US007238778B2

(12) United States Patent
Apolito et al.

(10) Patent No.: US 7,238,778 B2
(45) Date of Patent: Jul. 3, 2007

(54) CRYSTALLIZED GLUCOCORTICOID RECEPTOR LIGAND BINDING DOMAIN POLYPEPTIDE AND SCREENING METHODS EMPLOYING SAME

(75) Inventors: Christopher J. Apolito, Durham, NC (US); Randy K. Bledsoe, Durham, NC (US); Millard H. Lambert, III, Durham, NC (US); David D. McKee, Durham, NC (US); Valerie Gail Montana, Durham, NC (US); Kenneth H. Pearce, Durham, NC (US); Thomas B. Stanley, Durham, NC (US); Huaqiang Eric Xu, Grand Rapids, MI (US); Christopher J Delves, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 256 days.

(21) Appl. No.: 10/484,061

(22) PCT Filed: Jul. 17, 2002

(86) PCT No.: PCT/US02/22648

§ 371 (c)(1),
(2), (4) Date: Jan. 16, 2004

(87) PCT Pub. No.: WO03/015692

PCT Pub. Date: Feb. 27, 2003

(65) Prior Publication Data

US 2005/0181362 A1 Aug. 18, 2005

Related U.S. Application Data

(60) Provisional application No. 60/305,902, filed on Jul. 17, 2001.

(51) Int. Cl.
*A61K 38/00* (2006.01)
*A61K 38/16* (2006.01)

(52) U.S. Cl. ........................................ 530/350

(58) Field of Classification Search ................ 530/350
See application file for complete search history.

(56) References Cited

U.S. PATENT DOCUMENTS 6,004,757 A 12/1999 Cantley et al.
6,699,686 B1 * 3/2004 Brocard et al. ............ 435/69.1

FOREIGN PATENT DOCUMENTS

WO WO 00/52050 9/2000

OTHER PUBLICATIONS

Bourguet et al. Molecular Cell, vol. 5, 289-298, 2000.*

Bledsoe et al., "Crystal structure of the glucocorticoid receptor ligand binding domain reveals a novel mode of receptor dimerization and coactivator recognition," *Cell* 110:93-105 (Jul. 2002).

Dey et al., "Homology modeling of the ligand-binding domain of glucocorticoid receptor: binding site interactions with cortisol and corticosterone," *Protein Engineering* 14(8):565-571 (2001).

Jagerschmidt et al., "Residues in the ligand binding domain that confer progestin or glucocorticoid specificity and modulate the receptor transactivation capacity," *Molecular Endocrinology* 14(7):1028-1037 (2000).

Chan et al., "Investigating the substrate specificity of the HER2/Neu tyrosine kinase using peptide libraries," *Cancer Letters* 160(2):159-169 (Nov. 2000).

Chen et al., "Selection of substrate recognition sequence of protein kinase with ferric chelation affinity chromatography," *Science in China Series C* 40(2):184-193 (Apr. 1997).

Erdjument-Bromage et al., "Examination of micro-tip reversed-phase liquid chromatographic extraction of peptide pools for mass spectrometric analysis," *Journal of Chromatography* 826(2):167-181 (Nov. 1998).

Irvine, "Size exclusion high-performance liquid chromatography of peptides: a review," *Analytica Chimica Acta* 352(1-3):387-397 (Oct. 1997).

Posewitz et al., "Immobilized gallium(III) affinity chromatography of phosphopeptides," *Analytical Chemistry* 71(14):2883-2892 (Jul. 1999).

* cited by examiner

*Primary Examiner*—Michael Borin
(74) *Attorney, Agent, or Firm*—Eric J. Kron

(57) ABSTRACT

A method of modifying a test nuclear receptor (NR) polypeptide is disclosed. The method provides a test NR polypeptide sequence having a characteristic that is targeted for modification; aligning the test NR polypeptide sequence with at least one reference NR polypeptide sequence for which an X-ray structure is available; building a three-dimensional model for the test NR polypeptide using the three-dimensional coordinates of the X-ray structure(s) of at least one reference polypeptide and its sequence alignment with the test NR polypeptide sequence; examining the three-dimensional model of the test NR polypeptide sequence for characteristic differences with the reference polypeptide; and mutating at least one amino acid residue in the test NR polypeptide sequence at a characteristic difference, whereby the test NR polypeptide is modified.

4 Claims, 17 Drawing Sheets

FIGURE 5

```
GR  527 QLTPTLVSLLEVIEPEVLYAGYDSSVPDSTWRIMTTLNMLGGRQV
MR  733 ALTPSPVMVLENIEPEIVYAGYDSSKPDTAENLLSTLNRLAGKQM
PR  682 QLIPPLINLLMSIEPDVIYAGHDNTKPDTSSSLLTSLNQLGERQL
AR  668 ECQPIFLNVLEAIEPGVVCAGHDNNQPDSFAALLSSLNELGERQL
ERA 310 LTADQMVSALLDAEPPILYSEYDPTRPFSEASMMGLLTNLADREL
ERB 263 LSPEQLVLTLLEAEPPHVLIS-RPSAPFTEASMMMSLTKLADKEL
                  helix-1                         helix-3

GR  572 IAAVKWAKAIPGFRNLHLDDQMTLLQYSWMSLMAFALGWRSYRQS
MR  778 IQVVKWAKVLPGFKNLPLEDQITLLQYSWMCLSSFALSWRSYKHT
PR  727 LSVVKWSKSLPGFRNLHIDDQITLIQYSWMSLMVFGLGWRSYKHV
AR  713 VHVVKWAKALPGFRNLHVDDQMAVIQYSWMGLMVFAMGWRSFTNV
ERA 355 VHMINWAKRVPGFVDLTLHDQVHLLECAWLEILMIGLVWRSMEH-
ERB 307 VHMISWAKKIPGFVELSLFDQVRLLESCWMEVLMMGLMWRSIDH-
                     helix-3'  helix-4      helix-5

GR  617 SANLLCFAPDLIINEQRMT-LPCMYDQCKHMLYVSSELHRLQVSY
MR  823 NSQFLYFAPDLVFNEEKMH-QSAMYELCQGMHQISLQFVRLQLTF
PR  772 SGQMLYFAPDLILNEQRMK-ESSFYSLCLTMWQIPQEFVKLQVSQ
AR  758 NSRMLYFAPDLVFNEYRMH-KSRMYSQCVRMRHLSQEFGWLQITP
ERA 399 -PGKLLFAPNLLLDRNQGKCVEGMVEIFDMLLATSSRFRMMNLQG
ERB 351 -PGKLIFAPDLVLDRDEGKCVEGILEIFDMLLATTSRFRELKLQH
           beta-3  beta-4 helix-6          helix-7

GR  661 EEYLCMKTLLLLS-------SVPKDGLKSQELFDEIRMTYIKELG
MR  867 EEYTIMKVLLLLS-------TIPKDGLKSQAAFEEMRTNYIKELR
PR  816 EEFLCMKVLLLLN-------TIPLEGLRSQTQFEEMRSSYIRELI
AR  802 QEFLCMKALLLFS-------IIPVDGLKNQKFFDELRMNYIKELD
ERA 443 EEFVCLKSIILLNSGVYTFLSSTLKSLEEKDHIHRVLDKITDTLI
ERB 395 KEYLCVKAMILLNSSMYPLV-TATQDADSSRKLAHLLNAVTDALV
          helix-8            beta-5              helix-9

GR  699 KAIVKREGNSSQNWQRFYQLTKLLDSMHEVVENLLNYCFQTFLD-
MR  905 KNVTKCPNNSGQSWQRFYQLTKLLDSMHDLVSDLLEFCFYTFRES
PR  854 KAIGLRQKGVVSSSQRFYQLTKLLDNLHDLVKQLHLYCLNTFIQS
AR  840 RIIACKRKNPTSCSRRFYQLTKLLDSVQPIARELHQFTFDLLIKS
ERA 488 HLMAKAGLTLQQQHQRLAQLLLILSHIRHMSNKGMEHLYSMKCKN
ERB 439 WVIAKSGISSQQQSMRLANLLMLLSHVRHASNKGMEHLLNMKCKN
                                   helix-10

GR  743 KTMSIEFPEMLAEIITNQIPKYSNGNIKKLLFHQK----------
MR  950 HALKVEFPAMLVEIISDQLPKVESGNAKPLYFHRK----------
PR  899 RALSVEFPEMMSEVIAAQLPKILAGMVKPLLFHKK----------
AR  885 HMVSVDFPEMMAEIISVQVPKILSGKVKPIYFHTQ----------
ERA 533 ---VVPLYDLLLEMLDAHRLHAPTSRGGASVEETDQSHLATAGST
ERB 484 ---VVPVYDLLLEMLNAHVLRGCKSSITGSECSPAEDSKSKEGSQ
                  helix-AF           beta-6

ERA 575 SSHSLQKYYITGEAEGFPATV
ERB 526 NPQSQ----------------
```

CRYSTALLIZED GLUCOCORTICOID RECEPTOR LIGAND BINDING DOMAIN POLYPEPTIDE AND SCREENING METHODS EMPLOYING SAME

CROSS REFERENCE TO RELATED APPLICATIONS

This application is filed pursuant to 35 U.S.C. § 371 as a United States National Phase Application of International Application No. PCT/US02/22648 filed Jul. 17, 2002, which claims priority from U.S. Provisional Application No. 60/305,902 filed Jul. 17, 2001.

TECHNICAL FIELD

The present invention relates generally to a modified glucocortcoid receptor polypeptide, to a modified glucocortcoid receptor ligand binding domain polypeptide, to the structure of a glucocorticoid receptor ligand binding domain, and to the structure of a glucocorticoid receptor ligand binding domain in complex with a ligand and a co-activator. The invention further relates to methods by which a soluble glucocorticoid polypeptide can be generated and by which modulators and ligands of nuclear receptors, particularly steroid receptors and more particularly glucosteroid receptors and the ligand binding domains thereof can be identified.

| Abbreviations | |
|---|---|
| ATP | adenosine triphosphate |
| ADP | adenosine diphosphate |
| AR | androgen receptor |
| CAT | chloramphenicol acyltransferase |
| CBP | CREB binding protein |
| cDNA | complementary DNA |
| DBD | DNA binding domain |
| DMSO | dimethyl sulfoxide |
| DNA | deoxyribonucleic acid |
| DTT | dithiothreitol |
| EDTA | ethylenediaminetetraacetic acid |
| ER | estrogen receptor |
| GR | glucocorticoid receptor |
| GRE | glucocorticoid responsive element |
| GST | glutathione S-transferase |
| HEPES | N-2-Hydroxyethylpiperazine-N'-2-ethanesulfonic acid |
| HSP | heat shock protein |
| kDa | kilodalton(s) |
| LBD | ligand binding domain |
| MR | mineralcorticoid receptor |
| NDP | nucleotide diphosphate |
| NID | nuclear receptor interaction domain |
| NTP | nucleotide triphosphate |
| PAGE | polyacrylamide gel electrophoresis |
| PCR | polymerase chain reaction |
| pI | isoelectric point |
| PPAR | peroxisome proliferator-activated receptor |
| PR | progesterone receptor |
| RAR | retinoid acid receptor |
| RXR | retinoid X receptor |
| SDS | sodium dodecyl sulfate |
| SDS-PAGE | sodium dodecyl sulfate polyacrylamide gel electrophoresis |
| TIF2 | transcription intermediary factor 2 |
| TR | thyroid receptor |
| VDR | vitamin D receptor |

Amino Acid Abbreviations

| Single-Letter Code | Three-Letter Code | Name |
|---|---|---|
| A | Ala | Alanine |
| V | Val | Valine |
| L | Leu | Leucine |
| I | Ile | Isoleucine |
| P | Pro | Proline |
| F | Phe | Phenylalanine |
| W | Trp | Tryptophan |
| M | Met | Methionine |
| G | Gly | Glycine |
| S | Ser | Serine |
| T | Thr | Threonine |
| C | Cys | Cysteine |
| Y | Tyr | Tyrosine |
| N | Asn | Asparagine |
| Q | Gln | Glutamine |
| D | Asp | Aspartic Acid |
| E | Glu | Glutamic Acid |
| K | Lys | Lysine |
| R | Arg | Arginine |
| H | His | Histidine |

Functionally Equivalent Codons

| Amino Acid | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Methionine | Met | M | AUG |
| Asparagine | Asn | N | AAC AAU |
| Proline | Pro | P | CCA CCC CCG CCU |
| Glutamine | Gln | Q | CAA CAG |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |
| Leucine | Leu | L | UUA UUG CUA CUC CUG CUU |
| Arginine | Arg | R | AGA AGG CGA CGC CGG CGU |
| Serine | Ser | S | ACG AGU UCA UCC UCG UCU |

BACKGROUND ART

Nuclear receptors reside in either the cytoplasm or nucleus of eukaryotic cells and represent a superfamily of proteins that specifically bind a physiologically relevant small molecule, such as a hormone or vitamin. As a result of a molecule binding to a nuclear receptor, the nuclear receptor changes the ability of a cell to transcribe DNA, i.e. nuclear receptors modulate the transcription of DNA. However, they can also have transcription independent actions.

Unlike integral membrane receptors and membrane-associated receptors, nuclear receptors reside in either the cytoplasm or nucleus of eukaryotic cells. Thus, nuclear receptors comprise a class of intracellular, soluble, ligand-regulated transcription factors. Nuclear receptors include but are not limited to receptors for androgens, mineralcorticoids, progestins, estrogens, thyroid hormones, vitamin D, retinoids, eicosanoids, peroxisome proliferators and, pertinently, glucocorticoids. Many nuclear receptors, identified by either sequence homology to known receptors (See, e.g., Drewes et al., (1996) *Mol. Cell. Biol.* 16:925–31) or based on their affinity for specific DNA binding sites in gene promoters (See, e.g., Sladek et al., *Genes Dev.* 4:2353–65), have unascertained ligands and are therefore commonly termed "orphan receptors".

Glucocorticoids are an example of a cellular molecule that has been associated with cellular proliferation. Glucocorticoids are known to induce growth arrest in the G1-phase of the cell cycle in a variety of cells, both in vivo and in vitro, and have been shown to be useful in the treatment of certain cancers. The glucocorticoid receptor (GR) belongs to an important class of transcription factors that alter the expression of target genes in response to a specific hormone signal. Accumulated evidence indicates that receptor associated proteins play key roles in regulating glucocorticoid signaling. The list of cellular proteins that can bind and co-purify with the GR is constantly expanding.

Glucocorticoids are also used for their anti-inflammatory effect on the skin, joints, and tendons. They are important for treatment of disorders where inflammation is thought to be caused by immune system activity. Representative disorders of this sort include but are not limited to rheumatoid arthritis, inflammatory bowel disease, glomerulonephritis, and connective tissue diseases like systemic lupus erythmatosus. Glucocorticoids are also used to treat asthma and are widely used with other drugs to prevent the rejection of organ transplants. Some cancers of the blood (leukemias) and lymphatic system (lymphomas) can also respond to corticosteroid drugs.

Glucocorticoids exert several effects in tissues that express receptors for them. They regulate the expression of several genes either positively or negatively and in a direct or indirect manner. They are also known to arrest the growth of certain lymphoid cells and in some cases cause cell death (Harmon et al., (1979) *J. Cell Physiol.* 98: 267–278; Yamamoto, (1985) *Ann. Rev. Genet.* 19: 209–252; Evans, (1988) *Science* 240:889–895; Beato, (1989) *Cell* 56:335–344; Thompson, (1989) *Cancer Res.* 49: 2259s–2265s.). Due in part to their ability to kill cells, glucocorticoids have been used for decades in the treatment of leukemias, lymphomas, breast cancer, solid tumors and other diseases involving irregular cell growth, e.g. psoriasis. The inclusion of glucocorticoids in chemotherapeutic regimens has contributed to a high rate of cure of certain leukemias and lymphomas which were formerly lethal (Homo-Delarche, (1984) *Cancer Res.* 44: 431–437). Although it is clear that glucocorticoids exert these effects after binding to their receptors, the mechanism of cell kill is not completely understood, although several hypotheses have been proposed. Among the more prominent hypotheses are: the deinduction of critical lymphokines, oncogenes and growth factors; the induction of supposed "lysis genes"; alterations in calcium ion influx; the induction of endonucleases; and the induction of a cyclic AMP-dependent protein kinase (McConkey et al., (1989) *Arch. Biochem. Biophys.* 269: 365–370; Cohen & Duke, (1984) *J. Immunol.* 152: 38–42; Eastman-Reks & Vedeckis, (1986) *Cancer Res.* 46: 2457–2462; Kelso & Munck, (1984) *J. Immunol.* 133:784–791; Gruol et al., (1989) *Molec. Endocrinol.* 3: 2119–2127; Yuh & Thompson, (1989) *J. Biol. Chem.* 264: 10904–10910).

Polypeptides, including the glucocorticoid receptor ligand binding domain, have a three-dimensional structure determined by the primary amino acid sequence and the environment surrounding the polypeptide. This three-dimensional structure establishes the polypeptide's activity, stability, binding affinity, binding specificity, and other biochemical attributes. Thus, knowledge of a protein's three-dimensional structure can provide much guidance in designing agents that mimic, inhibit, or improve its biological activity.

The three-dimensional structure of a polypeptide can be determined in a number of ways. Many of the most precise methods employ X-ray crystallography (See, e.g., Van Holde, (1971) *Physical Biochemistry*, Prentice-Hall, New Jersey, pp. 221–39). This technique relies on the ability of crystalline lattices to diffract X-rays or other forms of radiation. Dffraction experiments suitable for determining the three-dimensional structure of macromolecules typically require high-quality crystals. Unfortunately, such crystals have been unavailable for the ligand binding domain of a human glucocorticoid receptor, as well as many other proteins of interest. Thus, high-quality diffracting crystals of the ligand binding domain of a human glucocorticoid receptor in complex with a ligand and a peptide would greatly assist in the elucidation of its three-dimensional structure.

Clearly, the solved crystal structure of the ligand binding domain of a glucocorticoid receptor polypeptide would be useful in the design of modulators of activity mediated by the glucocorticoid receptor. Evaluation of the available sequence data shows that GRα is particularly similar to MR, PR and AR. The GRα LBD has approximately 56%, 54% and 50% sequence identity to the MR, PR and AR LBDs, respectively. The GRβ amino acid sequence is identical to the GRα amino acid sequence for residues 1–727, but the remaining 15 residues in GRβ show no significant similarity to the remaining 50 residues in GRα. If no X-ray structure were available for GRα, then one could build a model for GRα using the available X-ray structures of PR and/or AR as templates. These theoretical models have some utility, but cannot be as accurate as a true X-ray structure, such as the X-ray structure disclosed here. Because of their limited accuracy, a model for GRα will generally be less useful than an X-ray structure for the design of agonists, antagonists and modulators of GRα.

The solved GRα-ligand-co-activator crystal structure would provide structural details and insights necessary to design a modulator of GRα that maximizes preferred requirements for any modulator, i.e. potency and specificity. By exploiting the structural details obtained from a GRα-ligand-co-activator crystal structure, it would be possible to design a GRα modulator that, despite GRα's similarity with other steroid receptors and nuclear receptors, exploits the unique structural features of the ligand binding domain of human GRα. A GRα modulator developed using structureassisted design would take advantage of heretofore unknown GRα structural considerations and thus be more effective than a modulator developed using homology-based design. Potential or existent homology models cannot provide the necessary degree of specificity. A GRα modulator designed using the structural coordinates of a crystalline form of the ligand binding domain of GRα in complex with a ligand and a co-activator would also provide a starting point for the development of modulators of other nuclear receptors.

Although several journal articles have referred to GR mutants having "increased ligand efficacy" in cell-based assays, it has not been mentioned that such mutants could have improved solution properties so that they could provide a suitable reagent for purification, assay, and crystallization. See Garabedian & Yamamoto (1992) *Mol. Biol. Cell* 3: 1245–1257; Kralli, et al., (1995) *Proc. Natl. Acad. Sci.* 92: 4701–4705; Bohen (1995) *J. Biol. Chem.* 270: 29433–29438; Bohen (1998) *Mol. Cell. Biol.* 18: 3330–3339; Freeman et al., (2000) *Genes Dev.* 14: 422–434.

Indeed, it is well documented that GR associates with molecular chaperones (such as hsp90, hsc70, and p23). In the past, it has been considered that GR would either not be active or soluble if purified away from these binding partners. In fact, it has even been mentioned that GR must be in complex with hsp90 in order to adopt a high affinity steroid binding conformation. See Xu et al. (1998) *J. Biol. Chem.* 273: 13918–13924; Rajapandi et al. (2000) *J. Biol. Chem.* 275: 22597–22604.

Still other journal articles have reported *E. coli* expression of GST-GR, but also noted a failure to purify the purported polypeptide. See Ohara-Nemoto et al., (1990) *J. Steroid Biochem. Molec. Biol.* 37: 481–490; Caamano et al., (1994) *Annal. NY Acad. Sci.* 746: 68–77.

What is needed, therefore, is a purified, soluble GRα LBD polypeptide for use in structural studies, as well as methods for making the same. Such methods would also find application in the preparation of modified NRs in general.

What is also needed is a crystallized form of a GRα ligand binding domain, preferably in complex with a ligand and more preferably in complex with a ligand and a co-activator. Acquisition of crystals of the GRα ligand binding domain polypeptide permits the three-dimensional structure of a GRα ligand binding domain (LBD) polypeptide to be determined. Knowledge of the three dimensional structure can facilitate the design of modulators of GR-mediated activity. Such modulators can lead to therapeutic compounds to treat a wide range of conditions, including inflammation, tissue rejection, auto-immunity, malignancies such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the TH1/TH2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, inflammatory bowel disease, systemic lupus erythematosus, polyartitis nodosa, Wegener's granulomatosis, giant cell arteritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitus, erythema nodosum, acne, hirsutism, toxic epidermal necrolysis, erythema multiform, cutaneous T-cell lymphoma. Other applications of a GR modulator developed in accordance with the present invention can be employed to treat Human Immunodeficiency Virus (HIV), cell apoptosis, and can be employed in treating cancerous conditions including, but not limited to, Kaposi's sarcoma, immune system activation and modulation, desensitization of inflammatory responses, IL-1 expression, natural killer cell development, lymphocytic leukemia, treatment of retinitis pigmentosa. Other applications for such a modulator comprise modulating cognitive performance, memory and learning enhancement, depression, addiction, mood disorders, chronic fatigue syndrome, schizophrenia, stroke, sleep disorders, anxiety, immunostimulants, repressors, wound healing and a role as a tissue repair agent or in anti-retroviral therapy.

SUMMARY OF THE INVENTION

A method of modifying a test NR polypeptide is disclosed. The method can comprise: providing a test NR polypeptide sequence having a characteristic that is targeted for modification; aligning the test NR polypeptide sequence with at least one reference NR polypeptide sequence for which an X-ray structure is available, wherein the at least one reference NR polypeptide sequence has a characteristic that is desired for the test NR polypeptide; building a three-dimensional model for the test NR polypeptide using the three-dimensional coordinates of the X-ray structure(s) of the at least one reference polypeptide and its sequence alignment with the test NR polypeptide sequence; examining the three-dimensional model of the test NR polypeptide for differences with the at least one reference polypeptide that are associated with the desired characteristic; and mutating at least one amino acid residue in the test NR polypeptide sequence located at a difference identified above to a residue associated with the desired characteristic, whereby the test NR polypeptide is modified.

A method of altering the solubility of a test NR polypeptide is also disclosed in accordance with the present invention. In a preferred embodiment, the method comprises: (a) providing a reference NR polypeptide sequence and a test NR polypeptide sequence; (b) comparing the reference NR polypeptide sequence and the test NR polypeptide sequence to identify one or more residues in the test NR sequence that are more or less hydrophilic than a corresponding residue in the reference NR polypeptide sequence; and (c) mutating the residue in the test NR polypeptide sequence identified in step (b) to a residue having a different hydrophilicity, whereby the solubility of the test NR polypeptide is altered. Optionally, the reference NR polypeptide sequence is an AR or a PR sequence, and the test polypeptide sequence is a GR polypeptide sequence. Alternatively, the reference polypeptide sequence is a crystalline GR LBD. The comparing of step (b) is preferably by sequence alignment.

An isolated GR polypeptide comprising a mutation in a ligand binding domain, wherein the mutation alters the solubility of the ligand binding domain, is also disclosed. An isolated GR polypeptide, or functional portion thereof, having one or more mutations comprising a substitution of a hydrophobic amino acid residue by a hydrophilic amino acid residue in a ligand binding domain is also disclosed. Preferably, in each case, the mutation can be at a residue selected from the group consisting of V552, W557, F602, L636, Y648, W712, L741, L535, V538, C638, M691, V702, Y648, Y660, L685, M691, V702, W712, L733, Y764 and combinations thereof. More preferably, the mutation is selected from the group consisting of V552K, W557S, F602S, F602D, F602E, L636E, Y648Q, W712S, L741R, L535T, V538S, C638S, M691T, V702T, W712T and combinations thereof. Antibodies against such polypeptides are also disclosed, as are methods of detecting such polypeptides and methods of identifying substances that modulate the biological activity of such polypeptides.

An isolated nucleic acid molecule encoding a GR polypeptide comprising a mutation in a ligand binding domain, wherein the mutation alters the solubility of the ligand binding domain, or encoding a GR LBD polypeptide, or functional portion thereof, having one or more mutations comprising a substitution of a hydrophobic amino acid residue by a hydrophilic amino acid residue, is also disclosed. A chimeric gene, comprising the nucleic acid molecule operably linked to a heterologous promoter, a vector comprising the chimeric gene, and a host cell comprising the chimeric gene are also disclosed. Methods for detecting such a nucleic acid molecule are also disclosed.

A substantially pure GRα ligand binding domain polypeptide in crystalline form is disclosed. Preferably, the crystalline form has lattice constants of a=b=126.014 Å, c=86.312 Å, α=90°, β=90°, γ=120°. Preferably, the crystalline form is a hexagonal crystalline form. More preferably, the crystalline form has a space group of $P6_1$. Even more preferably, the GRα ligand binding domain polypeptide has the F602S amino acid sequence shown in Example 2. Even more preferably, the GRα ligand binding domain has a crystalline structure further characterized by the coordinates corresponding to Table 4.

Preferably, the GRα ligand binding domain polypeptide is in complex with a ligand. Optionally, the crystalline form contains two GRα ligand binding domain polypeptides in the asymmetric unit. Preferably, the crystalline form is such that the three-dimensional structure of the crystallized GRα ligand binding domain polypeptide can be determined to a resolution of about 2.8 Å or better. Even more preferably, the crystalline form contains one or more atoms having a molecular weight of 40 grams/mol or greater.

A method for determining the three-dimensional structure of a crystallized GR ligand binding domain polypeptide to a resolution of about 2.8 Å or better, the method comprising: (a) crystallizing a GR ligand binding domain polypeptide; and (b) analyzing the GR ligand binding domain polypeptide to determine the three-dimensional structure of the crystallized GR ligand binding domain polypeptide, whereby the three-dimensional structure of a crystallized GR ligand binding domain polypeptide is determined to a resolution of about 2.8 Å or better. Preferably, the analyzing is by X-ray diffraction. More preferably, the crystallization is accomplished by the hanging drop method, and wherein the GRα ligand binding domain is mixed with a reservoir.

A method of generating a crystallized GR ligand binding domain polypeptide, the method comprising: (a) incubating a solution comprising a GR ligand binding domain with a reservoir; and (b) crystallizing the GR ligand binding domain polypeptide using the hanging drop method, whereby a crystallized GR ligand binding domain polypeptide is generated.

A method of designing a modulator of a nuclear receptor, the method comprising: (a) designing a potential modulator of a nuclear receptor that will make interactions with amino acids in the ligand binding site of the nuclear receptor based upon the atomic structure coordinates of a GR ligand binding domain polypeptide; (b) synthesizing the modulator; and (c) determining whether the potential modulator modulates the activity of the nuclear receptor, whereby a modulator of a nuclear receptor is designed.

A method of designing a modulator that selectively modulates the activity of a GRα polypeptide the method comprising: (a) obtaining a crystalline form of a GRα ligand binding domain polypeptide; (b) determining the three-dimensional structure of the crystalline form of the GRα ligand binding domain polypeptide; and (c) synthesizing a modulator based on the three-dimensional structure of the crystalline form of the GRα ligand binding domain polypeptide, whereby a modulator that selectively modulates the activity of a GRα polypeptide is designed. Preferably, the method further comprises contacting a GRα ligand binding domain polypeptide with the potential modulator; and assaying the GRα ligand binding domain polypeptide for binding of the potential modulator, for a change in activity of the GRα ligand binding domain polypeptide, or both. More preferably, the crystalline form is in orthorhombic form. Even more preferably, the crystals are such that the three-dimensional structure of the crystallized GRα ligand binding domain polypeptide can be determined to a resolution of about 2.8 Å or better.

A method of screening a plurality of compounds for a modulator of a GR ligand binding domain polypeptide, the method comprising: (a) providing a library of test samples; (b) contacting a GR ligand binding domain polypeptide with each test sample; (c) detecting an interaction between a test sample and the GR ligand binding domain polypeptide; (d) identifying a test sample that interacts with the GR ligand binding domain polypeptide; and (e) isolating a test sample that interacts with the GR ligand binding domain polypeptide, whereby a plurality of compounds is screened for a modulator of a GR ligand binding domain polypeptide. Preferably, the test samples are bound to a substrate, and more preferably, the test samples are synthesized directly on a substrate. The GR ligand binding domain polypeptide can be in soluble or crystalline form.

A method for identifying a GR modulator is also disclosed. In a preferred embodiment, the method comprises: (a) providing atomic coordinates of a GR ligand binding domain to a computerized modeling system; and (b) modeling ligands that fit spatially into the binding pocket of the GR ligand binding domain to thereby identify a GR modulator, whereby a GR modulator is identified. Preferably, the method further comprises identifying in an assay for GR-mediated activity a modeled ligand that increases or decreases the activity of the GR.

A method of identifying modulator that selectively modulates the activity of a GRα polypeptide compared to other GR polypeptides, the method comprising: (a) providing atomic coordinates of a GRα ligand binding domain to a computerized modeling system; and (b) modeling a ligand that fits into the binding pocket of a GRα ligand binding domain and that interacts with conformationally constrained residues of a GRα conserved among GR subtypes, whereby a modulator that selectively modulates the activity of a GRα polypeptide compared to other polypeptides is identified. Preferably, the method further comprises identifying in a biological assay for GRα activity a modeled ligand that selectively binds to GRα and increases or decreases the activity of said GRα.

A method of designing a modulator of a GR polypeptide, the method comprising: (a) selecting a candidate GR ligand; (b) determining which amino acid or amino acids of a GR polypeptide interact with the ligand using a three-dimensional model of a crystallized protein comprising a GRα LBD; (c) identifying in a biological assay for GR activity a degree to which the ligand modulates the activity of the GR polypeptide; (d) selecting a chemical modification of the ligand wherein the interaction between the amino acids of the GR polypeptide and the ligand is predicted to be modulated by the chemical modification; (e) synthesizing a chemical compound with the selected chemical modification to form a modified ligand; (f) contacting the modified ligand with the GR polypeptide; (g) identifying in a biological assay for GR activity a degree to which the modified ligand modulates the biological activity of the GR polypeptide; and (h) comparing the biological activity of the GR polypeptide in the presence of modified ligand with the biological activity of the GR polypeptide in the presence of the unmodified ligand, whereby a modulator of a GR polypeptide is designed. Preferably, the GR polypeptide is a GRα polypeptide. More preferably, the three-dimensional model of a crystallized protein is a GRα LBD polypeptide with a bound ligand. Optionally, the method further comprises repeating steps (a) through (f) if the biological activity of the GR polypeptide in the presence of the modified ligand varies from the biological activity of the GR polypeptide in the presence of the unmodified ligand.

An assay method for identifying a compound that inhibits binding of a ligand to a GR polypeptide, the assay method comprising: (a) designing a test inhibitor compound based on the three dimensional atomic coordinates of GR; (b) incubating a GR polypeptide with a ligand in the presence of a test inhibitor compound; (c) determining an amount of ligand that is bound to the GR polypeptide, wherein decreased binding of ligand to the GR protein in the presence of the test inhibitor compound relative to binding of ligand in the absence of the test inhibitor compound is indicative of inhibition; and (d) identifying the test compound as an inhibitor of ligand binding if decreased ligand binding is observed, whereby a compound that inhibits binding of a ligand to a GR polypeptide is identified.

A method of identifying a NR modulator that selectively modulates the biological activity of one NR compared to GRα is also disclosed. The method comprises: (a) providing an atomic structure coordinate set describing a GRα ligand binding domain structure and at least one other atomic structure coordinate set describing a NR ligand binding domain, each ligand binding domain comprising a ligand binding site; (b) comparing the atomic structure coordinate sets to identify at least one diference between the sets; (c) designing a candidate ligand predicted to interact with the difference of step (b); (d) synthesizing the candidate ligand; and (e) testing the synthesized candidate ligand for an ability to selectively modulate a NR as compared to GRα, whereby a NR modulator that selectively modulates the biological activity NR compared to GRα is identified.

Accordingly, it is an object of the present invention to provide a three dimensional structure of the ligand binding domain of a GR. The object is achieved in whole or in part by the present invention.

An object of the invention having been stated hereinabove, other objects will be evident as the description proceeds, when taken in connection with the accompanying Drawings and Laboratory Examples as best described hereinbelow.

BRIEF DESCRIPTION OF THE DRAWINGS

FIG. 2A is a graph depicting the binding of 10 nM fluorescein dexamethasone to varied concentrations of GST-GR LBD (F602S) 521–777 (circles), GR LBD (F602S) 521–777 (triangles) and GR LBD (F602S) 521–777 in the presence of 100 uM unlabeled dexamethasone (squares) as measured by fluorescence polarization.

FIG. 2B is a graph depicting ligand-dependent binding of TIF2 LXXLL(SEQ ID NO:18) motif to GR LBD. The binding of varied concentrations of GST-GR LBD (F602S) 521–777 to immobilized TIF2 732–756 peptide (SEQ ID NO:17) in the presence of a five-fold excess of dexamethasone (triangles), RU486 (squares) and no compound (circles) was measured by surface plasmon resonance. Each point is the average of two determinations.

FIG. 2C is a graph depicting that TIF2 coactivator peptide enhances stability of GR dexamethasone binding activity. The effect of 25 uM coactivator peptide TIF2 732–756 (diamonds) or no peptide (squares) on the binding of GST-GR LBD (F602S) 521–777 to 10 nM fluorescein dexamethasone with time is determined by fluorescence polarization.

FIG. 5 is a sequence alignment of steroid receptors, particularly an alignment of the F602S GRα sequence (SEQ ID NO:31) with MR(SEQ ID NO:26), PR(SEQ ID NO:27), AR(SEQ ID NO:28), ERα(SEQ ID NO:29), and ERβ(SEQ ID NO:30). Residues that lie within 5.0 angstroms of the ligand are identified with small square boxes around the one-letter amino acid code. The ligands used for this calculation are dexamethasone (for GR), progesterone (for PR), dihydrotestosterone (for AR), estradiol (for ERα) and genistein (for ERβ). The alpha-helices and beta-strands observed in the X-ray structures are identified by the larger boxes and captions. Note that the secondary structure of MR is not publicly known at this time, and thus is not annotated in the Figure. More than one structure is available for PR, AR, ERα and ERβ, and, in some cases, the alpha-helices have different endpoints in these different X-ray structures. The variation in the alpha-helices is indicated here by using boxes with thicker and thinner linewidths, where the thicker linewidth box encompasses residues that adopt the same secondary structure in all available X-ray structures, and thinner linewidth boxes encompass residues that adopt an alpha-helical structure in some but not all X-ray structures. The secondary structures were determined by graphical examination of the X-ray structures.

BRIEF DESCRIPTION OF SEQUENCES IN THE SEQUENCE LISTING

Figure 1A:
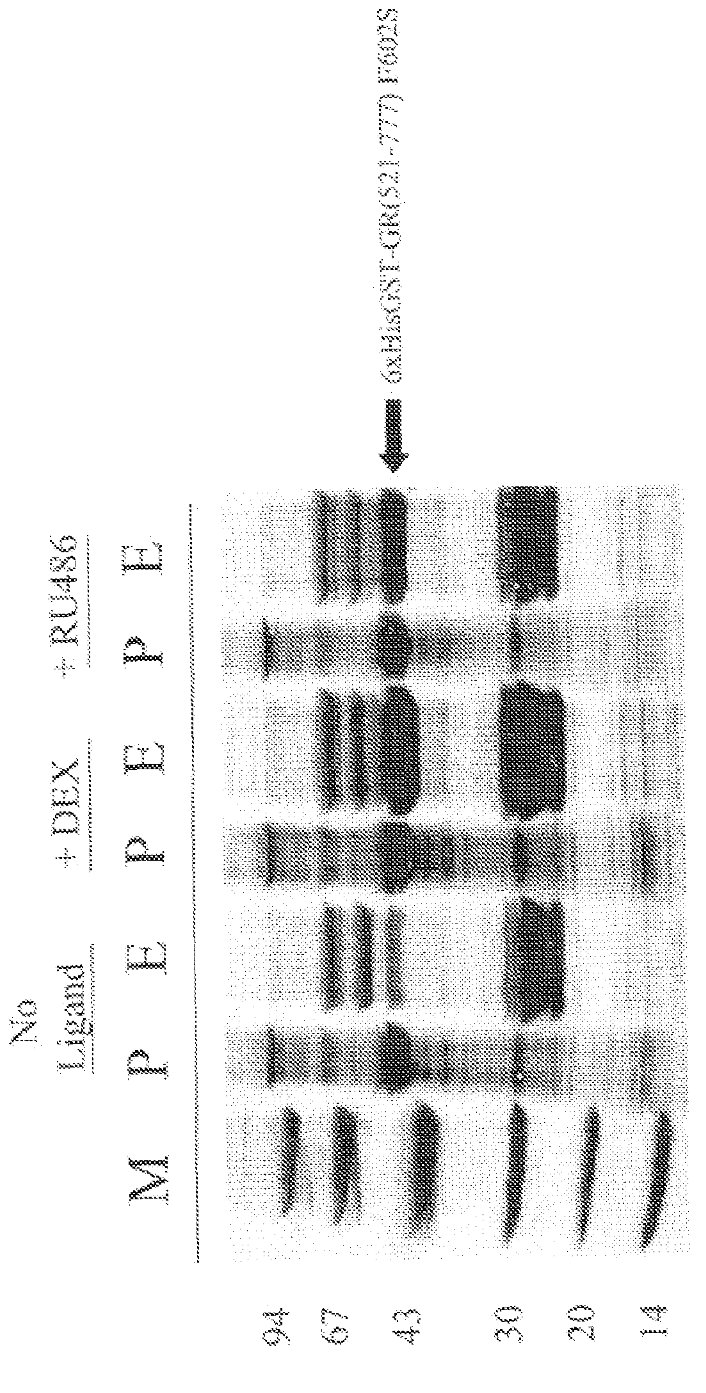
FIG. 1A depicts *E. coli* expression of mutant 6xHisGST-GR(521–777) F602S (SEQ ID NO:12) via SDS-PAGE. Staining was accomplished using the commercially available PROBLUE product.

SEQ ID NOs:1 and 2 are, respectively, a DNA sequence encoding a wild type full-length human glucocorticoid receptor (GenBank Accession No. 31679) and the amino acid sequence (GenBank Accession No. 121069) of a human glucocorticoid receptor encoded by the DNA sequence.

SEQ ID NOs:3 and 4 are, respectively, a DNA sequence encoding a F602S full-length human glucocorticoid receptor and the amino acid sequence of a human glucocorticoid receptor encoded by the DNA sequence.

SEQ ID NOs:5 and 6 are, respectively, a DNA sequence encoding a F602D full-length human glucocorticoid receptor and the amino acid sequence of a human glucocorticoid receptor encoded by the DNA sequence.

SEQ ID NOs:7 and 8 are, respectively, a DNA sequence encoding a preferred embodiment of a full-length human glucocorticoid receptor of the present invention and the amino acid sequence of a human glucocorticoid receptor encoded by the DNA sequence. These sequences thus include variable amino acids at the following locations: V552, W557, F602, L636, Y648, W712, L741, L535, V538, C638, M691, V702, Y648, Y660, L685, M691, V702, W712, L733, and Y764, thus reflecting the mutagenesis approach of the present invention disclosed herein below. Thus, a full length human glucocorticoid receptor of the present invention can include a mutation at any one of these residues, and/or at any combination of these residues.

SEQ ID NOs:9 and 10 are, respectively, a DNA sequence encoding a wild type ligand binding domain of a human glucocorticoid receptor and the amino acid sequence of a human glucocorticoid receptor encoded by the DNA sequence.

SEQ ID NOs:11 and 12 are, respectively, a DNA sequence encoding a ligand binding domain (residues 521–777) of a human glucocorticoid receptor containing a phenylalanine to serine mutation at residue 602 and the amino acid sequence of a human glucocorticoid receptor encoded by the DNA sequence.

SEQ ID NOs:13 and 14 are, respectively, a DNA sequence encoding a ligand binding domain (residues 521–777) of a human glucocorticoid receptor containing a phenylalanine to aspartic acid mutation at residue 602 and the amino acid sequence of a human glucocorticoid receptor encoded by the DNA sequence.

SEQ ID NOs:15 and 16 are, respectively, a DNA sequence encoding a preferred embodiment of a ligand binding domain of a human glucocorticoid receptor of the present invention and the amino acid sequence of a human glucocorticoid receptor encoded by the DNA sequence. These sequences thus include variable amino acids at the following locations: V552, W557, F602, L636, Y648, W712, L741, L535, V538, C638, M691, V702, Y648, Y660, L685, M691, V702, W712, L733, and Y764, thus reflecting the mutagenesis approach of the present invention disclosed herein below. Thus, a ligand binding domain of a human glucocorticoid receptor of the present invention can include a mutation at any one of these residues, and/or at any combination of these residues.

SEQ ID NO:17 is an amino acid sequence of amino acid residues 732–756 of the human TIF2 protein.

SEQ ID NO:18 is an LXXLL motif of the human TIF2 protein.

SEQ ID NOs:19–20 are oligonucleotide primers used to engineer a polyhistidine tag in frame to the sequence encoding glutathione S-transferase (GST).

SEQ ID NO:21 is the resulting amino acid sequence of the modified GST.

SEQ ID NOs:22–25 are oligonucleotide primers used in the mutagenesis approach of the present invention.

SEQ ID NOs:26–31 are the ligand binding domain pplypeptides of MR(SEQ ID NO:26), PR(SEQ ID NO:27), AR(SEQ ID NO:28), ERα(SEQ ID NO:29), ERβ(SEQ ID NO:30), and F602S GRα(SEQ ID NO:31) respectively. All of these sequences are also shown in FIG. 5. Note that the GRα sequence shown of SEQ ID NO:31 starts at residue 527, whereas the F602S sequence of SEQ ID NO:12 starts at residue 521.

SEQ ID NO:32 is an amino acid sequence of a ligand binding domain (residues 521–777) of a human glucocorticoid receptor containing a phenylalanine to serine mutation at residue 602, wherein the first two residues comprise a thrombin cleavage site encoded by vector.

SEQ ID NO: 33 is an amino acid sequence of a ligand binding domain (residues 521–777) of a human glucocorticoid receptor comprising a W557R mutation.

SEQ ID NO: 34 is an amino acid sequence of a ligand binding domain (residues 521–777) of a human glucocorticoid receptor comprising a Q615L mutation.

SEQ ID NO: 35 is an amino acid sequence of a ligand binding domain (residues 521–777) of a human glucocorticoid receptor comprising a Q615H mutation.

SEQ ID NO: 36 is an amino acid sequence of a ligand binding domain (residues 521–777) of a human glucocorticoid receptor comprising a A574T mutation.

SEQ ID NO: 37 is an amino acid sequence of a ligand binding domain (residues 521–777) of a human glucocorticoid receptor comprising a L620M mutation.

SEQ ID NO: 38 is an amino acid sequence of a ligand binding domain (residues 521–777) of a human glucocorticoid receptor comprising the double mutation F602L/A580T.

SEQ ID NO: 39 is an amino acid sequence of a ligand binding domain (residues 521–777) of a human glucocorticoid receptor comprising the double mutation L563F/G583C.

SEQ ID NO: 40 is an amino acid sequence of a ligand binding domain (residues 521–777) of a human glucocorticoid receptor comprising the double mutation L664H/M752T.

SEQ ID NO: 41 is an amino acid sequence of a ligand binding domain (residues 521–777) of a human glucocorticoid receptor comprising the double mutation L563F/T744N.

DETAILED DESCRIPTION OF THE INVENTION

The present invention provides for the generation of NR, SR and GR polypeptides and NR, SR or GR mutants (preferably GRα and GRα LBD mutants), and the ability to solve the crystal structures of those that crystallize. Indeed, a GRα LBD having a point mutation was crystallized and solved in one aspect of the present invention. Thus, an aspect of the present invention involves the use of both targeted and random mutagenesis of the GR gene for the production of a recombinant protein with improved solution characteristics for the purpose of crystallization, characterization of biologically relevant protein-protein interactions, and compound screening assays. The present invention, relating to GR LBD F602S and other LBD mutations, shows that GR can be overexpressed using an *E. coli* expression system and that active GR protein can be purified, assayed, and crystallized.

Until disclosure of the present invention presented herein, the ability to obtain crystalline forms of the ligand binding domain of GRα has not been realized. And until disclosure of the present invention presented herein, a detailed three-dimensional crystal structure of a GRα LBD polypeptide has not been solved.

In addition to providing structural information, crystalline polypeptides provide other advantages. For example, the crystallization process itself further purifies the polypeptide, and satisfies one of the classical criteria for homogeneity. In fact, crystallization frequently provides unparalleled purification quality, removing impurities that are not removed by other purification methods such as HPLC, dialysis, conventional column chromatography, and other methods. Moreover, crystalline polypeptides are sometimes stable at ambient temperatures and free of protease contamination and other degradation associated with solution storage. Crystalline polypeptides can also be useful as pharmaceutical preparations. Finally, crystallization techniques in general are largely free of problems such as denaturation associated with other stabilization methods (e.g., lyophilization). Once crystallization has been accomplished, crystallographic data provides useful structural information that can assist the design of compounds that can serve as modulators (e.g. agonists or antagonists), as described herein below. In addition, the crystal structure provides information useful to map a receptor binding domain, which can then be mimicked by a chemical entity that can serve as an antagonist or agonist.

I. Definitions

Following long-standing patent law convention, the terms "a" and "an" mean "one or more" when used in this application, including the claims.

As used herein, the term "agonist" means an agent that supplements or potentiates the bioactivity of a functional GR gene or protein or of a polypeptide encoded by a gene that is up- or down-regulated by a GR polypeptide and/or a polypeptide encoded by a gene that contains a GR binding site or response element in its promoter region. By way of specific example, an "agonist" is a compound that interacts with the steroid hormone receptor to promote a transcriptional response. An agonist can induce changes in a receptor that places the receptor in an active conformation that allows them to influence transcription, either positively or negatively. There can be several different ligand-induced changes in the receptors conformation. The term "agonist" specifically encompasses partial agonists.

As used herein, the terms "α-helix", "alpha-helix" and "alpha helix" are used interchangeably and mean the conformation of a polypeptide chain wherein the polypeptide backbone is wound around the long axis of the molecule in a left-handed or right-handed direction, and the R groups of the amino acids protrude outward from the helical backbone, wherein the repeating unit of the structure is a single turnoff the helix, which extends about 0.56 nm along the long axis.

As used herein, the term "antagonist" means an agent that decreases or inhibits the bioactivity of a functional GR gene or protein, or that supplements or potentiates the bioactivity of a naturally occurring or engineered non-functional GR gene or protein. Alternatively, an antagonist can decrease or inhibit the bioactivity of a functional gene or polypeptide encoded by a gene that is up- or down-regulated by a GR polypeptide and/or contains a GR binding site or response element in its promoter region. An antagonist can also supplement or potentiate the bioactivity of a naturally occurring or engineered non-functional gene or polypeptide encoded by a gene that is up- or down-regulated by a GR polypeptide, and/or contains a GR binding site or response element in its promoter region. By way of specific example, an "antagonist" is a compound that interacts with the steroid hormone receptor to inhibit a transcriptional response. An antagonist can bind to a receptor but fail to induce conformational changes that alter the receptor's transcriptional regulatory properties or physiologically relevant conformations. Binding of an antagonist can also block the binding and therefore the actions of an agonist. The term "antagonist" specifically encompasses partial antagonists.

As used herein, the terms "β-sheet", "beta-sheet" and "beta sheet" are used interchangeably and mean the conformation of a polypeptide chain stretched into an extended zig-zig conformation. Portions of polypeptide chains that run "parallel" all run in the same direction. Polypeptide chains that are "antiparallel" run in the opposite direction from the parallel chains.

As used herein, the terms "binding pocket of the GR ligand binding domain", "GR ligand binding pocket" and "GR binding pocket" are used interchangeably, and refer to the large cavity within the GR ligand binding domain where a ligand can bind. This cavity can be empty, or can contain water molecules or other molecules from the solvent, or can contain ligand atoms. The main binding pocket is the region of space encompassed the residues depicted FIG. 7. The binding pocket also includes regions of space near the "main" binding pocket that not occupied by atoms of GR but that are near the "main" binding pocket, and that are contiguous with the "main" binding pocket.

As used herein, the term "biological activity" means any observable effect flowing from interaction between a GR polypeptide and a ligand. Representative, but non-limiting, examples of biological activity in the context of the present invention include transcription regulation, ligand binding and peptide binding.

As used herein, the terms "candidate substance" and "candidate compound" are used interchangeably and refer to a substance that is believed to interact with another moiety, for example a given ligand that is believed to interact with a complete, or a fragment of, a GR polypeptide, and which can be subsequently evaluated for such an interaction. Representative candidate substances or compounds include xenobiotics such as drugs and other therapeutic agents, carcinogens and environmental pollutants, natural products and extracts, as well as endobiotics such as glucocorticosteroids, steroids, fatty acids and prostaglandins. Other examples of candidate compounds that can be investigated using the methods of the present invention include, but are not restricted to, agonists and antagonists of a GR polypeptide, toxins and venoms, viral epitopes, hormones (e.g., glucocorticosteroids, opioid peptides, steroids, etc.), hormone receptors, peptides, enzymes, enzyme substrates, cofactors, lectins, sugars, oligonucleotides or nucleic acids, oligosaccharides, proteins, small molecules and monoclonal antibodies.

As used herein, the terms "cells," "host cells" or "recombinant host cells" are used interchangeably and mean not only to the particular subject cell, but also to the progeny or potential progeny of such a cell. Because certain modifications can occur in succeeding generations due to either mutation or environmental influences, such progeny might not, in fact, be identical to the parent cell, but are still included within the scope of the term as used herein.

As used herein, the terms "chimeric protein" or "fusion protein" are used interchangeably and mean a fusion of a first amino acid sequence encoding a GR polypeptide with a second amino acid sequence defining a polypeptide domain foreign to, and not homologous with, any domain of a GR polypeptide. A chimeric protein can include a foreign domain that is found in an organism that also expresses the first protein, or it can be an "interspecies" or "intergenic" fusion of protein structures expressed by different kinds of organisms. In general, a fusion protein can be represented by the general formula X—GR—Y, wherein GR represents a portion of the protein which is derived from a GR polypeptide, and X and Y are independently absent or represent amino acid sequences which are not related to a GR sequence in an organism, which includes naturally occurring mutants.

As used herein, the term "co-activator" means an entity that has the ability to enhance transcription when it is bound to at least one other entity. The association of a co-activator with an entity has the ultimate effect of enhancing the transciption of one or more sequences of DNA. In the context of the present invention, transcription is preferably nuclear receptor-mediated. By way of specific example, in the present invention TIF2 (the human analog of mouse glucocorticoid receptor interaction protein 1 (GRIP1)) can bind to a site on the glucorticoid receptor, an event that can enhance transcription. TIF2 is therefore a co-activator of the glucocorticoid receptor. Other GR co-activators can include SRC1.

As used herein, the term "co-repressor" means an entity that has the ability to repress transcription when it is bound to at least one other entity. In the context of the present invention, transcription is preferably nuclear receptor-mediated. The association of a co-repressor with an entity has the ultimate effect of repressing the transciption of one or more sequences of DNA.

As used herein, the term "crystal laftice" means the array of points defined by the vertices of packed unit cells.

As used herein, the term "detecting" means confirming the presence of a target entity by observing the occurrence of a detectable signal, such as a radiologic or spectroscopic signal that will appear exclusively in the presence of the target entity.

As used herein, the term "DNA segment" means a DNA molecule that has been isolated free of total genomic DNA of a particular species. In a preferred embodiment, a DNA segment encoding a GR polypeptide refers to a DNA segment that comprises any of the odd numbered SEQ ID NOs:1–16, but can optionally comprise fewer or additional nucleic acids, yet is isolated away from, or purified free from, total genomic DNA of a source species, such as *Homo sapiens*. Included within the term "DNA segment" are DNA segments and smaller fragments of such segments, and also recombinant vectors, including, for example, plasmids, cosmids, phages, viruses, and the like.

As used herein, the term "DNA sequence encoding a GR polypeptide" can refer to one or more coding sequences within a particular individual. Moreover, certain differences in nucleotide sequences can exist between individual organisms, which are called alleles. It is possible that such allelic differences might or might not result in differences in amino acid sequence of the encoded polypeptide yet still encode a protein with the same biological activity. As is well known, genes for a particular polypeptide can exist in single or multiple copies within the genome of an individual. Such duplicate genes can be identical or can have certain modifications, including nucleotide substitutions, additions or deletions, all of which still code for polypeptides having substantially the same activity.

As used herein, the phrase "enhancer-promoter" means a composite unit that contains both enhancer and promoter elements. An enhancer-promoter is operatively linked to a coding sequence that encodes at least one gene product.

As used herein, the term "expression" generally refers to the cellular processes by which a biologically active polypeptide is produced.

As used herein, the term "gene" is used for simplicity to refer to a functional protein, polypeptide or peptide encoding unit. As will be understood by those in the art, this functional term includes both genomic sequences and cDNA sequences. Preferred embodiments of genomic and cDNA sequences are disclosed herein.

As used herein, the term "glucocorticoid" means a steroid hormone glucocorticoid. "Glucocorticoids" are agonists for the glucocorticoid receptor. Compounds which mimic glucocorticoids are also be defined as glucocorticoid receptor agonists. A preferred glucocorticoid receptor agonist is dexamethasone. Other common glucocorticoid receptor agonists include cortisol, cortisone, prednisolone, prednisone, methylprednisolone, trimcinolone, hydrocortisone, and corticosterone. As used herein, glucocorticoid is intended to include, for example, the following generic and brand name corticosteroids: cortisone (CORTONE ACETATE, ADRESON, ALTESONA, CORTELAN, CORTISTAB, CORTISYL, CORTOGEN, CORTONE, SCHEROSON); dexamethasone-oral (DECADRON-ORAL, DEXAMETH, DEXONE, HEXADROL-ORAL, DEXAMETHASONE INTENSOL, DEXONE 0.5, DEXONE 0.75, DEXONE 1.5, DEXONE 4); hydrocortisone-oral (CORTEF, HYDROCORTONE); hydrocortisone cypionate (CORTEF ORAL SUSPENSION); methylprednisolone-oral (MEDROL-ORAL); prednisolone-oral (PRELONE, DELTA-CORTEF, PEDIAPRED, ADNISOLONE, CORTALONE, DELTA-CORTRIL, DELTASOLONE, DELTASTAB, DI-ADRESON F, ENCORTOLONE, HYDROCORTANCYL, MEDISOLONE, METICORTELONE, OPREDSONE, PANAAFCORTELONE, PRECORTISYL, PRENISOLONA, SCHERISOLONA, SCHERISOLONE); prednisone (DELTASONE, LIQUID PRED, METICORTEN, ORASONE 1, ORASONE 5, ORASONE 10, ORASONE 20, ORASONE 50, PREDNICEN-M, PREDNISONE INTENSOL, STERAPRED, STERAPRED DS, ADASONE, CARTANCYL, COLISONE, CORDROL, CORTAN, DACORTIN, DECORTIN, DECORTISYL, DELCORTIN, DELLACORT, DELTADOME, DELTACORTENE, DELTISONA, DIADRESON, ECONOSONE, ENCORTON, FERNISONE, NISONA, NOVOPREDNISONE, PANAFCORT, PANASOL, PARACORT, PARMENISON, PEHACORT, PREDELTIN, PREDNICORT, PREDNICOT, PREDNIDIB, PREDNIMENT, RECTODELT, ULTRACORTEN, WINPRED); triamcinolone-oral (KENACORT, ARISTOCORT, ATOLONE, SHOLOG A, TRAMACORT-D, TRI-MED, TRIAMCOT, TRISTO-PLEX, TRYLONE D, U-TRI-LONE).

As used herein, the term "glucocorticoid receptor," abbreviated herein as "GR," means the receptor for a steroid hormone glucocorticoid. A glucocorticoid receptor is a steroid receptor and, consequently, a nuclear receptor, since steroid receptors are a subfamily of the superfamily of nuclear receptors. The term "GR" means any polypeptide sequence that can be aligned with human GR such that at least 70%, preferably at least 75%, of the amino acids are identical to the corresponding amino acid in the human GR. The term "GR" also encompasses nucleic acid sequences where the corresponding translated protein sequence can be considered to be a GR. The term "GR" includes invertebrate homologs, whether now known or hereafter identified; preferably, GR nucleic acids and polypeptides are isolated from eukaryotic sources. "GR" further includes vertebrate homologs of GR family members, including, but not limited to, mammalian and avian homologs. Representative mammalian homologs of GR family members include, but are not limited to, murine and human homologs. "GR" specifically encompasses all GR isoforms, including GRα and GRβ. GRβ is a splicing variant with 100% identity to GRα, except at the C-terminus, where 50 residues in GRα have been replaced with 15 residues in GRβ.

As used herein, the terms "GR gene product, UGR protein", "GR polypeptide", and "GR peptide" are used interchangeably and mean peptides having amino acid sequences which are substantially identical to native amino acid sequences from the organism of interest and which are biologically active in that they comprise all or a part of the amino acid sequence of a GR polypeptide, or cross-react with antibodies raised against a GR polypeptide, or retain all or some of the biological activity (e.g., DNA or ligand binding ability and/or transcriptional regulation) of the native amino acid sequence or protein. Such biological activity can include immunogenicity. Representative embodiments are set forth in any even numbered SEQ ID NOs:2–16. The terms "GR gene product", "GR protein", "GR polypeptide", and "GR peptide" also include analogs of a GR polypeptide. By "analog" is intended that a DNA or peptide sequence can contain alterations relative to the sequences disclosed herein, yet retain all or some of the biological activity of those sequences. Analogs can be derived from genomic nucleotide sequences as are disclosed herein or from other organisms, or can be created synthetically. Those skilled in the art will appreciate that other analogs, as yet undisclosed or undiscovered, can be used to design and/or construct GR analogs. There is no need for a "GR gene product", "GR protein", "GR polypeptide", or "GR peptide" to comprise all or substantially all of the amino acid sequence of a GR polypeptide gene product. Shorter or longer sequences are anticipated to be of use in the invention; shorter sequences are herein referred to as "segments". Thus, the terms "GR gene product", "GR protein", "GR polypeptide", and "GR peptide" also include fusion or recombinant GR polypeptides and proteins comprising sequences of the present invention. Methods of preparing such proteins are disclosed herein and are known in the art.

As used herein, the terms "GR gene" and "recombinant GR gene" mean a nucleic acid molecule comprising an open reading frame encoding a GR polypeptide of the present invention, including both exon and (optionally) intron sequences.

As used herein, "hexagonal unit cell" means a unit cell wherein a=b≠c; and α=β=90, γ=120°. The vectors a, b and c describe the unit cell edges and the angles α, β, and γ describe the unit cell angles. In a preferred embodiment of the present invention, the unit cell has lattice constants of a=b=126.014 Å, c=86.312 Å, α=90°, β=90°, γ=120°. While preferred lattice constants are provided, a crystalline polypeptide of the present invention also comprises variations from the preferred lattice constants, wherein the varations range from about one to about two percent. Thus, for example, a crystalline polypeptide of the present invention can also comprise lattice constants of about 125 or about 127.

As used herein, the term "hybridization" means the binding of a probe molecule, a molecule to which a detectable moiety has been bound, to a target sample.

As used herein, the term "interact" means detectable interactions between molecules, such as can be detected using, for example, a yeast two hybrid assay. The term "interact" is also meant to include "binding" interactions between molecules. Interactions can, for example, be protein-protein or protein-nucleic acid in nature.

As used herein, the term "intron" means a DNA sequence present in a given gene that is not translated into protein.

As used herein, the term "isolated" means oligonucleotides substantially free of other nucleic acids, proteins, lipids, carbohydrates or other materials with which they can be associated, such association being either in cellular material or in a synthesis medium. The term can also be applied to polypeptides, in which case the polypeptide will be substantially free of nucleic acids, carbohydrates, lipids and other undesired polypeptides.

As used herein, the term "labeled" means the attachment of a moiety, capable of detection by spectroscopic, radiologic or other methods, to a probe molecule.

As used herein, the term "modified" means an alteration from an entity's normally occurring state. An entity can be modified by removing discrete chemical units or by adding discrete chemical units. The term "modified" encompasses detectable labels as well as those entities added as aids in purification.

As used herein, the term "modulate" means an increase, decrease, or other alteration of any or all chemical and biological activities or properties of a wild-type or mutant GR polypeptide, preferably a wild-type or mutant GR polypeptide. The term "modulation" as used herein refers to both upregulation (i.e., activation or stimulation) and down-regulation (i.e. inhibition or suppression) of a response, and includes responses that are upregulated in one cell type or tissue, and down-regulated in another cell type or tissue.

As used herein, the term "molecular replacement" means a method that involves generating a preliminary model of the wild-type GR ligand binding domain, or a GR mutant crystal whose structure coordinates are unknown, by orienting and positioning a molecule or model whose structure coordinates are known (e.g., a nuclear receptor) within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown crystal. See, e.g., Lattman, (1985) *Method Enzymol.,* 115: 55–77; Rossmann, ed, (1972) *The Molecular Replacement Method*, Gordon & Breach, New York. Using the structure coordinates of the ligand binding domain of GR provided by this invention, molecular replacement can be used to determine the structure coordinates of a crystalline mutant or homologue of the GR ligand binding domain, or of a different crystal form of the GR ligand binding domain.

As used herein, the term "mutation" carries its traditional connotation and means a change, inherited, naturally occurring or introduced, in a nucleic acid or polypeptide sequence, and is used in its sense as generally known to those of skill in the art.

As used herein, the term "nuclear receptor", occasionally abbreviated herein as "NR", means a member of the superfamily of receptors that comprises at least the subfamilies of steroid receptors, thryroid hormone receptors, retinoic acid receptors and vitamin D receptors. Thus, a given nuclear receptor can be further classified as a member of a subfamily while retaining its status as a nuclear receptor.

As used herein, the phrase "operatively linked" means that an enhancer-promoter is connected to a coding sequence in such a way that the transcription of that coding sequence is controlled and regulated by that enhancer-promoter. Techniques for operatively linking an enhancer-promoter to a coding sequence are well known in the art; the precise orientation and location relative to a coding sequence of interest is dependent, inter alia, upon the specific nature of the enhancer-promoter.

As used herein, the term "partial agonist" means an entity that can bind to a receptor and induce only part of the changes in the receptors that are induced by agonists. The differences can be qualitative or quantitative. Thus, a partial agonist can induce some of the conformation changes induced by agonists, but not others, or it can only induce certain changes to a limited extent.

As used herein, the term "partial antagonist" means an entity that can bind to a receptor and inhibit only part of the changes in the receptors that are induced by antagonists. The differences can be qualitative or quantitative. Thus, a partial antagonist can inhibit some of the conformation changes induced by an antagonist, but not others, or it can inhibit certain changes to a limited extent.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably herein when referring to a gene product.

As used herein, the term "primer" means a sequence comprising two or more deoxyribonucleotides or ribonucleotides, preferably more than three, and more preferably more than eight and most preferably at least about 20 nucleotides of an exonic or intronic region. Such oligonucleotides are preferably between ten and thirty bases in length.

As used herein, the term "sequencing" means the determining the ordered linear sequence of nucleic acids or amino acids of a DNA or protein target sample, using conventional manual or automated laboratory techniques.

As used herein, the term "space group" means the arrangement of symmetry elements of a crystal.

As used herein, the term "steroid receptor" means a nuclear receptor that can bind or associate with a steroid compound. Steroid receptors are a subfamily of the superfamily of nuclear receptors. The subfamily of steroid receptors comprises glucocorticoid receptors and, therefore, a glucocorticoid receptor is a member of the subfamily of steroid receptors and the superfamily of nuclear receptors.

As used herein, the terms "structure coordinates" and "structural coordinates" mean mathematical coordinates derived from mathematical equations related to the patterns obtained on diffraction of a monochromatic beam of X-rays by the atoms (scattering centers) of a molecule in crystal form. The diffraction data are used to calculate an electron density map of the repeating unit of the crystal. The electron density maps are used to establish the positions of the individual atoms within the unit cell of the crystal.

Those of skill in the art understand that a set of coordinates determined by X-ray crystallography is not without standard error. In general, the error in the coordinates tends to be reduced as the resolution is increased, since more experimental diffraction data is available for the model fitting and refinement. Thus, for example, more diffraction data can be collected from a crystal that diffracts to a resolution of 2.8 angstroms than from a crystal that diffracts to a lower resolution, such as 3.5 angstroms. Consequently, the refined structural coordinates will usually be more accurate when fitted and refined using data from a crystal that diffracts to higher resolution. The design of ligands and modulators for GR or any other NR depends on the accuracy of the structural coordinates. If the coordinates are not sufficiently accurate, then the design process will be ineffective. In most cases, it is very difficult or impossible to collect sufficient diffraction data to define atomic coordinates precisely when the crystals diffract to a resolution of only 3.5 angstroms or poorer. Thus, in most cases, it is difficult to use X-ray structures in structure-based ligand design when the X-ray structures are based on crystals that diffract to a resolution of only 3.5 angstroms or poorer. However, common experience has shown that crystals diffracting to 2.8 angstroms or better can yield X-ray structures with sufficient accuracy to greatly facilitate structure-based drug design. Further improvement in the resolution can further facilitate structure-based design, but the coordinates obtained at 2.8 angstroms resolution are generally adequate for most purposes.

Also, those of skill in the art will understand that NR proteins can adopt different conformations when different ligands are bound. In particular, NR proteins will adopt substantially different conformations when agonists and antagonists are bound. Subtle variations in the conformation can also occur when different agonists are bound, and when different antagonists are bound. These variations can be difficult or impossible to predict from a single X-ray structure. Generally, structure-based design of GR modulators depends to some degree on a knowledge of the differences in conformation that occur when agonists and antagonists are bound. Thus, structure-based modulator design is most facilitated by the availability of X-ray structures of complexes with potent agonists as well as potent antagonists.

As used herein, the term "substantially pure" means that the polynucleotide or polypeptide is substantially free of the sequences and molecules with which it is associated in its natural state, and those molecules used in the isolation procedure. The term "substantially free" means that the sample is at least 50%, preferably at least 70%, more preferably 80% and most preferably 90% free of the materials and compounds with which is it associated in nature.

As used herein, the term "target cell" refers to a cell, into which it is desired to insert a nucleic acid sequence or polypeptide, or to otherwise effect a modification from conditions known to be standard in the unmodified cell. A nucleic acid sequence introduced into a target cell can be of variable length. Additionally, a nucleic acid sequence can enter a target cell as a component of a plasmid or other vector or as a naked sequence.

As used herein, the term "transcription" means a cellular process involving the interaction of an RNA polymerase with a gene that directs the expression as RNA of the structural information present in the coding sequences of the gene. The process includes, but is not limited to the following steps: (a) the transcription initiation, (b) transcript elongation, (c) transcript splicing, (d) transcript capping, (e) transcript termination, (f) transcript polyadenylation, (g) nuclear export of the transcript, (h) transcript editing, and (i) stabilizing the transcript.

As used herein, the term "transcription factor" means a cytoplasmic or nuclear protein which binds to such gene, or binds to an RNA transcript of such gene, or binds to another protein which binds to such gene or such RNA transcript or another protein which in turn binds to such gene or such RNA transcript, so as to thereby modulate expression of the gene. Such modulation can additionally be achieved by other mechanisms; the essence of "transcription factor for a gene" is that the level of transcription of the gene is altered in some way.

As used herein, the term "unit cell" means a basic parallelipiped shaped block. The entire volume of a crystal can be constructed by regular assembly of such blocks. Each unit cell comprises a complete representation of the unit of pattern, the repetition of which builds up the crystal. Thus, the term "unit cell" means the fundamental portion of a crystal structure that is repeated infinitely by translation in three dimensions. A unit cell is characterized by three vectors a, b, and c, not located in one plane, which form the edges of a parallelepiped. Angles α, β, and γ define the angles between the vectors: angle α is the angle between vectors b and c; angle β is the angle between vectors a and c; and angle γ is the angle between vectors a and b. The entire volume of a crystal can be constructed by regular assembly of unit cells; each unit cell comprises a complete representation of the unit of pattern, the repetition of which builds up the crystal.

II. Description of Tables

Table 1 is chart of sequence identity between the ligand binding domains of several nuclear receptors.

Table 2 is a table listing mutations of the GR LBD (521–777) gene for testing solution solubility and stability. SEQ ID NOs:7–8 and 15–16 also comprise these mutations. Candidate mutated residues include but are not limited to Cys, Asn, Tyr, Lys, Ser, Asp, Glu, Gln, Arg or Thr.

Table 2A is a table listing mutations that were discovered using the LacI-based "peptides-on-plasmids" technique with GR LBD.

Table 3 is a table summarizing the crystal and data statistics obtained from the crystallized ligand binding domain of GRα LBD that was co-crystallized with dexamethasone and a fragment of the co-activator TIF2. Data on the unit cell are presented, including data on the crystal space group, unit cell dimensions, molecules per asymmetric cell and crystal resolution.

Table 4 is a table of the atomic structure coordinate data obtained from X-ray diffraction from the ligand binding domain of GR (residues 521–777) in complex with desamethasone and a fragment of the co-activator TIF2.

Table 5 is a table of the atomic structure coordinates used as the initial model to solve the structure of the GR/TIF2/dexamethasone complex by molecular replacement. The GR model is a homology model built on the published structure of the progesterone receptor LBD and the SRC1 coactivator peptide from the PPARα/Compound 1/SRC1 structure.

III. General Considerations

The present invention will usually be applicable *mutatis mutandis* to nuclear receptors in general, more particularly to steroid receptors and even more particularly to glucocorticoid receptors, including GR isoforms, as discussed herein, based, in part, on the patterns of nuclear receptor and steroid receptor structure and modulation that have emerged as a consequence of the present disclosure, which in part discloses determining the three dimensional structure of the ligand binding domain of GRα in complex with dexamethasone and a fragment of the co-activator TIF2.

The nuclear receptor superfamily has been subdivided into two subfamilies: the GR subfamily (also referred to as the steroid receptors and denoted SRs), comprising GR, AR (androgen receptor), MR (mineralcorticoid receptor) and PR (progesterone receptor) and the thyroid hormone receptor (TR) subfamily, comprising TR, vitamin D receptor (VDR), retinoic acid receptor (RAR), retinoid X receptor (RXR), and most orphan receptors. This division has been made on the basis of DNA binding domain structures, interactions with heat shock proteins (HSP), and ability to form dimers.

Steroid receptors (SRs) form a subset of the superfamily of nuclear receptors. The glucocorticoid receptor is a steroid receptor and thus a member of the superfamily of nuclear receptors and the subset of steroid receptors. The human glucocorticoid receptor exists in two isoforms, GRα which consists of 777 amino acids and GRβ which consists of 742 amino acids. As noted, the alpha isoform of human glucocorticoid receptor is made up of 777 amino acids and is predominantly cytoplasmic in its unactivated, non-DNA binding form. When activated, it translocates to the nucleus. In order to understand the role played by the glucocorticoid receptor in the different cell processes, the receptor was mapped by transfecting receptor-negative and glucocorticoid-resistant cells with different steroid receptor constructs and reporter genes like chloramphenicol acyltransferase (CAT) or luciferase which had been covalently linked to a glucocorticoid responsive element (GRE). From these and other studies, four major functional domains have become evident.

From amino to carboxyl terminal end, these functional domains include the tau 1, DNA binding, and ligand binding domains in succession. The tau 1 domain spans amino acid positions 77–262 and regulates gene activation. The DNA binding domain is from amino acid positions 421–486 and has nine cysteine residues, eight of which are organized in the form of two zinc fingers analogous to *Xenopus* transcription factor IIIA. The DNA binding domain binds to the regulatory sequences of genes that are induced or deinduced by glucocorticoids. Amino acids 521 to 777 form the ligand binding domain, which binds glucocorticoid to activate the receptor. This region of the receptor also has the nuclear localization signal. Deletion of this carboxyl terminal end results in a receptor that is constitutively active for gene induction (up to 30% of wild type activity) and even more active for cell kill (up to 150% of wild type activity) (Giguere et al., (1986) *Cell* 46: 645–652; Hollenberg et al., (1987) *Cell* 49: 39–46; Hollenberg & Evans, (1988) *Cell* 55: 899–906; Hollenberg et al., (1989) *Cancer Res.* 49: 2292s–2294s; Oro et al., (1988) *Cell* 55: 1109–1114; Evans, (1989) in *Recent Progress in Hormone Research* (Clark, ed.) Vol. 45, pp. 1–27, Academic Press, San Diego, Calif.; Green & Chambon, (1987) *Nature* 325: 75–78; Picard & Yamamoto, (1987) *EMBO J.* 6: 3333–3340; Picard et al., (1990) *Cell Regul.* 1: 291–299; Godowski et al., (1987) *Nature* 325: 365–368; Miesfeld et al., (1987) *Science* 236:423–27; Danielsen et al., (1989) *Cancer Res.* 49: 2286s–2291s; Danielsen et al., (1987) *Molec. Endocrinol.* 1: 816–822; Umesono & Evans, (1989) *Cell* 57: 1139–1146.). Despite the aforementioned indirect characterization of the structure of GRα, until the present disclosure, a detailed three-dimensional model of the ligand binding domain of GRα has not been achieved.

GR subgroup members are tightly bound by heat shock protein(s) (HSP) in the absence of ligand, dimerize following ligand binding and dissociation of HSP, and show homology in the DNA half sites to which they bind. These half sites also tend to be arranged as palindromes. TR subgroup members tend to be bound to DNA or other chromatin molecules when unliganded, can bind to DNA as monomers and dimers, but tend to form heterodimers, and bind DNA elements with a variety of orientations and spacings of the half sites, and also show homology with respect to the nucleotide sequences of the half sites. ER does not belong to either subfamily, since it resembles the GR subfamily in hsp interactions, and the TR subfamily in nuclear localization and DNA-binding properties.

Most members of the superfamily, including orphan receptors, possess at least two transcription activation subdomains, one of which is constitutive and resides in the amino terminal domain (AF-1), and the other of which (AF-2) resides in the ligand binding domain, whose activity is regulated by binding of an agonist ligand. The function of AF-2 requires an activation domain (also called transactivation domain) that is highly conserved among the receptor superfamily. Most LBDs contain an activation domain. Some mutations in this domain abolish AF-2 function, but leave ligand binding and other functions unaffected. Ligand binding allows the activation domain to serve as an interaction site for essential co-activator proteins that function to stimulate (or in some cases, inhibit) transcription.

Analysis and alignment of amino acid sequences, and X-ray and NMR structure determinations, have shown that nuclear receptors have a modular architecture with three main domains:

1) a variable amino-terminal domain;

2) a highly conserved DNA-binding domain (DBD); and 3) a less conserved carboxy-terminal ligand binding domain (LBD).

In addition, nuclear receptors can have linker segments of variable length between these major domains. Sequence analysis and X-ray crystallography, including the disclosure of the present invention, have confirmed that GR also has the same general modular architecture, with the same three domains. The function of GR in human cells presumably requires all three domains in a single amino acid sequence. However, the modularity of GR permits different domains of each protein to separately accomplish certain functions. Some of the functions of a domain within the full-length receptor are preserved when that particular domain is isolated from the remainder of the protein. Using conventional protein chemistry techniques, a modular domain can sometimes be separated from the parent protein. Using conventional molecular biology techniques, each domain can usually be separately expressed with its original function intact or, as discussed herein below, chimeras comprising two different proteins can be constructed, wherein the chimeras retain the properties of the individual functional domains of the respective nuclear receptors from which the chimeras were generated.

The carboxy-terminal activation subdomain, is in close three dimensional proximity in the LBD to the ligand, so as to allow for ligands bound to the LBD to coordinate (or interact) with amino acid(s) in the activation subdomain. As described herein, the LBD of a nuclear receptor can be expressed, crystallized, its three dimensional structure determined with a ligand bound (either using crystal data from the same receptor or a different receptor or a combination thereof), and computational methods used to design ligands to its LBD, particularly ligands that contain an extension moiety that coordinates the activation domain of the nuclear receptor.

The LBD is the second most highly conserved domain in these receptors. As its name suggests, the LBD binds ligands. With many nuclear receptors, including GR, binding of the ligand can induce a conformational change in the LBD that can, in turn, activate transcription of certain target genes. Whereas integrity of several different LBD subdomains is important for ligand binding, truncated molecules containing only the LBD retain normal ligand-binding activity. This domain also participates in other functions, including dimerization, nuclear translocation and transcriptional activation, as described herein.

Nuclear receptors usually have HSP binding domains that present a region for binding to the LBD and can be modulated by the binding of a ligand to the LBD. For many of the nuclear receptors ligand binding induces a dissociation of heat shock proteins such that the receptors can form dimers in most cases, after which the receptors bind to DNA and regulate transcription. Consequently, a ligand that stabilizes the binding or contact of the heat shock protein binding domain with the LBD can be designed using the computational methods described herein.

With the receptors that are associated with the HSP in the absence of the ligand, dissociation of the HSP results in dimerization of the receptors. Dimerization is due to receptor domains in both the DBD and the LBD. Although the main stimulus for dimerization is dissociation of the HSP, the ligand-induced conformational changes in the receptors can have an additional facilitative influence. With the receptors that are not associated with HSP in the absence of the ligand, particularly with the TR, ligand binding can affect the pattern of dimerization. The influence depends on the DNA binding site context, and can also depend on the promoter context with respect to other proteins that can interact with the receptors. A common pattern is to discourage monomer formation, with a resulting preference for heterodimer formation over dimer formation on DNA.

Nuclear receptor LBDs usually have dimerization domains that present a region for binding to another nuclear receptor and can be modulated by the binding of a ligand to the LBD. Consequently, a ligand that disrupts the binding or contact of the dimerization domain can be designed using the computational methods described herein to produce a partial agonist or antagonist.

The amino terminal domain of GR is the least conserved of the three domains. This domain is involved in transcriptional activation and, its uniqueness might dictate selective receptor-DNA binding and activation of target genes by GR subtypes. This domain can display synergistic and antagonistic interactions with the domains of the LBD.

The DNA binding domain has the most highly conserved amino acid sequence amongst the GRs. It typically comprises about 70 amino acids that fold into two zinc finger motifs, wherein a zinc atom coordinates four cysteines. The DBD comprises two perpendicularly oriented α-helixes that extend from the base of the first and second zinc fingers. The two zinc fingers function in concert along with non-zinc finger residues to direct the GR to specific target sites on DNA and to align receptor dimer interfaces. Various amino acids in the DBD influence spacing between two half-sites (which usually comprises six nucleotides) for receptor dimerization. The optimal spacings facilitate cooperative interactions between DBDs, and D box residues are part of the dimerization interface. Other regions of the DBD facilitate DNA-protein and protein-protein interactions are involved in dimerization.

In nuclear receptors that bind to a HSP, the ligand-induced dissociation of HSP with consequent dimer formation allows, and therefore, promotes DNA binding. With receptors that are not associated (as in the absence of ligand), ligand binding tends to stimulate DNA binding of heterodimers and dimers, and to discourage monomer binding to DNA. However, with DNA containing only a single half site, the ligand tends to stimulate the receptor's binding to DNA. The effects are modest and depend on the nature of the DNA site and probably on the presence of other proteins that can interact with the receptors. Nuclear receptors usually have DBD (DNA binding domains) that present a region for binding to DNA and this binding can be modulated by the binding of a ligand to the LBD.

The modularity of the members of the nuclear receptor superfamily permits different domains of each protein to separately accomplish different functions, although the domains can influence each other. The separate function of a domain is usually preserved when a particular domain is isolated from the remainder of the protein. Using conventional protein chemistry techniques a modular domain can sometimes be separated from the parent protein. By employing conventional molecular biology techniques each domain can usually be separately expressed with its original function intact or chimerics of two different nuclear receptors can be constructed, wherein the chimerics retain the properties of the individual functional domains of the respective nuclear receptors from which the chimerics were generated.

Various structures have indicated that most nuclear receptor LBDs adopt the same general folding pattern. This fold consists of 10–12 alpha helices arranged in a bundle, together with several beta-strands, and linking segments. A preferred GRα LBD structure of the present invention has 10–11 helices, depending on whether helix-3' is counted. Structural studies have shown that most of the alpha-helices and beta-strands have the same general position and orientation in all nuclear receptor structures, whether ligand is bound or not. However, the AF2 helix has been found in different positions and orientations relative to the main bundle, depending on the presence or absence of the ligand, and also on the chemical nature of the ligand. These structural studies have suggested that many nuclear receptors share a common mechanism of activation, where binding of activating ligands helps to stabilize the AF2 helix in a position and orientation adjacent to helices-3, -4, and -10, covering an opening to the ligand binding site. This position and orientation of the AF2 helix, which will be called the "active conformation", creates a binding site for co-activators: See, e.g., Nolte et al., (1998) *Nature* 395:137–43; Shiau et al., (1998) *Cell* 95: 927–37. This co-activator binding site has a central lipophilic pocket that can accommodate leucine side-chains from co-activators, as well as a "charge-clamp" structure consisting essentially of a lysine residue from helix-3 and a glutamic acid residue from the AF2 helix.

Structural studies have shown that co-activator peptides containing the sequence LXXLL (where L is leucine and X can be a different amino acid in different cases) can bind to this co-activator binding site by making interactions with the charge clamp lysine and glutamic acid residues, as well as the central lipophilic region. This co-activator binding site is disrupted when the AF2 helix is shifted into other positions and orientations. In PPARγ, activating ligands such as rosiglitazone (BRL49653) make a hydrogen bonding interaction with tyrosine-473 in the AF2 helix. Nolte et al., (1998) *Nature* 395:137–43; Gampe et al., (2000) *Mol. Cell* 5: 545–55. Similarly, in GR, the dexamethasone ligand makes van der Waals interaction with the side chain of leucine-753 from the AF2 helix. This interaction is believed in part to stabilize the AF2 helix in the active conformation, thereby allowing co-activators to bind and thus activating transcription from target genes.

With certain antagonist ligands, or in the absence of any ligand, the AF2 helix can be held less tightly in the active conformation, or can be free to adopt other conformations. This would either destabilize or disrupt the co-activator binding site, thereby reducing or eliminating co-activator binding and transcription from certain target genes. Some of the functions of the GR protein depend on having the full-length amino acid sequence and certain partner molecules, such as co-activators and DNA. However, other functions, including ligand binding and ligand-dependent conformational changes, can be observed experimentally using isolated domains, chimeras and mutant molecules.

As described herein, the LBD of a GR can be mutated or engineered, expressed, crystallized, its three dimensional structure determined with a ligand bound as disclosed in the present invention, and computational methods can be used to design ligands to nuclear receptors, preferably to steroid receptors, and more preferably to glucocorticoid receptors.

IV. The Dexamethasone Ligand

Ligand binding can induce transcriptional activation functions in a variety of ways. One way is through the dissociation of the HSP from receptors. This dissociation, with consequent dimerization of the receptors and their binding to DNA or other proteins in the nuclear chromatin, allows transcriptional regulatory properties of the receptors to be manifest. This can be especially true of such functions on the amino terminus of the receptors.

Another way is to alter the receptor to interact with other proteins involved in transcription. These could be proteins that interact directly or indirectly with elements of the proximal promoter or proteins of the proximal promoter. Alternatively, the interactions can be through other transcription factors that themselves interact directly or indirectly with proteins of the proximal promoter. Several different proteins have been described that bind to the receptors in a ligand-dependent manner. In addition, it is possible that in some cases, the ligand-induced conformational changes do not affect the binding of other proteins to the receptor, but do affect their abilities to regulate transcription.

In one aspect of the present invention, a GR LBD was co-crystallized with a fragment of the co-activator TIF2 and the ligand dexamethasone. Dexamethasone is a synthetic adrenocortical steroid with a molecular weight of 392.47. The IUPAC name for dexamethasone is (11β, 16α)-9-fluoro-11β,17,21-trihydroxy-16α-methylpregna-1-4-diene-3,20-dione. The empirical formula for dexamethasone is $C_{22}H_{29}FO_5$. Dexamethasone is represented by the chemical structure:

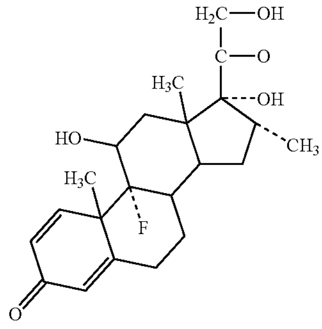

Dexamethasone-based therapeutics are commercially available in a variety of forms and formulations. Dexamethasone can also be purchased from various suppliers such as Sigma (St. Louis Mo.), as well as starting materials for the synthesis of dexamethasone. The synthesis of dexamethasone, and dexamethasone derivatives, is known and described in a variety of sources, including Arth et al., (1958) *J. Am. Chem. Soc.* 80: 3161; Oliveto et al., (1958) *J. Am. Chem. Soc.* 4431, Fried & Sabo, (1954) *J. Am Chem. Soc.* 76: 1455; Hirschman et al., (1956) *J. Am. Chem. Soc.* 78: 4957 and U.S. Pat. No. 3,007,923 to Muller et al., all of which are incorporated herein in their entirety.

V. The TIF2 Fragment

The nuclear receptor co-activator TIF2 (SEQ ID NO:17) was co-crystallized in one aspect of the present invention. Structurally, the nuclear receptor coactivator TIF2 comprises one domain that reacts with a nuclear receptor (nuclear receptor interaction domain, abbreviated "NID") and two autonomous activation domains, AD1 and AD2 (Voegel et al., (1998) *EMBO J.* 17: 507–519). The TIF2 NID comprises three NR-interacting modules, with each module comprising the motif, LXXLL (SEQ ID NO:18) (Voegel et al., (1998) *EMBO J.* 17: 507–519). Mutation of the motif abrogates TIF2's ability to interact with the ligand-induced activation function-2 (AF-2) found in the ligand-binding domains (LBDs) of many NRs. Presently, it is thought that TIF2 AD1 activity is mediated by CREB binding protein (CBP), however, TIF2 AD2 activity does not appear to involve interaction with CBP (Voegel et al., (1998) *EMBO J.* 17: 507–519).

In the present invention, residues 732–756 of the TIF2 protein (SEQ ID NO:17) were co-crystallized with GR and dexamethasone. These residues comprise the LXXLL (SEQ ID NO:18) of AD-2, the third motif in the linear sequence of TIF2. The TIF2 fragment is 25 residues in length and was synthesized using an automated peptide synthesis apparatus. SEQ ID NO:17, and other sequences corresponding to TIF2 and other co-activators and co-repressors, can be similarly synthesized using automated apparatuses.

VI. Production of NR, SR and GR Polypeptides

In a preferred embodiment, the present invention provides for the first time for the expression of a soluble GR polypeptide in bacteria, more preferably, in *E. coli*. The GR polypeptides of the present invention, disclosed herein, can thus now provide a variety of host-expression vector systems to express an NR, SR or GR coding sequence. These include but are not limited to microorganisms such as bacteria transformed with recombinant bacteriophage DNA, plasmid DNA or cosmid DNA expression vectors containing an NR, SR or GR coding sequence; yeast transformed with recombinant yeast expression vectors containing an NR, SR or GR coding sequence; insect cell systems infected with recombinant virus expression vectors (e.g., baculovirus) containing an NR, SR or GR coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing an NR, SR or GR coding sequence; or animal cell systems. The expression elements of these systems vary in their strength and specificities. Methods for constructing expression vectors that comprise a partial or the entire native or mutated NR and GR polypeptide coding sequence and appropriate transcriptional/translational control signals include in vitro recombinant DNA techniques, synthetic techniques and in vivo recombination/genetic recombination. See, for example, the techniques described throughout Sambrook et al., (1989) *Molecular Cloning: A Laboratory Manual*, Cold Spring Harbor Laboratory, New York, and Ausubel et al., (1989) *Current Protocols in Molecular Biology*, Greene Publishing Associates and Wiley Interscience, New York, both incorporated herein in their entirety.

Depending on the host/vector system utilized, any of a number of suitable transcription and translation elements, including constitutive and inducible promoters, can be used in the expression vector. For example, when cloning in bacterial systems, inducible promoters such as pL of bacteriophage λ, plac, ptrp, ptac (ptrp-lac hybrid promoter) and the like can be used. When cloning in insect cell systems, promoters such as the baculovirus polyhedrin promoter can be used. When cloning in plant cell systems, promoters derived from the genome of plant cells, such as heat shock promoters; the promoter for the small subunit of RUBISCO; the promoter for the chlorophyll a/b binding protein) or from plant viruses (e.g., the 35S RNA promoter of CaMV; the coat protein promoter of TMV) can be used. When cloning in mammalian cell systems, promoters derived from the genome of mammalian cells (e.g., metallothionein promoter) or from mammalian viruses (e.g., the adenovirus late promoter; the vaccinia virus 7.5K promoter) can be used. When generating cell lines that contain multiple copies of the tyrosine kinase domain DNA, SV40-, BPV- and EBV-based vectors can be used with an appropriate selectable marker.

Adequate levels of expression of nuclear receptor LBDs can be obtained by the novel approaches described herein. High level expression in *E. coli* of ligand binding domains of TR and other nuclear receptors, including members of the steroid/thyroid receptor superfamily, such as the estrogen (ER), androgen (AR), mineralocorticoid (MR), progesterone (PR), RAR, RXR and vitamin D (VDR) receptors can also be achieved after review of the expression of a soluble GR polypeptide in bacteria, more preferably, *E. coli* disclosed herein. The GR polypeptides of the present invention, disclosed herein, can thus now provide a variety of host-expression vector systems. Yeast and other eukaryotic expression systems can be used with nuclear receptors that bind heat shock proteins since these nuclear receptors are generally more difficult to express in bacteria, with the exception of ER, which can be expressed in bacteria. In a preferred embodiment of the present invention, as disclosed in the Examples, a GR LBD is expressed in *E. coli.*

Representative nuclear receptors or their ligand binding domains have been cloned and sequenced, including human RARα, human RARγ, human RXRα, human RXRβ, human PPARα, human PPARβ or δ (delta), human PPARγ, human VDR, human ER (as described in Seielstad et al., (1995) *Mol. Endocrinol.* 9: 647–658), human GR, human PR, human MR, and human AR. The ligand binding domain of each of these nuclear receptors has been identified. Using this information in conjunction with the methods described herein, one of ordinary skill in the art can express and purify LBDs of any of the nuclear receptors, bind it to an appropriate ligand, and crystallize the nuclear receptor's LBD with a bound ligand, if desired.

Extracts of expressing cells are a suitable source of receptor for purification and preparation of crystals of the chosen receptor. To obtain such expression, a vector can be constructed in a manner similar to that employed for expression of the rat TR alpha (Apriletti et al., (1995) *Protein Expression and Purification,* 6: 368–370). The nucleotides encoding the amino acids encompassing the ligand binding domain of the receptor to be expressed can be inserted into an expression vector such as the one employed by Apriletti et al (1995). Stretches of adjacent amino acid sequences can be included if more structural information is desired.

The native and mutated nuclear receptors in general, and more particularly SR and GR polypeptides, and fragments thereof, of the present invention can also be chemically synthesized in whole or part using techniques that are known in the art (See, e.g., Creighton, (1983) *Proteins: Structures and Molecular Principles*, W.H. Freeman & Co., New York, incorporated herein in its entirety).

In a preferred embodiment, the present invention provides for the first time for the expression of a soluble GR polypeptide in bacteria, more preferably, *E. coli*, and subsequent purification thereof. Representative purification techniques are also disclosed in the Examples, particularly Example 1. The GR polypeptides of the present invention, disclosed herein, can thus now provide the ability to employ additional purification techniques for both liganded and unliganded NRs. Thus, it is envisioned, based upon the disclosure of the present invention, that purification of the unliganded or liganded NR, SR or GR receptor can be obtained by conventional techniques, such as hydrophobic interaction chromatography (HPLC), ion exchange chromatography (HPLC), and heparin affinity chromatography. To achieve higher purification for improved crystals of nuclear receptors it is sometimes preferable to ligand shift purify the nuclear receptor using a column that separates the receptor according to charge, such as an ion exchange or hydrophobic interaction column, and then bind the eluted receptor with a ligand. The ligand induces a change in the receptor's surface charge such that when re-chromatographed on the same column, the receptor then elutes at the position of the liganded receptor and is removed by the original column run with the unliganded receptor. Typically, saturating concentrations of ligand can be used in the column and the protein can be preincubated with the ligand prior to passing it over the column.

More recently developed methods involve engineering a "tag" such as with histidine placed on the end of the protein, such as on the amino terminus, and then using a nickel chelation column for purification. See Janknecht, (1991) *Proc. Natl. Acad. Sci. U.S.A.* 88: 8972–8976 (1991), incorporated by reference.

VII. Formation of NR, SR and GR Ligand Binding Domain Crystals

In one embodiment, the present invention provides crystals of GRα LBD. The crystals were obtained using the methodology disclosed in the Laboratory Examples. The GRα LBD crystals, which can be native crystals, derivative crystals or co-crystals, have hexagonal unit cells (a hexagonal unit cell is a unit cell wherein a=b≠c, and wherein α=β=90°, and γ=120°) and space group symmetry $P6_1$. There are two GRα LBD molecule in the asymmetric unit. In this GRα crystalline form, the unit cell has dimensions of a=b=126.014 Å, c=86.312 Å, and α=β=90°, and γ=120°. This crystal form can be formed in a crystallization reservoir as described in the Examples.

VII.A. Preparation of NR, SR and GR Crystals

The native and derivative co-crystals, and fragments thereof, disclosed in the present invention can be obtained by a variety of techniques, including batch, liquid bridge, dialysis, vapor diffusion and hanging drop methods (See, e.g., McPherson, (1982) *Preparation and Analysis of Protein Crystals*, John Wiley, New York; McPherson, (1990) *Eur. J. Biochem.* 189:1–23; Weber, (1991) *Adv. Protein Chem.* 41:1–36). In a preferred embodiment, the vapor diffusion and hanging drop methods are used for the crystallization of NR, SR and GR polypeptides and fragments thereof. A more preferred hanging drop method technique is disclosed in the Examples.

In general, native crystals of the present invention are grown by dissolving substantially pure NR, SR or GR polypeptide or a fragment thereof in an aqueous buffer containing a precipitant at a concentration just below that necessary to precipitate the protein. Water is removed by controlled evaporation to produce precipitating conditions, which are maintained until crystal growth ceases.

In one embodiment of the invention, native crystals are grown by vapor diffusion (See, e.g., McPherson, (1982) *Preparation and Analysis of Protein Crystals*, John Wiley, New York.; McPherson, (1990) *Eur. J. Biochem.* 189:1–23). In this method, the polypeptide/precipitant solution is allowed to equilibrate in a closed container with a larger aqueous reservoir having a precipitant concentration optimal for producing crystals. Generally, less than about 25 μL of NR, SR or GR polypeptide solution is mixed with an equal volume of reservoir solution, giving a precipitant concentration about half that required for crystallization. This solution is suspended as a droplet underneath a coverslip, which is sealed onto the top of the reservoir. The sealed container is allowed to stand, until crystals grow. Crystals generally form within two to six weeks, and are suitable for data collection within approximately seven to ten weeks. Of course, those of skill in the art will recognize that the above-described crystallization procedures and conditions can be varied.

VII.B. Preparation of Derivative Crystals

Derivative crystals of the present invention, e.g. heavy atom derivative crystals, can be obtained by soaking native crystals in mother liquor containing salts of heavy metal atoms. Such derivative crystals are useful for phase analysis in the solution of crystals of the present invention. In a preferred embodiment of the present invention, for example, soaking a native crystal in a solution containing methylmercury chloride provides derivative crystals suitable for use as isomorphous replacements in determining the X-ray crystal structure of a NR, SR or GR polypeptide. Additional reagents useful for the preparation of the derivative crystals of the present invention will be apparent to those of skill in the art after review of the disclosure of the present invention presented herein.

VII.C. Preparation of Co-Crystals

Co-crystals of the present invention can be obtained by soaking a native crystal in mother liquor containing compounds known or predicted to bind the LBD of a NR, SR or GR, or a fragment thereof. Alternatively, co-crystals can be obtained by co-crystallizing a NR, SR or GR LBD polypeptide or a fragment thereof in the presence of one or more compounds known or predicted to bind the polypeptide. In a preferred embodiment, as disclosed in the Examples, such a compound is dexamethasone.

VII.D. Solving a Crystal Structure of the Present Invention

Crystal structures of the present invention can be solved using a variety of techniques including, but not limited to, isomorphous replacement, anomalous scattering or molecular replacement methods. Computer software packages are also helpful in solving a crystal structure of the present invention. Applicable software packages include but are not limited to the CCP4 package disclosed in the Examples, the X-PLOR™ program (Brünger, (1992) X-PLOR, Version 3.1. *A System for X-ray Crystallography and NMR*, Yale University Press, New Haven, Conn.; X-PLOR is available from Molecular Simulations, Inc., San Diego, Calif.), Xtal View (McRee, (1992) *J. Mol. Graphics* 10: 44–46; X-tal View is available from the San Diego Supercomputer Center). SHELXS 97 (Sheldrick (1990) *Acta Ctyst.* A46: 467; SHELX 97 is available from the Institute of Inorganic Chemistry, Georg-August-Universität, Göttingen, Germany), HEAVY (Terwilliger, Los Alamos National Laboratory) and SHAKE-AND-BAKE (Hauptman, (1997) *Curr. Opin. Struct. Biol.* 7: 672–80; Weeks et al., (1993) *Acta Cryst.* D49: 179; available from the Hauptman-Woodward Medical Research Institute, Buffalo, N.Y.) can be used. See also, Ducruix & Geige, (1992) *Crystallization of Nucleic Acids and Proteins: A Practical Approach*, IRL Press, Oxford, England, and references cited therein.

VIII. Characterization and Solution of a GRα Ligand Binding Domain Crystal

Figure 3A:
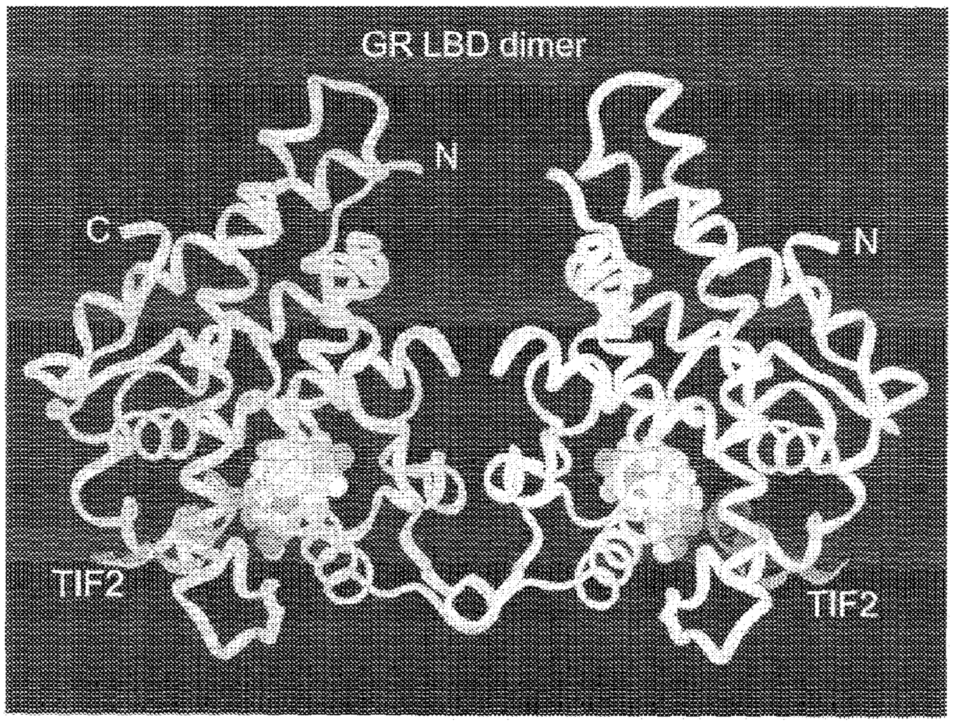
FIG. 3A is a worm/ribbon diagram depicting the overall arrangement of the GR LBD diamers. Two GR LBDs are shown in white and gray worm representation. TIF2 peptides are shown in gray ribbon and the two dexamethasone ligands are shown in space filling.

Referring now to FIG. 3A, the overall arrangement of the GR LBD dimer is depicted in a ribbon/worm diagram that was derived from the crystalline polypeptide of the present invention. The two GR LBDs are shown in white and gray worm representation. The TIF2 peptides TIF2 are shown in gray ribbon and two dexamethasone ligands DEX are shown in space filling. The N terminus and C terminus of each GR LBD are labeled with a C and N, respectively. There is an interface between the two LBDs at beta turns and beta strands.

Figure 3B:
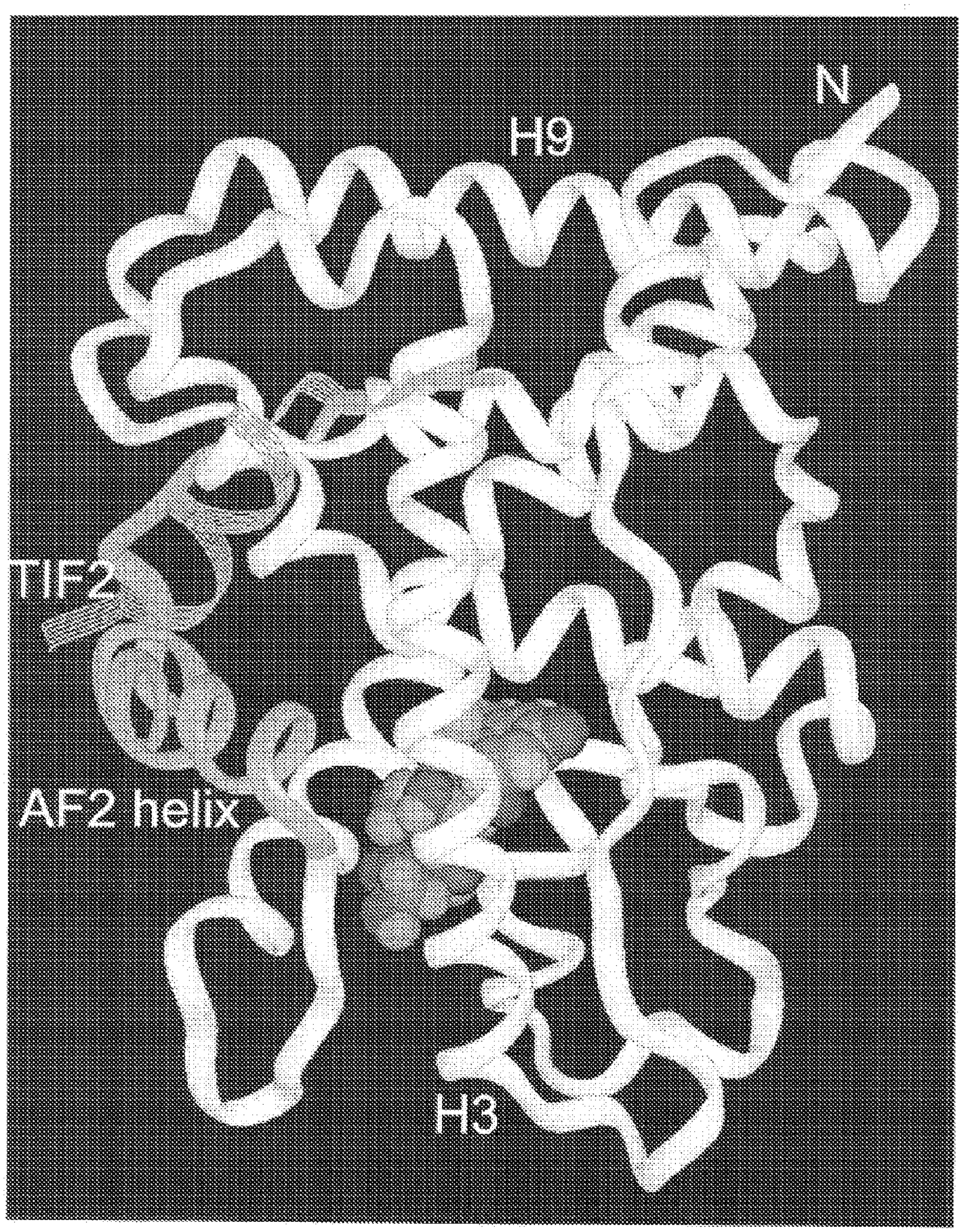
FIG. 3B is a worm/ribbon diagram depicting one orientation of the GR/TIF2/Dex complex. TIF peptide is shown in ribbon and GR is shown in worm. The AF2 helix of the GR is shown in gray worm. The key structural elements are marked and are described herein below.
Figure 3C:
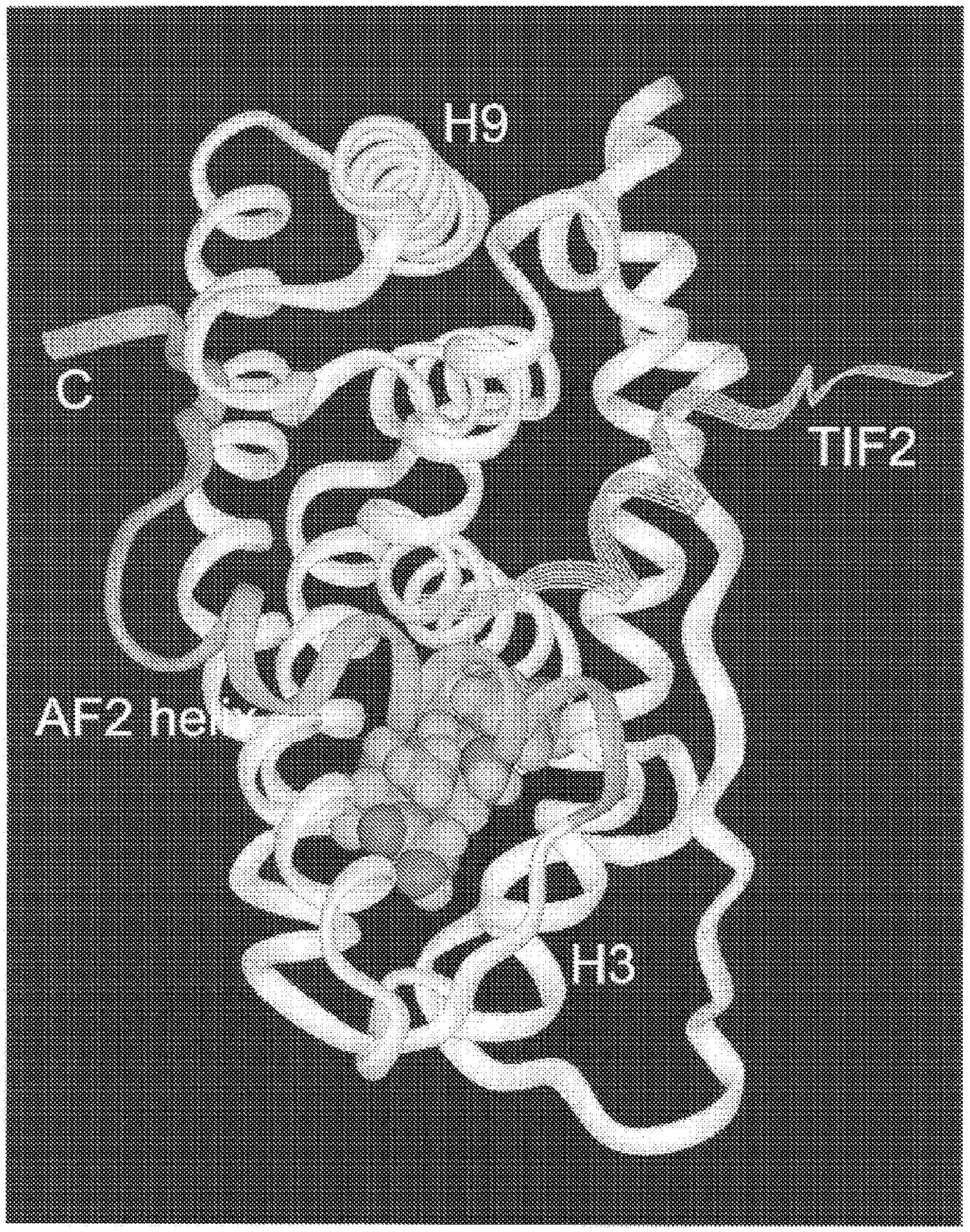
FIG. 3C is a worm/ribbon diagram depicting a second orientation of the GR/TIF2/DEX complex. TIF2 peptide is shown in ribbon and GR is shown in worm. The AF2 helix of GR is shown in gray worm. The key structural elements are marked and are described herein below.

Referring now to FIGS. 3B and 3C, two orientations of the GR/TIF2/DEX complex are depicted. In each figure, the TIF2 peptide TIF2 is shown in ribbon and the GR LBD is shown in worm. The AF2 helix AF2 of GR is shown in gray worm in each figure. The key structural elements helix 9 H9 and helix 3 H3 are indicated, as is the N terminus N. The DEX compound DEX is shown in dark gray shading. In FIGS. 3B and 3C, the interaction of helix 3 H3 and the AF2 helix AF2 with dexamethasone DEX can be seen.

Figure 4A:
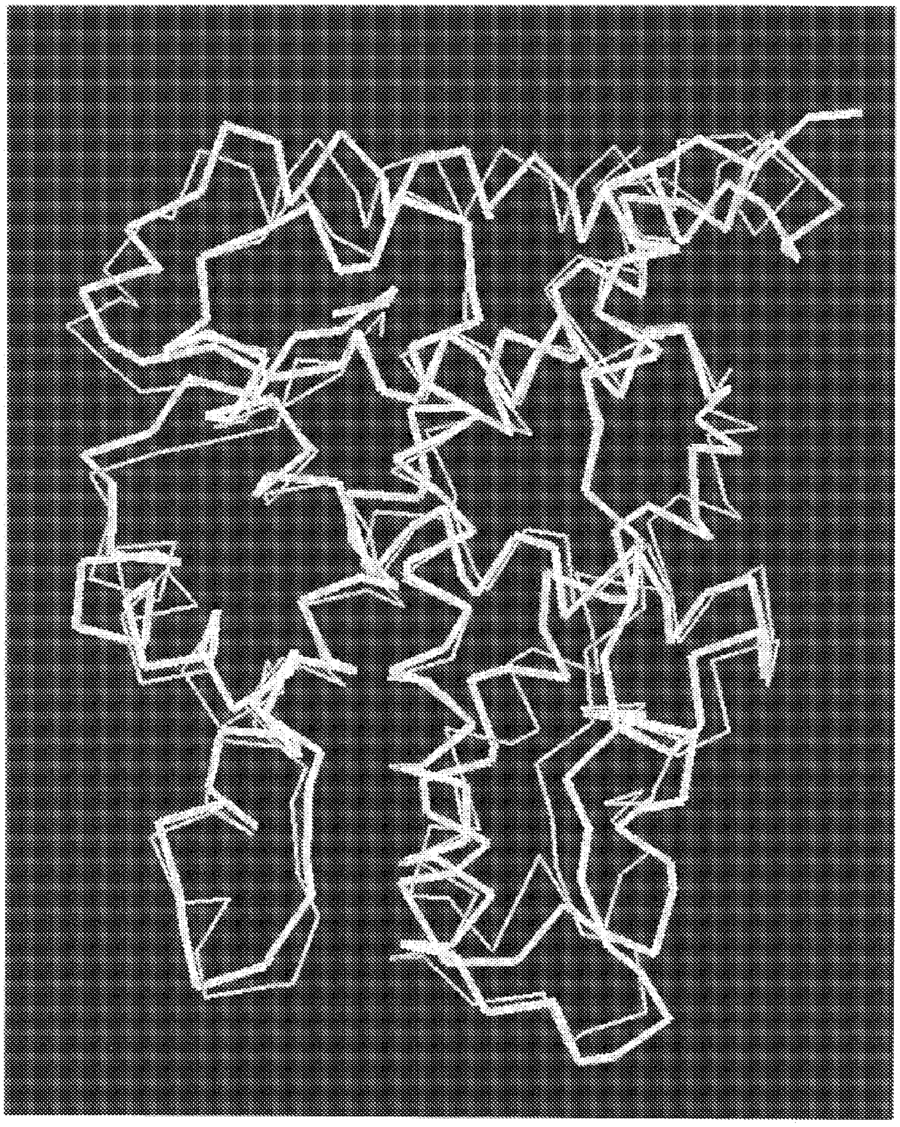
FIGS. 4A and 4B depict the overlap of the GR LBD with the AR LBD (FIG. 4A) and the PR LBD (FIG. 4B). The GR is in thick line. AR and PR are in the thin line. Only the backbone C alpha atoms are shown.
Figure 4B:
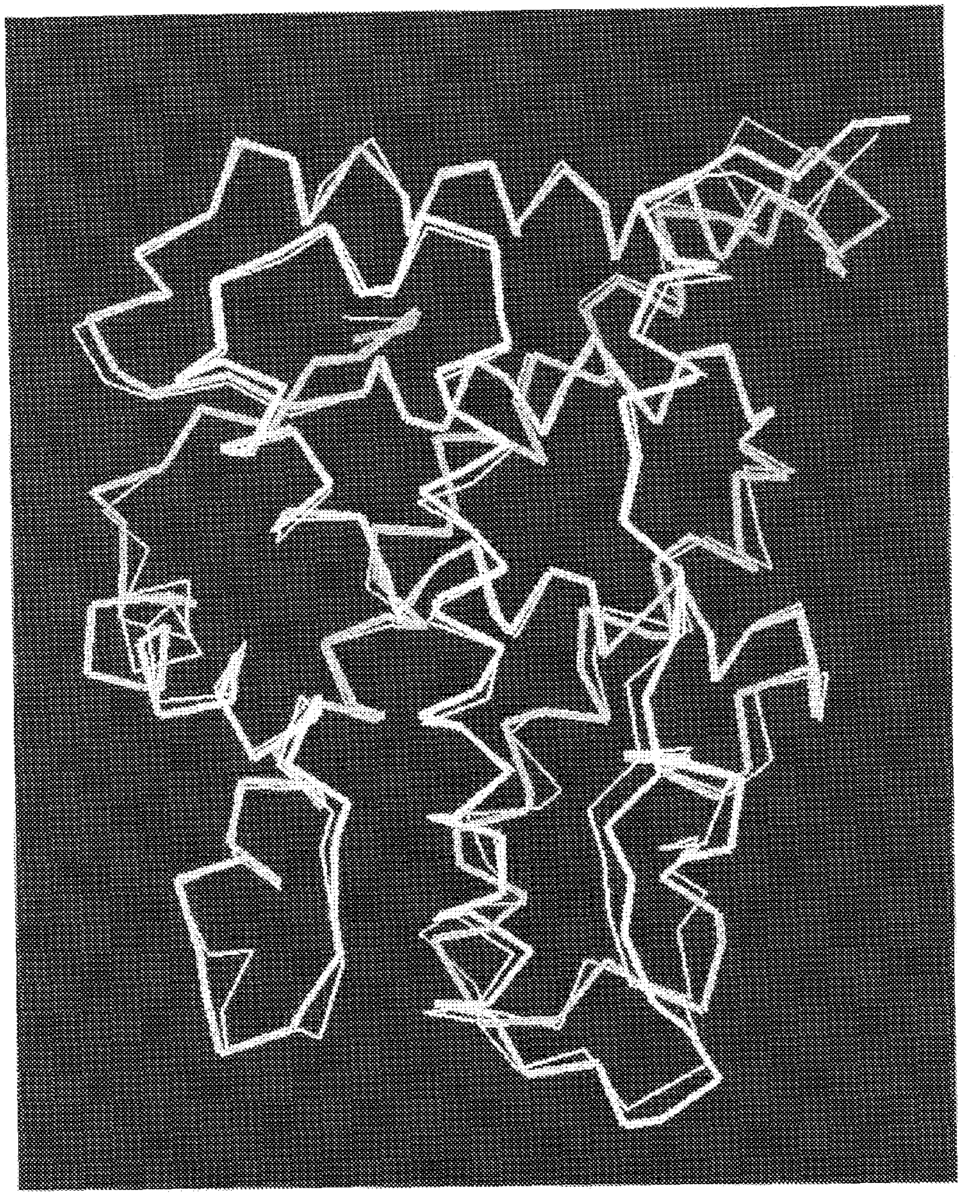

Referring now to FIGS. 4A and 4B, the overlap of GR LBD with the LBDs of the AR and PR (FIGS. 4A and 4B, respectively) is depicted. The AR and PR are shown as a thin line, while the GR is shown as a thick line. Backbone Calpha atoms are also shown. This superposition is consistent with the sequence alignment approach taken in the design of the GR LBD polypeptide disclosed herein.

RMS deviation calculation results were as follows:

| | GR | PR | AR |
|---|---|---|---|
| GR | 0.00 | 0.94 | 1.56 |
| PR | 0.94 | 0.00 | 1.34 |
| AR | 1.56 | 1.34 | 0.00 |

where in each of the three calculations, the RMS deviation was computed using 980 N, backbone C alpha, C, O atoms from 245 aligned residues. These 245 residues are GR:531–775, PR:686–987, 899–931 and AR:672–883, 885–917. Several GR and PR residues before helix-1 were omitted in the calculations, as was one residue at the C-terminus, to correspond to the shorter AR construct. One residue (PR:898 and AR:884) was also omitted in the 10-AF2 loop because of the deletion in GR. The RMS deviations suggest that the AR structure has diverged away from GR and PR, and graphical examination confirmed this at least qualitatively.

Referring now to FIG. 5, a sequence alignment of steroid receptors, particularly an alignment of the F602S GRα sequence with MR, PR, AR, ERα, and Erβ is depicted. Residues that lie within 5.0 angstroms of the ligand are identified with small square boxes around the one-letter amino acid code. The ligands used for this calculation are dexamethasone (for GR), progesterone (for PR), dihydrotestosterone (for AR), estradiol (for ERα) and genistein (for ERβ). The alpha-helices and beta-strands observed in the X-ray structures are identified by the larger boxes and captions. Note that the secondary structure of MR is not publicly known at this time, and is thus not annotated in the Figure. More than one structure is available for PR, AR, ERα and ERβ, and, in some cases, the alpha-helices have different endpoints in these different X-ray structures. The variation in the alpha-helices is indicated here by using boxes with thicker and thinner linewidths, where the thicker linewidth box encompasses residues that adopt the same secondary structure in all available X-ray structures, and thinner linewidth boxes encompass residues that adopt an alpha-helical structure in some but not all X-ray structures. The secondary structures were determined by graphical examination of the X-ray structures.

It is also noted that, within the ligand binding domains (LBDs), the sequence identity is as follows:

TABLE 1

| Sequence Identity of NR LBDs | | | | |
|---|---|---|---|---|
| | GR | MR | PR | AR |
| GR | 100% | 56% | 54% | 50% |
| MR | 56% | 100% | 55% | 51% |
| PR | 54% | 55% | 100% | 55% |
| AR | 50% | 51% | 55% | 100% |

VIII.A Unique Structural Differences Between GRα and Other SRs

Figure 6A:
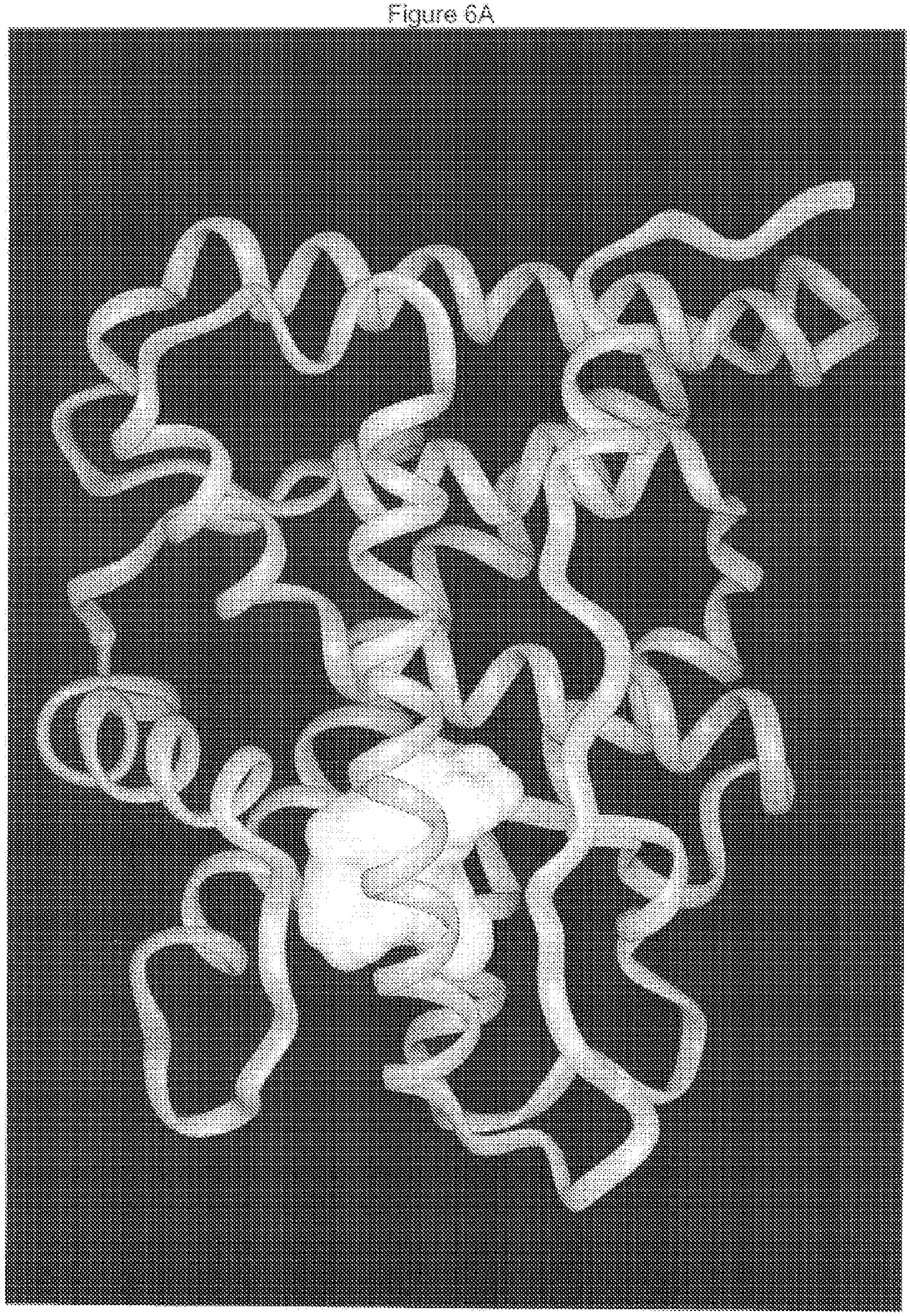
FIG. 6A depicts the GR ligand binding pocket. The GR LBD is shown in a worm representation and the pocket is shown with a white surface.

Even though the GR LBD shares over 50% sequence identity with PR and AR and fold into a similar three-layer helical sandwich (FIGS. 4A and 4B), there are a number of unique structural differences in their structures. The most distinct differences are noted in the extended strand between helices 1 and 3, and the position of helix 7. These differences contribute a unique shape of the binding pocket for each receptor (FIGS. 6A and 6B) and may thus provide a molecular basis for steroid specificity of these receptors. The detailed structural information about the GR LBD and the pocket provided herein can be further exploited to design receptor specific agonists or antagoinists.

VIII.B Dexamethasone

The ligand binding domain of GRα was co-crystallized with dexamethasone, which has the IUPAC name (11β, 16α)-9-fluoro-11β,17,21-trihydroxy-16α-methylpregna-1-4-diene-3,20-dione and is shown below.

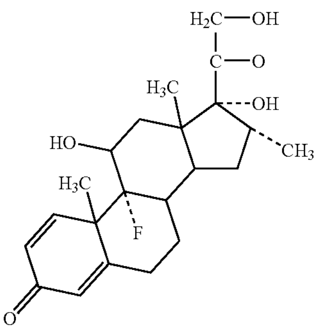

Dexamethasone is an agonist of GRα and is useful for treatment of GRα-mediated diseases or conditions including inflammation, tissue rejection, auto-immunity, malignancies such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, and Little's syndrome as well as many other conditions.

VIII.C. Characterization of the GRα Binding Pocket and Interactions Between GRα and Dexamethasone Referring now to FIG. 6A, the GR ligand binding pocket is depicted schematically. The GR ligand binding pocket is shown in a worm representation and the pocket is shown with a white surface. The gross shape of the binding pocket is depicted here with a smooth surface that covers the available volume within the binding pocket. The available volume is mapped by placing the protein within a grid, and then checking, for each grid point, whether a spherical probe atom can fit at that point without bumping into the protein. The spacing of grid points was taken as 0.50 Å, and the radius of the probe atom was taken as 1.40 Å. Atoms in the protein were represented as spheres with a radius of 1.20 Å for hydrogen, 1.70 Å for carbon, 1.55 Å for nitrogen, 1.52 Å for oxygen and 1.80 Å for sulfur. These are esssentially the atomic radius values suggested by Bondi (A. Bondi, "van der Waals Volumes and Radii," Journal of Physical Chemistry, 68, 441–451 (1964)). The protein was represented with all hydrogen atoms in order to handle its volume more accurately. These hydrogen atoms where added to obtain the protonation states expected at pH 7 using the MVP program. The MVP program adds hydrogens using standard geometry, and then refines the initial coordinates with energy minimization, holding all heavy atoms fixed. The "available" grid points are defined as those for which the probe sphere does not bump into any sphere corresponding to a protein atom. The smooth surface was then constructed over these available binding site grid points using the dot surface program of Connolly (Michael L. Connolly, "Solvent-Accessible Surfaces of Proteins and Nucleic Acids," Science 221, 709–713 (1983)) with a probe radius of 1.30 Å. The protein chain is shown with a backbone ribbon depiction.

Figure 6B:
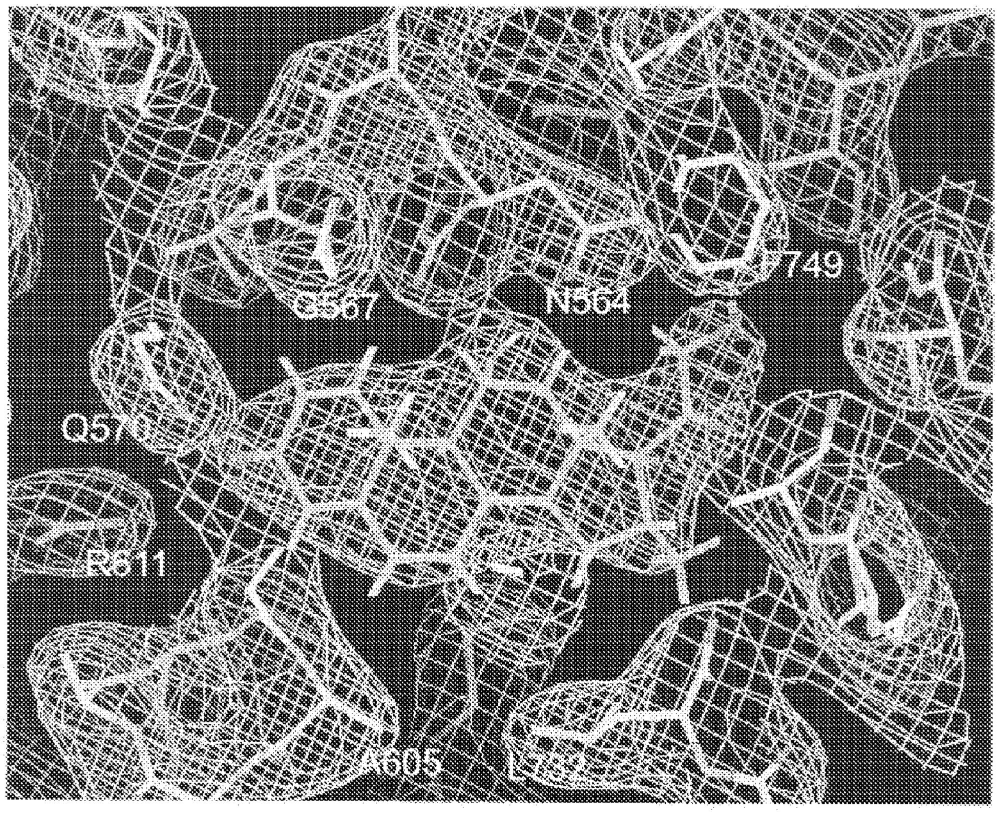
FIG. 6B is a diagram that depicts surfaces at the GR-dexamethasone interface. The electron density is calculated with Fo coefficiency and shown at a one sigma cutoff. Key residues surrounding the ligand are also labeled, as described herein below.

Referring now to FIG. 6B, electron density in the GR-dexamethasone interface is depicted. The electron density is calculated with Fo coefficiency and shown in a one sigma cutoff. The ligand DEX is in the center of the figure. Key residues L732, A605, R611, Q570, G567, N564, and F749 encircle ligand DEX. Ligand DEX displays a good spatial fit, with no overlaps and no apparent charge repulsions.

Figure 7:
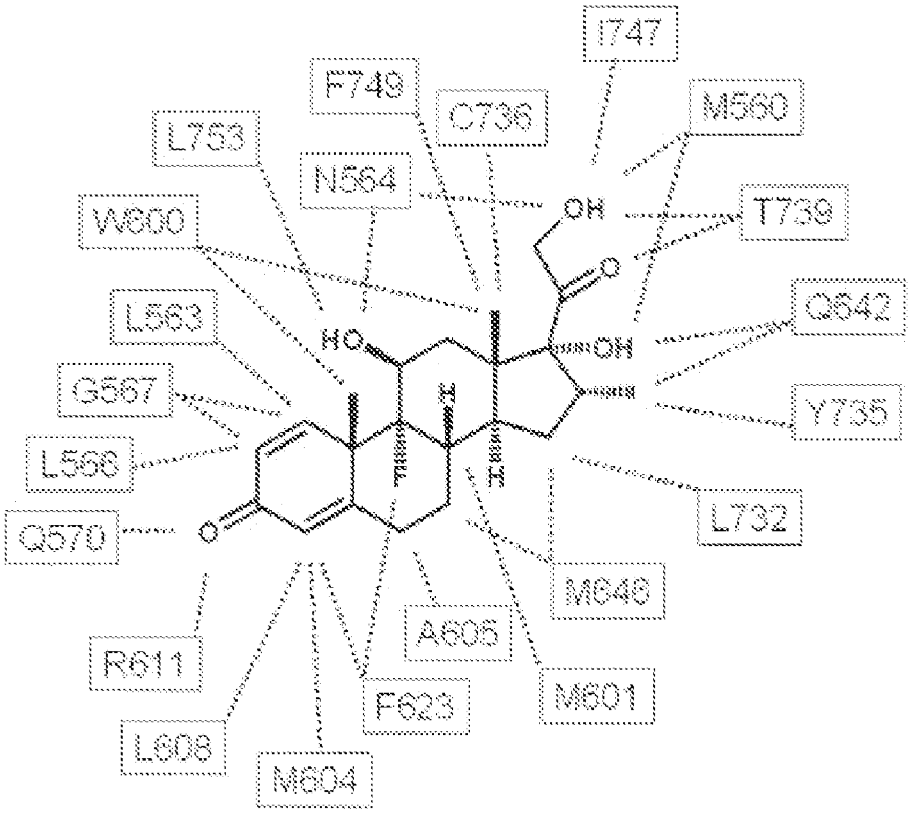
FIG. 7 is a diagram of molecular interactions between GR and dexamethasone. Both Van der Waals contacts and hydrogen bonds are indicated with dotted lines.

Referring now to FIG. 7, molecular interactions between the GR protein and the dexamethasone are depicted. There are 22 residues from GR involved in direct interactions with the dexamethasone, and the residues are Q570, L566, G567, L563, W600, L753, N564, F749, C736, I747, M560, T739, Q642, Y735, L732, M646, M601, A605, F623, M604, L608, and R611.

Figure 8:
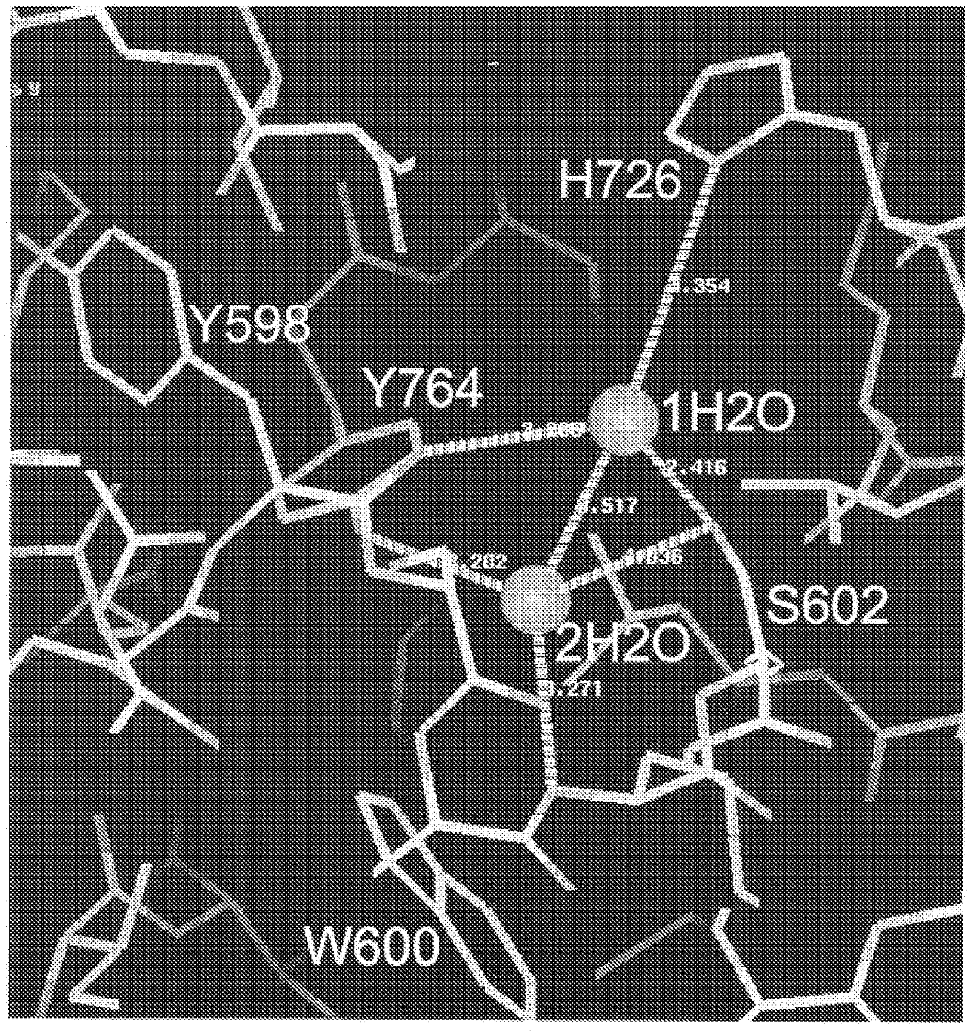
FIG. 8 is a wire frame diagram showing the structure around the F602 mutation in the GRα LBD polypeptide. The lipophilic F602 side-chain of the wild-type GRα protein would be located in a hydrophilic environment and could destabilize the protein. Changing the phenylalanine (F) to a serine (S) allows the S602 side-chain and NH group to make direct hydrogen bonds with two water molecules (1H2O and 2H2O). Other residues involved with the two water molecules are also shown and are described herein below.

VIII.D. Structural Mechanism of Improving Protein Solubility by the F602S Mutation FIG. 8 is a wire frame diagram that provides a closer look at the F602S mutation. The F602 is lipophilic but resides in the hydrophilic environment, a situation that could destabilize the protein. The mutation of the phenylalanine (F) to the serine (S) allows the S602 side chain to make direct hydrogen bonds with two water molecules, shown as $1H_2O$ and $2H_2O$ in FIG. 8. Association distances of 2.416 and 4.036 are indicated between S602 and $1H_2O$ and $2H_2O$, respectively. Other residues are also shown in interaction with $1H_2O$ and $2H_2O$, and these include H726 (which is also coordinated with water molecule $1H_2O$), Y764 (which is also coordinated with water molecules $1H_2O$ and $2H_2O$), Y598 and W600. An association distance of 4.354 is shown between $1H_2O$ and H726; and an association distance of 3.286 is shown with Y764. An association distance of 3.157 is shown between $1H_2O$ and $2H_2O$. It is envisioned that this complex hydrogen bond network initiated by the F602S mutation and the two water molecules improves the protein stability thus the solubility as well.

VIII.E. Generation of Easily-Solved NR, SR and GR Crystals

The present invention discloses a substantially pure GR LBD polypeptide in crystalline form. In a preferred embodiment, exemplified in the Figures and Laboratory Examples, GRα is crystallized with bound ligand. Crystals can be formed from NR, SR and GR LBD polypeptides that are usually expressed by a cell culture, such as *E. coli*. Bromo- and iodo-substitutions can be included during the preparation of crystal forms and can act as heavy atom substitutions in GR ligands and crystals of NRs, SRs and GRs. This method can be advantageous for the phasing of the crystal, which is a crucial, and sometimes limiting, step in solving the three-dimensional structure of a crystallized entity. Thus, the need for generating the heavy metal derivatives traditionally employed in crystallography can be eliminated. After the three-dimensional structure of a NR, SR or GR, or an NR, SR or GR LBD with or without a ligand bound is determined, the resultant three-dimensional structure can be used in computational methods to design synthetic ligands for NR, SR or GR and for other NR, SR or GR polypeptides. Further activity structure relationships can be determined through routine testing, using assays disclosed herein and known in the art.

IX. Uses of NR, SR and GR Crystals and the Three-Dimensional Structure of the Ligand Binding Domain of GRα

The solved crystal structure of the present invention is useful in the design of modulators of activity mediated by the glucocorticoid receptor and by other nuclear receptors. Evaluation of the available sequence data shows that GRα is particularly similar to MR, PR and AR. The GRα LBD has approximately 55%, 54% and 50% sequence identity to the MR, PR and AR LBDs, respectively. The GRβ amino acid sequence is identical to the GRα amino acid sequence for residues 1–726, but the remaining 16 residues in GRβ show no significant similarity to the remaining 51 residues in GRα.

The present GRα X-ray structure can also be used to build models for targets where no X-ray structure is available, such as with GRβ and MR. Indeed, a model for GRα using the available X-ray structures of PR and/or AR as templates was built and used by the present co-inventors to obtain a starting model for the molecular replacement calculation used in solving the X-ray structure of GRα disclosed herein. These models will be less accurate than X-ray structures, but can help in the design of compounds targeted for GRβ and MR, for example. Also, these models can aid the design of compounds to selectively modulate any desired subset of GRα, GRβ, MR, PR, AR and other related nuclear receptors.

IX.A. Design and Development of NR, SR and GR Modulators

The present invention, particularly the computational methods, can be used to design drugs for a variety of nuclear receptors, such as receptors for glucocorticoids (GRs), androgens (ARs), mineralocorticoids (MRs), progestins (PRs), estrogens (ERs), thyroid hormones (TRs), vitamin D (VDRs), retinoid (RARs and RXRs) and peroxisomal proliferators (PPARs). The present invention can also be applied to the "orphan receptors," as they are structurally homologous in terms of modular domains and primary structure to classic nuclear receptors, such as steroid and thyroid receptors. The amino acid homologies of orphan receptors with other nuclear receptors ranges from very low (<15%) to in the range of 35% when compared to rat RARα and human TRβ receptors, for example.

The knowledge of the structure of the GRα ligand binding domain (LBD), an aspect of the present invention, provides a tool for investigating the mechanism of action of GRα and other NR, SR and GR polypeptides in a subject. For example, various computer modelleing programs, as described herein, can predict the binding of various ligand molecules to the LBD of GRβ, or another steroid receptor or, more generally, nuclear receptor. Upon discovering that such binding in fact takes place, knowledge of the protein structure then allows design and synthesis of small molecules that mimic the functional binding of the ligand to the LBD of GRα, and to the LBDs of other polypeptides. This is the method of "rational" drug design, further described herein.

Use of the isolated and purified GRα crystalline structure of the present invention in rational drug design is thus provided in accordance with the present invention. Additional rational drug design techniques are described in U.S. Pat. Nos. 5,834,228 and 5,872,011, incorporated herein in their entirety.

Thus, in addition to the compounds described herein, other sterically similar compounds can be formulated to interact with the key structural regions of an NR, SR or GR in general, or of GRα in particular. The generation of a structural functional equivalent can be achieved by the techniques of modeling and chemical design known to those of skill in the art and described herein. It will be understood that all such sterically similar constructs fall within the scope of the present invention.

IX.A.1. Rational Drug Design

The three-dimensional structure of ligand-binding GRα is unprecedented and will greatly aid in the development of new synthetic ligands for NR, SR and GR polypeptides, such as GR agonists and antagonists, including those that bind exclusively to any one of the GR subtypes. In addition, NRs, SRs and GRs are well suited to modern methods, including three-dimensional structure elucidation and combinatorial chemistry, such as those disclosed in U.S. Pat. Nos. 5,463,564, and 6,236,946 incorporated herein by reference. Structure determination using X-ray crystallography is possible because of the solubility properties of NRs SRs and GRs. Computer programs that use crystallography data when practicing the present invention will enable the rational design of ligands to these receptors.

Programs such as RASMOL (Biomolecular Structures Group, Glaxo Wellcome Research & Development Stevenage, Hertfordshire, UK Version 2.6, August 1995, Version 2.6.4, December 1998, Copyright© Roger Sayle 1992–1999) and Protein Explorer (Version 1.87, Jul. 3, 2001, © Eric Martz, 2001 and available online at http://www.umass.edu/microbio/chime/explorer/index.htm) can be used with the atomic structural coordinates from crystals generated by practicing the invention or used to practice the invention by generating three-dimensional models and/or determining the structures involved in ligand binding. Computer programs such as those sold under the registered trademark INSIGHT II® and the programs GRASP (Nicholls et al., (1991) *Proteins* 11: 281) and SYBYL™ (available from Tripos, Inc. of St. Louis, Mo.) allow for further manipulations and the ability to introduce new structures. In addition, high throughput binding and bioactivity assays can be devised using purified recombinant protein and modern reporter gene transcription assays known to those of skill in the art in order to refine the activity of a designed ligand.

A method of identifying modulators of the activity of an NR, SR or GR polypeptide using rational drug design is thus provided in accordance with the present invention. The method comprises designing a potential modulator for an NR, SR or GR polypeptide of the present invention that will form non-covalent interactions with amino acids in the ligand binding pocket based upon the crystalline structure of the GRα LBD polypeptide; synthesizing the modulator; and determining whether the potential modulator modulates the activity of the NR, SR or GR polypeptide. In a preferred embodiment, the modulator is designed for an SR polypeptide. In a more preferred embodiment, the modulator is designed for a GRα polypeptide. Preferably, the GRα polypeptide comprises the amino acid sequence of any of SEQ ID NOs:2, 4, 6 and 8, and more preferably, the GRα LBD comprises the amino acid sequence of any of SEQ ID NOs:10, 12, 14, 16 and 31. The determination of whether the modulator modulates the biological activity of an NR, SR or GR polypeptide is made in accordance with the screening methods disclosed herein, or by other screening methods known to those of skill in the art. Modulators can be synthesized using techniques known to those of ordinary skill in the art.

In an alternative embodiment, a method of designing a modulator of an NR, SR or GR polypeptide in accordance with the present invention is disclosed comprising: (a) selecting a candidate NR, SR or GR ligand; (b) determining which amino acid or amino acids of an NR, SR or GR polypeptide interact with the ligand using a three-dimensional model of a crystallized GRα LBD; (c) identifying in a biological assay for NR, SR or GR activity a degree to which the ligand modulates the activity of the NR, SR or GR polypeptide; (d) selecting a chemical modification of the ligand wherein the interaction between the amino acids of the NR, SR or GR polypeptide and the ligand is predicted to be modulated by the chemical modification; (e) synthesizing a chemical compound with the selected chemical modification to form a modified ligand; (f) contacting the modified ligand with the NR, SR or GR polypeptide; (g) identifying in a biological assay for NR, SR or GR activity a degree to which the modified ligand modulates the biological activity of the NR, SR or GR polypeptide; and (h) comparing the biological activity of the NR, SR or GR polypeptide in the presence of modified ligand with the biological activity of the NR, SR or GR polypeptide in the presence of the unmodified ligand, whereby a modulator of an NR, SR or GR polypeptide is designed.

An additional method of designing modulators of an NR, SR or GR or an NR, SR or GR LBD can comprise: (a) determining which amino acid or amino acids of an NR, SR or GR LBD interacts with a first chemical moiety (at least one) of the ligand using a three dimensional model of a crystallized protein comprising an NR, SR or GR LBD in complex with a bound ligand and a co-activator; and (b) selecting one or more chemical modifications of the first chemical moiety to produce a second chemical moiety with a structure to either decrease or increase an interaction between the interacting amino acid and the second chemical moiety compared to the interaction between the interacting amino acid and the first chemical moiety. This is a general strategy only, however, and variations on this disclosed protocol would be apparent to those of skill in the art upon consideration of the present disclosure.

Once a candidate modulator is synthesized as described herein and as will be known to those of skill in the art upon contemplation of the present invention, it can be tested using assays to establish its activity as an agonist, partial agonist or antagonist, and affinity, as described herein. After such testing, a candidate modulator can be further refined by generating LBD crystals with the candidate modulator bound to the LBD. The structure of the candidate modulator can then be further refined using the chemical modification methods described herein for three dimensional models to improve the activity or affinity of the candidate modulator and make second generation modulators with improved properties, such as that of a super agonist or antagonist, as described herein.

IX.A.2. Methods for Using the GRα LBD Structural Coordinates for Molecular Design For the first time, the present invention permits the use of molecular design techniques to design, select and synthesize chemical entities and compounds, including modulatory compounds, capable of binding to the ligand binding pocket or an accessory binding site of an NR, SR or GR and an NR, SR or GR LBD, in whole or in part. Correspondingly, the present invention also provides for the application of similar techniques in the design of modulators of any NR, SR or GR polypeptide.

In accordance with a preferred embodiment of the present invention, the structure coordinates of a crystalline GRα LBD can be used to design compounds that bind to a GR LBD (more preferably a GRα LBD) and alter the properties of a GR LBD (for example, the dimerization ability, ligand binding ability or effect on transcription) in different ways. One aspect of the present invention provides for the design of compounds that can compete with natural or engineered ligands of a GR polypeptide by binding to all, or a portion of, the binding sites on a GR LBD. The present invention also provides for the design of compounds that can bind to all, or a portion of, an accessory binding site on a GR that is already binding a ligand. Similarly, non-competitive agonists/ligands that bind to and modulate GR LBD activity, whether or not it is bound to another chemical entity, and partial agonists and antagonists can be designed using the GR LBD structure coordinates of this invention.

A second design approach is to probe an NR, SR or GR or an NR, SR or GR LBD (preferably a GRα or GRα LBD) crystal with molecules comprising a variety of different chemical entities to determine optimal sites for interaction between candidate NR, SR or GR or NR, SR or GR LBD modulators and the polypeptide. For example, high resolution X-ray diffraction data collected from crystals saturated with solvent allows the determination of the site where each type of solvent molecule adheres. Small molecules that bind tightly to those sites can then be designed and synthesized and tested for their an NR, SR or GR modulator activity. Representative designs are also disclosed in published PCT application WO 99/26966.

Once a computationally-designed ligand is synthesized using the methods of the present invention or other methods known to those of skill in the art, assays can be used to establish its efficacy of the ligand as a modulator of NR, SR or GR (preferably GRα) activity. After such assays, the ligands can be further refined by generating intact NR, SR or GR, or NR, SR or GR LBD, crystals with a ligand bound to the LBD. The structure of the ligand can then be further refined using the chemical modification methods described herein and known to those of skill in the art, in order to improve the modulation activity or the binding affinity of the ligand. This process can lead to second generation ligands with improved properties.

Ligands also can be selected that modulate NR, SR or GR responsive gene transcription by the method of altering the interaction of co-activators and co-repressors with their cognate NR, SR or GR. For example, agonistic ligands can be selected that block or dissociate a co-repressor from interacting with a GR, and/or that promote binding or association of a co-activator. Antagonistic ligands can be selected that block co-activator interaction and/or promote co-repressor interaction with a target receptor. Selection can be done via binding assays that screen for designed ligands having the desired modulatory properties. Preferably, interactions of a GRα polypeptide are targeted. A suitable assay for screening that can be employed, *mutatis mutandis* in the present invention, as described in Oberfield, J. L., et al., *Proc Natl Acad Sci USA*. (1999) May 25; 96(11):6102–6, incorporated herein in its entirety by reference. Other examples of suitable screening assays for GR function include an in vitro peptide binding assay representing ligand-induced interaction with coactivator (Zhou, et al., (1998) *Mol. Endocrinol.* 12: 1594–1604; Parks et al., (1999) *Science* 284: 1365–1368) or a cell-based reporter assay related to transcription from a GRE (reviewed in Jenkins et al., (2001) *Trends Endocrinol. Metab.* 12: 122–126) or a cell-based reporter assay related to repression of genes driven via NF-kB. DeBosscher et al., (2000) *Proc Natl Acad Sci USA*. 97: 3919–3924.

IX.A.3. Methods of Designing NR, SR or GR LBD Modulator Compounds

Knowledge of the three-dimensional structure of the GR LBD complex of the present invention can facilitate a general model for modulator (e.g. agonist, partial agonist, antagonist and partial antagonist) design. Other ligand-receptor complexes belonging to the nuclear receptor superfamily can have a ligand binding pocket similar to that of GR and therefore the present invention can be employed in agonist/antagonist design for other members of the nuclear receptor superfamily and the steroid receptor subfamily. Examples of suitable receptors include those of the NR superfamily and those of the SR subfamily.

The design of candidate substances, also referred to as "compounds" or "candidate compounds", that bind to or inhibit NR, SR or GR LBD-mediated activity according to the present invention generally involves consideration of two factors. First, the compound must be capable of physically and structurally associating with a NR, SR or GR LBD. Non-covalent molecular interactions important in the association of a NR, SR or GR LBD with its substrate include hydrogen bonding, van der Waals interactions and hydrophobic interactions.

The interaction between an atom of a LBD amino acid and an atom of an LBD ligand can be made by any force or attraction described in nature. Usually the interaction between the atom of the amino acid and the ligand will be the result of a hydrogen bonding interaction, charge interaction, hydrophobic interaction, van der Waals interaction or dipole interaction. In the case of the hydrophobic interaction it is recognized that this is not a per se interaction between the amino acid and ligand, but rather the usual result, in part, of the repulsion of water or other hydrophilic group from a hydrophobic surface. Reducing or enhancing the interaction of the LBD and a ligand can be measured by calculating or testing binding energies, computationally or using thermodynamic or kinetic methods as known in the art.

Second, the compound must be able to assume a conformation that allows it to associate with a NR, SR or GR LBD. Although certain portions of the compound will not directly participate in this association with a NR, SR or GR LBD, those portions can still influence the overall conformation of the molecule. This, in tum, can have a significant impact on potency. Such conformational requirements include the overall three-dimensional structure and orientation of the chemical entity or compound in relation to all or a portion of the binding site, e.g., the ligand binding pocket or an accessory binding site of a NR, SR or GR LBD, or the spacing between functional groups of a compound comprising several chemical entities that directly interact with a NR, SR or GR LBD.

Chemical modifications will often enhance or reduce interactions of an atom of a LBD amino acid and an atom of an LBD ligand. Steric hinderance can be a common means of changing the interaction of a LBD binding pocket with an activation domain. Chemical modifications are preferably introduced at C—H, C— and C—OH positions in a ligand, where the carbon is part of the ligand structure that remains the same after modification is complete. In the case of C—H, C could have 1, 2 or 3 hydrogens, but usually only one hydrogen will be replaced. The H or OH can be removed after modification is complete and replaced with a desired chemical moiety.

The potential modulatory or binding effect of a chemical compound on a NR, SR or GR LBD can be analyzed prior to its actual synthesis and testing by the use of computer modeling techniques that employ the coordinates of a crystalline GRα LBD polypeptide of the present invention. If the theoretical structure of the given compound suggests insufficient interaction and association between it and a NR, SR or GR LBD, synthesis and testing of the compound is obviated. However, if computer modeling indicates a strong interaction, the molecule can then be synthesized and tested for its ability to bind and modulate the activity of a NR, SR or GR LBD. In this manner, synthesis of unproductive or inoperative compounds can be avoided.

A modulatory or other binding compound of a NR, SR or GR LBD polypeptide (preferably a GRα LBD) can be computationally evaluated and designed via a series of steps in which chemical entities or fragments are screened and selected for their ability to associate with an individual binding site or other area of a crystalline GRα LBD polypeptide of the present invention and to interact with the amino acids disposed in the binding sites.

Interacting amino acids forming contacts with a ligand and the atoms of the interacting amino acids are usually 2 to 4 angstroms away from the center of the atoms of the ligand. Generally these distances are determined by computer as discussed herein and in McRee (McRee, (1993) *Practical Protein Crystallography*, Academic Press, New York), however distances can be determined manually once the three dimensional model is made. More commonly, the atoms of the ligand and the atoms of interacting amino acids are 3 to 4 angstroms apart. A ligand can also interact with distant amino acids, after chemical modification of the ligand to create a new ligand. Distant amino acids are generally not in contact with the ligand before chemical modification. A chemical modification can change the structure of the ligand to make as new ligand that interacts with a distant amino acid usually at least 4.5 angstroms away from the ligand. Often distant amino acids will not line the surface of the binding cavity for the ligand, as they are too far away from the ligand to be part of a pocket or surface of the binding cavity.

A variety of methods can be used to screen chemical entities or fragments for their ability to associate with an NR, SR or GR LBD and, more particularly, with the individual binding sites of an NR, SR or GR LBD, such as ligand binding pocket or an accessory binding site. This process can begin by visual inspection of, for example, the ligand binding pocket on a computer screen based on the GRα LBD atomic coordinates in Table 4, as described herein. Selected fragments or chemical entities can then be positioned in a variety of orientations, or docked, within an individual binding site of a GRα LBD as defined herein above. Docking can be accomplished using software programs such as those available under the tradenames QUANTA™ (Molecular Simulations Inc., San Diego, Calif.) and SYBYL™ (Tripos, Inc., St. Louis, Mo.), followed by energy minimization and molecular dynamics with standard molecular mechanics forcefields, such as CHARM (Brooks et al., (1983) *J. Comp. Chem.,* 8: 132) and AMBER 5 (Case et al., (1997), AMBER 5, University of California, San Francisco; Pearlman et al., (1995) *Comput. Phys. Commun.* 91: 1–41).

Specialized computer programs can also assist in the process of selecting fragments or chemical entities. These include:

1. GRID™ program, version 17 (Goodford, (1985) *J. Med. Chem.* 28: 849–57), which is available from Molecular Discovery Ltd., Oxford, UK;

2. MCSS™ program (Miranker & Karplus, (1991) *Proteins* 11: 29–34), which is available from Molecular Simulations, Inc., San Diego, Calif.;

3. AUTODOCK™ 3.0 program (Goodsell & Olsen, (1990) *Proteins* 8: 195–202), which is available from the Scripps Research Institute, La Jolla, Calif.;

4. DOCK™ 4.0 program (Kuntz et al., (1992) *J. Mol. Biol.* 161: 269–88), which is available from the University of California, San Francisco, Calif.;

5. FLEX-X™ program (See, Rarey et al., (1996) *J. Comput. Aid. Mol. Des.* 10:41–54), which is available from Tripos, Inc., St. Louis, Mo.;

6. MVP program (Lambert, (1997) in *Practical Application of Computer-Aided Drug Design*, (Charifson, ed.) Marcel-Dekker, New York, pp. 243–303); and 7. LUDI™ program (Bohm, (1992) *J. Comput. Aid. Mol. Des.,* 6: 61–78), which is available from Molecular Simulations, Inc., San Diego, Calif.

Once suitable chemical entities or fragments have been selected, they can be assembled into a single compound or modulator. Assembly can proceed by visual inspection of the relationship of the fragments to each other on the three-dimensional image displayed on a computer screen in relation to the structure coordinates of a GRα LBD. Manual model building using software such as QUANTA™ or SYBYL™ typically follows.

Useful programs to aid one of ordinary skill in the art in connecting the individual chemical entities or fragments include:

1. CAVEAT™ program (Bartlett et al., (1989) *Special Pub., Royal Chem. Soc.* 78: 182–96), which is available from the University of California, Berkeley, Calif.;

2. 3D Database systems, such as MACCS-3D™ system program, which is available from MDL Information Systems, San Leandro, Calif. This area is reviewed in Martin, (1992) *J. Med. Chem.* 35: 2145–54; and 3. HOOK™ program (Eisen et al., (1994). *Proteins* 19: 199–221), which is available from Molecular Simulations, Inc., San Diego, Calif.

Instead of proceeding to build a GR LBD modulator (preferably a GRα LBD modulator) in a step-wise fashion one fragment or chemical entity at a time as described above, modulatory or other binding compounds can be designed as a whole or de novo using the structural coordinates of a crystalline GRα LBD polypeptide of the present invention and either an empty binding site or optionally including some portion(s) of a known modulator(s). Applicable methods can employ the following software programs:

1. LUDI™ program (Bohm, (1992) *J. Comput. Aid. Mol. Des.,* 6: 61–78), which is available from Molecular Simulations, Inc., San Diego, Calif.;

2. LEGEND™ program (Nishibata & Itai, (1991) *Tetrahedron* 47: 8985); and

3. LEAPFROG™, which is available from Tripos Associates, St. Louis, Mo.

Other molecular modeling techniques can also be employed in accordance with this invention. See, e.g., Cohen et al., (1990) *J. Med. Chem.* 33: 883–94. See also, Navia & Murcko, (1992) *Curr. Opin. Struc. Biol.* 2: 202–10; U.S. Pat. No. 6,008,033, herein incorporated by reference.

Once a compound has been designed or selected by the above methods, the efficiency with which that compound can bind to a NR, SR or GR LBD can be tested and optimized by computational evaluation. By way of particular example, a compound that has been designed or selected to function as a NR, SR or GR LBD modulator should also preferably traverse a volume not overlapping that occupied by the binding site when it is bound to its native ligand. Additionally, an effective NR, SR or GR LBD modulator should preferably demonstrate a relatively small difference in energy between its bound and free states (i.e., a small deformation energy of binding). Thus, the most efficient NR, SR and GR LBD modulators should preferably be designed with a deformation energy of binding of not greater than about 10 kcal/mole, and preferably, not greater than 7 kcal/mole. It is possible for NR, SR and GR LBD modulators to interact with the polypeptide in more than one conformation that is similar in overall binding energy. In those cases, the deformation energy of binding is taken to be the difference between the energy of the free compound and the average energy of the conformations observed when the modulator binds to the polypeptide.

A compound designed or selected as binding to an NR, SR or GR polypeptide (preferably a GRα LBD polypeptide) can be further computationally optimized so that in its bound state it would preferably lack repulsive electrostatic interaction with the target polypeptide. Such non-complementary (e.g., electrostatic) interactions include repulsive charge-charge, dipole-dipole and charge-dipole interactions. Specifically, the sum of all electrostatic interactions between the modulator and the polypeptide when the modulator is bound to an NR, SR or GR LBD preferably make a neutral or favorable contribution to the enthalpy of binding.

Specific computer software is available in the art to evaluate compound deformation energy and electrostatic interaction. Examples of programs designed for such uses include:

1. Gaussian 98™, which is available from Gaussian, Inc., Pittsburgh, Pa.;

2. AMBER™ program, version 6.0, which is available from the University of California at San Francisco;

3. QUANTA™ program, which is available from Molecular Simulations, Inc., San Diego, Calif.;

4. CHARMm® program, which is available from Molecular Simulations, Inc., San Diego, Calif.; and 4. Insight II® program, which is available from Molecular Simulations, Inc., San Diego, Calif.

These programs can be implemented using a suitable computer system. Other hardware systems and software packages will be apparent to those skilled in the art after review of the disclosure of the present invention presented herein.

Once an NR, SR or GR LBD modulating compound has been optimally selected or designed, as described above, substitutions can then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation are preferably avoided. Such substituted chemical compounds can then be analyzed for efficiency of fit to an NR, SR or GR LBD binding site using the same computer-based approaches described in detail above.

IX.B. Distinguishing Between GR Subtypes and Between NRs

The present invention also is applicable to generating new synthetic ligands to distinguish nuclear receptor subtypes. As described herein, modulators can be generated that distinguish between subtypes, thereby allowing the generation of either tissue specific or function specific synthetic ligands. For instance, the GRα gene can be translated from its mRNA by alternative initiation from an internal ATG codon (Yudt & Cidlowski (2001) *Molec. Endocrinol.* 15: 1093–1103). This codon codes for methionine at position 27 and translation from this position produces a slightly smaller protein. These two isoforms, translated from the same gene, are referred to as GR-A and GR-B. It has been shown in a cellular system that the shorter GR-B form is more effective in initiating transcription from a GRE compared to GR-A. Additionally, another form of GR, called GRβ is produced by an alternative splicing event. The GRβ protein differs from GRα at the very C-terminus, where the final 50 amino acids are replaced with a 15 amino acid segment. These two isoforms are 100% identical up to amino acid 727. No sequence similarity exists between GRα and GRβ at the C-terminus beyond position 727. GRβ has been shown to be a dominant negative regulator of GRα-mediated gene transcription (Oakley, Sar & Cidlowski (1996) *J. Biol. Chem.* 271: 9550–9559). It has been suggested that some of the tissue specific effects observed with glucocorticoid treatment may in part be due to the presence of varying amounts of isoform in certain cell-types. This method is also applicable to any other subfamily so organized.

The present invention discloses the ability to generate new synthetic ligands to distinguish between GR subtypes. As described herein, computer-designed ligands (i.e. candidate modulators and modulators) can be generated that distinguish between GR subtypes, thereby allowing the generation of either tissue specific or function specific ligands. The atomic structural coordinates disclosed in the present invention reveal structural details unique to GRα. These structural details can be exploited when a novel ligand is designed using the methods of the present invention or other ligand design methods known in the art. The structural features that differentiate, for example, a GRα from a GRβ can be targeted in ligand design. Thus, for example, a ligand can be designed that will recognize GRα, while not interacting with other GRs or even with moieties having similar structural features. Prior to the disclosure of the present invention, the ability to target a GR subtype was unattainable.

The present invention also pertains to a method for designing an agonist or modulator with desired levels of activity on at least two subtypes, GRα and GRβ. In a preferred embodiment, the method comprises obtaining atomic coordinates for structures of the GRα and/or GRβ ligand binding domains. The structures can comprise GRα and GRβ, each bound to various different ligands, and also can comprise structures where no ligand is present. The structures can also comprise models where a compound has been docked into a particular GR using a molecular docking procedure, such as the MVP program disclosed herein. Optionally, the structures are rotated and translated so as to superimpose corresponding Cα or backbone atoms; this facilitates the comparison of structures.

The GRα and GRβ structures can also be compared using a computer graphics system to identify regions of the ligand binding site that have similar shape and electrostatic character, and to identify regions of the ligand binding site that are narrowed or constricted in one or both of the GRs, particularly as compared to other NRs. Since these three GRs are subject to conformational changes, attention is paid to the range of motion observed for each protein atom over the whole collection of structures. The ligand structures, including both those determined by X-ray crystallography and those modeled using molecular docking procedures, can be examined using a computer graphics system to identify ligands where a chemical modification could increase or decrease binding to a particular GR, or decrease activity against a particular GR. Additionally or alternatively, the chemical modification can introduce a group into a volume that is normally occupied by an atom of that GR.

Optionally, to selectively decrease activity against a particular GR, the chemical modification can be made so as to occupy volume that is normally occupied by atoms of that particular GR, but not by atoms of the other GRs. To increase activity against a particular GR, a chemical modification can be made that improves interactions with that particular GR. To selectively increase activity against a particular GR, a chemical modification can be made that improves the interactions with that particular GR, but does not improve the interactions with the other GRs. Other design principles can also be used to increase or decrease activity on a particular GR.

Thus, various possible compounds and chemical modifications can be considered and compared graphically, and with molecular modeling tools, for synthetic feasibility and likelihood of achieving the desired profile of activation of GRα and GRβ. Compounds that appear synthetically feasible and that have a good likelihood of achieving the desired profile are synthesized. The compounds can then be tested for binding and/or activation of GRα and GRβ, and tested for their overall biological effect.

A method of identifying a NR modulator that selectively modulates the biological activity of one NR compared to GRα is also disclosed. In one embodiment, the method comprises: (a) providing an atomic structure coordinate set describing a GRα ligand binding domain structure and at least one other atomic structure coordinate set describing a NR ligand binding domain, each ligand binding domain comprising a ligand binding site; (b) comparing the atomic structure coordinate sets to identify at least one diference between the sets; (c) designing a candidate ligand predicted to interact with the difference of step (b); (d) synthesizing the candidate ligand; and (e) testing the synthesized candidate ligand for an ability to selectively modulate a NR as compared to GRα, whereby a NR modulator that selectively modulates the biological activity NR compared to GRα is identified.

Preferably, the GRα atomic structure coordinate set is the atomic structure coordinate set shown in Table 4. Optionally, the NR is selected from the group consisting of MR, PR, AR, GRβ and isoforms thereof that have ligands that also bind GRα.

IX.C. Method of Screening for Chemical and Biological Modulators of the Biological Activity of an NR, SR or GR A candidate substance identified according to a screening assay of the present invention has an ability to modulate the biological activity of an NR, SR or GR or an NR, SR or GR LBD polypeptide. In a preferred embodiment, such a candidate compound can have utility in the treatment of disorders and/or conditions and/or biological events associated with the biological activity of an NR, SR or GR or an NR, SR or GR LBD polypeptide, including transcription modulation.

In a cell-free system, the method comprises the steps of establishing a control system comprising a GRα polypeptide and a ligand which is capable of binding to the polypeptide; establishing a test system comprising a GRα polypeptide, the ligand, and a candidate compound; and determining whether the candidate compound modulates the activity of the polypeptide by comparison of the test and control systems. A representative ligand can comprise dexamethasone or other small molecule, and in this embodiment, the biological activity or property screened can include binding affinity or transcription regulation. The GRα polypeptide can be in soluble or crystalline form.

In another embodiment of the invention, a soluble or a crystalline form of a GRα polypeptide or a catalytic or immunogenic fragment or oligopeptide thereof, can be used for screening libraries of compounds in any of a variety of drug screening techniques. The fragment employed in such a screening can be affixed to a solid support. The formation of binding complexes, between a soluble or a crystalline GRα polypeptide and the agent being tested, will be detected. In a preferred embodiment, the soluble or crystalline GRα polypeptide has an amino acid sequence of any of SEQ ID NOs:4, 6, 8 or 10. When a GRα LBD polypeptide is employed, a preferred embodiment will include a soluble or a crystalline GRα polypeptide having the amino acid sequence of any of SEQ ID NOs:12, 14, 16 or 31.

Another technique for drug screening which can be used provides for high throughput screening of compounds having suitable binding affinity to the protein of interest as described in published PCT application WO 84/03564, herein incorporated by reference. In this method, as applied to a soluble or crystalline polypeptide of the present invention, large numbers of different small test compounds are synthesized on a solid substrate, such as plastic pins or some other surface. The test compounds are reacted with the soluble or crystalline polypeptide, or fragments thereof. Bound polypeptide is then detected by methods known to those of skill in the art. The soluble or crystalline polypeptide can also be placed directly onto plates for use in the aforementioned drug screening techniques.

In yet another embodiment, a method of screening for a modulator of an NR, SR or GR or an NR, SR or GR LBD polypeptide comprises: providing a library of test samples; contacting a soluble or a crystalline form of an NR, SR or GR or a soluble or crystalline form of an NR, SR or GR LBD polypeptide with each test sample; detecting an interaction between a test sample and a soluble or a crystalline form of an NR, SR or GR or a soluble or a crystalline form of an NR, SR or GR LBD polypeptide; identifying a test sample that interacts with a soluble or a crystalline form of an NR, SR or GR or a soluble or a crystalline form of an NR, SR or GR LBD polypeptide; and isolating a test sample that interacts with a soluble or a crystalline form of an NR, SR or GR or a soluble or a crystalline form of an NR, SR or GR LBD polypeptide.

In each of the foregoing embodiments, an interaction can be detected spectrophotometrically, radiologically, calorimetrically or immunologically. An interaction between a soluble or a crystalline form of an NR, SR or GR or a soluble or a crystalline form of an NR, SR or GR LBD polypeptide and a test sample can also be quantified using methodology known to those of skill in the art.

In accordance with the present invention there is also provided a rapid and high throughput screening method that relies on the methods described above. This screening method comprises separately contacting each of a plurality of substantially identical samples with a soluble or a crystalline form of an NR, SR or GR or a soluble or a crystalline form of an NR, SR or GR LBD and detecting a resulting binding complex. In such a screening method the plurality of samples preferably comprises more than about $10^4$ samples, or more preferably comprises more than about $5\times10^4$ samples.

In another embodiment, a method for identifying a substance that modulates GR LBD function is also provided. In a preferred embodiment, the method comprises: (a) isolating a GR polypeptide of the present invention; (b) exposing the isolated GR polypeptide to a plurality of substances; (c) assaying binding of a substance to the isolated GR polypeptide; and (d) selecting a substance that demonstrates specific binding to the isolated GR LBD polypeptide. By the term "exposing the GR polypeptide to a plurality of substances", it is meant both in pools and as mutiple samples of "discrete" pure substances.

IX.D. Method of Identifying Compounds Which Inhibit Ligand Binding

In one aspect of the present invention, an assay method for identifying a compound that inhibits binding of a ligand to an NR, SR or GR polypeptide is disclosed. A ligand, such as dexamethasone (which associates with at least GR), can be used in the assay method as the ligand against which the inhibition by a test compound is gauged. In the following discussion of Section IX.D., it will be understood that although GR is used as an example, the method is equally applicable to any of NR, SR or GR polypeptide The method comprises (a) incubating a GR polypeptide with a ligand in the presence of a test inhibitor compound; (b) determining an amount of ligand that is bound to the GR polypeptide, wherein decreased binding of ligand to the GR polypeptide in the presence of the test inhibitor compound relative to binding in the absence of the test inhibitor compound is indicative of inhibition; and (c) identifying the test compound as an inhibitor of ligand binding if decreased ligand binding is observed. Preferably, the ligand is dexamethasone.

In another aspect of the present invention, the disclosed assay method can be used in the structural refinement of candidate GR inhibitors. For example, multiple rounds of optimization can be followed by gradual structural changes in a strategy of inhibitor design. A strategy such as this is made possible by the disclosure of the atomic coordinates of the GRα LBD.

X. Design, Preparation and Structural Analysis of Additional NR, SR and GR Polypeptides and NR, SR and GR LBD Mutants and Structural Equivalents The present invention provides for the generation of NR, SR and GR polypeptides and NR, SR or GR mutants (preferably GRα and GRα LBD mutants), and the ability to solve the crystal structures of those that crystallize. Indeed, a GRα LBD havingfa point mutation was crystallized and solved in one aspect of the present invention. Thus, an aspect of the present invention involves the use of both targeted and random mutagenesis of the GR gene for the production of a recombinant protein with improved or desired characteristics for the purpose of crystallization, characterization of biologically relevant protein-protein interactions, and compound screening assays, or for the production of a recombinant protein having other desirable characteristic(s). Polypeptide products produced by the methods of the present invention are also disclosed herein.

The structure coordinates of a NR, SR or GR LBD provided in accordance with the present invention also facilitate the identification of related proteins or enzymes analogous to GRα in function, structure or both, (for example, a GRβ which can lead to novel therapeutic modes for treating or preventing a range of disease states. More particularly, through the provision of the mutagenesis approaches as well as the three-dimensional structure of a GRα LBD disclosed herein, desirable sites for mutation are identified.

X.A. Sterically Similar Compounds

A further aspect of the present invention is that sterically similar compounds can be formulated to mimic the key portions of an NR, SR or GR LBD structure. Such compounds are functional equivalents. The generation of a structural functional equivalent can be achieved by the techniques of modeling and chemical design known to those of skill in the art and described herein. Modeling and chemical design of NR, SR or GR and NR, SR or GR LBD structural equivalents can be based on the structure coordinates of a crystalline GRα LBD polypeptide of the present invention. It will be understood that all such sterically similar constructs fall within the scope of the present invention.

X.B. NR, SR and GR Polypeptides The generation of chimeric GR polypeptides is also an aspect of the present invention. Such a chimeric polypeptide can comprise an NR, SR or GR LBD polypeptide or a portion of an NR, SR or GR LBD, (e.g. a GRα LBD) that is fused to a candidate polypeptide or a suitable region of the candidate polypeptide, for example GRβ. Throughout the present disclosure it is intended that the term "mutant" encompass not only mutants of an NR, SR or GR LBD polypeptide but chimeric proteins generated using an NR, SR or GR LBD as well. It is thus intended that the following discussion of mutant NR, SR and GR LBDs apply *mutatis mutandis* to chimeric NR, SR and GR polypeptides and NR, SR and GR LBD polypeptides and to structural equivalents thereof.

In accordance with the present invention, a mutation can be directed to a particular site or combination of sites of a wild-type NR, SR or GR LBD. For example, an accessory binding site or the binding pocket can be chosen for mutagenesis. Similarly, a residue having a location on, at or near the surface of the polypeptide can be replaced, resulting in an altered surface charge of one or more charge units, as compared to the wild-type NR, SR or GR and NR, SR or GR LBDs. Alternatively, an amino acid residue in an NR, SR or GR or an NR, SR or GR LBD can be chosen for replacement based on its hydrophilic or hydrophobic characteristics.

Such mutants can be characterized by any one of several different properties, i.e. a "desired" or "predetermined" characteristic as compared with the wild type NR, SR or GR LBD. For example, such mutants can have an altered surface charge of one or more charge units, or can have an increase in overall stability. Other mutants can have altered substrate specificity in comparison with, or a higher specific activity than, a wild-type NR, SR or GR or an NR, SR or GR LBD.

NR, SR or GR and NR, SR or GR LBD mutants of the present invention can be generated in a number of ways. For example, the wild-type sequence of an NR, SR or GR or an NR, SR or GR LBD can be mutated at those sites identified using this invention as desirable for mutation, by means of oligonucleotide-directed mutagenesis or other conventional methods, such as deletion. Alternatively, mutants of an NR, SR or GR or an NR, SR or GR LBD can be generated by the site-specific replacement of a particular amino acid with an unnaturally occurring amino acid. In addition, NR, SR or GR or NR, SR or GR LBD mutants can be generated through replacement of an amino acid residue, for example, a particular cysteine or methionine residue, with selenocysteine or selenomethionine. This can be achieved by growing a host organism capable of expressing either the wild-type or mutant polypeptide on a growth medium depleted of either natural cysteine or methionine (or both) but enriched in selenocysteine or selenomethionine (or both).

As disclosed in the Examples presented below, mutations can be introduced into a DNA sequence coding for an NR, SR or GR or an NR, SR or GR LBD using synthetic oligonucleotides. These oligonucleotides contain nucleotide sequences flanking the desired mutation sites. Mutations can be generated in the full-length DNA sequence of an NR, SR or GR or an NR, SR or GR LBD or in any sequence coding for polypeptide fragments of an NR, SR or GR or an NR, SR or GR LBD.

According to the present invention, a mutated NR, SR or GR or NR, SR or GR LBD DNA sequence produced by the methods described above, or any alternative methods known in the art, can be expressed using an expression vector. An expression vector, as is well known to those of skill in the art, typically includes elements that permit autonomous replication in a host cell independent of the host genome, and one or more phenotypic markers for selection purposes. Either prior to or after insertion of the DNA sequences surrounding the desired NR, SR or GR or NR, SR or GR LBD mutant coding sequence, an expression vector also will include control sequences encoding a promoter, operator, ribosome binding site, translation initiation signal, and, optionally, a repressor gene or various activator genes and a signal for termination. In some embodiments, where secretion of the produced mutant is desired, nucleotides encoding a "signal sequence" can be inserted prior to an NR, SR or GR or an NR, SR or GR LBD mutant coding sequence. For expression under the direction of the control sequences, a desired DNA sequence must be operatively linked to the control sequences; that is, the sequence must have an appropriate start signal in front of the DNA sequence encoding the NR, SR or GR or NR, SR or GR LBD mutant, and the correct reading frame to permit expression of that sequence under the control of the control sequences and production of the desired product encoded by that NR, SR or GR or NR, SR or GR LBD sequence must be maintained.

After a review of the disclosure of the present invention presented herein, any of a wide variety of well-known available expression vectors can be useful to express a mutated coding sequence of this invention. These include for example, vectors consisting of segments of chromosomal, non-chromosomal and synthetic DNA sequences, such as various known derivatives of SV40, known bacterial plasmids, e.g., plasmids from *E. coli* including col E1, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and filamentous single stranded DNA phages, yeast plasmids and vectors derived from combinations of plasmids and phage DNAs, such as plasmids which have been modified to employ phage DNA or other expression control sequences. In the preferred embodiments of this invention, vectors amenable to expression in a pET-based expression system are employed. The pET expression system is available from Novagen/Invitrogen, Inc., Carlsbad, Calif. Expression and screening of a polypeptide of the present invention in bacteria, preferably *E. coli*, is a preferred aspect of the present invention.

In addition, any of a wide variety of expression control sequences—sequences that control the expression of a DNA sequence when operatively linked to it—can be used in these vectors to express the mutated DNA sequences according to this invention. Such useful expression control sequences, include, for example, the early and late promoters of SV40 for animal cells, the lac system, the trp system the TAC or TRC system, the major operator and promoter regions of phage λ, the control regions of fd coat protein, all for *E. coli*, the promoter for 3-phosphoglycerate kinase or other glycolytic enzymes, the promoters of acid phosphatase, e.g., Pho5, the promoters of the yeast α-mating factors for yeast, and other sequences known to control the expression of genes of prokaryotic or eukaryotic cells or their viruses, and various combinations thereof.

A wide variety of hosts are also useful for producing mutated NR, SR or GR and NR, SR or GR LBD polypeptides according to this invention. These hosts include, for example, bacteria, such as *E. coli, Bacillus* and *Streptomyces*, fungi, such as yeasts, and animal cells, such as CHO and COS-1 cells, plant cells, insect cells, such as SF9 cells, and transgenic host cells. Expression and screening of a polypeptide of the present invention in bacteria, preferably *E. coli*, is a preferred aspect of the present invention.

It should be understood that not all expression vectors and expression systems function in the same way to express mutated DNA sequences of this invention, and to produce modified NR, SR or GR and NR, SR or GR LBD polypeptides or NR, SR or GR or NR, SR or GR LBD mutants. Neither do all hosts function equally well with the same expression system. One of skill in the art can, however, make a selection among these vectors, expression control sequences and hosts without undue experimentation and without departing from the scope of this invention. For example, an important consideration in selecting a vector will be the ability of the vector to replicate in a given host. The copy number of the vector, the ability to control that copy number, and the expression of any other proteins encoded by the vector, such as antibiotic markers, should also be considered.

In selecting an expression control sequence, a variety of factors should also be considered. These include, for example, the relative strength of the system, its controllability and its compatibility with the DNA sequence encoding a modified NR, SR or GR or NR, SR or GR LBD polypeptide of this invention, with particular regard to the formation of potential secondary and tertiary structures.

Hosts should be selected by consideration of their compatibility with the chosen vector, the toxicity of a modified polypeptide to them, their ability to express mature products, their ability to fold proteins correctly, their fermentation requirements, the ease of purification of a modified GR or GR LBD and safety. Within these parameters, one of skill in the art can select various vector/expression control system/host combinations that will produce useful amounts of a mutant polypeptide. A mutant polypeptide produced in these systems can be purified, for example, via the approaches disclosed in the Examples.

Once a mutation(s) has been generated in the desired location, such as an active site or dimerization site, the mutants can be tested for any one of several properties of interest, i.e. "desired" or "predetermined" positions. For example, mutants can be screened for an altered charge at physiological pH. This property can be determined by measuring the mutant polypeptide isoelectric point (pI) and comparing the observed value with that of the wild-type parent. Isoelectric point can be measured by gel-electrophoresis according to the method of Wellner (Wellner, (1971) *Anal. Chem.* 43: 597). A mutant polypeptide containing a replacement amino acid located at the surface of the enzyme, as provided by the structural information of this invention, can lead to an altered surface charge and an altered pI.

X.C. Generation of an Engineered NR, SR or GR or NR, SR or GR LBD Mutants

In another aspect of the present invention, a unique NR, SR or GR or NR, SR or GR LBD polypeptide is generated. Such a mutant can facilitate purification and the study of the structure and the ligand-binding abilities of a NR, SR or GR polypeptide. Thus, an aspect of the present invention involves the use of both targeted and random mutagenesis of the GR gene for the production of a recombinant protein with improved solution characteristics for the purpose of crystallization, characterization of biologically relevant protein-protein interactions, and compound screening assays, or for the production of a recombinant polypeptide having other characteristics of interest. Expression of the polypeptide in bacteria, preferably *E. coli*, is also an aspect of the present invention.

In one embodiment, targeted mutagenesis was performed using a sequence alignment of several nuclear receptors, primarily steroid receptors. Several residues that were hydrophobic in GR and hydrophilic in other receptors were chosen for mutagenesis. Most of these residues were predicted to be solvent exposed hydrophobic residues in GR. Therefore, mutations were made to change these hydrophobic residues to hydrophilic in attempt to improve the solubility and stability of *E. coli*-expressed GR LBD. Table 2 immediately below presents a list of mutations (for that were made and tested for expression in *E. coli*.

TABLE 2

Mutations of the GR LBD (521–777) Gene for Testing Solution Solubility and Stability

| Single mutations | Double mutations | Triple mutations |
|---|---|---|
| V552K | L535T/V538S | M691T/V702T/W712T |
| W557S | V552K/W557S | |
| F602S | L636E/C638S | |
| F602D | | |
| F602E | | |
| L636E | | |
| Y648Q | | |
| W712S | | |
| L741R | | |
| F602Y | | |
| F602T | | |
| F602N | | |
| F602C | | |

Random mutagenesis can be performed on residues where a significant difference, hydrophobic versus hydrophilic, is observed between GR and other steroid receptors based on sequence alignment. Such positions can be randomized by oligo-directed or cassette mutagenesis. A GR LBD protein library can be sorted by an appropriate display system to select mutants with improved solution properties. Residues in GR that meet the criteria for such an approach include: V538, V552, W557, F602, L636, Y648, Y660, L685, M691, V702, W712, L733, and Y764. In addition, residues predicted to neighbor these positions could also be randomized.

In another embodiment, complete random mutagenesis can be performed on any residue within the context of the GR LBD. A method such as error incorporating PCR or chemical-based mutagenesis can be used to introduce mutations in an unbiased manner. These methods randomize the position of mutation as well as the nature of the mutated residue. A completely random GR LBD library can be screened for improved expression with the appropriate expression or display system. Ideally, the selection method should identify mutant proteins with increased expression, solubility, stability, and/or activity. A technique well suited for this purpose is the "peptides-on-plasmid" display system that utilizes the DNA-binding activity of the lac repressor (Lacl). GR, or another nuclear receptor LBD, can be expressed as a fusion to either Lacl or a fragment of Lacl, such as the "headpiece dimer", that comprises the DNA-binding domain. Because the plasmid that expresses the fusion protein also comprises a lac operon binding site, the protein will be physically coupled to the plasmid. GR mutants that produce soluble protein can then be isolated using either the coactivator peptide- or ligand-binding activity of the receptor. Table 2A below shows mutations that were prepared using the Lacl-based "peptides-on-plasmids" technique with GR LBD.

TABLE 2A

Random Mutations of the GR LBD (521–777) Gene for Improving Solution Solubility and Stability

| Single mutations | SEQ ID NO | Double Mutations | SEQ ID NO |
|---|---|---|---|
| W557R | 33 | F602L/A580T | 38 |
| Q615L | 34 | L563F/G583C | 39 |
| Q615H | 35 | L664H/M752T | 40 |
| A574T | 36 | L563F/T744N | 41 |
| L620M | 37 | | |

A method of modifying a test NR polypeptide is thus disclosed. The method can comprise: providing a test NR polypeptide sequence having a characteristic that is targeted for modification; aligning the test NR polypeptide sequence with at least one reference NR polypeptide sequence for which an X-ray structure is available, wherein the at least one reference NR polypeptide sequence has a characteristic that is desired for the test NR polypeptide; building a three-dimensional model for the test NR polypeptide using the three-dimensional coordinates of the X-ray structure(s) of the at least one reference polypeptide and its sequence alignment with the test NR polypeptide sequence; examining the three-dimensional model of the test NR polypeptide for differences with the at least one reference polypeptide that are associated with the desired characteristic; and mutating at least one amino acid residue in the test NR polypeptide sequence located at a difference identified above to a residue associated with the desired characteristic, whereby the test NR polypeptide is modified. By the term "associated with a desired characteristic" it is meant that a residue is found in the reference polypeptide at a point of difference wherein the difference provides a desired characteristic or phenotype in the reference polypeptide.

A method of altering the solubility of a test NR polypeptide is also disclosed in accordance with the present invention. In a preferred embodiment, the method comprises: (a) providing a reference NR polypeptide sequence and a test NR polypeptide sequence; (b) comparing the reference NR polypeptide sequence and the test NR polypeptide sequence to identify one or more residues in the test NR sequence that are more or less hydrophilic than a corresponding residue in the reference NR polypeptide sequence; and (c) mutating the residue in the test NR polypeptide sequence identified in step (b) to a residue having a different hydrophilicity, whereby the solubility of the test NR polypeptide is altered.

By the term "altering" it is meant any change in the solubility of the test NR polypeptide, including preferably a change to make the polypeptide more soluble. Such approaches to obtain soluble proteins for crystallization studies have been successfully demonstrated in the case of HIV integration intergrase and the human leptin cytokine. See Dyda, F., et al., *Science* (1994) December 23; 266 (5193):1981–6; and Zhang et al., *Nature* (1997) May 8; 387(6629):206–9.

Typically, such a change involves substituting a residue that is more hydrophilic than the wild type residue. Hydrophobicity and hydrophilicity criteria and comparision information are set forth herein below. Optionally, the reference NR polypeptide sequence is an AR or a PR sequence, and the test polypeptide sequence is a GR polypeptide sequence. Alternatively, the reference polypeptide sequence is a crystalline GR LBD. The comparing of step (b) is preferably by sequence alignment. More preferably, the screening is carried out in bacteria, even more preferably, in *E coli*.

A method for modifying a test NR polypeptide to alter and preferably improve the solubility, stability in solution and other solution behavior, to alter and preferably improve the folding and stability of the folded structure, and to alter and preferably improve the ability to form ordered crystals is also provided in accordance with the present invention. The aforementioned characteristics are representative "desired" or "predetermined characteristics or phenotypes.

In a preferred embodiment, the method comprises:

(a) providing a test NR polypeptide sequence for which the solubility, stability in solution, other solution behavior, tendency to fold properly, ability to form ordered crystals, or combination thereof is different from that desired;

(b) aligning the test NR polypeptide sequence with the sequences of other reference NR polypeptides for which the X-ray structure is available and for which the solution properties, folding behavior and crystallization properties are closer to those desired;

(c) building a three-dimensional model for the test NR polypeptide using the three-dimensional coordinates of the X-ray structure(s) of one or more of the reference polypeptides and their sequence alignment with the test NR polypetide sequence;

(d) optionally, optimizing the side-chain conformations in the three-dimensional model by generating many alternative side-chain conformations, refining by energy minimization, and selecting side-chain conformations with lower energy;

(e) examining the three-dimensional model for the test NR graphically for lipophilic side-chains that are exposed to solvent, for clusters of two or more lipophilic side-chains exposed to solvent, for lipophilic pockets and clefts on the surface of the protein model, and in particular for sites on the surface of the protein model that are more lipophilic than the corresponding sites on the structure(s) of the reference NR polypeptide(s);

(f) for each residue identified in step (e), mutating the amino acid to an amino acid with different hydrophilicity, and usually to a more hydrophilic amino acid, whereby the exposed lipophilic sites are reduced, and the solution properties improved;

(g) examining the three-dimensional model graphically at each site where the amino acid in the test NR polypeptide is different from the amino acid at the corresponding position in the reference NR polypeptide, and checking whether the amino acid in the test NR polypeptide makes favorable interactions with the atoms that lie around it in the three-dimensional model, considering the side-chain conformations predicted in steps (c) and, optionally step (d), as well as likely alternative conformations of the side-chains, and also considering the possible presence of water molecules (for this analysis, an amino acid is considered to make "favorable interactions with the atoms that lie around it" if these interactions are more favorable than the interactions that would be obtained if it was replaced by any of the 19 other naturally-occurring amino acids);

(h) for each residue identified in step (g) as not making favorable interactions with the atoms that lie around it, mutating the residue to another amino acid that could make better interactions with the atoms that lie around it, thereby promoting the tendency for the test NR polypeptide to fold into a stable structure with improved solution properties, less tendency to unfold, and greater tendency to form ordered crystals;

(i) examining the three-dimensional model graphically at each residue position where the amino acid in the test NR polypeptide is different from the amino acid at the corresponding position in the reference NR polypeptide, and checking whether the steric packing, hydrogen bonding and other energetic interactions could be improved by mutating that residue or any one or more of the surrounding residues lying within 8 angstroms in the three-dimensional model;

(j) for each residue position identified in step (i) as potentially allowing an improvement in the packing, hydrogen bonding and energetic interactions, mutating those residues individually or in combination to residues that could improve the packing, hydrogen bonding and energetic interactions, thereby promoting the tendency for the test NR polypeptide to fold into a stable structure with improved solution properties, less tendency to unfold, and greater tendency to form ordered crystals.

By the term "graphically" it is meant through the use of computer aided graphics, such by the use of a software package disclosed herein above. Optionally, in this embodiment, the reference NR polypeptide is AR, or preferably PR, when the test NR polypeptide is GRα. Alternatively, the reference NR polypeptide is GRα, and the test NR polypeptide is GRβ or MR.

An isolated GR polypeptide comprising a mutation in a ligand binding domain, wherein the mutation alters the solubility of the ligand binding domain, is also disclosed. An isolated GR polypeptide, or functional portion thereof, having one or more mutations comprising a substitution of a hydrophobic amino acid residue by a hydrophilic amino acid residue in a ligand binding domain is also disclosed. Preferably, in each case, the mutation can be at a residue selected from the group consisting of V552, W557, F602, L636, Y648, W712, L741, L535, V538, C638, M691, V702, Y648, Y660, L685, M691, V702, W712, L733, Y764 and combinations thereof. More preferably, the mutation is selected from the group consisting of V552K, W557S, F602S, F602D, F602E, F602Y, F602T, F602N, F602C, L636E, Y648Q, W712S, L741 R, L535T, V538S, C638S, M691T, V702T, W712T and combinations thereof. Even more preferably, the mutation is made by targeted point or randomizing mutagenesis. Hydrophobicity and hyrdrophilicity criteria and comparision information are set forth herein below.

As discussed above, the GRα gene can be translated from its mRNA by alternative initiation from an internal ATG codon (Yudt & Cidlowski (2001) *Molec. Endocrinol.* 15: 1093–1103). This codon codes for methionine at position 27 and translation from this position produces a slightly smaller protein. These two isoforms, translated from the same gene, are referred to as GR-A and GR-B. It has been shown in a cellular system that the shorter GR-B form is more effective in initiating transcription from a GRE compared to GR-A. Additionally, another form of GR, called GRβ is produced by an alternative splicing event. The GRβ protein differs from GRα at the very C-terminus, where the final 50 amino acids are replaced with a 15 amino acid segment. These two isoforms are 100% identical up to amino acid 727. No sequence similarity exists between GRα and GRβ at the C-terminus beyond position 727. GRβ has been shown to be a dominant negative regulator of GRα-mediated gene transcription (Oakley, Sar & Cidlowski (1996) *J. Biol. Chem.* 271: 9550–9559). It has been suggested that some of the tissue specific effects observed with glucocorticoid treatment may in part be due to the presence of varying amounts of isoform in certain cell-types. This method is also applicable to any other subfamily so organized. Thus, while the amino acid residue numbers referenced above pertain to GR-A, the polypeptides of the present invention also have a mutation at an analogous position in any polypeptide based on a sequence alignment (such as prepared by BLAST or other approach disclosed herein or known in the art) to GRα, which are not forth herein for convenience.

As used in the following discussion, the terms "engineered NR, SR or GR", "engineered NR, SR or GR LDB", "NR, SR or GR mutant", and "NR, SR or GR LBD mutant" refers to polypeptides having amino acid sequences that contain at least one mutation in the wild-type sequence, including at an analogous position in any polypeptide based on a sequence alignment to GRα. The terms also refer to NR, SR or GR and NR, SR or GR LBD polypeptides which are capable of exerting a biological effect in that they comprise all or a part of the amino acid sequence of an engineered mutant polypeptide of the present invention, or cross-react with antibodies raised against an engineered mutant polypeptide, or retain all or some or an enhanced degree of the biological activity of the engineered mutant amino acid sequence or protein. Such biological activity can include the binding of small molecules in general, the binding of glucocorticoids in particular and even more particularly the binding of dexamethasone.

The terms "engineered NR, SR or GR LBD" and "NR, SR or GR LBD mutant" also includes analogs of an engineered NR, SR or GR polypeptide or NR, SR or GR LBD or GR LBD mutant polypeptide. By "analog" is intended that a DNA or polypeptide sequence can contain alterations relative to the sequences disclosed herein, yet retain all or some or an enhanced degree of the biological activity of those sequences. Analogs can be derived from genomic nucleotide sequences or from other organisms, or can be created synthetically. Those of skill in the art will appreciate that other analogs, as yet undisclosed or undiscovered, can be used to design and/or construct mutant analogs. There is no need for an engineered mutant polypeptide to comprise all or substantially all of the amino acid sequence of the wild type polypeptide (e.g. SEQ ID NOs:2 or 10). Shorter or longer sequences are anticipated to be of use in the invention; shorter sequences are herein referred to as "segments". Thus, the terms "engineered NR, SR or GR LBD" and "NR, SR or GR LBD mutant" also includes fusion, chimeric or recombinant engineered NR, SR or GR LBD or NR, SR or GR LBD mutant polypeptides and proteins comprising sequences of the present invention. Methods of preparing such proteins are disclosed herein above.

X.D. Sequence Similarity and Identity

As used herein, the term "substantially similar" as applied to GR means that a particular sequence varies from nucleic acid sequence of any of odd numbered SEQ ID NOs:1–15, or the amino acid sequence of any of even numbered SEQ ID NOs:2–16 by one or more deletions, substitutions, or additions, the net effect of which is to retain at least some of biological activity of the natural gene, gene product, or sequence. Such sequences include "mutant" or "polymorphic" sequences, or sequences in which the biological activity and/or the physical properties are altered to some degree but retains at least some or an enhanced degree of the original biological activity and/or physical properties. In determining nucleic acid sequences, all subject nucleic acid sequences capable of encoding substantially similar amino acid sequences are considered to be substantially similar to a reference nucleic acid sequence, regardless of differences in codon sequences or substitution of equivalent amino acids to create biologically functional equivalents.

X.D.1. Sequences That are Substantially Identical to an Engineered NR, SR or GR or NR, SR or GR LBD Mutant Sequence of the Present Invention Nucleic acids that are substantially identical to a nucleic acid sequence of an engineered NR, SR or GR or NR, SR or GR LBD mutant of the present invention, e.g. allelic variants, genetically altered versions of the gene, etc., bind to an engineered NR, SR or GR or NR, SR or GR LBD mutant sequence under stringent hybridization conditions. By using probes, particularly labeled probes of DNA sequences, one can isolate homologous or related genes. The source of homologous genes can be any species, e.g. primate species; rodents, such as rats and mice, canines, felines, bovines, equines, yeast, nematodes, etc.

Between mammalian species, e.g. human and mouse, homologs have substantial sequence similarity, i.e. at least 75% sequence identity between nucleotide sequences. Sequence similarity is calculated based on a reference sequence, which can be a subset of a larger sequence, such as a conserved motif, coding region, flanking region, etc. A reference sequence will usually be at least about 18 nt long, more usually at least about 30 nt long, and can extend to the complete sequence that is being compared. Algorithms for sequence analysis are known in the art, such as BLAST, described in Altschul et al., (1990) *J. Mol. Biol.* 215: 403–10. Software for performing BLAST analyses is publicly available through the National Center for Biotechnology Information (http://www.ncbi.nlm.nih.gov/).

This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, (1989) *Proc Natl Acad Sci U.S.A.* 89: 10915.

In addition to calculating percent sequence identity, the BLAST algorithm also performs a statistical analysis of the similarity between two sequences. See, e.g., Karlin and Altschul, (1993) *Proc Natl Acad Sci U.S.A.* 90: 5873–5887. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Percent identity or percent similarity of a DNA or peptide sequence can be determined, for example, by comparing sequence information using the GAP computer program, available from the University of Wisconsin Geneticist Computer Group. The GAP program utilizes the alignment method of Needleman et al., (1970) *J. Mol. Biol.* 48: 443, as revised by Smith et al., (1981) *Adv. Appl. Math.* 2:482. Briefly, the GAP program defines similarity as the number of aligned symbols (i.e., nucleotides or amino acids) which are similar, divided by the total number of symbols in the shorter of the two sequences. The preferred parameters for the GAP program are the default parameters, which do not impose a penalty for end gaps. See, e.g., Schwartz et al., eds., (1979), *Atlas of Protein Sequence and Structure, National Biomedical Research Foundation,* pp. 357–358, and Gribskov et al., (1986) *Nucl. Acids. Res.* 14: 6745.

The term "similarity" is contrasted with the term "identity". Similarity is defined as above; "identity", however, means a nucleic acid or amino acid sequence having the same amino acid at the same relative position in a given family member of a gene family. Homology and similarity are generally viewed as broader terms than the term identity. Biochemically similar amino acids, for example leucine/isoleucine or glutamate/aspartate, can be present at the same position—these are not identical per se, but are biochemically "similar." As disclosed herein, these are referred to as conservative differences or conservative substitutions. This differs from a conservative mutation at the DNA level, which changes the nucleotide sequence without making a change in the encoded amino acid, e.g. TCC to TCA, both of which encode serine.

As used herein, DNA analog sequences are "substantially identical" to specific DNA sequences disclosed herein if: (a) the DNA analog sequence is derived from coding regions of the nucleic acid sequence shown in any one of odd numbered SEQ ID NOs:1–15 or (b) the DNA analog sequence is capable of hybridization with DNA sequences of (a) under stringent conditions and which encode a biologically active GRα or GRα LBD gene product; or (c) the DNA sequences are degenerate as a result of alternative genetic code to the DNA analog sequences defined in (a) and/or (b). Substantially identical analog proteins and nucleic acids will have between about 70% and 80%, preferably between about 81% to about 90% or even more preferably between about 91% and 99% sequence identity with the corresponding sequence of the native protein or nucleic acid. Sequences having lesser degrees of identity but comparable biological activity are considered to be equivalents.

As used herein, "stringent conditions" means conditions of high stringency, for example 6×SSC, 0.2% polyvinylpyrrolidone, 0.2% Ficoll, 0.2% bovine serum albumin, 0.1% sodium dodecyl sulfate, 100 μg/ml salmon sperm DNA and 15% formamide at 68° C. For the purposes of specifying additional conditions of high stringency, preferred conditions are salt concentration of about 200 mM and temperature of about 45° C. One example of such stringent conditions is hybridization at 4×SSC, at 65° C., followed by a washing in 0.1×SSC at 65° C. for one hour. Another exemplary stringent hybridization scheme uses 50% formamide, 4×SSC at 42° C.

In contrast, nucleic acids having sequence similarity are detected by hybridization under lower stringency conditions. Thus, sequence identity can be determined by hybridization under lower stringency conditions, for example, at 50° C. or higher and 0.1×SSC (9 mM NaCl/0.9 mM sodium citrate) and the sequences will remain bound when subjected to washing at 55° C. in 1×SSC.

As used herein, the term "complementary sequences" means nucleic acid sequences that are base-paired according to the standard Watson-Crick complementarity rules. The present invention also encompasses the use of nucleotide segments that are complementary to the sequences of the present invention.

Hybridization can also be used for assessing complementary sequences and/or isolating complementary nucleotide sequences. As discussed above, nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of about 30° C., typically in excess of about 37° C., and preferably in excess of about 45° C. Stringent salt conditions will ordinarily be less than about 1,000. mM, typically less than about 500 mM, and preferably less than about 200 mM. However, the combination of parameters is much more important than the measure of any single parameter. See, e.g., Wetmur & Davidson, (1968) *J. Mol. Biol.* 31: 349–70. Determining appropriate hybridization conditions to identify and/or isolate sequences containing high levels of homology is well known in the art. See, e.g., Sambrook et al., (1989) *Molecular Cloning: A Laboratory Manual,* Cold Spring Harbor, N.Y.

X.D.2. Functional Equivalents of an Engineered NR, SR or GR or NR, SR, GR LBD Mutant Nucleic Acid Sequence of the Present Invention As used herein, the term "functionally equivalent codon" is used to refer to codons that encode the same amino acid, such as the ACG and AGU codons for serine. For example, GRα or GRα LBD-encoding nucleic acid sequences comprising any one of odd numbered SEQ ID NOs:1–15, which have functionally equivalent codons are covered by the present invention. Thus, when referring to the sequence example presented in odd numbered SEQ ID NOs:1–15, applicants provide substitution of functionally equivalent codons into the sequence example of in odd numbered SEQ ID NOs:1–15. Thus, applicants are in possession of amino acid and nucleic acids sequences which include such substitutions but which are not set forth herein in their entirety for convenience.

It will also be understood by those of skill in the art that amino acid and nucleic acid sequences can include additional residues, such as additional N- or C-terminal amino acids or 5' or 3' nucleic acid sequences, and yet still be essentially as set forth in one of the sequences disclosed herein, so long as the sequence retains biological protein activity where polypeptide expression is concerned. The addition of terminal sequences particularly applies to nucleic acid sequences which can, for example, include various non-coding sequences flanking either of the 5' or 3' portions of the coding region or can include various internal sequences, i.e., introns, which are known to occur within genes.

X.D.3. Biological Equivalents

The present invention envisions and includes biological equivalents of a engineered NR, SR or GR or NR, SR or GR LBD mutant polypeptide of the present invention. The term "biological equivalent" refers to proteins having amino acid sequences which are substantially identical to the amino acid sequence of an engineered NR, SR or GR LBD mutant of the present invention and which are capable of exerting a biological effect in that they are capable of binding small molecules or cross-reacting with anti- NR, SR or GR or NR, SR or GR LBD mutant antibodies raised against an engineered mutant NR, SR or GR or NR, SR or GR LBD polypeptide of the present invention.

For example, certain amino acids can be substituted for other amino acids in a protein structure without appreciable loss of interactive capacity with, for example, structures in the nucleus of a cell. Since it is the interactive capacity and nature of a protein that defines that protein's biological functional activity, certain amino acid sequence substitutions can be made in a protein sequence (or the nucleic acid sequence encoding it) to obtain a protein with the same, enhanced, or antagonistic properties. Such properties can be achieved by interaction with the normal targets of the protein, but this need not be the case, and the biological activity of the invention is not limited to a particular mechanism of action. It is thus in accordance with the present invention that various changes can be made in the amino acid sequence of an engineered NR, SR or GR or NR, SR or GR LBD mutant polypeptide of the present invention or its underlying nucleic acid sequence without appreciable loss of biological utility or activity.

Biologically equivalent polypeptides, as used herein, are polypeptides in which certain, but not most or all, of the amino acids can be substituted. Thus, when referring to the sequence examples presented in any of even numbered SEQ ID NOs:2–16, applicants envision substitution of codons that encode biologically equivalent amino acids, as described herein, into a sequence example of even numbered SEQ ID NOs: 2–16, respectively. Thus, applicants are in possession of amino acid and nucleic acids sequences which include such substitutions but which are not set forth herein in their entirety for convenience.

Alternatively, functionally equivalent proteins or peptides can be created via the application of recombinant DNA technology, in which changes in the protein structure can be engineered, based on considerations of the properties of the amino acids being exchanged, e.g. substitution of Ile for Leu. Changes designed by man can be introduced through the application of site-directed mutagenesis techniques, e.g., to introduce improvements to the antigenicity of the protein or to test an engineered mutant polypeptide of the present invention in order to modulate lipid-binding or other activity, at the molecular level.

Amino acid substitutions, such as those which might be employed in modifying an engineered mutant polypeptide of the present invention are generally, but not necessarily, based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all of similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. Those of skill in the art will appreciate other biologically functionally equivalent changes. It is implicit in the above discussion, however, that one of skill in the art can appreciate that a radical, rather than a conservative substitution is warranted in a given situation. Non-conservative substitutions in engineered mutant LBD polypeptides of the present invention are also an aspect of the present invention.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, (1982), *J. Mol. Biol.* 157: 105–132, incorporated herein by reference). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

Thus, it will also be understood that this invention is not limited to the particular amino acid and nucleic acid sequences of any of SEQ ID NOs:1–16. Recombinant vectors and isolated DNA segments can therefore variously include an engineered NR, SR or GR or NR, SR or GR LBD mutant polypeptide-encoding region itself, include coding regions bearing selected alterations or modifications in the basic coding region, or include larger polypeptides which nevertheless comprise an NR, SR or GR or NR, SR or GR LBD mutant polypeptide-encoding regions or can encode biologically functional equivalent proteins or polypeptides which have variant amino acid sequences. Biological activity of an engineered NR, SR or GR or NR, SR or GR LBD mutant polypeptide can be determined, for example, by transcription assays known to those of skill in the art.

The nucleic acid segments of the present invention, regardless of the length of the coding sequence itself, can be combined with other DNA sequences, such as promoters, enhancers, polyadenylation signals, additional restriction enzyme sites, multiple cloning sites, other coding segments, and the like, such that their overall length can vary considerably. It is therefore contemplated that a nucleic acid fragment of almost any length can be employed, with the total length preferably being limited by the ease of preparation and use in the intended recombinant DNA protocol. For example, nucleic acid fragments can be prepared which include a short stretch complementary to a nucleic acid sequence set forth in any of odd numbered SEQ ID NOs: 1–15, such as about 10 nucleotides, and which are up to 10,000 or 5,000 base pairs in length. DNA segments with total lengths of about 4,000, 3,000, 2,000, 1,000, 500, 200, 100, and about 50 base pairs in length are also useful.

The DNA segments of the present invention encompass biologically functional equivalents of engineered NR, SR or GR, or NR, SR or GR LBD mutant polypeptides. Such sequences can rise as a consequence of codon redundancy and functional equivalency that are known to occur naturally within nucleic acid sequences and the proteins thus encoded. Alternatively, functionally equivalent proteins or polypeptides can be created via the application of recombinant DNA technology, in which changes in the protein structure can be engineered, based on considerations of the properties of the amino acids being exchanged. Changes can be introduced through the application of site-directed mutagenesis techniques, e.g., to introduce improvements to the antigenicity of the protein or to test variants of an engineered mutant of the present invention in order to examine the degree of binding activity, or other activity at the molecular level. Various site-directed mutagenesis techniques are known to those of skill in the art and can be employed in the present invention.

The invention further encompasses fusion proteins and peptides wherein an engineered mutant coding region of the present invention is aligned within the same expression unit with other proteins or peptides having desired functions, such as for purification or immunodetection purposes.

Recombinant vectors form important further aspects of the present invention. Particularly useful vectors are those in which the coding portion of the DNA segment is positioned under the control of a promoter. The promoter can be that naturally associated with an NR, SR or GR gene, as can be obtained by isolating the 5' non-coding sequences located upstream of the coding segment or exon, for example, using recombinant cloning and/or PCR technology and/or other methods known in the art, in conjunction with the compositions disclosed herein.

In other embodiments, certain advantages will be gained by positioning the coding DNA segment under the control of a recombinant, or heterologous, promoter. As used herein, a recombinant or heterologous promoter is a promoter that is not normally associated with an NR, SR or GR gene in its natural environment. Such promoters can include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology (See, e.g., Sambrook et al., (1989) *Molecular Cloning: A Laboratory Manual*, Cold Spring Harbor Laboratory, New York, specifically incorporated herein by reference). The promoters employed can be constitutive or inducible and can be used under the appropriate conditions to direct high level expression of the introduced DNA segment, such as is advantageous in the large-scale production of recombinant proteins or peptides. One preferred promoter system contemplated for use in high-level expression is a T7 promoter-based system.

X.E. Antibodies to an Engineered NR, SR or GR or NR, SR, GR LBD Mutant Polypeptide of the Present Invention The present invention also provides an antibody that specifically binds a engineered NR, SR or GR or NR, SR, GR LBD mutant polypeptide and methods to generate same. The term "antibody" indicates an immunoglobulin protein, or functional portion thereof, including a polyclonal antibody, a monoclonal antibody, a chimeric antibody, a single chain antibody, Fab fragments, and a Fab expression library. "Functional portion" refers to the part of the protein that binds a molecule of interest. In a preferred embodiment, an antibody of the invention is a monoclonal antibody. Techniques for preparing and characterizing antibodies are well known in the art (See, e.g., Harlow & Lane (1988) *Antibodies: A Laboratory Manual*, Cold Spring Harbor Laboratory Press, Cold Spring Harbor, N.Y.). A monoclonal antibody of the present invention can be readily prepared through use of well-known techniques such as the hybridoma techniques exemplified in U.S. Pat. No 4,196,265 and the phage-displayed techniques disclosed in U.S. Pat. No. 5,260,203.

The phrase "specifically (or selectively) binds to an antibody", or "specifically (or selectively) immunoreactive with", when referring to a protein or peptide, refers to a binding reaction which is determinative of the presence of the protein in a heterogeneous population of proteins and other biological materials. Thus, under designated immunoassay conditions, the specified antibodies bind to a particular protein and do not show significant binding to other proteins present in the sample. Specific binding to an antibody under such conditions can require an antibody that is selected for its specificity for a particular protein. For example, antibodies raised to a protein with an amino acid sequence encoded by any of the nucleic acid sequences of the invention can be selected to obtain antibodies specifically immunoreactive with that protein and not with unrelated proteins.

The use of a molecular cloning approach to generate antibodies, particularly monoclonal antibodies, and more particularly single chain monoclonal antibodies, are also provided. The production of single chain antibodies has been described in the art. See, e.g., U.S. Pat. No. 5,260,203. For this approach, combinatorial immunoglobulin phagemid libraries are prepared from RNA isolated from the spleen of the immunized animal, and phagemids expressing appropriate antibodies are selected by panning on endothelial tissue. The advantages of this approach over conventional hybridoma techniques are that approximately $10^4$ times as many antibodies can be produced and screened in a single round, and that new specificities are generated by heavy (H) and light (L) chain combinations in a single chain, which further increases the chance of finding appropriate antibodies. Thus, an antibody of the present invention, or a "derivative" of an antibody of the present invention, pertains to a single polypeptide chain binding molecule which has binding specificity and affinity substantially similar to the binding specificity and affinity of the light and heavy chain aggregate variable region of an antibody described herein.

The term "immunochemical reaction", as used herein, refers to any of a variety of immunoassay formats used to detect antibodies specifically bound to a particular protein, including but not limited to competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (e.g., using colloidal gold, enzyme or radioisotope labels), western blots, precipitation reactions, agglutination assays (e.g., gel agglutination assays, hemagglutination assays), complement fixation assays, immunofluorescence assays, protein A assays, and immunoelectrophoresis assays, etc. See Harlow & Lane (1988) for a description of immunoassay formats and conditions.

X.F. Method for Detecting an Engineered NR, SR or GR or NR, SR, GR LBD Mutant Polypeptide or an Nucleic Acid Molecule Encoding the Same In another aspect of the invention, a method is provided for detecting a level of an engineered NR, SR or GR or NR, SR, GR LBD mutant polypeptide using an antibody that specifically recognizes an engineered NR, SR or GR or NR, SR, GR LBD mutant polypeptide, or portion thereof. In a preferred embodiment, biological samples from an experimental subject and a control subject are obtained, and an engineered NR, SR or GR or NR, SR, GR LBD mutant polypeptide is detected in each sample by immunochemical reaction with the antibody. More preferably, the antibody recognizes amino acids of any one of the even-numbered SEQ ID NOs:4, 6, 8, 12, 14, and 16, and is prepared according to a method of the present invention for producing such an antibody.

In one embodiment, an antibody is used to screen a biological sample for the presence of an engineered NR, SR or GR or NR, SR, GR LBD mutant polypeptide. A biological sample to be screened can be a biological fluid such as extracellular or intracellular fluid, or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide. In accordance with a screening assay method, a biological sample is exposed to an antibody immunoreactive with an engineered NR, SR or GR or NR, SR, GR LBD mutant polypeptide whose presence is being assayed, and the formation of antibody-polypeptide complexes is detected. Techniques for detecting such antibody-antigen conjugates or complexes are well known in the art and include but are not limited to centrifugation, affinity chromatography and the like, and binding of a labeled secondary antibody to the antibody-candidate receptor complex.

In another aspect of the invention, a method is provided for detecting a nucleic acid molecule that encodes an engineered NR, SR or GR or NR, SR, GR LBD mutant polypeptide. According to the method, a biological sample having nucleic acid material is procured and hybridized under stringent hybridization conditions to an engineered NR, SR or GR or NR, SR, GR LBD mutant polypeptide-encoding nucleic acid molecule of the present invention. Such hybridization enables a nucleic acid molecule of the biological sample and an engineered NR, SR or GR or NR, SR, GR LBD mutant polypeptide encoding-nucleic acid molecule to form a detectable duplex structure. Preferably, the an engineered NR, SR or GR or NR, SR, GR LBD mutant polypeptide encoding-nucleic acid molecule includes some or all nucleotides of any one of the odd-numbered SEQ ID NOs:3, 5, 7, 11, 13, and 15. Also preferably, the biological sample comprises human nucleic acid material.

XI. The Role of the Three-Dimensional Structure of the GRα LDB in Solving Additional NR, SR or GR Crystals Because polypeptides can crystallize in more than one crystal form, the structural coordinates of a GRα LBD, or portions thereof, as provided by the present invention, are particularly useful in solving the structure of other crystal forms of GRα and the crystalline forms of other NRs, SRs and GRs. The coordinates provided in the present invention can also be used to solve the structure of NR, SR or GR and NR, SR or GR LBD mutants (such as those described in Sections IX and X above), NR, SR or GR LDB co-complexes, or of the crystalline form of any other protein with significant amino acid sequence homology to any functional domain of NR, SR or GR.

XI.A. Determining the Three-Dimensional Structure of a Polypeptide Using the Three-Dimensional Structure of the GRα LBD as a Template in Molecular Replacement One method that can be employed for the purpose of solving additional GR crystal structures is molecular replacement. See generally, Rossmann, ed, (1972) *The Molecular Replacement Method*, Gordon & Breach, New York. In the molecular replacement method, the unknown crystal structure, whether it is another crystal form of a GRα or a GRα LBD, (i.e. a GRα or a GRα LBD mutant), or an NR, SR or GR or an NR, SR or GR LBD polypeptide complexed with another compound (a "co-complex"), or the crystal of some other protein with significant amino acid sequence homology to any functional region of the GRα LBD, can be determined using the GRα LBD structure coordinates provided in Table 4. This method provides an accurate structural form for the unknown crystal more quickly and efficiently than attempting to determine such information ab initio.

In addition, in accordance with this invention, NR, SR or GR and NR, SR or GR LBD mutants can be crystallized in complex with known modulators. The crystal structures of a series of such complexes can then be solved by molecular replacement and compared with that of the wild-type NR, SR or GR or the wild-type NR, SR or GR LBD. Potential sites for modification within the various binding sites of the enzyme can thus be identified. This information provides an additional tool for determining the most efficient binding interactions, for example, increased hydrophobic interactions, between the GRα LBD and a chemical entity or compound.

All of the complexes referred to in the present disclosure can be studied using X-ray diffraction techniques (See, e.g., Blundell & Johnson (1985) *Method. Enzymol.,* 114A & 115B, (Wyckoff et al., eds.), Academic Press; McRee, (1993) *Practical Protein Crystallography*, Academic Press, New York) and can be refined using computer software, such as the X-PLOR™ program (Brünger, (1992) *X-PLOR, Version* 3.1. *A System for X-ray Crystallography and NMR*, Yale University Press, New Haven, Conn.; X-PLOR is available from Molecular Simulations, Inc., San Diego, Calif.) and the XTAL-VIEW program (McRee, (1992) *J. Mol. Graphics* 10: 44–46; McRee, (1993) *Practical Protein Crystallography*, Academic Press, San Diego, Calif.). This information can thus be used to optimize known classes of GR and GR LBD modulators, and more importantly, to design and synthesize novel classes of GR and GR LBD modulators.

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Example 1

Construction of the Modified pET24 Expression Vector

The expression vector pGEX-2T (Amersham Pharmacia Biotech, Piscataway, N.J.) was used as a template in a polymerase chain reaction to engineer a polyhistidine tag in frame to the sequence encoding glutathione S-transferase (GST) and a thrombin protease site. The forward primer contained a Nde I site (5' CGG CGG CGC CATATG AAA AAA GGT $(CAT)_6$ GGT TCC CCT ATA CTA GGT TAT TGG A 3') (SEQ ID NO:19) and the reverse primer (5' CGG CGG CGC GGATCC ACG CGG MC CAG ATC CGA 3') (SEQ ID NO:20) contained a BamH I site which allowed for direct cloning of the amplfied product into pET24a (Novagen, Inc., Madison, Wis.) following restiction enzyme digestion. The resulting sequence of the modified GST (SEQ ID NO:21) (last six residues are thrombin protease site) is below:

```
MKKGHHHHHH HGSPILGYWK IKGLVQPTRL LLEYLEEKYE EHLYERDEGD      50

KWRNKKFELG LEFPNLPYYI DGDVKLTQSM AIIRYIADKH NMLGGCPKER     100

AEISMLEGAV LDIRYGVSRI AYSKDFETLK VDFLSKLPEM LKMFEDRLCH     150

KTYLNGDHVT HPDFMLYDAL DVVLYMDPMC LDAFPKLVCF KKRIEAIPQI     200

DKYLKSSKYI AWPLQGWQAT FGGGDHPPKS DLVPRGS                  237
```

Example 2

Mutagenesis (F602S AND F602D) of Human GR Ligand Binding Domain (LBD)

Two complimentary oligonucleotides for each desired mutation were constructed. The following sequences represent the oligonucleotides for the Phenylalanine 602 Serine mutation:

```
                                    (SEQ ID NO:22)
Forward Primer (F602S):
5' TAC TCC TGG ATG TCC CTT ATG GCA TTT GCT CT 3'

                                    (SEQ ID NO:23)
Reverse Primer (F602S):
5' AG AGC AAA TGC CAT AAG GGA CAT CCA GGA GTA 3'
```

Another separate mutation was also constructed. The sequences below represent the oligonucleotides for the Phenylalanine 602 Aspartic Acid mutation:

```
                                    (SEQ ID NO:24)
Forward Primer (F602D):
5' TAC TCC TGG ATG GAC CTT ATG GCA TTT GCT CT 3'

                                    (SEQ ID NO:25)
Reverse Primer (F602D):
5' AG AGC AAA TGC CAT AAG GTC CAT CCA GGA GTA 3'
```

The underlined letters depict the base changes from the wild type human GR sequence. The GR LBD (amino acids 521–777) (SEQ ID NOs:9–10) previously cloned into the pRSET A vector (Invitrogen of Carlsbad, Calif.) was used as the backbone to create the mutants. The procedure used to make the mutation is outlined in the QuickChange Site-Directed Mutagenesis Kit sold by Stratagene, La Jolla, Calif. (Catalog #200518). After the constructs were sequence verified, the mutants of GR-LBD were subcloned inframe with the glutathione S-transferase in the modified pET24 expression vector. A thrombin protease site at the C-terminus of the glutathione S-transferase allows for cleavage of the resultant fusion protein following expression.

The resulting final amino acid sequences for the mutant GR LBDs are below. The underlined, bolded amino acids depict the changes from the wild type human GR sequence.

```
GR-LBD(521-777) F602S
VPATLPQLTP TLVSLLEVIE PEVLYAGYDS SVPDSTWRIM TTLNMLGGRQ (SEQ ID NO:12)

VIAAVKWAKA IPGFRNLHLD DQMTLLQYSW MSLMAFALGW RSYRQSSANL

LCFAPDLIIN EQRMTLPCMY DQCKHMLYVS SELHRLQVSY EEYLCMKTLL

LLSSVPKDGL KSQELFDEIR MTYIKELGKA IVKREGNSSQ NWQRFYQLTK

LLDSMHEVVE NLLNYCFQTF LDKTMSIEFP EMLAEIITNQ IPKYSNGNIK

KLLFHQK

GR-LBD(521-777) F602D
VPATLPQLTP TLVSLLEVIE PEVLYAGYDS SVPDSTWRIM TTLNMLGGRQ (SEQ ID NO:14)

VIAAVKWAKA IPGFRNLHLD DQMTLLQYSW MDLMAFALGW RSYRQSSANL

LCFAPDLIIN EQRMTLPCMY DQCKHMLYVS SELHRLQVSY EEYLCMKTLL

LLSSVPKDGL KSQELFDEIR MTYIKELGKA IVKREGNSSQ NWQRFYQLTK

LLDSMHEVVE NLLNYCFQTF LDKTMSIEFP EMLAEIITNQ IPKYSNGNIK

KLLFHQK
```

Example 3

Expression of the Fusion Protein

BL21(DE3) cells (Novagen, Inc., Madison, Wis.) were transformed following established protocols. Following overnight incubation at 37° C. a single colony was used to inoculate a 10 ml LB culture containing 50 µg/ml kanamycin (Sigma Chemical Company, St. Louis, Mo.). The culture was grown for ~12 hrs at 37° C. and then a 500 µl aliquot was used to inoculate flasks containing 1 liter Circle Grow media (Biol01, Inc., now Qbiogene of Carlsbad, Calif.) and the required antibiotic. The cells were then grown at 22° C.

to an OD600 between 1 and 2 and then cooled to 16° C. Following a 30 min equilibration at that temperature, dexamethasone (Spectrum, Gardena, Calif.) (10 μM final concentration) was added. Induction of expression was achieved by adding IPTG (BACHEM AG, Switzerland) (final concentration 1 mM) to the cultures. Expression at 16° C. was continued for ~24 hrs. Cells were then harvested and frozen at −80° C.

Referring now to FIG. 1A, *E. coli* expression of mutant 6xHisGST-GR(521–777) F602S is shown. Shown are the pellet (P—insoluble) and eluent (E—soluble Ni++ binding) fractions of protein expressed in the absence of ligand (NL—lanes 2 and 3) or in the presence (10 micromolar) of dexamethasone (DEX), lanes 4 and 5, or RU486, lanes 6 and 7. The positions of molecular mass (kDa) markers M (lane 1) (94, 67, 43, 30, 20 and 14 kDa, respectively) and of the expressed protein are indicated to the left and right sides of the panel, respectively.

Figure 1B:
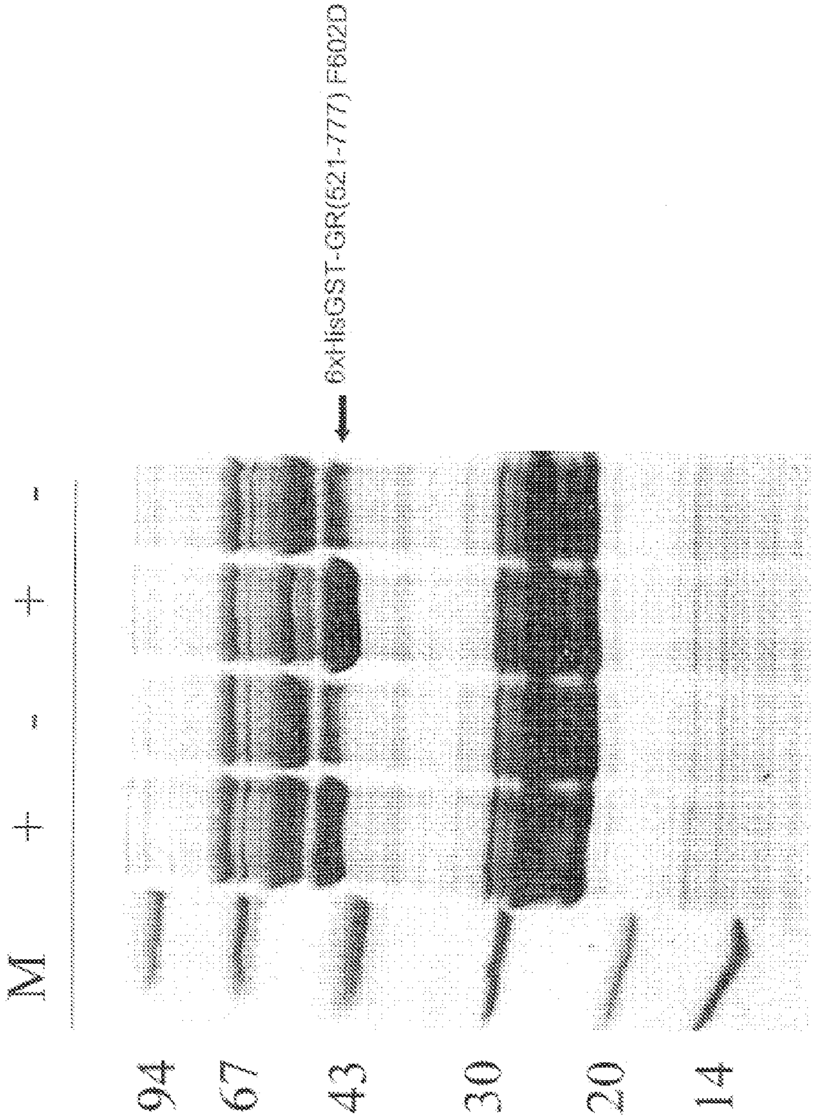
FIG. 1B depicts *E coli* expression of mutant 6xHisGST-GR(521–777) F602D (SEQ ID NO:14) via SDS-PAGE. Staining was accomplished using the commercially available PROBLUE product.
Figure 1C:
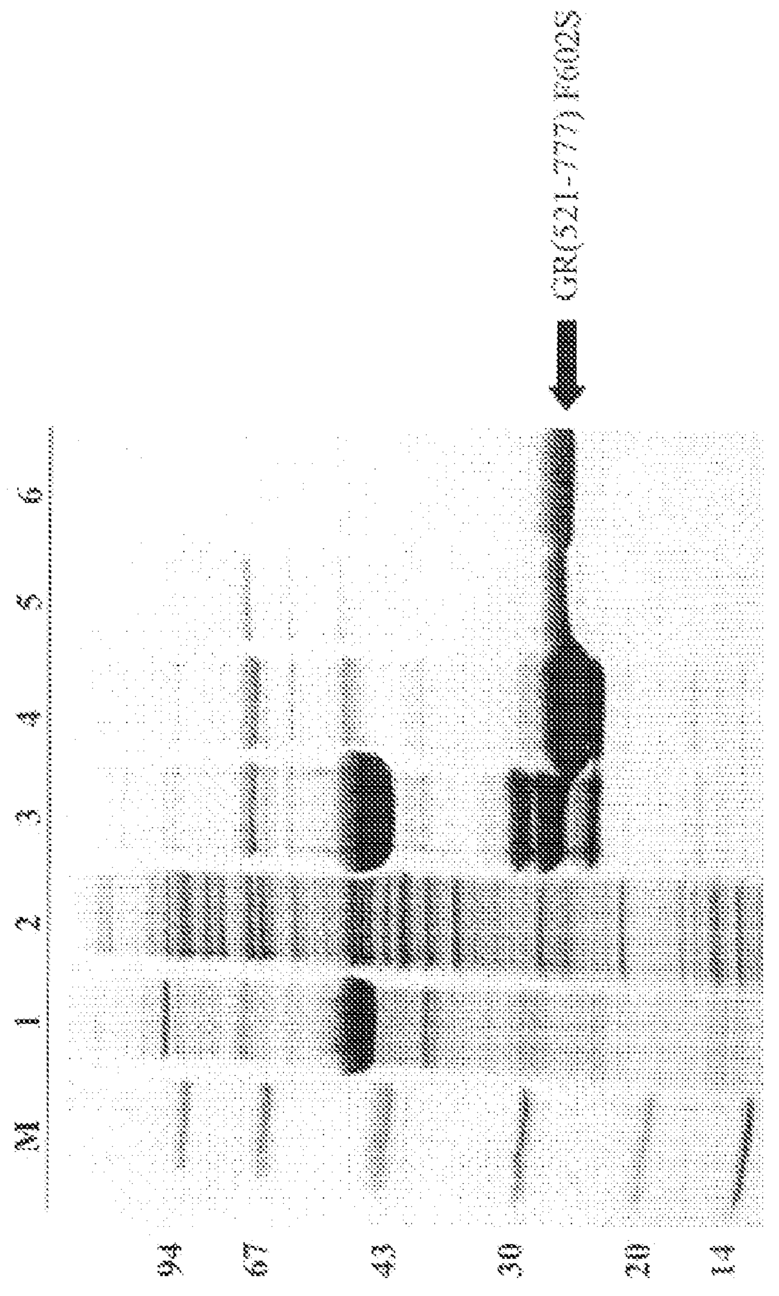
FIG. 1C depicts purification of *E. coli* expressed GR(521–777)F602S (SEQ ID NO:12) via SDS-PAGE. Staining was accomplished using the commercially available PROBLUE product.

Referring now to FIG. 1B, *E coli* expression of mutant 6xHisGST-GR(521–777) F602D is shown. Shown are eluent fractions from Ni++ chelated resin of two separate samples. Protein was expressed in either the presence (+, lanes 2 and 4, 10 micromolar) or absence (−, lanes 3 and 5) of dexamethasone. The positions of molecular mass (kDa) markers M (lane 1) (94, 67, 43, 30, 20 and 14 kDa, respectively) and of the expressed protein are indicated to the left and right sides of the panel, respectively.

Example 4

Purification Of GR-LBD (F602S)

~200 g cells were resuspended in 700 mL lysis buffer (50 mM Tris pH=8.0, 150 mM NaCl, 2M Urea, 10% glycerol and 100 μM dexamethasone) and lysed by passing 3 times through an APV Lab 2000 homogenizer. The lysate was subjected to centrifugation (45 minutes, 20,000 g, 4° C.), followed by a second 20 min spin at 20,000 g, 4°. The cleared supernatant was filtered through coarse pre-filters and 50 mM Tris, pH=8.0, containing 150 mM NaCl, 10% glycerol and 1M imidazole was added to obtain a final imidazole concentration of 50 mM. This lysate was loaded onto a XK-26 column (Pharmacia, Peapack, N.J.) packed with SEPHAROSE® [$Ni^{++}$ charged] Chelation resin (Pharmacia, Peapack, N.J.) and pre-equilibrated with lysis buffer supplemented with 50 mM imidazole. Following loading, the column was washed to baseline absorbance with equilibration buffer and a linear urea gradient (2M to 0). For elution the column was developed with a linear gradient from 50 to 500 mM Imidazole in 50 mM Tris pH=8.0, 150 mM NaCl, 10% glycerol and 30 μM dexamethasone. Column fractions of interest were pooled and 500 units of thrombin protease (Amersham Pharmacia Biotech, Piscataway, N.J.) were added for the cleavage of the fusion protein.

This solution was then dialyzed against 1 liter of 50 mM Tris pH=8.0, 150 mM NaCl, 10% glycerol and 20 μM dexamethasone for ~10 hrs at 4° C. The digested protein sample was filtered and then reloaded onto the same re-equilibrated column. The cleaved GR-LBD was collected in the flow through fraction. The diluted protein sample was concentrated with Centri-prep™ 10K centrifugal filtration devices (Amicon/Millpore, Bedford, Mass.) to a volume of 30 mls and then diluted 5 fold with 50 mM Tris pH=8.0, 10% glycerol, 10 mM DTT, 0.5 mM EDTA and 30 μM dexamethasone. The sample was then loaded onto a pre-equilibrated XK-26 column (Pharmacia, Peapack, N.J.) packed with Poros HQ resin (PerSeptive Biosystems, Framingham, Mass.). The cleaved GR LBD was collected in the flowthrough. The NaCl concentration was adjusted to 500 mM and the dexamethasone concentration was adjusted to 50 μM before the purified protein was concentrated to ~1 mg/ml using the Centri-prep™ 10K centrifugal filtration devices.

FIG. 1A depicts purification of *E. coli* expressed GR(521–777) F602S by SDS-PAGE. Lane 1 contains the insoluble pellet fraction. Lane 2 contains the soluble supernatant fraction. Lane 3 contains pooled eluent from intial $Ni^{++}$ column. Lane 4 contains the sample after thrombin digestion. Lane 5 contains the flow through fraction after reload of the $Ni^{++}$ column. Lane 6 contains the concentrated protein after anion exchange. The positions of molecular mass (kDa) markers (in Lane M, 94, 67, 43, 30, 20 and 14 kDa, respectively) and of the expressed protein are indicated to the left and right sides of the panel, respectively. Purification provides for the removal of any remaining associated bacterial HSPs.

The final resultant sequence (SEQ ID NO:32) of the purified protein is below. The first two residues (underlined and bolded) are vector derived and represent the remaining residues of the thrombin cleavage site following digestion.

```
GSVPATLPQL TPTLVSLLEV IEPEVLYAGY DSSVPDSTWR
IMTTLNMLGG RQVIAAVKWA KAIPGFRNLH LDDQMTLLQY
SWMSLMAFAL GWRSYRQSSA NLLCFAPDLI INEQRMTLPC
MYDQCKHMLY VSSELHRLQV SYEEYLCMKT LLLLSSVPKD
GLKSQELFDE IRMTYIKELG KAIVKREGNS SQNWQRFYQL
TKLLDSMHEV VENLLNYCFQ TFLDKTMSIE FPEMLAEIIT
NQIPKYSNGN IKKLLFHQK
```

Example 5

Ligand and Coactivator Binding of GR

All experiments were conducted with buffer containing 10 mM HEPES pH 7.4, 0.15 M NaCl, 3 mM EDTA, 0.005% polysorbate-20 and 5 mM DTT. For activity determinations, 10 nM of fluorescein dexamethasone (Molecular Probes, Eugene, Ore.) was titrated with increasing concentrations of the glucocorticoid receptor in black 96-well plates (CoStar, Cambridge, Mass.). The fluorescence polarization values for each concentration of receptor were determined using a BMG PolarStar Galaxy fluorescence plate reader (BMG Labtechnologies GmbH, Offenburg, Germany) with 485 nm excitation and 520 nm emission filters. Binding isotherms were constructed and apparent EC50 values were determined by non-linear least squares fit of the data to an equation for a simple 1:1 interaction. Note that these EC50 values are not corrected for the unlabeled dexamethasone present in the GR receptor preparations. For stability studies, the fluorescent polarization of 10 nM fluorescein dexamethasone with 1 μM GST-GR LBD 521–777 (F602S) is read at specific time intervals in the presence or absence of 25 uM of a peptide derived from the coactivator TIF2.

(SEQ ID NO:17)
(TIF2 732–756: QEPVSPKKKENALLRYLLDKDDTKD).

Figure 2A:
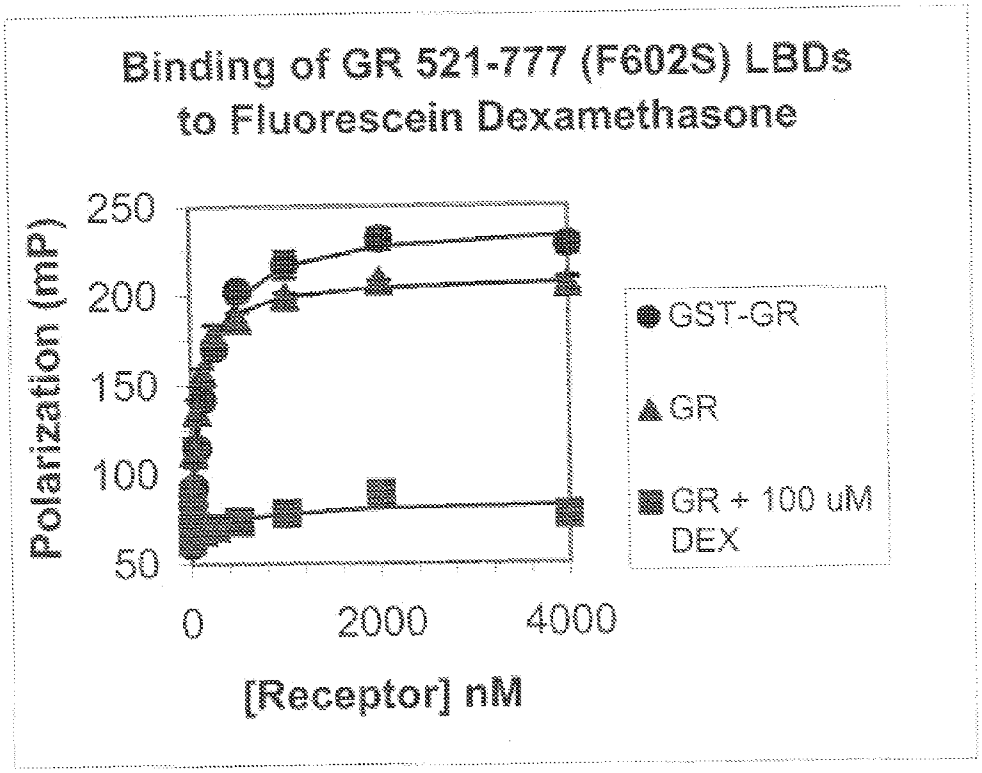
FIGS. 2A–2C depict characterization of GR binding to dexamethasone and the TIF2 LXXLL (SEQ ID NO:18) motif.
Figure 2B:
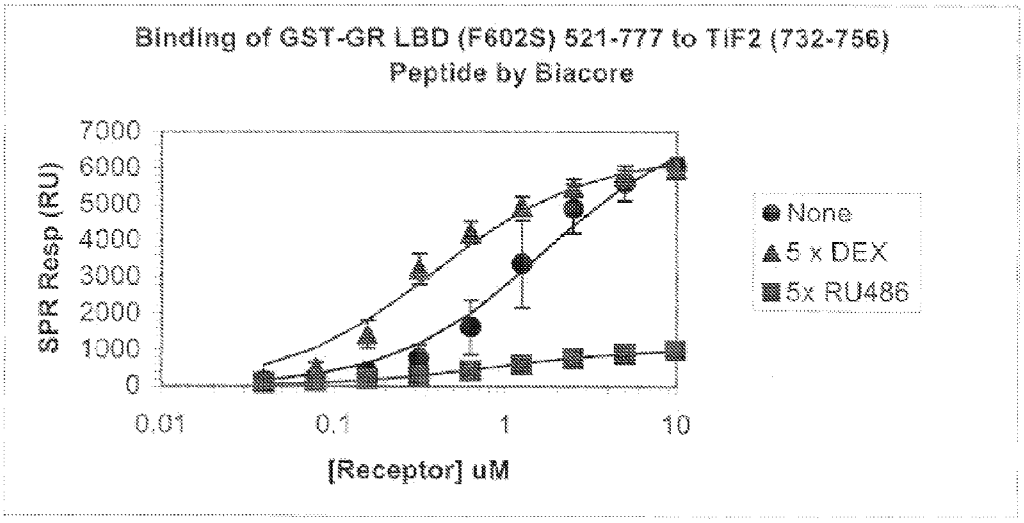
Figure 2C:
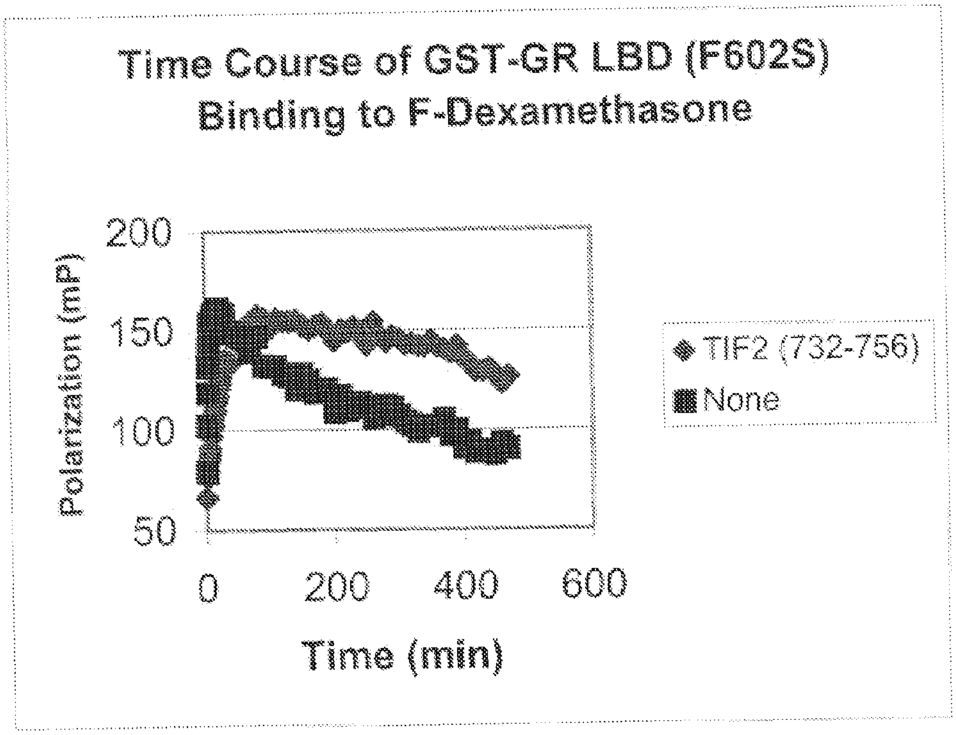

Data from these experiments are presented graphically in FIGS. 2A–2C. These studies demonstrate that the GST-GR fusion protein and the cleaved GR LBD alone bind dexamethasone in a saturable and competable manner (FIG. 2A). It was also found that the GST-GR fusion protein binds a peptide from the coactivator TIF2 with a submicromolar affinity. Binding of the GST-GR fusion protein is enhanced by the agonist dexamethasone (DEX) and inhibited by the antagonist RU486 (FIG. 2B). Finally, it was also found that the addition of the TIF2 peptide stabilizes the dexamethasone binding activity of the GST-GR fusion protein.

FIG. 2B was generated using Biacore techniques. Biacore relies on changes in the refractive index at the surface layer upon binding of a ligand to a protein immobilized on the layer. In this system, a collection of small ligands is injected sequentially in a 2–5 microliter cell, wherein the protein is immobilized within the cell. Binding is detected by surface plasmon resonance (SPR) by recording laser light refracting from the surface. In general, the refractive index change for a given change of mass concentration at the surface layer is practically the same for all proteins and peptides, allowing a single method to be applicable for any protein (Liedberg et al. (1983) *Sensors Actuators* 4:299–304; Malmquist (1993) *Nature* 361:186–187). The purified protein is then used in the assay without further preparation. A synthetic peptide with an amino-terminal biotin is coupled to a sensor chip immobilized with streptavidin. The chip thus prepared is then exposed to the potential ligand via the delivery system incorporated in the instruments sold by Biacore (Uppsala, Sweden) to pipet the ligands in a sequential manner (autosampler). The SPR signal on the chip is recorded and changes in the refractive index indicate an interaction between the immobilized target and the ligand. Analysis of the signal kinetics of on rate and off rate allows the discrimination between non-specific and specific interaction.

Example 6

Preparation of the GR/TIF2/Dex Complex

The GR/TIF2/Dex complex was prepared by adding a 2-fold excess of a TIF2 peptide containing sequence of QEPVSPKKKENALLRYLLDKDDTKD (SEQ ID NO:17). The above complex was diluted 10 folds with a buffer containing 500 mM ammonium acetate ($NH_4OAC$), 50 mM Tris, pH 8.0, 10% glycerol, 10 mM dithiothreitol (DTT), 0.5 mM EDTA, and 0.05% beta-N-octoglucoside (b-OG), and was slowly concentrated to 6.3 mg/ml, then aliquoted and stored at −80° C.

Example 7

Crystallization and Data Collection

The GR/TIF2/DEX crystals were grown at room temperature in hanging drops containing 3.0 ul of the above protein-ligand solutions, and 0.5 ul of well buffer (50 mM HEPES, pH 7.5–8.5 (preferred pH range is 8.0 to 8.5), and 1.7–2.3M ammonium formate). Crystals were also obtained with mixing of the above protein solution and the well buffer at various volume ratios. Crystals appeared overnight and continously grew to a size up to 300 micron within a week. Before data collection, crystals were transiently mixed with the well buffer that contained an additional 25% glycerol, and were then flash frozen in liquid nitrogen.

The GR/TIF2/DEX crystals formed in the $P6_1$ space group, with a=b=126.014 Å, c=86.312 Å, α=β=90°, and γ=120°. Each asymmetry unit contains two molecules of the GR LBD with 56% of solvent content. Data were collected with a Rigaku Raxis IV detector in house. The observed reflections were reduced, merged and scaled with DENZO and SCALEPACK in the HKL2000 package (Z. Otwinowski and W. Minor (1997)).

Example 8

Structure Determination and Refinement

Table 5 is a table of the atomic structure coordinates used as the initial model to solve the structure of the GR/TIF2/dexamethasone complex by molecular replacement. The GR model is a homology model built on the published structure of the progesterone receptor LBD and the SRC1 coactivator peptide from the PPARα/Compound 1/SRC1 structure.

Compound 1 is an agonist of hPPARα, and has the IUPAC name 2-methyl-2-[4-{[(4-methyl-2-[4-trifluoromethylphenyl] thiazol-5-yl-carbonyl) amino] methyl} phenoxy] propionic acid.

Compound 1

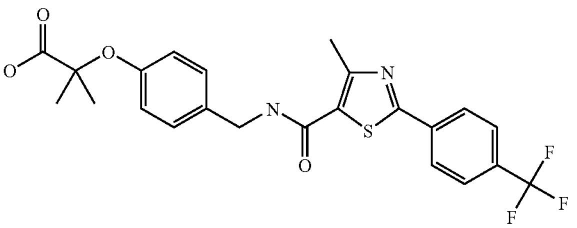

The initial model for the molecular replacement calculation comprised coordinates for residues 527–776 of wild-type GR together with coordinates for residues 685–697 of SRC-1, a coactivator very similar to TIF2. The model for GR was built from the crystal struture of PR bound to progesterone (Shawn P. Williams and Paul B. Sigler, *Nature* 393, 392–396 (1998)) using the MVP program (Lambert, 1997). The coordinates for SRC-1 were obtained from a crystal structure of PPARα bound to SRC-1. The SRC-1 model was positioned in the coactivator binding site of GR by rotating the GR model and PPARα/SRC-1 complex into a common orientation that superimposed their backbone atoms.

It is noted that the amino acid sequence for SRC-1 differs substantially from that of TIF2, although both coactivator sequences have the LXXLL motif. Model building, including conversion of side-chains from the SRC-1 and wild-type GR sequences to the actual TIF2 and GR F602S sequences, respectively, was carried out with QUANTA™.

This model was used in molecular replacement search with the CCP4 AmoRe™ program (Collaborative Computational Project Number 4, 1994, "The CCP4 Suite: Programs for Protein Crystallography", *Acta Cryst.* D50, 760–763; J. Navaza, *Acta Cryst.* A50, 157–163 (1994)) to determine the initial structure solutions. Two solutions were obtained from the molecular replacement search with a correlation coefficiency of 43% and an R-factor of 45.3%, consistent with two complexes within each asymmetry unit. The calculated phase from the molecular replacement solutions was improved with solvent flattening, histogram matching and the two-fold noncrystallographic averaging as implement in the CCP4 dm program, and produced a clear map for the GR LBD, the TIF2 peptide and the dexamethasone. As noted above, model building proceeded with QUANTA™, and refinement progressed with CNX (Accelrys, Princeton, N.J.) and multiple cycle of manual rebuilding. The statistics of the structure are summarized in Table 3 and coordinates are presented in FIG. 4.

Surface areas calculated with the Connolly MS program (Michael L. Connolly, "Solvent-Accessible Surfaces of Proteins and Nucleic Acids," *Science* 221, 709–713 (1983)) and the MVP program (Lambert, 1997). The pocket volume and binding site accessible waters were calculated with MVP.

Example 9

Random Mutant Library of GR LBD and Selection Using the Lacl Fusion System

The expression vector pJS142 Å (Affymax Inc., Palo Alto, Calif.) containing the Lacl protein was used to clone the wild type GR LBD in frame with the Lacl gene. Using standard error-incorporating PCR techniques, a random mutant library was created within the context of the GR LBD. An advantage of the Lacl expression system is that the protein expressed has the ability to bind the plasmid DNA from which it was derived. The mutant fusion proteins produced by the random library were expressed in *E. Coli* at 37° C. Lysis of the cell cultures was achieved using lysozyme. The cell lysates were then added to a microtiter plate containing the immobilized coactivator peptide biotinylated-TIF2 NR BoxIII. The plasmid DNA was eluted from the DNA-protein complex bound to the plate using 1 mM IPTG (Life Technologies). The eluted DNA was then re-transformed and individual clones were isolated for sequence analysis. Mutant fusion proteins with increased solubility and activity (ability to bind coactivator) should be selected for after rounds of panning and increased stringency washes. Once the sequence of the mutant Lacl-GR LBD was identified, the same mutation was also made in the pET24 expression vector (see Example 1). The expression and partial purification of the mutant Lacl-derived GST-GR LBD fusion proteins were performed in the same manner as described in Examples 3 and 4.

Figure 1D:
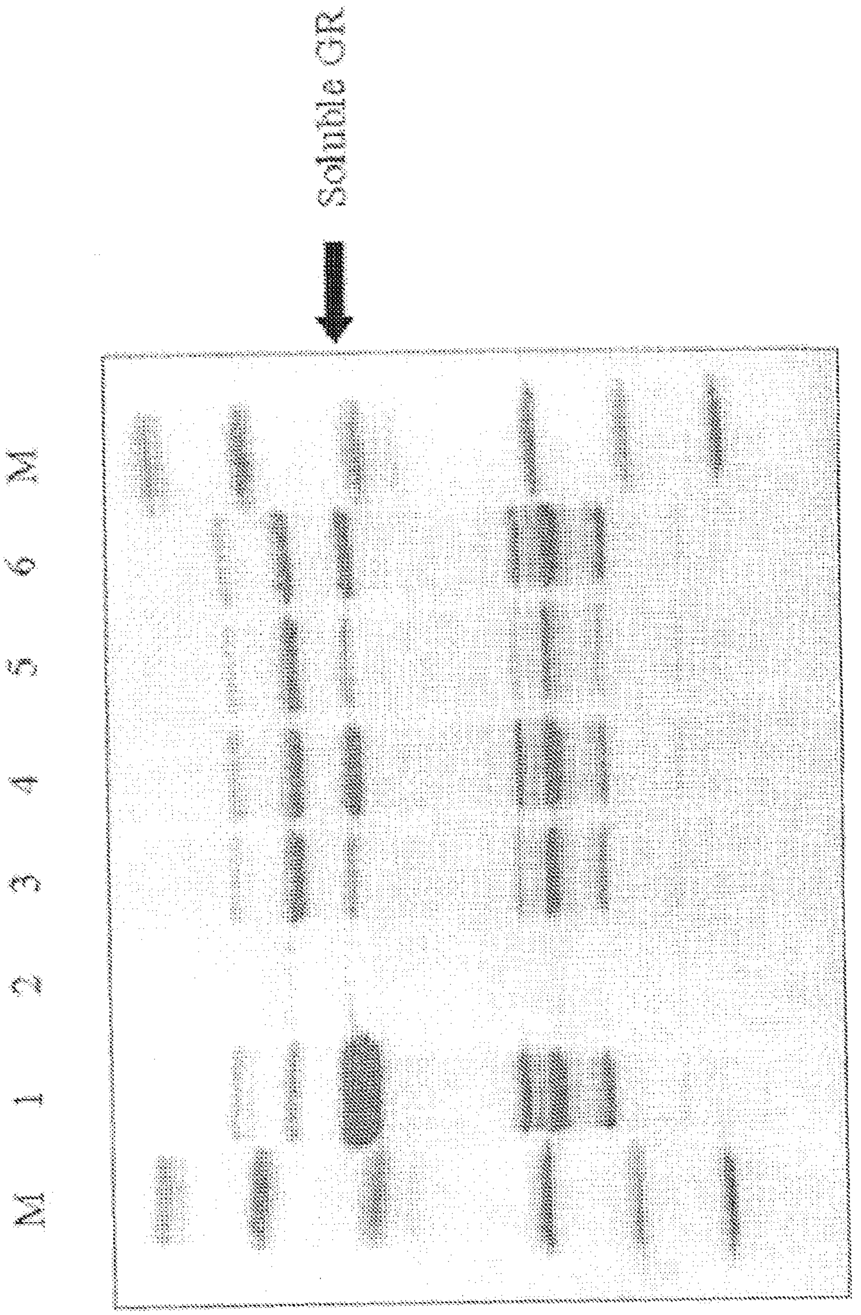
FIG. 1D shows the partial purification of *E. Coli* expressed GR (521–777) for several mutants isolated by the Lacl Fusion system.

FIG. 1D depicts the partial purification of *E. Coli* expressed GR (521–777) for several mutants isolated by the Lacl Fusion system. For solubility testing, these mutants are expressed as a fusion to 6xHis-GST using the modified pET24 expression vector. Continuing with FIG. 1D, Lane 1 contains the soluble fraction of GST-GR (521–777) F602S, Lane 2: GR (521–777) wild type, Lane 3: GST-GR (521–777) A580T/F602L, Lane 4: GST-GR (521–777) A574T, Lane 5: GST-GR (521–777) Q615H, and Lane 6: GST-GR (521–777) Q615L. Molecular weight markers (kD) are shown in Lane M.

TABLE 3

Statistics of Crystallographic Data and Structure

| Crystals | GR/TIF2 with dexamethasone |
|---|---|
| Space group | $P6_1$ |
| resolution (Å) | 20.0–2.8 |
| Unique reflections (N) | 18,923 |
| completeness (%) | 99.7 |
| I/σ (last shell) | 25.6 (2.2) |
| $R_{sym}{}^a$ (%) | 8.5 |

TABLE 3-continued

Statistics of Crystallographic Data and Structure

| Crystals | GR/TIF2 with dexamethasone |
|---|---|
| refinement statistics | |
| R factor$^b$ (%) | 33.4 |
| R free (%) | 29.6 |
| r.m.s.d. bond lengths (Å) | 0.015 |
| r.m.s.d. bond angles(degrees) | 1.795 |
| Number of H2O | 53 |
| total non-hydrogen atoms | 4444 |

r.m.s.d is the root mean square deviation from ideal geometry.

$^aR_{sym} = \Sigma|Iavg - Ii|/\Sigma Ii$ $^bR_{factor} = \Sigma|F_P - F_{Pcalc}|/\Sigma F_P$, where $F_P$ and $F_{pcalc}$ are observed and calculated structure factors, $R_{free}$ is calculated from a randomly chosen 8% of reflections that never be used in refinement and $R_{factor}$ is calculated for the remaining 92% of reflections.

REFERENCES

The references listed below as well as all references cited in the specification are incorporated herein by reference to the extent that they supplement, explain, provide a background for or teach methodology, techniques and/or compositions employed herein.

Altschul et al., (1990) *J. Mol. Biol.* 215: 403–10

Apriletti et al., (1995) *Protein Expression and Purification,* 6: 368–370

Arth et al., (1958) *J. Am. Chem. Soc.* 80: 3161

Ausubel et al., (1989) *Current Protocols in Molecular Biology*

Bartlett et al., (1989) *Special Pub., Royal Chem. Soc.* 78: 182–96

Beato, (1989) *Cell* 56:335–344

Blundell & Johnson, (1985) *Method. Enzymol.,* 114A & 115B

Bohm, (1992) *J. Comput. Aid. Mol. Des.,* 6: 61–78

Brooks et al., (1983) *J. Comp. Chem.,* 8: 132

Brünger, (1992) *X-PLOR, Version* 3.1. *A System for X-ray Crystallography and NMR*, Yale University Press, New Haven, Conn.

Case et al., (1997), AMBER 5, University of California, San Francisco

Cohen & Duke, (1984) *J. Immunol.* 152: 38–42

Cohen et al., (1990) *J. Med. Chem.* 33: 883–94

Crameri, A., et al., *Nature Biotechnology* 14, 315–319.

Creighton, (1983) *Proteins: Structures and Molecular Principles*, W.H. Freeman & Co., New York

*Crystallography*, Academic Press, San Diego, Calif.

Cull et al., (1992) *Proc. Natl. Acad. Sci.* 89:1865–1869.

Danielsen et al., (1987) *Molec. Endocrinol.* 1: 816–822

Danielsen et al., (1989) *Cancer Res.* 49: 2286s-2291s

Drewes et al., (1996) *Mol. Cell. Biol.* 16:925–31

Ducruix & Geige, (1992) *Crystallization of Nucleic Acids and Proteins: A Practical Approach*, IRL Press, Oxford, England Eastman-Reks & Vedeckis, (1986) *Cancer Res.* 46: 2457–2462

Eisen et al., (1994). *Proteins* 19: 199–221

Evans, (1988) *Science* 240:889–895

Evans, (1989) in *Recent Progress in Horrnone Research* (Clark, ed.) Vol. 45, pp. 1–27, Academic Press, San Diego, Calif.
Fried & Sabo, (1954) *J. Am Chem. Soc.* 76: 1455
Gampe et al., (2000) *Mol. Cell* 5: 545–55
Giguere et al., (1986) *Cell* 46: 645–652
Godowski et al., (1987) *Nature* 325: 365–368
Goodford, (1985) *J. Med. Chem.* 28: 849–57
Goodsell & Olsen, (1990) *Proteins* 8: 195–202
Green & Chambon, (1987) *Nature* 325: 75–78
Gribskov et al., (1986) *Nucl. Acids. Res.* 14: 6745
Gruol et al., (1989) *Molec. Endocrinol.* 3: 2119–2127
Harmon et al., (1979) *J. Cell Physiol.* 98: 267–278
Hauptman, (1997) *Curr. Opin. Struct. Biol.* 7: 672–80
Henikoff & Henikoff, (1989) *Proc Natl Acad Sci U.S.A.* 89: 10915
Hirschman et al., (1956) *J. Am. Chem. Soc.* 78: 4957
Hollenberg & Evans, (1988) *Cell* 55: 899–906
Hollenberg et al., (1987) *Cell* 49: 39–46
Hollenberg et al., (1989) *Cancer Res.* 49: 2292s–2294s
Homo-Delarche, (1984) *Cancer Res.* 44: 431–437
Janknecht, (1991) *Proc. Natl. Acad. Sci. U.S.A.* 88: 8972–8976
Jung, S., Honegger, A., and Pluckthun, A. (1999) *J. Mol. Biol.* 294, 163–180
Karlin and Altschul, (1993) *Proc Natl Acad Sci U.S.A.* 90: 5873–5887
Kelso & Munck, (1984) *J. Immunol.* 133:784–791
Kuntz et al., (1992) *J. Mol. Biol.* 161: 269–88
Kyte & Doolittle, (1982), *J. Mol. Biol.* 157: 105–132
Lambert, (1997) in *Practical Application of Computer-Aided Drug Design*, (Charifson, ed.) Marcel-Dekker, New York, pp. 243–303
Martin, (1992) *J. Med. Chem.* 35: 2145–54
McConkey et al., (1989) *Arch. Biochem. Biophys.* 269: 365–370
McPherson, (1982) *Preparation and Analysis of Protein Crystals*, John Wiley, New York
McPherson, (1990) *Eur. J. Biochem.* 189:1–23
McRee, (1992) *J. Mol. Graphics* 10: 44–46
McRee, (1993) *Practical Protein Crystallography*, Academic Press, New York
Miesfeld et al., (1987) *Science* 236:423–427
Miranker & Karplus, (1991) *Proteins* 11: 29–34
Navia & Murcko, (1992) *Curr. Opin. Struc. Bio.* 2: 202–10
Needleman et al., (1970) *J. Mol. Biol.* 48: 443
Nicholls et al., (1991) *Proteins* 11: 281
Nishibata & Itai, (1991) *Tetrahedron* 47: 8985
Nolte et al., (1998) *Nature* 395:137–43
Oberfield, J. L., et al., *Proc Natl Acad Sci USA.* (1999) May 25; 96(11):6102–6
Oliveto et al., (1958) *J. Am. Chem. Soc.* 4431
Oro et al., (1988) *Cell* 55: 1109–1114
Z. Otwinowski and W. Minor (1997), *Methods in Enzymology*, Volume 276: Macromolecular Crystallography, part A, p.307–326, 1997, C. W. Carter, Jr. & R. M. Sweet, Eds., Academic Press (New York).
Pearlman et al., (1995) *Comput. Phys. Commun.* 91: 1–41
Picard & Yamamoto, (1987) *EMBO J.* 6: 3333–3340
Picard et al., (1990) *Cell Regul.* 1: 291–299
Pjura, P., and Matthews, B. W. (1993) *Protein Science* 2, 2226–2236
Rarey et al., (1996) *J. Comput. Aid. Mol. Des.* 10:41–54
Rossmann, ed, (1972) *The Molecular Replacement Method*, Gordon & Breach, New York
Sambrook et al., (1989) *Molecular Cloning: A Laboratory Manual*, Cold Spring Harbor Laboratory, New York
Schatz et al., (1996) *Methods Enzymol.* 267:171–191
Schwartz et al., eds., (1979), *Atlas of Protein Sequence and Structure*, National Biomedical Research Foundation, pp. 357–358
Seielstad et al., (1995) *Mol. Endocrinol.* 9: 647–658
Sheldrick (1990) *Acta Cryst.* A46: 467
Shiau et al., (1998) *Cell* 95: 927–37
Sladek et al., *Genes Dev.* 4:2353–65
Smith et al., (1981) *Adv. Appl. Math.* 2:482
Thompson, (1989) *Cancer Res.* 49: 2259s–2265s.
Umesono & Evans, (1989) *Cell* 57: 1139–1146
Van Holde, (1971) *Physical Biochemistry*, Prentice-Hall, New Jersey, pp. 221–39
Voegel et al., (1998) *EMBO J.* 17: 507–519
Weber, (1991) *Adv. Protein Chem.* 41:1–36
Weeks et al., (1993) *Acta Cryst.* D49: 179
Wellner, (1971) *Anal. Chem.* 43: 597
Wetmur & Davidson, (1968) *J. Mol. Biol.* 31: 349–70
Wyckoff et al., eds., Academic Press
Yamamoto, (1985) *Ann. Rev. Genet.* 19: 209–252
Yuh & Thompson, (1989) *J. Biol. Chem.* 264: 10904–10910
U.S. Pat. No. 3,007,923
U.S. Pat. No. 6,008,033
U.S. Pat. No. 4,554,101
U.S. Pat. No. 5,463,564
U.S. Pat. No. 5,834,228
U.S. Pat. No. 5,872,011
U.S. Pat. No. 6,236,946
U.S. Pat. No. 5,338,665
WO 84/03564
WO 99/26966

TABLE 4

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1 | CB | GLN | 527 | 60.207 | 9.806 | 35.497 | 1.00 | 60.77 |
| 2 | CG | GLN | 527 | 60.501 | 11.318 | 35.564 | 1.00 | 60.74 |
| 3 | CD | GLN | 527 | 60.595 | 11.993 | 34.172 | 1.00 | 63.52 |
| 4 | OE1 | GLN | 527 | 60.493 | 13.224 | 34.058 | 1.00 | 61.80 |
| 5 | NE2 | GLN | 527 | 60.794 | 11.187 | 33.121 | 1.00 | 61.21 |
| 6 | C | GLN | 527 | 62.073 | 8.590 | 36.647 | 1.00 | 62.83 |
| 7 | O | GLN | 527 | 63.240 | 8.191 | 36.724 | 1.00 | 59.67 |
| 8 | N | GLN | 527 | 61.009 | 7.618 | 34.618 | 1.00 | 58.91 |
| 9 | CA | GLN | 527 | 61.426 | 8.890 | 35.289 | 1.00 | 62.13 |
| 10 | N | LEU | 528 | 61.308 | 8.776 | 37.716 | 1.00 | 62.73 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 11 | CA | LEU | 528 | 61.816 | 8.538 | 39.064 | 1.00 | 65.02 |
| 12 | CB | LEU | 528 | 62.105 | 9.889 | 39.733 | 1.00 | 62.65 |
| 13 | CG | LEU | 528 | 62.864 | 10.872 | 38.813 | 1.00 | 59.23 |
| 14 | CD1 | LEU | 528 | 62.071 | 12.198 | 38.675 | 1.00 | 63.52 |
| 15 | CD2 | LEU | 528 | 64.283 | 11.105 | 39.356 | 1.00 | 60.04 |
| 16 | C | LEU | 528 | 60.823 | 7.690 | 39.888 | 1.00 | 59.38 |
| 17 | O | LEU | 528 | 60.586 | 6.527 | 39.527 | 1.00 | 63.35 |
| 18 | N | THR | 529 | 60.247 | 8.256 | 40.960 | 1.00 | 60.40 |
| 19 | CA | THR | 529 | 59.282 | 7.539 | 41.835 | 1.00 | 60.79 |
| 20 | CB | THR | 529 | 57.841 | 8.227 | 41.847 | 1.00 | 63.67 |
| 21 | OG1 | THR | 529 | 57.918 | 9.561 | 42.382 | 1.00 | 60.60 |
| 22 | CG2 | THR | 529 | 56.867 | 7.410 | 42.706 | 1.00 | 62.04 |
| 23 | C | THR | 529 | 59.134 | 6.056 | 41.397 | 1.00 | 61.38 |
| 24 | O | THR | 529 | 58.454 | 5.754 | 40.398 | 1.00 | 59.93 |
| 25 | N | PRO | 530 | 59.743 | 5.117 | 42.163 | 1.00 | 61.16 |
| 26 | CD | PRO | 530 | 60.110 | 5.411 | 43.563 | 1.00 | 60.38 |
| 27 | CA | PRO | 530 | 59.753 | 3.660 | 41.928 | 1.00 | 62.39 |
| 28 | CB | PRO | 530 | 60.388 | 3.109 | 43.213 | 1.00 | 58.06 |
| 29 | CG | PRO | 530 | 59.914 | 4.071 | 44.249 | 1.00 | 64.31 |
| 30 | C | PRO | 530 | 58.453 | 2.927 | 41.537 | 1.00 | 63.39 |
| 31 | O | PRO | 530 | 57.400 | 3.542 | 41.363 | 1.00 | 59.17 |
| 32 | N | THR | 531 | 58.554 | 1.603 | 41.419 | 1.00 | 62.27 |
| 33 | CA | THR | 531 | 57.455 | 0.742 | 40.997 | 1.00 | 61.68 |
| 34 | CB | THR | 531 | 57.989 | −0.404 | 40.058 | 1.00 | 60.38 |
| 35 | OG1 | THR | 531 | 57.209 | −0.461 | 38.853 | 1.00 | 60.25 |
| 36 | CG2 | THR | 531 | 57.937 | −1.760 | 40.757 | 1.00 | 60.67 |
| 37 | C | THR | 531 | 56.629 | 0.125 | 42.117 | 1.00 | 60.82 |
| 38 | O | THR | 531 | 55.533 | −0.361 | 41.864 | 1.00 | 62.20 |
| 39 | N | LEU | 532 | 57.122 | 0.128 | 43.348 | 1.00 | 60.85 |
| 40 | CA | LEU | 532 | 56.324 | −0.465 | 44.418 | 1.00 | 60.11 |
| 41 | CB | LEU | 532 | 57.183 | −0.775 | 45.637 | 1.00 | 64.22 |
| 42 | CG | LEU | 532 | 56.388 | −1.514 | 46.704 | 1.00 | 63.74 |
| 43 | CD1 | LEU | 532 | 55.677 | −2.694 | 46.082 | 1.00 | 62.66 |
| 44 | CD2 | LEU | 532 | 57.317 | −1.968 | 47.806 | 1.00 | 63.22 |
| 45 | C | LEU | 532 | 55.143 | 0.422 | 44.817 | 1.00 | 62.08 |
| 46 | O | LEU | 532 | 54.047 | −0.075 | 45.061 | 1.00 | 61.27 |
| 47 | N | VAL | 533 | 55.366 | 1.733 | 44.883 | 1.00 | 59.27 |
| 48 | CA | VAL | 533 | 54.297 | 2.677 | 45.222 | 1.00 | 62.90 |
| 49 | CB | VAL | 533 | 54.858 | 4.050 | 45.638 | 1.00 | 64.91 |
| 50 | CG1 | VAL | 533 | 55.572 | 4.693 | 44.465 | 1.00 | 60.86 |
| 51 | CG2 | VAL | 533 | 53.746 | 4.941 | 46.102 | 1.00 | 61.00 |
| 52 | C | VAL | 533 | 53.422 | 2.874 | 43.979 | 1.00 | 62.21 |
| 53 | O | VAL | 533 | 52.281 | 3.321 | 44.065 | 1.00 | 61.72 |
| 54 | N | SER | 534 | 53.981 | 2.553 | 42.817 | 1.00 | 60.92 |
| 55 | CA | SER | 534 | 53.249 | 2.665 | 41.564 | 1.00 | 61.24 |
| 56 | CB | SER | 534 | 54.196 | 2.474 | 40.386 | 1.00 | 61.92 |
| 57 | OG | SER | 534 | 53.468 | 2.355 | 39.183 | 1.00 | 61.38 |
| 58 | C | SER | 534 | 52.209 | 1.557 | 41.566 | 1.00 | 64.31 |
| 59 | O | SER | 534 | 51.105 | 1.691 | 41.027 | 1.00 | 62.62 |
| 60 | N | LEU | 535 | 52.581 | 0.452 | 42.193 | 1.00 | 61.91 |
| 61 | CA | LEU | 535 | 51.697 | −0.684 | 42.288 | 1.00 | 60.97 |
| 62 | CB | LEU | 535 | 52.479 | −1.922 | 42.730 | 1.00 | 66.65 |
| 63 | CG | LEU | 535 | 51.949 | −3.225 | 42.131 | 1.00 | 63.58 |
| 64 | CD1 | LEU | 535 | 52.657 | −3.505 | 40.827 | 1.00 | 62.14 |
| 65 | CD2 | LEU | 535 | 52.175 | −4.364 | 43.090 | 1.00 | 61.95 |
| 66 | C | LEU | 535 | 50.588 | −0.353 | 43.285 | 1.00 | 59.91 |
| 67 | O | LEU | 535 | 49.432 | −0.684 | 43.060 | 1.00 | 63.02 |
| 68 | N | LEU | 536 | 50.933 | 0.315 | 44.381 | 1.00 | 62.58 |
| 69 | CA | LEU | 536 | 49.932 | 0.683 | 45.376 | 1.00 | 59.17 |
| 70 | CB | LEU | 536 | 50.583 | 1.413 | 46.541 | 1.00 | 61.74 |
| 71 | CG | LEU | 536 | 51.501 | 0.625 | 47.460 | 1.00 | 58.87 |
| 72 | CD1 | LEU | 536 | 51.953 | 1.545 | 48.553 | 1.00 | 59.54 |
| 73 | CD2 | LEU | 536 | 50.781 | −0.575 | 48.045 | 1.00 | 63.64 |
| 74 | C | LEU | 536 | 48.821 | 1.569 | 44.812 | 1.00 | 63.31 |
| 75 | O | LEU | 536 | 47.672 | 1.489 | 45.256 | 1.00 | 61.67 |
| 76 | N | GLU | 537 | 49.171 | 2.415 | 43.845 | 1.00 | 59.21 |
| 77 | CA | GLU | 537 | 48.231 | 3.343 | 43.213 | 1.00 | 59.76 |
| 78 | CB | GLU | 537 | 48.984 | 4.292 | 42.302 | 1.00 | 59.81 |
| 79 | CG | GLU | 537 | 48.816 | 5.744 | 42.625 | 1.00 | 60.10 |
| 80 | CD | GLU | 537 | 48.907 | 6.616 | 41.385 | 1.00 | 64.34 |
| 81 | OE1 | GLU | 537 | 47.868 | 6.813 | 40.707 | 1.00 | 57.41 |
| 82 | OE2 | GLU | 537 | 50.024 | 7.091 | 41.084 | 1.00 | 62.84 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 83 | C | GLU | 537 | 47.139 | 2.698 | 42.371 | 1.00 | 61.66 |
| 84 | O | GLU | 537 | 45.973 | 3.101 | 42.433 | 1.00 | 60.28 |
| 85 | N | VAL | 538 | 47.536 | 1.717 | 41.564 | 1.00 | 60.48 |
| 86 | CA | VAL | 538 | 46.606 | 1.045 | 40.674 | 1.00 | 63.41 |
| 87 | CB | VAL | 538 | 47.325 | 0.448 | 39.442 | 1.00 | 64.15 |
| 88 | CG1 | VAL | 538 | 48.334 | 1.444 | 38.903 | 1.00 | 60.29 |
| 89 | CG2 | VAL | 538 | 47.973 | −0.883 | 39.797 | 1.00 | 63.88 |
| 90 | C | VAL | 538 | 45.768 | −0.046 | 41.311 | 1.00 | 57.99 |
| 91 | O | VAL | 538 | 44.828 | −0.530 | 40.683 | 1.00 | 58.71 |
| 92 | N | ILE | 539 | 46.094 | −0.454 | 42.535 | 1.00 | 61.14 |
| 93 | CA | ILE | 539 | 45.282 | −1.484 | 43.186 | 1.00 | 60.23 |
| 94 | CB | ILE | 539 | 46.141 | −2.499 | 44.010 | 1.00 | 65.32 |
| 95 | CG2 | ILE | 539 | 47.243 | −3.066 | 43.140 | 1.00 | 61.32 |
| 96 | CG1 | ILE | 539 | 46.775 | −1.833 | 45.228 | 1.00 | 63.80 |
| 97 | CD1 | ILE | 539 | 47.356 | −2.833 | 46.207 | 1.00 | 60.85 |
| 98 | C | ILE | 539 | 44.259 | −0.811 | 44.097 | 1.00 | 61.40 |
| 99 | O | ILE | 539 | 43.321 | −1.447 | 44.573 | 1.00 | 63.49 |
| 100 | N | GLU | 540 | 44.451 | 0.489 | 44.310 | 1.00 | 61.12 |
| 101 | CA | GLU | 540 | 43.584 | 1.307 | 45.153 | 1.00 | 60.76 |
| 102 | CB | GLU | 540 | 44.109 | 2.753 | 45.173 | 1.00 | 58.26 |
| 103 | CG | GLU | 540 | 43.466 | 3.684 | 46.191 | 1.00 | 61.15 |
| 104 | CD | GLU | 540 | 43.598 | 3.183 | 47.619 | 1.00 | 61.95 |
| 105 | OE1 | GLU | 540 | 44.656 | 2.591 | 47.950 | 1.00 | 59.71 |
| 106 | OE2 | GLU | 540 | 42.649 | 3.397 | 48.410 | 1.00 | 62.96 |
| 107 | C | GLU | 540 | 42.169 | 1.264 | 44.585 | 1.00 | 61.78 |
| 108 | O | GLU | 540 | 41.928 | 1.709 | 43.459 | 1.00 | 61.36 |
| 109 | N | PRO | 541 | 41.214 | 0.713 | 45.352 | 1.00 | 63.77 |
| 110 | CD | PRO | 541 | 41.365 | 0.053 | 46.659 | 1.00 | 58.98 |
| 111 | CA | PRO | 541 | 39.830 | 0.632 | 44.876 | 1.00 | 60.14 |
| 112 | CB | PRO | 541 | 39.131 | −0.149 | 45.988 | 1.00 | 59.62 |
| 113 | CG | PRO | 541 | 39.978 | 0.122 | 47.195 | 1.00 | 60.56 |
| 114 | C | PRO | 541 | 39.180 | 1.991 | 44.592 | 1.00 | 62.36 |
| 115 | O | PRO | 541 | 39.455 | 2.982 | 45.283 | 1.00 | 59.45 |
| 116 | N | GLU | 542 | 38.332 | 2.039 | 43.563 | 1.00 | 60.43 |
| 117 | CA | GLU | 542 | 37.653 | 3.279 | 43.198 | 1.00 | 62.04 |
| 118 | CB | GLU | 542 | 37.091 | 3.201 | 41.770 | 1.00 | 62.84 |
| 119 | CG | GLU | 542 | 36.130 | 2.050 | 41.511 | 1.00 | 63.24 |
| 120 | CD | GLU | 542 | 35.745 | 1.911 | 40.031 | 1.00 | 63.39 |
| 121 | OE1 | GLU | 542 | 36.622 | 2.095 | 39.153 | 1.00 | 60.50 |
| 122 | OE2 | GLU | 542 | 34.568 | 1.599 | 39.743 | 1.00 | 59.31 |
| 123 | C | GLU | 542 | 36.548 | 3.515 | 44.208 | 1.00 | 63.11 |
| 124 | O | GLU | 542 | 35.941 | 2.564 | 44.697 | 1.00 | 59.70 |
| 125 | N | VAL | 543 | 36.304 | 4.783 | 44.528 | 1.00 | 61.53 |
| 126 | CA | VAL | 543 | 35.299 | 5.148 | 45.518 | 1.00 | 63.47 |
| 127 | CB | VAL | 543 | 35.334 | 6.661 | 45.801 | 1.00 | 62.60 |
| 128 | CG1 | VAL | 543 | 34.467 | 6.984 | 46.987 | 1.00 | 60.93 |
| 129 | CG2 | VAL | 543 | 36.762 | 7.103 | 46.064 | 1.00 | 59.59 |
| 130 | C | VAL | 543 | 33.886 | 4.748 | 45.126 | 1.00 | 61.39 |
| 131 | O | VAL | 543 | 33.495 | 4.877 | 43.965 | 1.00 | 60.79 |
| 132 | N | LEU | 544 | 33.128 | 4.267 | 46.109 | 1.00 | 62.56 |
| 133 | CA | LEU | 544 | 31.759 | 3.836 | 45.882 | 1.00 | 60.63 |
| 134 | CB | LEU | 544 | 31.501 | 2.486 | 46.547 | 1.00 | 63.18 |
| 135 | CG | LEU | 544 | 32.666 | 1.512 | 46.682 | 1.00 | 61.92 |
| 136 | CD1 | LEU | 544 | 33.702 | 2.114 | 47.638 | 1.00 | 62.67 |
| 137 | CD2 | LEU | 544 | 32.163 | 0.172 | 47.225 | 1.00 | 61.02 |
| 138 | C | LEU | 544 | 30.754 | 4.844 | 46.423 | 1.00 | 58.48 |
| 139 | O | LEU | 544 | 31.097 | 5.715 | 47.225 | 1.00 | 59.01 |
| 140 | N | TYR | 545 | 29.508 | 4.698 | 45.974 | 1.00 | 60.35 |
| 141 | CA | TYR | 545 | 28.394 | 5.559 | 46.356 | 1.00 | 58.86 |
| 142 | CB | TYR | 545 | 27.616 | 5.977 | 45.105 | 1.00 | 59.62 |
| 143 | CG | TYR | 545 | 28.421 | 6.799 | 44.122 | 1.00 | 60.54 |
| 144 | CD1 | TYR | 545 | 29.815 | 6.803 | 44.162 | 1.00 | 59.00 |
| 145 | CE1 | TYR | 545 | 30.561 | 7.563 | 43.270 | 1.00 | 61.22 |
| 146 | CD2 | TYR | 545 | 27.791 | 7.579 | 43.153 | 1.00 | 63.95 |
| 147 | CE2 | TYR | 545 | 28.534 | 8.348 | 42.256 | 1.00 | 59.17 |
| 148 | CZ | TYR | 545 | 29.914 | 8.336 | 42.325 | 1.00 | 60.43 |
| 149 | OH | TYR | 545 | 30.654 | 9.120 | 41.478 | 1.00 | 60.96 |
| 150 | C | TYR | 545 | 27.501 | 4.743 | 47.269 | 1.00 | 64.48 |
| 151 | O | TYR | 545 | 27.449 | 3.517 | 47.151 | 1.00 | 60.43 |
| 152 | N | ALA | 546 | 26.789 | 5.415 | 48.168 | 1.00 | 62.22 |
| 153 | CA | ALA | 546 | 25.918 | 4.720 | 49.112 | 1.00 | 61.72 |
| 154 | CB | ALA | 546 | 25.780 | 5.540 | 50.378 | 1.00 | 60.83 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 155 | C | ALA | 546 | 24.536 | 4.377 | 48.570 | 1.00 | 61.54 |
| 156 | O | ALA | 546 | 23.886 | 3.461 | 49.065 | 1.00 | 58.65 |
| 157 | N | GLY | 547 | 24.089 | 5.100 | 47.549 | 1.00 | 60.89 |
| 158 | CA | GLY | 547 | 22.768 | 4.841 | 47.014 | 1.00 | 59.44 |
| 159 | C | GLY | 547 | 21.765 | 5.212 | 48.088 | 1.00 | 59.45 |
| 160 | O | GLY | 547 | 20.849 | 4.460 | 48.392 | 1.00 | 58.64 |
| 161 | N | TYR | 548 | 21.966 | 6.387 | 48.671 | 1.00 | 59.64 |
| 162 | CA | TYR | 548 | 21.119 | 6.921 | 49.733 | 1.00 | 61.47 |
| 163 | CB | TYR | 548 | 21.912 | 7.970 | 50.520 | 1.00 | 64.12 |
| 164 | CG | TYR | 548 | 21.244 | 8.421 | 51.783 | 1.00 | 58.90 |
| 165 | CD1 | TYR | 548 | 21.049 | 7.534 | 52.833 | 1.00 | 61.61 |
| 166 | CE1 | TYR | 548 | 20.414 | 7.927 | 53.992 | 1.00 | 63.67 |
| 167 | CD2 | TYR | 548 | 20.785 | 9.726 | 51.926 | 1.00 | 60.05 |
| 168 | CE2 | TYR | 548 | 20.144 | 10.129 | 53.084 | 1.00 | 60.57 |
| 169 | CZ | TYR | 548 | 19.964 | 9.218 | 54.112 | 1.00 | 64.94 |
| 170 | OH | TYR | 548 | 19.319 | 9.579 | 55.262 | 1.00 | 63.47 |
| 171 | C | TYR | 548 | 19.907 | 7.569 | 49.080 | 1.00 | 63.87 |
| 172 | O | TYR | 548 | 19.755 | 7.481 | 47.867 | 1.00 | 60.53 |
| 173 | N | ASP | 549 | 19.043 | 8.207 | 49.871 | 1.00 | 60.86 |
| 174 | CA | ASP | 549 | 17.881 | 8.882 | 49.307 | 1.00 | 62.83 |
| 175 | CB | ASP | 549 | 16.590 | 8.410 | 49.958 | 1.00 | 61.82 |
| 176 | CG | ASP | 549 | 15.487 | 8.213 | 48.935 | 1.00 | 59.25 |
| 177 | OD1 | ASP | 549 | 14.321 | 7.942 | 49.306 | 1.00 | 61.06 |
| 178 | OD2 | ASP | 549 | 15.810 | 8.328 | 47.734 | 1.00 | 61.75 |
| 179 | C | ASP | 549 | 17.979 | 10.402 | 49.411 | 1.00 | 62.83 |
| 180 | O | ASP | 549 | 18.158 | 11.075 | 48.400 | 1.00 | 60.57 |
| 181 | N | SER | 550 | 17.875 | 10.954 | 50.617 | 1.00 | 59.81 |
| 182 | CA | SER | 550 | 17.953 | 12.415 | 50.793 | 1.00 | 62.38 |
| 183 | CB | SER | 550 | 19.325 | 12.951 | 50.386 | 1.00 | 56.99 |
| 184 | OG | SER | 550 | 19.438 | 13.020 | 48.978 | 1.00 | 62.06 |
| 185 | C | SER | 550 | 16.894 | 13.126 | 49.957 | 1.00 | 62.44 |
| 186 | O | SER | 550 | 16.893 | 14.350 | 49.843 | 1.00 | 61.89 |
| 187 | N | SER | 551 | 16.018 | 12.343 | 49.343 | 1.00 | 61.48 |
| 188 | CA | SER | 551 | 14.924 | 12.875 | 48.557 | 1.00 | 60.05 |
| 189 | CB | SER | 551 | 14.507 | 11.886 | 47.487 | 1.00 | 62.39 |
| 190 | OG | SER | 551 | 13.838 | 10.800 | 48.100 | 1.00 | 61.65 |
| 191 | C | SER | 551 | 13.850 | 12.904 | 49.615 | 1.00 | 60.87 |
| 192 | O | SER | 551 | 12.799 | 13.512 | 49.452 | 1.00 | 59.31 |
| 193 | N | VAL | 552 | 14.142 | 12.200 | 50.703 | 1.00 | 61.91 |
| 194 | CA | VAL | 552 | 13.252 | 12.096 | 51.849 | 1.00 | 60.13 |
| 195 | CB | VAL | 552 | 12.584 | 10.695 | 51.895 | 1.00 | 60.55 |
| 196 | CG1 | VAL | 552 | 11.242 | 10.744 | 51.187 | 1.00 | 59.77 |
| 197 | CG2 | VAL | 552 | 13.461 | 9.674 | 51.211 | 1.00 | 62.73 |
| 198 | C | VAL | 552 | 14.035 | 12.388 | 53.141 | 1.00 | 58.44 |
| 199 | O | VAL | 552 | 15.269 | 12.482 | 53.116 | 1.00 | 60.59 |
| 200 | N | PRO | 553 | 13.326 | 12.571 | 54.278 | 1.00 | 59.91 |
| 201 | CD | PRO | 553 | 11.861 | 12.614 | 54.440 | 1.00 | 61.19 |
| 202 | CA | PRO | 553 | 13.974 | 12.859 | 55.559 | 1.00 | 59.95 |
| 203 | CB | PRO | 553 | 12.865 | 12.572 | 56.556 | 1.00 | 62.02 |
| 204 | CG | PRO | 553 | 11.701 | 13.166 | 55.851 | 1.00 | 62.09 |
| 205 | C | PRO | 553 | 15.263 | 12.093 | 55.839 | 1.00 | 62.80 |
| 206 | O | PRO | 553 | 15.525 | 11.035 | 55.259 | 1.00 | 61.14 |
| 207 | N | ASP | 554 | 16.058 | 12.646 | 56.748 | 1.00 | 58.85 |
| 208 | CA | ASP | 554 | 17.357 | 12.084 | 57.104 | 1.00 | 60.06 |
| 209 | CB | ASP | 554 | 18.462 | 13.098 | 56.755 | 1.00 | 61.56 |
| 210 | CG | ASP | 554 | 18.836 | 13.106 | 55.280 | 1.00 | 62.42 |
| 211 | OD1 | ASP | 554 | 17.961 | 12.964 | 54.390 | 1.00 | 59.77 |
| 212 | OD2 | ASP | 554 | 20.038 | 13.286 | 55.014 | 1.00 | 59.95 |
| 213 | C | ASP | 554 | 17.535 | 11.703 | 58.575 | 1.00 | 56.92 |
| 214 | O | ASP | 554 | 18.402 | 12.273 | 59.229 | 1.00 | 61.20 |
| 215 | N | SER | 555 | 16.767 | 10.761 | 59.116 | 1.00 | 62.60 |
| 216 | CA | SER | 555 | 16.970 | 10.398 | 60.526 | 1.00 | 63.72 |
| 217 | CB | SER | 555 | 15.998 | 9.296 | 60.948 | 1.00 | 63.32 |
| 218 | OG | SER | 555 | 16.267 | 8.089 | 60.255 | 1.00 | 60.75 |
| 219 | C | SER | 555 | 18.404 | 9.905 | 60.749 | 1.00 | 61.32 |
| 220 | O | SER | 555 | 19.093 | 9.556 | 59.794 | 1.00 | 59.49 |
| 221 | N | THR | 556 | 18.855 | 9.877 | 62.002 | 1.00 | 63.20 |
| 222 | CA | THR | 556 | 20.211 | 9.407 | 62.308 | 1.00 | 62.68 |
| 223 | CB | THR | 556 | 20.554 | 9.487 | 63.826 | 1.00 | 62.64 |
| 224 | OG1 | THR | 556 | 20.893 | 10.831 | 64.183 | 1.00 | 62.26 |
| 225 | CG2 | THR | 556 | 21.739 | 8.582 | 64.158 | 1.00 | 62.40 |
| 226 | C | THR | 556 | 20.387 | 7.955 | 61.902 | 1.00 | 62.17 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 227 | O | THR | 556 | 21.196 | 7.633 | 61.030 | 1.00 | 63.77 |
| 228 | N | TRP | 557 | 19.624 | 7.082 | 62.554 | 1.00 | 63.04 |
| 229 | CA | TRP | 557 | 19.696 | 5.652 | 62.294 | 1.00 | 60.39 |
| 230 | CB | TRP | 557 | 18.505 | 4.923 | 62.964 | 1.00 | 61.26 |
| 231 | CG | TRP | 557 | 17.324 | 4.805 | 62.064 | 1.00 | 64.02 |
| 232 | CD2 | TRP | 557 | 17.074 | 3.747 | 61.123 | 1.00 | 60.71 |
| 233 | CE2 | TRP | 557 | 15.970 | 4.142 | 60.332 | 1.00 | 58.32 |
| 234 | CE3 | TRP | 557 | 17.684 | 2.511 | 60.865 | 1.00 | 62.45 |
| 235 | CD1 | TRP | 557 | 16.378 | 5.760 | 61.825 | 1.00 | 60.50 |
| 236 | NE1 | TRP | 557 | 15.562 | 5.373 | 60.780 | 1.00 | 59.73 |
| 237 | CZ2 | TRP | 557 | 15.464 | 3.341 | 59.296 | 1.00 | 61.79 |
| 238 | CZ3 | TRP | 557 | 17.184 | 1.716 | 59.836 | 1.00 | 62.55 |
| 239 | CH2 | TRP | 557 | 16.084 | 2.136 | 59.065 | 1.00 | 57.76 |
| 240 | C | TRP | 557 | 19.731 | 5.362 | 60.783 | 1.00 | 61.95 |
| 241 | O | TRP | 557 | 20.479 | 4.493 | 60.332 | 1.00 | 59.61 |
| 242 | N | ARG | 558 | 18.946 | 6.099 | 60.001 | 1.00 | 61.85 |
| 243 | CA | ARG | 558 | 18.898 | 5.873 | 58.555 | 1.00 | 64.57 |
| 244 | CB | ARG | 558 | 17.744 | 6.651 | 57.926 | 1.00 | 59.03 |
| 245 | CG | ARG | 558 | 17.303 | 6.107 | 56.582 | 1.00 | 62.63 |
| 246 | CD | ARG | 558 | 16.012 | 6.780 | 56.133 | 1.00 | 59.07 |
| 247 | NE | ARG | 558 | 16.221 | 7.958 | 55.288 | 1.00 | 61.76 |
| 248 | CZ | ARG | 558 | 16.594 | 7.911 | 54.011 | 1.00 | 63.52 |
| 249 | NH1 | ARG | 558 | 16.805 | 6.745 | 53.420 | 1.00 | 63.08 |
| 250 | NH2 | ARG | 558 | 16.750 | 9.031 | 53.319 | 1.00 | 60.97 |
| 251 | C | ARG | 558 | 20.200 | 6.222 | 57.841 | 1.00 | 64.20 |
| 252 | O | ARG | 558 | 20.573 | 5.566 | 56.869 | 1.00 | 65.47 |
| 253 | N | ILE | 559 | 20.877 | 7.266 | 58.307 | 1.00 | 62.87 |
| 254 | CA | ILE | 559 | 22.156 | 7.678 | 57.726 | 1.00 | 59.66 |
| 255 | CB | ILE | 559 | 22.639 | 9.040 | 58.329 | 1.00 | 62.98 |
| 256 | CG2 | ILE | 559 | 24.101 | 9.278 | 57.993 | 1.00 | 59.64 |
| 257 | CG1 | ILE | 559 | 21.794 | 10.196 | 57.791 | 1.00 | 61.72 |
| 258 | CD1 | ILE | 559 | 22.091 | 10.556 | 56.351 | 1.00 | 60.58 |
| 259 | C | ILE | 559 | 23.152 | 6.585 | 58.119 | 1.00 | 62.05 |
| 260 | O | ILE | 559 | 23.838 | 5.995 | 57.274 | 1.00 | 61.48 |
| 261 | N | MET | 560 | 23.188 | 6.332 | 59.425 | 1.00 | 60.47 |
| 262 | CA | MET | 560 | 24.056 | 5.340 | 60.036 | 1.00 | 59.72 |
| 263 | CB | MET | 560 | 23.799 | 5.286 | 61.554 | 1.00 | 61.50 |
| 264 | CG | MET | 560 | 24.863 | 6.016 | 62.358 | 1.00 | 59.68 |
| 265 | SD | MET | 560 | 24.765 | 5.946 | 64.183 | 1.00 | 62.00 |
| 266 | CE | MET | 560 | 25.827 | 7.029 | 64.314 | 1.00 | 56.75 |
| 267 | C | MET | 560 | 23.910 | 3.950 | 59.421 | 1.00 | 63.13 |
| 268 | O | MET | 560 | 24.908 | 3.299 | 59.122 | 1.00 | 60.43 |
| 269 | N | THR | 561 | 22.680 | 3.493 | 59.215 | 1.00 | 59.86 |
| 270 | CA | THR | 561 | 22.487 | 2.183 | 58.619 | 1.00 | 62.03 |
| 271 | CB | THR | 561 | 21.005 | 1.771 | 58.603 | 1.00 | 60.73 |
| 272 | OG1 | THR | 561 | 20.483 | 1.777 | 59.938 | 1.00 | 58.44 |
| 273 | CG2 | THR | 561 | 20.862 | 0.370 | 58.025 | 1.00 | 59.27 |
| 274 | C | THR | 561 | 23.005 | 2.192 | 57.190 | 1.00 | 62.25 |
| 275 | O | THR | 561 | 23.565 | 1.211 | 56.724 | 1.00 | 59.53 |
| 276 | N | THR | 562 | 22.813 | 3.296 | 56.482 | 1.00 | 61.35 |
| 277 | CA | THR | 562 | 23.305 | 3.365 | 55.112 | 1.00 | 62.18 |
| 278 | CB | THR | 562 | 22.728 | 4.593 | 54.342 | 1.00 | 58.86 |
| 279 | OG1 | THR | 562 | 21.338 | 4.375 | 54.051 | 1.00 | 58.36 |
| 280 | CG2 | THR | 562 | 23.473 | 4.805 | 53.033 | 1.00 | 58.66 |
| 281 | C | THR | 562 | 24.830 | 3.432 | 55.157 | 1.00 | 62.40 |
| 282 | O | THR | 562 | 25.509 | 3.011 | 54.225 | 1.00 | 59.62 |
| 283 | N | LEU | 563 | 25.374 | 3.949 | 56.252 | 1.00 | 60.06 |
| 284 | CA | LEU | 563 | 26.825 | 4.026 | 56.382 | 1.00 | 61.98 |
| 285 | CB | LEU | 563 | 27.230 | 5.045 | 57.451 | 1.00 | 59.10 |
| 286 | CG | LEU | 563 | 27.004 | 6.519 | 57.119 | 1.00 | 62.03 |
| 287 | CD1 | LEU | 563 | 27.667 | 7.377 | 58.180 | 1.00 | 59.83 |
| 288 | CD2 | LEU | 563 | 27.574 | 6.827 | 55.745 | 1.00 | 63.51 |
| 289 | C | LEU | 563 | 27.406 | 2.657 | 56.730 | 1.00 | 63.21 |
| 290 | O | LEU | 563 | 28.592 | 2.410 | 56.529 | 1.00 | 59.14 |
| 291 | N | ASN | 564 | 26.567 | 1.773 | 57.264 | 1.00 | 59.68 |
| 292 | CA | ASN | 564 | 27.001 | 0.427 | 57.606 | 1.00 | 62.50 |
| 293 | CB | ASN | 564 | 26.110 | −0.166 | 58.689 | 1.00 | 61.63 |
| 294 | CG | ASN | 564 | 26.456 | 0.349 | 60.058 | 1.00 | 62.37 |
| 295 | OD1 | ASN | 564 | 27.625 | 0.513 | 60.381 | 1.00 | 62.36 |
| 296 | ND2 | ASN | 564 | 25.447 | 0.590 | 60.881 | 1.00 | 59.03 |
| 297 | C | ASN | 564 | 26.949 | −0.442 | 56.356 | 1.00 | 61.40 |
| 298 | O | ASN | 564 | 27.823 | −1.266 | 56.121 | 1.00 | 61.63 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 299 | N | MET | 565 | 25.923 | −0.251 | 55.543 | 1.00 | 62.42 |
| 300 | CA | MET | 565 | 25.804 | −1.022 | 54.320 | 1.00 | 63.45 |
| 301 | CB | MET | 565 | 24.483 | −0.701 | 53.632 | 1.00 | 59.10 |
| 302 | CG | MET | 565 | 23.266 | −0.999 | 54.488 | 1.00 | 62.52 |
| 303 | SD | MET | 565 | 23.154 | −2.742 | 54.883 | 1.00 | 63.35 |
| 304 | CE | MET | 565 | 22.918 | −2.702 | 56.627 | 1.00 | 60.16 |
| 305 | C | MET | 565 | 26.967 | −0.669 | 53.410 | 1.00 | 62.27 |
| 306 | O | MET | 565 | 27.475 | −1.509 | 52.677 | 1.00 | 62.01 |
| 307 | N | LEU | 566 | 27.382 | 0.590 | 53.462 | 1.00 | 62.25 |
| 308 | CA | LEU | 566 | 28.495 | 1.064 | 52.656 | 1.00 | 60.20 |
| 309 | CB | LEU | 566 | 28.596 | 2.594 | 52.741 | 1.00 | 59.50 |
| 310 | CG | LEU | 566 | 29.801 | 3.267 | 52.076 | 1.00 | 64.18 |
| 311 | CD1 | LEU | 566 | 29.685 | 3.195 | 50.565 | 1.00 | 61.46 |
| 312 | CD2 | LEU | 566 | 29.869 | 4.700 | 52.516 | 1.00 | 62.10 |
| 313 | C | LEU | 566 | 29.756 | 0.424 | 53.218 | 1.00 | 62.85 |
| 314 | O | LEU | 566 | 30.576 | −0.116 | 52.474 | 1.00 | 60.20 |
| 315 | N | GLY | 567 | 29.886 | 0.477 | 54.542 | 1.00 | 59.45 |
| 316 | CA | GLY | 567 | 31.040 | −0.095 | 55.207 | 1.00 | 59.94 |
| 317 | C | GLY | 567 | 31.316 | −1.516 | 54.768 | 1.00 | 60.71 |
| 318 | O | GLY | 567 | 32.461 | −1.890 | 54.520 | 1.00 | 59.79 |
| 319 | N | GLY | 568 | 30.261 | −2.310 | 54.667 | 1.00 | 61.99 |
| 320 | CA | GLY | 568 | 30.417 | −3.687 | 54.254 | 1.00 | 59.73 |
| 321 | C | GLY | 568 | 31.050 | −3.836 | 52.888 | 1.00 | 60.65 |
| 322 | O | GLY | 568 | 32.008 | −4.590 | 52.724 | 1.00 | 63.15 |
| 323 | N | ARG | 569 | 30.529 | −3.112 | 51.907 | 1.00 | 58.99 |
| 324 | CA | ARG | 569 | 31.049 | −3.208 | 50.557 | 1.00 | 60.81 |
| 325 | CB | ARG | 569 | 30.109 | −2.483 | 49.600 | 1.00 | 60.57 |
| 326 | CG | ARG | 569 | 28.696 | −3.029 | 49.701 | 1.00 | 61.60 |
| 327 | CD | ARG | 569 | 27.806 | −2.602 | 48.556 | 1.00 | 64.73 |
| 328 | NE | ARG | 569 | 27.561 | −1.168 | 48.564 | 1.00 | 61.17 |
| 329 | CZ | ARG | 569 | 27.939 | −0.352 | 47.590 | 1.00 | 60.00 |
| 330 | NH1 | ARG | 569 | 28.577 | −0.841 | 46.532 | 1.00 | 60.46 |
| 331 | NH2 | ARG | 569 | 27.681 | 0.946 | 47.680 | 1.00 | 63.69 |
| 332 | C | ARG | 569 | 32.462 | −2.676 | 50.447 | 1.00 | 61.15 |
| 333 | O | ARG | 569 | 33.249 | −3.137 | 49.620 | 1.00 | 60.59 |
| 334 | N | GLN | 570 | 32.788 | −1.713 | 51.295 | 1.00 | 60.73 |
| 335 | CA | GLN | 570 | 34.123 | −1.132 | 51.300 | 1.00 | 62.31 |
| 336 | CB | GLN | 570 | 34.143 | 0.150 | 52.120 | 1.00 | 59.04 |
| 337 | CG | GLN | 570 | 33.608 | 1.361 | 51.417 | 1.00 | 62.03 |
| 338 | CD | GLN | 570 | 33.782 | 2.606 | 52.247 | 1.00 | 56.35 |
| 339 | OE1 | GLN | 570 | 33.460 | 3.698 | 51.801 | 1.00 | 62.86 |
| 340 | NE2 | GLN | 570 | 34.295 | 2.449 | 53.467 | 1.00 | 63.17 |
| 341 | C | GLN | 570 | 35.144 | −2.093 | 51.882 | 1.00 | 61.15 |
| 342 | O | GLN | 570 | 36.293 | −2.134 | 51.441 | 1.00 | 60.50 |
| 343 | N | VAL | 571 | 34.732 | −2.837 | 52.903 | 1.00 | 60.99 |
| 344 | CA | VAL | 571 | 35.615 | −3.792 | 53.554 | 1.00 | 61.91 |
| 345 | CB | VAL | 571 | 35.054 | −4.200 | 54.930 | 1.00 | 58.42 |
| 346 | CG1 | VAL | 571 | 35.822 | −5.393 | 55.485 | 1.00 | 61.27 |
| 347 | CG2 | VAL | 571 | 35.160 | −3.007 | 55.891 | 1.00 | 60.58 |
| 348 | C | VAL | 571 | 35.805 | −5.007 | 52.665 | 1.00 | 62.66 |
| 349 | O | VAL | 571 | 36.698 | −5.820 | 52.885 | 1.00 | 58.99 |
| 350 | N | ILE | 572 | 34.958 | −5.116 | 51.652 | 1.00 | 63.61 |
| 351 | CA | ILE | 572 | 35.042 | −6.206 | 50.695 | 1.00 | 63.76 |
| 352 | CB | ILE | 572 | 33.649 | −6.539 | 50.103 | 1.00 | 60.98 |
| 353 | CG2 | ILE | 572 | 33.794 | −7.443 | 48.883 | 1.00 | 63.63 |
| 354 | CG1 | ILE | 572 | 32.782 | −7.192 | 51.183 | 1.00 | 61.03 |
| 355 | CD1 | ILE | 572 | 31.346 | −7.366 | 50.801 | 1.00 | 62.17 |
| 356 | C | ILE | 572 | 35.999 | −5.772 | 49.589 | 1.00 | 60.35 |
| 357 | O | ILE | 572 | 36.733 | −6.587 | 49.042 | 1.00 | 62.13 |
| 358 | N | ALA | 573 | 35.984 | −4.481 | 49.265 | 1.00 | 62.76 |
| 359 | CA | ALA | 573 | 36.879 | −3.936 | 48.251 | 1.00 | 58.47 |
| 360 | CB | ALA | 573 | 36.502 | −2.496 | 47.940 | 1.00 | 61.48 |
| 361 | C | ALA | 573 | 38.271 | −3.997 | 48.872 | 1.00 | 61.14 |
| 362 | O | ALA | 573 | 39.294 | −4.088 | 48.180 | 1.00 | 60.46 |
| 363 | N | ALA | 574 | 38.273 | −3.964 | 50.200 | 1.00 | 60.84 |
| 364 | CA | ALA | 574 | 39.477 | −4.008 | 51.003 | 1.00 | 61.42 |
| 365 | CB | ALA | 574 | 39.098 | −3.888 | 52.465 | 1.00 | 60.18 |
| 366 | C | ALA | 574 | 40.294 | −5.282 | 50.771 | 1.00 | 58.96 |
| 367 | O | ALA | 574 | 41.506 | −5.217 | 50.518 | 1.00 | 61.38 |
| 368 | N | VAL | 575 | 39.631 | −6.435 | 50.861 | 1.00 | 59.99 |
| 369 | CA | VAL | 575 | 40.296 | −7.720 | 50.664 | 1.00 | 59.60 |
| 370 | CB | VAL | 575 | 39.309 | −8.898 | 50.732 | 1.00 | 56.06 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 371 | CG1 | VAL | 575 | 40.070 | −10.197 | 50.570 | 1.00 | 62.55 |
| 372 | CG2 | VAL | 575 | 38.547 | −8.880 | 52.057 | 1.00 | 63.34 |
| 373 | C | VAL | 575 | 41.009 | −7.779 | 49.318 | 1.00 | 60.96 |
| 374 | O | VAL | 575 | 42.222 | −7.981 | 49.264 | 1.00 | 62.47 |
| 375 | N | LYS | 576 | 40.265 | −7.584 | 48.236 | 1.00 | 59.97 |
| 376 | CA | LYS | 576 | 40.851 | −7.628 | 46.901 | 1.00 | 62.25 |
| 377 | CB | LYS | 576 | 39.770 | −7.391 | 45.860 | 1.00 | 60.99 |
| 378 | CG | LYS | 576 | 40.115 | −7.866 | 44.462 | 1.00 | 61.35 |
| 379 | CD | LYS | 576 | 38.905 | −7.708 | 43.568 | 1.00 | 63.13 |
| 380 | CE | LYS | 576 | 37.667 | −8.234 | 44.276 | 1.00 | 62.07 |
| 381 | NZ | LYS | 576 | 36.420 | −7.912 | 43.531 | 1.00 | 59.76 |
| 382 | C | LYS | 576 | 41.957 | −6.593 | 46.742 | 1.00 | 63.69 |
| 383 | O | LYS | 576 | 42.673 | −6.573 | 45.742 | 1.00 | 59.32 |
| 384 | N | TRP | 577 | 42.074 | −5.723 | 47.734 | 1.00 | 62.59 |
| 385 | CA | TRP | 577 | 43.091 | −4.694 | 47.734 | 1.00 | 62.15 |
| 386 | CB | TRP | 577 | 42.556 | −3.432 | 48.424 | 1.00 | 60.50 |
| 387 | CG | TRP | 577 | 43.620 | −2.458 | 48.780 | 1.00 | 63.03 |
| 388 | CD2 | TRP | 577 | 44.140 | −2.200 | 50.090 | 1.00 | 58.79 |
| 389 | CE2 | TRP | 577 | 45.189 | −1.272 | 49.945 | 1.00 | 64.04 |
| 390 | CE3 | TRP | 577 | 43.824 | −2.668 | 51.372 | 1.00 | 60.56 |
| 391 | CD1 | TRP | 577 | 44.346 | −1.698 | 47.924 | 1.00 | 62.09 |
| 392 | NE1 | TRP | 577 | 45.293 | −0.983 | 48.611 | 1.00 | 61.93 |
| 393 | CZ2 | TRP | 577 | 45.930 | −0.798 | 51.032 | 1.00 | 61.40 |
| 394 | CZ3 | TRP | 577 | 44.566 | −2.197 | 52.458 | 1.00 | 59.59 |
| 395 | CH2 | TRP | 577 | 45.607 | −1.271 | 52.277 | 1.00 | 61.92 |
| 396 | C | TRP | 577 | 44.263 | −5.272 | 48.509 | 1.00 | 64.09 |
| 397 | O | TRP | 577 | 45.403 | −5.238 | 48.055 | 1.00 | 61.89 |
| 398 | N | ALA | 578 | 43.958 | −5.824 | 49.678 | 1.00 | 60.10 |
| 399 | CA | ALA | 578 | 44.974 | −6.411 | 50.541 | 1.00 | 61.99 |
| 400 | CB | ALA | 578 | 44.342 | −6.937 | 51.828 | 1.00 | 57.97 |
| 401 | C | ALA | 578 | 45.704 | −7.526 | 49.828 | 1.00 | 61.84 |
| 402 | O | ALA | 578 | 46.890 | −7.718 | 50.034 | 1.00 | 60.47 |
| 403 | N | LYS | 579 | 44.988 | −8.251 | 48.979 | 1.00 | 61.79 |
| 404 | CA | LYS | 579 | 45.573 | −9.354 | 48.233 | 1.00 | 60.65 |
| 405 | CB | LYS | 579 | 44.472 | −10.320 | 47.784 | 1.00 | 62.20 |
| 406 | CG | LYS | 579 | 43.479 | −10.656 | 48.893 | 1.00 | 63.14 |
| 407 | CD | LYS | 579 | 42.688 | −11.944 | 48.636 | 1.00 | 58.27 |
| 408 | CE | LYS | 579 | 41.775 | −11.862 | 47.419 | 1.00 | 58.47 |
| 409 | NZ | LYS | 579 | 41.093 | −13.167 | 47.129 | 1.00 | 62.99 |
| 410 | C | LYS | 579 | 46.389 | −8.895 | 47.024 | 1.00 | 61.02 |
| 411 | O | LYS | 579 | 47.014 | −9.713 | 46.356 | 1.00 | 63.16 |
| 412 | N | ALA | 580 | 46.383 | −7.596 | 46.738 | 1.00 | 61.84 |
| 413 | CA | ALA | 580 | 47.153 | −7.079 | 45.610 | 1.00 | 58.94 |
| 414 | CB | ALA | 580 | 46.339 | −6.062 | 44.817 | 1.00 | 61.14 |
| 415 | C | ALA | 580 | 48.439 | −6.446 | 46.137 | 1.00 | 60.40 |
| 416 | O | ALA | 580 | 49.378 | −6.190 | 45.374 | 1.00 | 60.45 |
| 417 | N | ILE | 581 | 48.465 | −6.197 | 47.445 | 1.00 | 60.82 |
| 418 | CA | ILE | 581 | 49.631 | −5.631 | 48.111 | 1.00 | 60.29 |
| 419 | CB | ILE | 581 | 49.375 | −5.412 | 49.630 | 1.00 | 58.24 |
| 420 | CG2 | ILE | 581 | 50.654 | −4.997 | 50.324 | 1.00 | 63.40 |
| 421 | CG1 | ILE | 581 | 48.295 | −4.353 | 49.847 | 1.00 | 62.12 |
| 422 | CD1 | ILE | 581 | 47.769 | −4.324 | 51.257 | 1.00 | 62.13 |
| 423 | C | ILE | 581 | 50.690 | −6.706 | 47.965 | 1.00 | 62.02 |
| 424 | O | ILE | 581 | 50.541 | −7.805 | 48.500 | 1.00 | 61.29 |
| 425 | N | PRO | 582 | 51.773 | −6.412 | 47.233 | 1.00 | 62.24 |
| 426 | CD | PRO | 582 | 52.137 | −5.123 | 46.623 | 1.00 | 61.16 |
| 427 | CA | PRO | 582 | 52.837 | −7.397 | 47.041 | 1.00 | 64.30 |
| 428 | CB | PRO | 582 | 53.983 | −6.563 | 46.486 | 1.00 | 61.32 |
| 429 | CG | PRO | 582 | 53.294 | −5.515 | 45.720 | 1.00 | 57.84 |
| 430 | C | PRO | 582 | 53.208 | −8.082 | 48.341 | 1.00 | 62.26 |
| 431 | O | PRO | 582 | 53.291 | −7.451 | 49.390 | 1.00 | 61.55 |
| 432 | N | GLY | 583 | 53.413 | −9.386 | 48.268 | 1.00 | 60.04 |
| 433 | CA | GLY | 583 | 53.788 | −10.138 | 49.447 | 1.00 | 63.24 |
| 434 | C | GLY | 583 | 52.721 | −10.313 | 50.509 | 1.00 | 58.28 |
| 435 | O | GLY | 583 | 52.976 | −10.962 | 51.519 | 1.00 | 61.03 |
| 436 | N | PHE | 584 | 51.527 | −9.758 | 50.320 | 1.00 | 59.53 |
| 437 | CA | PHE | 584 | 50.517 | −9.932 | 51.354 | 1.00 | 60.33 |
| 438 | CB | PHE | 584 | 49.356 | −8.960 | 51.200 | 1.00 | 59.83 |
| 439 | CG | PHE | 584 | 48.314 | −9.107 | 52.276 | 1.00 | 62.69 |
| 440 | CD1 | PHE | 584 | 48.583 | −8.699 | 53.576 | 1.00 | 65.80 |
| 441 | CD2 | PHE | 584 | 47.075 | −9.677 | 52.000 | 1.00 | 59.15 |
| 442 | CE1 | PHE | 584 | 47.636 | −8.854 | 54.586 | 1.00 | 63.90 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 443 | CE2 | PHE | 584 | 46.123 | −9.837 | 53.000 | 1.00 | 62.77 |
| 444 | CZ | PHE | 584 | 46.405 | −9.423 | 54.296 | 1.00 | 62.23 |
| 445 | C | PHE | 584 | 49.960 | −11.336 | 51.359 | 1.00 | 59.87 |
| 446 | O | PHE | 584 | 49.874 | −11.967 | 52.415 | 1.00 | 60.23 |
| 447 | N | ARG | 585 | 49.584 | −11.848 | 50.193 | 1.00 | 61.22 |
| 448 | CA | ARG | 585 | 49.021 | −13.183 | 50.207 | 1.00 | 62.87 |
| 449 | CB | ARG | 585 | 48.025 | −13.405 | 49.042 | 1.00 | 61.05 |
| 450 | CG | ARG | 585 | 48.486 | −13.212 | 47.602 | 1.00 | 62.14 |
| 451 | CD | ARG | 585 | 47.253 | −13.326 | 46.690 | 1.00 | 59.51 |
| 452 | NE | ARG | 585 | 46.321 | −14.325 | 47.226 | 1.00 | 57.83 |
| 453 | CZ | ARG | 585 | 45.253 | −14.826 | 46.592 | 1.00 | 62.40 |
| 454 | NH1 | ARG | 585 | 44.934 | −14.430 | 45.360 | 1.00 | 64.51 |
| 455 | NH2 | ARG | 585 | 44.509 | −15.752 | 47.194 | 1.00 | 62.15 |
| 456 | C | ARG | 585 | 50.053 | −14.290 | 50.303 | 1.00 | 61.04 |
| 457 | O | ARG | 585 | 49.781 | −15.436 | 49.962 | 1.00 | 59.18 |
| 458 | N | ASN | 586 | 51.232 | −13.935 | 50.811 | 1.00 | 59.32 |
| 459 | CA | ASN | 586 | 52.319 | −14.893 | 51.021 | 1.00 | 62.11 |
| 460 | CB | ASN | 586 | 53.659 | −14.329 | 50.545 | 1.00 | 57.88 |
| 461 | CG | ASN | 586 | 53.910 | −14.596 | 49.071 | 1.00 | 62.73 |
| 462 | OD1 | ASN | 586 | 54.772 | −13.964 | 48.450 | 1.00 | 64.87 |
| 463 | ND2 | ASN | 586 | 53.164 | −15.551 | 48.504 | 1.00 | 63.32 |
| 464 | C | ASN | 586 | 52.396 | −15.218 | 52.503 | 1.00 | 61.24 |
| 465 | O | ASN | 586 | 53.093 | −16.138 | 52.916 | 1.00 | 62.45 |
| 466 | N | LEU | 587 | 51.692 | −14.446 | 53.314 | 1.00 | 62.98 |
| 467 | CA | LEU | 587 | 51.677 | −14.732 | 54.735 | 1.00 | 63.89 |
| 468 | CB | LEU | 587 | 51.210 | −13.502 | 55.522 | 1.00 | 63.58 |
| 469 | CG | LEU | 587 | 52.163 | −12.299 | 55.501 | 1.00 | 63.59 |
| 470 | CD1 | LEU | 587 | 51.405 | −11.009 | 55.348 | 1.00 | 58.78 |
| 471 | CD2 | LEU | 587 | 52.967 | −12.280 | 56.773 | 1.00 | 60.86 |
| 472 | C | LEU | 587 | 50.679 | −15.879 | 54.848 | 1.00 | 61.92 |
| 473 | O | LEU | 587 | 50.000 | −16.209 | 53.865 | 1.00 | 61.57 |
| 474 | N | HIS | 588 | 50.598 | −16.497 | 56.024 | 1.00 | 57.84 |
| 475 | CA | HIS | 588 | 49.676 | −17.609 | 56.235 | 1.00 | 62.30 |
| 476 | CB | HIS | 588 | 49.674 | −18.016 | 57.710 | 1.00 | 63.47 |
| 477 | CG | HIS | 588 | 49.180 | −19.411 | 57.962 | 1.00 | 62.99 |
| 478 | CD2 | HIS | 588 | 49.817 | −20.502 | 58.447 | 1.00 | 58.47 |
| 479 | ND1 | HIS | 588 | 47.886 | −19.808 | 57.705 | 1.00 | 57.63 |
| 480 | CE1 | HIS | 588 | 47.748 | −21.083 | 58.021 | 1.00 | 60.07 |
| 481 | NE2 | HIS | 588 | 48.905 | −21.527 | 58.474 | 1.00 | 61.65 |
| 482 | C | HIS | 588 | 48.304 | −17.100 | 55.839 | 1.00 | 61.24 |
| 483 | O | HIS | 588 | 48.137 | −15.900 | 55.641 | 1.00 | 58.81 |
| 484 | N | LEU | 589 | 47.325 | −17.990 | 55.714 | 1.00 | 60.37 |
| 485 | CA | LEU | 589 | 45.990 | −17.542 | 55.346 | 1.00 | 63.23 |
| 486 | CB | LEU | 589 | 45.219 | −18.626 | 54.588 | 1.00 | 60.24 |
| 487 | CG | LEU | 589 | 44.233 | −18.127 | 53.516 | 1.00 | 59.80 |
| 488 | CD1 | LEU | 589 | 43.798 | −19.286 | 52.630 | 1.00 | 65.35 |
| 489 | CD2 | LEU | 589 | 43.025 | −17.486 | 54.148 | 1.00 | 61.31 |
| 490 | C | LEU | 589 | 45.249 | −17.184 | 56.616 | 1.00 | 59.85 |
| 491 | O | LEU | 589 | 44.150 | −16.645 | 56.563 | 1.00 | 59.20 |
| 492 | N | ASP | 590 | 45.852 | −17.469 | 57.763 | 1.00 | 60.93 |
| 493 | CA | ASP | 590 | 45.200 | −17.158 | 59.027 | 1.00 | 61.82 |
| 494 | CB | ASP | 590 | 45.551 | −18.204 | 60.097 | 1.00 | 62.69 |
| 495 | CG | ASP | 590 | 44.823 | −19.529 | 59.898 | 1.00 | 58.29 |
| 496 | OD1 | ASP | 590 | 44.642 | −19.955 | 58.738 | 1.00 | 59.06 |
| 497 | OD2 | ASP | 590 | 44.447 | −20.159 | 60.910 | 1.00 | 64.34 |
| 498 | C | ASP | 590 | 45.608 | −15.771 | 59.504 | 1.00 | 59.77 |
| 499 | O | ASP | 590 | 44.915 | −15.153 | 60.314 | 1.00 | 60.73 |
| 500 | N | ASP | 591 | 46.734 | −15.278 | 59.001 | 1.00 | 59.62 |
| 501 | CA | ASP | 591 | 47.211 | −13.960 | 59.401 | 1.00 | 61.48 |
| 502 | CB | ASP | 591 | 48.733 | −13.861 | 59.240 | 1.00 | 60.79 |
| 503 | CG | ASP | 591 | 49.479 | −14.900 | 60.065 | 1.00 | 57.79 |
| 504 | OD1 | ASP | 591 | 49.012 | −15.239 | 61.176 | 1.00 | 66.77 |
| 505 | OD2 | ASP | 591 | 50.543 | −15.366 | 59.606 | 1.00 | 65.51 |
| 506 | C | ASP | 591 | 46.531 | −12.927 | 58.529 | 1.00 | 62.56 |
| 507 | O | ASP | 591 | 46.255 | −11.812 | 58.967 | 1.00 | 59.26 |
| 508 | N | GLN | 592 | 46.278 | −13.323 | 57.285 | 1.00 | 62.10 |
| 509 | CA | GLN | 592 | 45.613 | −12.473 | 56.316 | 1.00 | 61.30 |
| 510 | CB | GLN | 592 | 45.432 | −13.227 | 54.998 | 1.00 | 62.26 |
| 511 | CG | GLN | 592 | 46.751 | −13.456 | 54.277 | 1.00 | 60.59 |
| 512 | CD | GLN | 592 | 46.595 | −14.100 | 52.909 | 1.00 | 59.32 |
| 513 | OE1 | GLN | 592 | 45.597 | −13.887 | 52.213 | 1.00 | 62.27 |
| 514 | NE2 | GLN | 592 | 47.600 | −14.875 | 52.505 | 1.00 | 62.12 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 515 | C | GLN | 592 | 44.269 | −12.097 | 56.906 | 1.00 | 64.75 |
| 516 | O | GLN | 592 | 43.768 | −10.993 | 56.706 | 1.00 | 62.08 |
| 517 | N | MET | 593 | 43.701 | −13.028 | 57.660 | 1.00 | 59.14 |
| 518 | CA | MET | 593 | 42.413 | −12.815 | 58.302 | 1.00 | 61.78 |
| 519 | CB | MET | 593 | 41.740 | −14.162 | 58.597 | 1.00 | 58.91 |
| 520 | CG | MET | 593 | 41.290 | −14.935 | 57.357 | 1.00 | 64.30 |
| 521 | SD | MET | 593 | 40.510 | −16.524 | 57.776 | 1.00 | 58.06 |
| 522 | CE | MET | 593 | 39.514 | −16.029 | 59.273 | 1.00 | 61.88 |
| 523 | C | MET | 593 | 42.571 | −12.014 | 59.594 | 1.00 | 61.38 |
| 524 | O | MET | 593 | 41.802 | −11.089 | 59.837 | 1.00 | 60.42 |
| 525 | N | THR | 594 | 43.565 | −12.361 | 60.415 | 1.00 | 61.83 |
| 526 | CA | THR | 594 | 43.781 | −11.648 | 61.674 | 1.00 | 61.88 |
| 527 | CB | THR | 594 | 44.924 | −12.267 | 62.518 | 1.00 | 57.74 |
| 528 | OG1 | THR | 594 | 45.252 | −13.571 | 62.023 | 1.00 | 65.18 |
| 529 | CG2 | THR | 594 | 44.489 | −12.393 | 63.977 | 1.00 | 62.23 |
| 530 | C | THR | 594 | 44.127 | −10.194 | 61.378 | 1.00 | 62.61 |
| 531 | O | THR | 594 | 43.673 | −9.279 | 62.071 | 1.00 | 60.17 |
| 532 | N | LEU | 595 | 44.927 | −9.987 | 60.337 | 1.00 | 60.31 |
| 533 | CA | LEU | 595 | 45.325 | −8.647 | 59.938 | 1.00 | 61.48 |
| 534 | CB | LEU | 595 | 46.372 | −8.712 | 58.826 | 1.00 | 62.70 |
| 535 | CG | LEU | 595 | 47.788 | −9.074 | 59.266 | 1.00 | 60.61 |
| 536 | CD1 | LEU | 595 | 48.711 | −9.054 | 58.067 | 1.00 | 63.20 |
| 537 | CD2 | LEU | 595 | 48.268 | −8.083 | 60.316 | 1.00 | 62.58 |
| 538 | C | LEU | 595 | 44.128 | −7.823 | 59.475 | 1.00 | 63.38 |
| 539 | O | LEU | 595 | 43.835 | −6.779 | 60.051 | 1.00 | 60.70 |
| 540 | N | LEU | 596 | 43.439 | −8.290 | 58.436 | 1.00 | 60.66 |
| 541 | CA | LEU | 596 | 42.282 | −7.571 | 57.924 | 1.00 | 60.47 |
| 542 | CB | LEU | 596 | 41.703 | −8.278 | 56.699 | 1.00 | 60.10 |
| 543 | CG | LEU | 596 | 42.351 | −7.811 | 55.392 | 1.00 | 60.73 |
| 544 | CD1 | LEU | 596 | 42.036 | −8.767 | 54.254 | 1.00 | 59.40 |
| 545 | CD2 | LEU | 596 | 41.859 | −6.407 | 55.073 | 1.00 | 62.48 |
| 546 | C | LEU | 596 | 41.223 | −7.424 | 58.989 | 1.00 | 58.32 |
| 547 | O | LEU | 596 | 40.451 | −6.480 | 58.965 | 1.00 | 61.48 |
| 548 | N | GLN | 597 | 41.201 | −8.354 | 59.935 | 1.00 | 62.48 |
| 549 | CA | GLN | 597 | 40.230 | −8.327 | 61.031 | 1.00 | 64.28 |
| 550 | CB | GLN | 597 | 40.128 | −9.712 | 61.685 | 1.00 | 59.49 |
| 551 | CG | GLN | 597 | 38.936 | −10.561 | 61.279 | 1.00 | 64.66 |
| 552 | CD | GLN | 597 | 38.972 | −11.940 | 61.920 | 1.00 | 60.50 |
| 553 | OE1 | GLN | 597 | 39.080 | −12.078 | 63.149 | 1.00 | 60.07 |
| 554 | NE2 | GLN | 597 | 38.881 | −12.975 | 61.087 | 1.00 | 65.01 |
| 555 | C | GLN | 597 | 40.612 | −7.314 | 62.110 | 1.00 | 61.61 |
| 556 | O | GLN | 597 | 39.780 | −6.933 | 62.932 | 1.00 | 61.06 |
| 557 | N | TYR | 598 | 41.875 | −6.896 | 62.097 | 1.00 | 64.61 |
| 558 | CA | TYR | 598 | 42.418 | −5.958 | 63.075 | 1.00 | 60.76 |
| 559 | CB | TYR | 598 | 43.761 | −6.468 | 63.588 | 1.00 | 59.35 |
| 560 | CG | TYR | 598 | 43.692 | −7.564 | 64.613 | 1.00 | 63.67 |
| 561 | CD1 | TYR | 598 | 42.509 | −8.257 | 64.850 | 1.00 | 61.84 |
| 562 | CE1 | TYR | 598 | 42.451 | −9.262 | 65.812 | 1.00 | 61.13 |
| 563 | CD2 | TYR | 598 | 44.820 | −7.906 | 65.358 | 1.00 | 61.13 |
| 564 | CE2 | TYR | 598 | 44.774 | −8.915 | 66.322 | 1.00 | 62.04 |
| 565 | CZ | TYR | 598 | 43.588 | −9.583 | 66.544 | 1.00 | 60.04 |
| 566 | OH | TYR | 598 | 43.536 | −10.549 | 67.519 | 1.00 | 62.57 |
| 567 | C | TYR | 598 | 42.639 | −4.553 | 62.549 | 1.00 | 62.24 |
| 568 | O | TYR | 598 | 43.158 | −3.690 | 63.256 | 1.00 | 61.45 |
| 569 | N | SER | 599 | 42.278 | −4.312 | 61.305 | 1.00 | 58.28 |
| 570 | CA | SER | 599 | 42.491 | −2.988 | 60.774 | 1.00 | 62.69 |
| 571 | CB | SER | 599 | 43.837 | −2.949 | 60.046 | 1.00 | 62.55 |
| 572 | OG | SER | 599 | 44.008 | −4.083 | 59.216 | 1.00 | 62.72 |
| 573 | C | SER | 599 | 41.365 | −2.525 | 59.867 | 1.00 | 64.40 |
| 574 | O | SER | 599 | 41.398 | −1.405 | 59.367 | 1.00 | 62.40 |
| 575 | N | TRP | 600 | 40.358 | −3.375 | 59.677 | 1.00 | 59.48 |
| 576 | CA | TRP | 600 | 39.245 | −3.026 | 58.807 | 1.00 | 62.88 |
| 577 | CB | TRP | 600 | 38.073 | −4.031 | 58.932 | 1.00 | 64.17 |
| 578 | CG | TRP | 600 | 37.282 | −3.951 | 60.198 | 1.00 | 62.02 |
| 579 | CD2 | TRP | 600 | 36.105 | −3.166 | 60.420 | 1.00 | 58.67 |
| 580 | CE2 | TRP | 600 | 35.754 | −3.311 | 61.781 | 1.00 | 61.68 |
| 581 | CE3 | TRP | 600 | 35.314 | −2.350 | 59.603 | 1.00 | 62.68 |
| 582 | CD1 | TRP | 600 | 37.583 | −4.533 | 61.395 | 1.00 | 58.92 |
| 583 | NE1 | TRP | 600 | 36.672 | −4.151 | 62.355 | 1.00 | 64.28 |
| 584 | CZ2 | TRP | 600 | 34.648 | −2.666 | 62.342 | 1.00 | 61.17 |
| 585 | CZ3 | TRP | 600 | 34.217 | −1.711 | 60.159 | 1.00 | 58.94 |
| 586 | CH2 | TRP | 600 | 33.894 | −1.871 | 61.516 | 1.00 | 61.08 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 587 | C | TRP | 600 | 38.789 | −1.630 | 59.169 | 1.00 | 62.61 |
| 588 | O | TRP | 600 | 38.533 | −0.805 | 58.308 | 1.00 | 62.45 |
| 589 | N | MET | 601 | 38.744 | −1.344 | 60.458 | 1.00 | 63.90 |
| 590 | CA | MET | 601 | 38.298 | −0.049 | 60.884 | 1.00 | 60.96 |
| 591 | CB | MET | 601 | 37.968 | −0.064 | 62.351 | 1.00 | 60.46 |
| 592 | CG | MET | 601 | 37.139 | 1.112 | 62.702 | 1.00 | 61.28 |
| 593 | SD | MET | 601 | 35.774 | 1.420 | 61.631 | 1.00 | 59.33 |
| 594 | CE | MET | 601 | 34.684 | 1.638 | 62.889 | 1.00 | 64.63 |
| 595 | C | MET | 601 | 39.225 | 1.129 | 60.577 | 1.00 | 61.08 |
| 596 | O | MET | 601 | 38.758 | 2.167 | 60.114 | 1.00 | 60.27 |
| 597 | N | SER | 602 | 40.521 | 0.979 | 60.854 | 1.00 | 61.23 |
| 598 | CA | SER | 602 | 41.488 | 2.035 | 60.581 | 1.00 | 59.98 |
| 599 | CB | SER | 602 | 42.872 | 1.647 | 61.083 | 1.00 | 60.99 |
| 600 | OG | SER | 602 | 42.783 | 1.022 | 62.350 | 1.00 | 66.17 |
| 601 | C | SER | 602 | 41.536 | 2.214 | 59.079 | 1.00 | 60.99 |
| 602 | O | SER | 602 | 41.609 | 3.327 | 58.581 | 1.00 | 64.11 |
| 603 | N | LEU | 603 | 41.494 | 1.108 | 58.351 | 1.00 | 59.44 |
| 604 | CA | LEU | 603 | 41.522 | 1.185 | 56.901 | 1.00 | 61.46 |
| 605 | CB | LEU | 603 | 41.402 | −0.212 | 56.280 | 1.00 | 59.31 |
| 606 | CG | LEU | 603 | 42.646 | −1.097 | 56.346 | 1.00 | 61.54 |
| 607 | CD1 | LEU | 603 | 42.415 | −2.362 | 55.549 | 1.00 | 63.99 |
| 608 | CD2 | LEU | 603 | 43.828 | −0.346 | 55.787 | 1.00 | 63.36 |
| 609 | C | LEU | 603 | 40.386 | 2.061 | 56.408 | 1.00 | 60.47 |
| 610 | O | LEU | 603 | 40.599 | 3.062 | 55.731 | 1.00 | 63.39 |
| 611 | N | MET | 604 | 39.173 | 1.688 | 56.784 | 1.00 | 63.54 |
| 612 | CA | MET | 604 | 38.000 | 2.417 | 56.365 | 1.00 | 62.81 |
| 613 | CB | MET | 604 | 36.770 | 1.623 | 56.723 | 1.00 | 58.90 |
| 614 | CG | MET | 604 | 36.632 | 0.429 | 55.842 | 1.00 | 59.86 |
| 615 | SD | MET | 604 | 37.633 | 0.438 | 54.374 | 1.00 | 62.53 |
| 616 | CE | MET | 604 | 36.663 | −0.510 | 53.559 | 1.00 | 60.72 |
| 617 | C | MET | 604 | 37.898 | 3.832 | 56.856 | 1.00 | 60.43 |
| 618 | O | MET | 604 | 37.397 | 4.695 | 56.132 | 1.00 | 62.37 |
| 619 | N | ALA | 605 | 38.375 | 4.076 | 58.072 | 1.00 | 59.95 |
| 620 | CA | ALA | 605 | 38.357 | 5.409 | 58.664 | 1.00 | 60.49 |
| 621 | CB | ALA | 605 | 38.667 | 5.317 | 60.132 | 1.00 | 59.15 |
| 622 | C | ALA | 605 | 39.381 | 6.309 | 57.985 | 1.00 | 61.50 |
| 623 | O | ALA | 605 | 39.071 | 7.427 | 57.583 | 1.00 | 59.82 |
| 624 | N | PHE | 606 | 40.608 | 5.810 | 57.870 | 1.00 | 63.59 |
| 625 | CA | PHE | 606 | 41.700 | 6.554 | 57.258 | 1.00 | 60.15 |
| 626 | CB | PHE | 606 | 42.981 | 5.713 | 57.285 | 1.00 | 63.75 |
| 627 | CG | PHE | 606 | 44.237 | 6.490 | 56.999 | 1.00 | 64.30 |
| 628 | CD1 | PHE | 606 | 44.723 | 7.424 | 57.913 | 1.00 | 61.77 |
| 629 | CD2 | PHE | 606 | 44.957 | 6.265 | 55.829 | 1.00 | 60.74 |
| 630 | CE1 | PHE | 606 | 45.910 | 8.118 | 57.665 | 1.00 | 64.00 |
| 631 | CE2 | PHE | 606 | 46.145 | 6.955 | 55.575 | 1.00 | 62.47 |
| 632 | CZ | PHE | 606 | 46.620 | 7.879 | 56.496 | 1.00 | 63.95 |
| 633 | C | PHE | 606 | 41.362 | 6.933 | 55.825 | 1.00 | 61.96 |
| 634 | O | PHE | 606 | 41.751 | 7.991 | 55.356 | 1.00 | 60.07 |
| 635 | N | ALA | 607 | 40.644 | 6.063 | 55.126 | 1.00 | 62.00 |
| 636 | CA | ALA | 607 | 40.264 | 6.338 | 53.745 | 1.00 | 57.50 |
| 637 | CB | ALA | 607 | 39.888 | 5.051 | 53.039 | 1.00 | 59.69 |
| 638 | C | ALA | 607 | 39.105 | 7.324 | 53.684 | 1.00 | 64.88 |
| 639 | O | ALA | 607 | 38.931 | 8.030 | 52.703 | 1.00 | 59.60 |
| 640 | N | LEU | 608 | 38.292 | 7.361 | 54.723 | 1.00 | 59.93 |
| 641 | CA | LEU | 608 | 37.196 | 8.307 | 54.725 | 1.00 | 61.70 |
| 642 | CB | LEU | 608 | 36.222 | 7.972 | 55.883 | 1.00 | 59.57 |
| 643 | CG | LEU | 608 | 35.125 | 8.918 | 56.402 | 1.00 | 62.57 |
| 644 | CD1 | LEU | 608 | 34.229 | 9.360 | 55.287 | 1.00 | 63.51 |
| 645 | CD2 | LEU | 608 | 34.298 | 8.246 | 57.488 | 1.00 | 59.98 |
| 646 | C | LEU | 608 | 37.862 | 9.662 | 54.935 | 1.00 | 61.71 |
| 647 | O | LEU | 608 | 37.500 | 10.645 | 54.294 | 1.00 | 57.56 |
| 648 | N | GLY | 609 | 38.869 | 9.692 | 55.806 | 1.00 | 59.60 |
| 649 | CA | GLY | 609 | 39.583 | 10.920 | 56.086 | 1.00 | 60.49 |
| 650 | C | GLY | 609 | 40.232 | 11.505 | 54.850 | 1.00 | 59.17 |
| 651 | O | GLY | 609 | 40.189 | 12.710 | 54.625 | 1.00 | 61.65 |
| 652 | N | TRP | 610 | 40.835 | 10.650 | 54.039 | 1.00 | 62.47 |
| 653 | CA | TRP | 610 | 41.488 | 11.102 | 52.823 | 1.00 | 61.40 |
| 654 | CB | TRP | 610 | 42.141 | 9.917 | 52.123 | 1.00 | 62.68 |
| 655 | CG | TRP | 610 | 42.744 | 10.264 | 50.817 | 1.00 | 62.61 |
| 656 | CD2 | TRP | 610 | 43.955 | 10.991 | 50.604 | 1.00 | 61.10 |
| 657 | CE2 | TRP | 610 | 44.139 | 11.095 | 49.209 | 1.00 | 62.45 |
| 658 | CE3 | TRP | 610 | 44.906 | 11.565 | 51.457 | 1.00 | 63.78 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 659 | CD1 | TRP | 610 | 42.254 | 9.965 | 49.582 | 1.00 | 58.08 |
| 660 | NE1 | TRP | 610 | 43.086 | 10.459 | 48.608 | 1.00 | 62.17 |
| 661 | CZ2 | TRP | 610 | 45.238 | 11.751 | 48.646 | 1.00 | 60.53 |
| 662 | CZ3 | TRP | 610 | 46.001 | 12.219 | 50.896 | 1.00 | 62.27 |
| 663 | CH2 | TRP | 610 | 46.156 | 12.305 | 49.505 | 1.00 | 60.31 |
| 664 | C | TRP | 610 | 40.517 | 11.797 | 51.874 | 1.00 | 60.80 |
| 665 | O | TRP | 610 | 40.797 | 12.866 | 51.358 | 1.00 | 60.72 |
| 666 | N | ARG | 611 | 39.368 | 11.191 | 51.639 | 1.00 | 61.36 |
| 667 | CA | ARG | 611 | 38.412 | 11.790 | 50.738 | 1.00 | 58.33 |
| 668 | CB | ARG | 611 | 37.254 | 10.817 | 50.486 | 1.00 | 62.33 |
| 669 | CG | ARG | 611 | 37.684 | 9.490 | 49.873 | 1.00 | 60.18 |
| 670 | CD | ARG | 611 | 36.476 | 8.686 | 49.426 | 1.00 | 59.83 |
| 671 | NE | ARG | 611 | 35.604 | 8.333 | 50.544 | 1.00 | 61.17 |
| 672 | CZ | ARG | 611 | 35.817 | 7.308 | 51.366 | 1.00 | 59.54 |
| 673 | NH1 | ARG | 611 | 36.875 | 6.528 | 51.187 | 1.00 | 61.47 |
| 674 | NH2 | ARG | 611 | 34.988 | 7.072 | 52.376 | 1.00 | 62.25 |
| 675 | C | ARG | 611 | 37.898 | 13.128 | 51.277 | 1.00 | 62.93 |
| 676 | O | ARG | 611 | 37.610 | 14.051 | 50.502 | 1.00 | 61.13 |
| 677 | N | SER | 612 | 37.806 | 13.234 | 52.603 | 1.00 | 60.26 |
| 678 | CA | SER | 612 | 37.321 | 14.450 | 53.263 | 1.00 | 63.90 |
| 679 | CB | SER | 612 | 37.057 | 14.172 | 54.736 | 1.00 | 62.00 |
| 680 | OG | SER | 612 | 36.011 | 13.234 | 54.875 | 1.00 | 59.62 |
| 681 | C | SER | 612 | 38.263 | 15.637 | 53.137 | 1.00 | 61.68 |
| 682 | O | SER | 612 | 37.831 | 16.776 | 52.975 | 1.00 | 59.32 |
| 683 | N | TYR | 613 | 39.552 | 15.352 | 53.226 | 1.00 | 64.48 |
| 684 | CA | TYR | 613 | 40.600 | 16.351 | 53.111 | 1.00 | 60.97 |
| 685 | CB | TYR | 613 | 41.920 | 15.725 | 53.587 | 1.00 | 56.65 |
| 686 | CG | TYR | 613 | 43.169 | 16.122 | 52.830 | 1.00 | 60.73 |
| 687 | CD1 | TYR | 613 | 43.569 | 17.456 | 52.746 | 1.00 | 64.60 |
| 688 | CE1 | TYR | 613 | 44.737 | 17.812 | 52.086 | 1.00 | 60.79 |
| 689 | CD2 | TYR | 613 | 43.971 | 15.153 | 52.229 | 1.00 | 61.29 |
| 690 | CE2 | TYR | 613 | 45.142 | 15.500 | 51.564 | 1.00 | 63.40 |
| 691 | CZ | TYR | 613 | 45.522 | 16.830 | 51.497 | 1.00 | 61.75 |
| 692 | OH | TYR | 613 | 46.690 | 17.173 | 50.854 | 1.00 | 62.46 |
| 693 | C | TYR | 613 | 40.712 | 16.822 | 51.667 | 1.00 | 62.41 |
| 694 | O | TYR | 613 | 40.954 | 17.996 | 51.395 | 1.00 | 61.34 |
| 695 | N | ARG | 614 | 40.511 | 15.896 | 50.745 | 1.00 | 61.73 |
| 696 | CA | ARG | 614 | 40.623 | 16.190 | 49.328 | 1.00 | 61.64 |
| 697 | CB | ARG | 614 | 40.835 | 14.880 | 48.545 | 1.00 | 62.80 |
| 698 | CG | ARG | 614 | 42.274 | 14.328 | 48.621 | 1.00 | 58.30 |
| 699 | CD | ARG | 614 | 42.908 | 14.348 | 47.242 | 1.00 | 60.57 |
| 700 | NE | ARG | 614 | 44.369 | 14.448 | 47.262 | 1.00 | 61.63 |
| 701 | CZ | ARG | 614 | 45.056 | 15.421 | 47.868 | 1.00 | 63.66 |
| 702 | NH1 | ARG | 614 | 44.414 | 16.386 | 48.521 | 1.00 | 61.59 |
| 703 | NH2 | ARG | 614 | 46.389 | 15.451 | 47.797 | 1.00 | 64.70 |
| 704 | C | ARG | 614 | 39.440 | 16.960 | 48.776 | 1.00 | 58.09 |
| 705 | O | ARG | 614 | 39.613 | 17.922 | 48.041 | 1.00 | 63.07 |
| 706 | N | GLN | 615 | 38.239 | 16.538 | 49.137 | 1.00 | 64.09 |
| 707 | CA | GLN | 615 | 37.033 | 17.192 | 48.660 | 1.00 | 61.67 |
| 708 | CB | GLN | 615 | 35.840 | 16.259 | 48.801 | 1.00 | 62.84 |
| 709 | CG | GLN | 615 | 35.738 | 15.162 | 47.795 | 1.00 | 62.14 |
| 710 | CD | GLN | 615 | 34.290 | 14.775 | 47.573 | 1.00 | 58.76 |
| 711 | OE1 | GLN | 615 | 33.532 | 14.598 | 48.525 | 1.00 | 62.70 |
| 712 | NE2 | GLN | 615 | 33.897 | 14.651 | 46.314 | 1.00 | 61.03 |
| 713 | C | GLN | 615 | 36.677 | 18.478 | 49.396 | 1.00 | 59.82 |
| 714 | O | GLN | 615 | 36.200 | 19.441 | 48.784 | 1.00 | 60.64 |
| 715 | N | SER | 616 | 36.901 | 18.480 | 50.709 | 1.00 | 62.12 |
| 716 | CA | SER | 616 | 36.522 | 19.615 | 51.545 | 1.00 | 62.52 |
| 717 | CB | SER | 616 | 35.199 | 19.297 | 52.239 | 1.00 | 61.86 |
| 718 | OG | SER | 616 | 35.408 | 18.310 | 53.240 | 1.00 | 59.96 |
| 719 | C | SER | 616 | 37.514 | 20.090 | 52.612 | 1.00 | 61.77 |
| 720 | O | SER | 616 | 37.110 | 20.501 | 53.703 | 1.00 | 63.13 |
| 721 | N | SER | 617 | 38.804 | 20.026 | 52.321 | 1.00 | 59.65 |
| 722 | CA | SER | 617 | 39.796 | 20.502 | 53.279 | 1.00 | 60.19 |
| 723 | CB | SER | 617 | 39.818 | 22.033 | 53.253 | 1.00 | 60.71 |
| 724 | OG | SER | 617 | 39.578 | 22.511 | 51.942 | 1.00 | 63.01 |
| 725 | C | SER | 617 | 39.569 | 20.029 | 54.724 | 1.00 | 59.81 |
| 726 | O | SER | 617 | 40.164 | 20.577 | 55.654 | 1.00 | 63.66 |
| 727 | N | ALA | 618 | 38.700 | 19.036 | 54.903 | 1.00 | 64.87 |
| 728 | CA | ALA | 618 | 38.393 | 18.444 | 56.210 | 1.00 | 62.57 |
| 729 | CB | ALA | 618 | 39.673 | 18.327 | 57.064 | 1.00 | 60.83 |
| 730 | C | ALA | 618 | 37.277 | 19.059 | 57.053 | 1.00 | 59.66 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 731 | O | ALA | 618 | 37.238 | 18.817 | 58.260 | 1.00 | 60.80 |
| 732 | N | ASN | 619 | 36.375 | 19.839 | 56.451 | 1.00 | 63.98 |
| 733 | CA | ASN | 619 | 35.262 | 20.411 | 57.227 | 1.00 | 61.08 |
| 734 | CB | ASN | 619 | 35.129 | 21.934 | 57.042 | 1.00 | 61.69 |
| 735 | CG | ASN | 619 | 35.946 | 22.453 | 55.912 | 1.00 | 62.23 |
| 736 | OD1 | ASN | 619 | 35.664 | 22.172 | 54.751 | 1.00 | 61.72 |
| 737 | ND2 | ASN | 619 | 36.980 | 23.217 | 56.239 | 1.00 | 61.09 |
| 738 | C | ASN | 619 | 33.907 | 19.755 | 56.958 | 1.00 | 60.70 |
| 739 | O | ASN | 619 | 32.856 | 20.374 | 57.157 | 1.00 | 60.32 |
| 740 | N | LEU | 620 | 33.951 | 18.505 | 56.500 | 1.00 | 59.87 |
| 741 | CA | LEU | 620 | 32.767 | 17.686 | 56.237 | 1.00 | 59.97 |
| 742 | CB | LEU | 620 | 31.777 | 18.358 | 55.270 | 1.00 | 59.52 |
| 743 | CG | LEU | 620 | 32.162 | 19.088 | 53.990 | 1.00 | 61.28 |
| 744 | CD1 | LEU | 620 | 31.041 | 18.989 | 52.971 | 1.00 | 64.28 |
| 745 | CD2 | LEU | 620 | 32.459 | 20.539 | 54.330 | 1.00 | 65.45 |
| 746 | C | LEU | 620 | 33.147 | 16.307 | 55.712 | 1.00 | 61.40 |
| 747 | O | LEU | 620 | 33.869 | 16.178 | 54.720 | 1.00 | 61.10 |
| 748 | N | LEU | 621 | 32.660 | 15.280 | 56.407 | 1.00 | 58.95 |
| 749 | CA | LEU | 621 | 32.926 | 13.891 | 56.050 | 1.00 | 61.88 |
| 750 | CB | LEU | 621 | 32.394 | 12.947 | 57.123 | 1.00 | 63.38 |
| 751 | CG | LEU | 621 | 33.031 | 13.049 | 58.503 | 1.00 | 60.66 |
| 752 | CD1 | LEU | 621 | 32.383 | 12.036 | 59.434 | 1.00 | 59.80 |
| 753 | CD2 | LEU | 621 | 34.524 | 12.808 | 58.390 | 1.00 | 62.77 |
| 754 | C | LEU | 621 | 32.283 | 13.540 | 54.728 | 1.00 | 62.48 |
| 755 | O | LEU | 621 | 31.092 | 13.751 | 54.531 | 1.00 | 61.33 |
| 756 | N | CYS | 622 | 33.077 | 12.972 | 53.833 | 1.00 | 59.02 |
| 757 | CA | CYS | 622 | 32.585 | 12.609 | 52.523 | 1.00 | 62.42 |
| 758 | CB | CYS | 622 | 33.453 | 13.304 | 51.479 | 1.00 | 59.42 |
| 759 | SG | CYS | 622 | 33.715 | 15.064 | 51.889 | 1.00 | 59.94 |
| 760 | C | CYS | 622 | 32.566 | 11.094 | 52.329 | 1.00 | 59.63 |
| 761 | O | CYS | 622 | 33.248 | 10.552 | 51.451 | 1.00 | 58.28 |
| 762 | N | PHE | 623 | 31.766 | 10.421 | 53.156 | 1.00 | 62.39 |
| 763 | CA | PHE | 623 | 31.645 | 8.972 | 53.088 | 1.00 | 60.88 |
| 764 | CB | PHE | 623 | 30.387 | 8.490 | 53.841 | 1.00 | 59.68 |
| 765 | CG | PHE | 623 | 30.461 | 8.686 | 55.344 | 1.00 | 58.52 |
| 766 | CD1 | PHE | 623 | 30.338 | 9.948 | 55.906 | 1.00 | 66.23 |
| 767 | CD2 | PHE | 623 | 30.688 | 7.612 | 56.191 | 1.00 | 63.42 |
| 768 | CE1 | PHE | 623 | 30.443 | 10.139 | 57.292 | 1.00 | 60.25 |
| 769 | CE2 | PHE | 623 | 30.795 | 7.796 | 57.576 | 1.00 | 58.96 |
| 770 | CZ | PHE | 623 | 30.673 | 9.059 | 58.124 | 1.00 | 57.60 |
| 771 | C | PHE | 623 | 31.618 | 8.532 | 51.630 | 1.00 | 61.75 |
| 772 | O | PHE | 623 | 32.502 | 7.802 | 51.179 | 1.00 | 60.41 |
| 773 | N | ALA | 624 | 30.624 | 8.995 | 50.888 | 1.00 | 64.49 |
| 774 | CA | ALA | 624 | 30.517 | 8.644 | 49.476 | 1.00 | 61.68 |
| 775 | CB | ALA | 624 | 29.429 | 7.592 | 49.276 | 1.00 | 60.07 |
| 776 | C | ALA | 624 | 30.179 | 9.912 | 48.700 | 1.00 | 60.93 |
| 777 | O | ALA | 624 | 30.002 | 10.981 | 49.297 | 1.00 | 60.98 |
| 778 | N | PRO | 625 | 30.130 | 9.828 | 47.355 | 1.00 | 62.43 |
| 779 | CD | PRO | 625 | 30.706 | 8.811 | 46.459 | 1.00 | 62.52 |
| 780 | CA | PRO | 625 | 29.795 | 11.035 | 46.593 | 1.00 | 59.45 |
| 781 | CB | PRO | 625 | 29.949 | 10.582 | 45.146 | 1.00 | 62.18 |
| 782 | CG | PRO | 625 | 31.089 | 9.653 | 45.245 | 1.00 | 59.91 |
| 783 | C | PRO | 625 | 28.366 | 11.397 | 46.928 | 1.00 | 62.94 |
| 784 | O | PRO | 625 | 28.111 | 12.382 | 47.622 | 1.00 | 59.36 |
| 785 | N | ASP | 626 | 27.433 | 10.572 | 46.468 | 1.00 | 58.86 |
| 786 | CA | ASP | 626 | 26.036 | 10.848 | 46.741 | 1.00 | 60.61 |
| 787 | CB | ASP | 626 | 25.126 | 9.882 | 45.939 | 1.00 | 65.12 |
| 788 | CG | ASP | 626 | 25.227 | 8.421 | 46.393 | 1.00 | 60.28 |
| 789 | OD1 | ASP | 626 | 25.311 | 8.160 | 47.612 | 1.00 | 60.31 |
| 790 | OD2 | ASP | 626 | 25.189 | 7.526 | 45.518 | 1.00 | 59.51 |
| 791 | C | ASP | 626 | 25.680 | 10.825 | 48.248 | 1.00 | 58.60 |
| 792 | O | ASP | 626 | 24.510 | 10.636 | 48.616 | 1.00 | 62.03 |
| 793 | N | LEU | 627 | 26.668 | 11.051 | 49.119 | 1.00 | 63.43 |
| 794 | CA | LEU | 627 | 26.392 | 11.020 | 50.552 | 1.00 | 61.63 |
| 795 | CB | LEU | 627 | 26.175 | 9.573 | 51.007 | 1.00 | 58.45 |
| 796 | CG | LEU | 627 | 25.874 | 9.407 | 52.496 | 1.00 | 63.46 |
| 797 | CD1 | LEU | 627 | 24.401 | 9.669 | 52.770 | 1.00 | 60.41 |
| 798 | CD2 | LEU | 627 | 26.241 | 8.013 | 52.919 | 1.00 | 65.05 |
| 799 | C | LEU | 627 | 27.435 | 11.665 | 51.459 | 1.00 | 61.00 |
| 800 | O | LEU | 627 | 28.320 | 10.988 | 51.985 | 1.00 | 62.27 |
| 801 | N | ILE | 628 | 27.301 | 12.965 | 51.682 | 1.00 | 59.87 |
| 802 | CA | ILE | 628 | 28.230 | 13.686 | 52.537 | 1.00 | 61.72 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 803 | CB | ILE | 628 | 28.796 | 14.887 | 51.787 | 1.00 | 61.79 |
| 804 | CG2 | ILE | 628 | 29.848 | 15.575 | 52.618 | 1.00 | 61.82 |
| 805 | CG1 | ILE | 628 | 29.391 | 14.418 | 50.461 | 1.00 | 58.81 |
| 806 | CD1 | ILE | 628 | 29.806 | 15.542 | 49.554 | 1.00 | 61.23 |
| 807 | C | ILE | 628 | 27.541 | 14.162 | 53.815 | 1.00 | 59.57 |
| 808 | O | ILE | 628 | 26.396 | 14.611 | 53.779 | 1.00 | 61.09 |
| 809 | N | ILE | 629 | 28.221 | 14.044 | 54.951 | 1.00 | 60.22 |
| 810 | CA | ILE | 629 | 27.638 | 14.493 | 56.208 | 1.00 | 60.98 |
| 811 | CB | ILE | 629 | 28.261 | 13.766 | 57.423 | 1.00 | 65.92 |
| 812 | CG2 | ILE | 629 | 28.292 | 14.681 | 58.647 | 1.00 | 62.88 |
| 813 | CG1 | ILE | 629 | 27.419 | 12.536 | 57.768 | 1.00 | 64.60 |
| 814 | CD1 | ILE | 629 | 26.917 | 11.766 | 56.571 | 1.00 | 63.67 |
| 815 | C | ILE | 629 | 27.852 | 15.989 | 56.319 | 1.00 | 60.46 |
| 816 | O | ILE | 629 | 28.935 | 16.452 | 56.676 | 1.00 | 60.38 |
| 817 | N | ASN | 630 | 26.797 | 16.729 | 55.994 | 1.00 | 61.49 |
| 818 | CA | ASN | 630 | 26.789 | 18.187 | 56.015 | 1.00 | 61.95 |
| 819 | CB | ASN | 630 | 25.655 | 18.685 | 55.149 | 1.00 | 60.74 |
| 820 | CG | ASN | 630 | 24.348 | 18.042 | 55.516 | 1.00 | 63.39 |
| 821 | OD1 | ASN | 630 | 24.011 | 17.949 | 56.688 | 1.00 | 62.29 |
| 822 | ND2 | ASN | 630 | 23.603 | 17.591 | 54.525 | 1.00 | 63.08 |
| 823 | C | ASN | 630 | 26.616 | 18.786 | 57.402 | 1.00 | 63.46 |
| 824 | O | ASN | 630 | 26.311 | 18.085 | 58.369 | 1.00 | 63.49 |
| 825 | N | GLU | 631 | 26.794 | 20.103 | 57.475 | 1.00 | 60.97 |
| 826 | CA | GLU | 631 | 26.658 | 20.840 | 58.729 | 1.00 | 59.85 |
| 827 | CB | GLU | 631 | 26.743 | 22.349 | 58.484 | 1.00 | 62.90 |
| 828 | CG | GLU | 631 | 26.784 | 23.166 | 59.774 | 1.00 | 60.34 |
| 829 | CD | GLU | 631 | 25.819 | 24.340 | 59.761 | 1.00 | 60.36 |
| 830 | OE1 | GLU | 631 | 24.688 | 24.184 | 60.288 | 1.00 | 62.28 |
| 831 | OE2 | GLU | 631 | 26.191 | 25.406 | 59.213 | 1.00 | 56.78 |
| 832 | C | GLU | 631 | 25.313 | 20.519 | 59.367 | 1.00 | 59.95 |
| 833 | O | GLU | 631 | 25.223 | 20.250 | 60.564 | 1.00 | 61.19 |
| 834 | N | GLN | 632 | 24.268 | 20.540 | 58.552 | 1.00 | 60.53 |
| 835 | CA | GLN | 632 | 22.933 | 20.248 | 59.046 | 1.00 | 60.62 |
| 836 | CB | GLN | 632 | 21.930 | 20.354 | 57.895 | 1.00 | 64.85 |
| 837 | CG | GLN | 632 | 22.121 | 21.610 | 57.031 | 1.00 | 59.39 |
| 838 | CD | GLN | 632 | 22.081 | 22.917 | 57.841 | 1.00 | 63.65 |
| 839 | OE1 | GLN | 632 | 21.068 | 23.248 | 58.473 | 1.00 | 59.92 |
| 840 | NE2 | GLN | 632 | 23.193 | 23.663 | 57.821 | 1.00 | 62.67 |
| 841 | C | GLN | 632 | 22.873 | 18.860 | 59.697 | 1.00 | 63.23 |
| 842 | O | GLN | 632 | 22.554 | 18.741 | 60.882 | 1.00 | 61.37 |
| 843 | N | ARG | 633 | 23.213 | 17.827 | 58.929 | 1.00 | 62.09 |
| 844 | CA | ARG | 633 | 23.190 | 16.444 | 59.406 | 1.00 | 61.43 |
| 845 | CB | ARG | 633 | 23.762 | 15.504 | 58.345 | 1.00 | 60.38 |
| 846 | CG | ARG | 633 | 22.863 | 15.388 | 57.142 | 1.00 | 58.68 |
| 847 | CD | ARG | 633 | 23.419 | 14.459 | 56.102 | 1.00 | 63.71 |
| 848 | NE | ARG | 633 | 22.589 | 14.486 | 54.905 | 1.00 | 62.14 |
| 849 | CZ | ARG | 633 | 22.885 | 13.852 | 53.780 | 1.00 | 60.28 |
| 850 | NH1 | ARG | 633 | 23.996 | 13.136 | 53.704 | 1.00 | 60.27 |
| 851 | NH2 | ARG | 633 | 22.075 | 13.937 | 52.733 | 1.00 | 60.98 |
| 852 | C | ARG | 633 | 23.833 | 16.137 | 60.753 | 1.00 | 64.07 |
| 853 | O | ARG | 633 | 23.495 | 15.117 | 61.348 | 1.00 | 60.29 |
| 854 | N | MET | 634 | 24.758 | 16.970 | 61.236 | 1.00 | 61.53 |
| 855 | CA | MET | 634 | 25.334 | 16.721 | 62.560 | 1.00 | 60.63 |
| 856 | CB | MET | 634 | 26.429 | 17.747 | 62.859 | 1.00 | 60.06 |
| 857 | CG | MET | 634 | 27.598 | 17.688 | 61.874 | 1.00 | 53.30 |
| 858 | SD | MET | 634 | 28.604 | 16.178 | 62.057 | 1.00 | 63.04 |
| 859 | CE | MET | 634 | 30.133 | 16.562 | 61.162 | 1.00 | 60.95 |
| 860 | C | MET | 634 | 24.150 | 16.834 | 63.555 | 1.00 | 60.65 |
| 861 | O | MET | 634 | 23.899 | 17.897 | 64.149 | 1.00 | 63.14 |
| 862 | N | THR | 635 | 23.420 | 15.714 | 63.670 | 1.00 | 63.54 |
| 863 | CA | THR | 635 | 22.220 | 15.523 | 64.504 | 1.00 | 61.73 |
| 864 | CB | THR | 635 | 21.180 | 14.557 | 63.819 | 1.00 | 59.70 |
| 865 | OG1 | THR | 635 | 20.987 | 14.911 | 62.442 | 1.00 | 57.94 |
| 866 | CG2 | THR | 635 | 19.829 | 14.609 | 64.552 | 1.00 | 63.34 |
| 867 | C | THR | 635 | 22.593 | 14.861 | 65.825 | 1.00 | 61.33 |
| 868 | O | THR | 635 | 23.570 | 15.251 | 66.464 | 1.00 | 63.49 |
| 869 | N | LEU | 636 | 21.796 | 13.851 | 66.198 | 1.00 | 60.18 |
| 870 | CA | LEU | 636 | 21.953 | 13.057 | 67.420 | 1.00 | 61.62 |
| 871 | CB | LEU | 636 | 22.112 | 11.577 | 67.095 | 1.00 | 60.70 |
| 872 | CG | LEU | 636 | 22.867 | 10.855 | 68.213 | 1.00 | 62.64 |
| 873 | CD1 | LEU | 636 | 21.904 | 10.048 | 69.070 | 1.00 | 63.15 |
| 874 | CD2 | LEU | 636 | 23.910 | 9.960 | 67.603 | 1.00 | 60.79 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 875 | C | LEU | 636 | 23.183 | 13.478 | 68.172 | 1.00 | 61.59 |
| 876 | O | LEU | 636 | 24.287 | 13.372 | 67.626 | 1.00 | 60.57 |
| 877 | N | PRO | 637 | 23.029 | 13.907 | 69.442 | 1.00 | 59.83 |
| 878 | CD | PRO | 637 | 22.008 | 13.402 | 70.379 | 1.00 | 57.71 |
| 879 | CA | PRO | 637 | 24.225 | 14.321 | 70.182 | 1.00 | 61.11 |
| 880 | CB | PRO | 637 | 23.810 | 14.133 | 71.639 | 1.00 | 61.28 |
| 881 | CG | PRO | 637 | 22.862 | 12.966 | 71.555 | 1.00 | 61.68 |
| 882 | C | PRO | 637 | 25.417 | 13.433 | 69.793 | 1.00 | 61.18 |
| 883 | O | PRO | 637 | 26.457 | 13.928 | 69.331 | 1.00 | 61.45 |
| 884 | N | CYS | 638 | 25.243 | 12.117 | 69.920 | 1.00 | 63.53 |
| 885 | CA | CYS | 638 | 26.333 | 11.211 | 69.588 | 1.00 | 61.78 |
| 886 | CB | CYS | 638 | 26.024 | 9.787 | 70.065 | 1.00 | 62.20 |
| 887 | SG | CYS | 638 | 24.449 | 9.498 | 70.917 | 1.00 | 60.82 |
| 888 | C | CYS | 638 | 26.722 | 11.209 | 68.101 | 1.00 | 61.50 |
| 889 | O | CYS | 638 | 27.863 | 10.844 | 67.765 | 1.00 | 61.11 |
| 890 | N | MET | 639 | 25.816 | 11.625 | 67.214 | 1.00 | 57.65 |
| 891 | CA | MET | 639 | 26.186 | 11.638 | 65.817 | 1.00 | 60.56 |
| 892 | CB | MET | 639 | 25.103 | 12.211 | 64.924 | 1.00 | 66.32 |
| 893 | CG | MET | 639 | 25.612 | 12.161 | 63.532 | 1.00 | 60.47 |
| 894 | SD | MET | 639 | 25.084 | 11.084 | 62.238 | 1.00 | 57.31 |
| 895 | CE | MET | 639 | 25.984 | 11.962 | 61.115 | 1.00 | 58.45 |
| 896 | C | MET | 639 | 27.478 | 12.449 | 65.637 | 1.00 | 62.26 |
| 897 | O | MET | 639 | 28.361 | 12.083 | 64.857 | 1.00 | 61.35 |
| 898 | N | TYR | 640 | 27.589 | 13.543 | 66.383 | 1.00 | 61.78 |
| 899 | CA | TYR | 640 | 28.797 | 14.339 | 66.340 | 1.00 | 61.48 |
| 900 | CB | TYR | 640 | 28.569 | 15.755 | 66.872 | 1.00 | 60.05 |
| 901 | CG | TYR | 640 | 29.871 | 16.511 | 66.956 | 1.00 | 61.42 |
| 902 | CD1 | TYR | 640 | 30.530 | 16.927 | 65.795 | 1.00 | 62.42 |
| 903 | CE1 | TYR | 640 | 31.800 | 17.472 | 65.846 | 1.00 | 61.93 |
| 904 | CD2 | TYR | 640 | 30.519 | 16.680 | 68.175 | 1.00 | 59.45 |
| 905 | CE2 | TYR | 640 | 31.785 | 17.222 | 68.235 | 1.00 | 63.13 |
| 906 | CZ | TYR | 640 | 32.425 | 17.612 | 67.068 | 1.00 | 58.88 |
| 907 | OH | TYR | 640 | 33.711 | 18.103 | 67.130 | 1.00 | 60.76 |
| 908 | C | TYR | 640 | 29.842 | 13.646 | 67.215 | 1.00 | 60.30 |
| 909 | O | TYR | 640 | 31.041 | 13.847 | 67.034 | 1.00 | 63.06 |
| 910 | N | ASP | 641 | 29.397 | 12.830 | 68.168 | 1.00 | 61.14 |
| 911 | CA | ASP | 641 | 30.349 | 12.136 | 69.035 | 1.00 | 62.18 |
| 912 | CB | ASP | 641 | 29.674 | 11.669 | 70.323 | 1.00 | 59.68 |
| 913 | CG | ASP | 641 | 29.145 | 12.828 | 71.135 | 1.00 | 60.96 |
| 914 | OD1 | ASP | 641 | 27.930 | 13.090 | 71.062 | 1.00 | 61.07 |
| 915 | OD2 | ASP | 641 | 29.950 | 13.493 | 71.824 | 1.00 | 63.74 |
| 916 | C | ASP | 641 | 30.991 | 10.971 | 68.313 | 1.00 | 60.81 |
| 917 | O | ASP | 641 | 32.047 | 10.482 | 68.721 | 1.00 | 60.52 |
| 918 | N | GLN | 642 | 30.349 | 10.542 | 67.229 | 1.00 | 59.76 |
| 919 | CA | GLN | 642 | 30.860 | 9.456 | 66.396 | 1.00 | 63.97 |
| 920 | CB | GLN | 642 | 29.721 | 8.763 | 65.687 | 1.00 | 61.51 |
| 921 | CG | GLN | 642 | 28.690 | 8.348 | 66.642 | 1.00 | 61.79 |
| 922 | CD | GLN | 642 | 27.547 | 7.724 | 65.978 | 1.00 | 62.69 |
| 923 | OE1 | GLN | 642 | 27.709 | 6.684 | 65.308 | 1.00 | 61.01 |
| 924 | NE2 | GLN | 642 | 26.355 | 8.326 | 66.145 | 1.00 | 60.03 |
| 925 | C | GLN | 642 | 31.766 | 10.069 | 65.359 | 1.00 | 62.81 |
| 926 | O | GLN | 642 | 32.954 | 9.760 | 65.294 | 1.00 | 61.10 |
| 927 | N | CYS | 643 | 31.190 | 10.957 | 64.556 | 1.00 | 60.88 |
| 928 | CA | CYS | 643 | 31.931 | 11.628 | 63.504 | 1.00 | 61.65 |
| 929 | CB | CYS | 643 | 30.977 | 12.508 | 62.694 | 1.00 | 61.95 |
| 930 | SG | CYS | 643 | 29.662 | 11.585 | 61.843 | 1.00 | 63.26 |
| 931 | C | CYS | 643 | 33.081 | 12.455 | 64.071 | 1.00 | 61.30 |
| 932 | O | CYS | 643 | 34.102 | 12.652 | 63.418 | 1.00 | 61.90 |
| 933 | N | LYS | 644 | 32.911 | 12.923 | 65.299 | 1.00 | 62.82 |
| 934 | CA | LYS | 644 | 33.923 | 13.730 | 65.951 | 1.00 | 58.73 |
| 935 | CB | LYS | 644 | 33.634 | 13.827 | 67.449 | 1.00 | 63.83 |
| 936 | CG | LYS | 644 | 34.630 | 14.686 | 68.207 | 1.00 | 59.96 |
| 937 | CD | LYS | 644 | 34.226 | 14.891 | 69.665 | 1.00 | 59.57 |
| 938 | CE | LYS | 644 | 35.160 | 15.902 | 70.358 | 1.00 | 59.22 |
| 939 | NZ | LYS | 644 | 35.201 | 17.239 | 69.668 | 1.00 | 61.66 |
| 940 | C | LYS | 644 | 35.328 | 13.182 | 65.747 | 1.00 | 61.72 |
| 941 | O | LYS | 644 | 36.296 | 13.941 | 65.673 | 1.00 | 61.77 |
| 942 | N | HIS | 645 | 35.451 | 11.864 | 65.655 | 1.00 | 61.41 |
| 943 | CA | HIS | 645 | 36.769 | 11.262 | 65.474 | 1.00 | 59.96 |
| 944 | CB | HIS | 645 | 36.856 | 9.943 | 66.209 | 1.00 | 60.26 |
| 945 | CG | HIS | 645 | 37.109 | 10.100 | 67.667 | 1.00 | 59.75 |
| 946 | CD2 | HIS | 645 | 38.254 | 10.338 | 68.346 | 1.00 | 58.42 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 947 | ND1 | HIS | 645 | 36.103 | 10.041 | 68.606 | 1.00 | 61.77 |
| 948 | CE1 | HIS | 645 | 36.621 | 10.232 | 69.805 | 1.00 | 58.75 |
| 949 | NE2 | HIS | 645 | 37.924 | 10.415 | 69.675 | 1.00 | 57.48 |
| 950 | C | HIS | 645 | 37.165 | 11.038 | 64.037 | 1.00 | 60.84 |
| 951 | O | HIS | 645 | 38.352 | 11.000 | 63.727 | 1.00 | 62.12 |
| 952 | N | MET | 646 | 36.172 | 10.856 | 63.174 | 1.00 | 63.11 |
| 953 | CA | MET | 646 | 36.432 | 10.651 | 61.759 | 1.00 | 62.74 |
| 954 | CB | MET | 646 | 35.135 | 10.211 | 61.023 | 1.00 | 61.50 |
| 955 | CG | MET | 646 | 34.686 | 8.771 | 61.338 | 1.00 | 58.88 |
| 956 | SD | MET | 646 | 32.994 | 8.315 | 60.876 | 1.00 | 61.92 |
| 957 | CE | MET | 646 | 32.426 | 8.134 | 62.441 | 1.00 | 62.24 |
| 958 | C | MET | 646 | 36.948 | 11.972 | 61.168 | 1.00 | 63.61 |
| 959 | O | MET | 646 | 37.709 | 11.962 | 60.197 | 1.00 | 63.12 |
| 960 | N | LEU | 647 | 36.543 | 13.093 | 61.772 | 1.00 | 60.39 |
| 961 | CA | LEU | 647 | 36.963 | 14.419 | 61.325 | 1.00 | 61.16 |
| 962 | CB | LEU | 647 | 36.105 | 15.510 | 61.965 | 1.00 | 62.09 |
| 963 | CG | LEU | 647 | 34.661 | 15.778 | 61.551 | 1.00 | 62.69 |
| 964 | CD1 | LEU | 647 | 34.144 | 16.850 | 62.479 | 1.00 | 59.66 |
| 965 | CD2 | LEU | 647 | 34.553 | 16.232 | 60.098 | 1.00 | 61.60 |
| 966 | C | LEU | 647 | 38.400 | 14.652 | 61.731 | 1.00 | 62.99 |
| 967 | O | LEU | 647 | 39.164 | 15.329 | 61.042 | 1.00 | 62.41 |
| 968 | N | TYR | 648 | 38.750 | 14.087 | 62.876 | 1.00 | 60.24 |
| 969 | CA | TYR | 648 | 40.087 | 14.202 | 63.431 | 1.00 | 60.92 |
| 970 | CB | TYR | 648 | 40.190 | 13.339 | 64.685 | 1.00 | 59.63 |
| 971 | CG | TYR | 648 | 41.486 | 13.510 | 65.428 | 1.00 | 60.33 |
| 972 | CD1 | TYR | 648 | 42.672 | 12.950 | 64.952 | 1.00 | 62.96 |
| 973 | CE1 | TYR | 648 | 43.876 | 13.160 | 65.609 | 1.00 | 61.51 |
| 974 | CD2 | TYR | 648 | 41.537 | 14.280 | 66.585 | 1.00 | 57.67 |
| 975 | CE2 | TYR | 648 | 42.735 | 14.500 | 67.252 | 1.00 | 62.62 |
| 976 | CZ | TYR | 648 | 43.902 | 13.938 | 66.759 | 1.00 | 60.16 |
| 977 | OH | TYR | 648 | 45.089 | 14.157 | 67.426 | 1.00 | 64.40 |
| 978 | C | TYR | 648 | 41.164 | 13.787 | 62.435 | 1.00 | 61.32 |
| 979 | O | TYR | 648 | 42.045 | 14.575 | 62.099 | 1.00 | 62.83 |
| 980 | N | VAL | 649 | 41.107 | 12.545 | 61.971 | 1.00 | 65.90 |
| 981 | CA | VAL | 649 | 42.105 | 12.079 | 61.027 | 1.00 | 60.14 |
| 982 | CB | VAL | 649 | 41.862 | 10.578 | 60.642 | 1.00 | 59.02 |
| 983 | CG1 | VAL | 649 | 40.528 | 10.109 | 61.218 | 1.00 | 60.92 |
| 984 | CG2 | VAL | 649 | 41.930 | 10.372 | 59.122 | 1.00 | 59.70 |
| 985 | C | VAL | 649 | 42.072 | 12.982 | 59.814 | 1.00 | 61.99 |
| 986 | O | VAL | 649 | 43.105 | 13.378 | 59.297 | 1.00 | 60.55 |
| 987 | N | SER | 650 | 40.873 | 13.339 | 59.390 | 1.00 | 61.60 |
| 988 | CA | SER | 650 | 40.705 | 14.191 | 58.226 | 1.00 | 61.66 |
| 989 | CB | SER | 650 | 39.224 | 14.356 | 57.914 | 1.00 | 61.34 |
| 990 | OG | SER | 650 | 39.069 | 14.979 | 56.662 | 1.00 | 64.56 |
| 991 | C | SER | 650 | 41.344 | 15.555 | 58.429 | 1.00 | 61.44 |
| 992 | O | SER | 650 | 41.800 | 16.181 | 57.476 | 1.00 | 58.88 |
| 993 | N | SER | 651 | 41.365 | 16.013 | 59.677 | 1.00 | 59.26 |
| 994 | CA | SER | 651 | 41.960 | 17.298 | 60.029 | 1.00 | 62.47 |
| 995 | CB | SER | 651 | 41.578 | 17.637 | 61.483 | 1.00 | 58.62 |
| 996 | OG | SER | 651 | 42.537 | 18.441 | 62.154 | 1.00 | 60.41 |
| 997 | C | SER | 651 | 43.480 | 17.204 | 59.849 | 1.00 | 61.76 |
| 998 | O | SER | 651 | 44.087 | 18.019 | 59.164 | 1.00 | 62.09 |
| 999 | N | GLU | 652 | 44.070 | 16.172 | 60.441 | 1.00 | 60.41 |
| 1000 | CA | GLU | 652 | 45.509 | 15.927 | 60.395 | 1.00 | 60.48 |
| 1001 | CB | GLU | 652 | 45.837 | 14.680 | 61.220 | 1.00 | 65.10 |
| 1002 | CG | GLU | 652 | 45.488 | 14.822 | 62.677 | 1.00 | 59.36 |
| 1003 | CD | GLU | 652 | 46.160 | 16.021 | 63.289 | 1.00 | 62.29 |
| 1004 | OE1 | GLU | 652 | 47.399 | 15.970 | 63.444 | 1.00 | 60.10 |
| 1005 | OE2 | GLU | 652 | 45.451 | 17.014 | 63.592 | 1.00 | 60.61 |
| 1006 | C | GLU | 652 | 46.100 | 15.773 | 59.001 | 1.00 | 59.16 |
| 1007 | O | GLU | 652 | 47.238 | 16.166 | 58.755 | 1.00 | 59.92 |
| 1008 | N | LEU | 653 | 45.335 | 15.180 | 58.094 | 1.00 | 60.01 |
| 1009 | CA | LEU | 653 | 45.807 | 14.984 | 56.731 | 1.00 | 61.61 |
| 1010 | CB | LEU | 653 | 44.874 | 14.048 | 55.960 | 1.00 | 64.78 |
| 1011 | CG | LEU | 653 | 44.860 | 12.600 | 56.432 | 1.00 | 63.03 |
| 1012 | CD1 | LEU | 653 | 43.723 | 11.868 | 55.768 | 1.00 | 60.96 |
| 1013 | CD2 | LEU | 653 | 46.179 | 11.941 | 56.122 | 1.00 | 62.70 |
| 1014 | C | LEU | 653 | 45.878 | 16.328 | 56.037 | 1.00 | 60.72 |
| 1015 | O | LEU | 653 | 46.805 | 16.588 | 55.269 | 1.00 | 61.12 |
| 1016 | N | HIS | 654 | 44.895 | 17.182 | 56.303 | 1.00 | 62.78 |
| 1017 | CA | HIS | 654 | 44.894 | 18.497 | 55.698 | 1.00 | 61.32 |
| 1018 | CB | HIS | 654 | 43.513 | 19.141 | 55.805 | 1.00 | 63.28 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1019 | CG | HIS | 654 | 43.517 | 20.607 | 55.518 | 1.00 | 61.88 |
| 1020 | CD2 | HIS | 654 | 43.210 | 21.296 | 54.394 | 1.00 | 59.76 |
| 1021 | ND1 | HIS | 654 | 43.946 | 21.543 | 56.436 | 1.00 | 58.15 |
| 1022 | CE1 | HIS | 654 | 43.905 | 22.744 | 55.889 | 1.00 | 62.74 |
| 1023 | NE2 | HIS | 654 | 43.463 | 22.622 | 54.650 | 1.00 | 60.79 |
| 1024 | C | HIS | 654 | 45.935 | 19.319 | 56.440 | 1.00 | 62.39 |
| 1025 | O | HIS | 654 | 46.667 | 20.112 | 55.851 | 1.00 | 62.10 |
| 1026 | N | ARG | 655 | 46.012 | 19.098 | 57.743 | 1.00 | 62.07 |
| 1027 | CA | ARG | 655 | 46.968 | 19.804 | 58.572 | 1.00 | 62.85 |
| 1028 | CB | ARG | 655 | 46.882 | 19.277 | 60.008 | 1.00 | 58.45 |
| 1029 | CG | ARG | 655 | 47.082 | 20.314 | 61.111 | 1.00 | 57.53 |
| 1030 | CD | ARG | 655 | 48.522 | 20.368 | 61.565 | 1.00 | 58.48 |
| 1031 | NE | ARG | 655 | 48.968 | 19.079 | 62.082 | 1.00 | 61.43 |
| 1032 | CZ | ARG | 655 | 50.206 | 18.831 | 62.503 | 1.00 | 59.99 |
| 1033 | NH1 | ARG | 655 | 51.125 | 19.790 | 62.472 | 1.00 | 61.84 |
| 1034 | NH2 | ARG | 655 | 50.537 | 17.625 | 62.950 | 1.00 | 60.75 |
| 1035 | C | ARG | 655 | 48.367 | 19.599 | 57.999 | 1.00 | 60.66 |
| 1036 | O | ARG | 655 | 49.086 | 20.566 | 57.753 | 1.00 | 62.69 |
| 1037 | N | LEU | 656 | 48.735 | 18.340 | 57.759 | 1.00 | 60.05 |
| 1038 | CA | LEU | 656 | 50.060 | 18.008 | 57.224 | 1.00 | 61.69 |
| 1039 | CB | LEU | 656 | 50.575 | 16.697 | 57.832 | 1.00 | 60.63 |
| 1040 | CG | LEU | 656 | 50.902 | 16.651 | 59.330 | 1.00 | 60.12 |
| 1041 | CD1 | LEU | 656 | 51.059 | 15.205 | 59.759 | 1.00 | 61.83 |
| 1042 | CD2 | LEU | 656 | 52.161 | 17.440 | 59.632 | 1.00 | 61.33 |
| 1043 | C | LEU | 656 | 50.164 | 17.922 | 55.706 | 1.00 | 60.82 |
| 1044 | O | LEU | 656 | 51.187 | 17.491 | 55.184 | 1.00 | 63.77 |
| 1045 | N | GLN | 657 | 49.119 | 18.321 | 54.995 | 1.00 | 62.25 |
| 1046 | CA | GLN | 657 | 49.165 | 18.291 | 53.543 | 1.00 | 62.13 |
| 1047 | CB | GLN | 657 | 50.018 | 19.442 | 53.026 | 1.00 | 59.95 |
| 1048 | CG | GLN | 657 | 49.412 | 20.805 | 53.219 | 1.00 | 60.54 |
| 1049 | CD | GLN | 657 | 48.109 | 20.944 | 52.480 | 1.00 | 59.94 |
| 1050 | OE1 | GLN | 657 | 47.043 | 20.616 | 52.997 | 1.00 | 61.59 |
| 1051 | NE2 | GLN | 657 | 48.189 | 21.413 | 51.250 | 1.00 | 59.69 |
| 1052 | C | GLN | 657 | 49.756 | 16.998 | 53.027 | 1.00 | 64.37 |
| 1053 | O | GLN | 657 | 50.684 | 17.013 | 52.230 | 1.00 | 60.80 |
| 1054 | N | VAL | 658 | 49.233 | 15.876 | 53.487 | 1.00 | 59.26 |
| 1055 | CA | VAL | 658 | 49.730 | 14.589 | 53.048 | 1.00 | 60.79 |
| 1056 | CB | VAL | 658 | 49.044 | 13.466 | 53.856 | 1.00 | 61.35 |
| 1057 | CG1 | VAL | 658 | 49.169 | 12.130 | 53.154 | 1.00 | 61.79 |
| 1058 | CG2 | VAL | 658 | 49.663 | 13.406 | 55.240 | 1.00 | 61.37 |
| 1059 | C | VAL | 658 | 49.494 | 14.416 | 51.552 | 1.00 | 60.15 |
| 1060 | O | VAL | 658 | 48.452 | 14.798 | 51.025 | 1.00 | 60.95 |
| 1061 | N | SER | 659 | 50.485 | 13.862 | 50.869 | 1.00 | 63.41 |
| 1062 | CA | SER | 659 | 50.399 | 13.615 | 49.438 | 1.00 | 58.10 |
| 1063 | CB | SER | 659 | 51.797 | 13.685 | 48.834 | 1.00 | 59.86 |
| 1064 | OG | SER | 659 | 52.018 | 12.643 | 47.905 | 1.00 | 62.03 |
| 1065 | C | SER | 659 | 49.777 | 12.242 | 49.157 | 1.00 | 62.11 |
| 1066 | O | SER | 659 | 49.781 | 11.353 | 50.015 | 1.00 | 61.38 |
| 1067 | N | TYR | 660 | 49.243 | 12.062 | 47.956 | 1.00 | 60.30 |
| 1068 | CA | TYR | 660 | 48.633 | 10.789 | 47.601 | 1.00 | 61.68 |
| 1069 | CB | TYR | 660 | 48.100 | 10.860 | 46.177 | 1.00 | 61.85 |
| 1070 | CG | TYR | 660 | 47.411 | 9.605 | 45.727 | 1.00 | 59.67 |
| 1071 | CD1 | TYR | 660 | 46.561 | 8.911 | 46.581 | 1.00 | 63.51 |
| 1072 | CE1 | TYR | 660 | 45.893 | 7.783 | 46.152 | 1.00 | 60.60 |
| 1073 | CD2 | TYR | 660 | 47.576 | 9.134 | 44.431 | 1.00 | 60.37 |
| 1074 | CE2 | TYR | 660 | 46.911 | 8.011 | 43.990 | 1.00 | 64.13 |
| 1075 | CZ | TYR | 660 | 46.072 | 7.339 | 44.851 | 1.00 | 63.85 |
| 1076 | OH | TYR | 660 | 45.393 | 6.229 | 44.402 | 1.00 | 62.07 |
| 1077 | C | TYR | 660 | 49.584 | 9.594 | 47.749 | 1.00 | 59.81 |
| 1078 | O | TYR | 660 | 49.175 | 8.510 | 48.165 | 1.00 | 64.86 |
| 1079 | N | GLU | 661 | 50.853 | 9.789 | 47.411 | 1.00 | 60.25 |
| 1080 | CA | GLU | 661 | 51.814 | 8.703 | 47.527 | 1.00 | 62.48 |
| 1081 | CB | GLU | 661 | 53.119 | 9.034 | 46.788 | 1.00 | 61.23 |
| 1082 | CG | GLU | 661 | 53.209 | 8.405 | 45.395 | 1.00 | 63.67 |
| 1083 | CD | GLU | 661 | 54.517 | 8.708 | 44.672 | 1.00 | 65.78 |
| 1084 | OE1 | GLU | 661 | 55.602 | 8.472 | 45.247 | 1.00 | 60.21 |
| 1085 | OE2 | GLU | 661 | 54.462 | 9.174 | 43.517 | 1.00 | 60.28 |
| 1086 | C | GLU | 661 | 52.096 | 8.354 | 48.980 | 1.00 | 61.69 |
| 1087 | O | GLU | 661 | 52.247 | 7.183 | 49.312 | 1.00 | 61.32 |
| 1088 | N | GLU | 662 | 52.160 | 9.348 | 49.854 | 1.00 | 62.68 |
| 1089 | CA | GLU | 662 | 52.405 | 9.048 | 51.252 | 1.00 | 63.61 |
| 1090 | CB | GLU | 662 | 52.605 | 10.340 | 52.032 | 1.00 | 61.04 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1091 | CG | GLU | 662 | 53.485 | 11.321 | 51.309 | 1.00 | 61.12 |
| 1092 | CD | GLU | 662 | 53.768 | 12.555 | 52.117 | 1.00 | 62.85 |
| 1093 | OE1 | GLU | 662 | 52.822 | 13.164 | 52.637 | 1.00 | 58.86 |
| 1094 | OE2 | GLU | 662 | 54.945 | 12.931 | 52.227 | 1.00 | 61.02 |
| 1095 | C | GLU | 662 | 51.193 | 8.277 | 51.784 | 1.00 | 59.86 |
| 1096 | O | GLU | 662 | 51.333 | 7.263 | 52.466 | 1.00 | 63.08 |
| 1097 | N | TYR | 663 | 50.007 | 8.771 | 51.436 | 1.00 | 61.62 |
| 1098 | CA | TYR | 663 | 48.716 | 8.186 | 51.812 | 1.00 | 62.54 |
| 1099 | CB | TYR | 663 | 47.601 | 8.921 | 51.068 | 1.00 | 63.89 |
| 1100 | CG | TYR | 663 | 46.266 | 8.230 | 51.167 | 1.00 | 61.84 |
| 1101 | CD1 | TYR | 663 | 45.619 | 8.109 | 52.392 | 1.00 | 59.60 |
| 1102 | CE1 | TYR | 663 | 44.407 | 7.458 | 52.498 | 1.00 | 58.52 |
| 1103 | CD2 | TYR | 663 | 45.659 | 7.676 | 50.043 | 1.00 | 58.65 |
| 1104 | CE2 | TYR | 663 | 44.441 | 7.019 | 50.138 | 1.00 | 60.83 |
| 1105 | CZ | TYR | 663 | 43.820 | 6.916 | 51.368 | 1.00 | 62.58 |
| 1106 | OH | TYR | 663 | 42.601 | 6.287 | 51.477 | 1.00 | 61.21 |
| 1107 | C | TYR | 663 | 48.565 | 6.680 | 51.537 | 1.00 | 59.94 |
| 1108 | O | TYR | 663 | 48.090 | 5.918 | 52.389 | 1.00 | 60.92 |
| 1109 | N | LEU | 664 | 48.930 | 6.274 | 50.325 | 1.00 | 60.84 |
| 1110 | CA | LEU | 664 | 48.846 | 4.881 | 49.908 | 1.00 | 61.56 |
| 1111 | CB | LEU | 664 | 49.261 | 4.757 | 48.438 | 1.00 | 60.37 |
| 1112 | CG | LEU | 664 | 48.363 | 5.402 | 47.382 | 1.00 | 64.33 |
| 1113 | CD1 | LEU | 664 | 49.036 | 5.350 | 46.023 | 1.00 | 64.49 |
| 1114 | CD2 | LEU | 664 | 47.032 | 4.687 | 47.351 | 1.00 | 59.02 |
| 1115 | C | LEU | 664 | 49.744 | 4.001 | 50.777 | 1.00 | 60.21 |
| 1116 | O | LEU | 664 | 49.369 | 2.889 | 51.161 | 1.00 | 61.89 |
| 1117 | N | CYS | 665 | 50.933 | 4.519 | 51.071 | 1.00 | 61.72 |
| 1118 | CA | CYS | 665 | 51.915 | 3.823 | 51.882 | 1.00 | 58.12 |
| 1119 | CB | CYS | 665 | 53.272 | 4.508 | 51.737 | 1.00 | 62.31 |
| 1120 | SG | CYS | 665 | 54.006 | 4.295 | 50.123 | 1.00 | 59.12 |
| 1121 | C | CYS | 665 | 51.516 | 3.771 | 53.348 | 1.00 | 59.84 |
| 1122 | O | CYS | 665 | 51.726 | 2.766 | 54.024 | 1.00 | 61.71 |
| 1123 | N | MET | 666 | 50.953 | 4.862 | 53.845 | 1.00 | 63.34 |
| 1124 | CA | MET | 666 | 50.524 | 4.910 | 55.228 | 1.00 | 58.59 |
| 1125 | CB | MET | 666 | 50.199 | 6.341 | 55.627 | 1.00 | 59.71 |
| 1126 | CG | MET | 666 | 51.408 | 7.189 | 55.867 | 1.00 | 62.55 |
| 1127 | SD | MET | 666 | 50.921 | 8.891 | 56.036 | 1.00 | 61.95 |
| 1128 | CE | MET | 666 | 50.313 | 8.927 | 57.659 | 1.00 | 64.15 |
| 1129 | C | MET | 666 | 49.303 | 4.023 | 55.437 | 1.00 | 63.86 |
| 1130 | O | MET | 666 | 49.146 | 3.420 | 56.495 | 1.00 | 59.48 |
| 1131 | N | LYS | 667 | 48.446 | 3.950 | 54.421 | 1.00 | 58.08 |
| 1132 | CA | LYS | 667 | 47.241 | 3.129 | 54.482 | 1.00 | 61.17 |
| 1133 | CB | LYS | 667 | 46.318 | 3.429 | 53.305 | 1.00 | 66.33 |
| 1134 | CG | LYS | 667 | 45.013 | 2.663 | 53.338 | 1.00 | 59.73 |
| 1135 | CD | LYS | 667 | 43.951 | 3.382 | 52.532 | 1.00 | 60.07 |
| 1136 | CE | LYS | 667 | 44.313 | 3.462 | 51.063 | 1.00 | 62.82 |
| 1137 | NZ | LYS | 667 | 44.134 | 2.158 | 50.390 | 1.00 | 62.44 |
| 1138 | C | LYS | 667 | 47.592 | 1.658 | 54.468 | 1.00 | 63.84 |
| 1139 | O | LYS | 667 | 46.867 | 0.838 | 55.011 | 1.00 | 61.95 |
| 1140 | N | THR | 668 | 48.705 | 1.318 | 53.838 | 1.00 | 63.32 |
| 1141 | CA | THR | 668 | 49.114 | −0.069 | 53.801 | 1.00 | 61.88 |
| 1142 | CB | THR | 668 | 50.080 | −0.304 | 52.657 | 1.00 | 60.27 |
| 1143 | OG1 | THR | 668 | 49.463 | 0.124 | 51.439 | 1.00 | 62.16 |
| 1144 | CG2 | THR | 668 | 50.417 | −1.775 | 52.547 | 1.00 | 58.76 |
| 1145 | C | THR | 668 | 49.761 | −0.413 | 55.137 | 1.00 | 62.68 |
| 1146 | O | THR | 668 | 49.707 | −1.559 | 55.591 | 1.00 | 62.61 |
| 1147 | N | LEU | 669 | 50.350 | 0.597 | 55.773 | 1.00 | 62.26 |
| 1148 | CA | LEU | 669 | 50.995 | 0.427 | 57.068 | 1.00 | 61.58 |
| 1149 | CB | LEU | 669 | 51.888 | 1.626 | 57.378 | 1.00 | 62.50 |
| 1150 | CG | LEU | 669 | 53.265 | 1.643 | 56.712 | 1.00 | 57.56 |
| 1151 | CD1 | LEU | 669 | 54.041 | 2.847 | 57.205 | 1.00 | 60.97 |
| 1152 | CD2 | LEU | 669 | 54.012 | 0.355 | 57.037 | 1.00 | 59.22 |
| 1153 | C | LEU | 669 | 49.987 | 0.249 | 58.194 | 1.00 | 61.00 |
| 1154 | O | LEU | 669 | 50.354 | −0.119 | 59.310 | 1.00 | 61.30 |
| 1155 | N | LEU | 670 | 48.718 | 0.520 | 57.911 | 1.00 | 62.31 |
| 1156 | CA | LEU | 670 | 47.686 | 0.365 | 58.925 | 1.00 | 62.17 |
| 1157 | CB | LEU | 670 | 46.511 | 1.305 | 58.638 | 1.00 | 64.37 |
| 1158 | CG | LEU | 670 | 46.784 | 2.784 | 58.942 | 1.00 | 60.87 |
| 1159 | CD1 | LEU | 670 | 45.516 | 3.597 | 58.766 | 1.00 | 63.22 |
| 1160 | CD2 | LEU | 670 | 47.293 | 2.922 | 60.365 | 1.00 | 58.85 |
| 1161 | C | LEU | 670 | 47.227 | −1.090 | 58.976 | 1.00 | 63.40 |
| 1162 | O | LEU | 670 | 46.846 | −1.599 | 60.026 | 1.00 | 63.58 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1163 | N | LEU | 671 | 47.281 | −1.750 | 57.827 | 1.00 | 61.89 |
| 1164 | CA | LEU | 671 | 46.913 | −3.150 | 57.716 | 1.00 | 60.74 |
| 1165 | CB | LEU | 671 | 46.946 | −3.574 | 56.249 | 1.00 | 62.54 |
| 1166 | CG | LEU | 671 | 46.501 | −4.997 | 55.921 | 1.00 | 62.48 |
| 1167 | CD1 | LEU | 671 | 45.015 | −5.180 | 56.251 | 1.00 | 63.63 |
| 1168 | CD2 | LEU | 671 | 46.768 | −5.260 | 54.449 | 1.00 | 63.52 |
| 1169 | C | LEU | 671 | 47.967 | −3.928 | 58.500 | 1.00 | 61.46 |
| 1170 | O | LEU | 671 | 47.688 | −4.971 | 59.110 | 1.00 | 60.81 |
| 1171 | N | LEU | 672 | 49.182 | −3.388 | 58.479 | 1.00 | 62.75 |
| 1172 | CA | LEU | 672 | 50.320 | −3.974 | 59.163 | 1.00 | 62.92 |
| 1173 | CB | LEU | 672 | 51.562 | −3.883 | 58.280 | 1.00 | 60.56 |
| 1174 | CG | LEU | 672 | 51.399 | −4.164 | 56.786 | 1.00 | 62.90 |
| 1175 | CD1 | LEU | 672 | 52.776 | −4.394 | 56.183 | 1.00 | 60.90 |
| 1176 | CD2 | LEU | 672 | 50.519 | −5.373 | 56.558 | 1.00 | 61.77 |
| 1177 | C | LEU | 672 | 50.576 | −3.232 | 60.468 | 1.00 | 61.14 |
| 1178 | O | LEU | 672 | 51.722 | −3.064 | 60.883 | 1.00 | 63.28 |
| 1179 | N | SER | 673 | 49.502 | −2.795 | 61.116 | 1.00 | 62.86 |
| 1180 | CA | SER | 673 | 49.616 | −2.056 | 62.368 | 1.00 | 62.27 |
| 1181 | CB | SER | 673 | 48.582 | −0.910 | 62.405 | 1.00 | 61.42 |
| 1182 | OG | SER | 673 | 47.241 | −1.383 | 62.404 | 1.00 | 59.49 |
| 1183 | C | SER | 673 | 49.468 | −2.925 | 63.616 | 1.00 | 63.23 |
| 1184 | O | SER | 673 | 50.026 | −2.608 | 64.664 | 1.00 | 59.71 |
| 1185 | N | SER | 674 | 48.720 | −4.017 | 63.517 | 1.00 | 61.92 |
| 1186 | CA | SER | 674 | 48.538 | −4.875 | 64.680 | 1.00 | 60.38 |
| 1187 | CB | SER | 674 | 47.225 | −4.506 | 65.401 | 1.00 | 62.70 |
| 1188 | OG | SER | 674 | 46.204 | −4.115 | 64.495 | 1.00 | 56.91 |
| 1189 | C | SER | 674 | 48.590 | −6.373 | 64.405 | 1.00 | 61.52 |
| 1190 | O | SER | 674 | 48.122 | −6.849 | 63.377 | 1.00 | 61.47 |
| 1191 | N | VAL | 675 | 49.192 | −7.101 | 65.336 | 1.00 | 64.16 |
| 1192 | CA | VAL | 675 | 49.305 | −8.556 | 65.256 | 1.00 | 61.09 |
| 1193 | CB | VAL | 675 | 50.722 | −9.025 | 64.816 | 1.00 | 62.88 |
| 1194 | CG1 | VAL | 675 | 50.962 | −8.679 | 63.362 | 1.00 | 59.26 |
| 1195 | CG2 | VAL | 675 | 51.787 | −8.394 | 65.710 | 1.00 | 61.45 |
| 1196 | C | VAL | 675 | 49.039 | −9.116 | 66.652 | 1.00 | 62.60 |
| 1197 | O | VAL | 675 | 49.265 | −8.433 | 67.656 | 1.00 | 61.24 |
| 1198 | N | PRO | 676 | 48.550 | −10.363 | 66.735 | 1.00 | 59.77 |
| 1199 | CD | PRO | 676 | 48.219 | −11.265 | 65.616 | 1.00 | 57.51 |
| 1200 | CA | PRO | 676 | 48.260 | −11.001 | 68.020 | 1.00 | 62.72 |
| 1201 | CB | PRO | 676 | 48.026 | −12.452 | 67.623 | 1.00 | 60.61 |
| 1202 | CG | PRO | 676 | 47.362 | −12.317 | 66.283 | 1.00 | 59.30 |
| 1203 | C | PRO | 676 | 49.424 | −10.847 | 68.994 | 1.00 | 61.35 |
| 1204 | O | PRO | 676 | 50.585 | −10.758 | 68.576 | 1.00 | 63.84 |
| 1205 | N | LYS | 677 | 49.117 | −10.818 | 70.290 | 1.00 | 62.54 |
| 1206 | CA | LYS | 677 | 50.154 | −10.673 | 71.314 | 1.00 | 60.54 |
| 1207 | CB | LYS | 677 | 49.510 | −10.646 | 72.702 | 1.00 | 61.63 |
| 1208 | CG | LYS | 677 | 50.472 | −10.433 | 73.853 | 1.00 | 58.65 |
| 1209 | CD | LYS | 677 | 49.861 | −10.969 | 75.143 | 1.00 | 62.01 |
| 1210 | CE | LYS | 677 | 50.912 | −11.109 | 76.241 | 1.00 | 63.79 |
| 1211 | NZ | LYS | 677 | 50.350 | −11.727 | 77.491 | 1.00 | 60.49 |
| 1212 | C | LYS | 677 | 51.162 | −11.828 | 71.222 | 1.00 | 61.45 |
| 1213 | O | LYS | 677 | 52.102 | −11.917 | 72.023 | 1.00 | 59.62 |
| 1214 | N | ASP | 678 | 50.955 | −12.698 | 70.231 | 1.00 | 59.93 |
| 1215 | CA | ASP | 678 | 51.809 | −13.862 | 69.994 | 1.00 | 60.14 |
| 1216 | CB | ASP | 678 | 51.041 | −15.126 | 70.367 | 1.00 | 60.09 |
| 1217 | CG | ASP | 678 | 50.390 | −15.023 | 71.735 | 1.00 | 61.43 |
| 1218 | OD1 | ASP | 678 | 51.110 | −14.940 | 72.749 | 1.00 | 62.42 |
| 1219 | OD2 | ASP | 678 | 49.151 | −15.016 | 71.797 | 1.00 | 60.77 |
| 1220 | C | ASP | 678 | 52.273 | −13.947 | 68.535 | 1.00 | 63.29 |
| 1221 | O | ASP | 678 | 52.771 | −14.981 | 68.090 | 1.00 | 59.36 |
| 1222 | N | GLY | 679 | 52.098 | −12.854 | 67.797 | 1.00 | 59.82 |
| 1223 | CA | GLY | 679 | 52.512 | −12.823 | 66.408 | 1.00 | 58.14 |
| 1224 | C | GLY | 679 | 51.639 | −13.640 | 65.481 | 1.00 | 58.50 |
| 1225 | O | GLY | 679 | 50.600 | −14.179 | 65.870 | 1.00 | 58.88 |
| 1226 | N | LEU | 680 | 52.082 | −13.723 | 64.237 | 1.00 | 62.95 |
| 1227 | CA | LEU | 680 | 51.375 | −14.459 | 63.209 | 1.00 | 63.18 |
| 1228 | CB | LEU | 680 | 51.233 | −13.564 | 61.981 | 1.00 | 65.44 |
| 1229 | CG | LEU | 680 | 50.941 | −12.101 | 62.324 | 1.00 | 60.24 |
| 1230 | CD1 | LEU | 680 | 50.994 | −11.260 | 61.069 | 1.00 | 60.21 |
| 1231 | CD2 | LEU | 680 | 49.582 | −11.979 | 62.974 | 1.00 | 60.11 |
| 1232 | C | LEU | 680 | 52.221 | −15.685 | 62.881 | 1.00 | 63.74 |
| 1233 | O | LEU | 680 | 53.430 | −15.689 | 63.110 | 1.00 | 62.10 |
| 1234 | N | LYS | 681 | 51.598 | −16.729 | 62.354 | 1.00 | 60.36 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1235 | CA | LYS | 681 | 52.348 | −17.922 | 62.000 | 1.00 | 60.78 |
| 1236 | CB | LYS | 681 | 51.406 | −18.969 | 61.418 | 1.00 | 60.11 |
| 1237 | CG | LYS | 681 | 50.209 | −19.253 | 62.289 | 1.00 | 61.43 |
| 1238 | CD | LYS | 681 | 49.295 | −20.221 | 61.579 | 1.00 | 63.30 |
| 1239 | CE | LYS | 681 | 47.908 | −20.186 | 62.160 | 1.00 | 61.77 |
| 1240 | NZ | LYS | 681 | 46.983 | −20.886 | 61.244 | 1.00 | 62.13 |
| 1241 | C | LYS | 681 | 53.429 | −17.551 | 60.973 | 1.00 | 61.58 |
| 1242 | O | LYS | 681 | 54.401 | −18.286 | 60.784 | 1.00 | 63.01 |
| 1243 | N | SER | 682 | 53.250 | −16.410 | 60.309 | 1.00 | 60.35 |
| 1244 | CA | SER | 682 | 54.211 | −15.932 | 59.314 | 1.00 | 62.36 |
| 1245 | CB | SER | 682 | 53.515 | −15.613 | 57.989 | 1.00 | 61.24 |
| 1246 | OG | SER | 682 | 53.066 | −16.788 | 57.346 | 1.00 | 63.18 |
| 1247 | C | SER | 682 | 54.885 | −14.674 | 59.826 | 1.00 | 64.68 |
| 1248 | O | SER | 682 | 55.289 | −13.814 | 59.051 | 1.00 | 59.53 |
| 1249 | N | GLN | 683 | 55.012 | −14.579 | 61.140 | 1.00 | 64.92 |
| 1250 | CA | GLN | 683 | 55.614 | −13.411 | 61.754 | 1.00 | 62.89 |
| 1251 | CB | GLN | 683 | 55.862 | −13.679 | 63.240 | 1.00 | 63.65 |
| 1252 | CG | GLN | 683 | 56.282 | −12.452 | 64.059 | 1.00 | 64.38 |
| 1253 | CD | GLN | 683 | 55.318 | −11.274 | 63.954 | 1.00 | 64.26 |
| 1254 | OE1 | GLN | 683 | 55.688 | −10.205 | 63.476 | 1.00 | 63.72 |
| 1255 | NE2 | GLN | 683 | 54.085 | −11.465 | 64.407 | 1.00 | 61.52 |
| 1256 | C | GLN | 683 | 56.893 | −12.938 | 61.069 | 1.00 | 60.69 |
| 1257 | O | GLN | 683 | 56.981 | −11.782 | 60.669 | 1.00 | 62.35 |
| 1258 | N | GLU | 684 | 57.880 | −13.811 | 60.913 | 1.00 | 60.59 |
| 1259 | CA | GLU | 684 | 59.119 | −13.378 | 60.279 | 1.00 | 61.72 |
| 1260 | CB | GLU | 684 | 60.039 | −14.567 | 59.970 | 1.00 | 61.83 |
| 1261 | CG | GLU | 684 | 60.015 | −15.013 | 58.511 | 1.00 | 61.93 |
| 1262 | CD | GLU | 684 | 61.383 | −15.418 | 57.979 | 1.00 | 60.75 |
| 1263 | OE1 | GLU | 684 | 61.457 | −15.813 | 56.792 | 1.00 | 60.52 |
| 1264 | OE2 | GLU | 684 | 62.375 | −15.342 | 58.744 | 1.00 | 58.72 |
| 1265 | C | GLU | 684 | 58.801 | −12.623 | 58.993 | 1.00 | 60.55 |
| 1266 | O | GLU | 684 | 59.196 | −11.474 | 58.823 | 1.00 | 63.55 |
| 1267 | N | LEU | 685 | 58.064 | −13.263 | 58.100 | 1.00 | 63.64 |
| 1268 | CA | LEU | 685 | 57.710 | −12.649 | 56.834 | 1.00 | 57.80 |
| 1269 | CB | LEU | 685 | 56.921 | −13.649 | 55.985 | 1.00 | 59.68 |
| 1270 | CG | LEU | 685 | 57.165 | −13.734 | 54.476 | 1.00 | 63.20 |
| 1271 | CD1 | LEU | 685 | 55.839 | −14.063 | 53.829 | 1.00 | 59.43 |
| 1272 | CD2 | LEU | 685 | 57.699 | −12.434 | 53.902 | 1.00 | 62.25 |
| 1273 | C | LEU | 685 | 56.882 | −11.370 | 57.040 | 1.00 | 62.31 |
| 1274 | O | LEU | 685 | 56.953 | −10.432 | 56.242 | 1.00 | 61.77 |
| 1275 | N | PHE | 686 | 56.095 | −11.326 | 58.109 | 1.00 | 60.23 |
| 1276 | CA | PHE | 686 | 55.272 | −10.149 | 58.374 | 1.00 | 61.37 |
| 1277 | CB | PHE | 686 | 54.409 | −10.365 | 59.609 | 1.00 | 64.14 |
| 1278 | CG | PHE | 686 | 53.663 | −9.143 | 60.023 | 1.00 | 61.62 |
| 1279 | CD1 | PHE | 686 | 52.639 | −8.650 | 59.236 | 1.00 | 60.24 |
| 1280 | CD2 | PHE | 686 | 54.008 | −8.460 | 61.178 | 1.00 | 62.13 |
| 1281 | CE1 | PHE | 686 | 51.971 | −7.493 | 59.592 | 1.00 | 58.68 |
| 1282 | CE2 | PHE | 686 | 53.347 | −7.304 | 61.543 | 1.00 | 61.95 |
| 1283 | CZ | PHE | 686 | 52.326 | −6.818 | 60.749 | 1.00 | 61.43 |
| 1284 | C | PHE | 686 | 56.109 | −8.897 | 58.596 | 1.00 | 59.14 |
| 1285 | O | PHE | 686 | 56.247 | −8.051 | 57.714 | 1.00 | 61.44 |
| 1286 | N | ASP | 687 | 56.651 | −8.791 | 59.802 | 1.00 | 64.05 |
| 1287 | CA | ASP | 687 | 57.483 | −7.668 | 60.195 | 1.00 | 60.85 |
| 1288 | CB | ASP | 687 | 58.102 | −7.960 | 61.567 | 1.00 | 56.84 |
| 1289 | CG | ASP | 687 | 59.033 | −9.162 | 61.536 | 1.00 | 64.67 |
| 1290 | OD1 | ASP | 687 | 59.482 | −9.610 | 62.622 | 1.00 | 60.21 |
| 1291 | OD2 | ASP | 687 | 59.322 | −9.655 | 60.414 | 1.00 | 63.02 |
| 1292 | C | ASP | 687 | 58.573 | −7.383 | 59.142 | 1.00 | 61.59 |
| 1293 | O | ASP | 687 | 59.262 | −6.358 | 59.214 | 1.00 | 61.60 |
| 1294 | N | GLU | 688 | 58.725 | −8.289 | 58.172 | 1.00 | 60.82 |
| 1295 | CA | GLU | 688 | 59.700 | −8.104 | 57.098 | 1.00 | 59.68 |
| 1296 | CB | GLU | 688 | 60.246 | −9.433 | 56.604 | 1.00 | 62.54 |
| 1297 | CG | GLU | 688 | 61.434 | −9.252 | 55.674 | 1.00 | 60.98 |
| 1298 | CD | GLU | 688 | 61.479 | −10.289 | 54.569 | 1.00 | 58.58 |
| 1299 | OE1 | GLU | 688 | 61.323 | −9.898 | 53.387 | 1.00 | 61.73 |
| 1300 | OE2 | GLU | 688 | 61.663 | −11.490 | 54.882 | 1.00 | 60.24 |
| 1301 | C | GLU | 688 | 59.031 | −7.387 | 55.931 | 1.00 | 60.97 |
| 1302 | O | GLU | 688 | 59.684 | −6.719 | 55.137 | 1.00 | 62.27 |
| 1303 | N | ILE | 689 | 57.721 | −7.552 | 55.809 | 1.00 | 61.23 |
| 1304 | CA | ILE | 689 | 56.979 | −6.864 | 54.767 | 1.00 | 61.00 |
| 1305 | CB | ILE | 689 | 55.641 | −7.592 | 54.451 | 1.00 | 63.41 |
| 1306 | CG2 | ILE | 689 | 54.655 | −6.650 | 53.759 | 1.00 | 59.25 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1307 | CG1 | ILE | 689 | 55.916 | −8.808 | 53.568 | 1.00 | 57.54 |
| 1308 | CD1 | ILE | 689 | 54.667 | −9.526 | 53.121 | 1.00 | 62.29 |
| 1309 | C | ILE | 689 | 56.704 | −5.479 | 55.345 | 1.00 | 58.97 |
| 1310 | O | ILE | 689 | 56.778 | −4.473 | 54.645 | 1.00 | 61.54 |
| 1311 | N | ARG | 690 | 56.411 | −5.439 | 56.641 | 1.00 | 60.16 |
| 1312 | CA | ARG | 690 | 56.135 | −4.185 | 57.319 | 1.00 | 61.28 |
| 1313 | CB | ARG | 690 | 55.855 | −4.434 | 58.799 | 1.00 | 60.29 |
| 1314 | CG | ARG | 690 | 55.548 | −3.170 | 59.582 | 1.00 | 60.74 |
| 1315 | CD | ARG | 690 | 54.679 | −3.480 | 60.770 | 1.00 | 56.91 |
| 1316 | NE | ARG | 690 | 54.190 | −2.280 | 61.437 | 1.00 | 66.99 |
| 1317 | CZ | ARG | 690 | 54.967 | −1.378 | 62.026 | 1.00 | 64.04 |
| 1318 | NH1 | ARG | 690 | 56.283 | −1.533 | 62.029 | 1.00 | 58.19 |
| 1319 | NH2 | ARG | 690 | 54.427 | −0.327 | 62.623 | 1.00 | 62.52 |
| 1320 | C | ARG | 690 | 57.274 | −3.179 | 57.177 | 1.00 | 57.93 |
| 1321 | O | ARG | 690 | 57.037 | −1.977 | 57.067 | 1.00 | 59.25 |
| 1322 | N | MET | 691 | 58.512 | −3.660 | 57.190 | 1.00 | 58.75 |
| 1323 | CA | MET | 691 | 59.664 | −2.783 | 57.048 | 1.00 | 64.96 |
| 1324 | CB | MET | 691 | 60.928 | −3.542 | 57.450 | 1.00 | 61.53 |
| 1325 | CG | MET | 691 | 62.247 | −3.016 | 56.886 | 1.00 | 59.40 |
| 1326 | SD | MET | 691 | 62.942 | −4.201 | 55.673 | 1.00 | 61.45 |
| 1327 | CE | MET | 691 | 63.225 | −5.669 | 56.764 | 1.00 | 60.93 |
| 1328 | C | MET | 691 | 59.775 | −2.254 | 55.621 | 1.00 | 61.68 |
| 1329 | O | MET | 691 | 60.130 | −1.099 | 55.405 | 1.00 | 63.95 |
| 1330 | N | THR | 692 | 59.459 | −3.097 | 54.646 | 1.00 | 59.70 |
| 1331 | CA | THR | 692 | 59.519 | −2.698 | 53.243 | 1.00 | 60.57 |
| 1332 | CB | THR | 692 | 59.105 | −3.855 | 52.323 | 1.00 | 62.51 |
| 1333 | OG1 | THR | 692 | 59.796 | −5.046 | 52.714 | 1.00 | 59.90 |
| 1334 | CG2 | THR | 692 | 59.437 | −3.523 | 50.879 | 1.00 | 60.93 |
| 1335 | C | THR | 692 | 58.586 | −1.523 | 52.962 | 1.00 | 60.46 |
| 1336 | O | THR | 692 | 58.890 | −0.655 | 52.143 | 1.00 | 59.04 |
| 1337 | N | TYR | 693 | 57.439 | −1.516 | 53.634 | 1.00 | 61.66 |
| 1338 | CA | TYR | 693 | 56.459 | −0.458 | 53.461 | 1.00 | 60.32 |
| 1339 | CB | TYR | 693 | 55.045 | −1.033 | 53.553 | 1.00 | 59.81 |
| 1340 | CG | TYR | 693 | 54.665 | −1.802 | 52.302 | 1.00 | 61.04 |
| 1341 | CD1 | TYR | 693 | 54.552 | −1.153 | 51.073 | 1.00 | 63.46 |
| 1342 | CE1 | TYR | 693 | 54.292 | −1.865 | 49.909 | 1.00 | 65.96 |
| 1343 | CD2 | TYR | 693 | 54.497 | −3.185 | 52.332 | 1.00 | 59.82 |
| 1344 | CE2 | TYR | 693 | 54.236 | −3.906 | 51.170 | 1.00 | 63.54 |
| 1345 | CZ | TYR | 693 | 54.137 | −3.242 | 49.967 | 1.00 | 62.96 |
| 1346 | OH | TYR | 693 | 53.901 | −3.961 | 48.822 | 1.00 | 59.68 |
| 1347 | C | TYR | 693 | 56.663 | 0.664 | 54.458 | 1.00 | 58.94 |
| 1348 | O | TYR | 693 | 55.877 | 1.600 | 54.527 | 1.00 | 59.49 |
| 1349 | N | ILE | 694 | 57.720 | 0.555 | 55.248 | 1.00 | 63.16 |
| 1350 | CA | ILE | 694 | 58.052 | 1.598 | 56.195 | 1.00 | 61.35 |
| 1351 | CB | ILE | 694 | 58.734 | 1.042 | 57.462 | 1.00 | 59.89 |
| 1352 | CG2 | ILE | 694 | 59.652 | 2.101 | 58.077 | 1.00 | 62.13 |
| 1353 | CG1 | ILE | 694 | 57.668 | 0.580 | 58.457 | 1.00 | 63.95 |
| 1354 | CD1 | ILE | 694 | 58.216 | 0.168 | 59.793 | 1.00 | 61.57 |
| 1355 | C | ILE | 694 | 59.028 | 2.478 | 55.430 | 1.00 | 58.86 |
| 1356 | O | ILE | 694 | 58.989 | 3.701 | 55.541 | 1.00 | 62.76 |
| 1357 | N | LYS | 695 | 59.890 | 1.838 | 54.643 | 1.00 | 61.80 |
| 1358 | CA | LYS | 695 | 60.869 | 2.539 | 53.821 | 1.00 | 60.19 |
| 1359 | CB | LYS | 695 | 61.987 | 1.607 | 53.364 | 1.00 | 61.05 |
| 1360 | CG | LYS | 695 | 62.768 | 0.892 | 54.438 | 1.00 | 60.54 |
| 1361 | CD | LYS | 695 | 63.876 | 0.081 | 53.767 | 1.00 | 63.44 |
| 1362 | CE | LYS | 695 | 64.516 | −0.947 | 54.699 | 1.00 | 61.61 |
| 1363 | NZ | LYS | 695 | 65.330 | −1.962 | 53.942 | 1.00 | 62.18 |
| 1364 | C | LYS | 695 | 60.206 | 3.074 | 52.559 | 1.00 | 61.44 |
| 1365 | O | LYS | 695 | 60.706 | 4.010 | 51.946 | 1.00 | 61.23 |
| 1366 | N | GLU | 696 | 59.101 | 2.452 | 52.156 | 1.00 | 61.65 |
| 1367 | CA | GLU | 696 | 58.381 | 2.862 | 50.961 | 1.00 | 60.70 |
| 1368 | CB | GLU | 696 | 57.289 | 1.851 | 50.635 | 1.00 | 62.74 |
| 1369 | CG | GLU | 696 | 56.806 | 1.901 | 49.200 | 1.00 | 63.74 |
| 1370 | CD | GLU | 696 | 57.927 | 1.725 | 48.187 | 1.00 | 63.24 |
| 1371 | OE1 | GLU | 696 | 58.903 | 1.002 | 48.494 | 1.00 | 61.23 |
| 1372 | OE2 | GLU | 696 | 57.824 | 2.299 | 47.079 | 1.00 | 62.98 |
| 1373 | C | GLU | 696 | 57.775 | 4.215 | 51.260 | 1.00 | 61.27 |
| 1374 | O | GLU | 696 | 57.594 | 5.051 | 50.366 | 1.00 | 61.63 |
| 1375 | N | LEU | 697 | 57.468 | 4.414 | 52.540 | 1.00 | 59.99 |
| 1376 | CA | LEU | 697 | 56.912 | 5.668 | 53.022 | 1.00 | 63.89 |
| 1377 | CB | LEU | 697 | 56.314 | 5.493 | 54.418 | 1.00 | 58.18 |
| 1378 | CG | LEU | 697 | 55.831 | 6.810 | 55.016 | 1.00 | 62.97 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1379 | CD1 | LEU | 697 | 54.754 | 7.370 | 54.127 | 1.00 | 59.80 |
| 1380 | CD2 | LEU | 697 | 55.319 | 6.606 | 56.425 | 1.00 | 59.24 |
| 1381 | C | LEU | 697 | 58.029 | 6.709 | 53.072 | 1.00 | 61.66 |
| 1382 | O | LEU | 697 | 57.807 | 7.871 | 52.774 | 1.00 | 60.35 |
| 1383 | N | GLY | 698 | 59.228 | 6.283 | 53.460 | 1.00 | 59.57 |
| 1384 | CA | GLY | 698 | 60.348 | 7.198 | 53.523 | 1.00 | 61.15 |
| 1385 | C | GLY | 698 | 60.570 | 7.770 | 52.146 | 1.00 | 60.91 |
| 1386 | O | GLY | 698 | 60.748 | 8.977 | 51.988 | 1.00 | 61.15 |
| 1387 | N | LYS | 699 | 60.557 | 6.880 | 51.156 | 1.00 | 60.97 |
| 1388 | CA | LYS | 699 | 60.729 | 7.219 | 49.745 | 1.00 | 60.90 |
| 1389 | CB | LYS | 699 | 60.526 | 5.983 | 48.875 | 1.00 | 66.06 |
| 1390 | CG | LYS | 699 | 61.729 | 5.098 | 48.621 | 1.00 | 61.25 |
| 1391 | CD | LYS | 699 | 61.290 | 3.930 | 47.737 | 1.00 | 59.41 |
| 1392 | CE | LYS | 699 | 62.371 | 3.498 | 46.765 | 1.00 | 61.62 |
| 1393 | NZ | LYS | 699 | 63.066 | 2.246 | 47.178 | 1.00 | 60.87 |
| 1394 | C | LYS | 699 | 59.710 | 8.256 | 49.289 | 1.00 | 58.54 |
| 1395 | O | LYS | 699 | 60.019 | 9.127 | 48.482 | 1.00 | 59.98 |
| 1396 | N | ALA | 700 | 58.483 | 8.128 | 49.777 | 1.00 | 63.02 |
| 1397 | CA | ALA | 700 | 57.423 | 9.048 | 49.408 | 1.00 | 61.82 |
| 1398 | CB | ALA | 700 | 56.094 | 8.540 | 49.926 | 1.00 | 65.26 |
| 1399 | C | ALA | 700 | 57.712 | 10.422 | 49.977 | 1.00 | 60.36 |
| 1400 | O | ALA | 700 | 57.545 | 11.434 | 49.298 | 1.00 | 62.77 |
| 1401 | N | ILE | 701 | 58.137 | 10.446 | 51.235 | 1.00 | 65.16 |
| 1402 | CA | ILE | 701 | 58.471 | 11.683 | 51.917 | 1.00 | 64.84 |
| 1403 | CB | ILE | 701 | 58.931 | 11.406 | 53.338 | 1.00 | 61.36 |
| 1404 | CG2 | ILE | 701 | 59.509 | 12.670 | 53.953 | 1.00 | 63.03 |
| 1405 | CG1 | ILE | 701 | 57.761 | 10.874 | 54.151 | 1.00 | 61.61 |
| 1406 | CD1 | ILE | 701 | 58.167 | 10.364 | 55.495 | 1.00 | 60.05 |
| 1407 | C | ILE | 701 | 59.574 | 12.455 | 51.195 | 1.00 | 61.64 |
| 1408 | O | ILE | 701 | 59.597 | 13.683 | 51.228 | 1.00 | 58.62 |
| 1409 | N | VAL | 702 | 60.500 | 11.749 | 50.555 | 1.00 | 63.95 |
| 1410 | CA | VAL | 702 | 61.560 | 12.438 | 49.831 | 1.00 | 57.69 |
| 1411 | CB | VAL | 702 | 62.815 | 11.532 | 49.665 | 1.00 | 63.59 |
| 1412 | CG1 | VAL | 702 | 63.310 | 11.093 | 51.024 | 1.00 | 59.75 |
| 1413 | CG2 | VAL | 702 | 62.494 | 10.330 | 48.819 | 1.00 | 64.22 |
| 1414 | C | VAL | 702 | 61.038 | 12.907 | 48.466 | 1.00 | 61.62 |
| 1415 | O | VAL | 702 | 61.328 | 14.014 | 48.031 | 1.00 | 61.64 |
| 1416 | N | LYS | 703 | 60.244 | 12.065 | 47.814 | 1.00 | 61.58 |
| 1417 | CA | LYS | 703 | 59.666 | 12.387 | 46.516 | 1.00 | 60.75 |
| 1418 | CB | LYS | 703 | 58.475 | 11.474 | 46.201 | 1.00 | 56.80 |
| 1419 | CG | LYS | 703 | 57.419 | 12.161 | 45.293 | 1.00 | 59.93 |
| 1420 | CD | LYS | 703 | 55.967 | 11.815 | 45.660 | 1.00 | 60.60 |
| 1421 | CE | LYS | 703 | 54.962 | 12.848 | 45.088 | 1.00 | 57.15 |
| 1422 | NZ | LYS | 703 | 55.070 | 13.064 | 43.605 | 1.00 | 62.62 |
| 1423 | C | LYS | 703 | 59.169 | 13.814 | 46.392 | 1.00 | 61.49 |
| 1424 | O | LYS | 703 | 59.454 | 14.472 | 45.404 | 1.00 | 58.34 |
| 1425 | N | ARG | 704 | 58.390 | 14.271 | 47.367 | 1.00 | 63.00 |
| 1426 | CA | ARG | 704 | 57.826 | 15.621 | 47.321 | 1.00 | 60.60 |
| 1427 | CB | ARG | 704 | 56.331 | 15.590 | 47.661 | 1.00 | 62.95 |
| 1428 | CG | ARG | 704 | 56.026 | 15.010 | 49.033 | 1.00 | 61.71 |
| 1429 | CD | ARG | 704 | 54.728 | 15.553 | 49.548 | 1.00 | 60.30 |
| 1430 | NE | ARG | 704 | 54.931 | 16.417 | 50.702 | 1.00 | 62.33 |
| 1431 | CZ | ARG | 704 | 53.983 | 17.200 | 51.204 | 1.00 | 60.19 |
| 1432 | NH1 | ARG | 704 | 52.784 | 17.213 | 50.640 | 1.00 | 61.68 |
| 1433 | NH2 | ARG | 704 | 54.225 | 17.965 | 52.263 | 1.00 | 63.26 |
| 1434 | C | ARG | 704 | 58.520 | 16.607 | 48.249 | 1.00 | 63.14 |
| 1435 | O | ARG | 704 | 58.732 | 17.772 | 47.885 | 1.00 | 60.41 |
| 1436 | N | GLU | 705 | 58.842 | 16.155 | 49.458 | 1.00 | 60.89 |
| 1437 | CA | GLU | 705 | 59.528 | 17.018 | 50.412 | 1.00 | 62.58 |
| 1438 | CB | GLU | 705 | 59.814 | 16.288 | 51.730 | 1.00 | 60.91 |
| 1439 | CG | GLU | 705 | 58.605 | 16.091 | 52.605 | 1.00 | 62.30 |
| 1440 | CD | GLU | 705 | 57.847 | 17.384 | 52.817 | 1.00 | 64.22 |
| 1441 | OE1 | GLU | 705 | 56.684 | 17.460 | 52.347 | 1.00 | 58.55 |
| 1442 | OE2 | GLU | 705 | 58.419 | 18.317 | 53.440 | 1.00 | 61.42 |
| 1443 | C | GLU | 705 | 60.848 | 17.456 | 49.801 | 1.00 | 62.10 |
| 1444 | O | GLU | 705 | 61.869 | 16.761 | 49.939 | 1.00 | 59.78 |
| 1445 | N | GLY | 706 | 60.823 | 18.597 | 49.115 | 1.00 | 60.22 |
| 1446 | CA | GLY | 706 | 62.036 | 19.100 | 48.500 | 1.00 | 61.75 |
| 1447 | C | GLY | 706 | 63.159 | 19.239 | 49.518 | 1.00 | 60.44 |
| 1448 | O | GLY | 706 | 64.168 | 18.519 | 49.450 | 1.00 | 61.54 |
| 1449 | N | ASN | 707 | 62.974 | 20.148 | 50.477 | 1.00 | 61.06 |
| 1450 | CA | ASN | 707 | 63.989 | 20.387 | 51.491 | 1.00 | 60.61 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1451 | CB | ASN | 707 | 63.561 | 21.505 | 52.443 | 1.00 | 63.06 |
| 1452 | CG | ASN | 707 | 64.731 | 22.048 | 53.258 | 1.00 | 60.50 |
| 1453 | OD1 | ASN | 707 | 64.663 | 23.152 | 53.803 | 1.00 | 61.18 |
| 1454 | ND2 | ASN | 707 | 65.815 | 21.269 | 53.342 | 1.00 | 61.75 |
| 1455 | C | ASN | 707 | 64.355 | 19.143 | 52.281 | 1.00 | 61.56 |
| 1456 | O | ASN | 707 | 63.685 | 18.767 | 53.250 | 1.00 | 63.56 |
| 1457 | N | SER | 708 | 65.446 | 18.525 | 51.837 | 1.00 | 62.02 |
| 1458 | CA | SER | 708 | 66.024 | 17.326 | 52.427 | 1.00 | 60.22 |
| 1459 | CB | SER | 708 | 67.379 | 17.070 | 51.737 | 1.00 | 58.91 |
| 1460 | OG | SER | 708 | 68.112 | 15.998 | 52.305 | 1.00 | 62.15 |
| 1461 | C | SER | 708 | 66.200 | 17.500 | 53.945 | 1.00 | 63.60 |
| 1462 | O | SER | 708 | 66.754 | 16.635 | 54.624 | 1.00 | 60.95 |
| 1463 | N | SER | 709 | 65.713 | 18.619 | 54.474 | 1.00 | 61.83 |
| 1464 | CA | SER | 709 | 65.826 | 18.922 | 55.894 | 1.00 | 61.35 |
| 1465 | CB | SER | 709 | 66.279 | 20.373 | 56.065 | 1.00 | 65.65 |
| 1466 | OG | SER | 709 | 67.479 | 20.615 | 55.332 | 1.00 | 62.14 |
| 1467 | C | SER | 709 | 64.516 | 18.684 | 56.641 | 1.00 | 59.54 |
| 1468 | O | SER | 709 | 64.497 | 18.583 | 57.874 | 1.00 | 61.29 |
| 1469 | N | GLN | 710 | 63.416 | 18.586 | 55.900 | 1.00 | 62.57 |
| 1470 | CA | GLN | 710 | 62.131 | 18.347 | 56.533 | 1.00 | 61.59 |
| 1471 | CB | GLN | 710 | 61.087 | 19.333 | 56.007 | 1.00 | 58.05 |
| 1472 | CG | GLN | 710 | 61.469 | 20.792 | 56.249 | 1.00 | 62.98 |
| 1473 | CD | GLN | 710 | 60.344 | 21.776 | 55.943 | 1.00 | 59.84 |
| 1474 | OE1 | GLN | 710 | 59.363 | 21.882 | 56.696 | 1.00 | 60.97 |
| 1475 | NE2 | GLN | 710 | 60.481 | 22.502 | 54.831 | 1.00 | 65.14 |
| 1476 | C | GLN | 710 | 61.683 | 16.917 | 56.297 | 1.00 | 58.31 |
| 1477 | O | GLN | 710 | 60.512 | 16.586 | 56.466 | 1.00 | 60.42 |
| 1478 | N | ASN | 711 | 62.625 | 16.063 | 55.916 | 1.00 | 61.21 |
| 1479 | CA | ASN | 711 | 62.309 | 14.666 | 55.673 | 1.00 | 63.02 |
| 1480 | CB | ASN | 711 | 63.407 | 14.033 | 54.819 | 1.00 | 60.49 |
| 1481 | CG | ASN | 711 | 63.508 | 14.675 | 53.449 | 1.00 | 65.80 |
| 1482 | OD1 | ASN | 711 | 62.565 | 15.303 | 52.977 | 1.00 | 63.88 |
| 1483 | ND2 | ASN | 711 | 64.646 | 14.507 | 52.801 | 1.00 | 60.91 |
| 1484 | C | ASN | 711 | 62.090 | 13.879 | 56.974 | 1.00 | 63.26 |
| 1485 | O | ASN | 711 | 61.055 | 13.238 | 57.155 | 1.00 | 58.14 |
| 1486 | N | TRP | 712 | 63.054 | 13.930 | 57.883 | 1.00 | 61.93 |
| 1487 | CA | TRP | 712 | 62.915 | 13.234 | 59.148 | 1.00 | 59.49 |
| 1488 | CB | TRP | 712 | 64.259 | 13.185 | 59.833 | 1.00 | 62.44 |
| 1489 | CG | TRP | 712 | 65.169 | 12.333 | 59.088 | 1.00 | 62.60 |
| 1490 | CD2 | TRP | 712 | 65.485 | 10.980 | 59.388 | 1.00 | 61.74 |
| 1491 | CE2 | TRP | 712 | 66.331 | 10.516 | 58.366 | 1.00 | 62.04 |
| 1492 | CE3 | TRP | 712 | 65.130 | 10.108 | 60.426 | 1.00 | 60.92 |
| 1493 | CD1 | TRP | 712 | 65.815 | 12.637 | 57.934 | 1.00 | 57.10 |
| 1494 | NE1 | TRP | 712 | 66.517 | 11.552 | 57.490 | 1.00 | 63.63 |
| 1495 | CZ2 | TRP | 712 | 66.832 | 9.215 | 58.345 | 1.00 | 63.94 |
| 1496 | CZ3 | TRP | 712 | 65.625 | 8.817 | 60.407 | 1.00 | 65.64 |
| 1497 | CH2 | TRP | 712 | 66.470 | 8.381 | 59.370 | 1.00 | 62.08 |
| 1498 | C | TRP | 712 | 61.903 | 13.954 | 60.021 | 1.00 | 59.14 |
| 1499 | O | TRP | 712 | 61.372 | 13.410 | 60.996 | 1.00 | 59.32 |
| 1500 | N | GLN | 713 | 61.637 | 15.191 | 59.640 | 1.00 | 60.06 |
| 1501 | CA | GLN | 713 | 60.705 | 16.043 | 60.345 | 1.00 | 63.93 |
| 1502 | CB | GLN | 713 | 60.853 | 17.455 | 59.793 | 1.00 | 59.11 |
| 1503 | CG | GLN | 713 | 60.727 | 18.564 | 60.802 | 1.00 | 61.74 |
| 1504 | CD | GLN | 713 | 59.352 | 19.135 | 60.838 | 1.00 | 60.27 |
| 1505 | OE1 | GLN | 713 | 58.660 | 19.154 | 59.824 | 1.00 | 58.27 |
| 1506 | NE2 | GLN | 713 | 58.942 | 19.628 | 61.998 | 1.00 | 65.68 |
| 1507 | C | GLN | 713 | 59.296 | 15.522 | 60.107 | 1.00 | 57.87 |
| 1508 | O | GLN | 713 | 58.472 | 15.465 | 61.018 | 1.00 | 63.21 |
| 1509 | N | ARG | 714 | 59.051 | 15.125 | 58.864 | 1.00 | 62.15 |
| 1510 | CA | ARG | 714 | 57.758 | 14.626 | 58.424 | 1.00 | 57.88 |
| 1511 | CB | ARG | 714 | 57.668 | 14.782 | 56.907 | 1.00 | 65.30 |
| 1512 | CG | ARG | 714 | 56.272 | 14.971 | 56.382 | 1.00 | 62.96 |
| 1513 | CD | ARG | 714 | 56.301 | 15.439 | 54.940 | 1.00 | 62.68 |
| 1514 | NE | ARG | 714 | 55.029 | 15.200 | 54.267 | 1.00 | 62.08 |
| 1515 | CZ | ARG | 714 | 53.899 | 15.828 | 54.561 | 1.00 | 62.26 |
| 1516 | NH1 | ARG | 714 | 53.877 | 16.741 | 55.515 | 1.00 | 59.12 |
| 1517 | NH2 | ARG | 714 | 52.788 | 15.535 | 53.906 | 1.00 | 57.33 |
| 1518 | C | ARG | 714 | 57.573 | 13.171 | 58.831 | 1.00 | 60.95 |
| 1519 | O | ARG | 714 | 56.531 | 12.787 | 59.368 | 1.00 | 60.00 |
| 1520 | N | PHE | 715 | 58.594 | 12.363 | 58.571 | 1.00 | 59.93 |
| 1521 | CA | PHE | 715 | 58.551 | 10.960 | 58.940 | 1.00 | 61.38 |
| 1522 | CB | PHE | 715 | 59.934 | 10.328 | 58.799 | 1.00 | 60.45 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1523 | CG | PHE | 715 | 59.921 | 8.834 | 58.843 | 1.00 | 63.37 |
| 1524 | CD1 | PHE | 715 | 59.016 | 8.119 | 58.063 | 1.00 | 61.57 |
| 1525 | CD2 | PHE | 715 | 60.824 | 8.136 | 59.636 | 1.00 | 59.17 |
| 1526 | CE1 | PHE | 715 | 59.005 | 6.732 | 58.067 | 1.00 | 60.07 |
| 1527 | CE2 | PHE | 715 | 60.824 | 6.740 | 59.648 | 1.00 | 58.03 |
| 1528 | CZ | PHE | 715 | 59.904 | 6.038 | 58.856 | 1.00 | 61.29 |
| 1529 | C | PHE | 715 | 58.118 | 10.923 | 60.394 | 1.00 | 61.16 |
| 1530 | O | PHE | 715 | 57.409 | 10.017 | 60.821 | 1.00 | 61.52 |
| 1531 | N | TYR | 716 | 58.541 | 11.925 | 61.153 | 1.00 | 62.10 |
| 1532 | CA | TYR | 716 | 58.178 | 11.989 | 62.550 | 1.00 | 61.74 |
| 1533 | CB | TYR | 716 | 58.962 | 13.092 | 63.256 | 1.00 | 60.58 |
| 1534 | CG | TYR | 716 | 58.729 | 13.117 | 64.748 | 1.00 | 60.86 |
| 1535 | CD1 | TYR | 716 | 59.376 | 12.213 | 65.586 | 1.00 | 58.32 |
| 1536 | CE1 | TYR | 716 | 59.159 | 12.226 | 66.952 | 1.00 | 59.67 |
| 1537 | CD2 | TYR | 716 | 57.852 | 14.032 | 65.318 | 1.00 | 60.64 |
| 1538 | CE2 | TYR | 716 | 57.625 | 14.052 | 66.679 | 1.00 | 63.17 |
| 1539 | CZ | TYR | 716 | 58.283 | 13.152 | 67.493 | 1.00 | 58.37 |
| 1540 | OH | TYR | 716 | 58.090 | 13.194 | 68.856 | 1.00 | 59.28 |
| 1541 | C | TYR | 716 | 56.688 | 12.280 | 62.662 | 1.00 | 61.28 |
| 1542 | O | TYR | 716 | 55.952 | 11.578 | 63.356 | 1.00 | 61.70 |
| 1543 | N | GLN | 717 | 56.249 | 13.318 | 61.967 | 1.00 | 62.49 |
| 1544 | CA | GLN | 717 | 54.858 | 13.716 | 62.009 | 1.00 | 63.77 |
| 1545 | CB | GLN | 717 | 54.694 | 15.061 | 61.304 | 1.00 | 63.18 |
| 1546 | CG | GLN | 717 | 55.613 | 16.126 | 61.888 | 1.00 | 62.93 |
| 1547 | CD | GLN | 717 | 55.418 | 17.512 | 61.288 | 1.00 | 62.21 |
| 1548 | OE1 | GLN | 717 | 55.545 | 17.709 | 60.073 | 1.00 | 59.68 |
| 1549 | NE2 | GLN | 717 | 55.125 | 18.487 | 62.147 | 1.00 | 58.70 |
| 1550 | C | GLN | 717 | 53.910 | 12.674 | 61.426 | 1.00 | 61.09 |
| 1551 | O | GLN | 717 | 52.907 | 12.338 | 62.064 | 1.00 | 61.62 |
| 1552 | N | LEU | 718 | 54.228 | 12.154 | 60.237 | 1.00 | 62.25 |
| 1553 | CA | LEU | 718 | 53.384 | 11.144 | 59.589 | 1.00 | 60.93 |
| 1554 | CB | LEU | 718 | 53.880 | 10.833 | 58.166 | 1.00 | 61.18 |
| 1555 | CG | LEU | 718 | 53.823 | 11.915 | 57.078 | 1.00 | 60.69 |
| 1556 | CD1 | LEU | 718 | 54.322 | 11.353 | 55.764 | 1.00 | 59.94 |
| 1557 | CD2 | LEU | 718 | 52.411 | 12.419 | 56.916 | 1.00 | 64.72 |
| 1558 | C | LEU | 718 | 53.308 | 9.847 | 60.391 | 1.00 | 61.41 |
| 1559 | O | LEU | 718 | 52.241 | 9.270 | 60.530 | 1.00 | 62.27 |
| 1560 | N | THR | 719 | 54.441 | 9.387 | 60.911 | 1.00 | 62.60 |
| 1561 | CA | THR | 719 | 54.469 | 8.162 | 61.706 | 1.00 | 61.77 |
| 1562 | CB | THR | 719 | 55.902 | 7.717 | 62.001 | 1.00 | 63.38 |
| 1563 | OG1 | THR | 719 | 56.590 | 8.749 | 62.715 | 1.00 | 59.25 |
| 1564 | CG2 | THR | 719 | 56.626 | 7.420 | 60.716 | 1.00 | 64.41 |
| 1565 | C | THR | 719 | 53.744 | 8.362 | 63.034 | 1.00 | 64.18 |
| 1566 | O | THR | 719 | 53.365 | 7.398 | 63.702 | 1.00 | 59.43 |
| 1567 | N | LYS | 720 | 53.562 | 9.619 | 63.421 | 1.00 | 60.48 |
| 1568 | CA | LYS | 720 | 52.864 | 9.913 | 64.652 | 1.00 | 60.21 |
| 1569 | CB | LYS | 720 | 53.414 | 11.194 | 65.281 | 1.00 | 63.61 |
| 1570 | CG | LYS | 720 | 52.661 | 11.630 | 66.532 | 1.00 | 60.31 |
| 1571 | CD | LYS | 720 | 52.340 | 10.450 | 67.448 | 1.00 | 57.45 |
| 1572 | CE | LYS | 720 | 51.254 | 10.801 | 68.472 | 1.00 | 57.33 |
| 1573 | NZ | LYS | 720 | 50.621 | 9.562 | 69.037 | 1.00 | 61.89 |
| 1574 | C | LYS | 720 | 51.364 | 10.023 | 64.345 | 1.00 | 60.76 |
| 1575 | O | LYS | 720 | 50.523 | 10.016 | 65.246 | 1.00 | 60.43 |
| 1576 | N | LEU | 721 | 51.030 | 10.110 | 63.061 | 1.00 | 65.16 |
| 1577 | CA | LEU | 721 | 49.634 | 10.162 | 62.659 | 1.00 | 59.83 |
| 1578 | CB | LEU | 721 | 49.505 | 10.724 | 61.235 | 1.00 | 59.18 |
| 1579 | CG | LEU | 721 | 48.264 | 11.548 | 60.867 | 1.00 | 63.18 |
| 1580 | CD1 | LEU | 721 | 48.219 | 11.751 | 59.366 | 1.00 | 62.00 |
| 1581 | CD2 | LEU | 721 | 47.005 | 10.851 | 61.327 | 1.00 | 62.08 |
| 1582 | C | LEU | 721 | 49.163 | 8.696 | 62.703 | 1.00 | 61.87 |
| 1583 | O | LEU | 721 | 48.041 | 8.405 | 63.117 | 1.00 | 62.35 |
| 1584 | N | LEU | 722 | 50.052 | 7.788 | 62.282 | 1.00 | 62.99 |
| 1585 | CA | LEU | 722 | 49.813 | 6.339 | 62.250 | 1.00 | 58.34 |
| 1586 | CB | LEU | 722 | 50.988 | 5.635 | 61.570 | 1.00 | 59.92 |
| 1587 | CG | LEU | 722 | 51.194 | 5.933 | 60.084 | 1.00 | 60.23 |
| 1588 | CD1 | LEU | 722 | 52.500 | 5.333 | 59.636 | 1.00 | 58.33 |
| 1589 | CD2 | LEU | 722 | 50.050 | 5.373 | 59.264 | 1.00 | 59.18 |
| 1590 | C | LEU | 722 | 49.624 | 5.754 | 63.651 | 1.00 | 62.26 |
| 1591 | O | LEU | 722 | 48.827 | 4.835 | 63.860 | 1.00 | 60.80 |
| 1592 | N | ASP | 723 | 50.389 | 6.282 | 64.597 | 1.00 | 60.29 |
| 1593 | CA | ASP | 723 | 50.321 | 5.870 | 65.989 | 1.00 | 61.98 |
| 1594 | CB | ASP | 723 | 51.409 | 6.583 | 66.780 | 1.00 | 62.74 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1595 | CG | ASP | 723 | 52.652 | 5.759 | 66.935 | 1.00 | 62.09 |
| 1596 | OD1 | ASP | 723 | 52.840 | 4.814 | 66.146 | 1.00 | 62.64 |
| 1597 | OD2 | ASP | 723 | 53.445 | 6.066 | 67.848 | 1.00 | 60.13 |
| 1598 | C | ASP | 723 | 48.970 | 6.275 | 66.554 | 1.00 | 61.71 |
| 1599 | O | ASP | 723 | 48.281 | 5.496 | 67.202 | 1.00 | 61.64 |
| 1600 | N | SER | 724 | 48.612 | 7.524 | 66.305 | 1.00 | 62.20 |
| 1601 | CA | SER | 724 | 47.362 | 8.090 | 66.784 | 1.00 | 61.12 |
| 1602 | CB | SER | 724 | 47.329 | 9.579 | 66.449 | 1.00 | 63.08 |
| 1603 | OG | SER | 724 | 47.513 | 9.767 | 65.057 | 1.00 | 61.03 |
| 1604 | C | SER | 724 | 46.098 | 7.419 | 66.246 | 1.00 | 59.27 |
| 1605 | O | SER | 724 | 45.015 | 7.664 | 66.772 | 1.00 | 61.79 |
| 1606 | N | MET | 725 | 46.229 | 6.594 | 65.203 | 1.00 | 60.63 |
| 1607 | CA | MET | 725 | 45.077 | 5.893 | 64.615 | 1.00 | 60.05 |
| 1608 | CB | MET | 725 | 45.425 | 5.228 | 63.272 | 1.00 | 60.16 |
| 1609 | CG | MET | 725 | 45.452 | 6.151 | 62.055 | 1.00 | 66.62 |
| 1610 | SD | MET | 725 | 43.992 | 7.180 | 61.838 | 1.00 | 58.95 |
| 1611 | CE | MET | 725 | 42.904 | 6.134 | 61.000 | 1.00 | 61.36 |
| 1612 | C | MET | 725 | 44.573 | 4.833 | 65.576 | 1.00 | 64.25 |
| 1613 | O | MET | 725 | 43.382 | 4.543 | 65.627 | 1.00 | 59.89 |
| 1614 | N | HIS | 726 | 45.492 | 4.251 | 66.334 | 1.00 | 62.22 |
| 1615 | CA | HIS | 726 | 45.122 | 3.249 | 67.313 | 1.00 | 60.86 |
| 1616 | CB | HIS | 726 | 46.356 | 2.746 | 68.064 | 1.00 | 58.90 |
| 1617 | CG | HIS | 726 | 47.183 | 1.772 | 67.286 | 1.00 | 59.73 |
| 1618 | CD2 | HIS | 726 | 48.518 | 1.706 | 67.070 | 1.00 | 60.15 |
| 1619 | ND1 | HIS | 726 | 46.635 | 0.682 | 66.646 | 1.00 | 61.70 |
| 1620 | CE1 | HIS | 726 | 47.598 | −0.014 | 66.069 | 1.00 | 61.05 |
| 1621 | NE2 | HIS | 726 | 48.750 | 0.586 | 66.311 | 1.00 | 60.76 |
| 1622 | C | HIS | 726 | 44.141 | 3.880 | 68.291 | 1.00 | 61.09 |
| 1623 | O | HIS | 726 | 43.146 | 3.268 | 68.650 | 1.00 | 60.43 |
| 1624 | N | GLU | 727 | 44.425 | 5.109 | 68.714 | 1.00 | 61.91 |
| 1625 | CA | GLU | 727 | 43.548 | 5.825 | 69.642 | 1.00 | 58.28 |
| 1626 | CB | GLU | 727 | 44.218 | 7.109 | 70.159 | 1.00 | 63.92 |
| 1627 | CG | GLU | 727 | 43.254 | 8.102 | 70.846 | 1.00 | 59.43 |
| 1628 | CD | GLU | 727 | 43.073 | 9.413 | 70.053 | 1.00 | 61.79 |
| 1629 | OE1 | GLU | 727 | 44.079 | 10.150 | 69.874 | 1.00 | 60.96 |
| 1630 | OE2 | GLU | 727 | 41.931 | 9.707 | 69.607 | 1.00 | 63.98 |
| 1631 | C | GLU | 727 | 42.220 | 6.187 | 68.993 | 1.00 | 60.97 |
| 1632 | O | GLU | 727 | 41.163 | 6.009 | 69.596 | 1.00 | 58.72 |
| 1633 | N | VAL | 728 | 42.263 | 6.699 | 67.769 | 1.00 | 60.50 |
| 1634 | CA | VAL | 728 | 41.022 | 7.073 | 67.105 | 1.00 | 60.74 |
| 1635 | CB | VAL | 728 | 41.289 | 7.922 | 65.828 | 1.00 | 58.90 |
| 1636 | CG1 | VAL | 728 | 42.719 | 7.804 | 65.415 | 1.00 | 58.73 |
| 1637 | CG2 | VAL | 728 | 40.382 | 7.494 | 64.703 | 1.00 | 65.58 |
| 1638 | C | VAL | 728 | 40.192 | 5.842 | 66.773 | 1.00 | 59.91 |
| 1639 | O | VAL | 728 | 38.971 | 5.844 | 66.931 | 1.00 | 61.17 |
| 1640 | N | VAL | 729 | 40.872 | 4.792 | 66.326 | 1.00 | 61.77 |
| 1641 | CA | VAL | 729 | 40.243 | 3.522 | 65.974 | 1.00 | 62.39 |
| 1642 | CB | VAL | 729 | 41.277 | 2.578 | 65.332 | 1.00 | 60.27 |
| 1643 | CG1 | VAL | 729 | 40.946 | 1.131 | 65.606 | 1.00 | 61.53 |
| 1644 | CG2 | VAL | 729 | 41.298 | 2.815 | 63.866 | 1.00 | 60.01 |
| 1645 | C | VAL | 729 | 39.586 | 2.830 | 67.173 | 1.00 | 61.69 |
| 1646 | O | VAL | 729 | 38.718 | 1.971 | 67.009 | 1.00 | 59.65 |
| 1647 | N | GLU | 730 | 39.999 | 3.199 | 68.377 | 1.00 | 59.90 |
| 1648 | CA | GLU | 730 | 39.411 | 2.601 | 69.558 | 1.00 | 60.27 |
| 1649 | CB | GLU | 730 | 40.308 | 2.812 | 70.755 | 1.00 | 59.45 |
| 1650 | CG | GLU | 730 | 39.878 | 2.014 | 71.942 | 1.00 | 66.48 |
| 1651 | CD | GLU | 730 | 40.681 | 2.348 | 73.167 | 1.00 | 62.84 |
| 1652 | OE1 | GLU | 730 | 41.912 | 2.547 | 73.039 | 1.00 | 61.03 |
| 1653 | OE2 | GLU | 730 | 40.081 | 2.400 | 74.263 | 1.00 | 60.34 |
| 1654 | C | GLU | 730 | 38.085 | 3.291 | 69.804 | 1.00 | 62.24 |
| 1655 | O | GLU | 730 | 37.031 | 2.660 | 69.869 | 1.00 | 60.10 |
| 1656 | N | ASN | 731 | 38.154 | 4.606 | 69.941 | 1.00 | 61.01 |
| 1657 | CA | ASN | 731 | 36.967 | 5.409 | 70.157 | 1.00 | 60.41 |
| 1658 | CB | ASN | 731 | 37.356 | 6.880 | 70.212 | 1.00 | 62.98 |
| 1659 | CG | ASN | 731 | 37.593 | 7.333 | 71.613 | 1.00 | 59.54 |
| 1660 | OD1 | ASN | 731 | 36.657 | 7.385 | 72.410 | 1.00 | 58.59 |
| 1661 | ND2 | ASN | 731 | 38.841 | 7.638 | 71.945 | 1.00 | 58.18 |
| 1662 | C | ASN | 731 | 35.917 | 5.165 | 69.081 | 1.00 | 61.30 |
| 1663 | O | ASN | 731 | 34.720 | 5.345 | 69.317 | 1.00 | 60.95 |
| 1664 | N | LEU | 732 | 36.364 | 4.750 | 67.902 | 1.00 | 60.39 |
| 1665 | CA | LEU | 732 | 35.442 | 4.475 | 66.820 | 1.00 | 61.55 |
| 1666 | CB | LEU | 732 | 36.141 | 4.550 | 65.471 | 1.00 | 59.24 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1667 | CG | LEU | 732 | 36.184 | 5.931 | 64.813 | 1.00 | 64.00 |
| 1668 | CD1 | LEU | 732 | 36.712 | 5.787 | 63.374 | 1.00 | 62.90 |
| 1669 | CD2 | LEU | 732 | 34.771 | 6.561 | 64.818 | 1.00 | 60.26 |
| 1670 | C | LEU | 732 | 34.841 | 3.108 | 66.997 | 1.00 | 60.27 |
| 1671 | O | LEU | 732 | 33.648 | 2.922 | 66.774 | 1.00 | 61.79 |
| 1672 | N | LEU | 733 | 35.673 | 2.148 | 67.399 | 1.00 | 58.72 |
| 1673 | CA | LEU | 733 | 35.214 | 0.770 | 67.612 | 1.00 | 60.63 |
| 1674 | CB | LEU | 733 | 36.376 | −0.153 | 67.969 | 1.00 | 60.85 |
| 1675 | CG | LEU | 733 | 37.087 | −0.798 | 66.782 | 1.00 | 56.83 |
| 1676 | CD1 | LEU | 733 | 38.344 | −1.474 | 67.266 | 1.00 | 63.66 |
| 1677 | CD2 | LEU | 733 | 36.159 | −1.786 | 66.083 | 1.00 | 56.09 |
| 1678 | C | LEU | 733 | 34.158 | 0.663 | 68.696 | 1.00 | 60.11 |
| 1679 | O | LEU | 733 | 33.092 | 0.098 | 68.458 | 1.00 | 60.20 |
| 1680 | N | ASN | 734 | 34.456 | 1.192 | 69.883 | 1.00 | 64.88 |
| 1681 | CA | ASN | 734 | 33.503 | 1.148 | 70.988 | 1.00 | 60.87 |
| 1682 | CB | ASN | 734 | 33.874 | 2.130 | 72.099 | 1.00 | 64.42 |
| 1683 | CG | ASN | 734 | 35.076 | 1.683 | 72.896 | 1.00 | 60.85 |
| 1684 | OD1 | ASN | 734 | 35.499 | 0.526 | 72.817 | 1.00 | 60.20 |
| 1685 | ND2 | ASN | 734 | 35.627 | 2.597 | 73.686 | 1.00 | 62.04 |
| 1686 | C | ASN | 734 | 32.157 | 1.544 | 70.455 | 1.00 | 59.98 |
| 1687 | O | ASN | 734 | 31.209 | 0.755 | 70.478 | 1.00 | 59.10 |
| 1688 | N | TYR | 735 | 32.085 | 2.778 | 69.969 | 1.00 | 61.85 |
| 1689 | CA | TYR | 735 | 30.844 | 3.294 | 69.421 | 1.00 | 63.27 |
| 1690 | CB | TYR | 735 | 31.075 | 4.640 | 68.743 | 1.00 | 60.68 |
| 1691 | CG | TYR | 735 | 29.867 | 5.515 | 68.853 | 1.00 | 62.56 |
| 1692 | CD1 | TYR | 735 | 28.777 | 5.328 | 67.975 | 1.00 | 60.84 |
| 1693 | CE1 | TYR | 735 | 27.586 | 6.030 | 68.168 | 1.00 | 60.10 |
| 1694 | CD2 | TYR | 735 | 29.722 | 6.421 | 69.889 | 1.00 | 62.93 |
| 1695 | CE2 | TYR | 735 | 28.543 | 7.127 | 70.084 | 1.00 | 62.59 |
| 1696 | CZ | TYR | 735 | 27.483 | 6.916 | 69.221 | 1.00 | 60.99 |
| 1697 | OH | TYR | 735 | 26.305 | 7.561 | 69.418 | 1.00 | 56.15 |
| 1698 | C | TYR | 735 | 30.261 | 2.306 | 68.418 | 1.00 | 57.10 |
| 1699 | O | TYR | 735 | 29.052 | 2.158 | 68.321 | 1.00 | 60.19 |
| 1700 | N | CYS | 736 | 31.126 | 1.621 | 67.682 | 1.00 | 62.53 |
| 1701 | CA | CYS | 736 | 30.673 | 0.644 | 66.707 | 1.00 | 60.21 |
| 1702 | CB | CYS | 736 | 31.842 | 0.208 | 65.815 | 1.00 | 62.29 |
| 1703 | SG | CYS | 736 | 31.461 | −1.142 | 64.660 | 1.00 | 62.77 |
| 1704 | C | CYS | 736 | 30.063 | −0.572 | 67.399 | 1.00 | 62.99 |
| 1705 | O | CYS | 736 | 28.857 | −0.795 | 67.290 | 1.00 | 61.76 |
| 1706 | N | PHE | 737 | 30.892 | −1.346 | 68.111 | 1.00 | 60.76 |
| 1707 | CA | PHE | 737 | 30.435 | −2.546 | 68.835 | 1.00 | 61.61 |
| 1708 | CB | PHE | 737 | 31.454 | −3.013 | 69.889 | 1.00 | 65.67 |
| 1709 | CG | PHE | 737 | 32.718 | −3.575 | 69.321 | 1.00 | 61.17 |
| 1710 | CD1 | PHE | 737 | 32.732 | −4.173 | 68.069 | 1.00 | 62.43 |
| 1711 | CD2 | PHE | 737 | 33.904 | −3.515 | 70.049 | 1.00 | 62.09 |
| 1712 | CE1 | PHE | 737 | 33.908 | −4.704 | 67.544 | 1.00 | 60.80 |
| 1713 | CE2 | PHE | 737 | 35.083 | −4.042 | 69.536 | 1.00 | 61.51 |
| 1714 | CZ | PHE | 737 | 35.086 | −4.638 | 68.279 | 1.00 | 59.32 |
| 1715 | C | PHE | 737 | 29.151 | −2.266 | 69.581 | 1.00 | 60.98 |
| 1716 | O | PHE | 737 | 28.103 | −2.865 | 69.312 | 1.00 | 61.98 |
| 1717 | N | GLN | 738 | 29.274 | −1.356 | 70.542 | 1.00 | 64.21 |
| 1718 | CA | GLN | 738 | 28.183 | −0.934 | 71.399 | 1.00 | 63.22 |
| 1719 | CB | GLN | 738 | 28.613 | 0.301 | 72.173 | 1.00 | 64.29 |
| 1720 | CG | GLN | 738 | 27.542 | 0.896 | 73.021 | 1.00 | 59.02 |
| 1721 | CD | GLN | 738 | 27.555 | 2.392 | 72.920 | 1.00 | 61.20 |
| 1722 | OE1 | GLN | 738 | 27.116 | 2.962 | 71.916 | 1.00 | 60.80 |
| 1723 | NE2 | GLN | 738 | 28.082 | 3.048 | 73.948 | 1.00 | 57.12 |
| 1724 | C | GLN | 738 | 26.917 | −0.640 | 70.606 | 1.00 | 61.18 |
| 1725 | O | GLN | 738 | 25.827 | −1.017 | 71.009 | 1.00 | 61.34 |
| 1726 | N | THR | 739 | 27.056 | 0.037 | 69.478 | 1.00 | 61.45 |
| 1727 | CA | THR | 739 | 25.893 | 0.326 | 68.678 | 1.00 | 60.85 |
| 1728 | CB | THR | 739 | 26.208 | 1.297 | 67.542 | 1.00 | 55.90 |
| 1729 | OG1 | THR | 739 | 26.212 | 2.649 | 68.047 | 1.00 | 60.51 |
| 1730 | CG2 | THR | 739 | 25.193 | 1.200 | 66.444 | 1.00 | 62.24 |
| 1731 | C | THR | 739 | 25.330 | −0.969 | 68.085 | 1.00 | 62.53 |
| 1732 | O | THR | 739 | 24.122 | −1.107 | 67.898 | 1.00 | 60.85 |
| 1733 | N | PHE | 740 | 26.221 | −1.906 | 67.784 | 1.00 | 61.25 |
| 1734 | CA | PHE | 740 | 25.859 | −3.197 | 67.215 | 1.00 | 59.86 |
| 1735 | CB | PHE | 740 | 27.110 | −3.854 | 66.641 | 1.00 | 60.28 |
| 1736 | CG | PHE | 740 | 26.937 | −5.301 | 66.311 | 1.00 | 63.82 |
| 1737 | CD1 | PHE | 740 | 26.434 | −5.690 | 65.079 | 1.00 | 62.86 |
| 1738 | CD2 | PHE | 740 | 27.297 | −6.278 | 67.236 | 1.00 | 61.71 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1739 | CE1 | PHE | 740 | 26.295 | −7.042 | 64.763 | 1.00 | 60.86 |
| 1740 | CE2 | PHE | 740 | 27.165 | −7.623 | 66.938 | 1.00 | 60.83 |
| 1741 | CZ | PHE | 740 | 26.663 | −8.013 | 65.696 | 1.00 | 60.77 |
| 1742 | C | PHE | 740 | 25.200 | −4.140 | 68.238 | 1.00 | 60.76 |
| 1743 | O | PHE | 740 | 24.420 | −5.028 | 67.866 | 1.00 | 60.72 |
| 1744 | N | LEU | 741 | 25.538 | −3.965 | 69.515 | 1.00 | 62.82 |
| 1745 | CA | LEU | 741 | 24.976 | −4.793 | 70.584 | 1.00 | 61.57 |
| 1746 | CB | LEU | 741 | 25.991 | −5.012 | 71.708 | 1.00 | 59.14 |
| 1747 | CG | LEU | 741 | 27.187 | −5.904 | 71.404 | 1.00 | 62.48 |
| 1748 | CD1 | LEU | 741 | 28.083 | −5.956 | 72.627 | 1.00 | 58.13 |
| 1749 | CD2 | LEU | 741 | 26.708 | −7.294 | 71.021 | 1.00 | 60.31 |
| 1750 | C | LEU | 741 | 23.770 | −4.087 | 71.165 | 1.00 | 60.19 |
| 1751 | O | LEU | 741 | 23.577 | −4.055 | 72.389 | 1.00 | 59.64 |
| 1752 | N | ASP | 742 | 22.960 | −3.508 | 70.290 | 1.00 | 61.92 |
| 1753 | CA | ASP | 742 | 21.789 | −2.797 | 70.762 | 1.00 | 60.22 |
| 1754 | CB | ASP | 742 | 22.185 | −1.372 | 71.179 | 1.00 | 61.70 |
| 1755 | CG | ASP | 742 | 21.021 | −0.598 | 71.793 | 1.00 | 60.82 |
| 1756 | OD1 | ASP | 742 | 21.258 | 0.438 | 72.473 | 1.00 | 60.77 |
| 1757 | OD2 | ASP | 742 | 19.863 | −1.028 | 71.587 | 1.00 | 61.09 |
| 1758 | C | ASP | 742 | 20.689 | −2.769 | 69.710 | 1.00 | 61.90 |
| 1759 | O | ASP | 742 | 20.530 | −1.782 | 68.995 | 1.00 | 61.23 |
| 1760 | N | LYS | 743 | 19.934 | −3.864 | 69.623 | 1.00 | 63.29 |
| 1761 | CA | LYS | 743 | 18.833 | −3.975 | 68.664 | 1.00 | 62.18 |
| 1762 | CB | LYS | 743 | 18.045 | −5.273 | 68.888 | 1.00 | 63.55 |
| 1763 | CG | LYS | 743 | 18.054 | −6.243 | 67.705 | 1.00 | 62.77 |
| 1764 | CD | LYS | 743 | 17.301 | −5.691 | 66.489 | 1.00 | 59.38 |
| 1765 | CE | LYS | 743 | 17.291 | −6.724 | 65.349 | 1.00 | 62.80 |
| 1766 | NZ | LYS | 743 | 16.446 | −6.335 | 64.166 | 1.00 | 57.45 |
| 1767 | C | LYS | 743 | 17.899 | −2.786 | 68.822 | 1.00 | 62.93 |
| 1768 | O | LYS | 743 | 17.407 | −2.248 | 67.833 | 1.00 | 58.22 |
| 1769 | N | THR | 744 | 17.669 | −2.383 | 70.069 | 1.00 | 61.23 |
| 1770 | CA | THR | 744 | 16.808 | −1.247 | 70.400 | 1.00 | 61.48 |
| 1771 | CB | THR | 744 | 17.148 | −0.715 | 71.802 | 1.00 | 63.18 |
| 1772 | OG1 | THR | 744 | 17.199 | −1.817 | 72.719 | 1.00 | 59.84 |
| 1773 | CG2 | THR | 744 | 16.112 | 0.308 | 72.265 | 1.00 | 60.98 |
| 1774 | C | THR | 744 | 16.913 | −0.077 | 69.411 | 1.00 | 59.67 |
| 1775 | O | THR | 744 | 15.913 | 0.580 | 69.118 | 1.00 | 64.20 |
| 1776 | N | MET | 745 | 18.117 | 0.184 | 68.903 | 1.00 | 61.36 |
| 1777 | CA | MET | 745 | 18.322 | 1.282 | 67.961 | 1.00 | 62.05 |
| 1778 | CB | MET | 745 | 19.703 | 1.909 | 68.158 | 1.00 | 63.01 |
| 1779 | CG | MET | 745 | 20.029 | 2.189 | 69.614 | 1.00 | 61.21 |
| 1780 | SD | MET | 745 | 21.418 | 3.324 | 69.877 | 1.00 | 62.14 |
| 1781 | CE | MET | 745 | 20.934 | 4.087 | 71.538 | 1.00 | 61.78 |
| 1782 | C | MET | 745 | 18.175 | 0.824 | 66.517 | 1.00 | 59.56 |
| 1783 | O | MET | 745 | 18.382 | 1.605 | 65.585 | 1.00 | 62.58 |
| 1784 | N | SER | 746 | 17.817 | −0.442 | 66.334 | 1.00 | 59.78 |
| 1785 | CA | SER | 746 | 17.624 | −1.000 | 64.996 | 1.00 | 58.09 |
| 1786 | CB | SER | 746 | 16.169 | −0.786 | 64.541 | 1.00 | 58.34 |
| 1787 | OG | SER | 746 | 15.252 | −1.368 | 65.455 | 1.00 | 63.83 |
| 1788 | C | SER | 746 | 18.592 | −0.429 | 63.940 | 1.00 | 59.09 |
| 1789 | O | SER | 746 | 18.176 | 0.027 | 62.867 | 1.00 | 61.57 |
| 1790 | N | ILE | 747 | 19.882 | −0.432 | 64.269 | 1.00 | 62.10 |
| 1791 | CA | ILE | 747 | 20.905 | 0.022 | 63.342 | 1.00 | 61.22 |
| 1792 | CB | ILE | 747 | 22.021 | 0.814 | 64.054 | 1.00 | 63.05 |
| 1793 | CG2 | ILE | 747 | 23.241 | 0.930 | 63.145 | 1.00 | 64.60 |
| 1794 | CG1 | ILE | 747 | 21.499 | 2.205 | 64.426 | 1.00 | 61.38 |
| 1795 | CD1 | ILE | 747 | 22.576 | 3.198 | 64.804 | 1.00 | 63.35 |
| 1796 | C | ILE | 747 | 21.465 | −1.260 | 62.749 | 1.00 | 62.54 |
| 1797 | O | ILE | 747 | 22.169 | −2.011 | 63.419 | 1.00 | 60.09 |
| 1798 | N | GLU | 748 | 21.125 | −1.507 | 61.491 | 1.00 | 60.25 |
| 1799 | CA | GLU | 748 | 21.541 | −2.711 | 60.787 | 1.00 | 60.97 |
| 1800 | CB | GLU | 748 | 20.497 | −3.038 | 59.709 | 1.00 | 63.45 |
| 1801 | CG | GLU | 748 | 20.877 | −4.168 | 58.756 | 1.00 | 60.81 |
| 1802 | CD | GLU | 748 | 19.678 | −4.723 | 57.973 | 1.00 | 59.13 |
| 1803 | OE1 | GLU | 748 | 19.013 | −3.932 | 57.262 | 1.00 | 62.39 |
| 1804 | OE2 | GLU | 748 | 19.406 | −5.950 | 58.072 | 1.00 | 61.13 |
| 1805 | C | GLU | 748 | 22.940 | −2.658 | 60.175 | 1.00 | 61.28 |
| 1806 | O | GLU | 748 | 23.391 | −1.616 | 59.690 | 1.00 | 62.62 |
| 1807 | N | PHE | 749 | 23.622 | −3.800 | 60.231 | 1.00 | 62.73 |
| 1808 | CA | PHE | 749 | 24.963 | −3.959 | 59.667 | 1.00 | 59.35 |
| 1809 | CB | PHE | 749 | 25.974 | −4.421 | 60.733 | 1.00 | 59.45 |
| 1810 | CG | PHE | 749 | 26.299 | −3.389 | 61.759 | 1.00 | 64.74 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1811 | CD1 | PHE | 749 | 25.399 | −3.085 | 62.770 | 1.00 | 59.18 |
| 1812 | CD2 | PHE | 749 | 27.514 | −2.721 | 61.721 | 1.00 | 57.96 |
| 1813 | CE1 | PHE | 749 | 25.708 | −2.119 | 63.742 | 1.00 | 61.52 |
| 1814 | CE2 | PHE | 749 | 27.839 | −1.753 | 62.685 | 1.00 | 65.31 |
| 1815 | CZ | PHE | 749 | 26.934 | −1.451 | 63.697 | 1.00 | 59.87 |
| 1816 | C | PHE | 749 | 24.872 | −5.048 | 58.599 | 1.00 | 60.75 |
| 1817 | O | PHE | 749 | 24.047 | −5.952 | 58.705 | 1.00 | 62.03 |
| 1818 | N | PRO | 750 | 25.705 | −4.970 | 57.550 | 1.00 | 61.23 |
| 1819 | CD | PRO | 750 | 26.645 | −3.910 | 57.166 | 1.00 | 60.04 |
| 1820 | CA | PRO | 750 | 25.652 | −6.003 | 56.516 | 1.00 | 61.34 |
| 1821 | CB | PRO | 750 | 26.584 | −5.468 | 55.434 | 1.00 | 64.04 |
| 1822 | CG | PRO | 750 | 26.608 | −4.015 | 55.668 | 1.00 | 60.17 |
| 1823 | C | PRO | 750 | 26.240 | −7.235 | 57.172 | 1.00 | 60.83 |
| 1824 | O | PRO | 750 | 26.788 | −7.143 | 58.271 | 1.00 | 59.53 |
| 1825 | N | GLU | 751 | 26.139 | −8.386 | 56.523 | 1.00 | 60.43 |
| 1826 | CA | GLU | 751 | 26.719 | −9.572 | 57.122 | 1.00 | 61.33 |
| 1827 | CB | GLU | 751 | 26.350 | −10.834 | 56.311 | 1.00 | 62.90 |
| 1828 | CG | GLU | 751 | 25.560 | −10.608 | 55.002 | 1.00 | 60.51 |
| 1829 | CD | GLU | 751 | 26.436 | −10.142 | 53.837 | 1.00 | 57.86 |
| 1830 | OE1 | GLU | 751 | 27.420 | −10.844 | 53.519 | 1.00 | 60.97 |
| 1831 | OE2 | GLU | 751 | 26.138 | −9.084 | 53.240 | 1.00 | 59.16 |
| 1832 | C | GLU | 751 | 28.255 | −9.389 | 57.219 | 1.00 | 58.48 |
| 1833 | O | GLU | 751 | 28.850 | −9.561 | 58.292 | 1.00 | 59.47 |
| 1834 | N | MET | 752 | 28.891 | −9.004 | 56.115 | 1.00 | 64.26 |
| 1835 | CA | MET | 752 | 30.336 | −8.808 | 56.109 | 1.00 | 61.15 |
| 1836 | CB | MET | 752 | 30.777 | −8.060 | 54.857 | 1.00 | 63.84 |
| 1837 | CG | MET | 752 | 32.255 | −7.666 | 54.898 | 1.00 | 64.44 |
| 1838 | SD | MET | 752 | 33.383 | −9.076 | 55.043 | 1.00 | 67.15 |
| 1839 | CE | MET | 752 | 33.649 | −9.386 | 53.307 | 1.00 | 59.96 |
| 1840 | C | MET | 752 | 30.884 | −8.072 | 57.323 | 1.00 | 62.38 |
| 1841 | O | MET | 752 | 31.963 | −8.394 | 57.811 | 1.00 | 60.81 |
| 1842 | N | LEU | 753 | 30.163 | −7.067 | 57.796 | 1.00 | 59.19 |
| 1843 | CA | LEU | 753 | 30.627 | −6.323 | 58.957 | 1.00 | 62.39 |
| 1844 | CB | LEU | 753 | 30.187 | −4.862 | 58.881 | 1.00 | 61.65 |
| 1845 | CG | LEU | 753 | 31.214 | −3.835 | 58.397 | 1.00 | 61.49 |
| 1846 | CD1 | LEU | 753 | 31.713 | −4.171 | 57.010 | 1.00 | 61.11 |
| 1847 | CD2 | LEU | 753 | 30.567 | −2.471 | 58.411 | 1.00 | 63.29 |
| 1848 | C | LEU | 753 | 30.114 | −6.946 | 60.241 | 1.00 | 58.84 |
| 1849 | O | LEU | 753 | 30.779 | −6.885 | 61.273 | 1.00 | 61.39 |
| 1850 | N | ALA | 754 | 28.927 | −7.541 | 60.177 | 1.00 | 62.56 |
| 1851 | CA | ALA | 754 | 28.337 | −8.194 | 61.343 | 1.00 | 61.99 |
| 1852 | CB | ALA | 754 | 26.963 | −8.775 | 60.983 | 1.00 | 59.37 |
| 1853 | C | ALA | 754 | 29.287 | −9.313 | 61.747 | 1.00 | 66.01 |
| 1854 | O | ALA | 754 | 29.619 | −9.482 | 62.922 | 1.00 | 63.54 |
| 1855 | N | GLU | 755 | 29.724 | −10.044 | 60.722 | 1.00 | 63.92 |
| 1856 | CA | GLU | 755 | 30.632 | −11.194 | 60.795 | 1.00 | 59.42 |
| 1857 | CB | GLU | 755 | 30.674 | −11.851 | 59.407 | 1.00 | 60.24 |
| 1858 | CG | GLU | 755 | 31.733 | −12.933 | 59.190 | 1.00 | 62.29 |
| 1859 | CD | GLU | 755 | 31.348 | −14.260 | 59.811 | 1.00 | 59.60 |
| 1860 | OE1 | GLU | 755 | 30.318 | −14.834 | 59.388 | 1.00 | 60.67 |
| 1861 | OE2 | GLU | 755 | 32.075 | −14.728 | 60.719 | 1.00 | 62.46 |
| 1862 | C | GLU | 755 | 32.068 | −10.912 | 61.252 | 1.00 | 60.75 |
| 1863 | O | GLU | 755 | 32.906 | −11.809 | 61.240 | 1.00 | 61.42 |
| 1864 | N | ILE | 756 | 32.363 | −9.677 | 61.636 | 1.00 | 60.43 |
| 1865 | CA | ILE | 756 | 33.709 | −9.328 | 62.074 | 1.00 | 65.41 |
| 1866 | CB | ILE | 756 | 34.369 | −8.336 | 61.114 | 1.00 | 58.24 |
| 1867 | CG2 | ILE | 756 | 35.741 | −7.964 | 61.623 | 1.00 | 57.70 |
| 1868 | CG1 | ILE | 756 | 34.478 | −8.957 | 59.729 | 1.00 | 59.57 |
| 1869 | CD1 | ILE | 756 | 35.178 | −8.090 | 58.743 | 1.00 | 61.24 |
| 1870 | C | ILE | 756 | 33.625 | −8.693 | 63.439 | 1.00 | 63.18 |
| 1871 | O | ILE | 756 | 34.373 | −9.043 | 64.351 | 1.00 | 58.77 |
| 1872 | N | ILE | 757 | 32.705 | −7.740 | 63.548 | 1.00 | 59.89 |
| 1873 | CA | ILE | 757 | 32.434 | −7.024 | 64.785 | 1.00 | 61.90 |
| 1874 | CB | ILE | 757 | 31.115 | −6.254 | 64.668 | 1.00 | 64.77 |
| 1875 | CG2 | ILE | 757 | 30.778 | −5.602 | 65.991 | 1.00 | 62.61 |
| 1876 | CG1 | ILE | 757 | 31.224 | −5.237 | 63.529 | 1.00 | 62.60 |
| 1877 | CD1 | ILE | 757 | 29.902 | −4.649 | 63.097 | 1.00 | 59.02 |
| 1878 | C | ILE | 757 | 32.298 | −8.069 | 65.879 | 1.00 | 60.76 |
| 1879 | O | ILE | 757 | 32.990 | −8.016 | 66.890 | 1.00 | 60.98 |
| 1880 | N | THR | 758 | 31.396 | −9.022 | 65.660 | 1.00 | 59.72 |
| 1881 | CA | THR | 758 | 31.184 | −10.104 | 66.608 | 1.00 | 61.21 |
| 1882 | CB | THR | 758 | 30.224 | −11.141 | 66.017 | 1.00 | 58.63 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1883 | OG1 | THR | 758 | 30.260 | −11.028 | 64.592 | 1.00 | 60.88 |
| 1884 | CG2 | THR | 758 | 28.792 | −10.925 | 66.527 | 1.00 | 60.75 |
| 1885 | C | THR | 758 | 32.540 | −10.770 | 66.885 | 1.00 | 61.53 |
| 1886 | O | THR | 758 | 33.167 | −10.549 | 67.926 | 1.00 | 61.44 |
| 1887 | N | ASN | 759 | 32.979 | −11.572 | 65.924 | 1.00 | 62.04 |
| 1888 | CA | ASN | 759 | 34.240 | −12.305 | 65.965 | 1.00 | 60.58 |
| 1889 | CB | ASN | 759 | 34.426 | −13.001 | 64.623 | 1.00 | 60.54 |
| 1890 | CG | ASN | 759 | 33.242 | −12.774 | 63.689 | 1.00 | 60.06 |
| 1891 | OD1 | ASN | 759 | 32.581 | −11.723 | 63.736 | 1.00 | 59.27 |
| 1892 | ND2 | ASN | 759 | 32.976 | −13.747 | 62.825 | 1.00 | 59.97 |
| 1893 | C | ASN | 759 | 35.470 | −11.432 | 66.249 | 1.00 | 59.08 |
| 1894 | O | ASN | 759 | 36.564 | −11.710 | 65.734 | 1.00 | 63.02 |
| 1895 | N | GLN | 760 | 35.282 | −10.388 | 67.059 | 1.00 | 60.43 |
| 1896 | CA | GLN | 760 | 36.336 | −9.442 | 67.438 | 1.00 | 61.43 |
| 1897 | CB | GLN | 760 | 36.620 | −8.446 | 66.302 | 1.00 | 56.98 |
| 1898 | CG | GLN | 760 | 37.445 | −8.966 | 65.121 | 1.00 | 61.31 |
| 1899 | CD | GLN | 760 | 38.839 | −9.446 | 65.514 | 1.00 | 63.88 |
| 1900 | OE1 | GLN | 760 | 39.445 | −8.949 | 66.463 | 1.00 | 59.43 |
| 1901 | NE2 | GLN | 760 | 39.356 | −10.409 | 64.769 | 1.00 | 62.96 |
| 1902 | C | GLN | 760 | 35.850 | −8.659 | 68.651 | 1.00 | 59.31 |
| 1903 | O | GLN | 760 | 36.625 | −8.353 | 69.563 | 1.00 | 59.88 |
| 1904 | N | ILE | 761 | 34.546 | −8.371 | 68.649 | 1.00 | 61.08 |
| 1905 | CA | ILE | 761 | 33.861 | −7.606 | 69.704 | 1.00 | 64.40 |
| 1906 | CB | ILE | 761 | 32.318 | −7.582 | 69.469 | 1.00 | 60.77 |
| 1907 | CG2 | ILE | 761 | 31.759 | −8.983 | 69.575 | 1.00 | 61.46 |
| 1908 | CG1 | ILE | 761 | 31.626 | −6.686 | 70.500 | 1.00 | 61.86 |
| 1909 | CD1 | ILE | 761 | 30.115 | −6.703 | 70.390 | 1.00 | 62.34 |
| 1910 | C | ILE | 761 | 34.111 | −8.077 | 71.139 | 1.00 | 63.06 |
| 1911 | O | ILE | 761 | 33.900 | −7.317 | 72.087 | 1.00 | 60.11 |
| 1912 | N | PRO | 762 | 34.543 | −9.338 | 71.319 | 1.00 | 58.19 |
| 1913 | CD | PRO | 762 | 34.581 | −10.454 | 70.353 | 1.00 | 61.52 |
| 1914 | CA | PRO | 762 | 34.800 | −9.840 | 72.670 | 1.00 | 60.05 |
| 1915 | CB | PRO | 762 | 34.718 | −11.350 | 72.482 | 1.00 | 60.47 |
| 1916 | CG | PRO | 762 | 35.309 | −11.528 | 71.122 | 1.00 | 62.98 |
| 1917 | C | PRO | 762 | 36.160 | −9.419 | 73.230 | 1.00 | 59.07 |
| 1918 | O | PRO | 762 | 36.257 | −8.697 | 74.232 | 1.00 | 61.15 |
| 1919 | N | LYS | 763 | 37.203 | −9.887 | 72.558 | 1.00 | 59.41 |
| 1920 | CA | LYS | 763 | 38.580 | −9.637 | 72.960 | 1.00 | 61.27 |
| 1921 | CB | LYS | 763 | 39.424 | −10.882 | 72.594 | 1.00 | 61.66 |
| 1922 | CG | LYS | 763 | 40.926 | −10.651 | 72.347 | 1.00 | 62.08 |
| 1923 | CD | LYS | 763 | 41.206 | −9.910 | 71.025 | 1.00 | 58.99 |
| 1924 | CE | LYS | 763 | 40.834 | −10.723 | 69.776 | 1.00 | 60.53 |
| 1925 | NZ | LYS | 763 | 39.378 | −11.026 | 69.623 | 1.00 | 62.94 |
| 1926 | C | LYS | 763 | 39.256 | −8.359 | 72.438 | 1.00 | 63.01 |
| 1927 | O | LYS | 763 | 40.164 | −7.846 | 73.086 | 1.00 | 63.43 |
| 1928 | N | TYR | 764 | 38.820 | −7.847 | 71.289 | 1.00 | 64.75 |
| 1929 | CA | TYR | 764 | 39.428 | −6.653 | 70.673 | 1.00 | 58.42 |
| 1930 | CB | TYR | 764 | 38.399 | −5.865 | 69.876 | 1.00 | 62.63 |
| 1931 | CG | TYR | 764 | 38.901 | −5.590 | 68.486 | 1.00 | 65.16 |
| 1932 | CD1 | TYR | 764 | 38.708 | −6.516 | 67.467 | 1.00 | 57.96 |
| 1933 | CE1 | TYR | 764 | 39.190 | −6.287 | 66.180 | 1.00 | 61.30 |
| 1934 | CD2 | TYR | 764 | 39.600 | −4.422 | 68.192 | 1.00 | 61.22 |
| 1935 | CE2 | TYR | 764 | 40.092 | −4.183 | 66.902 | 1.00 | 61.36 |
| 1936 | CZ | TYR | 764 | 39.876 | −5.118 | 65.901 | 1.00 | 59.50 |
| 1937 | OH | TYR | 764 | 40.304 | −4.863 | 64.612 | 1.00 | 62.78 |
| 1938 | C | TYR | 764 | 40.204 | −5.654 | 71.535 | 1.00 | 61.96 |
| 1939 | O | TYR | 764 | 41.310 | −5.963 | 72.003 | 1.00 | 61.04 |
| 1940 | N | SER | 765 | 39.653 | −4.443 | 71.701 | 1.00 | 60.29 |
| 1941 | CA | SER | 765 | 40.324 | −3.419 | 72.519 | 1.00 | 61.03 |
| 1942 | CB | SER | 765 | 39.780 | −1.999 | 72.208 | 1.00 | 57.40 |
| 1943 | OG | SER | 765 | 38.359 | −1.934 | 72.144 | 1.00 | 59.00 |
| 1944 | C | SER | 765 | 40.207 | −3.760 | 74.016 | 1.00 | 59.80 |
| 1945 | O | SER | 765 | 39.574 | −3.046 | 74.809 | 1.00 | 60.59 |
| 1946 | N | ASN | 766 | 40.833 | −4.884 | 74.371 | 1.00 | 59.36 |
| 1947 | CA | ASN | 766 | 40.867 | −5.404 | 75.738 | 1.00 | 63.02 |
| 1948 | CB | ASN | 766 | 40.390 | −6.867 | 75.745 | 1.00 | 59.32 |
| 1949 | CG | ASN | 766 | 38.959 | −7.018 | 75.239 | 1.00 | 61.45 |
| 1950 | OD1 | ASN | 766 | 38.593 | −6.456 | 74.197 | 1.00 | 60.60 |
| 1951 | ND2 | ASN | 766 | 38.143 | −7.782 | 75.971 | 1.00 | 64.82 |
| 1952 | C | ASN | 766 | 42.301 | −5.305 | 76.311 | 1.00 | 62.76 |
| 1953 | O | ASN | 766 | 42.503 | −4.889 | 77.469 | 1.00 | 60.59 |
| 1954 | N | GLY | 767 | 43.281 | −5.673 | 75.478 | 1.00 | 59.11 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 1955 | CA | GLY | 767 | 44.689 | −5.653 | 75.860 | 1.00 | 59.91 |
| 1956 | C | GLY | 767 | 45.366 | −6.867 | 75.232 | 1.00 | 61.75 |
| 1957 | O | GLY | 767 | 46.588 | −6.912 | 75.041 | 1.00 | 61.17 |
| 1958 | N | ASN | 768 | 44.532 | −7.846 | 74.887 | 1.00 | 62.80 |
| 1959 | CA | ASN | 768 | 44.942 | −9.109 | 74.276 | 1.00 | 62.46 |
| 1960 | CB | ASN | 768 | 43.717 | −10.032 | 74.246 | 1.00 | 59.72 |
| 1961 | CG | ASN | 768 | 42.798 | −9.832 | 75.467 | 1.00 | 60.42 |
| 1962 | OD1 | ASN | 768 | 41.697 | −10.404 | 75.538 | 1.00 | 59.89 |
| 1963 | ND2 | ASN | 768 | 43.248 | −9.020 | 76.427 | 1.00 | 63.45 |
| 1964 | C | ASN | 768 | 45.543 | −8.940 | 72.855 | 1.00 | 63.10 |
| 1965 | O | ASN | 768 | 46.095 | −9.882 | 72.282 | 1.00 | 62.80 |
| 1966 | N | ILE | 769 | 45.418 | −7.744 | 72.284 | 1.00 | 58.10 |
| 1967 | CA | ILE | 769 | 45.984 | −7.464 | 70.967 | 1.00 | 60.18 |
| 1968 | CB | ILE | 769 | 45.006 | −6.713 | 70.036 | 1.00 | 61.64 |
| 1969 | CG2 | ILE | 769 | 45.569 | −6.703 | 68.614 | 1.00 | 59.97 |
| 1970 | CG1 | ILE | 769 | 43.623 | −7.361 | 70.051 | 1.00 | 65.54 |
| 1971 | CD1 | ILE | 769 | 42.605 | −6.626 | 69.175 | 1.00 | 65.14 |
| 1972 | C | ILE | 769 | 47.192 | −6.544 | 71.150 | 1.00 | 59.44 |
| 1973 | O | ILE | 769 | 47.217 | −5.701 | 72.058 | 1.00 | 61.97 |
| 1974 | N | LYS | 770 | 48.175 | −6.692 | 70.267 | 1.00 | 61.57 |
| 1975 | CA | LYS | 770 | 49.391 | −5.890 | 70.314 | 1.00 | 60.09 |
| 1976 | CB | LYS | 770 | 50.601 | −6.778 | 70.033 | 1.00 | 61.51 |
| 1977 | CG | LYS | 770 | 51.961 | −6.172 | 70.339 | 1.00 | 61.08 |
| 1978 | CD | LYS | 770 | 53.041 | −7.224 | 70.047 | 1.00 | 59.40 |
| 1979 | CE | LYS | 770 | 54.344 | −6.982 | 70.801 | 1.00 | 62.15 |
| 1980 | NZ | LYS | 770 | 55.339 | −8.089 | 70.604 | 1.00 | 63.19 |
| 1981 | C | LYS | 770 | 49.333 | −4.776 | 69.277 | 1.00 | 63.90 |
| 1982 | O | LYS | 770 | 49.439 | −5.031 | 68.071 | 1.00 | 62.08 |
| 1983 | N | LYS | 771 | 49.161 | −3.545 | 69.754 | 1.00 | 59.06 |
| 1984 | CA | LYS | 771 | 49.103 | −2.376 | 68.884 | 1.00 | 61.08 |
| 1985 | CB | LYS | 771 | 48.386 | −1.212 | 69.589 | 1.00 | 63.15 |
| 1986 | CG | LYS | 771 | 49.188 | −0.525 | 70.712 | 1.00 | 63.84 |
| 1987 | CD | LYS | 771 | 48.443 | 0.681 | 71.308 | 1.00 | 63.12 |
| 1988 | CE | LYS | 771 | 49.384 | 1.588 | 72.100 | 1.00 | 59.83 |
| 1989 | NZ | LYS | 771 | 48.821 | 2.970 | 72.186 | 1.00 | 60.16 |
| 1990 | C | LYS | 771 | 50.532 | −1.976 | 68.550 | 1.00 | 60.42 |
| 1991 | O | LYS | 771 | 51.276 | −1.561 | 69.430 | 1.00 | 62.03 |
| 1992 | N | LEU | 772 | 50.928 | −2.120 | 67.290 | 1.00 | 60.80 |
| 1993 | CA | LEU | 772 | 52.285 | −1.756 | 66.890 | 1.00 | 58.97 |
| 1994 | CB | LEU | 772 | 52.629 | −2.368 | 65.533 | 1.00 | 62.77 |
| 1995 | CG | LEU | 772 | 52.781 | −3.885 | 65.492 | 1.00 | 63.82 |
| 1996 | CD1 | LEU | 772 | 52.780 | −4.346 | 64.046 | 1.00 | 62.61 |
| 1997 | CD2 | LEU | 772 | 54.071 | −4.295 | 66.203 | 1.00 | 63.11 |
| 1998 | C | LEU | 772 | 52.405 | −0.243 | 66.812 | 1.00 | 61.57 |
| 1999 | O | LEU | 772 | 51.513 | 0.428 | 66.289 | 1.00 | 60.62 |
| 2000 | N | LEU | 773 | 53.499 | 0.296 | 67.341 | 1.00 | 59.76 |
| 2001 | CA | LEU | 773 | 53.704 | 1.734 | 67.317 | 1.00 | 60.00 |
| 2002 | CB | LEU | 773 | 53.602 | 2.320 | 68.725 | 1.00 | 59.66 |
| 2003 | CG | LEU | 773 | 52.221 | 2.321 | 69.380 | 1.00 | 62.80 |
| 2004 | CD1 | LEU | 773 | 52.290 | 2.999 | 70.729 | 1.00 | 61.23 |
| 2005 | CD2 | LEU | 773 | 51.233 | 3.053 | 68.490 | 1.00 | 65.68 |
| 2006 | C | LEU | 773 | 55.051 | 2.094 | 66.727 | 1.00 | 62.80 |
| 2007 | O | LEU | 773 | 55.911 | 1.234 | 66.517 | 1.00 | 61.81 |
| 2008 | N | PHE | 774 | 55.219 | 3.382 | 66.456 | 1.00 | 60.94 |
| 2009 | CA | PHE | 774 | 56.451 | 3.917 | 65.897 | 1.00 | 61.49 |
| 2010 | GB | PHE | 774 | 56.128 | 4.864 | 64.743 | 1.00 | 63.45 |
| 2011 | CG | PHE | 774 | 55.889 | 4.169 | 63.451 | 1.00 | 61.20 |
| 2012 | CD1 | PHE | 774 | 56.936 | 3.532 | 62.802 | 1.00 | 63.76 |
| 2013 | CD2 | PHE | 774 | 54.621 | 4.105 | 62.902 | 1.00 | 61.89 |
| 2014 | CE1 | PHE | 774 | 56.727 | 2.838 | 61.627 | 1.00 | 56.93 |
| 2015 | CE2 | PHE | 774 | 54.395 | 3.409 | 61.720 | 1.00 | 59.92 |
| 2016 | CZ | PHE | 774 | 55.451 | 2.773 | 61.081 | 1.00 | 62.56 |
| 2017 | C | PHE | 774 | 57.175 | 4.681 | 66.984 | 1.00 | 60.20 |
| 2018 | O | PHE | 774 | 58.400 | 4.702 | 67.046 | 1.00 | 60.03 |
| 2019 | N | HIS | 775 | 56.384 | 5.301 | 67.849 | 1.00 | 62.48 |
| 2020 | CA | HIS | 775 | 56.905 | 6.104 | 68.934 | 1.00 | 64.64 |
| 2021 | CB | HIS | 775 | 56.466 | 7.558 | 68.730 | 1.00 | 61.69 |
| 2022 | CG | HIS | 775 | 56.898 | 8.120 | 67.417 | 1.00 | 59.70 |
| 2023 | CD2 | HIS | 775 | 56.188 | 8.565 | 66.356 | 1.00 | 62.49 |
| 2024 | ND1 | HIS | 775 | 58.223 | 8.191 | 67.047 | 1.00 | 60.30 |
| 2025 | CE1 | HIS | 775 | 58.313 | 8.652 | 65.813 | 1.00 | 59.19 |
| 2026 | NE2 | HIS | 775 | 57.092 | 8.886 | 65.370 | 1.00 | 59.04 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2027 | C | HIS | 775 | 56.428 | 5.596 | 70.277 | 1.00 | 64.58 |
| 2028 | O | HIS | 775 | 55.390 | 4.948 | 70.373 | 1.00 | 58.66 |
| 2029 | N | GLN | 776 | 57.203 | 5.895 | 71.311 | 1.00 | 60.50 |
| 2030 | CA | GLN | 776 | 56.864 | 5.502 | 72.669 | 1.00 | 61.43 |
| 2031 | CB | GLN | 776 | 58.154 | 5.293 | 73.457 | 1.00 | 59.86 |
| 2032 | CG | GLN | 776 | 59.281 | 6.243 | 73.042 | 1.00 | 57.49 |
| 2033 | CD | GLN | 776 | 60.679 | 5.638 | 73.241 | 1.00 | 60.53 |
| 2034 | OE1 | GLN | 776 | 61.696 | 6.265 | 72.919 | 1.00 | 61.97 |
| 2035 | NE2 | GLN | 776 | 60.730 | 4.412 | 73.772 | 1.00 | 60.63 |
| 2036 | C | GLN | 776 | 55.993 | 6.583 | 73.335 | 1.00 | 60.06 |
| 2037 | O | GLN | 776 | 56.098 | 7.765 | 72.919 | 1.00 | 61.84 |
| 2038 | OXT | GLN | 776 | 55.219 | 6.239 | 74.268 | 1.00 | 60.74 |
| 2039 | CB | GLU | 741 | 35.922 | −16.424 | 65.488 | 1.00 | 58.89 |
| 2040 | CG | GLU | 741 | 36.766 | −17.078 | 64.386 | 1.00 | 67.76 |
| 2041 | CD | GLU | 741 | 38.144 | −16.463 | 64.277 | 1.00 | 60.66 |
| 2042 | OE1 | GLU | 741 | 38.838 | −16.698 | 63.252 | 1.00 | 59.66 |
| 2043 | OE2 | GLU | 741 | 38.524 | −15.741 | 65.233 | 1.00 | 61.27 |
| 2044 | C | GLU | 741 | 33.996 | −16.854 | 64.024 | 1.00 | 61.38 |
| 2045 | O | GLU | 741 | 33.681 | −15.808 | 63.464 | 1.00 | 63.70 |
| 2046 | N | GLU | 741 | 34.336 | −18.280 | 65.946 | 1.00 | 62.41 |
| 2047 | CA | GLU | 741 | 34.460 | −16.870 | 65.464 | 1.00 | 59.35 |
| 2048 | N | GLU | 742 | 33.995 | −18.034 | 63.422 | 1.00 | 58.35 |
| 2049 | CA | GLU | 742 | 33.594 | −18.184 | 62.036 | 1.00 | 63.61 |
| 2050 | CB | GLU | 742 | 32.158 | −17.672 | 61.824 | 1.00 | 60.80 |
| 2051 | CG | GLU | 742 | 31.516 | −18.155 | 60.518 | 1.00 | 62.06 |
| 2052 | CD | GLU | 742 | 31.783 | −19.645 | 60.238 | 1.00 | 63.64 |
| 2053 | OE1 | GLU | 742 | 31.146 | −20.190 | 59.309 | 1.00 | 64.92 |
| 2054 | OE2 | GLU | 742 | 32.632 | −20.276 | 60.925 | 1.00 | 62.96 |
| 2055 | C | GLU | 742 | 34.541 | −17.482 | 61.064 | 1.00 | 61.07 |
| 2056 | O | GLU | 742 | 35.655 | −17.950 | 60.825 | 1.00 | 59.51 |
| 2057 | N | ASN | 743 | 34.090 | −16.355 | 60.522 | 1.00 | 61.83 |
| 2058 | CA | ASN | 743 | 34.850 | −15.586 | 59.535 | 1.00 | 60.95 |
| 2059 | CB | ASN | 743 | 36.300 | −15.368 | 59.987 | 1.00 | 61.82 |
| 2060 | CG | ASN | 743 | 36.418 | −14.360 | 61.118 | 1.00 | 64.29 |
| 2061 | OD1 | ASN | 743 | 36.646 | −14.729 | 62.277 | 1.00 | 58.19 |
| 2062 | ND2 | ASN | 743 | 36.262 | −13.077 | 60.787 | 1.00 | 58.54 |
| 2063 | C | ASN | 743 | 34.842 | −16.318 | 58.192 | 1.00 | 60.80 |
| 2064 | O | ASN | 743 | 35.780 | −16.196 | 57.410 | 1.00 | 62.67 |
| 2065 | N | ALA | 744 | 33.779 | −17.075 | 57.935 | 1.00 | 59.69 |
| 2066 | CA | ALA | 744 | 33.640 | −17.827 | 56.696 | 1.00 | 61.76 |
| 2067 | CB | ALA | 744 | 32.350 | −18.623 | 56.729 | 1.00 | 60.04 |
| 2068 | C | ALA | 744 | 33.675 | −16.930 | 55.453 | 1.00 | 62.63 |
| 2069 | O | ALA | 744 | 34.423 | −17.199 | 54.503 | 1.00 | 58.54 |
| 2070 | N | LEU | 745 | 32.869 | −15.866 | 55.462 | 1.00 | 60.19 |
| 2071 | CA | LEU | 745 | 32.820 | −14.936 | 54.329 | 1.00 | 62.12 |
| 2072 | CB | LEU | 745 | 31.855 | −13.783 | 54.617 | 1.00 | 60.59 |
| 2073 | CG | LEU | 745 | 30.606 | −13.726 | 53.739 | 1.00 | 58.63 |
| 2074 | CD1 | LEU | 745 | 29.895 | −12.400 | 53.937 | 1.00 | 64.25 |
| 2075 | CD2 | LEU | 745 | 31.004 | −13.902 | 52.291 | 1.00 | 60.41 |
| 2076 | C | LEU | 745 | 34.190 | −14.360 | 53.952 | 1.00 | 61.72 |
| 2077 | O | LEU | 745 | 34.521 | −14.276 | 52.776 | 1.00 | 59.83 |
| 2078 | N | LEU | 746 | 34.978 | −13.961 | 54.946 | 1.00 | 57.79 |
| 2079 | CA | LEU | 746 | 36.311 | −13.413 | 54.691 | 1.00 | 60.45 |
| 2080 | CB | LEU | 746 | 36.898 | −12.849 | 55.989 | 1.00 | 61.06 |
| 2081 | CG | LEU | 746 | 37.673 | −11.534 | 55.956 | 1.00 | 61.13 |
| 2082 | CD1 | LEU | 746 | 38.380 | −11.374 | 57.275 | 1.00 | 61.70 |
| 2083 | CD2 | LEU | 746 | 38.664 | −11.520 | 54.823 | 1.00 | 61.56 |
| 2084 | C | LEU | 746 | 37.249 | −14.511 | 54.156 | 1.00 | 58.73 |
| 2085 | O | LEU | 746 | 37.905 | −14.356 | 53.120 | 1.00 | 62.68 |
| 2086 | N | ARG | 747 | 37.307 | −15.613 | 54.895 | 1.00 | 61.00 |
| 2087 | CA | ARG | 747 | 38.145 | −16.759 | 54.560 | 1.00 | 57.24 |
| 2088 | CB | ARG | 747 | 37.853 | −17.906 | 55.539 | 1.00 | 66.74 |
| 2089 | CG | ARG | 747 | 38.332 | −19.278 | 55.102 | 1.00 | 61.05 |
| 2090 | CD | ARG | 747 | 38.533 | −20.190 | 56.319 | 1.00 | 62.51 |
| 2091 | NE | ARG | 747 | 39.807 | −19.938 | 56.998 | 1.00 | 62.06 |
| 2092 | CZ | ARG | 747 | 39.952 | −19.867 | 58.321 | 1.00 | 63.78 |
| 2093 | NH1 | ARG | 747 | 38.894 | −20.023 | 59.118 | 1.00 | 60.31 |
| 2094 | NH2 | ARG | 747 | 41.156 | −19.637 | 58.848 | 1.00 | 60.80 |
| 2095 | C | ARG | 747 | 37.883 | −17.186 | 53.134 | 1.00 | 59.12 |
| 2096 | O | ARG | 747 | 38.793 | −17.589 | 52.418 | 1.00 | 62.02 |
| 2097 | N | TYR | 748 | 36.623 | −17.088 | 52.731 | 1.00 | 61.89 |
| 2098 | CA | TYR | 748 | 36.215 | −17.449 | 51.387 | 1.00 | 65.00 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2099 | CB | TYR | 748 | 34.685 | −17.413 | 51.301 | 1.00 | 58.95 |
| 2100 | CG | TYR | 748 | 34.136 | −17.350 | 49.897 | 1.00 | 62.12 |
| 2101 | CD1 | TYR | 748 | 34.256 | −18.429 | 49.021 | 1.00 | 63.79 |
| 2102 | CE1 | TYR | 748 | 33.805 | −18.342 | 47.715 | 1.00 | 61.69 |
| 2103 | CD2 | TYR | 748 | 33.544 | −16.185 | 49.430 | 1.00 | 61.63 |
| 2104 | CE2 | TYR | 748 | 33.091 | −16.084 | 48.127 | 1.00 | 60.08 |
| 2105 | CZ | TYR | 748 | 33.226 | −17.163 | 47.272 | 1.00 | 58.42 |
| 2106 | OH | TYR | 748 | 32.806 | −17.030 | 45.966 | 1.00 | 59.74 |
| 2107 | C | TYR | 748 | 36.832 | −16.447 | 50.419 | 1.00 | 61.75 |
| 2108 | O | TYR | 748 | 37.599 | −16.807 | 49.532 | 1.00 | 61.82 |
| 2109 | N | LEU | 749 | 36.501 | −15.178 | 50.628 | 1.00 | 60.52 |
| 2110 | CA | LEU | 749 | 36.974 | −14.069 | 49.800 | 1.00 | 61.53 |
| 2111 | CB | LEU | 749 | 36.380 | −12.757 | 50.303 | 1.00 | 63.00 |
| 2112 | CG | LEU | 749 | 34.873 | −12.741 | 50.535 | 1.00 | 57.09 |
| 2113 | CD1 | LEU | 749 | 34.508 | −11.427 | 51.167 | 1.00 | 62.85 |
| 2114 | CD2 | LEU | 749 | 34.113 | −12.954 | 49.233 | 1.00 | 62.37 |
| 2115 | C | LEU | 749 | 38.482 | −13.910 | 49.733 | 1.00 | 64.05 |
| 2116 | O | LEU | 749 | 38.991 | −13.275 | 48.807 | 1.00 | 61.97 |
| 2117 | N | LEU | 750 | 39.195 | −14.475 | 50.703 | 1.00 | 59.99 |
| 2118 | CA | LEU | 750 | 40.644 | −14.363 | 50.728 | 1.00 | 63.11 |
| 2119 | CB | LEU | 750 | 41.147 | −14.497 | 52.167 | 1.00 | 62.65 |
| 2120 | CG | LEU | 750 | 41.463 | −13.160 | 52.849 | 1.00 | 63.02 |
| 2121 | CD1 | LEU | 750 | 41.695 | −13.344 | 54.327 | 1.00 | 58.04 |
| 2122 | CD2 | LEU | 750 | 42.693 | −12.559 | 52.194 | 1.00 | 62.24 |
| 2123 | C | LEU | 750 | 41.436 | −15.294 | 49.803 | 1.00 | 64.30 |
| 2124 | O | LEU | 750 | 42.666 | −15.246 | 49.796 | 1.00 | 58.24 |
| 2125 | N | ASP | 751 | 40.745 | −16.129 | 49.024 | 1.00 | 59.30 |
| 2126 | CA | ASP | 751 | 41.396 | −17.048 | 48.068 | 1.00 | 62.49 |
| 2127 | CB | ASP | 751 | 41.860 | −18.337 | 48.764 | 1.00 | 62.90 |
| 2128 | CG | ASP | 751 | 40.921 | −18.784 | 49.855 | 1.00 | 62.09 |
| 2129 | OD1 | ASP | 751 | 40.342 | −17.900 | 50.526 | 1.00 | 62.68 |
| 2130 | OD2 | ASP | 751 | 40.779 | −20.014 | 50.051 | 1.00 | 60.33 |
| 2131 | C | ASP | 751 | 40.472 | −17.371 | 46.897 | 1.00 | 61.25 |
| 2132 | O | ASP | 751 | 39.476 | −18.065 | 47.053 | 1.00 | 61.96 |
| 2133 | N | LYS | 752 | 40.824 | −16.849 | 45.725 | 1.00 | 62.34 |
| 2134 | CA | LYS | 752 | 40.030 | −17.003 | 44.506 | 1.00 | 62.50 |
| 2135 | CB | LYS | 752 | 38.733 | −16.160 | 44.600 | 1.00 | 63.17 |
| 2136 | CG | LYS | 752 | 37.872 | −16.386 | 45.858 | 1.00 | 60.82 |
| 2137 | CD | LYS | 752 | 36.923 | −15.230 | 46.159 | 1.00 | 62.16 |
| 2138 | CE | LYS | 752 | 35.726 | −15.186 | 45.223 | 1.00 | 60.30 |
| 2139 | NZ | LYS | 752 | 36.101 | −15.095 | 43.779 | 1.00 | 61.47 |
| 2140 | C | LYS | 752 | 40.895 | −16.438 | 43.384 | 1.00 | 63.98 |
| 2141 | O | LYS | 752 | 42.043 | −16.833 | 43.212 | 1.00 | 60.08 |
| 2142 | N | ASP | 753 | 40.322 | −15.496 | 42.641 | 1.00 | 61.50 |
| 2143 | CA | ASP | 753 | 41.004 | −14.809 | 41.552 | 1.00 | 60.87 |
| 2144 | CB | ASP | 753 | 41.969 | −13.778 | 42.151 | 1.00 | 61.81 |
| 2145 | CG | ASP | 753 | 41.293 | −12.886 | 43.212 | 1.00 | 65.36 |
| 2146 | OD1 | ASP | 753 | 40.845 | −13.417 | 44.262 | 1.00 | 58.98 |
| 2147 | OD2 | ASP | 753 | 41.204 | −11.653 | 42.996 | 1.00 | 62.40 |
| 2148 | C | ASP | 753 | 41.712 | −15.723 | 40.533 | 1.00 | 62.25 |
| 2149 | O | ASP | 753 | 41.905 | −16.929 | 40.770 | 1.00 | 62.51 |
| 2150 | N | ASP | 754 | 42.076 | −15.125 | 39.394 | 1.00 | 59.26 |
| 2151 | CA | ASP | 754 | 42.713 | −15.818 | 38.271 | 1.00 | 62.08 |
| 2152 | CB | ASP | 754 | 42.118 | −15.302 | 36.949 | 1.00 | 60.51 |
| 2153 | CG | ASP | 754 | 41.121 | −14.148 | 37.150 | 1.00 | 60.95 |
| 2154 | OD1 | ASP | 754 | 40.683 | −13.555 | 36.135 | 1.00 | 61.57 |
| 2155 | OD2 | ASP | 754 | 40.762 | −13.831 | 38.304 | 1.00 | 61.61 |
| 2156 | C | ASP | 754 | 44.236 | −15.678 | 38.234 | 1.00 | 60.21 |
| 2157 | O | ASP | 754 | 44.946 | −16.712 | 38.264 | 1.00 | 63.29 |
| 2158 | OXT | ASP | 754 | 44.707 | −14.526 | 38.169 | 1.00 | 61.39 |
| 2159 | CB | GLN | 527 | 44.425 | 43.308 | 57.458 | 1.00 | 59.84 |
| 2160 | CG | GLN | 527 | 45.330 | 43.181 | 58.697 | 1.00 | 63.06 |
| 2161 | CD | GLN | 527 | 46.173 | 41.895 | 58.675 | 1.00 | 61.64 |
| 2162 | OE1 | GLN | 527 | 46.913 | 41.596 | 59.623 | 1.00 | 62.44 |
| 2163 | NE2 | GLN | 527 | 46.065 | 41.137 | 57.583 | 1.00 | 63.46 |
| 2164 | C | GLN | 527 | 43.994 | 44.763 | 55.475 | 1.00 | 60.61 |
| 2165 | O | GLN | 527 | 44.711 | 45.517 | 54.798 | 1.00 | 61.62 |
| 2166 | N | GLN | 527 | 42.843 | 45.238 | 57.671 | 1.00 | 62.80 |
| 2167 | CA | GLN | 527 | 44.095 | 44.745 | 57.006 | 1.00 | 60.11 |
| 2168 | N | LEU | 528 | 43.105 | 43.912 | 54.955 | 1.00 | 62.93 |
| 2169 | CA | LEU | 528 | 42.857 | 43.747 | 53.516 | 1.00 | 58.92 |
| 2170 | CB | LEU | 528 | 43.696 | 42.579 | 52.979 | 1.00 | 61.24 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2171 | CG | LEU | 528 | 45.210 | 42.751 | 53.124 | 1.00 | 58.97 |
| 2172 | CD1 | LEU | 528 | 45.858 | 41.410 | 53.501 | 1.00 | 57.95 |
| 2173 | CD2 | LEU | 528 | 45.778 | 43.371 | 51.831 | 1.00 | 60.61 |
| 2174 | C | LEU | 528 | 41.369 | 43.449 | 53.303 | 1.00 | 63.94 |
| 2175 | O | LEU | 528 | 40.531 | 44.290 | 53.650 | 1.00 | 62.36 |
| 2176 | N | THR | 529 | 41.067 | 42.256 | 52.748 | 1.00 | 59.95 |
| 2177 | CA | THR | 529 | 39.689 | 41.769 | 52.487 | 1.00 | 61.84 |
| 2178 | CB | THR | 529 | 39.396 | 40.430 | 53.232 | 1.00 | 59.05 |
| 2179 | OG1 | THR | 529 | 40.375 | 39.442 | 52.866 | 1.00 | 63.83 |
| 2180 | CG2 | THR | 529 | 37.997 | 39.920 | 52.882 | 1.00 | 59.80 |
| 2181 | C | THR | 529 | 38.725 | 42.842 | 52.992 | 1.00 | 61.32 |
| 2182 | O | THR | 529 | 37.988 | 42.645 | 53.973 | 1.00 | 61.35 |
| 2183 | N | PRO | 530 | 38.704 | 43.977 | 52.271 | 1.00 | 64.25 |
| 2184 | CD | PRO | 530 | 38.650 | 43.494 | 50.878 | 1.00 | 59.35 |
| 2185 | CA | PRO | 530 | 38.021 | 45.276 | 52.317 | 1.00 | 58.74 |
| 2186 | CB | PRO | 530 | 37.610 | 45.502 | 50.860 | 1.00 | 60.27 |
| 2187 | CG | PRO | 530 | 37.368 | 44.132 | 50.384 | 1.00 | 65.84 |
| 2188 | C | PRO | 530 | 36.839 | 45.387 | 53.239 | 1.00 | 62.92 |
| 2189 | O | PRO | 530 | 36.948 | 45.328 | 54.474 | 1.00 | 60.28 |
| 2190 | N | THR | 531 | 35.706 | 45.591 | 52.590 | 1.00 | 63.85 |
| 2191 | CA | THR | 531 | 34.443 | 45.708 | 53.246 | 1.00 | 62.34 |
| 2192 | CB | THR | 531 | 34.253 | 47.135 | 53.851 | 1.00 | 63.80 |
| 2193 | OG1 | THR | 531 | 33.854 | 47.016 | 55.230 | 1.00 | 64.25 |
| 2194 | CG2 | THR | 531 | 33.218 | 47.940 | 53.067 | 1.00 | 61.34 |
| 2195 | C | THR | 531 | 33.526 | 45.410 | 52.081 | 1.00 | 61.78 |
| 2196 | O | THR | 531 | 32.505 | 44.758 | 52.251 | 1.00 | 61.93 |
| 2197 | N | LEU | 532 | 33.917 | 45.822 | 50.877 | 1.00 | 62.02 |
| 2198 | CA | LEU | 532 | 33.060 | 45.545 | 49.722 | 1.00 | 60.94 |
| 2199 | CB | LEU | 532 | 33.410 | 46.445 | 48.528 | 1.00 | 57.32 |
| 2200 | CG | LEU | 532 | 32.463 | 46.285 | 47.329 | 1.00 | 64.49 |
| 2201 | CD1 | LEU | 532 | 31.027 | 46.313 | 47.771 | 1.00 | 61.90 |
| 2202 | CD2 | LEU | 532 | 32.702 | 47.377 | 46.344 | 1.00 | 62.84 |
| 2203 | C | LEU | 532 | 33.077 | 44.077 | 49.283 | 1.00 | 61.37 |
| 2204 | O | LEU | 532 | 32.016 | 43.461 | 49.149 | 1.00 | 62.65 |
| 2205 | N | VAL | 533 | 34.266 | 43.518 | 49.052 | 1.00 | 61.22 |
| 2206 | CA | VAL | 533 | 34.366 | 42.119 | 48.635 | 1.00 | 60.75 |
| 2207 | CB | VAL | 533 | 35.781 | 41.753 | 48.114 | 1.00 | 59.58 |
| 2208 | CG1 | VAL | 533 | 36.697 | 41.400 | 49.264 | 1.00 | 60.31 |
| 2209 | CG2 | VAL | 533 | 35.695 | 40.576 | 47.185 | 1.00 | 59.77 |
| 2210 | C | VAL | 533 | 34.062 | 41.240 | 49.840 | 1.00 | 63.61 |
| 2211 | O | VAL | 533 | 33.861 | 40.038 | 49.709 | 1.00 | 62.93 |
| 2212 | N | SER | 534 | 34.053 | 41.859 | 51.013 | 1.00 | 61.64 |
| 2213 | CA | SER | 534 | 33.774 | 41.170 | 52.260 | 1.00 | 60.61 |
| 2214 | CB | SER | 534 | 34.143 | 42.089 | 53.425 | 1.00 | 62.32 |
| 2215 | OG | SER | 534 | 34.391 | 41.364 | 54.612 | 1.00 | 60.70 |
| 2216 | C | SER | 534 | 32.276 | 40.880 | 52.270 | 1.00 | 62.67 |
| 2217 | O | SER | 534 | 31.799 | 39.906 | 52.854 | 1.00 | 59.90 |
| 2218 | N | LEU | 535 | 31.544 | 41.747 | 51.593 | 1.00 | 60.18 |
| 2219 | CA | LEU | 535 | 30.102 | 41.644 | 51.508 | 1.00 | 60.75 |
| 2220 | CB | LEU | 535 | 29.527 | 42.975 | 51.048 | 1.00 | 61.59 |
| 2221 | CG | LEU | 535 | 28.027 | 43.101 | 51.245 | 1.00 | 61.16 |
| 2222 | CD1 | LEU | 535 | 27.773 | 43.835 | 52.537 | 1.00 | 63.92 |
| 2223 | CD2 | LEU | 535 | 27.416 | 43.850 | 50.089 | 1.00 | 61.72 |
| 2224 | C | LEU | 535 | 29.688 | 40.547 | 50.543 | 1.00 | 60.18 |
| 2225 | O | LEU | 535 | 28.852 | 39.714 | 50.868 | 1.00 | 58.39 |
| 2226 | N | LEU | 536 | 30.269 | 40.552 | 49.349 | 1.00 | 60.57 |
| 2227 | CA | LEU | 536 | 29.950 | 39.536 | 48.355 | 1.00 | 63.14 |
| 2228 | CB | LEU | 536 | 30.813 | 39.719 | 47.115 | 1.00 | 61.69 |
| 2229 | CG | LEU | 536 | 30.671 | 40.980 | 46.284 | 1.00 | 63.99 |
| 2230 | CD1 | LEU | 536 | 31.622 | 40.864 | 45.118 | 1.00 | 60.60 |
| 2231 | CD2 | LEU | 536 | 29.247 | 41.145 | 45.801 | 1.00 | 62.81 |
| 2232 | C | LEU | 536 | 30.204 | 38.140 | 48.908 | 1.00 | 61.72 |
| 2233 | O | LEU | 536 | 29.703 | 37.141 | 48.379 | 1.00 | 60.04 |
| 2234 | N | GLU | 537 | 30.996 | 38.086 | 49.970 | 1.00 | 60.48 |
| 2235 | CA | GLU | 537 | 31.359 | 36.838 | 50.607 | 1.00 | 61.60 |
| 2236 | CB | GLU | 537 | 32.691 | 37.003 | 51.307 | 1.00 | 61.56 |
| 2237 | CG | GLU | 537 | 33.169 | 35.763 | 51.998 | 1.00 | 58.70 |
| 2238 | CD | GLU | 537 | 34.599 | 35.907 | 52.442 | 1.00 | 62.52 |
| 2239 | OE1 | GLU | 537 | 35.173 | 34.900 | 52.919 | 1.00 | 61.18 |
| 2240 | OE2 | GLU | 537 | 35.140 | 37.033 | 52.305 | 1.00 | 60.21 |
| 2241 | C | GLU | 537 | 30.344 | 36.288 | 51.592 | 1.00 | 59.30 |
| 2242 | O | GLU | 537 | 30.094 | 35.084 | 51.604 | 1.00 | 60.22 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2243 | N | VAL | 538 | 29.773 | 37.155 | 52.424 | 1.00 | 61.88 |
| 2244 | CA | VAL | 538 | 28.781 | 36.714 | 53.399 | 1.00 | 62.81 |
| 2245 | CB | VAL | 538 | 28.636 | 37.687 | 54.591 | 1.00 | 57.08 |
| 2246 | CG1 | VAL | 538 | 29.993 | 38.283 | 54.957 | 1.00 | 61.43 |
| 2247 | CG2 | VAL | 538 | 27.611 | 38.757 | 54.268 | 1.00 | 60.61 |
| 2248 | C | VAL | 538 | 27.420 | 36.586 | 52.752 | 1.00 | 61.99 |
| 2249 | O | VAL | 538 | 26.576 | 35.841 | 53.233 | 1.00 | 61.89 |
| 2250 | N | ILE | 539 | 27.203 | 37.322 | 51.669 | 1.00 | 61.34 |
| 2251 | CA | ILE | 539 | 25.931 | 37.263 | 50.977 | 1.00 | 60.88 |
| 2252 | CB | ILE | 539 | 25.628 | 38.548 | 50.209 | 1.00 | 57.53 |
| 2253 | CG2 | ILE | 539 | 26.034 | 39.737 | 51.035 | 1.00 | 63.74 |
| 2254 | CG1 | ILE | 539 | 26.365 | 38.550 | 48.869 | 1.00 | 64.95 |
| 2255 | CD1 | ILE | 539 | 25.847 | 39.584 | 47.898 | 1.00 | 61.40 |
| 2256 | C | ILE | 539 | 25.946 | 36.133 | 49.977 | 1.00 | 59.86 |
| 2257 | O | ILE | 539 | 24.984 | 35.934 | 49.251 | 1.00 | 60.95 |
| 2258 | N | GLU | 540 | 27.051 | 35.408 | 49.919 | 1.00 | 61.19 |
| 2259 | CA | GLU | 540 | 27.170 | 34.290 | 48.993 | 1.00 | 64.61 |
| 2260 | CB | GLU | 540 | 28.620 | 33.798 | 48.960 | 1.00 | 61.89 |
| 2261 | CG | GLU | 540 | 28.917 | 32.628 | 48.022 | 1.00 | 59.99 |
| 2262 | CD | GLU | 540 | 28.635 | 32.926 | 46.560 | 1.00 | 60.98 |
| 2263 | OE1 | GLU | 540 | 28.949 | 34.050 | 46.103 | 1.00 | 60.19 |
| 2264 | OE2 | GLU | 540 | 28.113 | 32.025 | 45.861 | 1.00 | 58.09 |
| 2265 | C | GLU | 540 | 26.241 | 33.181 | 49.469 | 1.00 | 60.25 |
| 2266 | O | GLU | 540 | 26.357 | 32.710 | 50.603 | 1.00 | 62.79 |
| 2267 | N | PRO | 541 | 25.289 | 32.766 | 48.614 | 1.00 | 59.70 |
| 2268 | CD | PRO | 541 | 24.961 | 33.287 | 47.275 | 1.00 | 61.01 |
| 2269 | CA | PRO | 541 | 24.362 | 31.703 | 49.013 | 1.00 | 61.09 |
| 2270 | CB | PRO | 541 | 23.361 | 31.665 | 47.861 | 1.00 | 63.13 |
| 2271 | CG | PRO | 541 | 24.138 | 32.177 | 46.694 | 1.00 | 57.00 |
| 2272 | C | PRO | 541 | 25.051 | 30.365 | 49.254 | 1.00 | 60.83 |
| 2273 | O | PRO | 541 | 25.979 | 29.988 | 48.535 | 1.00 | 60.28 |
| 2274 | N | GLU | 542 | 24.607 | 29.669 | 50.297 | 1.00 | 60.82 |
| 2275 | CA | GLU | 542 | 25.157 | 28.364 | 50.655 | 1.00 | 61.11 |
| 2276 | CB | GLU | 542 | 24.607 | 27.933 | 52.001 | 1.00 | 63.94 |
| 2277 | CG | GLU | 542 | 23.163 | 27.558 | 51.899 | 1.00 | 65.51 |
| 2278 | CD | GLU | 542 | 22.569 | 27.217 | 53.237 | 1.00 | 61.20 |
| 2279 | OE1 | GLU | 542 | 21.369 | 26.813 | 53.269 | 1.00 | 64.82 |
| 2280 | OE2 | GLU | 542 | 23.307 | 27.360 | 54.253 | 1.00 | 61.05 |
| 2281 | C | GLU | 542 | 24.668 | 27.393 | 49.584 | 1.00 | 60.85 |
| 2282 | O | GLU | 542 | 23.631 | 27.637 | 48.966 | 1.00 | 61.52 |
| 2283 | N | VAL | 543 | 25.369 | 26.291 | 49.353 | 1.00 | 62.89 |
| 2284 | CA | VAL | 543 | 24.879 | 25.397 | 48.316 | 1.00 | 61.20 |
| 2285 | CB | VAL | 543 | 26.029 | 24.589 | 47.676 | 1.00 | 60.15 |
| 2286 | CG1 | VAL | 543 | 27.366 | 25.164 | 48.116 | 1.00 | 61.25 |
| 2287 | CG2 | VAL | 543 | 25.903 | 23.132 | 48.011 | 1.00 | 64.25 |
| 2288 | C | VAL | 543 | 23.745 | 24.465 | 48.760 | 1.00 | 61.19 |
| 2289 | O | VAL | 543 | 23.506 | 24.232 | 49.955 | 1.00 | 61.59 |
| 2290 | N | LEU | 544 | 23.037 | 23.944 | 47.769 | 1.00 | 60.75 |
| 2291 | CA | LEU | 544 | 21.910 | 23.068 | 48.018 | 1.00 | 62.70 |
| 2292 | CB | LEU | 544 | 20.686 | 23.557 | 47.244 | 1.00 | 61.76 |
| 2293 | CG | LEU | 544 | 20.315 | 25.041 | 47.237 | 1.00 | 62.21 |
| 2294 | CD1 | LEU | 544 | 19.968 | 25.490 | 48.639 | 1.00 | 60.39 |
| 2295 | CD2 | LEU | 544 | 21.464 | 25.856 | 46.654 | 1.00 | 61.37 |
| 2296 | C | LEU | 544 | 22.209 | 21.639 | 47.591 | 1.00 | 61.62 |
| 2297 | O | LEU | 544 | 23.047 | 21.388 | 46.721 | 1.00 | 61.82 |
| 2298 | N | TYR | 545 | 21.504 | 20.713 | 48.222 | 1.00 | 60.41 |
| 2299 | CA | TYR | 545 | 21.623 | 19.306 | 47.915 | 1.00 | 64.14 |
| 2300 | CB | TYR | 545 | 21.436 | 18.495 | 49.189 | 1.00 | 59.96 |
| 2301 | CG | TYR | 545 | 22.566 | 18.713 | 50.160 | 1.00 | 66.69 |
| 2302 | CD1 | TYR | 545 | 22.715 | 17.908 | 51.287 | 1.00 | 63.31 |
| 2303 | CE1 | TYR | 545 | 23.810 | 18.056 | 52.122 | 1.00 | 61.54 |
| 2304 | CD2 | TYR | 545 | 23.537 | 19.684 | 49.907 | 1.00 | 62.21 |
| 2305 | CE2 | TYR | 545 | 24.632 | 19.843 | 50.739 | 1.00 | 61.49 |
| 2306 | CZ | TYR | 545 | 24.769 | 19.022 | 51.842 | 1.00 | 59.50 |
| 2307 | OH | TYR | 545 | 25.898 | 19.142 | 52.619 | 1.00 | 60.93 |
| 2308 | C | TYR | 545 | 20.482 | 19.111 | 46.949 | 1.00 | 58.64 |
| 2309 | O | TYR | 545 | 19.553 | 19.912 | 46.956 | 1.00 | 62.56 |
| 2310 | N | ALA | 546 | 20.532 | 18.077 | 46.115 | 1.00 | 57.51 |
| 2311 | CA | ALA | 546 | 19.461 | 17.886 | 45.145 | 1.00 | 59.14 |
| 2312 | CB | ALA | 546 | 20.026 | 17.390 | 43.845 | 1.00 | 60.50 |
| 2313 | C | ALA | 546 | 18.347 | 16.965 | 45.595 | 1.00 | 62.16 |
| 2314 | O | ALA | 546 | 17.352 | 16.821 | 44.895 | 1.00 | 62.38 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2315 | N | GLY | 547 | 18.493 | 16.338 | 46.755 | 1.00 | 59.60 |
| 2316 | CA | GLY | 547 | 17.441 | 15.445 | 47.203 | 1.00 | 63.46 |
| 2317 | C | GLY | 547 | 17.125 | 14.408 | 46.137 | 1.00 | 63.02 |
| 2318 | O | GLY | 547 | 15.968 | 14.068 | 45.890 | 1.00 | 60.60 |
| 2319 | N | TYR | 548 | 18.180 | 13.918 | 45.496 | 1.00 | 62.10 |
| 2320 | CA | TYR | 548 | 18.095 | 12.906 | 44.447 | 1.00 | 60.16 |
| 2321 | CB | TYR | 548 | 19.366 | 12.971 | 43.621 | 1.00 | 60.58 |
| 2322 | CG | TYR | 548 | 19.357 | 12.107 | 42.403 | 1.00 | 61.55 |
| 2323 | CD1 | TYR | 548 | 18.522 | 12.406 | 41.331 | 1.00 | 65.33 |
| 2324 | CE1 | TYR | 548 | 18.550 | 11.657 | 40.175 | 1.00 | 62.35 |
| 2325 | CD2 | TYR | 548 | 20.218 | 11.023 | 42.292 | 1.00 | 62.44 |
| 2326 | CE2 | TYR | 548 | 20.251 | 10.267 | 41.142 | 1.00 | 64.59 |
| 2327 | CZ | TYR | 548 | 19.416 | 10.594 | 40.086 | 1.00 | 60.42 |
| 2328 | OH | TYR | 548 | 19.467 | 9.877 | 38.925 | 1.00 | 60.60 |
| 2329 | C | TYR | 548 | 17.979 | 11.519 | 45.080 | 1.00 | 60.53 |
| 2330 | O | TYR | 548 | 18.584 | 11.272 | 46.114 | 1.00 | 61.95 |
| 2331 | N | ASP | 549 | 17.227 | 10.603 | 44.480 | 1.00 | 60.31 |
| 2332 | CA | ASP | 549 | 17.135 | 9.281 | 45.088 | 1.00 | 60.89 |
| 2333 | CB | ASP | 549 | 16.206 | 8.359 | 44.317 | 1.00 | 61.64 |
| 2334 | CG | ASP | 549 | 15.653 | 7.256 | 45.196 | 1.00 | 62.87 |
| 2335 | OD1 | ASP | 549 | 16.437 | 6.715 | 45.997 | 1.00 | 61.92 |
| 2336 | OD2 | ASP | 549 | 14.446 | 6.929 | 45.100 | 1.00 | 58.12 |
| 2337 | C | ASP | 549 | 18.525 | 8.656 | 45.152 | 1.00 | 62.05 |
| 2338 | O | ASP | 549 | 19.176 | 8.728 | 46.190 | 1.00 | 59.43 |
| 2339 | N | SER | 550 | 18.977 | 8.052 | 44.049 | 1.00 | 61.36 |
| 2340 | CA | SER | 550 | 20.312 | 7.425 | 43.963 | 1.00 | 61.16 |
| 2341 | CB | SER | 550 | 21.301 | 8.127 | 44.910 | 1.00 | 61.33 |
| 2342 | OG | SER | 550 | 22.637 | 8.055 | 44.435 | 1.00 | 65.58 |
| 2343 | C | SER | 550 | 20.286 | 5.923 | 44.268 | 1.00 | 62.72 |
| 2344 | O | SER | 550 | 21.025 | 5.138 | 43.662 | 1.00 | 61.37 |
| 2345 | N | SER | 551 | 19.422 | 5.543 | 45.206 | 1.00 | 60.55 |
| 2346 | CA | SER | 551 | 19.262 | 4.155 | 45.623 | 1.00 | 62.47 |
| 2347 | CB | SER | 551 | 18.461 | 4.092 | 46.927 | 1.00 | 59.78 |
| 2348 | OG | SER | 551 | 17.138 | 4.551 | 46.727 | 1.00 | 65.75 |
| 2349 | C | SER | 551 | 18.548 | 3.348 | 44.544 | 1.00 | 61.26 |
| 2350 | O | SER | 551 | 18.187 | 2.189 | 44.749 | 1.00 | 64.05 |
| 2351 | N | VAL | 552 | 18.349 | 3.976 | 43.394 | 1.00 | 61.88 |
| 2352 | CA | VAL | 552 | 17.683 | 3.338 | 42.268 | 1.00 | 61.07 |
| 2353 | CB | VAL | 552 | 16.146 | 3.536 | 42.346 | 1.00 | 61.01 |
| 2354 | CG1 | VAL | 552 | 15.781 | 4.362 | 43.582 | 1.00 | 62.13 |
| 2355 | CG2 | VAL | 552 | 15.642 | 4.194 | 41.084 | 1.00 | 63.59 |
| 2356 | C | VAL | 552 | 18.245 | 3.935 | 40.975 | 1.00 | 60.74 |
| 2357 | O | VAL | 552 | 18.423 | 5.151 | 40.872 | 1.00 | 60.94 |
| 2358 | N | PRO | 553 | 18.502 | 3.085 | 39.966 | 1.00 | 57.88 |
| 2359 | CD | PRO | 553 | 17.755 | 1.824 | 39.869 | 1.00 | 60.27 |
| 2360 | CA | PRO | 553 | 19.058 | 3.418 | 38.648 | 1.00 | 60.29 |
| 2361 | CB | PRO | 553 | 18.407 | 2.387 | 37.718 | 1.00 | 59.38 |
| 2362 | CG | PRO | 553 | 17.208 | 1.918 | 38.478 | 1.00 | 59.68 |
| 2363 | C | PRO | 553 | 18.933 | 4.837 | 38.105 | 1.00 | 61.75 |
| 2364 | O | PRO | 553 | 17.864 | 5.452 | 38.132 | 1.00 | 60.81 |
| 2365 | N | ASP | 554 | 20.055 | 5.352 | 37.616 | 1.00 | 59.48 |
| 2366 | CA | ASP | 554 | 20.061 | 6.676 | 37.032 | 1.00 | 59.15 |
| 2367 | CB | ASP | 554 | 21.477 | 7.212 | 36.819 | 1.00 | 62.17 |
| 2368 | CG | ASP | 554 | 22.222 | 7.452 | 38.101 | 1.00 | 62.93 |
| 2369 | OD1 | ASP | 554 | 21.591 | 7.655 | 39.164 | 1.00 | 60.70 |
| 2370 | OD2 | ASP | 554 | 23.467 | 7.455 | 38.017 | 1.00 | 60.19 |
| 2371 | C | ASP | 554 | 19.433 | 6.505 | 35.667 | 1.00 | 61.49 |
| 2372 | O | ASP | 554 | 18.898 | 5.446 | 35.354 | 1.00 | 59.51 |
| 2373 | N | SER | 555 | 19.536 | 7.557 | 34.859 | 1.00 | 60.31 |
| 2374 | CA | SER | 555 | 19.023 | 7.601 | 33.492 | 1.00 | 60.74 |
| 2375 | CB | SER | 555 | 17.576 | 7.113 | 33.419 | 1.00 | 64.15 |
| 2376 | OG | SER | 555 | 16.687 | 8.099 | 33.896 | 1.00 | 60.71 |
| 2377 | C | SER | 555 | 19.092 | 9.069 | 33.108 | 1.00 | 61.31 |
| 2378 | O | SER | 555 | 18.776 | 9.929 | 33.927 | 1.00 | 59.93 |
| 2379 | N | THR | 556 | 19.525 | 9.358 | 31.883 | 1.00 | 62.16 |
| 2380 | CA | THR | 556 | 19.636 | 10.742 | 31.434 | 1.00 | 61.52 |
| 2381 | CB | THR | 556 | 19.673 | 10.857 | 29.895 | 1.00 | 59.01 |
| 2382 | OG1 | THR | 556 | 20.850 | 10.212 | 29.391 | 1.00 | 60.60 |
| 2383 | CG2 | THR | 556 | 19.677 | 12.330 | 29.475 | 1.00 | 60.87 |
| 2384 | C | THR | 556 | 18.422 | 11.505 | 31.913 | 1.00 | 61.95 |
| 2385 | O | THR | 556 | 18.517 | 12.377 | 32.788 | 1.00 | 60.46 |
| 2386 | N | TRP | 557 | 17.285 | 11.145 | 31.318 | 1.00 | 60.92 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2387 | CA | TRP | 557 | 15.986 | 11.734 | 31.611 | 1.00 | 63.76 |
| 2388 | CB | TRP | 557 | 14.864 | 10.739 | 31.251 | 1.00 | 61.57 |
| 2389 | CG | TRP | 557 | 13.719 | 10.807 | 32.225 | 1.00 | 57.77 |
| 2390 | CD2 | TRP | 557 | 12.895 | 11.949 | 32.491 | 1.00 | 60.28 |
| 2391 | CE2 | TRP | 557 | 12.066 | 11.627 | 33.595 | 1.00 | 61.10 |
| 2392 | CE3 | TRP | 557 | 12.785 | 13.219 | 31.911 | 1.00 | 57.69 |
| 2393 | CD1 | TRP | 557 | 13.357 | 9.855 | 33.145 | 1.00 | 63.49 |
| 2394 | NE1 | TRP | 557 | 12.369 | 10.344 | 33.974 | 1.00 | 60.45 |
| 2395 | CZ2 | TRP | 557 | 11.132 | 12.535 | 34.132 | 1.00 | 61.64 |
| 2396 | CZ3 | TRP | 557 | 11.857 | 14.124 | 32.452 | 1.00 | 61.15 |
| 2397 | CH2 | TRP | 557 | 11.045 | 13.773 | 33.548 | 1.00 | 61.06 |
| 2398 | C | TRP | 557 | 15.816 | 12.176 | 33.063 | 1.00 | 61.03 |
| 2399 | O | TRP | 557 | 15.546 | 13.342 | 33.335 | 1.00 | 63.66 |
| 2400 | N | ARG | 558 | 15.972 | 11.228 | 33.982 | 1.00 | 62.37 |
| 2401 | CA | ARG | 558 | 15.798 | 11.466 | 35.413 | 1.00 | 63.98 |
| 2402 | CB | ARG | 558 | 15.806 | 10.116 | 36.134 | 1.00 | 61.30 |
| 2403 | CG | ARG | 558 | 15.389 | 10.127 | 37.590 | 1.00 | 62.22 |
| 2404 | CD | ARG | 558 | 15.189 | 8.686 | 38.070 | 1.00 | 59.18 |
| 2405 | NE | ARG | 558 | 16.210 | 8.204 | 39.005 | 1.00 | 60.75 |
| 2406 | CZ | ARG | 558 | 16.280 | 8.542 | 40.294 | 1.00 | 62.74 |
| 2407 | NH1 | ARG | 558 | 15.392 | 9.378 | 40.820 | 1.00 | 65.45 |
| 2408 | NH2 | ARG | 558 | 17.222 | 8.022 | 41.074 | 1.00 | 61.39 |
| 2409 | C | ARG | 558 | 16.814 | 12.416 | 36.056 | 1.00 | 63.08 |
| 2410 | O | ARG | 558 | 16.524 | 13.027 | 37.085 | 1.00 | 62.80 |
| 2411 | N | ILE | 559 | 17.991 | 12.548 | 35.451 | 1.00 | 63.40 |
| 2412 | CA | ILE | 559 | 19.036 | 13.423 | 35.983 | 1.00 | 59.67 |
| 2413 | CB | ILE | 559 | 20.459 | 12.828 | 35.701 | 1.00 | 59.65 |
| 2414 | CG2 | ILE | 559 | 21.437 | 13.905 | 35.250 | 1.00 | 56.03 |
| 2415 | CG1 | ILE | 559 | 20.982 | 12.150 | 36.968 | 1.00 | 58.33 |
| 2416 | CD1 | ILE | 559 | 22.212 | 11.327 | 36.744 | 1.00 | 61.31 |
| 2417 | C | ILE | 559 | 18.939 | 14.862 | 35.469 | 1.00 | 64.14 |
| 2418 | O | ILE | 559 | 18.843 | 15.792 | 36.281 | 1.00 | 63.80 |
| 2419 | N | MET | 560 | 18.964 | 15.060 | 34.151 | 1.00 | 58.15 |
| 2420 | CA | MET | 560 | 18.871 | 16.419 | 33.646 | 1.00 | 61.08 |
| 2421 | CB | MET | 560 | 18.753 | 16.460 | 32.095 | 1.00 | 60.65 |
| 2422 | CG | MET | 560 | 20.117 | 16.352 | 31.322 | 1.00 | 63.74 |
| 2423 | SD | MET | 560 | 20.038 | 16.357 | 29.422 | 1.00 | 63.49 |
| 2424 | CE | MET | 560 | 21.750 | 16.939 | 28.970 | 1.00 | 61.12 |
| 2425 | C | MET | 560 | 17.634 | 17.014 | 34.325 | 1.00 | 63.02 |
| 2426 | O | MET | 560 | 17.666 | 18.156 | 34.780 | 1.00 | 60.37 |
| 2427 | N | THR | 561 | 16.572 | 16.217 | 34.457 | 1.00 | 60.33 |
| 2428 | CA | THR | 561 | 15.351 | 16.677 | 35.123 | 1.00 | 60.71 |
| 2429 | CB | THR | 561 | 14.306 | 15.540 | 35.292 | 1.00 | 58.90 |
| 2430 | OG1 | THR | 561 | 14.006 | 14.959 | 34.025 | 1.00 | 60.27 |
| 2431 | CG2 | THR | 561 | 13.019 | 16.080 | 35.867 | 1.00 | 58.67 |
| 2432 | C | THR | 561 | 15.616 | 17.259 | 36.520 | 1.00 | 60.71 |
| 2433 | O | THR | 561 | 15.390 | 18.429 | 36.747 | 1.00 | 62.74 |
| 2434 | N | THR | 562 | 16.111 | 16.434 | 37.451 | 1.00 | 61.67 |
| 2435 | CA | THR | 562 | 16.387 | 16.821 | 38.860 | 1.00 | 62.60 |
| 2436 | CB | THR | 562 | 16.914 | 15.721 | 39.677 | 1.00 | 60.58 |
| 2437 | OG1 | THR | 562 | 18.152 | 15.292 | 39.081 | 1.00 | 59.96 |
| 2438 | CG2 | THR | 562 | 15.938 | 14.616 | 39.802 | 1.00 | 62.71 |
| 2439 | C | THR | 562 | 17.487 | 17.786 | 39.098 | 1.00 | 60.58 |
| 2440 | O | THR | 562 | 17.924 | 18.032 | 40.229 | 1.00 | 63.25 |
| 2441 | N | LEU | 563 | 17.993 | 18.325 | 38.047 | 1.00 | 60.71 |
| 2442 | CA | LEU | 563 | 19.148 | 19.110 | 38.123 | 1.00 | 61.15 |
| 2443 | CB | LEU | 563 | 20.009 | 18.485 | 37.164 | 1.00 | 61.40 |
| 2444 | CG | LEU | 563 | 21.445 | 18.268 | 37.247 | 1.00 | 60.76 |
| 2445 | CD1 | LEU | 563 | 21.882 | 17.094 | 38.118 | 1.00 | 59.56 |
| 2446 | CD2 | LEU | 563 | 21.705 | 18.012 | 35.810 | 1.00 | 62.29 |
| 2447 | C | LEU | 563 | 18.542 | 20.350 | 37.631 | 1.00 | 60.18 |
| 2448 | O | LEU | 563 | 19.115 | 21.393 | 37.453 | 1.00 | 62.51 |
| 2449 | N | ASN | 564 | 17.281 | 20.194 | 37.278 | 1.00 | 62.12 |
| 2450 | CA | ASN | 564 | 16.596 | 21.312 | 36.741 | 1.00 | 63.12 |
| 2451 | CB | ASN | 564 | 15.703 | 20.918 | 35.651 | 1.00 | 63.80 |
| 2452 | CG | ASN | 564 | 16.263 | 21.124 | 34.284 | 1.00 | 60.00 |
| 2453 | OD1 | ASN | 564 | 17.269 | 21.801 | 34.085 | 1.00 | 59.72 |
| 2454 | ND2 | ASN | 564 | 15.577 | 20.559 | 33.311 | 1.00 | 61.08 |
| 2455 | C | ASN | 564 | 15.740 | 21.719 | 37.867 | 1.00 | 61.56 |
| 2456 | O | ASN | 564 | 15.204 | 22.818 | 37.863 | 1.00 | 61.14 |
| 2457 | N | MET | 565 | 15.483 | 20.798 | 38.768 | 1.00 | 63.63 |
| 2458 | CA | MET | 565 | 14.643 | 21.083 | 39.872 | 1.00 | 60.96 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2459 | CB | MET | 565 | 14.164 | 19.773 | 40.504 | 1.00 | 61.63 |
| 2460 | CG | MET | 565 | 12.686 | 19.546 | 40.369 | 1.00 | 65.53 |
| 2461 | SD | MET | 565 | 12.013 | 20.320 | 38.903 | 1.00 | 61.09 |
| 2462 | CE | MET | 565 | 10.337 | 20.392 | 39.357 | 1.00 | 60.22 |
| 2463 | C | MET | 565 | 15.560 | 21.814 | 40.802 | 1.00 | 62.76 |
| 2464 | O | MET | 565 | 15.162 | 22.713 | 41.539 | 1.00 | 60.13 |
| 2465 | N | LEU | 566 | 16.826 | 21.447 | 40.746 | 1.00 | 62.63 |
| 2466 | CA | LEU | 566 | 17.794 | 22.101 | 41.590 | 1.00 | 58.73 |
| 2467 | CB | LEU | 566 | 19.007 | 21.188 | 41.764 | 1.00 | 59.94 |
| 2468 | CG | LEU | 566 | 20.381 | 21.435 | 42.410 | 1.00 | 60.09 |
| 2469 | CD1 | LEU | 566 | 21.236 | 21.209 | 41.243 | 1.00 | 60.52 |
| 2470 | CD2 | LEU | 566 | 20.687 | 22.805 | 43.045 | 1.00 | 59.08 |
| 2471 | C | LEU | 566 | 18.142 | 23.418 | 40.952 | 1.00 | 61.33 |
| 2472 | O | LEU | 566 | 18.373 | 24.398 | 41.652 | 1.00 | 61.14 |
| 2473 | N | GLY | 567 | 18.140 | 23.461 | 39.625 | 1.00 | 57.88 |
| 2474 | CA | GLY | 567 | 18.436 | 24.703 | 38.935 | 1.00 | 63.27 |
| 2475 | C | GLY | 567 | 17.469 | 25.785 | 39.351 | 1.00 | 60.49 |
| 2476 | O | GLY | 567 | 17.854 | 26.938 | 39.514 | 1.00 | 61.62 |
| 2477 | N | GLY | 568 | 16.206 | 25.412 | 39.526 | 1.00 | 63.72 |
| 2478 | CA | GLY | 568 | 15.212 | 26.382 | 39.936 | 1.00 | 60.34 |
| 2479 | C | GLY | 568 | 15.617 | 27.006 | 41.256 | 1.00 | 60.96 |
| 2480 | O | GLY | 568 | 15.913 | 28.195 | 41.332 | 1.00 | 61.39 |
| 2481 | N | ARG | 569 | 15.662 | 26.196 | 42.302 | 1.00 | 59.63 |
| 2482 | CA | ARG | 569 | 16.011 | 26.692 | 43.623 | 1.00 | 58.74 |
| 2483 | CB | ARG | 569 | 16.143 | 25.530 | 44.588 | 1.00 | 62.58 |
| 2484 | CG | ARG | 569 | 14.860 | 24.767 | 44.719 | 1.00 | 61.89 |
| 2485 | CD | ARG | 569 | 14.973 | 23.794 | 45.842 | 1.00 | 60.95 |
| 2486 | NE | ARG | 569 | 16.047 | 22.854 | 45.573 | 1.00 | 60.03 |
| 2487 | CZ | ARG | 569 | 16.734 | 22.229 | 46.513 | 1.00 | 60.68 |
| 2488 | NH1 | ARG | 569 | 16.459 | 22.447 | 47.793 | 1.00 | 65.06 |
| 2489 | NH2 | ARG | 569 | 17.697 | 21.391 | 46.169 | 1.00 | 63.36 |
| 2490 | C | ARG | 569 | 17.261 | 27.538 | 43.671 | 1.00 | 59.59 |
| 2491 | O | ARG | 569 | 17.395 | 28.397 | 44.539 | 1.00 | 58.49 |
| 2492 | N | GLN | 570 | 18.179 | 27.299 | 42.747 | 1.00 | 60.12 |
| 2493 | CA | GLN | 570 | 19.417 | 28.069 | 42.704 | 1.00 | 62.83 |
| 2494 | CB | GLN | 570 | 20.457 | 27.359 | 41.852 | 1.00 | 64.23 |
| 2495 | CG | GLN | 570 | 21.212 | 26.254 | 42.529 | 1.00 | 60.55 |
| 2496 | CD | GLN | 570 | 22.345 | 25.738 | 41.674 | 1.00 | 61.81 |
| 2497 | OE1 | GLN | 570 | 23.046 | 24.818 | 42.067 | 1.00 | 60.88 |
| 2498 | NE2 | GLN | 570 | 22.533 | 26.331 | 40.499 | 1.00 | 56.12 |
| 2499 | C | GLN | 570 | 19.195 | 29.462 | 42.135 | 1.00 | 59.62 |
| 2500 | O | GLN | 570 | 19.872 | 30.409 | 42.529 | 1.00 | 60.45 |
| 2501 | N | VAL | 571 | 18.273 | 29.571 | 41.182 | 1.00 | 64.99 |
| 2502 | CA | VAL | 571 | 17.953 | 30.851 | 40.576 | 1.00 | 62.98 |
| 2503 | CB | VAL | 571 | 17.141 | 30.653 | 39.278 | 1.00 | 62.20 |
| 2504 | CG1 | VAL | 571 | 16.363 | 31.906 | 38.929 | 1.00 | 61.93 |
| 2505 | CG2 | VAL | 571 | 18.090 | 30.312 | 38.140 | 1.00 | 61.13 |
| 2506 | C | VAL | 571 | 17.166 | 31.658 | 41.605 | 1.00 | 63.93 |
| 2507 | O | VAL | 571 | 17.379 | 32.865 | 41.763 | 1.00 | 65.46 |
| 2508 | N | ILE | 572 | 16.271 | 30.981 | 42.317 | 1.00 | 61.03 |
| 2509 | CA | ILE | 572 | 15.483 | 31.623 | 43.360 | 1.00 | 58.70 |
| 2510 | CB | ILE | 572 | 14.548 | 30.605 | 44.045 | 1.00 | 66.72 |
| 2511 | CG2 | ILE | 572 | 14.006 | 31.169 | 45.350 | 1.00 | 58.22 |
| 2512 | CG1 | ILE | 572 | 13.425 | 30.220 | 43.081 | 1.00 | 61.85 |
| 2513 | CD1 | ILE | 572 | 12.411 | 29.251 | 43.663 | 1.00 | 61.02 |
| 2514 | C | ILE | 572 | 16.456 | 32.186 | 44.390 | 1.00 | 59.43 |
| 2515 | O | ILE | 572 | 16.240 | 33.257 | 44.948 | 1.00 | 61.61 |
| 2516 | N | ALA | 573 | 17.531 | 31.446 | 44.628 | 1.00 | 62.51 |
| 2517 | CA | ALA | 573 | 18.562 | 31.844 | 45.571 | 1.00 | 63.19 |
| 2518 | CB | ALA | 573 | 19.467 | 30.662 | 45.875 | 1.00 | 59.65 |
| 2519 | C | ALA | 573 | 19.390 | 32.994 | 45.016 | 1.00 | 60.08 |
| 2520 | O | ALA | 573 | 19.853 | 33.852 | 45.765 | 1.00 | 61.27 |
| 2521 | N | ALA | 574 | 19.573 | 33.004 | 43.700 | 1.00 | 62.86 |
| 2522 | CA | ALA | 574 | 20.350 | 34.039 | 43.027 | 1.00 | 62.91 |
| 2523 | CB | ALA | 574 | 20.500 | 33.690 | 41.553 | 1.00 | 60.40 |
| 2524 | C | ALA | 574 | 19.729 | 35.426 | 43.176 | 1.00 | 61.54 |
| 2525 | O | ALA | 574 | 20.402 | 36.441 | 42.977 | 1.00 | 62.14 |
| 2526 | N | VAL | 575 | 18.447 | 35.461 | 43.535 | 1.00 | 63.11 |
| 2527 | CA | VAL | 575 | 17.721 | 36.716 | 43.708 | 1.00 | 61.22 |
| 2528 | CB | VAL | 575 | 16.214 | 36.502 | 43.529 | 1.00 | 61.11 |
| 2529 | CG1 | VAL | 575 | 15.500 | 37.835 | 43.568 | 1.00 | 63.45 |
| 2530 | CG2 | VAL | 575 | 15.950 | 35.795 | 42.218 | 1.00 | 55.96 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2531 | C | VAL | 575 | 17.970 | 37.386 | 45.063 | 1.00 | 61.67 |
| 2532 | O | VAL | 575 | 18.242 | 38.589 | 45.119 | 1.00 | 61.16 |
| 2533 | N | LYS | 576 | 17.866 | 36.618 | 46.148 | 1.00 | 63.44 |
| 2534 | CA | LYS | 576 | 18.103 | 37.169 | 47.477 | 1.00 | 61.90 |
| 2535 | CB | LYS | 576 | 17.913 | 36.120 | 48.576 | 1.00 | 60.65 |
| 2536 | CG | LYS | 576 | 16.569 | 35.385 | 48.633 | 1.00 | 62.95 |
| 2537 | CD | LYS | 576 | 16.370 | 34.812 | 50.045 | 1.00 | 61.64 |
| 2538 | CE | LYS | 576 | 15.453 | 33.594 | 50.101 | 1.00 | 61.27 |
| 2539 | NZ | LYS | 576 | 16.134 | 32.288 | 49.785 | 1.00 | 60.24 |
| 2540 | C | LYS | 576 | 19.554 | 37.616 | 47.498 | 1.00 | 62.75 |
| 2541 | O | LYS | 576 | 19.966 | 38.384 | 48.367 | 1.00 | 59.51 |
| 2542 | N | TRP | 577 | 20.320 | 37.103 | 46.534 | 1.00 | 64.04 |
| 2543 | CA | TRP | 577 | 21.741 | 37.407 | 46.382 | 1.00 | 63.24 |
| 2544 | CB | TRP | 577 | 22.447 | 36.277 | 45.610 | 1.00 | 61.04 |
| 2545 | CG | TRP | 577 | 23.852 | 36.613 | 45.166 | 1.00 | 62.92 |
| 2546 | CD2 | TRP | 577 | 24.285 | 36.919 | 43.828 | 1.00 | 59.92 |
| 2547 | CE2 | TRP | 577 | 25.663 | 37.212 | 43.892 | 1.00 | 60.22 |
| 2548 | CE3 | TRP | 577 | 23.637 | 36.978 | 42.584 | 1.00 | 61.13 |
| 2549 | CD1 | TRP | 577 | 24.956 | 36.729 | 45.958 | 1.00 | 63.10 |
| 2550 | NE1 | TRP | 577 | 26.045 | 37.088 | 45.201 | 1.00 | 58.91 |
| 2551 | CZ2 | TRP | 577 | 26.411 | 37.557 | 42.763 | 1.00 | 58.75 |
| 2552 | CZ3 | TRP | 577 | 24.378 | 37.325 | 41.461 | 1.00 | 63.87 |
| 2553 | CH2 | TRP | 577 | 25.754 | 37.611 | 41.559 | 1.00 | 60.61 |
| 2554 | C | TRP | 577 | 21.923 | 38.719 | 45.634 | 1.00 | 60.28 |
| 2555 | O | TRP | 577 | 22.654 | 39.597 | 46.083 | 1.00 | 61.57 |
| 2556 | N | ALA | 578 | 21.251 | 38.837 | 44.490 | 1.00 | 60.75 |
| 2557 | CA | ALA | 578 | 21.338 | 40.032 | 43.661 | 1.00 | 62.79 |
| 2558 | CB | ALA | 578 | 20.522 | 39.847 | 42.395 | 1.00 | 63.55 |
| 2559 | C | ALA | 578 | 20.869 | 41.274 | 44.409 | 1.00 | 60.84 |
| 2560 | O | ALA | 578 | 21.347 | 42.370 | 44.156 | 1.00 | 60.70 |
| 2561 | N | LYS | 579 | 19.937 | 41.105 | 45.339 | 1.00 | 62.74 |
| 2562 | CA | LYS | 579 | 19.423 | 42.234 | 46.107 | 1.00 | 60.13 |
| 2563 | CB | LYS | 579 | 18.016 | 41.900 | 46.640 | 1.00 | 60.85 |
| 2564 | CG | LYS | 579 | 16.969 | 41.709 | 45.532 | 1.00 | 61.81 |
| 2565 | CD | LYS | 579 | 15.725 | 40.942 | 45.986 | 1.00 | 61.28 |
| 2566 | CE | LYS | 579 | 14.910 | 41.704 | 47.020 | 1.00 | 61.64 |
| 2567 | NZ | LYS | 579 | 13.708 | 40.953 | 47.492 | 1.00 | 62.20 |
| 2568 | C | LYS | 579 | 20.372 | 42.613 | 47.252 | 1.00 | 60.67 |
| 2569 | O | LYS | 579 | 20.251 | 43.683 | 47.835 | 1.00 | 59.96 |
| 2570 | N | ALA | 580 | 21.322 | 41.738 | 47.564 | 1.00 | 59.98 |
| 2571 | CA | ALA | 580 | 22.288 | 42.011 | 48.630 | 1.00 | 60.27 |
| 2572 | CB | ALA | 580 | 22.721 | 40.713 | 49.304 | 1.00 | 64.73 |
| 2573 | C | ALA | 580 | 23.505 | 42.722 | 48.059 | 1.00 | 58.96 |
| 2574 | O | ALA | 580 | 24.349 | 43.229 | 48.801 | 1.00 | 61.59 |
| 2575 | N | ILE | 581 | 23.590 | 42.738 | 46.731 | 1.00 | 63.39 |
| 2576 | CA | ILE | 581 | 24.690 | 43.380 | 46.030 | 1.00 | 60.52 |
| 2577 | CB | ILE | 581 | 24.789 | 42.908 | 44.559 | 1.00 | 60.74 |
| 2578 | CG2 | ILE | 581 | 25.911 | 43.650 | 43.840 | 1.00 | 63.37 |
| 2579 | CG1 | ILE | 581 | 25.069 | 41.409 | 44.494 | 1.00 | 60.26 |
| 2580 | CD1 | ILE | 581 | 24.930 | 40.862 | 43.091 | 1.00 | 61.59 |
| 2581 | C | ILE | 581 | 24.426 | 44.873 | 46.025 | 1.00 | 63.62 |
| 2582 | O | ILE | 581 | 23.418 | 45.329 | 45.482 | 1.00 | 63.59 |
| 2583 | N | PRO | 582 | 25.329 | 45.655 | 46.634 | 1.00 | 62.76 |
| 2584 | CD | PRO | 582 | 26.596 | 45.257 | 47.270 | 1.00 | 63.28 |
| 2585 | CA | PRO | 582 | 25.162 | 47.104 | 46.681 | 1.00 | 64.52 |
| 2586 | CB | PRO | 582 | 26.505 | 47.589 | 47.226 | 1.00 | 62.45 |
| 2587 | CG | PRO | 582 | 26.934 | 46.473 | 48.106 | 1.00 | 59.21 |
| 2588 | C | PRO | 582 | 24.882 | 47.654 | 45.298 | 1.00 | 62.22 |
| 2589 | O | PRO | 582 | 25.518 | 47.252 | 44.323 | 1.00 | 61.69 |
| 2590 | N | GLY | 583 | 23.913 | 48.560 | 45.224 | 1.00 | 58.26 |
| 2591 | CA | GLY | 583 | 23.565 | 49.189 | 43.965 | 1.00 | 59.81 |
| 2592 | C | GLY | 583 | 22.640 | 48.446 | 43.028 | 1.00 | 61.92 |
| 2593 | O | GLY | 583 | 22.231 | 49.002 | 42.024 | 1.00 | 58.88 |
| 2594 | N | PHE | 584 | 22.302 | 47.201 | 43.327 | 1.00 | 62.92 |
| 2595 | CA | PHE | 584 | 21.418 | 46.459 | 42.438 | 1.00 | 61.83 |
| 2596 | CB | PHE | 584 | 21.563 | 44.953 | 42.677 | 1.00 | 62.46 |
| 2597 | CG | PHE | 584 | 20.863 | 44.104 | 41.650 | 1.00 | 57.96 |
| 2598 | CD1 | PHE | 584 | 21.406 | 43.921 | 40.390 | 1.00 | 63.14 |
| 2599 | CD2 | PHE | 584 | 19.646 | 43.514 | 41.938 | 1.00 | 62.84 |
| 2600 | CE1 | PHE | 584 | 20.746 | 43.166 | 39.437 | 1.00 | 61.42 |
| 2601 | CE2 | PHE | 584 | 18.980 | 42.759 | 40.991 | 1.00 | 60.47 |
| 2602 | CZ | PHE | 584 | 19.533 | 42.585 | 39.737 | 1.00 | 59.28 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2603 | C | PHE | 584 | 19.958 | 46.883 | 42.624 | 1.00 | 60.13 |
| 2604 | O | PHE | 584 | 19.210 | 46.996 | 41.653 | 1.00 | 61.49 |
| 2605 | N | ARG | 585 | 19.561 | 47.131 | 43.870 | 1.00 | 60.78 |
| 2606 | CA | ARG | 585 | 18.190 | 47.535 | 44.160 | 1.00 | 63.10 |
| 2607 | CB | ARG | 585 | 17.832 | 47.252 | 45.627 | 1.00 | 59.03 |
| 2608 | CG | ARG | 585 | 17.716 | 45.757 | 45.943 | 1.00 | 57.77 |
| 2609 | CD | ARG | 585 | 17.222 | 45.476 | 47.365 | 1.00 | 61.69 |
| 2610 | NE | ARG | 585 | 15.825 | 45.858 | 47.587 | 1.00 | 62.10 |
| 2611 | CZ | ARG | 585 | 14.800 | 45.492 | 46.817 | 1.00 | 62.77 |
| 2612 | NH1 | ARG | 585 | 14.996 | 44.724 | 45.744 | 1.00 | 60.63 |
| 2613 | NH2 | ARG | 585 | 13.569 | 45.893 | 47.126 | 1.00 | 59.26 |
| 2614 | C | ARG | 585 | 17.952 | 48.996 | 43.843 | 1.00 | 59.85 |
| 2615 | O | ARG | 585 | 16.833 | 49.487 | 43.965 | 1.00 | 61.84 |
| 2616 | N | ASN | 586 | 19.003 | 49.689 | 43.424 | 1.00 | 60.92 |
| 2617 | CA | ASN | 586 | 18.871 | 51.094 | 43.090 | 1.00 | 62.56 |
| 2618 | CB | ASN | 586 | 19.987 | 51.892 | 43.740 | 1.00 | 59.81 |
| 2619 | CG | ASN | 586 | 20.079 | 51.620 | 45.218 | 1.00 | 62.07 |
| 2620 | OD1 | ASN | 586 | 20.714 | 50.651 | 45.641 | 1.00 | 62.28 |
| 2621 | ND2 | ASN | 586 | 19.415 | 52.452 | 46.018 | 1.00 | 56.67 |
| 2622 | C | ASN | 586 | 18.865 | 51.271 | 41.592 | 1.00 | 63.34 |
| 2623 | O | ASN | 586 | 19.054 | 52.363 | 41.068 | 1.00 | 60.96 |
| 2624 | N | LEU | 587 | 18.648 | 50.163 | 40.907 | 1.00 | 62.25 |
| 2625 | CA | LEU | 587 | 18.551 | 50.166 | 39.467 | 1.00 | 60.33 |
| 2626 | CB | LEU | 587 | 19.304 | 48.971 | 38.887 | 1.00 | 63.97 |
| 2627 | CG | LEU | 587 | 20.823 | 49.075 | 38.847 | 1.00 | 59.84 |
| 2628 | CD1 | LEU | 587 | 21.410 | 47.701 | 38.948 | 1.00 | 62.41 |
| 2629 | CD2 | LEU | 587 | 21.262 | 49.748 | 37.572 | 1.00 | 64.48 |
| 2630 | C | LEU | 587 | 17.053 | 50.008 | 39.259 | 1.00 | 61.19 |
| 2631 | O | LEU | 587 | 16.355 | 49.541 | 40.164 | 1.00 | 61.87 |
| 2632 | N | HIS | 588 | 16.556 | 50.400 | 38.090 | 1.00 | 63.05 |
| 2633 | CA | HIS | 588 | 15.130 | 50.288 | 37.829 | 1.00 | 58.93 |
| 2634 | CB | HIS | 588 | 14.797 | 50.621 | 36.371 | 1.00 | 62.93 |
| 2635 | CG | HIS | 588 | 13.338 | 50.871 | 36.131 | 1.00 | 61.44 |
| 2636 | CD2 | HIS | 588 | 12.679 | 51.990 | 35.745 | 1.00 | 61.68 |
| 2637 | ND1 | HIS | 588 | 12.369 | 49.912 | 36.344 | 1.00 | 59.82 |
| 2638 | CE1 | HIS | 588 | 11.178 | 50.431 | 36.101 | 1.00 | 59.25 |
| 2639 | NE2 | HIS | 588 | 11.339 | 51.691 | 35.736 | 1.00 | 58.14 |
| 2640 | C | HIS | 588 | 14.723 | 48.860 | 38.128 | 1.00 | 61.41 |
| 2641 | O | HIS | 588 | 15.515 | 47.942 | 37.948 | 1.00 | 59.96 |
| 2642 | N | LEU | 589 | 13.492 | 48.686 | 38.598 | 1.00 | 59.88 |
| 2643 | CA | LEU | 589 | 12.974 | 47.370 | 38.929 | 1.00 | 61.54 |
| 2644 | CB | LEU | 589 | 11.602 | 47.509 | 39.599 | 1.00 | 60.80 |
| 2645 | CG | LEU | 589 | 10.980 | 46.337 | 40.367 | 1.00 | 62.36 |
| 2646 | CD1 | LEU | 589 | 10.643 | 45.192 | 39.424 | 1.00 | 59.67 |
| 2647 | CD2 | LEU | 589 | 11.934 | 45.887 | 41.449 | 1.00 | 61.30 |
| 2648 | C | LEU | 589 | 12.867 | 46.562 | 37.640 | 1.00 | 60.73 |
| 2649 | O | LEU | 589 | 12.841 | 45.332 | 37.667 | 1.00 | 59.26 |
| 2650 | N | ASP | 590 | 12.811 | 47.254 | 36.507 | 1.00 | 62.77 |
| 2651 | CA | ASP | 590 | 12.714 | 46.574 | 35.222 | 1.00 | 59.61 |
| 2652 | CB | ASP | 590 | 12.172 | 47.516 | 34.154 | 1.00 | 60.63 |
| 2653 | CG | ASP | 590 | 10.676 | 47.476 | 34.060 | 1.00 | 60.64 |
| 2654 | OD1 | ASP | 590 | 10.031 | 47.099 | 35.060 | 1.00 | 66.03 |
| 2655 | OD2 | ASP | 590 | 10.140 | 47.830 | 32.989 | 1.00 | 62.74 |
| 2656 | C | ASP | 590 | 14.077 | 46.079 | 34.801 | 1.00 | 64.03 |
| 2657 | O | ASP | 590 | 14.194 | 45.131 | 34.020 | 1.00 | 61.02 |
| 2658 | N | ASP | 591 | 15.109 | 46.734 | 35.319 | 1.00 | 61.76 |
| 2659 | CA | ASP | 591 | 16.481 | 46.364 | 34.993 | 1.00 | 61.72 |
| 2660 | CB | ASP | 591 | 17.425 | 47.557 | 35.224 | 1.00 | 60.28 |
| 2661 | CG | ASP | 591 | 17.174 | 48.709 | 34.250 | 1.00 | 66.48 |
| 2662 | OD1 | ASP | 591 | 16.782 | 48.445 | 33.092 | 1.00 | 56.28 |
| 2663 | OD2 | ASP | 591 | 17.393 | 49.877 | 34.639 | 1.00 | 63.43 |
| 2664 | C | ASP | 591 | 16.937 | 45.160 | 35.813 | 1.00 | 60.81 |
| 2665 | O | ASP | 591 | 17.642 | 44.292 | 35.306 | 1.00 | 61.99 |
| 2666 | N | GLN | 592 | 16.515 | 45.120 | 37.075 | 1.00 | 59.60 |
| 2667 | CA | GLN | 592 | 16.852 | 44.035 | 37.981 | 1.00 | 59.54 |
| 2668 | CB | GLN | 592 | 16.145 | 44.209 | 39.327 | 1.00 | 60.92 |
| 2669 | CG | GLN | 592 | 16.268 | 45.571 | 39.962 | 1.00 | 63.19 |
| 2670 | CD | GLN | 592 | 15.991 | 45.536 | 41.460 | 1.00 | 61.96 |
| 2671 | OE1 | GLN | 592 | 15.303 | 44.641 | 41.967 | 1.00 | 59.41 |
| 2672 | NE2 | GLN | 592 | 16.522 | 46.518 | 42.176 | 1.00 | 61.73 |
| 2673 | C | GLN | 592 | 16.409 | 42.711 | 37.376 | 1.00 | 58.77 |
| 2674 | O | GLN | 592 | 17.034 | 41.668 | 37.606 | 1.00 | 60.09 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2675 | N | MET | 593 | 15.319 | 42.762 | 36.611 | 1.00 | 61.89 |
| 2676 | CA | MET | 593 | 14.756 | 41.575 | 35.977 | 1.00 | 60.29 |
| 2677 | CB | MET | 593 | 13.257 | 41.746 | 35.768 | 1.00 | 61.65 |
| 2678 | CG | MET | 593 | 12.401 | 41.411 | 36.969 | 1.00 | 61.69 |
| 2679 | SD | MET | 593 | 10.676 | 41.232 | 36.456 | 1.00 | 62.68 |
| 2680 | CE | MET | 593 | 10.249 | 42.940 | 36.274 | 1.00 | 60.78 |
| 2681 | C | MET | 593 | 15.388 | 41.229 | 34.645 | 1.00 | 59.77 |
| 2682 | O | MET | 593 | 15.386 | 40.068 | 34.241 | 1.00 | 61.16 |
| 2683 | N | THR | 594 | 15.904 | 42.235 | 33.948 | 1.00 | 59.97 |
| 2684 | CA | THR | 594 | 16.541 | 42.008 | 32.655 | 1.00 | 61.96 |
| 2685 | CB | THR | 594 | 16.828 | 43.335 | 31.932 | 1.00 | 61.57 |
| 2686 | OG1 | THR | 594 | 15.726 | 44.234 | 32.127 | 1.00 | 61.11 |
| 2687 | CG2 | THR | 594 | 17.026 | 43.086 | 30.435 | 1.00 | 62.41 |
| 2688 | C | THR | 594 | 17.865 | 41.305 | 32.902 | 1.00 | 63.83 |
| 2689 | O | THR | 594 | 18.184 | 40.287 | 32.274 | 1.00 | 62.47 |
| 2690 | N | LEU | 595 | 18.634 | 41.865 | 33.829 | 1.00 | 61.96 |
| 2691 | CA | LEU | 595 | 19.924 | 41.308 | 34.184 | 1.00 | 62.86 |
| 2692 | CB | LEU | 595 | 20.585 | 42.172 | 35.265 | 1.00 | 61.42 |
| 2693 | CG | LEU | 595 | 20.937 | 43.615 | 34.885 | 1.00 | 63.11 |
| 2694 | CD1 | LEU | 595 | 21.680 | 44.276 | 36.031 | 1.00 | 63.10 |
| 2695 | CD2 | LEU | 595 | 21.791 | 43.634 | 33.636 | 1.00 | 59.45 |
| 2696 | C | LEU | 595 | 19.784 | 39.859 | 34.660 | 1.00 | 61.56 |
| 2697 | O | LEU | 595 | 20.438 | 38.960 | 34.136 | 1.00 | 62.15 |
| 2698 | N | LEU | 596 | 18.920 | 39.629 | 35.640 | 1.00 | 63.33 |
| 2699 | CA | LEU | 596 | 18.728 | 38.283 | 36.156 | 1.00 | 61.25 |
| 2700 | CB | LEU | 596 | 17.830 | 38.313 | 37.387 | 1.00 | 59.50 |
| 2701 | CG | LEU | 596 | 18.518 | 38.469 | 38.735 | 1.00 | 63.65 |
| 2702 | CD1 | LEU | 596 | 17.484 | 38.837 | 39.769 | 1.00 | 60.39 |
| 2703 | CD2 | LEU | 596 | 19.232 | 37.190 | 39.109 | 1.00 | 62.18 |
| 2704 | C | LEU | 596 | 18.159 | 37.293 | 35.140 | 1.00 | 57.46 |
| 2705 | O | LEU | 596 | 18.306 | 36.079 | 35.310 | 1.00 | 60.98 |
| 2706 | N | GLN | 597 | 17.507 | 37.800 | 34.095 | 1.00 | 60.24 |
| 2707 | CA | GLN | 597 | 16.915 | 36.953 | 33.055 | 1.00 | 59.39 |
| 2708 | CB | GLN | 597 | 15.727 | 37.660 | 32.413 | 1.00 | 63.86 |
| 2709 | CG | GLN | 597 | 14.431 | 37.528 | 33.171 | 1.00 | 63.29 |
| 2710 | CD | GLN | 597 | 13.365 | 38.466 | 32.648 | 1.00 | 58.84 |
| 2711 | OE1 | GLN | 597 | 13.389 | 38.873 | 31.484 | 1.00 | 61.11 |
| 2712 | NE2 | GLN | 597 | 12.414 | 38.811 | 33.505 | 1.00 | 60.83 |
| 2713 | C | GLN | 597 | 17.927 | 36.620 | 31.973 | 1.00 | 60.76 |
| 2714 | O | GLN | 597 | 17.829 | 35.597 | 31.302 | 1.00 | 63.58 |
| 2715 | N | TYR | 598 | 18.900 | 37.501 | 31.806 | 1.00 | 59.20 |
| 2716 | CA | TYR | 598 | 19.923 | 37.315 | 30.807 | 1.00 | 61.48 |
| 2717 | CB | TYR | 598 | 20.378 | 38.678 | 30.311 | 1.00 | 64.95 |
| 2718 | CG | TYR | 598 | 19.364 | 39.407 | 29.466 | 1.00 | 59.33 |
| 2719 | CD1 | TYR | 598 | 18.119 | 38.844 | 29.177 | 1.00 | 59.16 |
| 2720 | CE1 | TYR | 598 | 17.213 | 39.496 | 28.344 | 1.00 | 62.34 |
| 2721 | CD2 | TYR | 598 | 19.673 | 40.645 | 28.903 | 1.00 | 58.48 |
| 2722 | CE2 | TYR | 598 | 18.771 | 41.303 | 28.067 | 1.00 | 61.12 |
| 2723 | CZ | TYR | 598 | 17.551 | 40.721 | 27.794 | 1.00 | 63.18 |
| 2724 | OH | TYR | 598 | 16.680 | 41.371 | 26.960 | 1.00 | 63.83 |
| 2725 | C | TYR | 598 | 21.130 | 36.532 | 31.320 | 1.00 | 63.31 |
| 2726 | O | TYR | 598 | 21.850 | 35.900 | 30.550 | 1.00 | 62.59 |
| 2727 | N | SER | 599 | 21.356 | 36.554 | 32.623 | 1.00 | 62.16 |
| 2728 | CA | SER | 599 | 22.511 | 35.859 | 33.157 | 1.00 | 62.80 |
| 2729 | CB | SER | 599 | 23.420 | 36.885 | 33.845 | 1.00 | 60.71 |
| 2730 | OG | SER | 599 | 22.660 | 37.845 | 34.560 | 1.00 | 60.75 |
| 2731 | C | SER | 599 | 22.245 | 34.678 | 34.093 | 1.00 | 60.81 |
| 2732 | O | SER | 599 | 23.183 | 34.104 | 34.636 | 1.00 | 57.53 |
| 2733 | N | TRP | 600 | 20.986 | 34.293 | 34.272 | 1.00 | 62.86 |
| 2734 | CA | TRP | 600 | 20.683 | 33.187 | 35.180 | 1.00 | 60.85 |
| 2735 | CB | TRP | 600 | 19.186 | 32.813 | 35.134 | 1.00 | 60.84 |
| 2736 | CG | TRP | 600 | 18.745 | 32.104 | 33.887 | 1.00 | 61.86 |
| 2737 | CD2 | TRP | 600 | 18.561 | 30.697 | 33.726 | 1.00 | 61.60 |
| 2738 | CE2 | TRP | 600 | 18.300 | 30.461 | 32.362 | 1.00 | 64.40 |
| 2739 | CE3 | TRP | 600 | 18.599 | 29.611 | 34.602 | 1.00 | 59.75 |
| 2740 | CD1 | TRP | 600 | 18.574 | 32.653 | 32.650 | 1.00 | 60.08 |
| 2741 | NE1 | TRP | 600 | 18.311 | 31.672 | 31.724 | 1.00 | 59.13 |
| 2742 | CZ2 | TRP | 600 | 18.085 | 29.182 | 31.854 | 1.00 | 61.82 |
| 2743 | CZ3 | TRP | 600 | 18.383 | 28.342 | 34.097 | 1.00 | 63.01 |
| 2744 | CH2 | TRP | 600 | 18.131 | 28.137 | 32.737 | 1.00 | 62.11 |
| 2745 | C | TRP | 600 | 21.523 | 31.963 | 34.848 | 1.00 | 61.75 |
| 2746 | O | TRP | 600 | 21.973 | 31.238 | 35.732 | 1.00 | 60.91 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2747 | N | MET | 601 | 21.761 | 31.749 | 33.564 | 1.00 | 62.84 |
| 2748 | CA | MET | 601 | 22.504 | 30.591 | 33.172 | 1.00 | 60.19 |
| 2749 | CB | MET | 601 | 22.084 | 30.133 | 31.794 | 1.00 | 61.93 |
| 2750 | CG | MET | 601 | 22.616 | 28.786 | 31.496 | 1.00 | 63.07 |
| 2751 | SD | MET | 601 | 21.595 | 27.427 | 31.465 | 1.00 | 62.35 |
| 2752 | CE | MET | 601 | 22.357 | 26.773 | 32.529 | 1.00 | 60.74 |
| 2753 | C | MET | 601 | 24.008 | 30.766 | 33.243 | 1.00 | 61.35 |
| 2754 | O | MET | 601 | 24.732 | 29.790 | 33.391 | 1.00 | 62.01 |
| 2755 | N | SER | 602 | 24.483 | 32.002 | 33.146 | 1.00 | 59.64 |
| 2756 | CA | SER | 602 | 25.914 | 32.253 | 33.227 | 1.00 | 61.85 |
| 2757 | CB | SER | 602 | 26.249 | 33.637 | 32.675 | 1.00 | 63.12 |
| 2758 | OG | SER | 602 | 27.643 | 33.887 | 32.746 | 1.00 | 63.90 |
| 2759 | C | SER | 602 | 26.356 | 32.163 | 34.684 | 1.00 | 63.19 |
| 2760 | O | SER | 602 | 27.478 | 31.765 | 34.976 | 1.00 | 59.89 |
| 2761 | N | LEU | 603 | 25.452 | 32.537 | 35.588 | 1.00 | 59.89 |
| 2762 | CA | LEU | 603 | 25.703 | 32.527 | 37.027 | 1.00 | 63.05 |
| 2763 | CB | LEU | 603 | 24.673 | 33.413 | 37.748 | 1.00 | 60.06 |
| 2764 | CG | LEU | 603 | 24.752 | 34.936 | 37.606 | 1.00 | 58.80 |
| 2765 | CD1 | LEU | 603 | 23.591 | 35.588 | 38.334 | 1.00 | 59.17 |
| 2766 | CD2 | LEU | 603 | 26.051 | 35.422 | 38.175 | 1.00 | 63.89 |
| 2767 | C | LEU | 603 | 25.624 | 31.118 | 37.586 | 1.00 | 60.06 |
| 2768 | O | LEU | 603 | 26.337 | 30.753 | 38.519 | 1.00 | 58.30 |
| 2769 | N | MET | 604 | 24.745 | 30.323 | 37.004 | 1.00 | 62.50 |
| 2770 | CA | MET | 604 | 24.565 | 28.967 | 37.468 | 1.00 | 61.20 |
| 2771 | CB | MET | 604 | 23.151 | 28.541 | 37.166 | 1.00 | 59.34 |
| 2772 | CG | MET | 604 | 22.185 | 28.879 | 38.247 | 1.00 | 61.83 |
| 2773 | SD | MET | 604 | 22.610 | 30.141 | 39.388 | 1.00 | 62.09 |
| 2774 | CE | MET | 604 | 22.173 | 29.285 | 40.731 | 1.00 | 60.68 |
| 2775 | C | MET | 604 | 25.578 | 28.009 | 36.879 | 1.00 | 61.48 |
| 2776 | O | MET | 604 | 25.989 | 27.048 | 37.536 | 1.00 | 60.91 |
| 2777 | N | ALA | 605 | 25.988 | 28.292 | 35.646 | 1.00 | 58.39 |
| 2778 | CA | ALA | 605 | 26.970 | 27.493 | 34.943 | 1.00 | 62.30 |
| 2779 | CB | ALA | 605 | 26.934 | 27.812 | 33.472 | 1.00 | 63.55 |
| 2780 | C | ALA | 605 | 28.341 | 27.820 | 35.502 | 1.00 | 63.47 |
| 2781 | O | ALA | 605 | 29.194 | 26.944 | 35.590 | 1.00 | 60.63 |
| 2782 | N | PHE | 606 | 28.546 | 29.082 | 35.882 | 1.00 | 60.75 |
| 2783 | CA | PHE | 606 | 29.832 | 29.536 | 36.411 | 1.00 | 62.24 |
| 2784 | CB | PHE | 606 | 29.951 | 31.059 | 36.300 | 1.00 | 65.41 |
| 2785 | CG | PHE | 606 | 31.316 | 31.606 | 36.663 | 1.00 | 64.45 |
| 2786 | CD1 | PHE | 606 | 32.424 | 31.375 | 35.848 | 1.00 | 62.88 |
| 2787 | CD2 | PHE | 606 | 31.483 | 32.388 | 37.802 | 1.00 | 61.45 |
| 2788 | CE1 | PHE | 606 | 33.668 | 31.919 | 36.162 | 1.00 | 61.89 |
| 2789 | CE2 | PHE | 606 | 32.725 | 32.931 | 38.120 | 1.00 | 63.04 |
| 2790 | CZ | PHE | 606 | 33.814 | 32.696 | 37.296 | 1.00 | 66.17 |
| 2791 | C | PHE | 606 | 30.044 | 29.121 | 37.851 | 1.00 | 64.34 |
| 2792 | O | PHE | 606 | 31.154 | 28.764 | 38.234 | 1.00 | 61.04 |
| 2793 | N | ALA | 607 | 28.997 | 29.180 | 38.661 | 1.00 | 59.38 |
| 2794 | CA | ALA | 607 | 29.144 | 28.771 | 40.047 | 1.00 | 61.90 |
| 2795 | CB | ALA | 607 | 27.953 | 29.224 | 40.865 | 1.00 | 58.55 |
| 2796 | C | ALA | 607 | 29.269 | 27.246 | 40.073 | 1.00 | 58.23 |
| 2797 | O | ALA | 607 | 29.912 | 26.681 | 40.953 | 1.00 | 60.68 |
| 2798 | N | LEU | 608 | 28.656 | 26.571 | 39.110 | 1.00 | 61.24 |
| 2799 | CA | LEU | 608 | 28.771 | 25.121 | 39.086 | 1.00 | 60.02 |
| 2800 | CB | LEU | 608 | 27.928 | 24.526 | 37.958 | 1.00 | 62.86 |
| 2801 | CG | LEU | 608 | 27.703 | 23.018 | 37.693 | 1.00 | 60.90 |
| 2802 | CD1 | LEU | 608 | 27.926 | 22.923 | 36.222 | 1.00 | 62.46 |
| 2803 | CD2 | LEU | 608 | 28.630 | 22.033 | 38.439 | 1.00 | 60.02 |
| 2804 | C | LEU | 608 | 30.240 | 24.783 | 38.858 | 1.00 | 61.60 |
| 2805 | O | LEU | 608 | 30.758 | 23.870 | 39.479 | 1.00 | 62.78 |
| 2806 | N | GLY | 609 | 30.917 | 25.511 | 37.974 | 1.00 | 63.89 |
| 2807 | CA | GLY | 609 | 32.319 | 25.229 | 37.746 | 1.00 | 60.11 |
| 2808 | C | GLY | 609 | 33.143 | 25.391 | 39.018 | 1.00 | 61.05 |
| 2809 | O | GLY | 609 | 34.080 | 24.631 | 39.266 | 1.00 | 62.95 |
| 2810 | N | TRP | 610 | 32.783 | 26.374 | 39.838 | 1.00 | 62.51 |
| 2811 | CA | TRP | 610 | 33.499 | 26.652 | 41.073 | 1.00 | 63.33 |
| 2812 | CB | TRP | 610 | 32.917 | 27.885 | 41.741 | 1.00 | 59.08 |
| 2813 | CG | TRP | 610 | 33.617 | 28.226 | 43.008 | 1.00 | 60.29 |
| 2814 | CD2 | TRP | 610 | 34.910 | 28.821 | 43.127 | 1.00 | 61.56 |
| 2815 | CE2 | TRP | 610 | 35.194 | 28.930 | 44.501 | 1.00 | 59.81 |
| 2816 | CE3 | TRP | 610 | 35.860 | 29.273 | 42.200 | 1.00 | 57.77 |
| 2817 | CD1 | TRP | 610 | 33.178 | 28.002 | 44.279 | 1.00 | 61.04 |
| 2818 | NE1 | TRP | 610 | 34.121 | 28.423 | 45.183 | 1.00 | 63.24 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2819 | CZ2 | TRP | 610 | 36.387 | 29.472 | 44.973 | 1.00 | 58.16 |
| 2820 | CZ3 | TRP | 610 | 37.048 | 29.811 | 42.670 | 1.00 | 62.09 |
| 2821 | CH2 | TRP | 610 | 37.301 | 29.905 | 44.043 | 1.00 | 63.07 |
| 2822 | C | TRP | 610 | 33.516 | 25.510 | 42.073 | 1.00 | 62.56 |
| 2823 | O | TRP | 610 | 34.554 | 25.205 | 42.662 | 1.00 | 62.85 |
| 2824 | N | ARG | 611 | 32.360 | 24.896 | 42.288 | 1.00 | 64.01 |
| 2825 | CA | ARG | 611 | 32.268 | 23.784 | 43.222 | 1.00 | 61.00 |
| 2826 | CB | ARG | 611 | 30.803 | 23.396 | 43.440 | 1.00 | 60.82 |
| 2827 | CG | ARG | 611 | 29.973 | 24.437 | 44.180 | 1.00 | 60.63 |
| 2828 | CD | ARG | 611 | 28.568 | 23.899 | 44.480 | 1.00 | 63.65 |
| 2829 | NE | ARG | 611 | 27.830 | 23.608 | 43.250 | 1.00 | 60.05 |
| 2830 | CZ | ARG | 611 | 27.228 | 24.528 | 42.498 | 1.00 | 61.48 |
| 2831 | NH1 | ARG | 611 | 27.255 | 25.811 | 42.853 | 1.00 | 62.30 |
| 2832 | NH2 | ARG | 611 | 26.638 | 24.175 | 41.365 | 1.00 | 62.30 |
| 2833 | C | ARG | 611 | 33.049 | 22.606 | 42.648 | 1.00 | 64.56 |
| 2834 | O | ARG | 611 | 33.712 | 21.854 | 43.373 | 1.00 | 59.80 |
| 2835 | N | SER | 612 | 32.971 | 22.467 | 41.329 | 1.00 | 60.03 |
| 2836 | CA | SER | 612 | 33.664 | 21.403 | 40.624 | 1.00 | 62.69 |
| 2837 | CB | SER | 612 | 33.312 | 21.451 | 39.141 | 1.00 | 60.54 |
| 2838 | OG | SER | 612 | 31.976 | 21.038 | 38.947 | 1.00 | 61.90 |
| 2839 | C | SER | 612 | 35.163 | 21.542 | 40.815 | 1.00 | 60.18 |
| 2840 | O | SER | 612 | 35.842 | 20.597 | 41.209 | 1.00 | 62.35 |
| 2841 | N | TYR | 613 | 35.663 | 22.738 | 40.538 | 1.00 | 59.25 |
| 2842 | CA | TYR | 613 | 37.074 | 23.058 | 40.677 | 1.00 | 60.56 |
| 2843 | CB | TYR | 613 | 37.265 | 24.534 | 40.311 | 1.00 | 63.42 |
| 2844 | CG | TYR | 613 | 38.515 | 25.215 | 40.829 | 1.00 | 66.04 |
| 2845 | CD1 | TYR | 613 | 39.771 | 24.631 | 40.692 | 1.00 | 61.54 |
| 2846 | CE1 | TYR | 613 | 40.925 | 25.308 | 41.091 | 1.00 | 59.89 |
| 2847 | CD2 | TYR | 613 | 38.443 | 26.491 | 41.384 | 1.00 | 61.40 |
| 2848 | CE2 | TYR | 613 | 39.586 | 27.172 | 41.782 | 1.00 | 60.60 |
| 2849 | CZ | TYR | 613 | 40.823 | 26.577 | 41.633 | 1.00 | 61.69 |
| 2850 | OH | TYR | 613 | 41.950 | 27.258 | 42.022 | 1.00 | 57.50 |
| 2851 | C | TYR | 613 | 37.624 | 22.765 | 42.074 | 1.00 | 61.96 |
| 2852 | O | TYR | 613 | 38.665 | 22.130 | 42.219 | 1.00 | 62.16 |
| 2853 | N | ARG | 614 | 36.913 | 23.204 | 43.102 | 1.00 | 65.05 |
| 2854 | CA | ARG | 614 | 37.380 | 23.004 | 44.463 | 1.00 | 59.34 |
| 2855 | CB | ARG | 614 | 36.724 | 24.017 | 45.395 | 1.00 | 60.68 |
| 2856 | CG | ARG | 614 | 36.950 | 25.445 | 45.007 | 1.00 | 63.19 |
| 2857 | CD | ARG | 614 | 36.724 | 26.354 | 46.190 | 1.00 | 59.94 |
| 2858 | NE | ARG | 614 | 37.945 | 26.927 | 46.773 | 1.00 | 59.42 |
| 2859 | CZ | ARG | 614 | 39.115 | 27.068 | 46.145 | 1.00 | 60.26 |
| 2860 | NH1 | ARG | 614 | 40.141 | 27.628 | 46.776 | 1.00 | 60.62 |
| 2861 | NH2 | ARG | 614 | 39.288 | 26.619 | 44.906 | 1.00 | 59.69 |
| 2862 | C | ARG | 614 | 37.144 | 21.620 | 45.019 | 1.00 | 60.75 |
| 2863 | O | ARG | 614 | 37.899 | 21.144 | 45.869 | 1.00 | 61.95 |
| 2864 | N | GLN | 615 | 36.093 | 20.967 | 44.549 | 1.00 | 60.97 |
| 2865 | CA | GLN | 615 | 35.780 | 19.654 | 45.074 | 1.00 | 61.36 |
| 2866 | CB | GLN | 615 | 34.282 | 19.387 | 44.957 | 1.00 | 59.74 |
| 2867 | CG | GLN | 615 | 33.666 | 18.942 | 46.273 | 1.00 | 65.30 |
| 2868 | CD | GLN | 615 | 32.416 | 18.106 | 46.097 | 1.00 | 64.80 |
| 2869 | OE1 | GLN | 615 | 32.019 | 17.380 | 47.007 | 1.00 | 59.65 |
| 2870 | NE2 | GLN | 615 | 31.787 | 18.204 | 44.928 | 1.00 | 63.88 |
| 2871 | C | GLN | 615 | 36.547 | 18.523 | 44.419 | 1.00 | 61.87 |
| 2872 | O | GLN | 615 | 36.984 | 17.588 | 45.093 | 1.00 | 61.19 |
| 2873 | N | SER | 616 | 36.726 | 18.615 | 43.109 | 1.00 | 62.69 |
| 2874 | CA | SER | 616 | 37.408 | 17.559 | 42.387 | 1.00 | 60.64 |
| 2875 | CB | SER | 616 | 36.380 | 16.632 | 41.757 | 1.00 | 64.46 |
| 2876 | OG | SER | 616 | 35.731 | 17.299 | 40.688 | 1.00 | 63.47 |
| 2877 | C | SER | 616 | 38.347 | 18.047 | 41.298 | 1.00 | 59.36 |
| 2878 | O | SER | 616 | 38.444 | 17.424 | 40.246 | 1.00 | 61.79 |
| 2879 | N | SER | 617 | 39.021 | 19.163 | 41.534 | 1.00 | 62.74 |
| 2880 | CA | SER | 617 | 39.972 | 19.681 | 40.560 | 1.00 | 60.01 |
| 2881 | CB | SER | 617 | 41.253 | 18.847 | 40.638 | 1.00 | 56.86 |
| 2882 | OG | SER | 617 | 41.690 | 18.714 | 41.980 | 1.00 | 64.58 |
| 2883 | C | SER | 617 | 39.433 | 19.675 | 39.119 | 1.00 | 62.31 |
| 2884 | O | SER | 617 | 40.099 | 19.196 | 38.196 | 1.00 | 60.08 |
| 2885 | N | ALA | 618 | 38.230 | 20.213 | 38.931 | 1.00 | 62.60 |
| 2886 | CA | ALA | 618 | 37.600 | 20.261 | 37.612 | 1.00 | 62.84 |
| 2887 | CB | ALA | 618 | 38.399 | 21.165 | 36.676 | 1.00 | 61.64 |
| 2888 | C | ALA | 618 | 37.475 | 18.866 | 37.005 | 1.00 | 60.94 |
| 2889 | O | ALA | 618 | 37.175 | 18.725 | 35.820 | 1.00 | 63.12 |
| 2890 | N | ASN | 619 | 37.692 | 17.836 | 37.820 | 1.00 | 60.02 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2891 | CA | ASN | 619 | 37.610 | 16.465 | 37.330 | 1.00 | 60.02 |
| 2892 | CB | ASN | 619 | 38.467 | 15.523 | 38.178 | 1.00 | 61.65 |
| 2893 | CG | ASN | 619 | 39.881 | 15.426 | 37.663 | 1.00 | 65.19 |
| 2894 | OD1 | ASN | 619 | 40.813 | 15.986 | 38.241 | 1.00 | 58.62 |
| 2895 | ND2 | ASN | 619 | 40.047 | 14.729 | 36.547 | 1.00 | 59.93 |
| 2896 | C | ASN | 619 | 36.205 | 15.922 | 37.241 | 1.00 | 63.97 |
| 2897 | O | ASN | 619 | 35.933 | 15.005 | 36.469 | 1.00 | 61.24 |
| 2898 | N | LEU | 620 | 35.305 | 16.487 | 38.028 | 1.00 | 61.46 |
| 2899 | CA | LEU | 620 | 33.925 | 16.044 | 37.999 | 1.00 | 61.85 |
| 2900 | CB | LEU | 620 | 33.599 | 15.266 | 39.271 | 1.00 | 63.36 |
| 2901 | CG | LEU | 620 | 34.516 | 14.087 | 39.589 | 1.00 | 60.08 |
| 2902 | CD1 | LEU | 620 | 33.992 | 13.354 | 40.805 | 1.00 | 65.17 |
| 2903 | CD2 | LEU | 620 | 34.578 | 13.145 | 38.408 | 1.00 | 59.21 |
| 2904 | C | LEU | 620 | 33.031 | 17.266 | 37.890 | 1.00 | 63.79 |
| 2905 | O | LEU | 620 | 33.520 | 18.400 | 37.844 | 1.00 | 62.56 |
| 2906 | N | LEU | 621 | 31.728 | 17.022 | 37.808 | 1.00 | 60.88 |
| 2907 | CA | LEU | 621 | 30.757 | 18.096 | 37.739 | 1.00 | 60.93 |
| 2908 | CB | LEU | 621 | 29.822 | 17.930 | 36.545 | 1.00 | 59.84 |
| 2909 | CG | LEU | 621 | 30.365 | 18.564 | 35.272 | 1.00 | 61.52 |
| 2910 | CD1 | LEU | 621 | 29.302 | 18.516 | 34.204 | 1.00 | 61.79 |
| 2911 | CD2 | LEU | 621 | 30.776 | 19.998 | 35.547 | 1.00 | 62.82 |
| 2912 | C | LEU | 621 | 30.001 | 17.973 | 39.033 | 1.00 | 59.84 |
| 2913 | O | LEU | 621 | 29.267 | 17.009 | 39.249 | 1.00 | 59.39 |
| 2914 | N | CYS | 622 | 30.191 | 18.952 | 39.903 | 1.00 | 60.82 |
| 2915 | CA | CYS | 622 | 29.562 | 18.902 | 41.201 | 1.00 | 61.70 |
| 2916 | CB | CYS | 622 | 30.612 | 19.216 | 42.276 | 1.00 | 61.70 |
| 2917 | SG | CYS | 622 | 32.249 | 18.417 | 42.005 | 1.00 | 55.72 |
| 2918 | C | CYS | 622 | 28.360 | 19.822 | 41.333 | 1.00 | 60.92 |
| 2919 | O | CYS | 622 | 28.394 | 20.777 | 42.107 | 1.00 | 60.85 |
| 2920 | N | PHE | 623 | 27.299 | 19.518 | 40.584 | 1.00 | 62.83 |
| 2921 | CA | PHE | 623 | 26.057 | 20.298 | 40.618 | 1.00 | 61.52 |
| 2922 | CB | PHE | 623 | 24.944 | 19.578 | 39.827 | 1.00 | 63.16 |
| 2923 | CG | PHE | 623 | 25.174 | 19.562 | 38.332 | 1.00 | 64.30 |
| 2924 | CD1 | PHE | 623 | 25.946 | 18.565 | 37.734 | 1.00 | 62.97 |
| 2925 | CD2 | PHE | 623 | 24.667 | 20.580 | 37.527 | 1.00 | 59.44 |
| 2926 | CE1 | PHE | 623 | 26.214 | 18.585 | 36.354 | 1.00 | 60.51 |
| 2927 | CE2 | PHE | 623 | 24.931 | 20.607 | 36.152 | 1.00 | 61.00 |
| 2928 | CZ | PHE | 623 | 25.705 | 19.609 | 35.566 | 1.00 | 58.20 |
| 2929 | C | PHE | 623 | 25.631 | 20.512 | 42.074 | 1.00 | 62.99 |
| 2930 | O | PHE | 623 | 25.433 | 21.650 | 42.520 | 1.00 | 59.63 |
| 2931 | N | ALA | 624 | 25.489 | 19.404 | 42.798 | 1.00 | 60.19 |
| 2932 | CA | ALA | 624 | 25.146 | 19.426 | 44.220 | 1.00 | 60.71 |
| 2933 | CB | ALA | 624 | 23.953 | 18.540 | 44.505 | 1.00 | 65.97 |
| 2934 | C | ALA | 624 | 26.384 | 18.877 | 44.921 | 1.00 | 60.87 |
| 2935 | O | ALA | 624 | 27.278 | 18.328 | 44.276 | 1.00 | 61.88 |
| 2936 | N | PRO | 625 | 26.467 | 19.023 | 46.248 | 1.00 | 63.71 |
| 2937 | CD | PRO | 625 | 25.561 | 19.666 | 47.207 | 1.00 | 59.14 |
| 2938 | CA | PRO | 625 | 27.658 | 18.496 | 46.924 | 1.00 | 61.58 |
| 2939 | CB | PRO | 625 | 27.528 | 19.055 | 48.346 | 1.00 | 64.33 |
| 2940 | CG | PRO | 625 | 26.534 | 20.184 | 48.212 | 1.00 | 61.92 |
| 2941 | C | PRO | 625 | 27.593 | 16.960 | 46.904 | 1.00 | 61.41 |
| 2942 | O | PRO | 625 | 28.630 | 16.280 | 46.869 | 1.00 | 60.49 |
| 2943 | N | ASP | 626 | 26.353 | 16.450 | 46.913 | 1.00 | 61.38 |
| 2944 | CA | ASP | 626 | 26.036 | 15.016 | 46.914 | 1.00 | 61.12 |
| 2945 | CB | ASP | 626 | 25.050 | 14.730 | 48.038 | 1.00 | 59.24 |
| 2946 | CG | ASP | 626 | 23.643 | 15.219 | 47.706 | 1.00 | 60.93 |
| 2947 | OD1 | ASP | 626 | 23.518 | 16.271 | 47.036 | 1.00 | 62.15 |
| 2948 | OD2 | ASP | 626 | 22.658 | 14.564 | 48.112 | 1.00 | 64.40 |
| 2949 | C | ASP | 626 | 25.405 | 14.562 | 45.587 | 1.00 | 62.42 |
| 2950 | O | ASP | 626 | 24.526 | 13.703 | 45.568 | 1.00 | 60.54 |
| 2951 | N | LEU | 627 | 25.834 | 15.152 | 44.483 | 1.00 | 60.30 |
| 2952 | CA | LEU | 627 | 25.293 | 14.792 | 43.183 | 1.00 | 61.38 |
| 2953 | CB | LEU | 627 | 24.007 | 15.569 | 42.915 | 1.00 | 59.07 |
| 2954 | CG | LEU | 627 | 23.311 | 15.347 | 41.573 | 1.00 | 62.30 |
| 2955 | CD1 | LEU | 627 | 22.632 | 13.994 | 41.525 | 1.00 | 59.92 |
| 2956 | CD2 | LEU | 627 | 22.300 | 16.440 | 41.381 | 1.00 | 64.94 |
| 2957 | C | LEU | 627 | 26.349 | 15.143 | 42.152 | 1.00 | 59.24 |
| 2958 | O | LEU | 627 | 26.321 | 16.224 | 41.550 | 1.00 | 60.06 |
| 2959 | N | ILE | 628 | 27.284 | 14.219 | 41.958 | 1.00 | 59.89 |
| 2960 | CA | ILE | 628 | 28.380 | 14.422 | 41.030 | 1.00 | 60.40 |
| 2961 | CB | ILE | 628 | 29.729 | 14.056 | 41.692 | 1.00 | 62.59 |
| 2962 | CG2 | ILE | 628 | 30.850 | 14.267 | 40.716 | 1.00 | 59.44 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 2963 | CG1 | ILE | 628 | 29.990 | 14.940 | 42.909 | 1.00 | 61.86 |
| 2964 | CD1 | ILE | 628 | 29.045 | 14.711 | 44.049 | 1.00 | 62.51 |
| 2965 | C | ILE | 628 | 28.234 | 13.609 | 39.750 | 1.00 | 64.22 |
| 2966 | O | ILE | 628 | 28.028 | 12.402 | 39.787 | 1.00 | 60.75 |
| 2967 | N | ILE | 629 | 28.323 | 14.272 | 38.608 | 1.00 | 60.54 |
| 2968 | CA | ILE | 629 | 28.239 | 13.540 | 37.370 | 1.00 | 62.37 |
| 2969 | CB | ILE | 629 | 28.044 | 14.470 | 36.165 | 1.00 | 65.41 |
| 2970 | CG2 | ILE | 629 | 28.371 | 13.733 | 34.877 | 1.00 | 61.37 |
| 2971 | CG1 | ILE | 629 | 26.619 | 15.024 | 36.170 | 1.00 | 63.05 |
| 2972 | CD1 | ILE | 629 | 25.623 | 14.193 | 36.983 | 1.00 | 60.63 |
| 2973 | C | ILE | 629 | 29.575 | 12.839 | 37.270 | 1.00 | 60.22 |
| 2974 | O | ILE | 629 | 30.580 | 13.454 | 36.929 | 1.00 | 58.35 |
| 2975 | N | ASN | 630 | 29.580 | 11.556 | 37.611 | 1.00 | 60.04 |
| 2976 | CA | ASN | 630 | 30.776 | 10.726 | 37.570 | 1.00 | 60.83 |
| 2977 | CB | ASN | 630 | 30.674 | 9.637 | 38.632 | 1.00 | 62.77 |
| 2978 | CG | ASN | 630 | 29.368 | 8.868 | 38.556 | 1.00 | 60.79 |
| 2979 | OD1 | ASN | 630 | 29.051 | 8.248 | 37.541 | 1.00 | 61.32 |
| 2980 | ND2 | ASN | 630 | 28.603 | 8.908 | 39.632 | 1.00 | 62.90 |
| 2981 | C | ASN | 630 | 30.949 | 10.085 | 36.197 | 1.00 | 60.61 |
| 2982 | O | ASN | 630 | 30.016 | 10.041 | 35.403 | 1.00 | 62.50 |
| 2983 | N | GLU | 631 | 32.151 | 9.592 | 35.926 | 1.00 | 63.77 |
| 2984 | CA | GLU | 631 | 32.472 | 8.954 | 34.653 | 1.00 | 60.65 |
| 2985 | CB | GLU | 631 | 33.804 | 8.219 | 34.786 | 1.00 | 62.06 |
| 2986 | CG | GLU | 631 | 34.021 | 7.046 | 33.841 | 1.00 | 63.14 |
| 2987 | CD | GLU | 631 | 35.255 | 6.229 | 34.232 | 1.00 | 59.80 |
| 2988 | OE1 | GLU | 631 | 36.349 | 6.836 | 34.405 | 1.00 | 61.43 |
| 2989 | OE2 | GLU | 631 | 35.122 | 4.988 | 34.369 | 1.00 | 58.68 |
| 2990 | C | GLU | 631 | 31.381 | 7.986 | 34.254 | 1.00 | 61.07 |
| 2991 | O | GLU | 631 | 30.879 | 8.014 | 33.132 | 1.00 | 61.02 |
| 2992 | N | GLN | 632 | 31.011 | 7.126 | 35.186 | 1.00 | 63.77 |
| 2993 | CA | GLN | 632 | 29.978 | 6.151 | 34.916 | 1.00 | 61.66 |
| 2994 | CB | GLN | 632 | 29.732 | 5.285 | 36.159 | 1.00 | 61.41 |
| 2995 | CG | GLN | 632 | 30.936 | 4.415 | 36.579 | 1.00 | 65.26 |
| 2996 | CD | GLN | 632 | 31.704 | 3.828 | 35.393 | 1.00 | 64.37 |
| 2997 | OE1 | GLN | 632 | 31.109 | 3.357 | 34.420 | 1.00 | 60.73 |
| 2998 | NE2 | GLN | 632 | 33.034 | 3.847 | 35.480 | 1.00 | 59.46 |
| 2999 | C | GLN | 632 | 28.695 | 6.851 | 34.466 | 1.00 | 61.12 |
| 3000 | O | GLN | 632 | 28.055 | 6.417 | 33.512 | 1.00 | 62.13 |
| 3001 | N | ARG | 633 | 28.334 | 7.946 | 35.134 | 1.00 | 59.27 |
| 3002 | CA | ARG | 633 | 27.125 | 8.682 | 34.767 | 1.00 | 61.29 |
| 3003 | CB | ARG | 633 | 26.821 | 9.786 | 35.775 | 1.00 | 59.65 |
| 3004 | CG | ARG | 633 | 26.235 | 9.274 | 37.069 | 1.00 | 62.42 |
| 3005 | CD | ARG | 633 | 25.223 | 10.258 | 37.602 | 1.00 | 60.12 |
| 3006 | NE | ARG | 633 | 24.486 | 9.732 | 38.743 | 1.00 | 61.79 |
| 3007 | CZ | ARG | 633 | 24.739 | 10.038 | 40.011 | 1.00 | 64.89 |
| 3008 | NH1 | ARG | 633 | 25.717 | 10.878 | 40.308 | 1.00 | 60.64 |
| 3009 | NH2 | ARG | 633 | 24.014 | 9.501 | 40.984 | 1.00 | 62.92 |
| 3010 | C | ARG | 633 | 27.151 | 9.274 | 33.360 | 1.00 | 61.86 |
| 3011 | O | ARG | 633 | 26.086 | 9.401 | 32.750 | 1.00 | 59.63 |
| 3012 | N | MET | 634 | 28.337 | 9.643 | 32.855 | 1.00 | 64.70 |
| 3013 | CA | MET | 634 | 28.465 | 10.180 | 31.497 | 1.00 | 60.91 |
| 3014 | CB | MET | 634 | 29.921 | 10.556 | 31.189 | 1.00 | 59.90 |
| 3015 | CG | MET | 634 | 30.438 | 11.791 | 31.950 | 1.00 | 60.63 |
| 3016 | SD | MET | 634 | 30.042 | 13.425 | 31.192 | 1.00 | 60.35 |
| 3017 | CE | MET | 634 | 30.985 | 14.531 | 32.251 | 1.00 | 64.03 |
| 3018 | C | MET | 634 | 27.956 | 9.086 | 30.543 | 1.00 | 60.81 |
| 3019 | O | MET | 634 | 28.727 | 8.350 | 29.899 | 1.00 | 62.71 |
| 3020 | N | THR | 635 | 26.622 | 8.989 | 30.531 | 1.00 | 62.02 |
| 3021 | CA | THR | 635 | 25.820 | 8.059 | 29.738 | 1.00 | 62.69 |
| 3022 | CB | THR | 635 | 24.313 | 8.140 | 30.124 | 1.00 | 62.75 |
| 3023 | OG1 | THR | 635 | 24.150 | 7.893 | 31.528 | 1.00 | 60.63 |
| 3024 | CG2 | THR | 635 | 23.486 | 7.141 | 29.303 | 1.00 | 61.43 |
| 3025 | C | THR | 635 | 25.912 | 8.531 | 28.307 | 1.00 | 61.30 |
| 3026 | O | THR | 635 | 26.510 | 7.876 | 27.454 | 1.00 | 59.84 |
| 3027 | N | LEU | 636 | 25.315 | 9.694 | 28.077 | 1.00 | 61.92 |
| 3028 | CA | LEU | 636 | 25.270 | 10.317 | 26.765 | 1.00 | 60.40 |
| 3029 | CB | LEU | 636 | 23.901 | 10.968 | 26.586 | 1.00 | 63.75 |
| 3030 | CG | LEU | 636 | 22.679 | 10.156 | 26.167 | 1.00 | 61.04 |
| 3031 | CD1 | LEU | 636 | 22.623 | 8.760 | 26.811 | 1.00 | 59.92 |
| 3032 | CD2 | LEU | 636 | 21.476 | 11.011 | 26.536 | 1.00 | 55.92 |
| 3033 | C | LEU | 636 | 26.347 | 11.377 | 26.441 | 1.00 | 63.57 |
| 3034 | O | LEU | 636 | 26.834 | 12.087 | 27.327 | 1.00 | 58.28 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3035 | N | PRO | 637 | 26.754 | 11.471 | 25.155 | 1.00 | 61.79 |
| 3036 | CD | PRO | 637 | 26.479 | 10.631 | 23.987 | 1.00 | 63.46 |
| 3037 | CA | PRO | 637 | 27.744 | 12.476 | 24.794 | 1.00 | 60.89 |
| 3038 | CB | PRO | 637 | 28.363 | 11.932 | 23.490 | 1.00 | 63.07 |
| 3039 | CG | PRO | 637 | 27.855 | 10.482 | 23.398 | 1.00 | 62.95 |
| 3040 | C | PRO | 637 | 26.780 | 13.647 | 24.551 | 1.00 | 61.80 |
| 3041 | O | PRO | 637 | 27.038 | 14.531 | 23.736 | 1.00 | 60.33 |
| 3042 | N | CYS | 638 | 25.605 | 13.523 | 25.193 | 1.00 | 63.35 |
| 3043 | CA | CYS | 638 | 24.557 | 14.549 | 25.225 | 1.00 | 58.89 |
| 3044 | CB | CYS | 638 | 23.122 | 14.023 | 25.351 | 1.00 | 62.48 |
| 3045 | SG | CYS | 638 | 22.633 | 12.668 | 24.333 | 1.00 | 61.93 |
| 3046 | C | CYS | 638 | 24.925 | 14.896 | 26.642 | 1.00 | 59.34 |
| 3047 | O | CYS | 638 | 25.366 | 16.010 | 26.968 | 1.00 | 61.64 |
| 3048 | N | MET | 639 | 24.773 | 13.878 | 27.486 | 1.00 | 59.95 |
| 3049 | CA | MET | 639 | 25.094 | 14.058 | 28.870 | 1.00 | 62.51 |
| 3050 | CB | MET | 639 | 24.794 | 12.794 | 29.647 | 1.00 | 56.25 |
| 3051 | CG | MET | 639 | 24.597 | 13.021 | 31.126 | 1.00 | 59.11 |
| 3052 | SD | MET | 639 | 23.446 | 14.225 | 31.808 | 1.00 | 60.73 |
| 3053 | CE | MET | 639 | 24.286 | 14.281 | 33.307 | 1.00 | 59.61 |
| 3054 | C | MET | 639 | 26.567 | 14.451 | 28.934 | 1.00 | 60.92 |
| 3055 | O | MET | 639 | 27.074 | 14.783 | 30.000 | 1.00 | 59.57 |
| 3056 | N | TYR | 640 | 27.244 | 14.409 | 27.782 | 1.00 | 60.93 |
| 3057 | CA | TYR | 640 | 28.622 | 14.866 | 27.693 | 1.00 | 62.32 |
| 3058 | CB | TYR | 640 | 29.585 | 13.827 | 27.110 | 1.00 | 61.41 |
| 3059 | CG | TYR | 640 | 30.961 | 14.446 | 26.910 | 1.00 | 62.45 |
| 3060 | CD1 | TYR | 640 | 31.797 | 14.687 | 28.006 | 1.00 | 59.75 |
| 3061 | CE1 | TYR | 640 | 32.996 | 15.372 | 27.862 | 1.00 | 59.57 |
| 3062 | CD2 | TYR | 640 | 31.376 | 14.906 | 25.651 | 1.00 | 59.20 |
| 3063 | CE2 | TYR | 640 | 32.578 | 15.594 | 25.495 | 1.00 | 64.39 |
| 3064 | CZ | TYR | 640 | 33.381 | 15.827 | 26.608 | 1.00 | 62.16 |
| 3065 | OH | TYR | 640 | 34.554 | 16.542 | 26.485 | 1.00 | 62.68 |
| 3066 | C | TYR | 640 | 28.650 | 16.082 | 26.764 | 1.00 | 60.42 |
| 3067 | O | TYR | 640 | 29.264 | 17.104 | 27.075 | 1.00 | 62.43 |
| 3068 | N | ASP | 641 | 27.985 | 15.960 | 25.619 | 1.00 | 63.11 |
| 3069 | CA | ASP | 641 | 27.946 | 17.029 | 24.617 | 1.00 | 64.46 |
| 3070 | CB | ASP | 641 | 26.821 | 16.780 | 23.617 | 1.00 | 64.30 |
| 3071 | CG | ASP | 641 | 27.232 | 17.039 | 22.196 | 1.00 | 61.31 |
| 3072 | OD1 | ASP | 641 | 26.317 | 17.192 | 21.353 | 1.00 | 59.56 |
| 3073 | OD2 | ASP | 641 | 28.453 | 17.079 | 21.917 | 1.00 | 63.20 |
| 3074 | C | ASP | 641 | 27.729 | 18.401 | 25.222 | 1.00 | 61.02 |
| 3075 | O | ASP | 641 | 28.073 | 19.417 | 24.617 | 1.00 | 60.07 |
| 3076 | N | GLN | 642 | 27.124 | 18.417 | 26.406 | 1.00 | 63.30 |
| 3077 | CA | GLN | 642 | 26.801 | 19.653 | 27.115 | 1.00 | 60.83 |
| 3078 | CB | GLN | 642 | 25.298 | 19.837 | 27.180 | 1.00 | 63.77 |
| 3079 | CG | GLN | 642 | 24.570 | 18.590 | 26.781 | 1.00 | 59.93 |
| 3080 | CD | GLN | 642 | 24.905 | 18.192 | 25.345 | 1.00 | 61.47 |
| 3081 | OE1 | GLN | 642 | 24.656 | 17.063 | 24.922 | 1.00 | 59.50 |
| 3082 | NE2 | GLN | 642 | 25.462 | 19.135 | 24.580 | 1.00 | 60.78 |
| 3083 | C | GLN | 642 | 27.353 | 19.664 | 28.518 | 1.00 | 60.90 |
| 3084 | O | GLN | 642 | 27.430 | 20.714 | 29.136 | 1.00 | 60.17 |
| 3085 | N | CYS | 643 | 27.678 | 18.497 | 29.052 | 1.00 | 61.78 |
| 3086 | CA | CYS | 643 | 28.291 | 18.491 | 30.362 | 1.00 | 62.44 |
| 3087 | CB | CYS | 643 | 28.348 | 17.080 | 30.963 | 1.00 | 66.84 |
| 3088 | SG | CYS | 643 | 27.004 | 16.704 | 32.130 | 1.00 | 64.90 |
| 3089 | C | CYS | 643 | 29.691 | 18.976 | 30.015 | 1.00 | 61.39 |
| 3090 | O | CYS | 643 | 30.377 | 19.587 | 30.836 | 1.00 | 61.37 |
| 3091 | N | LYS | 644 | 30.093 | 18.726 | 28.768 | 1.00 | 63.75 |
| 3092 | CA | LYS | 644 | 31.415 | 19.128 | 28.308 | 1.00 | 59.22 |
| 3093 | CB | LYS | 644 | 31.708 | 18.603 | 26.889 | 1.00 | 57.84 |
| 3094 | CG | LYS | 644 | 31.163 | 19.462 | 25.740 | 1.00 | 63.56 |
| 3095 | CD | LYS | 644 | 31.637 | 18.994 | 24.350 | 1.00 | 63.09 |
| 3096 | CE | LYS | 644 | 33.034 | 19.520 | 23.983 | 1.00 | 63.23 |
| 3097 | NZ | LYS | 644 | 34.141 | 19.025 | 24.872 | 1.00 | 61.68 |
| 3098 | C | LYS | 644 | 31.560 | 20.641 | 28.319 | 1.00 | 61.63 |
| 3099 | O | LYS | 644 | 32.672 | 21.157 | 28.379 | 1.00 | 62.21 |
| 3100 | N | HIS | 645 | 30.444 | 21.359 | 28.267 | 1.00 | 59.46 |
| 3101 | CA | HIS | 645 | 30.518 | 22.809 | 28.261 | 1.00 | 61.40 |
| 3102 | CB | HIS | 645 | 29.338 | 23.380 | 27.490 | 1.00 | 62.01 |
| 3103 | CG | HIS | 645 | 29.548 | 23.365 | 26.009 | 1.00 | 61.11 |
| 3104 | CD2 | HIS | 645 | 30.591 | 23.797 | 25.261 | 1.00 | 62.23 |
| 3105 | ND1 | HIS | 645 | 28.628 | 22.845 | 25.123 | 1.00 | 62.89 |
| 3106 | CE1 | HIS | 645 | 29.097 | 22.957 | 23.892 | 1.00 | 60.35 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3107 | NE2 | HIS | 645 | 30.285 | 23.532 | 23.948 | 1.00 | 58.72 |
| 3108 | C | HIS | 645 | 30.626 | 23.413 | 29.652 | 1.00 | 60.22 |
| 3109 | O | HIS | 645 | 31.097 | 24.535 | 29.804 | 1.00 | 62.73 |
| 3110 | N | MET | 646 | 30.205 | 22.672 | 30.668 | 1.00 | 61.99 |
| 3111 | CA | MET | 646 | 30.320 | 23.173 | 32.027 | 1.00 | 60.02 |
| 3112 | CB | MET | 646 | 29.235 | 22.574 | 32.963 | 1.00 | 60.39 |
| 3113 | CG | MET | 646 | 27.846 | 22.502 | 32.348 | 1.00 | 59.13 |
| 3114 | SD | MET | 646 | 26.508 | 21.807 | 33.298 | 1.00 | 59.17 |
| 3115 | CE | MET | 646 | 25.617 | 21.251 | 31.946 | 1.00 | 56.97 |
| 3116 | C | MET | 646 | 31.712 | 22.761 | 32.539 | 1.00 | 61.22 |
| 3117 | O | MET | 646 | 32.329 | 23.495 | 33.304 | 1.00 | 59.33 |
| 3118 | N | LEU | 647 | 32.207 | 21.597 | 32.110 | 1.00 | 61.22 |
| 3119 | CA | LEU | 647 | 33.539 | 21.146 | 32.526 | 1.00 | 59.88 |
| 3120 | CB | LEU | 647 | 33.858 | 19.754 | 31.962 | 1.00 | 64.23 |
| 3121 | CG | LEU | 647 | 33.205 | 18.494 | 32.529 | 1.00 | 60.79 |
| 3122 | CD1 | LEU | 647 | 33.267 | 17.423 | 31.475 | 1.00 | 61.72 |
| 3123 | CD2 | LEU | 647 | 33.901 | 18.030 | 33.803 | 1.00 | 62.44 |
| 3124 | C | LEU | 647 | 34.571 | 22.141 | 31.997 | 1.00 | 62.52 |
| 3125 | O | LEU | 647 | 35.664 | 22.292 | 32.558 | 1.00 | 59.55 |
| 3126 | N | TYR | 648 | 34.220 | 22.816 | 30.907 | 1.00 | 61.57 |
| 3127 | CA | TYR | 648 | 35.126 | 23.785 | 30.320 | 1.00 | 63.01 |
| 3128 | CB | TYR | 648 | 34.597 | 24.318 | 28.997 | 1.00 | 64.69 |
| 3129 | CG | TYR | 648 | 35.477 | 25.427 | 28.499 | 1.00 | 60.08 |
| 3130 | CD1 | TYR | 648 | 36.741 | 25.148 | 27.989 | 1.00 | 62.71 |
| 3131 | CE1 | TYR | 648 | 37.617 | 26.170 | 27.642 | 1.00 | 56.16 |
| 3132 | CD2 | TYR | 648 | 35.104 | 26.764 | 28.646 | 1.00 | 65.58 |
| 3133 | CE2 | TYR | 648 | 35.974 | 27.795 | 28.305 | 1.00 | 64.32 |
| 3134 | CZ | TYR | 648 | 37.226 | 27.490 | 27.806 | 1.00 | 62.44 |
| 3135 | OH | TYR | 648 | 38.097 | 28.500 | 27.480 | 1.00 | 58.63 |
| 3136 | C | TYR | 648 | 35.380 | 24.969 | 31.241 | 1.00 | 60.50 |
| 3137 | O | TYR | 648 | 36.510 | 25.423 | 31.369 | 1.00 | 59.77 |
| 3138 | N | VAL | 649 | 34.331 | 25.490 | 31.865 | 1.00 | 61.19 |
| 3139 | CA | VAL | 649 | 34.521 | 26.625 | 32.754 | 1.00 | 62.10 |
| 3140 | CB | VAL | 649 | 33.164 | 27.231 | 33.257 | 1.00 | 63.18 |
| 3141 | CG1 | VAL | 649 | 32.254 | 27.546 | 32.089 | 1.00 | 60.09 |
| 3142 | CG2 | VAL | 649 | 32.476 | 26.282 | 34.202 | 1.00 | 59.25 |
| 3143 | C | VAL | 649 | 35.313 | 26.111 | 33.941 | 1.00 | 63.47 |
| 3144 | O | VAL | 649 | 36.188 | 26.791 | 34.465 | 1.00 | 58.78 |
| 3145 | N | SER | 650 | 35.010 | 24.884 | 34.340 | 1.00 | 61.57 |
| 3146 | CA | SER | 650 | 35.664 | 24.258 | 35.471 | 1.00 | 62.45 |
| 3147 | CB | SER | 650 | 35.032 | 22.901 | 35.727 | 1.00 | 63.87 |
| 3148 | OG | SER | 650 | 35.312 | 22.468 | 37.037 | 1.00 | 57.30 |
| 3149 | C | SER | 650 | 37.152 | 24.102 | 35.217 | 1.00 | 61.59 |
| 3150 | O | SER | 650 | 37.966 | 24.254 | 36.123 | 1.00 | 59.77 |
| 3151 | N | SER | 651 | 37.506 | 23.796 | 33.977 | 1.00 | 61.81 |
| 3152 | CA | SER | 651 | 38.904 | 23.629 | 33.615 | 1.00 | 59.44 |
| 3153 | CB | SER | 651 | 39.029 | 23.147 | 32.175 | 1.00 | 61.10 |
| 3154 | OG | SER | 651 | 40.285 | 23.527 | 31.635 | 1.00 | 62.25 |
| 3155 | C | SER | 651 | 39.638 | 24.942 | 33.755 | 1.00 | 62.21 |
| 3156 | O | SER | 651 | 40.736 | 24.994 | 34.299 | 1.00 | 59.39 |
| 3157 | N | GLU | 652 | 39.019 | 25.998 | 33.248 | 1.00 | 60.68 |
| 3158 | CA | GLU | 652 | 39.590 | 27.333 | 33.296 | 1.00 | 62.47 |
| 3159 | CB | GLU | 652 | 38.683 | 28.294 | 32.534 | 1.00 | 62.00 |
| 3160 | CG | GLU | 652 | 38.551 | 27.905 | 31.087 | 1.00 | 60.93 |
| 3161 | CD | GLU | 652 | 39.896 | 27.841 | 30.412 | 1.00 | 62.60 |
| 3162 | OE1 | GLU | 652 | 40.389 | 28.912 | 29.994 | 1.00 | 61.37 |
| 3163 | OE2 | GLU | 652 | 40.466 | 26.727 | 30.323 | 1.00 | 62.86 |
| 3164 | C | GLU | 652 | 39.803 | 27.829 | 34.719 | 1.00 | 59.21 |
| 3165 | O | GLU | 652 | 40.843 | 28.404 | 35.040 | 1.00 | 60.26 |
| 3166 | N | LEU | 653 | 38.812 | 27.613 | 35.573 | 1.00 | 62.17 |
| 3167 | CA | LEU | 653 | 38.939 | 28.039 | 36.949 | 1.00 | 61.29 |
| 3168 | CB | LEU | 653 | 37.630 | 27.816 | 37.702 | 1.00 | 62.27 |
| 3169 | CG | LEU | 653 | 36.539 | 28.833 | 37.355 | 1.00 | 63.87 |
| 3170 | CD1 | LEU | 653 | 35.239 | 28.428 | 38.009 | 1.00 | 60.88 |
| 3171 | CD2 | LEU | 653 | 36.969 | 30.220 | 37.805 | 1.00 | 66.93 |
| 3172 | C | LEU | 653 | 40.065 | 27.252 | 37.579 | 1.00 | 61.64 |
| 3173 | O | LEU | 653 | 40.705 | 27.711 | 38.526 | 1.00 | 62.53 |
| 3174 | N | HIS | 654 | 40.316 | 26.067 | 37.035 | 1.00 | 59.14 |
| 3175 | CA | HIS | 654 | 41.386 | 25.219 | 37.534 | 1.00 | 63.27 |
| 3176 | CB | HIS | 654 | 41.122 | 23.768 | 37.166 | 1.00 | 63.36 |
| 3177 | CG | HIS | 654 | 42.203 | 22.842 | 37.610 | 1.00 | 63.44 |
| 3178 | CD2 | HIS | 654 | 43.298 | 22.379 | 36.965 | 1.00 | 60.81 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3179 | ND1 | HIS | 654 | 42.281 | 22.360 | 38.898 | 1.00 | 62.60 |
| 3180 | CE1 | HIS | 654 | 43.382 | 21.642 | 39.027 | 1.00 | 56.60 |
| 3181 | NE2 | HIS | 654 | 44.017 | 21.639 | 37.870 | 1.00 | 63.72 |
| 3182 | C | HIS | 654 | 42.719 | 25.654 | 36.928 | 1.00 | 61.86 |
| 3183 | O | HIS | 654 | 43.691 | 25.906 | 37.636 | 1.00 | 63.73 |
| 3184 | N | ARG | 655 | 42.744 | 25.732 | 35.605 | 1.00 | 62.82 |
| 3185 | CA | ARG | 655 | 43.929 | 26.133 | 34.867 | 1.00 | 60.68 |
| 3186 | CB | ARG | 655 | 43.559 | 26.326 | 33.394 | 1.00 | 56.53 |
| 3187 | CG | ARG | 655 | 44.577 | 27.074 | 32.574 | 1.00 | 62.54 |
| 3188 | CD | ARG | 655 | 43.921 | 27.870 | 31.451 | 1.00 | 58.99 |
| 3189 | NE | ARG | 655 | 44.865 | 28.859 | 30.951 | 1.00 | 62.01 |
| 3190 | CZ | ARG | 655 | 46.081 | 28.544 | 30.503 | 1.00 | 59.65 |
| 3191 | NH1 | ARG | 655 | 46.475 | 27.269 | 30.488 | 1.00 | 58.86 |
| 3192 | NH2 | ARG | 655 | 46.926 | 29.491 | 30.103 | 1.00 | 59.91 |
| 3193 | C | ARG | 655 | 44.525 | 27.419 | 35.430 | 1.00 | 59.56 |
| 3194 | O | ARG | 655 | 45.741 | 27.524 | 35.595 | 1.00 | 60.27 |
| 3195 | N | LEU | 656 | 43.664 | 28.389 | 35.735 | 1.00 | 64.27 |
| 3196 | CA | LEU | 656 | 44.102 | 29.687 | 36.250 | 1.00 | 58.78 |
| 3197 | CB | LEU | 656 | 43.099 | 30.751 | 35.833 | 1.00 | 62.45 |
| 3198 | CG | LEU | 656 | 43.072 | 30.957 | 34.328 | 1.00 | 57.52 |
| 3199 | CD1 | LEU | 656 | 41.832 | 31.704 | 33.943 | 1.00 | 65.67 |
| 3200 | CD2 | LEU | 656 | 44.305 | 31.714 | 33.895 | 1.00 | 62.85 |
| 3201 | C | LEU | 656 | 44.340 | 29.761 | 37.757 | 1.00 | 61.09 |
| 3202 | O | LEU | 656 | 44.995 | 30.688 | 38.244 | 1.00 | 62.48 |
| 3203 | N | GLN | 657 | 43.816 | 28.783 | 38.489 | 1.00 | 59.08 |
| 3204 | CA | GLN | 657 | 43.979 | 28.736 | 39.936 | 1.00 | 63.09 |
| 3205 | CB | GLN | 657 | 45.469 | 28.663 | 40.307 | 1.00 | 58.16 |
| 3206 | CG | GLN | 657 | 46.052 | 27.250 | 40.286 | 1.00 | 63.46 |
| 3207 | CD | GLN | 657 | 45.307 | 26.310 | 41.225 | 1.00 | 59.61 |
| 3208 | OE1 | GLN | 657 | 44.607 | 25.392 | 40.785 | 1.00 | 64.27 |
| 3209 | NE2 | GLN | 657 | 45.442 | 26.547 | 42.529 | 1.00 | 59.12 |
| 3210 | C | GLN | 657 | 43.335 | 29.932 | 40.611 | 1.00 | 59.19 |
| 3211 | O | GLN | 657 | 43.926 | 30.539 | 41.498 | 1.00 | 61.22 |
| 3212 | N | VAL | 658 | 42.113 | 30.249 | 40.192 | 1.00 | 61.76 |
| 3213 | CA | VAL | 658 | 41.355 | 31.376 | 40.734 | 1.00 | 61.31 |
| 3214 | CB | VAL | 658 | 39.970 | 31.503 | 40.043 | 1.00 | 60.50 |
| 3215 | CG1 | VAL | 658 | 39.211 | 32.664 | 40.623 | 1.00 | 59.45 |
| 3216 | CG2 | VAL | 658 | 40.132 | 31.716 | 38.559 | 1.00 | 61.37 |
| 3217 | C | VAL | 658 | 41.115 | 31.283 | 42.240 | 1.00 | 58.30 |
| 3218 | O | VAL | 658 | 40.838 | 30.208 | 42.764 | 1.00 | 56.60 |
| 3219 | N | SER | 659 | 41.214 | 32.418 | 42.928 | 1.00 | 60.76 |
| 3220 | CA | SER | 659 | 40.979 | 32.465 | 44.369 | 1.00 | 59.93 |
| 3221 | CB | SER | 659 | 41.873 | 33.507 | 45.047 | 1.00 | 59.20 |
| 3222 | OG | SER | 659 | 41.582 | 34.817 | 44.608 | 1.00 | 62.34 |
| 3223 | C | SER | 659 | 39.518 | 32.789 | 44.656 | 1.00 | 62.94 |
| 3224 | O | SER | 659 | 38.784 | 33.247 | 43.780 | 1.00 | 58.10 |
| 3225 | N | TYR | 660 | 39.097 | 32.563 | 45.893 | 1.00 | 61.68 |
| 3226 | CA | TYR | 660 | 37.720 | 32.808 | 46.250 | 1.00 | 62.54 |
| 3227 | CB | TYR | 660 | 37.481 | 32.526 | 47.717 | 1.00 | 64.73 |
| 3228 | CG | TYR | 660 | 36.014 | 32.432 | 48.044 | 1.00 | 56.73 |
| 3229 | CD1 | TYR | 660 | 35.144 | 31.742 | 47.200 | 1.00 | 59.62 |
| 3230 | CE1 | TYR | 660 | 33.817 | 31.568 | 47.524 | 1.00 | 61.29 |
| 3231 | CD2 | TYR | 660 | 35.507 | 32.957 | 49.223 | 1.00 | 64.06 |
| 3232 | CE2 | TYR | 660 | 34.176 | 32.789 | 49.557 | 1.00 | 61.23 |
| 3233 | CZ | TYR | 660 | 33.336 | 32.085 | 48.705 | 1.00 | 60.34 |
| 3234 | OH | TYR | 660 | 32.032 | 31.840 | 49.064 | 1.00 | 61.17 |
| 3235 | C | TYR | 660 | 37.250 | 34.204 | 45.954 | 1.00 | 61.20 |
| 3236 | O | TYR | 660 | 36.162 | 34.383 | 45.433 | 1.00 | 65.37 |
| 3237 | N | GLU | 661 | 38.057 | 35.199 | 46.290 | 1.00 | 61.50 |
| 3238 | CA | GLU | 661 | 37.657 | 36.574 | 46.052 | 1.00 | 58.24 |
| 3239 | CB | GLU | 661 | 38.598 | 37.523 | 46.765 | 1.00 | 64.85 |
| 3240 | CG | GLU | 661 | 38.276 | 37.577 | 48.225 | 1.00 | 61.43 |
| 3241 | CD | GLU | 661 | 39.283 | 38.360 | 48.991 | 1.00 | 60.83 |
| 3242 | OE1 | GLU | 661 | 39.961 | 39.204 | 48.365 | 1.00 | 59.88 |
| 3243 | OE2 | GLU | 661 | 39.387 | 38.143 | 50.219 | 1.00 | 59.48 |
| 3244 | C | GLU | 661 | 37.548 | 36.918 | 44.591 | 1.00 | 58.50 |
| 3245 | O | GLU | 661 | 36.573 | 37.536 | 44.178 | 1.00 | 62.37 |
| 3246 | N | GLU | 662 | 38.529 | 36.516 | 43.798 | 1.00 | 63.69 |
| 3247 | CA | GLU | 662 | 38.453 | 36.784 | 42.374 | 1.00 | 59.27 |
| 3248 | CB | GLU | 662 | 39.646 | 36.158 | 41.657 | 1.00 | 57.91 |
| 3249 | CG | GLU | 662 | 40.974 | 36.663 | 42.122 | 1.00 | 62.43 |
| 3250 | CD | GLU | 662 | 42.104 | 35.948 | 41.436 | 1.00 | 62.15 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3251 | OE1 | GLU | 662 | 41.969 | 34.732 | 41.223 | 1.00 | 57.52 |
| 3252 | OE2 | GLU | 662 | 43.128 | 36.585 | 41.119 | 1.00 | 61.99 |
| 3253 | C | GLU | 662 | 37.138 | 36.188 | 41.831 | 1.00 | 61.83 |
| 3254 | O | GLU | 662 | 36.492 | 36.771 | 40.963 | 1.00 | 63.75 |
| 3255 | N | TYR | 663 | 36.751 | 35.031 | 42.361 | 1.00 | 59.76 |
| 3256 | CA | TYR | 663 | 35.525 | 34.336 | 41.962 | 1.00 | 62.22 |
| 3257 | CB | TYR | 663 | 35.439 | 32.992 | 42.694 | 1.00 | 58.01 |
| 3258 | CG | TYR | 663 | 34.073 | 32.342 | 42.676 | 1.00 | 62.53 |
| 3259 | CD1 | TYR | 663 | 33.536 | 31.831 | 41.499 | 1.00 | 60.26 |
| 3260 | CE1 | TYR | 663 | 32.298 | 31.201 | 41.495 | 1.00 | 62.40 |
| 3261 | CD2 | TYR | 663 | 33.330 | 32.212 | 43.850 | 1.00 | 58.63 |
| 3262 | CE2 | TYR | 663 | 32.096 | 31.590 | 43.855 | 1.00 | 62.25 |
| 3263 | CZ | TYR | 663 | 31.587 | 31.084 | 42.676 | 1.00 | 63.25 |
| 3264 | OH | TYR | 663 | 30.372 | 30.448 | 42.682 | 1.00 | 62.04 |
| 3265 | C | TYR | 663 | 34.240 | 35.125 | 42.228 | 1.00 | 61.08 |
| 3266 | O | TYR | 663 | 33.429 | 35.343 | 41.322 | 1.00 | 58.41 |
| 3267 | N | LEU | 664 | 34.055 | 35.528 | 43.480 | 1.00 | 60.59 |
| 3268 | CA | LEU | 664 | 32.876 | 36.270 | 43.884 | 1.00 | 61.06 |
| 3269 | CB | LEU | 664 | 32.976 | 36.618 | 45.369 | 1.00 | 63.96 |
| 3270 | CG | LEU | 664 | 33.063 | 35.440 | 46.343 | 1.00 | 63.81 |
| 3271 | CD1 | LEU | 664 | 33.322 | 35.929 | 47.750 | 1.00 | 60.79 |
| 3272 | CD2 | LEU | 664 | 31.786 | 34.656 | 46.283 | 1.00 | 58.66 |
| 3273 | C | LEU | 664 | 32.692 | 37.539 | 43.057 | 1.00 | 62.83 |
| 3274 | O | LEU | 664 | 31.558 | 37.955 | 42.812 | 1.00 | 59.88 |
| 3275 | N | CYS | 665 | 33.809 | 38.139 | 42.632 | 1.00 | 59.97 |
| 3276 | CA | CYS | 665 | 33.805 | 39.365 | 41.831 | 1.00 | 63.59 |
| 3277 | CB | CYS | 665 | 35.167 | 40.043 | 41.869 | 1.00 | 60.16 |
| 3278 | SG | CYS | 665 | 35.586 | 40.757 | 43.441 | 1.00 | 62.94 |
| 3279 | C | CYS | 665 | 33.475 | 39.091 | 40.388 | 1.00 | 60.01 |
| 3280 | O | CYS | 665 | 32.794 | 39.876 | 39.735 | 1.00 | 57.49 |
| 3281 | N | MET | 666 | 33.997 | 37.984 | 39.883 | 1.00 | 60.45 |
| 3282 | CA | MET | 666 | 33.752 | 37.601 | 38.510 | 1.00 | 61.35 |
| 3283 | CB | MET | 666 | 34.733 | 36.517 | 38.077 | 1.00 | 60.05 |
| 3284 | CG | MET | 666 | 36.156 | 36.993 | 37.902 | 1.00 | 63.77 |
| 3285 | SD | MET | 666 | 37.274 | 35.592 | 37.856 | 1.00 | 59.75 |
| 3286 | CE | MET | 666 | 37.139 | 35.071 | 36.150 | 1.00 | 62.17 |
| 3287 | C | MET | 666 | 32.338 | 37.078 | 38.411 | 1.00 | 61.52 |
| 3288 | O | MET | 666 | 31.681 | 37.255 | 37.388 | 1.00 | 60.47 |
| 3289 | N | LYS | 667 | 31.869 | 36.433 | 39.475 | 1.00 | 61.04 |
| 3290 | CA | LYS | 667 | 30.516 | 35.898 | 39.482 | 1.00 | 62.69 |
| 3291 | CB | LYS | 667 | 30.261 | 35.036 | 40.726 | 1.00 | 61.46 |
| 3292 | CG | LYS | 667 | 28.966 | 34.228 | 40.671 | 1.00 | 59.84 |
| 3293 | CD | LYS | 667 | 28.678 | 33.497 | 41.975 | 1.00 | 63.25 |
| 3294 | CE | LYS | 667 | 28.483 | 34.471 | 43.123 | 1.00 | 59.23 |
| 3295 | NZ | LYS | 667 | 27.639 | 33.891 | 44.192 | 1.00 | 61.97 |
| 3296 | C | LYS | 667 | 29.554 | 37.066 | 39.461 | 1.00 | 63.05 |
| 3297 | O | LYS | 667 | 28.459 | 36.945 | 38.942 | 1.00 | 60.65 |
| 3298 | N | THR | 668 | 29.981 | 38.201 | 40.011 | 1.00 | 61.58 |
| 3299 | CA | THR | 668 | 29.146 | 39.398 | 40.061 | 1.00 | 60.37 |
| 3300 | CB | THR | 668 | 29.609 | 40.357 | 41.149 | 1.00 | 59.81 |
| 3301 | OG1 | THR | 668 | 29.776 | 39.634 | 42.370 | 1.00 | 59.26 |
| 3302 | CG2 | THR | 668 | 28.588 | 41.442 | 41.365 | 1.00 | 57.52 |
| 3303 | C | THR | 668 | 29.174 | 40.146 | 38.746 | 1.00 | 60.69 |
| 3304 | O | THR | 668 | 28.184 | 40.749 | 38.348 | 1.00 | 61.79 |
| 3305 | N | LEU | 669 | 30.320 | 40.111 | 38.076 | 1.00 | 58.82 |
| 3306 | CA | LEU | 669 | 30.479 | 40.774 | 36.786 | 1.00 | 60.62 |
| 3307 | CB | LEU | 669 | 31.947 | 40.863 | 36.412 | 1.00 | 60.70 |
| 3308 | CG | LEU | 669 | 32.673 | 41.944 | 37.192 | 1.00 | 61.83 |
| 3309 | CD1 | LEU | 669 | 34.131 | 41.996 | 36.761 | 1.00 | 63.30 |
| 3310 | CD2 | LEU | 669 | 31.981 | 43.275 | 36.953 | 1.00 | 62.82 |
| 3311 | C | LEU | 669 | 29.736 | 40.028 | 35.707 | 1.00 | 63.57 |
| 3312 | O | LEU | 669 | 29.574 | 40.521 | 34.599 | 1.00 | 63.32 |
| 3313 | N | LEU | 670 | 29.303 | 38.823 | 36.034 | 1.00 | 62.04 |
| 3314 | CA | LEU | 670 | 28.558 | 38.030 | 35.087 | 1.00 | 64.79 |
| 3315 | CB | LEU | 670 | 28.662 | 36.542 | 35.432 | 1.00 | 63.41 |
| 3316 | CG | LEU | 670 | 29.983 | 35.838 | 35.078 | 1.00 | 62.66 |
| 3317 | CD1 | LEU | 670 | 29.918 | 34.407 | 35.554 | 1.00 | 61.38 |
| 3318 | CD2 | LEU | 670 | 30.239 | 35.867 | 33.580 | 1.00 | 61.74 |
| 3319 | C | LEU | 670 | 27.111 | 38.495 | 35.114 | 1.00 | 60.65 |
| 3320 | O | LEU | 670 | 26.405 | 38.402 | 34.119 | 1.00 | 60.67 |
| 3321 | N | LEU | 671 | 26.673 | 39.008 | 36.257 | 1.00 | 60.80 |
| 3322 | CA | LEU | 671 | 25.308 | 39.500 | 36.386 | 1.00 | 60.13 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3323 | CB | LEU | 671 | 24.977 | 39.756 | 37.852 | 1.00 | 55.83 |
| 3324 | CG | LEU | 671 | 23.636 | 40.403 | 38.198 | 1.00 | 59.73 |
| 3325 | CD1 | LEU | 671 | 22.495 | 39.498 | 37.819 | 1.00 | 58.32 |
| 3326 | CD2 | LEU | 671 | 23.606 | 40.677 | 39.673 | 1.00 | 59.37 |
| 3327 | C | LEU | 671 | 25.178 | 40.804 | 35.613 | 1.00 | 60.50 |
| 3328 | O | LEU | 671 | 24.076 | 41.295 | 35.377 | 1.00 | 61.24 |
| 3329 | N | LEU | 672 | 26.320 | 41.354 | 35.219 | 1.00 | 59.65 |
| 3330 | CA | LEU | 672 | 26.355 | 42.613 | 34.492 | 1.00 | 62.17 |
| 3331 | CB | LEU | 672 | 27.128 | 43.650 | 35.309 | 1.00 | 60.10 |
| 3332 | CG | LEU | 672 | 26.917 | 43.688 | 36.822 | 1.00 | 65.92 |
| 3333 | CD1 | LEU | 672 | 27.728 | 44.819 | 37.407 | 1.00 | 60.54 |
| 3334 | CD2 | LEU | 672 | 25.460 | 43.885 | 37.148 | 1.00 | 58.59 |
| 3335 | C | LEU | 672 | 27.027 | 42.456 | 33.131 | 1.00 | 62.29 |
| 3336 | O | LEU | 672 | 27.489 | 43.430 | 32.554 | 1.00 | 61.76 |
| 3337 | N | SER | 673 | 27.070 | 41.237 | 32.613 | 1.00 | 60.43 |
| 3338 | CA | SER | 673 | 27.732 | 40.980 | 31.342 | 1.00 | 60.60 |
| 3339 | CB | SER | 673 | 28.212 | 39.538 | 31.317 | 1.00 | 60.81 |
| 3340 | OG | SER | 673 | 27.281 | 38.718 | 31.987 | 1.00 | 56.49 |
| 3341 | C | SER | 673 | 26.949 | 41.280 | 30.074 | 1.00 | 60.41 |
| 3342 | O | SER | 673 | 27.542 | 41.502 | 29.020 | 1.00 | 60.96 |
| 3343 | N | SER | 674 | 25.625 | 41.267 | 30.160 | 1.00 | 62.26 |
| 3344 | CA | SER | 674 | 24.800 | 41.565 | 28.995 | 1.00 | 62.20 |
| 3345 | CB | SER | 674 | 24.359 | 40.281 | 28.298 | 1.00 | 61.34 |
| 3346 | OG | SER | 674 | 23.730 | 39.420 | 29.221 | 1.00 | 62.88 |
| 3347 | C | SER | 674 | 23.581 | 42.371 | 29.402 | 1.00 | 60.51 |
| 3348 | O | SER | 674 | 22.904 | 42.050 | 30.376 | 1.00 | 62.02 |
| 3349 | N | VAL | 675 | 23.321 | 43.432 | 28.653 | 1.00 | 61.79 |
| 3350 | CA | VAL | 675 | 22.190 | 44.299 | 25.911 | 1.00 | 61.63 |
| 3351 | CB | VAL | 675 | 22.670 | 45.712 | 29.194 | 1.00 | 59.56 |
| 3352 | CG1 | VAL | 675 | 23.388 | 45.748 | 30.517 | 1.00 | 62.21 |
| 3353 | CG2 | VAL | 675 | 23.598 | 46.164 | 28.078 | 1.00 | 63.23 |
| 3354 | C | VAL | 675 | 21.325 | 44.320 | 27.658 | 1.00 | 62.05 |
| 3355 | O | VAL | 675 | 21.757 | 43.861 | 26.603 | 1.00 | 62.28 |
| 3356 | N | PRO | 676 | 20.077 | 44.817 | 27.764 | 1.00 | 60.51 |
| 3357 | CD | PRO | 676 | 19.330 | 45.132 | 28.991 | 1.00 | 63.50 |
| 3358 | CA | PRO | 676 | 19.191 | 44.880 | 26.593 | 1.00 | 62.22 |
| 3359 | CB | PRO | 676 | 17.896 | 45.494 | 27.156 | 1.00 | 58.53 |
| 3360 | CG | PRO | 676 | 18.322 | 46.117 | 28.488 | 1.00 | 60.68 |
| 3361 | C | PRO | 676 | 19.839 | 45.746 | 25.514 | 1.00 | 58.14 |
| 3362 | O | PRO | 676 | 20.824 | 46.435 | 25.792 | 1.00 | 61.96 |
| 3363 | N | LYS | 677 | 19.309 | 45.710 | 24.293 | 1.00 | 60.64 |
| 3364 | CA | LYS | 677 | 19.906 | 46.501 | 23.215 | 1.00 | 59.47 |
| 3365 | CB | LYS | 677 | 19.025 | 46.521 | 21.970 | 1.00 | 61.69 |
| 3366 | CG | LYS | 677 | 19.782 | 46.912 | 20.707 | 1.00 | 61.32 |
| 3367 | CD | LYS | 677 | 18.832 | 47.051 | 19.514 | 1.00 | 61.48 |
| 3368 | CE | LYS | 677 | 19.604 | 47.129 | 18.198 | 1.00 | 62.13 |
| 3369 | NZ | LYS | 677 | 20.435 | 45.908 | 17.952 | 1.00 | 60.25 |
| 3370 | C | LYS | 677 | 20.145 | 47.929 | 23.686 | 1.00 | 59.29 |
| 3371 | O | LYS | 677 | 21.248 | 48.235 | 24.158 | 1.00 | 63.94 |
| 3372 | N | ASP | 678 | 19.129 | 48.796 | 23.580 | 1.00 | 61.98 |
| 3373 | CA | ASP | 678 | 19.302 | 50.178 | 24.028 | 1.00 | 61.19 |
| 3374 | CB | ASP | 678 | 18.178 | 51.083 | 23.506 | 1.00 | 60.11 |
| 3375 | CG | ASP | 678 | 18.515 | 52.582 | 23.647 | 1.00 | 60.40 |
| 3376 | OD1 | ASP | 678 | 18.311 | 53.325 | 22.652 | 1.00 | 60.21 |
| 3377 | OD2 | ASP | 678 | 18.980 | 53.011 | 24.745 | 1.00 | 61.19 |
| 3378 | C | ASP | 678 | 19.395 | 50.284 | 25.558 | 1.00 | 61.02 |
| 3379 | O | ASP | 678 | 18.592 | 50.955 | 26.210 | 1.00 | 61.94 |
| 3380 | N | GLY | 679 | 20.398 | 49.604 | 26.108 | 1.00 | 58.42 |
| 3381 | CA | GLY | 679 | 20.649 | 49.605 | 27.534 | 1.00 | 56.97 |
| 3382 | C | GLY | 679 | 19.449 | 49.444 | 28.438 | 1.00 | 56.85 |
| 3383 | O | GLY | 679 | 18.362 | 49.031 | 28.028 | 1.00 | 59.44 |
| 3384 | N | LEU | 680 | 19.674 | 49.788 | 29.696 | 1.00 | 63.29 |
| 3385 | CA | LEU | 680 | 18.655 | 49.704 | 30.727 | 1.00 | 62.45 |
| 3386 | CB | LEU | 680 | 19.297 | 49.181 | 32.017 | 1.00 | 64.86 |
| 3387 | CG | LEU | 680 | 20.118 | 47.895 | 31.832 | 1.00 | 59.84 |
| 3388 | CD1 | LEU | 680 | 20.946 | 47.595 | 33.068 | 1.00 | 59.62 |
| 3389 | CD2 | LEU | 680 | 19.181 | 46.760 | 31.543 | 1.00 | 61.01 |
| 3390 | C | LEU | 680 | 18.056 | 51.090 | 30.955 | 1.00 | 60.58 |
| 3391 | O | LEU | 680 | 18.433 | 52.063 | 30.298 | 1.00 | 62.60 |
| 3392 | N | LYS | 681 | 17.120 | 51.174 | 31.888 | 1.00 | 62.27 |
| 3393 | CA | LYS | 681 | 16.486 | 52.441 | 32.197 | 1.00 | 63.23 |
| 3394 | CB | LYS | 681 | 15.146 | 52.211 | 32.901 | 1.00 | 59.95 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3395 | CG | LYS | 681 | 14.188 | 51.417 | 32.034 | 1.00 | 60.87 |
| 3396 | CD | LYS | 681 | 12.837 | 51.183 | 32.665 | 1.00 | 61.02 |
| 3397 | CE | LYS | 681 | 12.004 | 50.295 | 31.740 | 1.00 | 64.07 |
| 3398 | NZ | LYS | 681 | 10.616 | 50.060 | 32.218 | 1.00 | 58.77 |
| 3399 | C | LYS | 681 | 17.414 | 53.242 | 33.072 | 1.00 | 60.18 |
| 3400 | O | LYS | 681 | 17.373 | 54.462 | 33.069 | 1.00 | 63.10 |
| 3401 | N | SER | 682 | 18.278 | 52.554 | 33.802 | 1.00 | 60.92 |
| 3402 | CA | SER | 682 | 19.214 | 53.240 | 34.681 | 1.00 | 62.50 |
| 3403 | CB | SER | 682 | 18.953 | 52.786 | 36.113 | 1.00 | 62.86 |
| 3404 | OG | SER | 682 | 17.564 | 52.589 | 36.296 | 1.00 | 61.69 |
| 3405 | C | SER | 682 | 20.682 | 52.993 | 34.272 | 1.00 | 58.65 |
| 3406 | O | SER | 682 | 21.558 | 52.781 | 35.120 | 1.00 | 60.76 |
| 3407 | N | GLN | 683 | 20.924 | 53.053 | 32.961 | 1.00 | 60.04 |
| 3408 | CA | GLN | 683 | 22.241 | 52.840 | 32.348 | 1.00 | 61.19 |
| 3409 | CB | GLN | 683 | 22.156 | 53.127 | 30.850 | 1.00 | 59.58 |
| 3410 | CG | GLN | 683 | 23.397 | 52.757 | 30.056 | 1.00 | 62.33 |
| 3411 | CD | GLN | 683 | 23.606 | 51.259 | 29.955 | 1.00 | 62.33 |
| 3412 | OE1 | GLN | 683 | 22.651 | 50.502 | 29.759 | 1.00 | 62.13 |
| 3413 | NE2 | GLN | 683 | 24.858 | 50.823 | 30.065 | 1.00 | 61.30 |
| 3414 | C | GLN | 683 | 23.397 | 53.655 | 32.934 | 1.00 | 61.70 |
| 3415 | O | GLN | 683 | 24.561 | 53.335 | 32.719 | 1.00 | 62.18 |
| 3416 | N | GLU | 684 | 23.083 | 54.710 | 33.666 | 1.00 | 64.02 |
| 3417 | CA | GLU | 684 | 24.117 | 55.539 | 34.257 | 1.00 | 60.92 |
| 3418 | CB | GLU | 684 | 23.541 | 56.904 | 34.590 | 1.00 | 62.70 |
| 3419 | CG | GLU | 684 | 22.396 | 56.780 | 35.574 | 1.00 | 62.30 |
| 3420 | CD | GLU | 684 | 21.884 | 58.112 | 36.063 | 1.00 | 61.33 |
| 3421 | OE1 | GLU | 684 | 21.260 | 58.120 | 37.153 | 1.00 | 61.85 |
| 3422 | OE2 | GLU | 684 | 22.092 | 59.135 | 35.363 | 1.00 | 62.66 |
| 3423 | C | GLU | 684 | 24.582 | 54.867 | 35.534 | 1.00 | 61.21 |
| 3424 | O | GLU | 684 | 25.741 | 54.979 | 35.924 | 1.00 | 63.65 |
| 3425 | N | LEU | 685 | 23.659 | 54.181 | 36.197 | 1.00 | 62.46 |
| 3426 | CA | LEU | 685 | 23.992 | 53.487 | 37.429 | 1.00 | 60.48 |
| 3427 | CB | LEU | 685 | 22.731 | 53.265 | 38.269 | 1.00 | 62.31 |
| 3428 | CG | LEU | 685 | 22.992 | 53.036 | 39.764 | 1.00 | 59.19 |
| 3429 | CD1 | LEU | 685 | 23.700 | 54.245 | 40.360 | 1.00 | 59.86 |
| 3430 | CD2 | LEU | 685 | 21.684 | 52.795 | 40.485 | 1.00 | 61.02 |
| 3431 | C | LEU | 685 | 24.657 | 52.148 | 37.086 | 1.00 | 61.95 |
| 3432 | O | LEU | 685 | 25.524 | 51.662 | 37.804 | 1.00 | 61.31 |
| 3433 | N | PHE | 686 | 24.264 | 51.566 | 35.964 | 1.00 | 60.07 |
| 3434 | CA | PHE | 686 | 24.832 | 50.302 | 35.560 | 1.00 | 60.10 |
| 3435 | CB | PHE | 686 | 24.147 | 49.785 | 34.311 | 1.00 | 61.65 |
| 3436 | CG | PHE | 686 | 24.500 | 48.372 | 33.990 | 1.00 | 62.45 |
| 3437 | CD1 | PHE | 686 | 24.148 | 47.352 | 34.860 | 1.00 | 58.40 |
| 3438 | CD2 | PHE | 686 | 25.204 | 48.057 | 32.839 | 1.00 | 57.88 |
| 3439 | CE1 | PHE | 686 | 24.493 | 46.038 | 34.589 | 1.00 | 58.59 |
| 3440 | CE2 | PHE | 686 | 25.558 | 46.741 | 32.558 | 1.00 | 63.31 |
| 3441 | CZ | PHE | 686 | 25.201 | 45.733 | 33.433 | 1.00 | 61.15 |
| 3442 | C | PHE | 686 | 26.321 | 50.423 | 35.287 | 1.00 | 61.88 |
| 3443 | O | PHE | 686 | 27.150 | 49.890 | 36.038 | 1.00 | 60.58 |
| 3444 | N | ASP | 687 | 26.657 | 51.113 | 34.199 | 1.00 | 62.94 |
| 3445 | CA | ASP | 687 | 28.048 | 51.291 | 33.817 | 1.00 | 61.00 |
| 3446 | CB | ASP | 687 | 28.171 | 52.397 | 32.776 | 1.00 | 59.08 |
| 3447 | CG | ASP | 687 | 27.327 | 52.131 | 31.555 | 1.00 | 63.32 |
| 3448 | OD1 | ASP | 687 | 27.089 | 50.940 | 31.271 | 1.00 | 59.10 |
| 3449 | OD2 | ASP | 687 | 26.914 | 53.098 | 30.875 | 1.00 | 63.48 |
| 3450 | C | ASP | 687 | 28.853 | 51.645 | 35.051 | 1.00 | 60.66 |
| 3451 | O | ASP | 687 | 29.988 | 51.203 | 35.213 | 1.00 | 60.12 |
| 3452 | N | GLU | 688 | 28.238 | 52.424 | 35.934 | 1.00 | 62.70 |
| 3453 | CA | GLU | 688 | 28.869 | 52.872 | 37.172 | 1.00 | 64.06 |
| 3454 | CB | GLU | 688 | 27.967 | 53.930 | 37.803 | 1.00 | 59.69 |
| 3455 | CG | GLU | 688 | 28.530 | 54.718 | 38.963 | 1.00 | 60.90 |
| 3456 | CD | GLU | 688 | 27.609 | 55.883 | 39.319 | 1.00 | 59.61 |
| 3457 | OE1 | GLU | 688 | 27.607 | 56.905 | 38.575 | 1.00 | 59.94 |
| 3458 | OE2 | GLU | 688 | 26.871 | 55.765 | 40.328 | 1.00 | 61.24 |
| 3459 | C | GLU | 688 | 29.137 | 51.726 | 38.164 | 1.00 | 62.60 |
| 3460 | O | GLU | 688 | 30.199 | 51.659 | 38.784 | 1.00 | 62.63 |
| 3461 | N | ILE | 689 | 28.166 | 50.833 | 38.314 | 1.00 | 61.42 |
| 3462 | CA | ILE | 689 | 28.296 | 49.691 | 39.207 | 1.00 | 64.18 |
| 3463 | CB | ILE | 689 | 26.919 | 49.043 | 39.453 | 1.00 | 57.30 |
| 3464 | CG2 | ILE | 689 | 27.080 | 47.686 | 40.125 | 1.00 | 62.29 |
| 3465 | CG1 | ILE | 689 | 26.055 | 49.980 | 40.297 | 1.00 | 63.30 |
| 3466 | CD1 | ILE | 689 | 24.668 | 49.458 | 40.545 | 1.00 | 63.34 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3467 | C | ILE | 689 | 29.235 | 48.654 | 38.590 | 1.00 | 62.15 |
| 3468 | O | ILE | 689 | 30.079 | 48.071 | 39.276 | 1.00 | 59.58 |
| 3469 | N | ARG | 690 | 29.083 | 48.416 | 37.290 | 1.00 | 63.61 |
| 3470 | CA | ARG | 690 | 29.938 | 47.455 | 36.606 | 1.00 | 64.65 |
| 3471 | CB | ARG | 690 | 29.619 | 47.429 | 35.111 | 1.00 | 61.26 |
| 3472 | CG | ARG | 690 | 30.319 | 46.331 | 34.331 | 1.00 | 60.27 |
| 3473 | CD | ARG | 690 | 29.665 | 46.159 | 32.967 | 1.00 | 61.69 |
| 3474 | NE | ARG | 690 | 30.153 | 44.983 | 32.247 | 1.00 | 64.60 |
| 3475 | CZ | ARG | 690 | 31.331 | 44.907 | 31.640 | 1.00 | 64.30 |
| 3476 | NH1 | ARG | 690 | 32.158 | 45.946 | 31.657 | 1.00 | 61.69 |
| 3477 | NH2 | ARG | 690 | 31.682 | 43.793 | 31.015 | 1.00 | 61.35 |
| 3478 | C | ARG | 690 | 31.387 | 47.863 | 36.824 | 1.00 | 62.11 |
| 3479 | O | ARG | 690 | 32.208 | 47.070 | 37.268 | 1.00 | 63.96 |
| 3480 | N | MET | 691 | 31.690 | 49.118 | 36.521 | 1.00 | 58.67 |
| 3481 | CA | MET | 691 | 33.029 | 49.642 | 36.689 | 1.00 | 62.38 |
| 3482 | CB | MET | 691 | 33.015 | 51.144 | 36.408 | 1.00 | 63.73 |
| 3483 | CG | MET | 691 | 34.366 | 51.723 | 36.003 | 1.00 | 63.05 |
| 3484 | SD | MET | 691 | 35.189 | 50.799 | 34.661 | 1.00 | 60.35 |
| 3485 | CE | MET | 691 | 36.714 | 50.382 | 35.462 | 1.00 | 57.09 |
| 3486 | C | MET | 691 | 33.533 | 49.367 | 38.106 | 1.00 | 61.62 |
| 3487 | O | MET | 691 | 34.653 | 48.907 | 38.300 | 1.00 | 60.31 |
| 3488 | N | THR | 692 | 32.691 | 49.633 | 39.095 | 1.00 | 61.56 |
| 3489 | CA | THR | 692 | 33.053 | 49.428 | 40.490 | 1.00 | 59.70 |
| 3490 | CB | THR | 692 | 31.899 | 49.838 | 41.404 | 1.00 | 61.08 |
| 3491 | OG1 | THR | 692 | 31.493 | 51.167 | 41.074 | 1.00 | 61.61 |
| 3492 | CG2 | THR | 692 | 32.331 | 49.794 | 42.860 | 1.00 | 61.81 |
| 3493 | C | THR | 692 | 33.478 | 47.997 | 40.837 | 1.00 | 61.92 |
| 3494 | O | THR | 692 | 34.349 | 47.799 | 41.695 | 1.00 | 59.04 |
| 3495 | N | TYR | 693 | 32.850 | 47.013 | 40.190 | 1.00 | 58.91 |
| 3496 | CA | TYR | 693 | 33.183 | 45.605 | 40.419 | 1.00 | 59.83 |
| 3497 | CB | TYR | 693 | 31.961 | 44.711 | 40.241 | 1.00 | 59.81 |
| 3498 | CG | TYR | 693 | 31.053 | 44.801 | 41.437 | 1.00 | 63.50 |
| 3499 | CD1 | TYR | 693 | 31.565 | 44.640 | 42.728 | 1.00 | 59.52 |
| 3500 | CE1 | TYR | 693 | 30.757 | 44.793 | 43.844 | 1.00 | 63.13 |
| 3501 | CD2 | TYR | 693 | 29.703 | 45.109 | 41.297 | 1.00 | 59.74 |
| 3502 | CE2 | TYR | 693 | 28.892 | 45.259 | 42.409 | 1.00 | 61.29 |
| 3503 | CZ | TYR | 693 | 29.428 | 45.101 | 43.671 | 1.00 | 62.95 |
| 3504 | OH | TYR | 693 | 28.625 | 45.264 | 44.760 | 1.00 | 60.97 |
| 3505 | C | TYR | 693 | 34.310 | 45.138 | 39.530 | 1.00 | 62.66 |
| 3506 | O | TYR | 693 | 34.856 | 44.059 | 39.732 | 1.00 | 60.97 |
| 3507 | N | ILE | 694 | 34.648 | 45.955 | 38.536 | 1.00 | 62.91 |
| 3508 | CA | ILE | 694 | 35.766 | 45.651 | 37.661 | 1.00 | 60.76 |
| 3509 | CB | ILE | 694 | 35.726 | 46.450 | 36.347 | 1.00 | 63.35 |
| 3510 | CG2 | ILE | 694 | 37.057 | 46.305 | 35.611 | 1.00 | 58.86 |
| 3511 | CG1 | ILE | 694 | 34.570 | 45.956 | 35.480 | 1.00 | 59.03 |
| 3512 | CD1 | ILE | 694 | 34.524 | 46.568 | 34.109 | 1.00 | 64.66 |
| 3513 | C | ILE | 694 | 36.947 | 46.106 | 38.496 | 1.00 | 59.29 |
| 3514 | O | ILE | 694 | 37.976 | 45.450 | 38.548 | 1.00 | 59.81 |
| 3515 | N | LYS | 695 | 36.788 | 47.235 | 39.171 | 1.00 | 60.10 |
| 3516 | CA | LYS | 695 | 37.850 | 47.718 | 40.031 | 1.00 | 59.42 |
| 3517 | CB | LYS | 695 | 37.530 | 49.111 | 40.577 | 1.00 | 62.71 |
| 3518 | CG | LYS | 695 | 37.525 | 50.194 | 39.543 | 1.00 | 56.74 |
| 3519 | CD | LYS | 695 | 37.579 | 51.556 | 40.199 | 1.00 | 62.01 |
| 3520 | CE | LYS | 695 | 37.453 | 52.666 | 39.170 | 1.00 | 62.05 |
| 3521 | NZ | LYS | 695 | 37.650 | 54.002 | 39.778 | 1.00 | 58.55 |
| 3522 | C | LYS | 695 | 37.996 | 46.741 | 41.193 | 1.00 | 60.49 |
| 3523 | O | LYS | 695 | 39.071 | 46.578 | 41.744 | 1.00 | 58.83 |
| 3524 | N | GLU | 696 | 36.906 | 46.084 | 41.559 | 1.00 | 58.96 |
| 3525 | CA | GLU | 696 | 36.924 | 45.135 | 42.663 | 1.00 | 63.14 |
| 3526 | CB | GLU | 696 | 35.489 | 44.813 | 43.080 | 1.00 | 62.85 |
| 3527 | CG | GLU | 696 | 35.338 | 44.392 | 44.513 | 1.00 | 61.99 |
| 3528 | CD | GLU | 696 | 35.888 | 45.410 | 45.497 | 1.00 | 62.60 |
| 3529 | OE1 | GLU | 696 | 35.609 | 46.616 | 45.353 | 1.00 | 60.89 |
| 3530 | OE2 | GLU | 696 | 36.596 | 44.999 | 46.438 | 1.00 | 59.40 |
| 3531 | C | GLU | 696 | 37.668 | 43.855 | 42.273 | 1.00 | 63.03 |
| 3532 | O | GLU | 696 | 38.281 | 43.198 | 43.120 | 1.00 | 61.00 |
| 3533 | N | LEU | 697 | 37.605 | 43.507 | 40.990 | 1.00 | 61.52 |
| 3534 | CA | LEU | 697 | 38.279 | 42.324 | 40.487 | 1.00 | 58.74 |
| 3535 | CB | LEU | 697 | 37.830 | 42.018 | 39.057 | 1.00 | 58.36 |
| 3536 | CG | LEU | 697 | 38.438 | 40.757 | 38.439 | 1.00 | 63.54 |
| 3537 | CD1 | LEU | 697 | 37.948 | 39.560 | 39.208 | 1.00 | 57.14 |
| 3538 | CD2 | LEU | 697 | 38.058 | 40.623 | 36.972 | 1.00 | 63.58 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3539 | C | LEU | 697 | 39.766 | 42.633 | 40.499 | 1.00 | 60.87 |
| 3540 | O | LEU | 697 | 40.599 | 41.748 | 40.683 | 1.00 | 64.34 |
| 3541 | N | GLY | 698 | 40.087 | 43.907 | 40.303 | 1.00 | 63.62 |
| 3542 | CA | GLY | 698 | 41.472 | 44.331 | 40.285 | 1.00 | 60.55 |
| 3543 | C | GLY | 698 | 42.053 | 44.398 | 41.677 | 1.00 | 61.55 |
| 3544 | O | GLY | 698 | 43.259 | 44.268 | 41.877 | 1.00 | 58.62 |
| 3545 | N | LYS | 699 | 41.180 | 44.621 | 42.644 | 1.00 | 60.41 |
| 3546 | CA | LYS | 699 | 41.596 | 44.689 | 44.027 | 1.00 | 61.47 |
| 3547 | CB | LYS | 699 | 40.437 | 45.189 | 44.903 | 1.00 | 62.58 |
| 3548 | CG | LYS | 699 | 40.251 | 46.712 | 44.942 | 1.00 | 64.44 |
| 3549 | CD | LYS | 699 | 39.111 | 47.088 | 45.889 | 1.00 | 59.70 |
| 3550 | CE | LYS | 699 | 39.375 | 48.368 | 46.707 | 1.00 | 60.92 |
| 3551 | NZ | LYS | 699 | 38.986 | 49.663 | 46.056 | 1.00 | 62.69 |
| 3552 | C | LYS | 699 | 42.000 | 43.284 | 44.447 | 1.00 | 64.59 |
| 3553 | O | LYS | 699 | 43.044 | 43.077 | 45.063 | 1.00 | 59.56 |
| 3554 | N | ALA | 700 | 41.161 | 42.322 | 44.080 | 1.00 | 58.13 |
| 3555 | CA | ALA | 700 | 41.376 | 40.927 | 44.415 | 1.00 | 62.66 |
| 3556 | CB | ALA | 700 | 40.219 | 40.103 | 43.908 | 1.00 | 59.89 |
| 3557 | C | ALA | 700 | 42.678 | 40.387 | 43.861 | 1.00 | 60.42 |
| 3558 | O | ALA | 700 | 43.430 | 39.743 | 44.577 | 1.00 | 61.59 |
| 3559 | N | ILE | 701 | 42.937 | 40.662 | 42.585 | 1.00 | 60.42 |
| 3560 | CA | ILE | 701 | 44.141 | 40.201 | 41.898 | 1.00 | 63.95 |
| 3561 | CB | ILE | 701 | 44.105 | 40.611 | 40.416 | 1.00 | 61.37 |
| 3562 | CG2 | ILE | 701 | 45.396 | 40.224 | 39.742 | 1.00 | 65.93 |
| 3563 | CG1 | ILE | 701 | 42.921 | 39.939 | 39.717 | 1.00 | 60.90 |
| 3564 | CD1 | ILE | 701 | 42.697 | 40.405 | 38.275 | 1.00 | 59.90 |
| 3565 | C | ILE | 701 | 45.465 | 40.675 | 42.514 | 1.00 | 61.05 |
| 3566 | O | ILE | 701 | 46.455 | 39.931 | 42.518 | 1.00 | 62.71 |
| 3567 | N | VAL | 702 | 45.495 | 41.901 | 43.030 | 1.00 | 64.20 |
| 3568 | CA | VAL | 702 | 46.723 | 42.409 | 43.637 | 1.00 | 61.51 |
| 3569 | CB | VAL | 702 | 46.690 | 43.949 | 43.841 | 1.00 | 61.28 |
| 3570 | CG1 | VAL | 702 | 46.285 | 44.645 | 42.546 | 1.00 | 61.75 |
| 3571 | CG2 | VAL | 702 | 45.753 | 44.305 | 44.983 | 1.00 | 63.42 |
| 3572 | C | VAL | 702 | 46.964 | 41.753 | 44.995 | 1.00 | 62.93 |
| 3573 | O | VAL | 702 | 48.101 | 41.598 | 45.432 | 1.00 | 62.05 |
| 3574 | N | LYS | 703 | 45.894 | 41.357 | 45.665 | 1.00 | 61.37 |
| 3575 | CA | LYS | 703 | 46.057 | 40.741 | 46.967 | 1.00 | 62.89 |
| 3576 | CB | LYS | 703 | 44.714 | 40.683 | 47.705 | 1.00 | 58.24 |
| 3577 | CG | LYS | 703 | 44.851 | 40.816 | 49.215 | 1.00 | 61.67 |
| 3578 | CD | LYS | 703 | 45.460 | 39.557 | 49.830 | 1.00 | 63.57 |
| 3579 | CE | LYS | 703 | 46.410 | 39.869 | 50.986 | 1.00 | 57.61 |
| 3580 | NZ | LYS | 703 | 46.656 | 38.664 | 51.838 | 1.00 | 61.16 |
| 3581 | C | LYS | 703 | 46.645 | 39.355 | 46.776 | 1.00 | 60.39 |
| 3582 | O | LYS | 703 | 46.974 | 38.668 | 47.731 | 1.00 | 61.26 |
| 3583 | N | ARG | 704 | 46.790 | 38.951 | 45.523 | 1.00 | 62.02 |
| 3584 | CA | ARG | 704 | 47.369 | 37.649 | 45.214 | 1.00 | 61.58 |
| 3585 | CB | ARG | 704 | 46.408 | 36.817 | 44.368 | 1.00 | 61.15 |
| 3586 | CG | ARG | 704 | 45.272 | 36.177 | 45.112 | 1.00 | 66.70 |
| 3587 | CD | ARG | 704 | 44.871 | 34.956 | 44.350 | 1.00 | 62.98 |
| 3588 | NE | ARG | 704 | 45.731 | 34.788 | 43.185 | 1.00 | 58.04 |
| 3589 | CZ | ARG | 704 | 45.973 | 33.619 | 42.601 | 1.00 | 65.26 |
| 3590 | NH1 | ARG | 704 | 45.422 | 32.513 | 43.080 | 1.00 | 60.05 |
| 3591 | NH2 | ARG | 704 | 46.761 | 33.552 | 41.538 | 1.00 | 60.69 |
| 3592 | C | ARG | 704 | 48.686 | 37.792 | 44.445 | 1.00 | 62.07 |
| 3593 | O | ARG | 704 | 49.779 | 37.725 | 45.029 | 1.00 | 60.23 |
| 3594 | N | GLU | 705 | 48.555 | 37.997 | 43.130 | 1.00 | 61.20 |
| 3595 | CA | GLU | 705 | 49.686 | 38.134 | 42.212 | 1.00 | 61.45 |
| 3596 | CB | GLU | 705 | 49.179 | 38.271 | 40.776 | 1.00 | 59.83 |
| 3597 | CG | GLU | 705 | 49.038 | 36.941 | 40.015 | 1.00 | 61.58 |
| 3598 | CD | GLU | 705 | 48.539 | 35.764 | 40.875 | 1.00 | 62.88 |
| 3599 | OE1 | GLU | 705 | 47.511 | 35.908 | 41.595 | 1.00 | 61.37 |
| 3600 | OE2 | GLU | 705 | 49.181 | 34.685 | 40.806 | 1.00 | 62.83 |
| 3601 | C | GLU | 705 | 50.601 | 39.296 | 42.542 | 1.00 | 60.29 |
| 3602 | O | GLU | 705 | 50.212 | 40.468 | 42.446 | 1.00 | 61.23 |
| 3603 | N | GLY | 706 | 51.832 | 38.935 | 42.896 | 1.00 | 60.12 |
| 3604 | CA | GLY | 706 | 52.855 | 39.883 | 43.288 | 1.00 | 62.85 |
| 3605 | C | GLY | 706 | 53.083 | 41.191 | 42.556 | 1.00 | 58.46 |
| 3606 | O | GLY | 706 | 52.603 | 42.244 | 42.991 | 1.00 | 60.65 |
| 3607 | N | ASN | 707 | 53.818 | 41.141 | 41.449 | 1.00 | 62.51 |
| 3608 | CA | ASN | 707 | 54.158 | 42.366 | 40.729 | 1.00 | 63.30 |
| 3609 | CB | ASN | 707 | 55.516 | 42.196 | 40.013 | 1.00 | 60.74 |
| 3610 | CG | ASN | 707 | 55.676 | 40.835 | 39.356 | 1.00 | 60.19 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3611 | OD1 | ASN | 707 | 55.354 | 39.797 | 39.950 | 1.00 | 59.76 |
| 3612 | ND2 | ASN | 707 | 56.195 | 40.833 | 38.128 | 1.00 | 59.34 |
| 3613 | C | ASN | 707 | 53.134 | 42.993 | 39.792 | 1.00 | 59.87 |
| 3614 | O | ASN | 707 | 52.054 | 42.451 | 39.569 | 1.00 | 63.44 |
| 3615 | N | SER | 708 | 53.501 | 44.161 | 39.265 | 1.00 | 60.90 |
| 3616 | CA | SER | 708 | 52.647 | 44.950 | 38.382 | 1.00 | 58.16 |
| 3617 | CB | SER | 708 | 53.218 | 46.366 | 38.244 | 1.00 | 62.09 |
| 3618 | OG | SER | 708 | 53.403 | 46.974 | 39.516 | 1.00 | 61.85 |
| 3619 | C | SER | 708 | 52.432 | 44.354 | 36.998 | 1.00 | 61.28 |
| 3620 | O | SER | 708 | 51.400 | 44.607 | 36.372 | 1.00 | 58.94 |
| 3621 | N | SER | 709 | 53.393 | 43.567 | 36.516 | 1.00 | 61.19 |
| 3622 | CA | SER | 709 | 53.266 | 42.952 | 35.193 | 1.00 | 59.82 |
| 3623 | CB | SER | 709 | 54.650 | 42.527 | 34.665 | 1.00 | 62.14 |
| 3624 | OG | SER | 709 | 54.658 | 42.353 | 33.249 | 1.00 | 61.67 |
| 3625 | C | SER | 709 | 52.338 | 41.743 | 35.318 | 1.00 | 59.05 |
| 3626 | O | SER | 709 | 51.508 | 41.479 | 34.442 | 1.00 | 63.30 |
| 3627 | N | GLN | 710 | 52.481 | 41.022 | 36.426 | 1.00 | 63.44 |
| 3628 | CA | GLN | 710 | 51.652 | 39.851 | 36.691 | 1.00 | 59.41 |
| 3629 | CB | GLN | 710 | 52.289 | 39.036 | 37.833 | 1.00 | 63.27 |
| 3630 | CG | GLN | 710 | 53.572 | 38.329 | 37.354 | 1.00 | 60.06 |
| 3631 | CD | GLN | 710 | 54.362 | 37.611 | 38.453 | 1.00 | 57.38 |
| 3632 | OE1 | GLN | 710 | 53.781 | 37.012 | 39.369 | 1.00 | 60.97 |
| 3633 | NE2 | GLN | 710 | 55.701 | 37.647 | 38.348 | 1.00 | 63.13 |
| 3634 | C | GLN | 710 | 50.209 | 40.281 | 37.010 | 1.00 | 62.98 |
| 3635 | O | GLN | 710 | 49.250 | 39.584 | 36.667 | 1.00 | 61.41 |
| 3636 | N | ASN | 711 | 50.087 | 41.451 | 37.641 | 1.00 | 59.07 |
| 3637 | CA | ASN | 711 | 48.815 | 42.048 | 38.017 | 1.00 | 59.32 |
| 3638 | CB | ASN | 711 | 49.053 | 43.439 | 38.610 | 1.00 | 62.53 |
| 3639 | CG | ASN | 711 | 49.400 | 43.398 | 40.096 | 1.00 | 65.70 |
| 3640 | OD1 | ASN | 711 | 49.886 | 44.388 | 40.663 | 1.00 | 59.52 |
| 3641 | ND2 | ASN | 711 | 49.140 | 42.259 | 40.736 | 1.00 | 62.62 |
| 3642 | C | ASN | 711 | 47.918 | 42.167 | 36.792 | 1.00 | 61.19 |
| 3643 | O | ASN | 711 | 46.796 | 41.644 | 36.778 | 1.00 | 59.41 |
| 3644 | N | TRP | 712 | 48.418 | 42.850 | 35.762 | 1.00 | 60.32 |
| 3645 | CA | TRP | 712 | 47.660 | 43.044 | 34.534 | 1.00 | 65.58 |
| 3646 | CB | TRP | 712 | 48.270 | 44.168 | 33.711 | 1.00 | 59.75 |
| 3647 | CG | TRP | 712 | 48.272 | 45.426 | 34.444 | 1.00 | 58.80 |
| 3648 | CD2 | TRP | 712 | 47.148 | 46.271 | 34.668 | 1.00 | 64.37 |
| 3649 | CE2 | TRP | 712 | 47.577 | 47.322 | 35.506 | 1.00 | 59.23 |
| 3650 | CE3 | TRP | 712 | 45.812 | 46.240 | 34.245 | 1.00 | 62.90 |
| 3651 | CD1 | TRP | 712 | 49.313 | 45.976 | 35.124 | 1.00 | 62.87 |
| 3652 | NE1 | TRP | 712 | 48.905 | 47.118 | 35.770 | 1.00 | 62.24 |
| 3653 | CZ2 | TRP | 712 | 46.719 | 48.335 | 35.935 | 1.00 | 60.25 |
| 3654 | CZ3 | TRP | 712 | 44.954 | 47.247 | 34.672 | 1.00 | 61.54 |
| 3655 | CH2 | TRP | 712 | 45.413 | 48.281 | 35.511 | 1.00 | 58.28 |
| 3656 | C | TRP | 712 | 47.538 | 41.811 | 33.663 | 1.00 | 61.45 |
| 3657 | O | TRP | 712 | 46.531 | 41.623 | 32.992 | 1.00 | 63.89 |
| 3658 | N | GLN | 713 | 48.561 | 40.974 | 33.646 | 1.00 | 62.44 |
| 3659 | CA | GLN | 713 | 48.493 | 39.778 | 32.823 | 1.00 | 60.84 |
| 3660 | CB | GLN | 713 | 49.865 | 39.088 | 32.761 | 1.00 | 59.49 |
| 3661 | CG | GLN | 713 | 50.495 | 39.114 | 31.371 | 1.00 | 61.40 |
| 3662 | CD | GLN | 713 | 49.624 | 38.414 | 30.336 | 1.00 | 60.98 |
| 3663 | OE1 | GLN | 713 | 49.306 | 38.980 | 29.285 | 1.00 | 60.97 |
| 3664 | NE2 | GLN | 713 | 49.232 | 37.173 | 30.629 | 1.00 | 62.19 |
| 3665 | C | GLN | 713 | 47.446 | 38.847 | 33.420 | 1.00 | 64.17 |
| 3666 | O | GLN | 713 | 46.843 | 38.037 | 32.722 | 1.00 | 62.77 |
| 3667 | N | ARG | 714 | 47.242 | 38.993 | 34.724 | 1.00 | 60.50 |
| 3668 | CA | ARG | 714 | 46.276 | 38.203 | 35.481 | 1.00 | 60.81 |
| 3669 | CB | ARG | 714 | 46.560 | 38.352 | 36.978 | 1.00 | 61.22 |
| 3670 | CG | ARG | 714 | 45.609 | 37.613 | 37.897 | 1.00 | 60.90 |
| 3671 | CD | ARG | 714 | 45.858 | 36.130 | 37.894 | 1.00 | 60.47 |
| 3672 | NE | ARG | 714 | 44.999 | 35.455 | 38.858 | 1.00 | 60.72 |
| 3673 | CZ | ARG | 714 | 44.777 | 34.145 | 38.860 | 1.00 | 62.42 |
| 3674 | NH1 | ARG | 714 | 45.358 | 33.382 | 37.943 | 1.00 | 57.63 |
| 3675 | NH2 | ARG | 714 | 43.967 | 33.601 | 39.762 | 1.00 | 61.24 |
| 3676 | C | ARG | 714 | 44.877 | 38.722 | 35.174 | 1.00 | 61.77 |
| 3677 | O | ARG | 714 | 43.930 | 37.949 | 35.007 | 1.00 | 61.51 |
| 3678 | N | PHE | 715 | 44.765 | 40.044 | 35.107 | 1.00 | 59.93 |
| 3679 | CA | PHE | 715 | 43.502 | 40.691 | 34.809 | 1.00 | 62.80 |
| 3680 | CB | PHE | 715 | 43.630 | 42.203 | 34.932 | 1.00 | 61.91 |
| 3681 | CG | PHE | 715 | 42.335 | 42.909 | 34.749 | 1.00 | 63.38 |
| 3682 | CD1 | PHE | 715 | 41.340 | 42.779 | 35.706 | 1.00 | 62.36 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3683 | CD2 | PHE | 715 | 42.062 | 43.610 | 33.581 | 1.00 | 62.07 |
| 3684 | CE1 | PHE | 715 | 40.091 | 43.323 | 35.504 | 1.00 | 60.49 |
| 3685 | CE2 | PHE | 715 | 40.815 | 44.162 | 33.365 | 1.00 | 62.56 |
| 3686 | CZ | PHE | 715 | 39.823 | 44.017 | 34.328 | 1.00 | 61.44 |
| 3687 | C | PHE | 715 | 43.046 | 40.353 | 33.395 | 1.00 | 60.17 |
| 3688 | O | PHE | 715 | 41.849 | 40.288 | 33.115 | 1.00 | 59.69 |
| 3689 | N | TYR | 716 | 44.017 | 40.157 | 32.507 | 1.00 | 61.56 |
| 3690 | CA | TYR | 716 | 43.749 | 39.820 | 31.116 | 1.00 | 60.99 |
| 3691 | CB | TYR | 716 | 45.043 | 39.870 | 30.297 | 1.00 | 62.72 |
| 3692 | CG | TYR | 716 | 44.810 | 39.609 | 28.828 | 1.00 | 61.29 |
| 3693 | CD1 | TYR | 716 | 44.115 | 40.530 | 28.047 | 1.00 | 57.90 |
| 3694 | CE1 | TYR | 716 | 43.790 | 40.253 | 26.728 | 1.00 | 62.63 |
| 3695 | CD2 | TYR | 716 | 45.188 | 38.399 | 28.242 | 1.00 | 65.06 |
| 3696 | CE2 | TYR | 716 | 44.866 | 38.111 | 26.923 | 1.00 | 60.30 |
| 3697 | CZ | TYR | 716 | 44.161 | 39.044 | 26.172 | 1.00 | 62.23 |
| 3698 | OH | TYR | 716 | 43.798 | 38.768 | 24.870 | 1.00 | 58.39 |
| 3699 | C | TYR | 716 | 43.157 | 38.419 | 31.036 | 1.00 | 62.09 |
| 3700 | O | TYR | 716 | 42.085 | 38.213 | 30.469 | 1.00 | 60.05 |
| 3701 | N | GLN | 717 | 43.875 | 37.460 | 31.611 | 1.00 | 62.41 |
| 3702 | CA | GLN | 717 | 43.449 | 36.071 | 31.623 | 1.00 | 60.55 |
| 3703 | CB | GLN | 717 | 44.409 | 35.222 | 32.465 | 1.00 | 59.06 |
| 3704 | CG | GLN | 717 | 45.855 | 35.166 | 31.978 | 1.00 | 60.27 |
| 3705 | CD | GLN | 717 | 46.758 | 34.357 | 32.919 | 1.00 | 60.87 |
| 3706 | OE1 | GLN | 717 | 46.844 | 34.639 | 34.124 | 1.00 | 61.07 |
| 3707 | NE2 | GLN | 717 | 47.437 | 33.352 | 32.369 | 1.00 | 62.22 |
| 3708 | C | GLN | 717 | 42.048 | 35.931 | 32.194 | 1.00 | 59.73 |
| 3709 | O | GLN | 717 | 41.156 | 35.383 | 31.545 | 1.00 | 64.26 |
| 3710 | N | LEU | 718 | 41.867 | 36.428 | 33.415 | 1.00 | 58.62 |
| 3711 | CA | LEU | 718 | 40.582 | 36.348 | 34.101 | 1.00 | 60.65 |
| 3712 | CB | LEU | 718 | 40.708 | 36.899 | 35.530 | 1.00 | 61.42 |
| 3713 | CG | LEU | 718 | 41.661 | 36.158 | 36.487 | 1.00 | 61.76 |
| 3714 | CD1 | LEU | 718 | 41.717 | 36.889 | 37.809 | 1.00 | 60.77 |
| 3715 | CD2 | LEU | 718 | 41.210 | 34.721 | 36.701 | 1.00 | 59.74 |
| 3716 | C | LEU | 718 | 39.427 | 37.034 | 33.375 | 1.00 | 59.70 |
| 3717 | O | LEU | 718 | 38.330 | 36.495 | 33.327 | 1.00 | 60.84 |
| 3718 | N | THR | 719 | 39.661 | 38.211 | 32.812 | 1.00 | 62.09 |
| 3719 | CA | THR | 719 | 38.608 | 38.925 | 32.095 | 1.00 | 59.89 |
| 3720 | CB | THR | 719 | 38.985 | 40.387 | 31.900 | 1.00 | 63.01 |
| 3721 | OG1 | THR | 719 | 40.248 | 40.465 | 31.237 | 1.00 | 63.25 |
| 3722 | CG2 | THR | 719 | 39.087 | 41.082 | 33.240 | 1.00 | 61.82 |
| 3723 | C | THR | 719 | 38.329 | 38.291 | 30.733 | 1.00 | 61.35 |
| 3724 | O | THR | 719 | 37.349 | 38.622 | 30.062 | 1.00 | 61.10 |
| 3725 | N | LYS | 720 | 39.203 | 37.371 | 30.341 | 1.00 | 62.98 |
| 3726 | CA | LYS | 720 | 39.074 | 36.651 | 29.079 | 1.00 | 61.71 |
| 3727 | CB | LYS | 720 | 40.460 | 36.209 | 28.588 | 1.00 | 62.48 |
| 3728 | CG | LYS | 720 | 40.500 | 35.805 | 27.128 | 1.00 | 58.53 |
| 3729 | CD | LYS | 720 | 40.038 | 36.972 | 26.251 | 1.00 | 59.89 |
| 3730 | CE | LYS | 720 | 39.616 | 36.524 | 24.842 | 1.00 | 58.48 |
| 3731 | NZ | LYS | 720 | 38.772 | 37.570 | 24.209 | 1.00 | 60.64 |
| 3732 | C | LYS | 720 | 38.184 | 35.430 | 29.331 | 1.00 | 61.74 |
| 3733 | O | LYS | 720 | 37.479 | 34.962 | 28.438 | 1.00 | 61.10 |
| 3734 | N | LEU | 721 | 38.228 | 34.923 | 30.560 | 1.00 | 61.01 |
| 3735 | CA | LEU | 721 | 37.417 | 33.776 | 30.938 | 1.00 | 64.67 |
| 3736 | CB | LEU | 721 | 37.897 | 33.187 | 32.268 | 1.00 | 59.87 |
| 3737 | CG | LEU | 721 | 37.656 | 31.707 | 32.594 | 1.00 | 61.04 |
| 3738 | CD1 | LEU | 721 | 37.766 | 31.549 | 34.095 | 1.00 | 57.32 |
| 3739 | CD2 | LEU | 721 | 36.292 | 31.224 | 32.130 | 1.00 | 59.37 |
| 3740 | C | LEU | 721 | 35.983 | 34.277 | 31.078 | 1.00 | 62.25 |
| 3741 | O | LEU | 721 | 35.031 | 33.533 | 30.860 | 1.00 | 57.52 |
| 3742 | N | LEU | 722 | 35.830 | 35.540 | 31.455 | 1.00 | 62.01 |
| 3743 | CA | LEU | 722 | 34.503 | 36.113 | 31.591 | 1.00 | 62.92 |
| 3744 | CB | LEU | 722 | 34.578 | 37.497 | 32.246 | 1.00 | 61.91 |
| 3745 | CG | LEU | 722 | 34.841 | 37.559 | 33.754 | 1.00 | 58.92 |
| 3746 | CD1 | LEU | 722 | 34.946 | 38.986 | 34.193 | 1.00 | 62.12 |
| 3747 | CD2 | LEU | 722 | 33.728 | 36.876 | 34.507 | 1.00 | 62.52 |
| 3748 | C | LEU | 722 | 33.949 | 36.226 | 30.180 | 1.00 | 59.20 |
| 3749 | O | LEU | 722 | 32.883 | 35.697 | 29.854 | 1.00 | 60.43 |
| 3750 | N | ASP | 723 | 34.714 | 36.911 | 29.344 | 1.00 | 60.22 |
| 3751 | CA | ASP | 723 | 34.379 | 37.143 | 27.952 | 1.00 | 60.07 |
| 3752 | CB | ASP | 723 | 35.607 | 37.697 | 27.248 | 1.00 | 59.74 |
| 3753 | CG | ASP | 723 | 35.437 | 39.115 | 26.832 | 1.00 | 60.94 |
| 3754 | OD1 | ASP | 723 | 34.869 | 39.890 | 27.626 | 1.00 | 63.82 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3755 | OD2 | ASP | 723 | 35.883 | 39.445 | 25.713 | 1.00 | 63.76 |
| 3756 | C | ASP | 723 | 33.909 | 35.899 | 27.214 | 1.00 | 61.21 |
| 3757 | O | ASP | 723 | 33.108 | 35.981 | 26.292 | 1.00 | 61.67 |
| 3758 | N | SER | 724 | 34.414 | 34.743 | 27.613 | 1.00 | 62.19 |
| 3759 | CA | SER | 724 | 34.054 | 33.521 | 26.923 | 1.00 | 62.38 |
| 3760 | CB | SER | 724 | 35.256 | 32.578 | 26.876 | 1.00 | 61.26 |
| 3761 | OG | SER | 724 | 35.743 | 32.308 | 28.175 | 1.00 | 62.27 |
| 3762 | C | SER | 724 | 32.869 | 32.823 | 27.539 | 1.00 | 63.42 |
| 3763 | O | SER | 724 | 32.419 | 31.785 | 27.054 | 1.00 | 60.80 |
| 3764 | N | MET | 725 | 32.352 | 33.395 | 28.613 | 1.00 | 61.24 |
| 3765 | CA | MET | 725 | 31.209 | 32.794 | 29.265 | 1.00 | 60.73 |
| 3766 | CB | MET | 725 | 30.955 | 33.461 | 30.608 | 1.00 | 62.85 |
| 3767 | CG | MET | 725 | 30.460 | 32.506 | 31.654 | 1.00 | 63.01 |
| 3768 | SD | MET | 725 | 31.773 | 31.403 | 32.092 | 1.00 | 57.07 |
| 3769 | CE | MET | 725 | 30.949 | 30.380 | 33.178 | 1.00 | 59.44 |
| 3770 | C | MET | 725 | 30.008 | 32.987 | 28.352 | 1.00 | 59.13 |
| 3771 | O | MET | 725 | 29.022 | 32.254 | 28.437 | 1.00 | 62.11 |
| 3772 | N | HIS | 726 | 30.105 | 33.973 | 27.465 | 1.00 | 58.55 |
| 3773 | CA | HIS | 726 | 29.021 | 34.267 | 26.547 | 1.00 | 60.99 |
| 3774 | CB | HIS | 726 | 29.302 | 35.554 | 25.769 | 1.00 | 62.45 |
| 3775 | CG | HIS | 726 | 29.036 | 36.801 | 26.557 | 1.00 | 59.03 |
| 3776 | CD2 | HIS | 726 | 27.909 | 37.248 | 27.161 | 1.00 | 60.25 |
| 3777 | ND1 | HIS | 726 | 30.003 | 37.753 | 26.800 | 1.00 | 61.07 |
| 3778 | CE1 | HIS | 726 | 29.484 | 38.731 | 27.520 | 1.00 | 61.93 |
| 3779 | NE2 | HIS | 726 | 28.215 | 38.451 | 27.752 | 1.00 | 59.78 |
| 3780 | C | HIS | 726 | 28.773 | 33.116 | 25.601 | 1.00 | 58.35 |
| 3781 | O | HIS | 726 | 27.638 | 32.696 | 25.438 | 1.00 | 61.58 |
| 3782 | N | GLU | 727 | 29.816 | 32.571 | 24.993 | 1.00 | 62.79 |
| 3783 | CA | GLU | 727 | 29.574 | 31.461 | 24.086 | 1.00 | 60.53 |
| 3784 | CB | GLU | 727 | 30.693 | 31.307 | 23.055 | 1.00 | 59.90 |
| 3785 | CG | GLU | 727 | 32.005 | 30.809 | 23.578 | 1.00 | 57.32 |
| 3786 | CD | GLU | 727 | 32.838 | 30.187 | 22.473 | 1.00 | 59.99 |
| 3787 | OE1 | GLU | 727 | 34.057 | 30.013 | 22.680 | 1.00 | 62.44 |
| 3788 | OE2 | GLU | 727 | 32.275 | 29.862 | 21.400 | 1.00 | 63.27 |
| 3789 | C | GLU | 727 | 29.351 | 30.138 | 24.791 | 1.00 | 59.24 |
| 3790 | O | GLU | 727 | 28.779 | 29.233 | 24.203 | 1.00 | 62.98 |
| 3791 | N | VAL | 728 | 29.812 | 29.992 | 26.029 | 1.00 | 60.19 |
| 3792 | CA | VAL | 728 | 29.546 | 28.732 | 26.721 | 1.00 | 58.29 |
| 3793 | CB | VAL | 728 | 30.493 | 28.481 | 27.956 | 1.00 | 58.87 |
| 3794 | CG1 | VAL | 728 | 31.261 | 29.728 | 28.304 | 1.00 | 60.81 |
| 3795 | CG2 | VAL | 728 | 29.694 | 28.002 | 29.152 | 1.00 | 61.95 |
| 3796 | C | VAL | 728 | 28.082 | 28.825 | 27.145 | 1.00 | 59.41 |
| 3797 | O | VAL | 728 | 27.335 | 27.848 | 27.046 | 1.00 | 61.38 |
| 3798 | N | VAL | 729 | 27.670 | 30.014 | 27.585 | 1.00 | 59.91 |
| 3799 | CA | VAL | 729 | 26.283 | 30.238 | 27.971 | 1.00 | 60.73 |
| 3800 | CB | VAL | 729 | 26.072 | 31.664 | 28.504 | 1.00 | 63.53 |
| 3801 | CG1 | VAL | 729 | 24.602 | 32.062 | 28.406 | 1.00 | 62.52 |
| 3802 | CG2 | VAL | 729 | 26.513 | 31.725 | 29.946 | 1.00 | 62.40 |
| 3803 | C | VAL | 729 | 25.397 | 30.004 | 26.749 | 1.00 | 62.11 |
| 3804 | O | VAL | 729 | 24.279 | 29.493 | 26.868 | 1.00 | 58.35 |
| 3805 | N | GLU | 730 | 25.894 | 30.372 | 25.571 | 1.00 | 59.30 |
| 3806 | CA | GLU | 730 | 25.133 | 30.146 | 24.347 | 1.00 | 61.37 |
| 3807 | CB | GLU | 730 | 25.940 | 30.546 | 23.125 | 1.00 | 57.56 |
| 3808 | CG | GLU | 730 | 25.202 | 31.467 | 22.199 | 1.00 | 61.79 |
| 3809 | CD | GLU | 730 | 25.875 | 31.569 | 20.859 | 1.00 | 62.47 |
| 3810 | OE1 | GLU | 730 | 27.039 | 32.032 | 20.811 | 1.00 | 62.43 |
| 3811 | OE2 | GLU | 730 | 25.235 | 31.178 | 19.858 | 1.00 | 61.70 |
| 3812 | C | GLU | 730 | 24.832 | 28.660 | 24.267 | 1.00 | 60.90 |
| 3813 | O | GLU | 730 | 23.701 | 28.244 | 24.449 | 1.00 | 63.19 |
| 3814 | N | ASN | 731 | 25.864 | 27.866 | 24.013 | 1.00 | 61.88 |
| 3815 | CA | ASN | 731 | 25.729 | 26.416 | 23.919 | 1.00 | 63.18 |
| 3816 | CB | ASN | 731 | 27.109 | 25.761 | 23.859 | 1.00 | 56.96 |
| 3817 | CG | ASN | 731 | 27.516 | 25.393 | 22.449 | 1.00 | 61.50 |
| 3818 | OD1 | ASN | 731 | 26.909 | 24.515 | 21.808 | 1.00 | 59.01 |
| 3819 | ND2 | ASN | 731 | 28.552 | 26.059 | 21.953 | 1.00 | 62.29 |
| 3820 | C | ASN | 731 | 24.927 | 25.773 | 25.045 | 1.00 | 62.97 |
| 3821 | O | ASN | 731 | 24.251 | 24.772 | 24.834 | 1.00 | 60.93 |
| 3822 | N | LEU | 732 | 25.002 | 26.330 | 26.246 | 1.00 | 59.50 |
| 3823 | CA | LEU | 732 | 24.241 | 25.737 | 27.326 | 1.00 | 57.74 |
| 3824 | CB | LEU | 732 | 24.826 | 26.120 | 28.668 | 1.00 | 61.00 |
| 3825 | CG | LEU | 732 | 25.964 | 25.172 | 29.078 | 1.00 | 60.69 |
| 3826 | CD1 | LEU | 732 | 26.278 | 25.584 | 30.458 | 1.00 | 63.28 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3827 | CD2 | LEU | 732 | 25.589 | 23.663 | 29.058 | 1.00 | 63.30 |
| 3828 | C | LEU | 732 | 22.761 | 26.089 | 27.240 | 1.00 | 61.98 |
| 3829 | O | LEU | 732 | 21.912 | 25.269 | 27.574 | 1.00 | 63.87 |
| 3830 | N | LEU | 733 | 22.456 | 27.294 | 26.762 | 1.00 | 63.36 |
| 3831 | CA | LEU | 733 | 21.073 | 27.744 | 26.596 | 1.00 | 57.15 |
| 3832 | CB | LEU | 733 | 21.040 | 29.241 | 26.290 | 1.00 | 60.30 |
| 3833 | CG | LEU | 733 | 21.134 | 30.193 | 27.481 | 1.00 | 57.97 |
| 3834 | CD1 | LEU | 733 | 21.471 | 31.571 | 26.956 | 1.00 | 62.48 |
| 3835 | CD2 | LEU | 733 | 19.824 | 30.212 | 28.272 | 1.00 | 62.63 |
| 3836 | C | LEU | 733 | 20.354 | 26.997 | 25.470 | 1.00 | 63.32 |
| 3837 | O | LEU | 733 | 19.256 | 26.475 | 25.655 | 1.00 | 61.30 |
| 3838 | N | ASN | 734 | 20.965 | 26.972 | 24.292 | 1.00 | 57.57 |
| 3839 | CA | ASN | 734 | 20.376 | 26.285 | 23.159 | 1.00 | 59.44 |
| 3840 | CB | ASN | 734 | 21.363 | 26.277 | 21.994 | 1.00 | 57.94 |
| 3841 | CG | ASN | 734 | 21.671 | 27.682 | 21.495 | 1.00 | 59.18 |
| 3842 | OD1 | ASN | 734 | 22.072 | 28.556 | 22.268 | 1.00 | 63.60 |
| 3843 | ND2 | ASN | 734 | 21.476 | 27.908 | 20.202 | 1.00 | 63.41 |
| 3844 | C | ASN | 734 | 20.038 | 24.872 | 23.594 | 1.00 | 60.75 |
| 3845 | O | ASN | 734 | 18.904 | 24.423 | 23.453 | 1.00 | 62.53 |
| 3846 | N | TYR | 735 | 21.017 | 24.177 | 24.151 | 1.00 | 61.37 |
| 3847 | CA | TYR | 735 | 20.762 | 22.823 | 24.597 | 1.00 | 58.79 |
| 3848 | CB | TYR | 735 | 22.058 | 22.201 | 25.158 | 1.00 | 58.40 |
| 3849 | CG | TYR | 735 | 22.087 | 20.717 | 24.978 | 1.00 | 60.44 |
| 3850 | CD1 | TYR | 735 | 21.309 | 19.890 | 25.780 | 1.00 | 60.76 |
| 3851 | CE1 | TYR | 735 | 21.240 | 18.509 | 25.562 | 1.00 | 60.42 |
| 3852 | CD2 | TYR | 735 | 22.815 | 20.134 | 23.938 | 1.00 | 61.19 |
| 3853 | CE2 | TYR | 735 | 22.750 | 18.758 | 23.696 | 1.00 | 62.36 |
| 3854 | CZ | TYR | 735 | 21.961 | 17.950 | 24.519 | 1.00 | 59.04 |
| 3855 | OH | TYR | 735 | 21.899 | 16.583 | 24.313 | 1.00 | 58.73 |
| 3856 | C | TYR | 735 | 19.649 | 22.877 | 25.657 | 1.00 | 61.17 |
| 3857 | O | TYR | 735 | 18.858 | 21.945 | 25.790 | 1.00 | 63.18 |
| 3858 | N | CYS | 736 | 19.574 | 23.995 | 26.373 | 1.00 | 63.51 |
| 3859 | CA | CYS | 736 | 18.563 | 24.202 | 27.403 | 1.00 | 65.29 |
| 3860 | CB | CYS | 736 | 18.922 | 25.433 | 28.228 | 1.00 | 64.15 |
| 3861 | SG | CYS | 736 | 17.642 | 25.957 | 29.339 | 1.00 | 60.76 |
| 3862 | C | CYS | 736 | 17.183 | 24.389 | 26.779 | 1.00 | 63.45 |
| 3863 | O | CYS | 736 | 16.251 | 23.645 | 27.090 | 1.00 | 61.32 |
| 3864 | N | PHE | 737 | 17.061 | 25.391 | 25.906 | 1.00 | 59.77 |
| 3865 | CA | PHE | 737 | 15.808 | 25.688 | 25.209 | 1.00 | 61.17 |
| 3866 | CB | PHE | 737 | 16.014 | 26.792 | 24.175 | 1.00 | 59.61 |
| 3867 | CG | PHE | 737 | 16.348 | 28.129 | 24.764 | 1.00 | 58.80 |
| 3868 | CD1 | PHE | 737 | 16.060 | 28.414 | 26.096 | 1.00 | 59.85 |
| 3869 | CD2 | PHE | 737 | 16.924 | 29.119 | 23.979 | 1.00 | 61.58 |
| 3870 | CE1 | PHE | 737 | 16.340 | 29.669 | 26.638 | 1.00 | 59.75 |
| 3871 | CE2 | PHE | 737 | 17.207 | 30.374 | 24.510 | 1.00 | 61.15 |
| 3872 | CZ | PHE | 737 | 16.914 | 30.649 | 25.843 | 1.00 | 59.90 |
| 3873 | C | PHE | 737 | 15.280 | 24.462 | 24.484 | 1.00 | 61.86 |
| 3874 | O | PHE | 737 | 14.153 | 24.024 | 24.714 | 1.00 | 64.04 |
| 3875 | N | GLN | 738 | 16.108 | 23.932 | 23.590 | 1.00 | 60.57 |
| 3876 | CA | GLN | 738 | 15.786 | 22.752 | 22.798 | 1.00 | 61.63 |
| 3877 | CB | GLN | 738 | 17.078 | 22.181 | 22.220 | 1.00 | 62.59 |
| 3878 | CG | GLN | 738 | 16.989 | 20.805 | 21.575 | 1.00 | 61.50 |
| 3879 | CD | GLN | 738 | 18.368 | 20.144 | 21.521 | 1.00 | 62.73 |
| 3880 | OE1 | GLN | 738 | 18.581 | 19.062 | 22.093 | 1.00 | 60.75 |
| 3881 | NE2 | GLN | 738 | 19.321 | 20.808 | 20.853 | 1.00 | 61.08 |
| 3882 | C | GLN | 738 | 15.043 | 21.677 | 23.591 | 1.00 | 62.87 |
| 3883 | O | GLN | 738 | 13.970 | 21.235 | 23.180 | 1.00 | 62.00 |
| 3884 | N | THR | 739 | 15.595 | 21.262 | 24.725 | 1.00 | 62.54 |
| 3885 | CA | THR | 739 | 14.937 | 20.228 | 25.513 | 1.00 | 62.00 |
| 3886 | CB | THR | 739 | 15.883 | 19.572 | 26.529 | 1.00 | 61.40 |
| 3887 | OG1 | THR | 739 | 16.041 | 20.437 | 27.659 | 1.00 | 59.46 |
| 3888 | CG2 | THR | 739 | 17.234 | 19.302 | 25.902 | 1.00 | 67.45 |
| 3889 | C | THR | 739 | 13.721 | 20.740 | 26.282 | 1.00 | 60.54 |
| 3890 | O | THR | 739 | 12.911 | 19.949 | 26.758 | 1.00 | 60.32 |
| 3891 | N | PHE | 740 | 13.589 | 22.049 | 26.433 | 1.00 | 60.26 |
| 3892 | CA | PHE | 740 | 12.426 | 22.572 | 27.136 | 1.00 | 60.59 |
| 3893 | CB | PHE | 740 | 12.645 | 24.013 | 27.586 | 1.00 | 60.53 |
| 3894 | CG | PHE | 740 | 11.387 | 24.682 | 28.073 | 1.00 | 60.33 |
| 3895 | CD1 | PHE | 740 | 10.976 | 24.543 | 29.399 | 1.00 | 60.24 |
| 3896 | CD2 | PHE | 740 | 10.591 | 25.417 | 27.196 | 1.00 | 60.88 |
| 3897 | CE1 | PHE | 740 | 9.794 | 25.124 | 29.842 | 1.00 | 62.19 |
| 3898 | CE2 | PHE | 740 | 9.407 | 26.001 | 27.629 | 1.00 | 63.06 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3899 | CZ | PHE | 740 | 9.005 | 25.857 | 28.954 | 1.00 | 59.45 |
| 3900 | C | PHE | 740 | 11.269 | 22.562 | 26.161 | 1.00 | 62.20 |
| 3901 | O | PHE | 740 | 10.102 | 22.514 | 26.560 | 1.00 | 60.22 |
| 3902 | N | LEU | 741 | 11.619 | 22.631 | 24.877 | 1.00 | 61.98 |
| 3903 | CA | LEU | 741 | 10.650 | 22.665 | 23.783 | 1.00 | 61.09 |
| 3904 | CB | LEU | 741 | 11.158 | 23.561 | 22.656 | 1.00 | 63.24 |
| 3905 | CG | LEU | 741 | 11.286 | 25.053 | 22.919 | 1.00 | 57.80 |
| 3906 | CD1 | LEU | 741 | 11.680 | 25.732 | 21.617 | 1.00 | 59.82 |
| 3907 | CD2 | LEU | 741 | 9.966 | 25.608 | 23.455 | 1.00 | 59.42 |
| 3908 | C | LEU | 741 | 10.313 | 21.316 | 23.170 | 1.00 | 60.22 |
| 3909 | O | LEU | 741 | 9.748 | 21.267 | 22.079 | 1.00 | 59.13 |
| 3910 | N | ASP | 742 | 10.662 | 20.230 | 23.845 | 1.00 | 61.37 |
| 3911 | CA | ASP | 742 | 10.388 | 18.914 | 23.309 | 1.00 | 61.75 |
| 3912 | CB | ASP | 742 | 11.679 | 18.315 | 22.733 | 1.00 | 62.29 |
| 3913 | CG | ASP | 742 | 11.476 | 16.916 | 22.145 | 1.00 | 59.85 |
| 3914 | OD1 | ASP | 742 | 12.450 | 16.354 | 21.576 | 1.00 | 62.02 |
| 3915 | OD2 | ASP | 742 | 10.348 | 16.378 | 22.253 | 1.00 | 63.60 |
| 3916 | C | ASP | 742 | 9.843 | 18.041 | 24.420 | 1.00 | 61.37 |
| 3917 | O | ASP | 742 | 10.614 | 17.412 | 25.153 | 1.00 | 62.69 |
| 3918 | N | LYS | 743 | 8.517 | 18.018 | 24.564 | 1.00 | 61.79 |
| 3919 | CA | LYS | 743 | 7.882 | 17.183 | 25.595 | 1.00 | 58.96 |
| 3920 | CB | LYS | 743 | 6.381 | 17.501 | 25.727 | 1.00 | 62.19 |
| 3921 | CG | LYS | 743 | 6.056 | 18.836 | 26.404 | 1.00 | 57.47 |
| 3922 | CD | LYS | 743 | 4.545 | 19.047 | 26.473 | 1.00 | 59.18 |
| 3923 | CE | LYS | 743 | 4.180 | 20.313 | 27.232 | 1.00 | 61.36 |
| 3924 | NZ | LYS | 743 | 2.699 | 20.507 | 27.295 | 1.00 | 57.73 |
| 3925 | C | LYS | 743 | 8.055 | 15.688 | 25.281 | 1.00 | 61.20 |
| 3926 | O | LYS | 743 | 7.912 | 14.843 | 26.165 | 1.00 | 60.18 |
| 3927 | N | THR | 744 | 8.366 | 15.380 | 24.020 | 1.00 | 59.67 |
| 3928 | CA | THR | 744 | 8.580 | 14.007 | 23.554 | 1.00 | 61.15 |
| 3929 | CB | THR | 744 | 8.792 | 13.974 | 22.047 | 1.00 | 59.67 |
| 3930 | OG1 | THR | 744 | 7.881 | 14.890 | 21.426 | 1.00 | 62.19 |
| 3931 | CG2 | THR | 744 | 8.550 | 12.574 | 21.513 | 1.00 | 63.96 |
| 3932 | C | THR | 744 | 9.818 | 13.406 | 24.202 | 1.00 | 61.58 |
| 3933 | O | THR | 744 | 9.976 | 12.195 | 24.261 | 1.00 | 62.58 |
| 3934 | N | MET | 745 | 10.711 | 14.279 | 24.646 | 1.00 | 57.60 |
| 3935 | CA | MET | 745 | 11.933 | 13.887 | 25.334 | 1.00 | 62.60 |
| 3936 | CB | MET | 745 | 12.982 | 14.976 | 25.147 | 1.00 | 59.01 |
| 3937 | CG | MET | 745 | 14.366 | 14.645 | 25.612 | 1.00 | 60.84 |
| 3938 | SD | MET | 745 | 15.440 | 15.948 | 24.965 | 1.00 | 58.90 |
| 3939 | CE | MET | 745 | 16.317 | 15.039 | 23.610 | 1.00 | 62.07 |
| 3940 | C | MET | 745 | 11.435 | 13.843 | 26.774 | 1.00 | 63.96 |
| 3941 | O | MET | 745 | 11.973 | 13.137 | 27.629 | 1.00 | 64.77 |
| 3942 | N | SER | 746 | 10.394 | 14.635 | 27.025 | 1.00 | 59.79 |
| 3943 | CA | SER | 746 | 9.744 | 14.657 | 28.326 | 1.00 | 60.83 |
| 3944 | CB | SER | 746 | 9.149 | 13.249 | 28.576 | 1.00 | 61.05 |
| 3945 | OG | SER | 746 | 8.512 | 13.111 | 29.842 | 1.00 | 61.76 |
| 3946 | C | SER | 746 | 10.597 | 15.089 | 29.533 | 1.00 | 61.97 |
| 3947 | O | SER | 746 | 10.576 | 14.408 | 30.545 | 1.00 | 61.88 |
| 3948 | N | ILE | 747 | 11.322 | 16.207 | 29.443 | 1.00 | 60.50 |
| 3949 | CA | ILE | 747 | 12.140 | 16.678 | 30.571 | 1.00 | 61.46 |
| 3950 | CB | ILE | 747 | 13.557 | 17.115 | 30.098 | 1.00 | 57.79 |
| 3951 | CG2 | ILE | 747 | 14.374 | 17.635 | 31.275 | 1.00 | 62.83 |
| 3952 | CG1 | ILE | 747 | 14.282 | 15.911 | 29.484 | 1.00 | 61.46 |
| 3953 | CD1 | ILE | 747 | 15.664 | 16.211 | 28.976 | 1.00 | 65.11 |
| 3954 | C | ILE | 747 | 11.441 | 17.829 | 31.318 | 1.00 | 63.68 |
| 3955 | O | ILE | 747 | 11.166 | 18.891 | 30.747 | 1.00 | 62.48 |
| 3956 | N | GLU | 748 | 11.167 | 17.597 | 32.601 | 1.00 | 59.16 |
| 3957 | CA | GLU | 748 | 10.457 | 18.546 | 33.466 | 1.00 | 62.34 |
| 3958 | CB | GLU | 748 | 9.803 | 17.736 | 34.620 | 1.00 | 60.97 |
| 3959 | CG | GLU | 748 | 8.628 | 18.410 | 35.400 | 1.00 | 63.60 |
| 3960 | CD | GLU | 748 | 7.998 | 17.505 | 36.516 | 1.00 | 59.56 |
| 3961 | OE1 | GLU | 748 | 8.753 | 16.918 | 37.340 | 1.00 | 61.60 |
| 3962 | OE2 | GLU | 748 | 6.744 | 17.396 | 36.574 | 1.00 | 62.18 |
| 3963 | C | GLU | 748 | 11.333 | 19.701 | 34.022 | 1.00 | 59.89 |
| 3964 | O | GLU | 748 | 12.503 | 19.498 | 34.367 | 1.00 | 59.20 |
| 3965 | N | PHE | 749 | 10.781 | 20.913 | 34.046 | 1.00 | 62.20 |
| 3966 | CA | PHE | 749 | 11.484 | 22.079 | 34.601 | 1.00 | 60.36 |
| 3967 | CB | PHE | 749 | 11.773 | 23.202 | 33.571 | 1.00 | 63.43 |
| 3968 | CG | PHE | 749 | 12.801 | 22.827 | 32.506 | 1.00 | 62.31 |
| 3969 | CD1 | PHE | 749 | 12.604 | 21.790 | 31.624 | 1.00 | 63.18 |
| 3970 | CD2 | PHE | 749 | 13.948 | 23.639 | 32.305 | 1.00 | 58.27 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 3971 | CE1 | PHE | 749 | 13.461 | 21.555 | 30.545 | 1.00 | 59.47 |
| 3972 | CE2 | PHE | 749 | 14.821 | 23.409 | 31.221 | 1.00 | 59.31 |
| 3973 | CZ | PHE | 749 | 14.566 | 22.379 | 30.341 | 1.00 | 60.26 |
| 3974 | C | PHE | 749 | 10.491 | 22.634 | 35.646 | 1.00 | 57.34 |
| 3975 | O | PHE | 749 | 9.296 | 22.348 | 35.598 | 1.00 | 62.05 |
| 3976 | N | PRO | 750 | 10.971 | 23.425 | 36.612 | 1.00 | 61.11 |
| 3977 | CD | PRO | 750 | 12.322 | 23.572 | 37.178 | 1.00 | 62.36 |
| 3978 | CA | PRO | 750 | 9.955 | 23.918 | 37.535 | 1.00 | 63.79 |
| 3979 | CB | PRO | 750 | 10.745 | 24.124 | 38.834 | 1.00 | 59.84 |
| 3980 | CG | PRO | 750 | 12.072 | 24.510 | 38.341 | 1.00 | 61.92 |
| 3981 | C | PRO | 750 | 9.283 | 25.174 | 37.042 | 1.00 | 61.44 |
| 3982 | O | PRO | 750 | 9.000 | 25.325 | 35.852 | 1.00 | 61.38 |
| 3983 | N | GLU | 751 | 9.016 | 26.087 | 37.962 | 1.00 | 61.10 |
| 3984 | CA | GLU | 751 | 8.375 | 27.335 | 37.604 | 1.00 | 59.57 |
| 3985 | CB | GLU | 751 | 7.535 | 27.828 | 38.778 | 1.00 | 60.79 |
| 3986 | CG | GLU | 751 | 6.534 | 26.804 | 39.190 | 1.00 | 60.87 |
| 3987 | CD | GLU | 751 | 5.716 | 26.358 | 38.013 | 1.00 | 58.45 |
| 3988 | OE1 | GLU | 751 | 6.004 | 26.825 | 36.889 | 1.00 | 58.76 |
| 3989 | OE2 | GLU | 751 | 4.768 | 25.564 | 38.205 | 1.00 | 62.99 |
| 3990 | C | GLU | 751 | 9.449 | 28.328 | 37.275 | 1.00 | 59.04 |
| 3991 | O | GLU | 751 | 9.644 | 28.698 | 36.115 | 1.00 | 63.48 |
| 3992 | N | MET | 752 | 10.154 | 28.736 | 38.319 | 1.00 | 62.70 |
| 3993 | CA | MET | 752 | 11.223 | 29.693 | 38.184 | 1.00 | 60.75 |
| 3994 | CB | MET | 752 | 12.241 | 29.499 | 39.306 | 1.00 | 60.00 |
| 3995 | CG | MET | 752 | 13.222 | 30.641 | 39.392 | 1.00 | 60.74 |
| 3996 | SD | MET | 752 | 12.305 | 32.203 | 39.387 | 1.00 | 61.02 |
| 3997 | CE | MET | 752 | 12.040 | 32.394 | 41.073 | 1.00 | 58.25 |
| 3998 | C | MET | 752 | 11.919 | 29.549 | 36.847 | 1.00 | 61.43 |
| 3999 | O | MET | 752 | 12.062 | 30.515 | 36.103 | 1.00 | 63.92 |
| 4000 | N | LEU | 753 | 12.329 | 28.326 | 36.537 | 1.00 | 61.53 |
| 4001 | CA | LEU | 753 | 13.044 | 28.081 | 35.307 | 1.00 | 63.94 |
| 4002 | CB | LEU | 753 | 13.749 | 26.729 | 35.370 | 1.00 | 61.07 |
| 4003 | CG | LEU | 753 | 15.278 | 26.834 | 35.432 | 1.00 | 59.22 |
| 4004 | CD1 | LEU | 753 | 15.720 | 27.666 | 36.636 | 1.00 | 60.65 |
| 4005 | CD2 | LEU | 753 | 15.870 | 25.436 | 35.488 | 1.00 | 56.88 |
| 4006 | C | LEU | 753 | 12.182 | 28.179 | 34.073 | 1.00 | 62.24 |
| 4007 | O | LEU | 753 | 12.539 | 28.882 | 33.138 | 1.00 | 61.75 |
| 4008 | N | ALA | 754 | 11.049 | 27.488 | 34.061 | 1.00 | 58.32 |
| 4009 | CA | ALA | 754 | 10.156 | 27.536 | 32.902 | 1.00 | 60.89 |
| 4010 | CB | ALA | 754 | 8.856 | 26.790 | 33.209 | 1.00 | 62.87 |
| 4011 | C | ALA | 754 | 9.851 | 28.995 | 32.581 | 1.00 | 60.33 |
| 4012 | O | ALA | 754 | 10.031 | 29.471 | 31.454 | 1.00 | 61.42 |
| 4013 | N | GLU | 755 | 9.406 | 29.698 | 33.615 | 1.00 | 62.19 |
| 4014 | CA | GLU | 755 | 9.040 | 31.101 | 33.535 | 1.00 | 60.87 |
| 4015 | CB | GLU | 755 | 8.481 | 31.550 | 34.891 | 1.00 | 60.79 |
| 4016 | CG | GLU | 755 | 7.821 | 32.911 | 34.858 | 1.00 | 62.93 |
| 4017 | CD | GLU | 755 | 6.333 | 32.829 | 35.097 | 1.00 | 56.10 |
| 4018 | OE1 | GLU | 755 | 5.741 | 31.746 | 34.841 | 1.00 | 59.07 |
| 4019 | OE2 | GLU | 755 | 5.761 | 33.857 | 35.531 | 1.00 | 65.63 |
| 4020 | C | GLU | 755 | 10.163 | 32.053 | 33.106 | 1.00 | 64.44 |
| 4021 | O | GLU | 755 | 10.006 | 33.269 | 33.209 | 1.00 | 61.31 |
| 4022 | N | ILE | 756 | 11.296 | 31.528 | 32.653 | 1.00 | 60.43 |
| 4023 | CA | ILE | 756 | 12.382 | 32.396 | 32.187 | 1.00 | 58.74 |
| 4024 | CB | ILE | 756 | 13.664 | 32.292 | 33.024 | 1.00 | 62.34 |
| 4025 | CG2 | ILE | 756 | 14.819 | 32.942 | 32.280 | 1.00 | 62.52 |
| 4026 | CG1 | ILE | 756 | 13.487 | 33.000 | 34.355 | 1.00 | 61.56 |
| 4027 | CD1 | ILE | 756 | 14.750 | 33.012 | 35.170 | 1.00 | 59.91 |
| 4028 | C | ILE | 756 | 12.725 | 31.933 | 30.799 | 1.00 | 61.14 |
| 4029 | O | ILE | 756 | 12.985 | 32.732 | 29.904 | 1.00 | 61.35 |
| 4030 | N | ILE | 757 | 12.728 | 30.618 | 30.639 | 1.00 | 58.95 |
| 4031 | CA | ILE | 757 | 13.026 | 30.016 | 29.362 | 1.00 | 60.81 |
| 4032 | CB | ILE | 757 | 12.990 | 28.467 | 29.480 | 1.00 | 60.69 |
| 4033 | CG2 | ILE | 757 | 12.522 | 27.838 | 28.197 | 1.00 | 64.94 |
| 4034 | CG1 | ILE | 757 | 14.378 | 27.948 | 29.883 | 1.00 | 60.19 |
| 4035 | CD1 | ILE | 757 | 14.463 | 27.436 | 31.313 | 1.00 | 62.89 |
| 4036 | C | ILE | 757 | 12.012 | 30.542 | 28.348 | 1.00 | 59.56 |
| 4037 | O | ILE | 757 | 12.397 | 30.991 | 27.276 | 1.00 | 61.79 |
| 4038 | N | THR | 758 | 10.726 | 30.521 | 28.702 | 1.00 | 61.66 |
| 4039 | CA | THR | 758 | 9.677 | 31.014 | 27.795 | 1.00 | 61.59 |
| 4040 | CB | THR | 758 | 8.224 | 30.722 | 28.323 | 1.00 | 63.29 |
| 4041 | OG1 | THR | 758 | 8.188 | 30.811 | 29.755 | 1.00 | 62.91 |
| 4042 | CG2 | THR | 758 | 7.754 | 29.343 | 27.874 | 1.00 | 61.73 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 4043 | C | THR | 758 | 9.809 | 32.516 | 27.566 | 1.00 | 60.10 |
| 4044 | O | THR | 758 | 9.735 | 33.002 | 26.423 | 1.00 | 59.44 |
| 4045 | N | ASN | 759 | 10.023 | 33.242 | 28.656 | 1.00 | 59.76 |
| 4046 | CA | ASN | 759 | 10.154 | 34.691 | 28.608 | 1.00 | 61.77 |
| 4047 | CB | ASN | 759 | 10.160 | 35.242 | 30.034 | 1.00 | 62.16 |
| 4048 | CG | ASN | 759 | 9.352 | 34.371 | 30.981 | 1.00 | 60.61 |
| 4049 | OD1 | ASN | 759 | 9.601 | 33.164 | 31.072 | 1.00 | 60.73 |
| 4050 | ND2 | ASN | 759 | 8.379 | 34.965 | 31.683 | 1.00 | 58.61 |
| 4051 | C | ASN | 759 | 11.430 | 35.091 | 27.886 | 1.00 | 63.83 |
| 4052 | O | ASN | 759 | 11.725 | 36.278 | 27.737 | 1.00 | 59.18 |
| 4053 | N | GLN | 760 | 12.191 | 34.099 | 27.439 | 1.00 | 60.77 |
| 4054 | CA | GLN | 760 | 13.431 | 34.395 | 26.742 | 1.00 | 60.74 |
| 4055 | CB | GLN | 760 | 14.637 | 34.295 | 27.690 | 1.00 | 63.92 |
| 4056 | CG | GLN | 760 | 14.546 | 35.101 | 28.992 | 1.00 | 63.35 |
| 4057 | CD | GLN | 760 | 15.114 | 36.508 | 28.896 | 1.00 | 61.91 |
| 4058 | OE1 | GLN | 760 | 16.231 | 36.714 | 28.423 | 1.00 | 61.24 |
| 4059 | NE2 | GLN | 760 | 14.351 | 37.482 | 29.367 | 1.00 | 62.64 |
| 4060 | C | GLN | 760 | 13.687 | 33.482 | 25.554 | 1.00 | 61.67 |
| 4061 | O | GLN | 760 | 14.390 | 33.898 | 24.631 | 1.00 | 58.73 |
| 4062 | N | ILE | 761 | 13.124 | 32.264 | 25.563 | 1.00 | 63.30 |
| 4063 | CA | ILE | 761 | 13.368 | 31.305 | 24.476 | 1.00 | 62.33 |
| 4064 | CB | ILE | 761 | 12.102 | 30.454 | 24.088 | 1.00 | 62.35 |
| 4065 | CG2 | ILE | 761 | 12.345 | 29.721 | 22.777 | 1.00 | 64.29 |
| 4066 | CG1 | ILE | 761 | 11.834 | 29.367 | 25.140 | 1.00 | 60.68 |
| 4067 | CD1 | ILE | 761 | 12.794 | 28.186 | 25.074 | 1.00 | 65.98 |
| 4068 | C | ILE | 761 | 13.925 | 32.069 | 23.273 | 1.00 | 60.92 |
| 4069 | O | ILE | 761 | 15.089 | 31.875 | 22.912 | 1.00 | 60.54 |
| 4070 | N | PRO | 762 | 13.128 | 32.938 | 22.626 | 1.00 | 60.85 |
| 4071 | CD | PRO | 762 | 11.810 | 32.652 | 22.044 | 1.00 | 60.12 |
| 4072 | CA | PRO | 762 | 13.999 | 33.474 | 21.571 | 1.00 | 60.84 |
| 4073 | CB | PRO | 762 | 13.355 | 32.980 | 20.264 | 1.00 | 58.66 |
| 4074 | CG | PRO | 762 | 12.240 | 32.017 | 20.716 | 1.00 | 58.17 |
| 4075 | C | PRO | 762 | 14.222 | 34.968 | 21.533 | 1.00 | 62.93 |
| 4076 | O | PRO | 762 | 14.168 | 35.566 | 20.457 | 1.00 | 59.88 |
| 4077 | N | LYS | 763 | 14.405 | 35.599 | 22.687 | 1.00 | 59.58 |
| 4078 | CA | LYS | 763 | 14.750 | 37.015 | 22.653 | 1.00 | 62.56 |
| 4079 | CB | LYS | 763 | 14.713 | 37.645 | 24.045 | 1.00 | 61.84 |
| 4080 | CG | LYS | 763 | 15.014 | 39.141 | 24.061 | 1.00 | 61.96 |
| 4081 | CD | LYS | 763 | 14.703 | 39.723 | 25.430 | 1.00 | 62.42 |
| 4082 | CE | LYS | 763 | 13.428 | 39.096 | 25.979 | 1.00 | 61.00 |
| 4083 | NZ | LYS | 763 | 12.992 | 39.651 | 27.285 | 1.00 | 62.85 |
| 4084 | C | LYS | 763 | 16.182 | 36.666 | 22.292 | 1.00 | 58.43 |
| 4085 | O | LYS | 763 | 16.780 | 37.217 | 21.354 | 1.00 | 59.83 |
| 4086 | N | TYR | 764 | 16.668 | 35.665 | 23.036 | 1.00 | 59.46 |
| 4087 | CA | TYR | 764 | 17.999 | 35.106 | 22.895 | 1.00 | 61.50 |
| 4088 | CB | TYR | 764 | 18.291 | 34.109 | 24.020 | 1.00 | 62.35 |
| 4089 | CG | TYR | 764 | 19.085 | 34.715 | 25.149 | 1.00 | 57.24 |
| 4090 | CD1 | TYR | 764 | 18.526 | 34.872 | 26.424 | 1.00 | 62.21 |
| 4091 | CE1 | TYR | 764 | 19.236 | 35.509 | 27.451 | 1.00 | 63.69 |
| 4092 | CD2 | TYR | 764 | 20.378 | 35.200 | 24.927 | 1.00 | 62.73 |
| 4093 | CE2 | TYR | 764 | 21.095 | 35.837 | 25.942 | 1.00 | 62.44 |
| 4094 | CZ | TYR | 764 | 20.516 | 35.992 | 27.195 | 1.00 | 65.70 |
| 4095 | OH | TYR | 764 | 21.206 | 36.670 | 28.168 | 1.00 | 63.44 |
| 4096 | C | TYR | 764 | 18.156 | 34.400 | 21.570 | 1.00 | 60.32 |
| 4097 | O | TYR | 764 | 17.580 | 34.816 | 20.556 | 1.00 | 60.80 |
| 4098 | N | SER | 765 | 18.922 | 33.310 | 21.597 | 1.00 | 62.63 |
| 4099 | CA | SER | 765 | 19.209 | 32.535 | 20.391 | 1.00 | 62.57 |
| 4100 | CB | SER | 765 | 17.908 | 31.971 | 19.777 | 1.00 | 63.02 |
| 4101 | OG | SER | 765 | 18.172 | 31.232 | 18.586 | 1.00 | 63.09 |
| 4102 | C | SER | 765 | 19.904 | 33.487 | 19.403 | 1.00 | 61.20 |
| 4103 | O | SER | 765 | 21.121 | 33.703 | 19.474 | 1.00 | 60.85 |
| 4104 | N | ASN | 766 | 19.099 | 34.064 | 18.513 | 1.00 | 59.31 |
| 4105 | CA | ASN | 766 | 19.520 | 35.005 | 17.477 | 1.00 | 61.38 |
| 4106 | CB | ASN | 766 | 18.344 | 35.932 | 17.155 | 1.00 | 63.73 |
| 4107 | CG | ASN | 766 | 17.006 | 35.195 | 17.116 | 1.00 | 60.04 |
| 4108 | OD1 | ASN | 766 | 16.493 | 34.720 | 18.153 | 1.00 | 64.69 |
| 4109 | ND2 | ASN | 766 | 16.433 | 35.091 | 15.916 | 1.00 | 59.73 |
| 4110 | C | ASN | 766 | 20.764 | 35.857 | 17.800 | 1.00 | 64.20 |
| 4111 | O | ASN | 766 | 21.906 | 35.462 | 17.491 | 1.00 | 60.72 |
| 4112 | N | GLY | 767 | 20.523 | 37.032 | 18.396 | 1.00 | 59.36 |
| 4113 | CA | GLY | 767 | 21.589 | 37.961 | 18.766 | 1.00 | 63.17 |
| 4114 | C | GLY | 767 | 21.096 | 39.388 | 19.032 | 1.00 | 61.77 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 4115 | O | GLY | 767 | 21.905 | 40.321 | 19.172 | 1.00 | 58.54 |
| 4116 | N | ASN | 768 | 19.772 | 39.550 | 19.118 | 1.00 | 61.70 |
| 4117 | CA | ASN | 768 | 19.115 | 40.849 | 19.347 | 1.00 | 60.25 |
| 4118 | CB | ASN | 768 | 17.603 | 40.673 | 19.163 | 1.00 | 61.86 |
| 4119 | CG | ASN | 768 | 17.257 | 39.882 | 17.898 | 1.00 | 63.48 |
| 4120 | OD1 | ASN | 768 | 17.602 | 38.702 | 17.772 | 1.00 | 58.87 |
| 4121 | ND2 | ASN | 768 | 16.579 | 40.534 | 16.956 | 1.00 | 59.56 |
| 4122 | C | ASN | 768 | 19.400 | 41.566 | 20.692 | 1.00 | 61.21 |
| 4123 | O | ASN | 768 | 18.781 | 42.595 | 20.987 | 1.00 | 57.65 |
| 4124 | N | ILE | 769 | 20.323 | 41.011 | 21.490 | 1.00 | 60.01 |
| 4125 | CA | ILE | 769 | 20.764 | 41.563 | 22.792 | 1.00 | 60.44 |
| 4126 | CB | ILE | 769 | 20.851 | 40.456 | 23.891 | 1.00 | 60.23 |
| 4127 | CG2 | ILE | 769 | 21.520 | 41.004 | 25.161 | 1.00 | 65.73 |
| 4128 | CG1 | ILE | 769 | 19.461 | 39.920 | 24.234 | 1.00 | 64.63 |
| 4129 | CD1 | ILE | 769 | 19.506 | 38.773 | 25.256 | 1.00 | 63.56 |
| 4130 | C | ILE | 769 | 22.197 | 42.097 | 22.594 | 1.00 | 60.12 |
| 4131 | O | ILE | 769 | 22.744 | 41.990 | 21.495 | 1.00 | 59.38 |
| 4132 | N | LYS | 770 | 22.799 | 42.660 | 23.643 | 1.00 | 58.87 |
| 4133 | CA | LYS | 770 | 24.173 | 43.171 | 23.568 | 1.00 | 63.22 |
| 4134 | CB | LYS | 770 | 24.210 | 44.693 | 23.711 | 1.00 | 61.35 |
| 4135 | CG | LYS | 770 | 25.615 | 45.304 | 23.656 | 1.00 | 60.38 |
| 4136 | CD | LYS | 770 | 25.617 | 46.682 | 24.324 | 1.00 | 59.38 |
| 4137 | CE | LYS | 770 | 26.765 | 47.580 | 23.858 | 1.00 | 63.47 |
| 4138 | NZ | LYS | 770 | 26.704 | 48.946 | 24.493 | 1.00 | 63.76 |
| 4139 | C | LYS | 770 | 25.039 | 42.568 | 24.665 | 1.00 | 59.00 |
| 4140 | O | LYS | 770 | 24.962 | 42.967 | 25.829 | 1.00 | 63.74 |
| 4141 | N | LYS | 771 | 25.868 | 41.604 | 24.292 | 1.00 | 59.72 |
| 4142 | CA | LYS | 771 | 26.742 | 40.984 | 25.268 | 1.00 | 60.78 |
| 4143 | CB | LYS | 771 | 27.024 | 39.525 | 24.871 | 1.00 | 59.33 |
| 4144 | CG | LYS | 771 | 27.854 | 39.345 | 23.619 | 1.00 | 62.03 |
| 4145 | CD | LYS | 771 | 28.351 | 37.906 | 23.466 | 1.00 | 63.82 |
| 4146 | CE | LYS | 771 | 29.538 | 37.838 | 22.501 | 1.00 | 59.76 |
| 4147 | NZ | LYS | 771 | 30.301 | 36.550 | 22.571 | 1.00 | 57.46 |
| 4148 | C | LYS | 771 | 28.044 | 41.798 | 25.413 | 1.00 | 61.42 |
| 4149 | O | LYS | 771 | 28.800 | 41.976 | 24.459 | 1.00 | 58.76 |
| 4150 | N | LEU | 772 | 28.271 | 42.302 | 26.623 | 1.00 | 61.95 |
| 4151 | CA | LEU | 772 | 29.444 | 43.107 | 26.948 | 1.00 | 60.44 |
| 4152 | CB | LEU | 772 | 29.187 | 43.864 | 28.260 | 1.00 | 59.38 |
| 4153 | CG | LEU | 772 | 27.923 | 44.730 | 28.267 | 1.00 | 63.13 |
| 4154 | CD1 | LEU | 772 | 27.630 | 45.253 | 29.656 | 1.00 | 60.11 |
| 4155 | CD2 | LEU | 772 | 28.102 | 45.873 | 27.289 | 1.00 | 62.17 |
| 4156 | C | LEU | 772 | 30.732 | 42.272 | 27.060 | 1.00 | 60.10 |
| 4157 | O | LEU | 772 | 30.764 | 41.233 | 27.718 | 1.00 | 60.79 |
| 4158 | N | LEU | 773 | 31.797 | 42.749 | 26.423 | 1.00 | 61.72 |
| 4159 | CA | LEU | 773 | 33.074 | 42.055 | 26.428 | 1.00 | 60.85 |
| 4160 | CB | LEU | 773 | 33.406 | 41.580 | 25.011 | 1.00 | 62.82 |
| 4161 | CG | LEU | 773 | 32.425 | 40.675 | 24.265 | 1.00 | 63.82 |
| 4162 | CD1 | LEU | 773 | 32.927 | 40.451 | 22.866 | 1.00 | 60.94 |
| 4163 | CD2 | LEU | 773 | 32.285 | 39.352 | 24.966 | 1.00 | 62.11 |
| 4164 | C | LEU | 773 | 34.205 | 42.942 | 26.933 | 1.00 | 63.04 |
| 4165 | O | LEU | 773 | 34.271 | 44.126 | 26.625 | 1.00 | 62.16 |
| 4166 | N | PHE | 774 | 35.101 | 42.352 | 27.712 | 1.00 | 60.13 |
| 4167 | CA | PHE | 774 | 36.246 | 43.072 | 28.248 | 1.00 | 61.57 |
| 4168 | CB | PHE | 774 | 36.893 | 42.279 | 29.377 | 1.00 | 66.09 |
| 4169 | CG | PHE | 774 | 36.280 | 42.543 | 30.698 | 1.00 | 61.67 |
| 4170 | CD1 | PHE | 774 | 36.524 | 43.741 | 31.355 | 1.00 | 59.42 |
| 4171 | CD2 | PHE | 774 | 35.385 | 41.650 | 31.248 | 1.00 | 56.29 |
| 4172 | CE1 | PHE | 774 | 35.879 | 44.050 | 32.536 | 1.00 | 64.79 |
| 4173 | CE2 | PHE | 774 | 34.729 | 41.948 | 32.435 | 1.00 | 61.83 |
| 4174 | CZ | PHE | 774 | 34.978 | 43.155 | 33.080 | 1.00 | 62.07 |
| 4175 | C | PHE | 774 | 37.243 | 43.261 | 27.143 | 1.00 | 58.09 |
| 4176 | O | PHE | 774 | 38.081 | 44.155 | 27.187 | 1.00 | 63.24 |
| 4177 | N | HIS | 775 | 37.131 | 42.398 | 26.143 | 1.00 | 61.71 |
| 4178 | CA | HIS | 775 | 38.022 | 42.419 | 25.007 | 1.00 | 60.58 |
| 4179 | CB | HIS | 775 | 39.060 | 41.319 | 25.175 | 1.00 | 63.99 |
| 4180 | CG | HIS | 775 | 39.763 | 41.365 | 26.492 | 1.00 | 62.38 |
| 4181 | CD2 | HIS | 775 | 39.696 | 40.548 | 27.567 | 1.00 | 61.52 |
| 4182 | ND1 | HIS | 775 | 40.616 | 42.389 | 26.838 | 1.00 | 62.48 |
| 4183 | CE1 | HIS | 775 | 41.042 | 42.202 | 28.074 | 1.00 | 59.32 |
| 4184 | NE2 | HIS | 775 | 40.498 | 41.092 | 28.538 | 1.00 | 62.24 |
| 4185 | C | HIS | 775 | 37.236 | 42.196 | 23.732 | 1.00 | 61.77 |
| 4186 | O | HIS | 775 | 36.461 | 41.252 | 23.633 | 1.00 | 62.62 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 4187 | N | GLN | 776 | 37.425 | 43.083 | 22.765 | 1.00 | 58.75 |
| 4188 | CA | GLN | 776 | 36.759 | 42.955 | 21.484 | 1.00 | 58.47 |
| 4189 | CB | GLN | 776 | 36.460 | 44.340 | 20.893 | 1.00 | 58.08 |
| 4190 | CG | GLN | 776 | 37.681 | 45.247 | 20.680 | 1.00 | 63.95 |
| 4191 | CD | GLN | 776 | 38.236 | 45.221 | 19.250 | 1.00 | 62.81 |
| 4192 | OE1 | GLN | 776 | 39.158 | 45.979 | 18.924 | 1.00 | 62.48 |
| 4193 | NE2 | GLN | 776 | 37.680 | 44.353 | 18.397 | 1.00 | 60.08 |
| 4194 | C | GLN | 776 | 37.724 | 42.163 | 20.599 | 1.00 | 60.33 |
| 4195 | O | GLN | 776 | 37.269 | 41.235 | 19.894 | 1.00 | 61.93 |
| 4196 | OXT | GLN | 776 | 38.936 | 42.474 | 20.642 | 1.00 | 63.26 |
| 4197 | CB | LYS | 741 | 7.500 | 39.003 | 28.905 | 1.00 | 62.43 |
| 4198 | CG | LYS | 741 | 8.600 | 39.530 | 28.004 | 1.00 | 60.91 |
| 4199 | CD | LYS | 741 | 9.141 | 40.875 | 28.431 | 1.00 | 59.52 |
| 4200 | CE | LYS | 741 | 10.182 | 41.314 | 27.418 | 1.00 | 62.38 |
| 4201 | NZ | LYS | 741 | 10.807 | 42.617 | 27.779 | 1.00 | 64.43 |
| 4202 | C | LYS | 741 | 6.303 | 36.975 | 29.773 | 1.00 | 61.31 |
| 4203 | O | LYS | 741 | 6.054 | 35.766 | 29.829 | 1.00 | 59.09 |
| 4204 | N | LYS | 741 | 6.417 | 37.458 | 27.272 | 1.00 | 62.30 |
| 4205 | CA | LYS | 741 | 7.109 | 37.544 | 28.597 | 1.00 | 59.65 |
| 4206 | N | GLU | 742 | 5.905 | 37.867 | 30.689 | 1.00 | 62.69 |
| 4207 | CA | GLU | 742 | 5.163 | 37.547 | 31.917 | 1.00 | 61.65 |
| 4208 | CB | GLU | 742 | 4.672 | 36.083 | 31.926 | 1.00 | 61.06 |
| 4209 | CG | GLU | 742 | 4.087 | 35.564 | 33.257 | 1.00 | 61.09 |
| 4210 | CD | GLU | 742 | 2.705 | 36.123 | 33.568 | 1.00 | 62.31 |
| 4211 | OE1 | GLU | 742 | 2.138 | 35.720 | 34.616 | 1.00 | 57.45 |
| 4212 | OE2 | GLU | 742 | 2.195 | 36.960 | 32.771 | 1.00 | 60.87 |
| 4213 | C | GLU | 742 | 6.112 | 37.794 | 33.099 | 1.00 | 63.06 |
| 4214 | O | GLU | 742 | 5.915 | 38.741 | 33.853 | 1.00 | 61.76 |
| 4215 | N | ASN | 743 | 7.151 | 36.967 | 33.238 | 1.00 | 63.03 |
| 4216 | CA | ASN | 743 | 8.116 | 37.101 | 34.341 | 1.00 | 61.82 |
| 4217 | CB | ASN | 743 | 9.276 | 38.040 | 33.958 | 1.00 | 58.35 |
| 4218 | CG | ASN | 743 | 10.217 | 37.445 | 32.909 | 1.00 | 59.24 |
| 4219 | OD1 | ASN | 743 | 10.071 | 37.693 | 31.699 | 1.00 | 60.28 |
| 4220 | ND2 | ASN | 743 | 11.198 | 36.658 | 33.372 | 1.00 | 60.70 |
| 4221 | C | ASN | 743 | 7.447 | 37.656 | 35.604 | 1.00 | 61.37 |
| 4222 | O | ASN | 743 | 8.010 | 38.522 | 36.284 | 1.00 | 60.15 |
| 4223 | N | ALA | 744 | 6.245 | 37.167 | 35.907 | 1.00 | 60.68 |
| 4224 | CA | ALA | 744 | 5.497 | 37.626 | 37.073 | 1.00 | 62.31 |
| 4225 | CB | ALA | 744 | 4.024 | 37.229 | 36.940 | 1.00 | 62.38 |
| 4226 | C | ALA | 744 | 6.080 | 37.067 | 38.364 | 1.00 | 61.35 |
| 4227 | O | ALA | 744 | 6.168 | 37.778 | 39.360 | 1.00 | 59.70 |
| 4228 | N | LEU | 745 | 6.490 | 35.801 | 38.346 | 1.00 | 61.20 |
| 4229 | CA | LEU | 745 | 7.062 | 35.182 | 39.538 | 1.00 | 59.93 |
| 4230 | CB | LEU | 745 | 7.419 | 33.710 | 39.276 | 1.00 | 63.15 |
| 4231 | CG | LEU | 745 | 7.255 | 32.720 | 40.448 | 1.00 | 63.24 |
| 4232 | CD1 | LEU | 745 | 8.022 | 31.429 | 40.158 | 1.00 | 59.45 |
| 4233 | CD2 | LEU | 745 | 7.759 | 33.342 | 41.745 | 1.00 | 59.90 |
| 4234 | C | LEU | 745 | 8.313 | 35.934 | 39.987 | 1.00 | 59.41 |
| 4235 | O | LEU | 745 | 8.520 | 36.123 | 41.182 | 1.00 | 59.83 |
| 4236 | N | LEU | 746 | 9.137 | 36.372 | 39.031 | 1.00 | 63.44 |
| 4237 | CA | LEU | 746 | 10.375 | 37.096 | 39.350 | 1.00 | 60.90 |
| 4238 | CB | LEU | 746 | 11.266 | 37.239 | 38.104 | 1.00 | 63.43 |
| 4239 | CG | LEU | 746 | 12.771 | 36.991 | 38.300 | 1.00 | 64.10 |
| 4240 | CD1 | LEU | 746 | 13.540 | 37.598 | 37.140 | 1.00 | 61.93 |
| 4241 | CD2 | LEU | 746 | 13.248 | 37.598 | 39.612 | 1.00 | 58.02 |
| 4242 | C | LEU | 746 | 10.120 | 38.485 | 39.950 | 1.00 | 65.26 |
| 4243 | O | LEU | 746 | 10.649 | 38.808 | 41.025 | 1.00 | 59.76 |
| 4244 | N | ARG | 747 | 9.334 | 39.308 | 39.255 | 1.00 | 61.19 |
| 4245 | CA | ARG | 747 | 9.012 | 40.641 | 39.762 | 1.00 | 61.73 |
| 4246 | CB | ARG | 747 | 7.844 | 41.256 | 38.975 | 1.00 | 59.04 |
| 4247 | CG | ARG | 747 | 7.475 | 42.676 | 39.421 | 1.00 | 57.13 |
| 4248 | CD | ARG | 747 | 6.596 | 43.434 | 38.407 | 1.00 | 58.93 |
| 4249 | NE | ARG | 747 | 7.362 | 44.324 | 37.522 | 1.00 | 59.01 |
| 4250 | CZ | ARG | 747 | 7.556 | 44.118 | 36.221 | 1.00 | 59.60 |
| 4251 | NH1 | ARG | 747 | 7.039 | 43.043 | 35.624 | 1.00 | 63.96 |
| 4252 | NH2 | ARG | 747 | 8.272 | 44.987 | 35.518 | 1.00 | 60.37 |
| 4253 | C | ARG | 747 | 8.651 | 40.511 | 41.247 | 1.00 | 61.37 |
| 4254 | O | ARG | 747 | 9.155 | 41.257 | 42.090 | 1.00 | 62.28 |
| 4255 | N | TYR | 748 | 7.799 | 39.541 | 41.565 | 1.00 | 62.06 |
| 4256 | CA | TYR | 748 | 7.399 | 39.306 | 42.941 | 1.00 | 60.54 |
| 4257 | CB | TYR | 748 | 6.517 | 38.050 | 43.003 | 1.00 | 60.69 |
| 4258 | CG | TYR | 748 | 6.287 | 37.521 | 44.401 | 1.00 | 59.67 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 4259 | CD1 | TYR | 748 | 7.077 | 36.488 | 44.908 | 1.00 | 60.21 |
| 4260 | CE1 | TYR | 748 | 6.926 | 36.044 | 46.209 | 1.00 | 60.77 |
| 4261 | CD2 | TYR | 748 | 5.329 | 38.093 | 45.240 | 1.00 | 63.30 |
| 4262 | CE2 | TYR | 748 | 5.174 | 37.654 | 46.550 | 1.00 | 61.08 |
| 4263 | CZ | TYR | 748 | 5.977 | 36.631 | 47.027 | 1.00 | 62.49 |
| 4264 | OH | TYR | 748 | 5.864 | 36.204 | 48.331 | 1.00 | 59.76 |
| 4265 | C | TYR | 748 | 8.593 | 39.190 | 43.908 | 1.00 | 63.27 |
| 4266 | O | TYR | 748 | 8.702 | 39.969 | 44.857 | 1.00 | 60.19 |
| 4267 | N | LEU | 749 | 9.484 | 38.229 | 43.663 | 1.00 | 62.27 |
| 4268 | CA | LEU | 749 | 10.661 | 38.008 | 44.516 | 1.00 | 62.12 |
| 4269 | CB | LEU | 749 | 11.454 | 36.792 | 44.020 | 1.00 | 64.20 |
| 4270 | CG | LEU | 749 | 10.690 | 35.476 | 43.873 | 1.00 | 58.72 |
| 4271 | CD1 | LEU | 749 | 11.058 | 34.828 | 42.554 | 1.00 | 61.26 |
| 4272 | CD2 | LEU | 749 | 10.986 | 34.565 | 45.039 | 1.00 | 61.68 |
| 4273 | C | LEU | 749 | 11.589 | 39.223 | 44.561 | 1.00 | 61.27 |
| 4274 | O | LEU | 749 | 12.241 | 39.497 | 45.571 | 1.00 | 60.09 |
| 4275 | N | LEU | 750 | 11.658 | 39.946 | 43.455 | 1.00 | 60.39 |
| 4276 | CA | LEU | 750 | 12.503 | 41.120 | 43.397 | 1.00 | 59.95 |
| 4277 | CB | LEU | 750 | 12.603 | 41.607 | 41.959 | 1.00 | 59.67 |
| 4278 | CG | LEU | 750 | 14.026 | 41.742 | 41.404 | 1.00 | 65.62 |
| 4279 | CD1 | LEU | 750 | 15.031 | 40.919 | 42.205 | 1.00 | 61.72 |
| 4280 | CD2 | LEU | 750 | 14.005 | 41.302 | 39.953 | 1.00 | 61.66 |
| 4281 | C | LEU | 750 | 11.954 | 42.216 | 44.298 | 1.00 | 58.16 |
| 4282 | O | LEU | 750 | 12.712 | 42.855 | 45.032 | 1.00 | 61.93 |
| 4283 | N | ASP | 751 | 10.637 | 42.423 | 44.242 | 1.00 | 60.02 |
| 4284 | CA | ASP | 751 | 9.969 | 43.428 | 45.073 | 1.00 | 61.63 |
| 4285 | CB | ASP | 751 | 8.539 | 43.658 | 44.616 | 1.00 | 59.82 |
| 4286 | CG | ASP | 751 | 8.381 | 44.973 | 43.912 | 1.00 | 60.49 |
| 4287 | OD1 | ASP | 751 | 9.166 | 45.214 | 42.968 | 1.00 | 59.40 |
| 4288 | OD2 | ASP | 751 | 7.491 | 45.767 | 44.298 | 1.00 | 59.17 |
| 4289 | C | ASP | 751 | 9.941 | 43.037 | 46.531 | 1.00 | 62.48 |
| 4290 | O | ASP | 751 | 10.367 | 43.813 | 47.383 | 1.00 | 63.09 |
| 4291 | N | LYS | 752 | 9.421 | 41.841 | 46.808 | 1.00 | 64.09 |
| 4292 | CA | LYS | 752 | 9.346 | 41.308 | 48.164 | 1.00 | 60.89 |
| 4293 | CB | LYS | 752 | 9.881 | 39.882 | 48.216 | 1.00 | 63.21 |
| 4294 | CG | LYS | 752 | 9.051 | 38.811 | 47.568 | 1.00 | 57.72 |
| 4295 | CD | LYS | 752 | 9.168 | 37.532 | 48.396 | 1.00 | 60.58 |
| 4296 | CE | LYS | 752 | 8.769 | 37.801 | 49.858 | 1.00 | 63.26 |
| 4297 | NZ | LYS | 752 | 8.598 | 36.571 | 50.686 | 1.00 | 60.07 |
| 4298 | C | LYS | 752 | 10.218 | 42.123 | 49.090 | 1.00 | 59.75 |
| 4299 | O | LYS | 752 | 11.426 | 42.228 | 48.869 | 1.00 | 61.26 |
| 4300 | N | ASP | 753 | 9.644 | 42.700 | 50.132 | 1.00 | 64.75 |
| 4301 | CA | ASP | 753 | 10.478 | 43.462 | 51.039 | 1.00 | 60.32 |
| 4302 | CB | ASP | 753 | 9.643 | 44.126 | 52.126 | 1.00 | 62.72 |
| 4303 | CG | ASP | 753 | 10.496 | 44.762 | 53.198 | 1.00 | 62.87 |
| 4304 | OD1 | ASP | 753 | 11.420 | 45.549 | 52.863 | 1.00 | 59.14 |
| 4305 | OD2 | ASP | 753 | 10.239 | 44.468 | 54.382 | 1.00 | 63.19 |
| 4306 | C | ASP | 753 | 11.455 | 42.468 | 51.647 | 1.00 | 60.33 |
| 4307 | O | ASP | 753 | 12.111 | 42.750 | 52.646 | 1.00 | 61.12 |
| 4308 | N | ALA | 754 | 11.528 | 41.304 | 51.008 | 1.00 | 59.93 |
| 4309 | CA | ALA | 754 | 12.396 | 40.177 | 51.356 | 1.00 | 61.16 |
| 4310 | CB | ALA | 754 | 12.896 | 39.509 | 50.053 | 1.00 | 64.36 |
| 4311 | C | ALA | 754 | 13.587 | 40.401 | 52.307 | 1.00 | 59.44 |
| 4312 | O | ALA | 754 | 14.700 | 39.937 | 52.047 | 1.00 | 61.71 |
| 4313 | N | THR | 755 | 13.355 | 41.108 | 53.403 | 1.00 | 60.67 |
| 4314 | CA | THR | 755 | 14.375 | 41.342 | 54.420 | 1.00 | 60.98 |
| 4315 | CB | THR | 755 | 15.250 | 42.613 | 54.137 | 1.00 | 63.96 |
| 4316 | OG1 | THR | 755 | 14.460 | 43.794 | 54.313 | 1.00 | 60.28 |
| 4317 | CG2 | THR | 755 | 15.824 | 42.582 | 52.696 | 1.00 | 57.43 |
| 4318 | C | THR | 755 | 13.505 | 41.499 | 55.671 | 1.00 | 59.27 |
| 4319 | O | THR | 755 | 13.323 | 42.586 | 56.237 | 1.00 | 60.51 |
| 4320 | N | ALA | 756 | 12.918 | 40.356 | 56.024 | 1.00 | 62.21 |
| 4321 | CA | ALA | 756 | 12.025 | 40.165 | 57.162 | 1.00 | 59.83 |
| 4322 | CB | ALA | 756 | 11.075 | 38.993 | 56.870 | 1.00 | 60.21 |
| 4323 | C | ALA | 756 | 12.890 | 39.842 | 58.372 | 1.00 | 61.08 |
| 4324 | O | ALA | 756 | 12.461 | 39.941 | 59.531 | 1.00 | 61.80 |
| 4325 | N | ALA | 757 | 14.115 | 39.426 | 58.072 | 1.00 | 62.43 |
| 4326 | CA | ALA | 757 | 15.087 | 39.099 | 59.092 | 1.00 | 60.57 |
| 4327 | CB | ALA | 757 | 16.415 | 38.753 | 58.431 | 1.00 | 60.81 |
| 4328 | C | ALA | 757 | 15.211 | 40.367 | 59.932 | 1.00 | 61.35 |
| 4329 | O | ALA | 757 | 15.146 | 41.460 | 59.327 | 1.00 | 62.10 |
| 4330 | OXT | ALA | 757 | 15.354 | 40.253 | 61.169 | 1.00 | 58.48 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 4331 | O | HOH | 1 | 62.349 | −1.370 | 59.183 | 1.00 | 61.82 |
| 4332 | O | HOH | 2 | 63.098 | 9.775 | 56.010 | 1.00 | 63.21 |
| 4333 | O | HOH | 3 | 29.467 | 50.468 | 47.493 | 1.00 | 60.82 |
| 4334 | O | HOH | 4 | 24.799 | 1.025 | 51.054 | 1.00 | 63.04 |
| 4335 | O | HOH | 5 | 25.120 | 35.371 | 29.890 | 1.00 | 58.53 |
| 4336 | O | HOH | 6 | 62.603 | 13.819 | 69.179 | 1.00 | 62.10 |
| 4337 | O | HOH | 7 | 43.394 | −0.575 | 64.086 | 1.00 | 61.07 |
| 4338 | O | HOH | 8 | 33.029 | 27.080 | 24.812 | 1.00 | 63.53 |
| 4339 | O | HOH | 9 | 40.476 | 0.604 | 50.517 | 1.00 | 62.87 |
| 4340 | O | HOH | 10 | 42.083 | 33.017 | 29.431 | 1.00 | 59.31 |
| 4341 | O | HOH | 11 | 40.224 | −1.905 | 63.310 | 1.00 | 60.38 |
| 4342 | O | HOH | 12 | 29.926 | 49.219 | 30.317 | 1.00 | 60.19 |
| 4343 | O | HOH | 13 | 63.481 | 3.211 | 57.703 | 1.00 | 62.93 |
| 4344 | O | HOH | 14 | 45.679 | 44.833 | 38.756 | 1.00 | 60.97 |
| 4345 | O | HOH | 15 | 21.388 | 1.839 | 41.400 | 1.00 | 61.41 |
| 4346 | O | HOH | 16 | 47.452 | −16.061 | 63.707 | 1.00 | 60.73 |
| 4347 | O | HOH | 17 | 52.653 | 15.955 | 63.901 | 1.00 | 64.75 |
| 4348 | O | HOH | 18 | 62.913 | 1.964 | 67.923 | 1.00 | 64.33 |
| 4349 | O | HOH | 19 | 62.507 | 3.936 | 69.792 | 1.00 | 60.95 |
| 4350 | O | HOH | 20 | 11.730 | 26.749 | 44.436 | 1.00 | 60.79 |
| 4351 | O | HOH | 21 | 48.735 | 13.308 | 64.587 | 1.00 | 62.06 |
| 4352 | O | HOH | 22 | 32.377 | 39.863 | 58.144 | 1.00 | 63.51 |
| 4353 | O | HOH | 23 | 58.924 | 9.831 | 70.947 | 1.00 | 61.40 |
| 4354 | O | HOH | 24 | 39.278 | 17.448 | 64.290 | 1.00 | 62.12 |
| 4355 | O | HOH | 25 | 40.573 | 48.042 | 36.816 | 1.00 | 60.96 |
| 4356 | O | HOH | 26 | 40.494 | 35.299 | 48.387 | 1.00 | 59.93 |
| 4357 | O | HOH | 27 | 61.454 | 1.678 | 61.901 | 1.00 | 60.51 |
| 4358 | O | HOH | 28 | 9.075 | 22.638 | 42.296 | 1.00 | 61.65 |
| 4359 | O | HOH | 29 | 51.369 | 13.900 | 63.592 | 1.00 | 64.00 |
| 4360 | O | HOH | 30 | 61.184 | −0.481 | 44.937 | 1.00 | 61.95 |
| 4361 | O | HOH | 31 | 19.041 | 16.035 | 52.737 | 1.00 | 60.85 |
| 4362 | O | HOH | 32 | 37.487 | 3.963 | 49.092 | 1.00 | 60.40 |
| 4363 | O | HOH | 33 | 31.183 | 34.399 | 55.395 | 1.00 | 61.32 |
| 4364 | O | HOH | 34 | 25.672 | 33.490 | 53.795 | 1.00 | 61.76 |
| 4365 | O | HOH | 35 | 24.467 | 27.177 | 45.107 | 1.00 | 62.37 |
| 4366 | O | HOH | 36 | 47.899 | 30.685 | 35.691 | 1.00 | 60.62 |
| 4367 | O | HOH | 37 | 31.250 | 45.014 | 24.427 | 1.00 | 63.26 |
| 4368 | O | HOH | 38 | 60.719 | −0.340 | 49.987 | 1.00 | 60.94 |
| 4369 | O | HOH | 39 | 48.761 | 14.305 | 46.147 | 1.00 | 59.45 |
| 4370 | O | HOH | 40 | 52.252 | 11.824 | 45.533 | 1.00 | 59.86 |
| 4371 | O | HOH | 41 | 40.704 | 30.604 | 47.765 | 1.00 | 62.04 |
| 4372 | O | HOH | 42 | 34.599 | 19.541 | 73.265 | 1.00 | 61.69 |
| 4373 | O | HOH | 43 | 44.135 | 32.951 | 48.092 | 1.00 | 60.11 |
| 4374 | O | HOH | 44 | 16.447 | 16.136 | 55.224 | 1.00 | 58.77 |
| 4375 | O | HOH | 45 | 37.470 | 21.079 | 29.057 | 1.00 | 61.47 |
| 4376 | O | HOH | 46 | 14.411 | 15.785 | 52.085 | 1.00 | 58.97 |
| 4377 | O | HOH | 47 | 27.199 | 25.588 | 51.919 | 1.00 | 58.58 |
| 4378 | O | HOH | 48 | 32.466 | 25.097 | 53.254 | 1.00 | 60.88 |
| 4379 | O | HOH | 49 | 17.927 | 39.612 | 49.972 | 1.00 | 61.48 |
| 4380 | O | HOH | 50 | 17.243 | 38.022 | 52.339 | 1.00 | 61.61 |
| 4381 | O | HOH | 51 | 65.714 | 6.374 | 72.458 | 1.00 | 61.45 |
| 4382 | O | HOH | 52 | 25.540 | 34.686 | 57.601 | 1.00 | 59.81 |
| 4383 | O | HOH | 53 | 22.812 | 3.452 | 38.767 | 1.00 | 62.42 |
| 4384 | C1 | DEX | 1 | 31.791 | 3.330 | 56.615 | 1.00 | 59.00 |
| 4385 | H1 | DEX | 1 | 30.892 | 2.719 | 56.626 | 1.00 | 59.00 |
| 4386 | C2 | DEX | 1 | 32.066 | 4.057 | 55.552 | 1.00 | 59.00 |
| 4387 | H2 | DEX | 1 | 31.418 | 4.016 | 54.717 | 1.00 | 59.00 |
| 4388 | C3 | DEX | 1 | 33.314 | 4.929 | 55.514 | 1.00 | 59.00 |
| 4389 | C4 | DEX | 1 | 34.176 | 5.061 | 56.733 | 1.00 | 59.00 |
| 4390 | H4 | DEX | 1 | 35.013 | 5.729 | 56.720 | 1.00 | 59.00 |
| 4391 | C5 | DEX | 1 | 33.915 | 4.329 | 57.855 | 1.00 | 59.00 |
| 4392 | C6 | DEX | 1 | 34.782 | 4.456 | 59.133 | 1.00 | 59.00 |
| 4393 | H61 | DEX | 1 | 35.558 | 5.172 | 59.015 | 1.00 | 59.00 |
| 4394 | H62 | DEX | 1 | 35.262 | 3.483 | 59.339 | 1.00 | 59.00 |
| 4395 | C7 | DEX | 1 | 33.905 | 4.834 | 60.331 | 1.00 | 59.00 |
| 4396 | H71 | DEX | 1 | 33.520 | 5.861 | 60.202 | 1.00 | 59.00 |
| 4397 | H72 | DEX | 1 | 34.515 | 4.837 | 61.236 | 1.00 | 59.00 |
| 4398 | C8 | DEX | 1 | 32.690 | 3.903 | 60.544 | 1.00 | 59.00 |
| 4399 | H8 | DEX | 1 | 33.063 | 2.878 | 60.787 | 1.00 | 59.00 |
| 4400 | C9 | DEX | 1 | 31.759 | 3.803 | 59.162 | 1.00 | 59.00 |
| 4401 | C10 | DEX | 1 | 32.677 | 3.304 | 57.900 | 1.00 | 59.00 |
| 4402 | C11 | DEX | 1 | 30.360 | 2.986 | 59.327 | 1.00 | 59.00 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 4403 | H11 | DEX | 1 | 29.743 | 3.203 | 58.478 | 1.00 | 59.00 |
| 4404 | C12 | DEX | 1 | 29.599 | 3.415 | 60.596 | 1.00 | 59.00 |
| 4405 | H121 | DEX | 1 | 28.744 | 2.788 | 60.729 | 1.00 | 59.00 |
| 4406 | H122 | DEX | 1 | 29.221 | 4.448 | 60.436 | 1.00 | 59.00 |
| 4407 | C13 | DEX | 1 | 30.518 | 3.414 | 61.924 | 1.00 | 59.00 |
| 4408 | C14 | DEX | 1 | 31.758 | 4.387 | 61.726 | 1.00 | 59.00 |
| 4409 | H14 | DEX | 1 | 31.359 | 5.403 | 61.401 | 1.00 | 59.00 |
| 4410 | C15 | DEX | 1 | 32.374 | 4.589 | 63.095 | 1.00 | 59.00 |
| 4411 | H151 | DEX | 1 | 32.893 | 5.547 | 63.111 | 1.00 | 59.00 |
| 4412 | H152 | DEX | 1 | 33.119 | 3.796 | 63.281 | 1.00 | 59.00 |
| 4413 | C16 | DEX | 1 | 31.175 | 4.486 | 64.093 | 1.00 | 59.00 |
| 4414 | H16 | DEX | 1 | 31.391 | 3.605 | 64.743 | 1.00 | 59.00 |
| 4415 | C17 | DEX | 1 | 29.863 | 4.144 | 63.168 | 1.00 | 59.00 |
| 4416 | C18 | DEX | 1 | 30.929 | 1.834 | 62.325 | 1.00 | 59.00 |
| 4417 | H181 | DEX | 1 | 31.535 | 1.833 | 63.241 | 1.00 | 59.00 |
| 4418 | H182 | DEX | 1 | 30.050 | 1.248 | 62.496 | 1.00 | 59.00 |
| 4419 | H183 | DEX | 1 | 31.537 | 1.374 | 61.558 | 1.00 | 59.00 |
| 4420 | C19 | DEX | 1 | 33.270 | 1.833 | 58.015 | 1.00 | 59.00 |
| 4421 | H191 | DEX | 1 | 33.916 | 1.724 | 58.905 | 1.00 | 59.00 |
| 4422 | H192 | DEX | 1 | 32.485 | 1.095 | 58.112 | 1.00 | 59.00 |
| 4423 | H193 | DEX | 1 | 33.870 | 1.605 | 57.134 | 1.00 | 59.00 |
| 4424 | C20 | DEX | 1 | 28.759 | 3.270 | 63.873 | 1.00 | 59.00 |
| 4425 | C21 | DEX | 1 | 27.338 | 3.348 | 63.353 | 1.00 | 59.00 |
| 4426 | H211 | DEX | 1 | 27.350 | 3.637 | 62.283 | 1.00 | 59.00 |
| 4427 | H212 | DEX | 1 | 26.827 | 4.148 | 63.876 | 1.00 | 59.00 |
| 4428 | C22 | DEX | 1 | 31.008 | 5.693 | 64.947 | 1.00 | 59.00 |
| 4429 | H221 | DEX | 1 | 30.160 | 5.560 | 65.619 | 1.00 | 59.00 |
| 4430 | H222 | DEX | 1 | 31.912 | 5.877 | 65.542 | 1.00 | 59.00 |
| 4431 | H223 | DEX | 1 | 30.811 | 6.588 | 64.313 | 1.00 | 59.00 |
| 4432 | F1 | DEX | 1 | 31.331 | 5.130 | 58.833 | 1.00 | 59.00 |
| 4433 | O1 | DEX | 1 | 33.617 | 5.512 | 54.507 | 1.00 | 59.00 |
| 4434 | O2 | DEX | 1 | 30.601 | 1.580 | 59.361 | 1.00 | 59.00 |
| 4435 | HO2 | DEX | 1 | 29.784 | 1.163 | 59.706 | 1.00 | 59.00 |
| 4436 | O3 | DEX | 1 | 29.236 | 5.409 | 62.711 | 1.00 | 59.00 |
| 4437 | H3 | DEX | 1 | 28.816 | 5.780 | 63.475 | 1.00 | 59.00 |
| 4438 | O4 | DEX | 1 | 29.058 | 2.511 | 64.818 | 1.00 | 59.00 |
| 4439 | O5 | DEX | 1 | 26.689 | 2.117 | 63.492 | 1.00 | 59.00 |
| 4440 | H5 | DEX | 1 | 25.816 | 2.344 | 63.756 | 1.00 | 59.00 |
| 4441 | C1 | DEX | 1 | 21.344 | 23.582 | 37.624 | 1.00 | 59.00 |
| 4442 | H1 | DEX | 1 | 20.325 | 23.208 | 37.634 | 1.00 | 59.00 |
| 4443 | C2 | DEX | 1 | 22.105 | 23.392 | 38.670 | 1.00 | 59.00 |
| 4444 | H2 | DEX | 1 | 21.710 | 22.910 | 39.509 | 1.00 | 59.00 |
| 4445 | C3 | DEX | 1 | 23.539 | 23.892 | 38.687 | 1.00 | 59.00 |
| 4446 | C4 | DEX | 1 | 24.137 | 24.501 | 37.450 | 1.00 | 59.00 |
| 4447 | H4 | DEX | 1 | 25.173 | 24.791 | 37.441 | 1.00 | 59.00 |
| 4448 | C5 | DEX | 1 | 23.372 | 24.700 | 36.346 | 1.00 | 59.00 |
| 4449 | C6 | DEX | 1 | 23.965 | 25.312 | 35.061 | 1.00 | 59.00 |
| 4450 | H61 | DEX | 1 | 24.996 | 25.542 | 35.157 | 1.00 | 59.00 |
| 4451 | H62 | DEX | 1 | 23.444 | 26.267 | 34.853 | 1.00 | 59.00 |
| 4452 | C7 | DEX | 1 | 23.752 | 24.345 | 33.877 | 1.00 | 59.00 |
| 4453 | H71 | DEX | 1 | 24.370 | 23.444 | 34.001 | 1.00 | 59.00 |
| 4454 | H72 | DEX | 1 | 24.092 | 24.829 | 32.956 | 1.00 | 59.00 |
| 4455 | C8 | DEX | 1 | 22.275 | 23.885 | 33.692 | 1.00 | 59.00 |
| 4456 | H8 | DEX | 1 | 21.638 | 24.764 | 33.460 | 1.00 | 59.00 |
| 4457 | C9 | DEX | 1 | 21.676 | 23.232 | 35.081 | 1.00 | 59.00 |
| 4458 | C10 | DEX | 1 | 21.819 | 24.294 | 36.329 | 1.00 | 59.00 |
| 4459 | C11 | DEX | 1 | 20.197 | 22.585 | 34.938 | 1.00 | 59.00 |
| 4460 | H11 | DEX | 1 | 20.028 | 21.974 | 35.784 | 1.00 | 59.00 |
| 4461 | C12 | DEX | 1 | 20.107 | 21.699 | 33.700 | 1.00 | 59.00 |
| 4462 | H121 | DEX | 1 | 19.130 | 21.365 | 33.602 | 1.00 | 59.00 |
| 4463 | H122 | DEX | 1 | 20.720 | 20.795 | 33.859 | 1.00 | 59.00 |
| 4464 | C13 | DEX | 1 | 20.600 | 22.429 | 32.344 | 1.00 | 59.00 |
| 4465 | C14 | DEX | 1 | 22.105 | 22.863 | 32.515 | 1.00 | 59.00 |
| 4466 | H14 | DEX | 1 | 22.701 | 21.953 | 32.834 | 1.00 | 59.00 |
| 4467 | C15 | DEX | 1 | 22.602 | 23.242 | 31.129 | 1.00 | 59.00 |
| 4468 | H151 | DEX | 1 | 23.685 | 23.110 | 31.097 | 1.00 | 59.00 |
| 4469 | H152 | DEX | 1 | 22.383 | 24.310 | 30.934 | 1.00 | 59.00 |
| 4470 | C16 | DEX | 1 | 21.806 | 22.306 | 30.152 | 1.00 | 59.00 |
| 4471 | H16 | DEX | 1 | 21.207 | 22.984 | 29.504 | 1.00 | 59.00 |
| 4472 | C17 | DEX | 1 | 20.783 | 21.450 | 31.097 | 1.00 | 59.00 |
| 4473 | C18 | DEX | 1 | 19.540 | 23.677 | 31.944 | 1.00 | 59.00 |
| 4474 | H181 | DEX | 1 | 19.873 | 24.157 | 31.015 | 1.00 | 59.00 |

TABLE 4-continued

ATOMIC STRUCTURE COORDINATE DATA OBTAINED FROM X-RAY DIFFRACTION FROM THE LIGAND BINDING DOMAIN OF GRα IN COMPLEX WITH DEXAMETHASONE

| ATOM | ATOM TYPE | RESIDUE | PROTEIN # | # | X | Y | OCC | B |
|---|---|---|---|---|---|---|---|---|
| 4475 | H182 | DEX | 1 | 18.547 | 23.297 | 31.792 | 1.00 | 59.00 |
| 4476 | H183 | DEX | 1 | 19.525 | 24.449 | 32.700 | 1.00 | 59.00 |
| 4477 | C19 | DEX | 1 | 20.959 | 25.638 | 36.205 | 1.00 | 59.00 |
| 4478 | H191 | DEX | 1 | 21.232 | 26.215 | 35.303 | 1.00 | 59.00 |
| 4479 | H192 | DEX | 1 | 19.899 | 25.426 | 36.127 | 1.00 | 59.00 |
| 4480 | H193 | DEX | 1 | 21.132 | 26.270 | 37.072 | 1.00 | 59.00 |
| 4481 | C20 | DEX | 1 | 19.417 | 21.067 | 30.421 | 1.00 | 59.00 |
| 4482 | C21 | DEX | 1 | 18.443 | 20.176 | 31.204 | 1.00 | 59.00 |
| 4483 | H211 | DEX | 1 | 17.932 | 20.800 | 31.959 | 1.00 | 59.00 |
| 4484 | H212 | DEX | 1 | 19.031 | 19.423 | 31.779 | 1.00 | 59.00 |
| 4485 | C22 | DEX | 1 | 22.671 | 21.454 | 29.301 | 1.00 | 59.00 |
| 4486 | H221 | DEX | 1 | 22.061 | 20.835 | 28.644 | 1.00 | 59.00 |
| 4487 | H222 | DEX | 1 | 23.334 | 22.077 | 28.688 | 1.00 | 59.00 |
| 4488 | H223 | DEX | 1 | 23.300 | 20.785 | 29.933 | 1.00 | 59.00 |
| 4489 | F1 | DEX | 1 | 22.519 | 22.128 | 35.397 | 1.00 | 59.00 |
| 4490 | O1 | DEX | 1 | 24.201 | 23.808 | 39.692 | 1.00 | 59.00 |
| 4491 | O2 | DEX | 1 | 19.179 | 23.598 | 34.905 | 1.00 | 59.00 |
| 4492 | HO2 | DEX | 1 | 18.367 | 23.168 | 34.580 | 1.00 | 59.00 |
| 4493 | O3 | DEX | 1 | 21.444 | 20.210 | 31.554 | 1.00 | 59.00 |
| 4494 | H3 | DEX | 1 | 21.502 | 19.648 | 30.802 | 1.00 | 59.00 |
| 4495 | O4 | DEX | 1 | 19.127 | 21.505 | 29.299 | 1.00 | 59.00 |
| 4496 | O5 | DEX | 1 | 17.530 | 19.572 | 30.381 | 1.00 | 59.00 |
| 4497 | H5 | DEX | 1 | 17.435 | 18.711 | 30.744 | 1.00 | 59.00 |

TABLE 5

ATOMIC COORDINATES FOR THE GR/SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1 | N | GLN | 527 | −10.228 | 40.054 | 15.641 | 1.00 | 69.36 |
| 2 | CA | GLN | 527 | −10.481 | 38.584 | 15.329 | 1.00 | 66.54 |
| 3 | C | GLN | 527 | −9.230 | 37.821 | 15.751 | 1.00 | 66.47 |
| 4 | O | GLN | 527 | −9.189 | 37.229 | 16.832 | 1.00 | 66.82 |
| 5 | CB | GLN | 527 | −10.824 | 38.264 | 13.878 | 1.00 | 68.47 |
| 6 | CG | GLN | 527 | −11.131 | 36.765 | 13.555 | 1.00 | 99.90 |
| 7 | CD | GLN | 527 | −11.424 | 36.357 | 12.106 | 1.00 | 99.90 |
| 8 | OE1 | GLN | 527 | −11.629 | 35.191 | 11.807 | 1.00 | 99.90 |
| 9 | NE2 | GLN | 527 | −11.432 | 37.263 | 11.161 | 1.00 | 99.90 |
| 10 | N | LEU | 528 | −8.211 | 37.835 | 14.896 | 1.00 | 63.30 |
| 11 | CA | LEU | 528 | −6.966 | 37.146 | 15.198 | 1.00 | 60.85 |
| 12 | C | LEU | 528 | −5.949 | 38.070 | 15.865 | 1.00 | 56.94 |
| 13 | O | LEU | 528 | −5.120 | 37.612 | 16.653 | 1.00 | 54.60 |
| 14 | CB | LEU | 528 | −6.361 | 36.538 | 13.925 | 1.00 | 61.13 |
| 15 | CG | LEU | 528 | −7.168 | 35.430 | 13.235 | 1.00 | 66.50 |
| 16 | CD1 | LEU | 528 | −6.400 | 34.910 | 12.020 | 1.00 | 60.00 |
| 17 | CD2 | LEU | 528 | −7.426 | 34.291 | 14.214 | 1.00 | 59.53 |
| 18 | N | THR | 529 | −6.012 | 39.362 | 15.551 | 1.00 | 52.97 |
| 19 | CA | THR | 529 | −5.083 | 40.319 | 16.141 | 1.00 | 48.69 |
| 20 | C | THR | 529 | −5.489 | 40.584 | 17.589 | 1.00 | 46.25 |
| 21 | O | THR | 529 | −6.595 | 41.044 | 17.853 | 1.00 | 41.04 |
| 22 | CB | THR | 529 | −5.082 | 41.664 | 15.381 | 1.00 | 52.18 |
| 23 | OG1 | THR | 529 | −4.666 | 41.475 | 14.034 | 1.00 | 99.90 |
| 24 | CG2 | THR | 529 | −4.139 | 42.758 | 15.927 | 1.00 | 99.90 |
| 25 | N | PRO | 530 | −4.595 | 40.292 | 18.548 | 1.00 | 40.66 |
| 26 | CA | PRO | 530 | −4.883 | 40.507 | 19.968 | 1.00 | 39.82 |
| 27 | C | PRO | 530 | −5.301 | 41.950 | 20.272 | 1.00 | 36.13 |
| 28 | O | PRO | 530 | −4.811 | 42.889 | 19.648 | 1.00 | 35.64 |
| 29 | CB | PRO | 530 | −3.570 | 40.108 | 20.640 | 1.00 | 34.22 |
| 30 | CG | PRO | 530 | −3.073 | 39.021 | 19.725 | 1.00 | 43.36 |
| 31 | CD | PRO | 530 | −3.240 | 39.737 | 18.398 | 1.00 | 40.38 |
| 32 | N | THR | 531 | −6.206 | 42.135 | 21.243 | 1.00 | 35.29 |
| 33 | CA | THR | 531 | −6.722 | 43.444 | 21.654 | 1.00 | 35.12 |
| 34 | C | THR | 531 | −5.642 | 44.469 | 21.993 | 1.00 | 30.01 |
| 35 | O | THR | 531 | −5.687 | 45.610 | 21.527 | 1.00 | 29.64 |
| 36 | CB | THR | 531 | −7.584 | 43.099 | 22.866 | 1.00 | 36.34 |
| 37 | OG1 | THR | 531 | −8.643 | 42.227 | 22.491 | 1.00 | 99.90 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 38 | CG2 | THR | 531 | −8.286 | 44.282 | 23.567 | 1.00 | 99.90 |
| 39 | N | LEU | 532 | −4.676 | 44.056 | 22.805 | 1.00 | 29.04 |
| 40 | CA | LEU | 532 | −3.597 | 44.958 | 23.211 | 1.00 | 28.23 |
| 41 | C | LEU | 532 | −2.763 | 45.434 | 22.022 | 1.00 | 26.62 |
| 42 | O | LEU | 532 | −2.299 | 46.580 | 21.984 | 1.00 | 25.82 |
| 43 | CB | LEU | 532 | −2.702 | 44.274 | 24.232 | 1.00 | 25.68 |
| 44 | CG | LEU | 532 | −1.563 | 45.146 | 24.757 | 1.00 | 34.63 |
| 45 | CD1 | LEU | 532 | −2.111 | 46.509 | 25.197 | 1.00 | 30.55 |
| 46 | CD2 | LEU | 532 | −0.867 | 44.418 | 25.902 | 1.00 | 30.65 |
| 47 | N | VAL | 533 | −2.571 | 44.555 | 21.045 | 1.00 | 27.06 |
| 48 | CA | VAL | 533 | −1.809 | 44.925 | 19.863 | 1.00 | 23.18 |
| 49 | C | VAL | 533 | −2.593 | 45.921 | 19.014 | 1.00 | 24.05 |
| 50 | O | VAL | 533 | −2.030 | 46.890 | 18.496 | 1.00 | 26.77 |
| 51 | CB | VAL | 533 | −1.442 | 43.683 | 19.053 | 1.00 | 23.51 |
| 52 | CG1 | VAL | 533 | −0.483 | 42.716 | 19.788 | 1.00 | 99.90 |
| 53 | CG2 | VAL | 533 | −0.787 | 43.933 | 17.666 | 1.00 | 99.90 |
| 54 | N | SER | 534 | −3.900 | 45.708 | 18.871 | 1.00 | 25.92 |
| 55 | CA | SER | 534 | −4.703 | 46.659 | 18.103 | 1.00 | 27.71 |
| 56 | C | SER | 534 | −4.657 | 48.017 | 18.811 | 1.00 | 22.00 |
| 57 | O | SER | 534 | −4.612 | 49.063 | 18.165 | 1.00 | 26.26 |
| 58 | CB | SER | 534 | −6.156 | 46.179 | 17.998 | 1.00 | 31.49 |
| 59 | OG | SER | 534 | −6.853 | 46.235 | 19.247 | 1.00 | 99.90 |
| 60 | N | LEU | 535 | −4.662 | 48.000 | 20.140 | 1.00 | 26.88 |
| 61 | CA | LEU | 535 | −4.620 | 49.258 | 20.894 | 1.00 | 25.43 |
| 62 | C | LEU | 535 | −3.296 | 49.974 | 20.628 | 1.00 | 27.05 |
| 63 | O | LEU | 535 | −3.273 | 51.177 | 20.377 | 1.00 | 26.07 |
| 64 | CB | LEU | 535 | −4.802 | 48.981 | 22.385 | 1.00 | 26.35 |
| 65 | CG | LEU | 535 | −4.863 | 50.186 | 23.336 | 1.00 | 35.60 |
| 66 | CD1 | LEU | 535 | −5.553 | 49.756 | 24.633 | 1.00 | 36.71 |
| 67 | CD2 | LEU | 535 | −3.464 | 50.735 | 23.618 | 1.00 | 30.46 |
| 68 | N | LEU | 536 | −2.197 | 49.230 | 20.652 | 1.00 | 25.73 |
| 69 | CA | LEU | 536 | −0.883 | 49.817 | 20.384 | 1.00 | 23.64 |
| 70 | C | LEU | 536 | −0.843 | 50.404 | 18.977 | 1.00 | 27.62 |
| 71 | O | LEU | 536 | −0.242 | 51.450 | 18.756 | 1.00 | 22.81 |
| 72 | CB | LEU | 536 | 0.221 | 48.764 | 20.527 | 1.00 | 24.64 |
| 73 | CG | LEU | 536 | 0.433 | 48.131 | 21.906 | 1.00 | 25.70 |
| 74 | CD1 | LEU | 536 | 1.559 | 47.084 | 21.835 | 1.00 | 21.63 |
| 75 | CD2 | LEU | 536 | 0.782 | 49.226 | 22.923 | 1.00 | 20.83 |
| 76 | N | GLU | 537 | −1.455 | 49.717 | 18.013 | 1.00 | 24.62 |
| 77 | CA | GLU | 537 | −1.488 | 50.230 | 16.646 | 1.00 | 27.60 |
| 78 | C | GLU | 537 | −2.257 | 51.555 | 16.668 | 1.00 | 27.94 |
| 79 | O | GLU | 537 | −1.850 | 52.543 | 16.060 | 1.00 | 25.86 |
| 80 | CB | GLU | 537 | −2.207 | 49.232 | 15.730 | 1.00 | 27.45 |
| 81 | CG | GLU | 537 | −2.284 | 49.639 | 14.284 | 1.00 | 39.52 |
| 82 | CD | GLU | 537 | −3.073 | 48.750 | 13.320 | 1.00 | 99.90 |
| 83 | OE1 | GLU | 537 | −3.217 | 49.017 | 12.134 | 1.00 | 99.90 |
| 84 | OE2 | GLU | 537 | −3.596 | 47.637 | 13.905 | 1.00 | 99.90 |
| 85 | N | VAL | 538 | −3.358 | 51.575 | 17.406 | 1.00 | 25.24 |
| 86 | CA | VAL | 538 | −4.180 | 52.769 | 17.476 | 1.00 | 31.97 |
| 87 | C | VAL | 538 | −3.512 | 53.961 | 18.152 | 1.00 | 29.88 |
| 88 | O | VAL | 538 | −3.776 | 55.107 | 17.786 | 1.00 | 28.14 |
| 89 | CB | VAL | 538 | −5.505 | 52.468 | 18.192 | 1.00 | 38.05 |
| 90 | CG1 | VAL | 538 | −6.415 | 51.472 | 17.434 | 1.00 | 99.90 |
| 91 | CG2 | VAL | 538 | −6.410 | 53.691 | 18.509 | 1.00 | 99.90 |
| 92 | N | ILE | 539 | −2.649 | 53.719 | 19.132 | 1.00 | 25.23 |
| 93 | CA | ILE | 539 | −2.029 | 54.861 | 19.808 | 1.00 | 26.22 |
| 94 | C | ILE | 539 | −0.676 | 55.270 | 19.251 | 1.00 | 23.06 |
| 95 | O | ILE | 539 | −0.047 | 56.183 | 19.773 | 1.00 | 24.41 |
| 96 | CB | ILE | 539 | −1.882 | 54.630 | 21.329 | 1.00 | 22.83 |
| 97 | CG1 | ILE | 539 | −0.980 | 53.420 | 21.599 | 1.00 | 22.20 |
| 98 | CG2 | ILE | 539 | −3.272 | 54.416 | 21.956 | 1.00 | 28.20 |
| 99 | CD1 | ILE | 539 | −0.532 | 53.297 | 23.062 | 1.00 | 22.62 |
| 100 | N | GLU | 540 | −0.226 | 54.598 | 18.192 | 1.00 | 26.89 |
| 101 | CA | GLU | 540 | 1.057 | 54.934 | 17.586 | 1.00 | 21.93 |
| 102 | C | GLU | 540 | 0.876 | 56.354 | 17.033 | 1.00 | 28.96 |
| 103 | O | GLU | 540 | −0.099 | 56.649 | 16.351 | 1.00 | 29.21 |
| 104 | CB | GLU | 540 | 1.375 | 53.934 | 16.466 | 1.00 | 34.17 |
| 105 | CG | GLU | 540 | 2.763 | 54.039 | 15.856 | 1.00 | 34.86 |
| 106 | CD | GLU | 540 | 3.897 | 53.587 | 16.769 | 1.00 | 45.46 |
| 107 | OE1 | GLU | 540 | 3.672 | 53.281 | 17.966 | 1.00 | 31.19 |
| 108 | OE2 | GLU | 540 | 5.046 | 53.539 | 16.270 | 1.00 | 49.30 |
| 109 | N | PRO | 541 | 1.795 | 57.264 | 17.354 | 1.00 | 32.33 |
| 110 | CA | PRO | 541 | 1.659 | 58.635 | 16.856 | 1.00 | 34.70 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 111 | C | PRO | 541 | 1.667 | 58.767 | 15.331 | 1.00 | 30.39 |
| 112 | O | PRO | 541 | 2.212 | 57.925 | 14.636 | 1.00 | 27.63 |
| 113 | CB | PRO | 541 | 2.849 | 59.338 | 17.508 | 1.00 | 38.27 |
| 114 | CG | PRO | 541 | 3.883 | 58.205 | 17.590 | 1.00 | 40.07 |
| 115 | CD | PRO | 541 | 2.996 | 57.145 | 18.198 | 1.00 | 34.72 |
| 116 | N | GLU | 542 | 1.059 | 59.843 | 14.830 | 1.00 | 38.27 |
| 117 | CA | GLU | 542 | 1.016 | 60.116 | 13.393 | 1.00 | 35.46 |
| 118 | C | GLU | 542 | 2.448 | 60.549 | 13.036 | 1.00 | 35.96 |
| 119 | O | GLU | 542 | 3.146 | 61.098 | 13.878 | 1.00 | 30.43 |
| 120 | CB | GLU | 542 | 0.019 | 61.240 | 13.114 | 1.00 | 44.25 |
| 121 | CG | GLU | 542 | 0.362 | 62.659 | 13.675 | 1.00 | 99.90 |
| 122 | CD | GLU | 542 | −0.666 | 63.779 | 13.498 | 1.00 | 99.90 |
| 123 | OE1 | GLU | 542 | −0.499 | 64.911 | 13.930 | 1.00 | 99.90 |
| 124 | OE2 | GLU | 542 | −1.781 | 63.396 | 12.815 | 1.00 | 99.90 |
| 125 | N | VAL | 543 | 2.894 | 60.309 | 11.807 | 1.00 | 32.80 |
| 126 | CA | VAL | 543 | 4.265 | 60.673 | 11.442 | 1.00 | 34.66 |
| 127 | C | VAL | 543 | 4.614 | 62.131 | 11.776 | 1.00 | 28.44 |
| 128 | O | VAL | 543 | 3.816 | 63.045 | 11.605 | 1.00 | 30.11 |
| 129 | CB | VAL | 543 | 4.552 | 60.403 | 9.937 | 1.00 | 41.68 |
| 130 | CG1 | VAL | 543 | 3.962 | 61.509 | 9.080 | 1.00 | 38.06 |
| 131 | CG2 | VAL | 543 | 6.058 | 60.258 | 9.715 | 1.00 | 45.80 |
| 132 | N | LEU | 544 | 5.823 | 62.324 | 12.280 | 1.00 | 30.17 |
| 133 | CA | LEU | 544 | 6.298 | 63.640 | 12.668 | 1.00 | 26.23 |
| 134 | C | LEU | 544 | 7.221 | 64.217 | 11.601 | 1.00 | 28.40 |
| 135 | O | LEU | 544 | 8.113 | 63.526 | 11.118 | 1.00 | 22.17 |
| 136 | CB | LEU | 544 | 7.089 | 63.668 | 14.010 | 1.00 | 28.58 |
| 137 | CG | LEU | 544 | 6.289 | 64.066 | 15.279 | 1.00 | 99.90 |
| 138 | CD1 | LEU | 544 | 5.742 | 65.511 | 15.198 | 1.00 | 99.90 |
| 139 | CD2 | LEU | 544 | 5.145 | 63.088 | 15.608 | 1.00 | 99.90 |
| 140 | N | TYR | 545 | 7.000 | 65.477 | 11.239 | 1.00 | 23.87 |
| 141 | CA | TYR | 545 | 7.839 | 66.165 | 10.260 | 1.00 | 27.94 |
| 142 | C | TYR | 545 | 8.960 | 66.895 | 10.979 | 1.00 | 28.04 |
| 143 | O | TYR | 545 | 8.794 | 67.338 | 12.116 | 1.00 | 24.24 |
| 144 | CB | TYR | 545 | 7.010 | 67.159 | 9.460 | 1.00 | 27.40 |
| 145 | CG | TYR | 545 | 6.083 | 66.476 | 8.487 | 1.00 | 34.60 |
| 146 | CD1 | TYR | 545 | 4.825 | 66.038 | 8.889 | 1.00 | 37.81 |
| 147 | CD2 | TYR | 545 | 6.489 | 66.207 | 7.181 | 1.00 | 38.29 |
| 148 | CE1 | TYR | 545 | 3.992 | 65.348 | 8.016 | 1.00 | 47.26 |
| 149 | CE2 | TYR | 545 | 5.661 | 65.516 | 6.295 | 1.00 | 39.38 |
| 150 | CZ | TYR | 545 | 4.414 | 65.090 | 6.724 | 1.00 | 41.71 |
| 151 | OH | TYR | 545 | 3.599 | 64.389 | 5.864 | 1.00 | 52.51 |
| 152 | N | ALA | 546 | 10.110 | 67.022 | 10.328 | 1.00 | 23.60 |
| 153 | CA | ALA | 546 | 11.213 | 67.720 | 10.964 | 1.00 | 26.37 |
| 154 | C | ALA | 546 | 11.100 | 69.231 | 10.756 | 1.00 | 29.47 |
| 155 | O | ALA | 546 | 11.688 | 70.011 | 11.510 | 1.00 | 28.14 |
| 156 | CB | ALA | 546 | 12.542 | 67.231 | 10.418 | 1.00 | 27.79 |
| 157 | N | GLY | 547 | 10.332 | 69.635 | 9.749 | 1.00 | 29.99 |
| 158 | CA | GLY | 547 | 10.213 | 71.051 | 9.439 | 1.00 | 32.21 |
| 159 | C | GLY | 547 | 11.541 | 71.501 | 8.836 | 1.00 | 39.13 |
| 160 | O | GLY | 547 | 11.964 | 72.645 | 8.992 | 1.00 | 40.76 |
| 161 | N | TYR | 548 | 12.206 | 70.581 | 8.140 | 1.00 | 38.38 |
| 162 | CA | TYR | 548 | 13.505 | 70.850 | 7.528 | 1.00 | 46.41 |
| 163 | C | TYR | 548 | 13.429 | 71.638 | 6.208 | 1.00 | 47.68 |
| 164 | O | TYR | 548 | 12.536 | 71.420 | 5.391 | 1.00 | 49.96 |
| 165 | CB | TYR | 548 | 14.242 | 69.521 | 7.333 | 1.00 | 42.73 |
| 166 | CG | TYR | 548 | 15.579 | 69.661 | 6.681 | 1.00 | 48.58 |
| 167 | CD1 | TYR | 548 | 16.740 | 69.612 | 7.459 | 1.00 | 99.90 |
| 168 | CD2 | TYR | 548 | 15.683 | 69.849 | 5.299 | 1.00 | 99.90 |
| 169 | CE1 | TYR | 548 | 17.990 | 69.755 | 6.864 | 1.00 | 99.90 |
| 170 | CE2 | TYR | 548 | 16.935 | 69.992 | 4.706 | 1.00 | 99.90 |
| 171 | CZ | TYR | 548 | 18.085 | 69.945 | 5.488 | 1.00 | 99.90 |
| 172 | OH | TYR | 548 | 19.311 | 70.089 | 4.902 | 1.00 | 99.90 |
| 173 | N | ASP | 549 | 14.389 | 72.543 | 6.016 | 1.00 | 51.90 |
| 174 | CA | ASP | 549 | 14.465 | 73.400 | 4.832 | 1.00 | 52.61 |
| 175 | C | ASP | 549 | 14.420 | 72.658 | 3.499 | 1.00 | 54.82 |
| 176 | O | ASP | 549 | 13.434 | 72.755 | 2.768 | 1.00 | 57.82 |
| 177 | CB | ASP | 549 | 15.727 | 74.257 | 4.903 | 1.00 | 52.84 |
| 178 | CG | ASP | 549 | 15.881 | 75.347 | 3.832 | 1.00 | 99.90 |
| 179 | OD1 | ASP | 549 | 16.948 | 75.607 | 3.295 | 1.00 | 99.90 |
| 180 | OD2 | ASP | 549 | 14.700 | 75.968 | 3.534 | 1.00 | 99.90 |
| 181 | N | SER | 550 | 15.499 | 71.940 | 3.190 | 1.00 | 55.70 |
| 182 | CA | SER | 550 | 15.638 | 71.176 | 1.951 | 1.00 | 56.60 |
| 183 | C | SER | 550 | 16.129 | 72.063 | 0.803 | 1.00 | 60.14 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 184 | O | SER | 550 | 17.143 | 71.764 | 0.160 | 1.00 | 61.18 |
| 185 | CB | SER | 550 | 14.308 | 70.509 | 1.579 | 1.00 | 57.02 |
| 186 | OG | SER | 550 | 13.309 | 71.449 | 1.168 | 1.00 | 99.90 |
| 187 | N | SER | 551 | 15.414 | 73.153 | 0.549 | 1.00 | 59.68 |
| 188 | CA | SER | 551 | 15.776 | 74.077 | −0.525 | 1.00 | 60.50 |
| 189 | C | SER | 551 | 17.217 | 74.596 | −0.418 | 1.00 | 61.78 |
| 190 | O | SER | 551 | 17.813 | 74.999 | −1.421 | 1.00 | 61.98 |
| 191 | CB | SER | 551 | 14.797 | 75.251 | −0.544 | 1.00 | 57.03 |
| 192 | OG | SER | 551 | 14.942 | 76.115 | 0.588 | 1.00 | 99.90 |
| 193 | N | VAL | 552 | 17.779 | 74.588 | 0.789 | 1.00 | 62.40 |
| 194 | CA | VAL | 552 | 19.146 | 75.067 | 0.984 | 1.00 | 64.42 |
| 195 | C | VAL | 552 | 20.127 | 73.906 | 1.141 | 1.00 | 66.61 |
| 196 | O | VAL | 552 | 19.730 | 72.783 | 1.477 | 1.00 | 64.83 |
| 197 | CB | VAL | 552 | 19.212 | 75.972 | 2.210 | 1.00 | 60.35 |
| 198 | CG1 | VAL | 552 | 18.401 | 77.282 | 2.067 | 1.00 | 99.90 |
| 199 | CG2 | VAL | 552 | 20.631 | 76.416 | 2.664 | 1.00 | 99.90 |
| 200 | N | PRO | 553 | 21.421 | 74.158 | 0.871 | 1.00 | 67.95 |
| 201 | CA | PRO | 553 | 22.478 | 73.146 | 0.982 | 1.00 | 69.09 |
| 202 | C | PRO | 553 | 22.696 | 72.762 | 2.450 | 1.00 | 68.98 |
| 203 | O | PRO | 553 | 23.139 | 73.581 | 3.258 | 1.00 | 70.54 |
| 204 | CB | PRO | 553 | 23.694 | 73.862 | 0.379 | 1.00 | 71.22 |
| 205 | CG | PRO | 553 | 23.056 | 74.901 | −0.556 | 1.00 | 69.09 |
| 206 | CD | PRO | 553 | 22.000 | 75.422 | 0.389 | 1.00 | 68.58 |
| 207 | N | ASP | 554 | 22.391 | 71.512 | 2.783 | 1.00 | 68.95 |
| 208 | CA | ASP | 554 | 22.527 | 71.018 | 4.150 | 1.00 | 68.41 |
| 209 | C | ASP | 554 | 23.968 | 70.915 | 4.646 | 1.00 | 65.11 |
| 210 | O | ASP | 554 | 24.764 | 70.158 | 4.094 | 1.00 | 67.29 |
| 211 | CB | ASP | 554 | 21.883 | 69.631 | 4.276 | 1.00 | 72.12 |
| 212 | CG | ASP | 554 | 20.413 | 69.618 | 3.875 | 1.00 | 74.27 |
| 213 | OD1 | ASP | 554 | 19.882 | 70.676 | 3.471 | 1.00 | 77.63 |
| 214 | OD2 | ASP | 554 | 19.791 | 68.538 | 3.964 | 1.00 | 75.63 |
| 215 | N | SER | 555 | 24.301 | 71.673 | 5.689 | 1.00 | 61.36 |
| 216 | CA | SER | 555 | 25.640 | 71.597 | 6.262 | 1.00 | 54.04 |
| 217 | C | SER | 555 | 25.561 | 70.578 | 7.393 | 1.00 | 53.38 |
| 218 | O | SER | 555 | 24.471 | 70.198 | 7.818 | 1.00 | 44.49 |
| 219 | CB | SER | 555 | 26.118 | 72.959 | 6.830 | 1.00 | 56.37 |
| 220 | OG | SER | 555 | 25.403 | 73.353 | 8.005 | 1.00 | 99.90 |
| 221 | N | THR | 556 | 26.710 | 70.123 | 7.873 | 1.00 | 47.04 |
| 222 | CA | THR | 556 | 26.725 | 69.148 | 8.945 | 1.00 | 48.03 |
| 223 | C | THR | 556 | 26.006 | 69.688 | 10.180 | 1.00 | 44.05 |
| 224 | O | THR | 556 | 25.178 | 68.999 | 10.773 | 1.00 | 41.23 |
| 225 | CB | THR | 556 | 28.189 | 68.850 | 9.368 | 1.00 | 50.15 |
| 226 | OG1 | THR | 556 | 28.903 | 68.203 | 8.319 | 1.00 | 99.90 |
| 227 | CG2 | THR | 556 | 28.263 | 68.016 | 10.654 | 1.00 | 99.90 |
| 228 | N | TRP | 557 | 26.306 | 70.925 | 10.556 | 1.00 | 37.98 |
| 229 | CA | TRP | 557 | 25.673 | 71.524 | 11.726 | 1.00 | 39.84 |
| 230 | C | TRP | 557 | 24.187 | 71.832 | 11.510 | 1.00 | 37.46 |
| 231 | O | TRP | 557 | 23.393 | 71.743 | 12.449 | 1.00 | 35.48 |
| 232 | CB | TRP | 557 | 26.399 | 72.802 | 12.203 | 1.00 | 40.58 |
| 233 | CG | TRP | 557 | 26.434 | 73.958 | 11.232 | 1.00 | 99.90 |
| 234 | CD1 | TRP | 557 | 27.544 | 74.313 | 10.390 | 1.00 | 99.90 |
| 235 | CD2 | TRP | 557 | 25.452 | 74.961 | 11.022 | 1.00 | 99.90 |
| 236 | NE1 | TRP | 557 | 27.245 | 75.473 | 9.684 | 1.00 | 99.90 |
| 237 | CE2 | TRP | 557 | 25.973 | 75.857 | 10.063 | 1.00 | 99.90 |
| 238 | CE3 | TRP | 557 | 24.158 | 75.198 | 11.599 | 1.00 | 99.90 |
| 239 | CZ2 | TRP | 557 | 25.272 | 77.008 | 9.578 | 1.00 | 99.90 |
| 240 | CZ3 | TRP | 557 | 23.408 | 76.344 | 11.133 | 1.00 | 99.90 |
| 241 | CH2 | TRP | 557 | 23.957 | 77.238 | 10.130 | 1.00 | 99.90 |
| 242 | N | ARG | 558 | 23.800 | 72.201 | 10.291 | 1.00 | 36.47 |
| 243 | CA | ARG | 558 | 22.391 | 72.504 | 10.047 | 1.00 | 34.65 |
| 244 | C | ARG | 558 | 21.619 | 71.191 | 10.107 | 1.00 | 31.60 |
| 245 | O | ARG | 558 | 20.506 | 71.126 | 10.623 | 1.00 | 28.24 |
| 246 | CB | ARG | 558 | 22.184 | 73.186 | 8.679 | 1.00 | 35.58 |
| 247 | CG | ARG | 558 | 20.779 | 73.811 | 8.448 | 1.00 | 99.90 |
| 248 | CD | ARG | 558 | 20.649 | 74.442 | 7.052 | 1.00 | 99.90 |
| 249 | NE | ARG | 558 | 19.294 | 75.048 | 6.898 | 1.00 | 99.90 |
| 250 | CZ | ARG | 558 | 18.852 | 75.678 | 5.814 | 1.00 | 99.90 |
| 251 | NH1 | ARG | 558 | 17.650 | 76.161 | 5.831 | 1.00 | 99.90 |
| 252 | NH2 | ARG | 558 | 19.562 | 75.839 | 4.733 | 1.00 | 99.90 |
| 253 | N | ILE | 559 | 22.229 | 70.139 | 9.588 | 1.00 | 27.90 |
| 254 | CA | ILE | 559 | 21.613 | 68.820 | 9.602 | 1.00 | 29.29 |
| 255 | C | ILE | 559 | 21.345 | 68.364 | 11.043 | 1.00 | 28.57 |
| 256 | O | ILE | 559 | 20.232 | 67.953 | 11.369 | 1.00 | 25.88 |

TABLE 5-continued

ATOMIC COORDINATES FOR THE GR/SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 257 | CB | ILE | 559 | 22.406 | 67.656 | 8.915 | 1.00 | 27.95 |
| 258 | CG2 | ILE | 559 | 21.832 | 66.259 | 9.270 | 1.00 | 99.90 |
| 259 | CG1 | ILE | 559 | 22.415 | 67.806 | 7.377 | 1.00 | 99.90 |
| 260 | CD1 | ILE | 559 | 23.458 | 66.951 | 6.630 | 1.00 | 99.90 |
| 261 | N | MET | 560 | 22.364 | 68.445 | 11.894 | 1.00 | 25.56 |
| 262 | CA | MET | 560 | 22.212 | 68.046 | 13.295 | 1.00 | 24.24 |
| 263 | C | MET | 560 | 21.180 | 68.886 | 13.992 | 1.00 | 22.49 |
| 264 | O | MET | 560 | 20.386 | 68.365 | 14.764 | 1.00 | 21.35 |
| 265 | CB | MET | 560 | 23.550 | 68.151 | 14.056 | 1.00 | 24.95 |
| 266 | CG | MET | 560 | 24.525 | 67.005 | 13.723 | 1.00 | 99.90 |
| 267 | SD | MET | 560 | 23.920 | 65.411 | 14.376 | 1.00 | 99.90 |
| 268 | CE | MET | 560 | 24.920 | 64.276 | 13.373 | 1.00 | 99.90 |
| 269 | N | THR | 561 | 21.176 | 70.188 | 13.712 | 1.00 | 21.24 |
| 270 | CA | THR | 561 | 20.191 | 71.086 | 14.293 | 1.00 | 24.54 |
| 271 | C | THR | 561 | 18.791 | 70.654 | 13.870 | 1.00 | 24.54 |
| 272 | O | THR | 561 | 17.868 | 70.652 | 14.680 | 1.00 | 21.07 |
| 273 | CB | THR | 561 | 20.428 | 72.551 | 13.849 | 1.00 | 24.90 |
| 274 | OG1 | THR | 561 | 21.608 | 73.099 | 14.433 | 1.00 | 26.56 |
| 275 | CG2 | THR | 561 | 19.251 | 73.435 | 14.239 | 1.00 | 23.35 |
| 276 | N | THR | 562 | 18.623 | 70.304 | 12.598 | 1.00 | 19.11 |
| 277 | CA | THR | 562 | 17.325 | 69.852 | 12.125 | 1.00 | 21.51 |
| 278 | C | THR | 562 | 16.950 | 68.510 | 12.763 | 1.00 | 19.84 |
| 279 | O | THR | 562 | 15.765 | 68.271 | 13.043 | 1.00 | 21.66 |
| 280 | CB | THR | 562 | 17.209 | 69.868 | 10.626 | 1.00 | 24.02 |
| 281 | OG1 | THR | 562 | 18.182 | 69.009 | 10.045 | 1.00 | 99.90 |
| 282 | CG2 | THR | 562 | 17.280 | 71.338 | 10.099 | 1.00 | 99.90 |
| 283 | N | LEU | 563 | 17.928 | 67.625 | 12.974 | 1.00 | 18.47 |
| 284 | CA | LEU | 563 | 17.608 | 66.344 | 13.600 | 1.00 | 20.90 |
| 285 | C | LEU | 563 | 17.233 | 66.563 | 15.064 | 1.00 | 20.84 |
| 286 | O | LEU | 563 | 16.408 | 65.823 | 15.626 | 1.00 | 20.00 |
| 287 | CB | LEU | 563 | 18.779 | 65.376 | 13.501 | 1.00 | 17.55 |
| 288 | CG | LEU | 563 | 19.050 | 64.828 | 12.100 | 1.00 | 19.20 |
| 289 | CD1 | LEU | 563 | 20.349 | 64.062 | 12.128 | 1.00 | 20.15 |
| 290 | CD2 | LEU | 563 | 17.907 | 63.924 | 11.653 | 1.00 | 19.08 |
| 291 | N | ASN | 564 | 17.833 | 67.569 | 15.695 | 1.00 | 17.81 |
| 292 | CA | ASN | 564 | 17.467 | 67.856 | 17.098 | 1.00 | 19.99 |
| 293 | C | ASN | 564 | 16.053 | 68.424 | 17.186 | 1.00 | 18.99 |
| 294 | O | ASN | 564 | 15.333 | 68.155 | 18.142 | 1.00 | 20.08 |
| 295 | CB | ASN | 564 | 18.437 | 68.841 | 17.766 | 1.00 | 22.67 |
| 296 | CG | ASN | 564 | 19.770 | 68.211 | 18.120 | 1.00 | 27.38 |
| 297 | OD1 | ASN | 564 | 19.868 | 66.996 | 18.368 | 1.00 | 24.69 |
| 298 | ND2 | ASN | 564 | 20.855 | 69.103 | 18.180 | 1.00 | 23.33 |
| 299 | N | MET | 565 | 15.665 | 69.235 | 16.207 | 1.00 | 18.44 |
| 300 | CA | MET | 565 | 14.315 | 69.814 | 16.170 | 1.00 | 21.61 |
| 301 | C | MET | 565 | 13.323 | 68.659 | 16.001 | 1.00 | 23.93 |
| 302 | O | MET | 565 | 12.274 | 68.623 | 16.642 | 1.00 | 18.25 |
| 303 | CB | MET | 565 | 14.184 | 70.806 | 15.004 | 1.00 | 22.65 |
| 304 | CG | MET | 565 | 12.747 | 71.298 | 14.744 | 1.00 | 26.41 |
| 305 | SD | MET | 565 | 12.649 | 72.592 | 13.455 | 1.00 | 99.90 |
| 306 | CE | MET | 565 | 13.095 | 74.057 | 14.453 | 1.00 | 99.90 |
| 307 | N | LEU | 566 | 13.671 | 67.699 | 15.143 | 1.00 | 19.58 |
| 308 | CA | LEU | 566 | 12.817 | 66.527 | 14.951 | 1.00 | 17.13 |
| 309 | C | LEU | 566 | 12.746 | 65.757 | 16.277 | 1.00 | 16.29 |
| 310 | O | LEU | 566 | 11.671 | 65.324 | 16.696 | 1.00 | 19.55 |
| 311 | CB | LEU | 566 | 13.387 | 65.627 | 13.840 | 1.00 | 17.00 |
| 312 | CG | LEU | 566 | 12.612 | 64.333 | 13.581 | 1.00 | 19.10 |
| 313 | CD1 | LEU | 566 | 11.169 | 64.658 | 13.155 | 1.00 | 18.65 |
| 314 | CD2 | LEU | 566 | 13.358 | 63.527 | 12.488 | 1.00 | 17.08 |
| 315 | N | GLY | 567 | 13.893 | 65.600 | 16.928 | 1.00 | 16.83 |
| 316 | CA | GLY | 567 | 13.964 | 64.895 | 18.202 | 1.00 | 17.42 |
| 317 | C | GLY | 567 | 13.076 | 65.551 | 19.250 | 1.00 | 24.76 |
| 318 | O | GLY | 567 | 12.414 | 64.868 | 20.039 | 1.00 | 19.56 |
| 319 | N | GLY | 568 | 13.060 | 66.880 | 19.270 | 1.00 | 20.84 |
| 320 | CA | GLY | 568 | 12.208 | 67.618 | 20.227 | 1.00 | 22.88 |
| 321 | C | GLY | 568 | 10.745 | 67.300 | 19.943 | 1.00 | 23.92 |
| 322 | O | GLY | 568 | 9.941 | 67.105 | 20.861 | 1.00 | 23.22 |
| 323 | N | ARG | 569 | 10.383 | 67.247 | 18.663 | 1.00 | 17.75 |
| 324 | CA | ARG | 569 | 9.003 | 66.943 | 18.297 | 1.00 | 19.86 |
| 325 | C | ARG | 569 | 8.645 | 65.488 | 18.579 | 1.00 | 18.81 |
| 326 | O | ARG | 569 | 7.487 | 65.185 | 18.891 | 1.00 | 20.56 |
| 327 | CB | ARG | 569 | 8.759 | 67.252 | 16.822 | 1.00 | 18.63 |
| 328 | CG | ARG | 569 | 8.968 | 68.720 | 16.487 | 1.00 | 24.16 |
| 329 | CD | ARG | 569 | 8.809 | 68.967 | 15.007 | 1.00 | 28.88 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 330 | NE | ARG | 569 | 9.078 | 70.364 | 14.697 | 1.00 | 27.71 |
| 331 | CZ | ARG | 569 | 8.799 | 70.947 | 13.543 | 1.00 | 32.19 |
| 332 | NH1 | ARG | 569 | 8.220 | 70.275 | 12.501 | 1.00 | 28.19 |
| 333 | NH2 | ARG | 569 | 9.059 | 72.280 | 13.407 | 1.00 | 35.89 |
| 334 | N | GLN | 570 | 9.610 | 64.584 | 18.434 | 1.00 | 19.77 |
| 335 | CA | GLN | 570 | 9.347 | 63.185 | 18.733 | 1.00 | 19.30 |
| 336 | C | GLN | 570 | 9.290 | 62.930 | 20.235 | 1.00 | 21.49 |
| 337 | O | GLN | 570 | 8.579 | 62.041 | 20.686 | 1.00 | 21.43 |
| 338 | CB | GLN | 570 | 10.402 | 62.278 | 18.090 | 1.00 | 19.47 |
| 339 | CG | GLN | 570 | 10.243 | 62.249 | 16.570 | 1.00 | 22.41 |
| 340 | CD | GLN | 570 | 11.136 | 61.224 | 15.896 | 1.00 | 30.53 |
| 341 | OE1 | GLN | 570 | 11.158 | 61.113 | 14.660 | 1.00 | 32.93 |
| 342 | NE2 | GLN | 570 | 11.855 | 60.320 | 16.694 | 1.00 | 27.09 |
| 343 | N | VAL | 571 | 10.026 | 63.719 | 21.013 | 1.00 | 21.82 |
| 344 | CA | VAL | 571 | 10.012 | 63.557 | 22.464 | 1.00 | 22.79 |
| 345 | C | VAL | 571 | 8.605 | 63.860 | 22.974 | 1.00 | 21.40 |
| 346 | O | VAL | 571 | 8.070 | 63.124 | 23.814 | 1.00 | 23.41 |
| 347 | CB | VAL | 571 | 11.050 | 64.461 | 23.230 | 1.00 | 19.53 |
| 348 | CG1 | VAL | 571 | 12.095 | 63.635 | 24.008 | 1.00 | 99.90 |
| 349 | CG2 | VAL | 571 | 10.473 | 65.473 | 24.249 | 1.00 | 99.90 |
| 350 | N | ILE | 572 | 8.003 | 64.934 | 22.463 | 1.00 | 18.00 |
| 351 | CA | ILE | 572 | 6.645 | 65.281 | 22.849 | 1.00 | 19.91 |
| 352 | C | ILE | 572 | 5.737 | 64.105 | 22.494 | 1.00 | 24.23 |
| 353 | O | ILE | 572 | 4.905 | 63.659 | 23.291 | 1.00 | 19.07 |
| 354 | CB | ILE | 572 | 6.158 | 66.513 | 22.085 | 1.00 | 21.64 |
| 355 | CG2 | ILE | 572 | 4.737 | 66.978 | 22.530 | 1.00 | 99.90 |
| 356 | CG1 | ILE | 572 | 7.116 | 67.745 | 22.156 | 1.00 | 99.90 |
| 357 | CD1 | ILE | 572 | 6.829 | 68.881 | 21.152 | 1.00 | 99.90 |
| 358 | N | ALA | 573 | 5.914 | 63.605 | 21.276 | 1.00 | 21.94 |
| 359 | CA | ALA | 573 | 5.113 | 62.497 | 20.783 | 1.00 | 21.38 |
| 360 | C | ALA | 573 | 5.250 | 61.280 | 21.696 | 1.00 | 20.10 |
| 361 | O | ALA | 573 | 4.249 | 60.628 | 22.014 | 1.00 | 22.32 |
| 362 | CB | ALA | 573 | 5.529 | 62.155 | 19.344 | 1.00 | 24.08 |
| 363 | N | ALA | 574 | 6.470 | 60.965 | 22.106 | 1.00 | 18.72 |
| 364 | CA | ALA | 574 | 6.727 | 59.847 | 23.015 | 1.00 | 20.27 |
| 365 | C | ALA | 574 | 6.016 | 59.998 | 24.355 | 1.00 | 18.31 |
| 366 | O | ALA | 574 | 5.435 | 59.040 | 24.866 | 1.00 | 19.16 |
| 367 | CB | ALA | 574 | 8.233 | 59.670 | 23.290 | 1.00 | 17.15 |
| 368 | N | VAL | 575 | 6.053 | 61.190 | 24.932 | 1.00 | 17.43 |
| 369 | CA | VAL | 575 | 5.395 | 61.372 | 26.212 | 1.00 | 21.44 |
| 370 | C | VAL | 575 | 3.881 | 61.250 | 26.044 | 1.00 | 19.86 |
| 371 | O | VAL | 575 | 3.229 | 60.652 | 26.888 | 1.00 | 21.47 |
| 372 | CB | VAL | 575 | 5.767 | 62.724 | 26.853 | 1.00 | 20.22 |
| 373 | CG1 | VAL | 575 | 5.044 | 62.890 | 28.196 | 1.00 | 21.24 |
| 374 | CG2 | VAL | 575 | 7.267 | 62.791 | 27.055 | 1.00 | 19.32 |
| 375 | N | LYS | 576 | 3.321 | 61.798 | 24.964 | 1.00 | 17.73 |
| 376 | CA | LYS | 576 | 1.887 | 61.669 | 24.724 | 1.00 | 22.58 |
| 377 | C | LYS | 576 | 1.511 | 60.201 | 24.534 | 1.00 | 23.23 |
| 378 | O | LYS | 576 | 0.505 | 59.724 | 25.073 | 1.00 | 20.64 |
| 379 | CB | LYS | 576 | 1.449 | 62.508 | 23.520 | 1.00 | 23.07 |
| 380 | CG | LYS | 576 | 1.382 | 64.007 | 23.862 | 1.00 | 25.92 |
| 381 | CD | LYS | 576 | 0.670 | 64.861 | 22.804 | 1.00 | 37.08 |
| 382 | CE | LYS | 576 | 1.481 | 65.021 | 21.529 | 1.00 | 48.50 |
| 383 | NZ | LYS | 576 | 0.886 | 65.984 | 20.514 | 1.00 | 49.18 |
| 384 | N | TRP | 577 | 2.324 | 59.485 | 23.767 | 1.00 | 18.73 |
| 385 | CA | TRP | 577 | 2.103 | 58.062 | 23.544 | 1.00 | 21.37 |
| 386 | C | TRP | 577 | 2.085 | 57.301 | 24.865 | 1.00 | 22.20 |
| 387 | O | TRP | 577 | 1.214 | 56.463 | 25.089 | 1.00 | 23.93 |
| 388 | CB | TRP | 577 | 3.212 | 57.516 | 22.647 | 1.00 | 21.47 |
| 389 | CG | TRP | 577 | 3.324 | 56.016 | 22.560 | 1.00 | 17.78 |
| 390 | CD1 | TRP | 577 | 2.491 | 55.147 | 21.892 | 1.00 | 20.71 |
| 391 | CD2 | TRP | 577 | 4.384 | 55.226 | 23.086 | 1.00 | 17.23 |
| 392 | NE1 | TRP | 577 | 2.986 | 53.867 | 21.972 | 1.00 | 19.88 |
| 393 | CE2 | TRP | 577 | 4.149 | 53.887 | 22.699 | 1.00 | 19.41 |
| 394 | CE3 | TRP | 577 | 5.525 | 55.520 | 23.852 | 1.00 | 19.83 |
| 395 | CZ2 | TRP | 577 | 5.018 | 52.839 | 23.050 | 1.00 | 18.15 |
| 396 | CZ3 | TRP | 577 | 6.395 | 54.472 | 24.201 | 1.00 | 20.23 |
| 397 | CH2 | TRP | 577 | 6.129 | 53.149 | 23.796 | 1.00 | 22.27 |
| 398 | N | ALA | 578 | 3.026 | 57.612 | 25.754 | 1.00 | 20.68 |
| 399 | CA | ALA | 578 | 3.119 | 56.904 | 27.029 | 1.00 | 22.57 |
| 400 | C | ALA | 578 | 1.893 | 57.109 | 27.916 | 1.00 | 20.83 |
| 401 | O | ALA | 578 | 1.580 | 56.253 | 28.722 | 1.00 | 22.59 |
| 402 | CB | ALA | 578 | 4.383 | 57.328 | 27.800 | 1.00 | 22.82 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 403 | N | LYS | 579 | 1.209 | 58.242 | 27.768 | 1.00 | 20.76 |
| 404 | CA | LYS | 579 | 0.034 | 58.523 | 28.591 | 1.00 | 25.82 |
| 405 | C | LYS | 579 | −1.139 | 57.644 | 28.160 | 1.00 | 26.99 |
| 406 | O | LYS | 579 | −2.099 | 57.463 | 28.917 | 1.00 | 24.98 |
| 407 | CB | LYS | 579 | −0.343 | 60.011 | 28.504 | 1.00 | 27.35 |
| 408 | CG | LYS | 579 | 0.830 | 60.916 | 28.818 | 1.00 | 34.69 |
| 409 | CD | LYS | 579 | 0.432 | 62.175 | 29.587 | 1.00 | 44.84 |
| 410 | CE | LYS | 579 | −0.567 | 63.030 | 28.838 | 1.00 | 49.64 |
| 411 | NZ | LYS | 579 | −1.041 | 64.247 | 29.618 | 1.00 | 49.55 |
| 412 | N | ALA | 580 | −1.063 | 57.101 | 26.947 | 1.00 | 23.17 |
| 413 | CA | ALA | 580 | −2.110 | 56.201 | 26.454 | 1.00 | 23.40 |
| 414 | C | ALA | 580 | −1.690 | 54.735 | 26.489 | 1.00 | 24.42 |
| 415 | O | ALA | 580 | −2.505 | 53.841 | 26.216 | 1.00 | 21.97 |
| 416 | CB | ALA | 580 | −2.504 | 56.563 | 25.016 | 1.00 | 24.11 |
| 417 | N | ILE | 581 | −0.427 | 54.480 | 26.834 | 1.00 | 19.77 |
| 418 | CA | ILE | 581 | 0.106 | 53.112 | 26.852 | 1.00 | 21.02 |
| 419 | C | ILE | 581 | −0.434 | 52.326 | 28.032 | 1.00 | 21.28 |
| 420 | O | ILE | 581 | −0.175 | 52.679 | 29.172 | 1.00 | 22.53 |
| 421 | CB | ILE | 581 | 1.639 | 53.156 | 26.928 | 1.00 | 23.10 |
| 422 | CG2 | ILE | 581 | 2.289 | 51.739 | 26.862 | 1.00 | 99.90 |
| 423 | CG1 | ILE | 581 | 2.320 | 54.053 | 25.845 | 1.00 | 99.90 |
| 424 | CD1 | ILE | 581 | 3.809 | 54.379 | 26.080 | 1.00 | 99.90 |
| 425 | N | PRO | 582 | −1.142 | 51.218 | 27.773 | 1.00 | 22.85 |
| 426 | CA | PRO | 582 | −1.688 | 50.455 | 28.903 | 1.00 | 24.25 |
| 427 | C | PRO | 582 | −0.693 | 50.121 | 30.008 | 1.00 | 25.32 |
| 428 | O | PRO | 582 | 0.380 | 49.563 | 29.756 | 1.00 | 25.05 |
| 429 | CB | PRO | 582 | −2.273 | 49.215 | 28.221 | 1.00 | 24.36 |
| 430 | CG | PRO | 582 | −2.742 | 49.779 | 26.893 | 1.00 | 23.83 |
| 431 | CD | PRO | 582 | −1.474 | 50.547 | 26.502 | 1.00 | 20.46 |
| 432 | N | GLY | 583 | −1.064 | 50.493 | 31.233 | 1.00 | 25.15 |
| 433 | CA | GLY | 583 | −0.240 | 50.226 | 32.397 | 1.00 | 25.65 |
| 434 | C | GLY | 583 | 0.794 | 51.272 | 32.770 | 1.00 | 23.09 |
| 435 | O | GLY | 583 | 1.172 | 51.397 | 33.932 | 1.00 | 25.86 |
| 436 | N | PHE | 584 | 1.247 | 52.055 | 31.804 | 1.00 | 22.74 |
| 437 | CA | PHE | 584 | 2.289 | 53.021 | 32.116 | 1.00 | 23.63 |
| 438 | C | PHE | 584 | 1.874 | 54.103 | 33.106 | 1.00 | 22.42 |
| 439 | O | PHE | 584 | 2.605 | 54.395 | 34.041 | 1.00 | 21.78 |
| 440 | CB | PHE | 584 | 2.800 | 53.696 | 30.832 | 1.00 | 21.38 |
| 441 | CG | PHE | 584 | 4.125 | 54.391 | 31.005 | 1.00 | 20.80 |
| 442 | CD1 | PHE | 584 | 5.284 | 53.639 | 31.225 | 1.00 | 22.81 |
| 443 | CD2 | PHE | 584 | 4.221 | 55.780 | 30.956 | 1.00 | 24.10 |
| 444 | CE1 | PHE | 584 | 6.512 | 54.254 | 31.389 | 1.00 | 24.39 |
| 445 | CE2 | PHE | 584 | 5.458 | 56.409 | 31.121 | 1.00 | 19.38 |
| 446 | CZ | PHE | 584 | 6.597 | 55.644 | 31.336 | 1.00 | 23.48 |
| 447 | N | ARG | 585 | 0.696 | 54.688 | 32.899 | 1.00 | 22.15 |
| 448 | CA | ARG | 585 | 0.230 | 55.780 | 33.752 | 1.00 | 25.70 |
| 449 | C | ARG | 585 | 0.022 | 55.358 | 35.192 | 1.00 | 24.37 |
| 450 | O | ARG | 585 | −0.142 | 56.197 | 36.080 | 1.00 | 24.34 |
| 451 | CB | ARG | 585 | −1.081 | 56.353 | 33.225 | 1.00 | 23.04 |
| 452 | CG | ARG | 585 | −2.193 | 55.320 | 33.145 | 1.00 | 24.68 |
| 453 | CD | ARG | 585 | −3.541 | 56.001 | 32.956 | 1.00 | 25.40 |
| 454 | NE | ARG | 585 | −4.603 | 55.003 | 32.931 | 1.00 | 24.48 |
| 455 | CZ | ARG | 585 | −5.894 | 55.292 | 32.940 | 1.00 | 20.47 |
| 456 | NH1 | ARG | 585 | −6.370 | 56.573 | 33.000 | 1.00 | 23.59 |
| 457 | NH2 | ARG | 585 | −6.788 | 54.265 | 32.887 | 1.00 | 26.38 |
| 458 | N | ASN | 586 | 0.040 | 54.056 | 35.420 | 1.00 | 27.20 |
| 459 | CA | ASN | 586 | −0.174 | 53.518 | 36.748 | 1.00 | 23.55 |
| 460 | C | ASN | 586 | 1.103 | 53.371 | 37.564 | 1.00 | 26.53 |
| 461 | O | ASN | 586 | 1.037 | 53.106 | 38.766 | 1.00 | 27.16 |
| 462 | CB | ASN | 586 | −0.930 | 52.210 | 36.617 | 1.00 | 32.06 |
| 463 | CG | ASN | 586 | −2.263 | 52.399 | 35.915 | 1.00 | 33.85 |
| 464 | OD1 | ASN | 586 | −2.792 | 51.484 | 35.293 | 1.00 | 37.94 |
| 465 | ND2 | ASN | 586 | −3.004 | 53.573 | 36.197 | 1.00 | 28.27 |
| 466 | N | LEU | 587 | 2.256 | 53.542 | 36.920 | 1.00 | 22.63 |
| 467 | CA | LEU | 587 | 3.532 | 53.511 | 37.620 | 1.00 | 22.51 |
| 468 | C | LEU | 587 | 3.617 | 54.863 | 38.294 | 1.00 | 19.73 |
| 469 | O | LEU | 587 | 2.941 | 55.801 | 37.907 | 1.00 | 23.16 |
| 470 | CB | LEU | 587 | 4.713 | 53.393 | 36.649 | 1.00 | 21.95 |
| 471 | CG | LEU | 587 | 4.686 | 52.151 | 35.762 | 1.00 | 20.73 |
| 472 | CD1 | LEU | 587 | 5.770 | 52.276 | 34.661 | 1.00 | 23.47 |
| 473 | CD2 | LEU | 587 | 4.890 | 50.905 | 36.624 | 1.00 | 22.85 |
| 474 | N | HIS | 588 | 4.454 | 54.948 | 39.308 | 1.00 | 21.02 |
| 475 | CA | HIS | 588 | 4.661 | 56.192 | 40.037 | 1.00 | 25.86 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 476 | C | HIS | 588 | 5.125 | 57.217 | 39.005 | 1.00 | 26.17 |
| 477 | O | HIS | 588 | 5.834 | 56.860 | 38.072 | 1.00 | 23.09 |
| 478 | CB | HIS | 588 | 5.727 | 55.921 | 41.100 | 1.00 | 28.77 |
| 479 | CG | HIS | 588 | 5.930 | 57.038 | 42.066 | 1.00 | 36.70 |
| 480 | ND1 | HIS | 588 | 6.543 | 58.220 | 41.718 | 1.00 | 34.14 |
| 481 | CD2 | HIS | 588 | 5.612 | 57.149 | 43.377 | 1.00 | 38.95 |
| 482 | CE1 | HIS | 588 | 6.598 | 59.012 | 42.775 | 1.00 | 39.45 |
| 483 | NE2 | HIS | 588 | 6.039 | 58.385 | 43.794 | 1.00 | 39.37 |
| 484 | N | LEU | 589 | 4.717 | 58.477 | 39.156 | 1.00 | 20.73 |
| 485 | CA | LEU | 589 | 5.113 | 59.520 | 38.215 | 1.00 | 27.73 |
| 486 | C | LEU | 589 | 6.627 | 59.635 | 38.061 | 1.00 | 27.07 |
| 487 | O | LEU | 589 | 7.137 | 59.841 | 36.948 | 1.00 | 24.14 |
| 488 | CB | LEU | 589 | 4.534 | 60.892 | 38.625 | 1.00 | 26.09 |
| 489 | CG | LEU | 589 | 2.993 | 61.022 | 38.767 | 1.00 | 99.90 |
| 490 | CD1 | LEU | 589 | 2.612 | 62.479 | 39.068 | 1.00 | 99.90 |
| 491 | CD2 | LEU | 589 | 2.238 | 60.537 | 37.518 | 1.00 | 99.90 |
| 492 | N | ASP | 590 | 7.362 | 59.511 | 39.164 | 1.00 | 24.97 |
| 493 | CA | ASP | 590 | 8.811 | 59.597 | 39.074 | 1.00 | 27.70 |
| 494 | C | ASP | 590 | 9.369 | 58.468 | 38.212 | 1.00 | 25.79 |
| 495 | O | ASP | 590 | 10.365 | 58.653 | 37.515 | 1.00 | 26.38 |
| 496 | CB | ASP | 590 | 9.479 | 59.536 | 40.452 | 1.00 | 33.81 |
| 497 | CG | ASP | 590 | 9.143 | 60.731 | 41.321 | 1.00 | 46.44 |
| 498 | OD1 | ASP | 590 | 8.821 | 61.801 | 40.763 | 1.00 | 51.31 |
| 499 | OD2 | ASP | 590 | 9.238 | 60.609 | 42.566 | 1.00 | 50.96 |
| 500 | N | ASP | 591 | 8.744 | 57.299 | 38.279 | 1.00 | 23.70 |
| 501 | CA | ASP | 591 | 9.199 | 56.177 | 37.478 | 1.00 | 22.43 |
| 502 | C | ASP | 591 | 8.872 | 56.433 | 36.012 | 1.00 | 19.90 |
| 503 | O | ASP | 591 | 9.691 | 56.138 | 35.140 | 1.00 | 22.60 |
| 504 | CB | ASP | 591 | 8.551 | 54.870 | 37.911 | 1.00 | 21.92 |
| 505 | CG | ASP | 591 | 8.827 | 54.538 | 39.355 | 1.00 | 33.42 |
| 506 | OD1 | ASP | 591 | 9.882 | 54.978 | 39.884 | 1.00 | 34.56 |
| 507 | OD2 | ASP | 591 | 7.996 | 53.817 | 39.949 | 1.00 | 39.54 |
| 508 | N | GLN | 592 | 7.698 | 57.001 | 35.742 | 1.00 | 19.31 |
| 509 | CA | GLN | 592 | 7.307 | 57.263 | 34.357 | 1.00 | 17.71 |
| 510 | C | GLN | 592 | 8.321 | 58.215 | 33.762 | 1.00 | 23.99 |
| 511 | O | GLN | 592 | 8.813 | 57.992 | 32.663 | 1.00 | 19.91 |
| 512 | CB | GLN | 592 | 5.924 | 57.901 | 34.270 | 1.00 | 19.37 |
| 513 | CG | GLN | 592 | 4.823 | 57.083 | 34.901 | 1.00 | 22.18 |
| 514 | CD | GLN | 592 | 3.473 | 57.742 | 34.779 | 1.00 | 22.76 |
| 515 | OE1 | GLN | 592 | 2.619 | 57.600 | 35.656 | 1.00 | 25.01 |
| 516 | NE2 | GLN | 592 | 3.183 | 58.456 | 33.594 | 1.00 | 18.79 |
| 517 | N | MET | 593 | 8.623 | 59.289 | 34.485 | 1.00 | 21.08 |
| 518 | CA | MET | 593 | 9.602 | 60.249 | 33.999 | 1.00 | 21.96 |
| 519 | C | MET | 593 | 10.973 | 59.607 | 33.797 | 1.00 | 24.64 |
| 520 | O | MET | 593 | 11.599 | 59.811 | 32.755 | 1.00 | 23.28 |
| 521 | CB | MET | 593 | 9.727 | 61.448 | 34.968 | 1.00 | 25.55 |
| 522 | CG | MET | 593 | 8.454 | 62.300 | 35.153 | 1.00 | 99.90 |
| 523 | SD | MET | 593 | 8.851 | 63.799 | 36.068 | 1.00 | 99.90 |
| 524 | CE | MET | 593 | 7.176 | 64.333 | 36.445 | 1.00 | 99.90 |
| 525 | N | THR | 594 | 11.439 | 58.840 | 34.785 | 1.00 | 19.75 |
| 526 | CA | THR | 594 | 12.733 | 58.166 | 34.705 | 1.00 | 20.18 |
| 527 | C | THR | 594 | 12.812 | 57.212 | 33.499 | 1.00 | 19.01 |
| 528 | O | THR | 594 | 13.815 | 57.184 | 32.799 | 1.00 | 18.23 |
| 529 | CB | THR | 594 | 13.014 | 57.344 | 35.986 | 1.00 | 24.15 |
| 530 | OG1 | THR | 594 | 13.099 | 58.173 | 37.142 | 1.00 | 26.23 |
| 531 | CG2 | THR | 594 | 14.347 | 56.633 | 35.879 | 1.00 | 23.53 |
| 532 | N | LEU | 595 | 11.761 | 56.428 | 33.256 | 1.00 | 17.46 |
| 533 | CA | LEU | 595 | 11.778 | 55.502 | 32.116 | 1.00 | 19.07 |
| 534 | C | LEU | 595 | 11.867 | 56.218 | 30.760 | 1.00 | 17.18 |
| 535 | O | LEU | 595 | 12.533 | 55.729 | 29.840 | 1.00 | 17.28 |
| 536 | CB | LEU | 595 | 10.544 | 54.590 | 32.139 | 1.00 | 18.92 |
| 537 | CG | LEU | 595 | 10.566 | 53.657 | 33.371 | 1.00 | 22.74 |
| 538 | CD1 | LEU | 595 | 9.226 | 52.941 | 33.555 | 1.00 | 22.99 |
| 539 | CD2 | LEU | 595 | 11.672 | 52.663 | 33.188 | 1.00 | 20.48 |
| 540 | N | LEU | 596 | 11.172 | 57.343 | 30.631 | 1.00 | 16.29 |
| 541 | CA | LEU | 596 | 11.231 | 58.127 | 29.386 | 1.00 | 23.76 |
| 542 | C | LEU | 596 | 12.630 | 58.735 | 29.234 | 1.00 | 22.00 |
| 543 | O | LEU | 596 | 13.213 | 58.713 | 28.148 | 1.00 | 17.05 |
| 544 | CB | LEU | 596 | 10.153 | 59.246 | 29.361 | 1.00 | 18.60 |
| 545 | CG | LEU | 596 | 8.665 | 58.830 | 29.513 | 1.00 | 99.90 |
| 546 | CD1 | LEU | 596 | 7.756 | 60.057 | 29.351 | 1.00 | 99.90 |
| 547 | CD2 | LEU | 596 | 8.247 | 57.740 | 28.512 | 1.00 | 99.90 |
| 548 | N | GLN | 597 | 13.180 | 59.275 | 30.318 | 1.00 | 21.43 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 549 | CA | GLN | 597 | 14.516 | 59.863 | 30.216 | 1.00 | 23.26 |
| 550 | C | GLN | 597 | 15.596 | 58.825 | 29.922 | 1.00 | 22.82 |
| 551 | O | GLN | 597 | 16.616 | 59.155 | 29.340 | 1.00 | 22.26 |
| 552 | CB | GLN | 597 | 14.856 | 60.678 | 31.478 | 1.00 | 21.04 |
| 553 | CG | GLN | 597 | 13.846 | 61.816 | 31.674 | 1.00 | 26.41 |
| 554 | CD | GLN | 597 | 14.176 | 62.744 | 32.833 | 1.00 | 34.88 |
| 555 | OE1 | GLN | 597 | 14.610 | 62.307 | 33.897 | 1.00 | 28.80 |
| 556 | NE2 | GLN | 597 | 13.918 | 64.117 | 32.626 | 1.00 | 32.80 |
| 557 | N | TYR | 598 | 15.376 | 57.571 | 30.312 | 1.00 | 21.10 |
| 558 | CA | TYR | 598 | 16.362 | 56.521 | 30.034 | 1.00 | 23.73 |
| 559 | C | TYR | 598 | 16.240 | 55.998 | 28.622 | 1.00 | 21.41 |
| 560 | O | TYR | 598 | 17.233 | 55.689 | 27.968 | 1.00 | 24.76 |
| 561 | CB | TYR | 598 | 16.150 | 55.309 | 30.946 | 1.00 | 22.41 |
| 562 | CG | TYR | 598 | 16.647 | 55.443 | 32.367 | 1.00 | 21.14 |
| 563 | CD1 | TYR | 598 | 17.195 | 56.628 | 32.840 | 1.00 | 22.56 |
| 564 | CD2 | TYR | 598 | 16.589 | 54.356 | 33.230 | 1.00 | 25.54 |
| 565 | CE1 | TYR | 598 | 17.682 | 56.729 | 34.154 | 1.00 | 27.58 |
| 566 | CE2 | TYR | 598 | 17.068 | 54.442 | 34.533 | 1.00 | 23.54 |
| 567 | CZ | TYR | 598 | 17.612 | 55.626 | 34.989 | 1.00 | 22.36 |
| 568 | OH | TYR | 598 | 18.085 | 55.737 | 36.276 | 1.00 | 29.42 |
| 569 | N | SER | 599 | 15.014 | 55.934 | 28.138 | 1.00 | 19.69 |
| 570 | CA | SER | 599 | 14.784 | 55.299 | 26.849 | 1.00 | 21.05 |
| 571 | C | SER | 599 | 14.475 | 56.110 | 25.608 | 1.00 | 20.67 |
| 572 | O | SER | 599 | 14.363 | 55.519 | 24.520 | 1.00 | 17.40 |
| 573 | CB | SER | 599 | 13.657 | 54.283 | 27.020 | 1.00 | 24.21 |
| 574 | OG | SER | 599 | 12.387 | 54.913 | 27.142 | 1.00 | 27.35 |
| 575 | N | TRP | 600 | 14.371 | 57.430 | 25.724 | 1.00 | 17.55 |
| 576 | CA | TRP | 600 | 13.998 | 58.207 | 24.546 | 1.00 | 21.93 |
| 577 | C | TRP | 600 | 14.874 | 57.931 | 23.320 | 1.00 | 18.91 |
| 578 | O | TRP | 600 | 14.350 | 57.773 | 22.223 | 1.00 | 20.07 |
| 579 | CB | TRP | 600 | 13.972 | 59.717 | 24.836 | 1.00 | 22.52 |
| 580 | CG | TRP | 600 | 15.298 | 60.318 | 25.168 | 1.00 | 23.08 |
| 581 | CD1 | TRP | 600 | 15.904 | 60.348 | 26.389 | 1.00 | 28.21 |
| 582 | CD2 | TRP | 600 | 16.200 | 60.938 | 24.252 | 1.00 | 24.51 |
| 583 | NE1 | TRP | 600 | 17.137 | 60.953 | 26.292 | 1.00 | 25.19 |
| 584 | CE2 | TRP | 600 | 17.342 | 61.325 | 24.989 | 1.00 | 26.64 |
| 585 | CE3 | TRP | 600 | 16.154 | 61.203 | 22.880 | 1.00 | 25.75 |
| 586 | CZ2 | TRP | 600 | 18.442 | 61.969 | 24.396 | 1.00 | 29.86 |
| 587 | CZ3 | TRP | 600 | 17.249 | 61.843 | 22.288 | 1.00 | 32.59 |
| 588 | CH2 | TRP | 600 | 18.375 | 62.218 | 23.048 | 1.00 | 30.85 |
| 589 | N | MET | 601 | 16.191 | 57.861 | 23.495 | 1.00 | 21.38 |
| 590 | CA | MET | 601 | 17.087 | 57.622 | 22.352 | 1.00 | 18.69 |
| 591 | C | MET | 601 | 16.823 | 56.265 | 21.715 | 1.00 | 23.20 |
| 592 | O | MET | 601 | 16.790 | 56.138 | 20.478 | 1.00 | 21.19 |
| 593 | CB | MET | 601 | 18.553 | 57.684 | 22.783 | 1.00 | 21.49 |
| 594 | CG | MET | 601 | 19.522 | 57.518 | 21.611 | 1.00 | 22.22 |
| 595 | SD | MET | 601 | 19.630 | 59.001 | 20.532 | 1.00 | 27.03 |
| 596 | CE | MET | 601 | 20.664 | 60.086 | 21.623 | 1.00 | 26.64 |
| 597 | N | PHE | 602 | 16.668 | 55.248 | 22.557 | 1.00 | 19.23 |
| 598 | CA | PHE | 602 | 16.383 | 53.904 | 22.078 | 1.00 | 22.32 |
| 599 | C | PHE | 602 | 15.085 | 53.867 | 21.295 | 1.00 | 20.68 |
| 600 | O | PHE | 602 | 15.028 | 53.277 | 20.224 | 1.00 | 21.09 |
| 601 | CB | PHE | 602 | 16.113 | 52.858 | 23.210 | 1.00 | 23.54 |
| 602 | CG | PHE | 602 | 17.192 | 52.587 | 24.232 | 1.00 | 99.90 |
| 603 | CD1 | PHE | 602 | 17.625 | 53.578 | 25.189 | 1.00 | 99.90 |
| 604 | CD2 | PHE | 602 | 17.732 | 51.253 | 24.325 | 1.00 | 99.90 |
| 605 | CE1 | PHE | 602 | 18.605 | 53.248 | 26.189 | 1.00 | 99.90 |
| 606 | CE2 | PHE | 602 | 18.716 | 50.929 | 25.313 | 1.00 | 99.90 |
| 607 | CZ | PHE | 602 | 19.158 | 51.927 | 26.246 | 1.00 | 99.90 |
| 608 | N | LEU | 603 | 14.035 | 54.487 | 21.830 | 1.00 | 20.06 |
| 609 | CA | LEU | 603 | 12.735 | 54.478 | 21.165 | 1.00 | 16.39 |
| 610 | C | LEU | 603 | 12.804 | 55.201 | 19.831 | 1.00 | 18.68 |
| 611 | O | LEU | 603 | 12.226 | 54.754 | 18.838 | 1.00 | 18.94 |
| 612 | CB | LEU | 603 | 11.679 | 55.173 | 22.038 | 1.00 | 14.15 |
| 613 | CG | LEU | 603 | 11.408 | 54.532 | 23.397 | 1.00 | 20.53 |
| 614 | CD1 | LEU | 603 | 10.488 | 55.448 | 24.208 | 1.00 | 20.07 |
| 615 | CD2 | LEU | 603 | 10.742 | 53.165 | 23.186 | 1.00 | 24.11 |
| 616 | N | MET | 604 | 13.503 | 56.329 | 19.810 | 1.00 | 18.42 |
| 617 | CA | MET | 604 | 13.597 | 57.094 | 18.587 | 1.00 | 19.21 |
| 618 | C | MET | 604 | 14.437 | 56.424 | 17.504 | 1.00 | 19.93 |
| 619 | O | MET | 604 | 14.071 | 56.492 | 16.322 | 1.00 | 23.09 |
| 620 | CB | MET | 604 | 14.113 | 58.499 | 18.889 | 1.00 | 21.20 |
| 621 | CG | MET | 604 | 13.084 | 59.331 | 19.684 | 1.00 | 21.45 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 622 | SD | MET | 604 | 13.619 | 61.014 | 19.956 | 1.00 | 25.97 |
| 623 | CE | MET | 604 | 12.389 | 61.557 | 21.170 | 1.00 | 26.52 |
| 624 | N | ALA | 605 | 15.545 | 55.793 | 17.873 | 1.00 | 18.66 |
| 625 | CA | ALA | 605 | 16.357 | 55.125 | 16.843 | 1.00 | 19.71 |
| 626 | C | ALA | 605 | 15.628 | 53.865 | 16.343 | 1.00 | 22.38 |
| 627 | O | ALA | 605 | 15.752 | 53.486 | 15.178 | 1.00 | 18.63 |
| 628 | CB | ALA | 605 | 17.774 | 54.744 | 17.363 | 1.00 | 20.60 |
| 629 | N | PHE | 606 | 14.871 | 53.230 | 17.233 | 1.00 | 18.16 |
| 630 | CA | PHE | 606 | 14.092 | 52.032 | 16.886 | 1.00 | 20.65 |
| 631 | C | PHE | 606 | 13.005 | 52.461 | 15.884 | 1.00 | 21.25 |
| 632 | O | PHE | 606 | 12.762 | 51.773 | 14.879 | 1.00 | 23.39 |
| 633 | CB | PHE | 606 | 13.479 | 51.439 | 18.173 | 1.00 | 19.84 |
| 634 | CG | PHE | 606 | 13.048 | 49.979 | 18.055 | 1.00 | 22.22 |
| 635 | CD1 | PHE | 606 | 13.982 | 48.980 | 17.790 | 1.00 | 22.72 |
| 636 | CD2 | PHE | 606 | 11.719 | 49.613 | 18.255 | 1.00 | 23.08 |
| 637 | CE1 | PHE | 606 | 13.609 | 47.639 | 17.726 | 1.00 | 23.74 |
| 638 | CE2 | PHE | 606 | 11.325 | 48.274 | 18.196 | 1.00 | 24.95 |
| 639 | CZ | PHE | 606 | 12.266 | 47.287 | 17.930 | 1.00 | 22.67 |
| 640 | N | ALA | 607 | 12.352 | 53.591 | 16.160 | 1.00 | 18.00 |
| 641 | CA | ALA | 607 | 11.335 | 54.114 | 15.266 | 1.00 | 19.15 |
| 642 | C | ALA | 607 | 11.932 | 54.472 | 13.914 | 1.00 | 19.60 |
| 643 | O | ALA | 607 | 11.307 | 54.266 | 12.866 | 1.00 | 17.94 |
| 644 | CB | ALA | 607 | 10.674 | 55.315 | 15.963 | 1.00 | 99.90 |
| 645 | N | LEU | 608 | 13.135 | 55.044 | 13.939 | 1.00 | 18.18 |
| 646 | CA | LEU | 608 | 13.841 | 55.382 | 12.710 | 1.00 | 18.82 |
| 647 | C | LEU | 608 | 14.041 | 54.100 | 11.907 | 1.00 | 20.32 |
| 648 | O | LEU | 608 | 13.869 | 54.087 | 10.671 | 1.00 | 21.06 |
| 649 | CB | LEU | 608 | 15.201 | 55.995 | 13.046 | 1.00 | 18.85 |
| 650 | CG | LEU | 608 | 16.256 | 56.031 | 11.928 | 1.00 | 15.12 |
| 651 | CD1 | LEU | 608 | 15.824 | 56.992 | 10.845 | 1.00 | 21.31 |
| 652 | CD2 | LEU | 608 | 17.592 | 56.443 | 12.524 | 1.00 | 22.01 |
| 653 | N | GLY | 609 | 14.406 | 53.031 | 12.610 | 1.00 | 19.32 |
| 654 | CA | GLY | 609 | 14.642 | 51.749 | 11.967 | 1.00 | 22.15 |
| 655 | C | GLY | 609 | 13.388 | 51.267 | 11.274 | 1.00 | 22.09 |
| 656 | O | GLY | 609 | 13.404 | 50.859 | 10.095 | 1.00 | 18.52 |
| 657 | N | TRP | 610 | 12.274 | 51.326 | 11.995 | 1.00 | 18.65 |
| 658 | CA | TRP | 610 | 11.011 | 50.885 | 11.424 | 1.00 | 21.70 |
| 659 | C | TRP | 610 | 10.602 | 51.712 | 10.189 | 1.00 | 20.69 |
| 660 | O | TRP | 610 | 10.218 | 51.156 | 9.162 | 1.00 | 20.73 |
| 661 | CB | TRP | 610 | 9.911 | 50.926 | 12.493 | 1.00 | 19.80 |
| 662 | CG | TRP | 610 | 8.584 | 50.462 | 11.980 | 1.00 | 20.60 |
| 663 | CD1 | TRP | 610 | 7.541 | 51.236 | 11.588 | 1.00 | 26.35 |
| 664 | CD2 | TRP | 610 | 8.204 | 49.104 | 11.712 | 1.00 | 22.75 |
| 665 | NE1 | TRP | 610 | 6.527 | 50.452 | 11.086 | 1.00 | 25.80 |
| 666 | CE2 | TRP | 610 | 6.909 | 49.137 | 11.151 | 1.00 | 27.72 |
| 667 | CE3 | TRP | 610 | 8.835 | 47.870 | 11.890 | 1.00 | 24.76 |
| 668 | CZ2 | TRP | 610 | 6.223 | 47.971 | 10.759 | 1.00 | 28.33 |
| 669 | CZ3 | TRP | 610 | 8.154 | 46.703 | 11.502 | 1.00 | 25.79 |
| 670 | CH2 | TRP | 610 | 6.862 | 46.771 | 10.944 | 1.00 | 23.99 |
| 671 | N | ARG | 611 | 10.686 | 53.038 | 10.273 | 1.00 | 20.81 |
| 672 | CA | ARG | 611 | 10.301 | 53.868 | 9.132 | 1.00 | 18.86 |
| 673 | C | ARG | 611 | 11.209 | 53.618 | 7.926 | 1.00 | 18.44 |
| 674 | O | ARG | 611 | 10.747 | 53.594 | 6.783 | 1.00 | 20.30 |
| 675 | CB | ARG | 611 | 10.341 | 55.357 | 9.493 | 1.00 | 18.28 |
| 676 | CG | ARG | 611 | 9.298 | 55.794 | 10.543 | 1.00 | 20.05 |
| 677 | CD | ARG | 611 | 9.320 | 57.317 | 10.695 | 1.00 | 25.08 |
| 678 | NE | ARG | 611 | 10.593 | 57.831 | 11.202 | 1.00 | 20.13 |
| 679 | CZ | ARG | 611 | 10.944 | 57.862 | 12.483 | 1.00 | 22.33 |
| 680 | NH1 | ARG | 611 | 10.128 | 57.409 | 13.478 | 1.00 | 22.73 |
| 681 | NH2 | ARG | 611 | 12.160 | 58.356 | 12.800 | 1.00 | 19.31 |
| 682 | N | SER | 612 | 12.490 | 53.431 | 8.187 | 1.00 | 20.91 |
| 683 | CA | SER | 612 | 13.459 | 53.185 | 7.117 | 1.00 | 18.59 |
| 684 | C | SER | 612 | 13.126 | 51.856 | 6.432 | 1.00 | 24.76 |
| 685 | O | SER | 612 | 13.088 | 51.761 | 5.208 | 1.00 | 19.96 |
| 686 | CB | SER | 612 | 14.869 | 53.159 | 7.709 | 1.00 | 19.66 |
| 687 | OG | SER | 612 | 15.287 | 54.391 | 8.280 | 1.00 | 23.01 |
| 688 | N | TYR | 613 | 12.852 | 50.847 | 7.248 | 1.00 | 20.64 |
| 689 | CA | TYR | 613 | 12.468 | 49.520 | 6.762 | 1.00 | 21.51 |
| 690 | C | TYR | 613 | 11.193 | 49.603 | 5.909 | 1.00 | 20.49 |
| 691 | O | TYR | 613 | 11.166 | 49.176 | 4.749 | 1.00 | 20.85 |
| 692 | CB | TYR | 613 | 12.255 | 48.625 | 7.993 | 1.00 | 20.88 |
| 693 | CG | TYR | 613 | 11.481 | 47.341 | 7.799 | 1.00 | 24.41 |
| 694 | CD1 | TYR | 613 | 11.853 | 46.392 | 6.843 | 1.00 | 24.71 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 695 | CD2 | TYR | 613 | 10.448 | 47.022 | 8.672 | 1.00 | 22.00 |
| 696 | CE1 | TYR | 613 | 11.208 | 45.137 | 6.787 | 1.00 | 21.58 |
| 697 | CE2 | TYR | 613 | 9.812 | 45.792 | 8.622 | 1.00 | 21.74 |
| 698 | CZ | TYR | 613 | 10.203 | 44.853 | 7.691 | 1.00 | 24.16 |
| 699 | OH | TYR | 613 | 9.579 | 43.627 | 7.637 | 1.00 | 22.86 |
| 700 | N | ARG | 614 | 10.147 | 50.203 | 6.467 | 1.00 | 19.61 |
| 701 | CA | ARG | 614 | 8.859 | 50.302 | 5.779 | 1.00 | 20.88 |
| 702 | C | ARG | 614 | 8.783 | 51.149 | 4.525 | 1.00 | 25.83 |
| 703 | O | ARG | 614 | 8.173 | 50.737 | 3.535 | 1.00 | 23.20 |
| 704 | CB | ARG | 614 | 7.789 | 50.821 | 6.744 | 1.00 | 26.26 |
| 705 | CG | ARG | 614 | 7.402 | 49.864 | 7.838 | 1.00 | 29.74 |
| 706 | CD | ARG | 614 | 6.455 | 48.756 | 7.353 | 1.00 | 34.33 |
| 707 | NE | ARG | 614 | 6.095 | 47.866 | 8.496 | 1.00 | 99.90 |
| 708 | CZ | ARG | 614 | 5.290 | 46.810 | 8.424 | 1.00 | 99.90 |
| 709 | NH1 | ARG | 614 | 5.065 | 46.135 | 9.507 | 1.00 | 99.90 |
| 710 | NH2 | ARG | 614 | 4.714 | 46.415 | 7.324 | 1.00 | 99.90 |
| 711 | N | GLN | 615 | 9.397 | 52.326 | 4.564 | 1.00 | 20.34 |
| 712 | CA | GLN | 615 | 9.314 | 53.278 | 3.458 | 1.00 | 25.32 |
| 713 | C | GLN | 615 | 10.398 | 53.227 | 2.392 | 1.00 | 24.30 |
| 714 | O | GLN | 615 | 10.153 | 53.590 | 1.243 | 1.00 | 23.64 |
| 715 | CB | GLN | 615 | 9.274 | 54.708 | 4.027 | 1.00 | 25.43 |
| 716 | CG | GLN | 615 | 9.138 | 55.864 | 2.982 | 1.00 | 99.90 |
| 717 | CD | GLN | 615 | 9.152 | 57.318 | 3.470 | 1.00 | 99.90 |
| 718 | OE1 | GLN | 615 | 9.089 | 58.249 | 2.682 | 1.00 | 99.90 |
| 719 | NE2 | GLN | 615 | 9.259 | 57.578 | 4.749 | 1.00 | 99.90 |
| 720 | N | SER | 616 | 11.596 | 52.791 | 2.759 | 1.00 | 24.39 |
| 721 | CA | SER | 616 | 12.680 | 52.765 | 1.789 | 1.00 | 25.76 |
| 722 | C | SER | 616 | 13.443 | 51.452 | 1.809 | 1.00 | 24.92 |
| 723 | O | SER | 616 | 14.609 | 51.399 | 1.451 | 1.00 | 27.56 |
| 724 | CB | SER | 616 | 13.650 | 53.978 | 2.014 | 1.00 | 27.85 |
| 725 | OG | SER | 616 | 14.409 | 53.867 | 3.223 | 1.00 | 99.90 |
| 726 | N | SER | 617 | 12.763 | 50.384 | 2.217 | 1.00 | 22.68 |
| 727 | CA | SER | 617 | 13.365 | 49.052 | 2.280 | 1.00 | 24.24 |
| 728 | C | SER | 617 | 14.686 | 48.997 | 3.021 | 1.00 | 22.19 |
| 729 | O | SER | 617 | 15.547 | 48.160 | 2.721 | 1.00 | 24.35 |
| 730 | CB | SER | 617 | 13.526 | 48.483 | 0.862 | 1.00 | 22.79 |
| 731 | OG | SER | 617 | 12.294 | 48.353 | 0.151 | 1.00 | 24.02 |
| 732 | N | ALA | 618 | 14.827 | 49.883 | 4.011 | 1.00 | 20.76 |
| 733 | CA | ALA | 618 | 16.026 | 49.916 | 4.830 | 1.00 | 21.80 |
| 734 | C | ALA | 618 | 17.254 | 50.449 | 4.123 | 1.00 | 20.80 |
| 735 | O | ALA | 618 | 18.352 | 50.403 | 4.676 | 1.00 | 25.34 |
| 736 | CB | ALA | 618 | 16.235 | 48.506 | 5.409 | 1.00 | 99.90 |
| 737 | N | ASN | 619 | 17.069 | 50.990 | 2.928 | 1.00 | 23.07 |
| 738 | CA | ASN | 619 | 18.203 | 51.479 | 2.156 | 1.00 | 23.42 |
| 739 | C | ASN | 619 | 18.560 | 52.962 | 2.319 | 1.00 | 25.60 |
| 740 | O | ASN | 619 | 19.512 | 53.440 | 1.703 | 1.00 | 23.56 |
| 741 | CB | ASN | 619 | 17.987 | 51.138 | 0.680 | 1.00 | 25.32 |
| 742 | CG | ASN | 619 | 17.774 | 49.661 | 0.332 | 1.00 | 99.90 |
| 743 | OD1 | ASN | 619 | 16.665 | 49.194 | 0.123 | 1.00 | 99.90 |
| 744 | ND2 | ASN | 619 | 18.813 | 48.871 | 0.281 | 1.00 | 99.90 |
| 745 | N | LEU | 620 | 17.787 | 53.687 | 3.121 | 1.00 | 21.96 |
| 746 | CA | LEU | 620 | 18.074 | 55.094 | 3.425 | 1.00 | 22.20 |
| 747 | C | LEU | 620 | 17.560 | 55.257 | 4.857 | 1.00 | 24.08 |
| 748 | O | LEU | 620 | 16.807 | 54.408 | 5.327 | 1.00 | 21.84 |
| 749 | CB | LEU | 620 | 17.311 | 56.048 | 2.499 | 1.00 | 23.95 |
| 750 | CG | LEU | 620 | 17.531 | 55.912 | 0.968 | 1.00 | 99.90 |
| 751 | CD1 | LEU | 620 | 16.772 | 57.020 | 0.225 | 1.00 | 99.90 |
| 752 | CD2 | LEU | 620 | 19.018 | 55.951 | 0.576 | 1.00 | 99.90 |
| 753 | N | LEU | 621 | 17.985 | 56.311 | 5.552 | 1.00 | 21.78 |
| 754 | CA | LEU | 621 | 17.505 | 56.553 | 6.924 | 1.00 | 22.28 |
| 755 | C | LEU | 621 | 16.356 | 57.545 | 6.837 | 1.00 | 20.07 |
| 756 | O | LEU | 621 | 16.541 | 58.727 | 6.544 | 1.00 | 21.05 |
| 757 | CB | LEU | 621 | 18.630 | 57.076 | 7.826 | 1.00 | 21.10 |
| 758 | CG | LEU | 621 | 19.759 | 56.060 | 8.074 | 1.00 | 24.71 |
| 759 | CD1 | LEU | 621 | 20.794 | 56.627 | 9.017 | 1.00 | 26.09 |
| 760 | CD2 | LEU | 621 | 19.174 | 54.777 | 8.653 | 1.00 | 23.43 |
| 761 | N | CYS | 622 | 15.154 | 57.041 | 7.070 | 1.00 | 20.52 |
| 762 | CA | CYS | 622 | 13.950 | 57.844 | 6.975 | 1.00 | 17.48 |
| 763 | C | CYS | 622 | 13.647 | 58.516 | 8.327 | 1.00 | 21.46 |
| 764 | O | CYS | 622 | 12.783 | 58.069 | 9.066 | 1.00 | 18.14 |
| 765 | CB | CYS | 622 | 12.729 | 57.025 | 6.493 | 1.00 | 20.38 |
| 766 | SG | CYS | 622 | 12.923 | 56.304 | 4.826 | 1.00 | 99.90 |
| 767 | N | PHE | 623 | 14.377 | 59.583 | 8.644 | 1.00 | 20.19 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 768 | CA | PHE | 623 | 14.147 | 60.288 | 9.903 | 1.00 | 22.33 |
| 769 | C | PHE | 623 | 12.734 | 60.881 | 9.946 | 1.00 | 19.77 |
| 770 | O | PHE | 623 | 12.036 | 60.799 | 10.953 | 1.00 | 20.69 |
| 771 | CB | PHE | 623 | 15.209 | 61.386 | 10.109 | 1.00 | 17.81 |
| 772 | CG | PHE | 623 | 16.565 | 60.855 | 10.420 | 1.00 | 19.78 |
| 773 | CD1 | PHE | 623 | 17.463 | 60.544 | 9.409 | 1.00 | 26.89 |
| 774 | CD2 | PHE | 623 | 16.942 | 60.616 | 11.737 | 1.00 | 21.49 |
| 775 | CE1 | PHE | 623 | 18.726 | 59.999 | 9.722 | 1.00 | 24.89 |
| 776 | CE2 | PHE | 623 | 18.193 | 60.073 | 12.051 | 1.00 | 21.92 |
| 777 | CZ | PHE | 623 | 19.087 | 59.766 | 11.043 | 1.00 | 25.29 |
| 778 | N | ALA | 624 | 12.311 | 61.478 | 8.846 | 1.00 | 18.84 |
| 779 | CA | ALA | 624 | 10.976 | 62.054 | 8.755 | 1.00 | 18.94 |
| 780 | C | ALA | 624 | 10.706 | 62.148 | 7.259 | 1.00 | 23.24 |
| 781 | O | ALA | 624 | 11.621 | 61.956 | 6.458 | 1.00 | 21.88 |
| 782 | CB | ALA | 624 | 10.948 | 63.442 | 9.399 | 1.00 | 19.00 |
| 783 | N | PRO | 625 | 9.452 | 62.382 | 6.864 | 1.00 | 24.08 |
| 784 | CA | PRO | 625 | 9.122 | 62.493 | 5.441 | 1.00 | 22.75 |
| 785 | C | PRO | 625 | 9.897 | 63.631 | 4.757 | 1.00 | 31.17 |
| 786 | O | PRO | 625 | 10.189 | 63.558 | 3.560 | 1.00 | 27.19 |
| 787 | CB | PRO | 625 | 7.618 | 62.742 | 5.476 | 1.00 | 23.42 |
| 788 | CG | PRO | 625 | 7.198 | 61.973 | 6.719 | 1.00 | 29.68 |
| 789 | CD | PRO | 625 | 8.225 | 62.532 | 7.668 | 1.00 | 19.66 |
| 790 | N | ASP | 626 | 10.240 | 64.671 | 5.514 | 1.00 | 24.25 |
| 791 | CA | ASP | 626 | 10.984 | 65.801 | 4.951 | 1.00 | 30.35 |
| 792 | C | ASP | 626 | 12.470 | 65.758 | 5.305 | 1.00 | 28.45 |
| 793 | O | ASP | 626 | 13.216 | 66.724 | 5.082 | 1.00 | 31.54 |
| 794 | CB | ASP | 626 | 10.362 | 67.106 | 5.439 | 1.00 | 33.03 |
| 795 | CG | ASP | 626 | 10.455 | 67.270 | 6.945 | 1.00 | 42.61 |
| 796 | OD1 | ASP | 626 | 10.274 | 66.273 | 7.681 | 1.00 | 37.30 |
| 797 | OD2 | ASP | 626 | 10.687 | 68.409 | 7.395 | 1.00 | 39.66 |
| 798 | N | LEU | 627 | 12.907 | 64.627 | 5.844 | 1.00 | 25.42 |
| 799 | CA | LEU | 627 | 14.290 | 64.464 | 6.238 | 1.00 | 23.61 |
| 800 | C | LEU | 627 | 14.689 | 62.992 | 6.078 | 1.00 | 25.27 |
| 801 | O | LEU | 627 | 14.650 | 62.200 | 7.018 | 1.00 | 21.60 |
| 802 | CB | LEU | 627 | 14.465 | 64.921 | 7.686 | 1.00 | 25.81 |
| 803 | CG | LEU | 627 | 15.903 | 65.214 | 8.098 | 1.00 | 26.41 |
| 804 | CD1 | LEU | 627 | 16.471 | 66.222 | 7.110 | 1.00 | 37.20 |
| 805 | CD2 | LEU | 627 | 15.944 | 65.796 | 9.499 | 1.00 | 23.25 |
| 806 | N | ILE | 628 | 15.038 | 62.634 | 4.849 | 1.00 | 20.00 |
| 807 | CA | ILE | 628 | 15.447 | 61.288 | 4.510 | 1.00 | 21.82 |
| 808 | C | ILE | 628 | 16.926 | 61.365 | 4.132 | 1.00 | 26.37 |
| 809 | O | ILE | 628 | 17.280 | 62.120 | 3.233 | 1.00 | 27.10 |
| 810 | CB | ILE | 628 | 14.659 | 60.791 | 3.287 | 1.00 | 19.86 |
| 811 | CG1 | ILE | 628 | 13.160 | 60.854 | 3.576 | 1.00 | 23.93 |
| 812 | CG2 | ILE | 628 | 15.107 | 59.369 | 2.935 | 1.00 | 26.69 |
| 813 | CD1 | ILE | 628 | 12.264 | 60.752 | 2.345 | 1.00 | 22.62 |
| 814 | N | ILE | 629 | 17.781 | 60.593 | 4.797 | 1.00 | 24.00 |
| 815 | CA | ILE | 629 | 19.203 | 60.626 | 4.478 | 1.00 | 30.39 |
| 816 | C | ILE | 629 | 19.745 | 59.395 | 3.756 | 1.00 | 28.22 |
| 817 | O | ILE | 629 | 19.446 | 58.251 | 4.116 | 1.00 | 27.38 |
| 818 | CB | ILE | 629 | 19.971 | 60.933 | 5.814 | 1.00 | 27.74 |
| 819 | CG2 | ILE | 629 | 21.443 | 61.321 | 5.592 | 1.00 | 99.90 |
| 820 | CG1 | ILE | 629 | 19.354 | 62.070 | 6.698 | 1.00 | 99.90 |
| 821 | CD1 | ILE | 629 | 19.296 | 63.491 | 6.094 | 1.00 | 99.90 |
| 822 | N | ASN | 630 | 20.560 | 59.665 | 2.739 | 1.00 | 37.87 |
| 823 | CA | ASN | 630 | 21.239 | 58.635 | 1.955 | 1.00 | 34.28 |
| 824 | C | ASN | 630 | 22.728 | 58.921 | 2.135 | 1.00 | 40.43 |
| 825 | O | ASN | 630 | 23.105 | 59.961 | 2.699 | 1.00 | 32.88 |
| 826 | CB | ASN | 630 | 20.868 | 58.724 | 0.473 | 1.00 | 43.78 |
| 827 | CG | ASN | 630 | 21.147 | 60.091 | −0.113 | 1.00 | 39.05 |
| 828 | OD1 | ASN | 630 | 22.203 | 60.674 | 0.123 | 1.00 | 56.25 |
| 829 | ND2 | ASN | 630 | 20.136 | 60.626 | −0.936 | 1.00 | 55.74 |
| 830 | N | GLU | 631 | 23.563 | 58.000 | 1.660 | 1.00 | 37.34 |
| 831 | CA | GLU | 631 | 25.015 | 58.123 | 1.773 | 1.00 | 41.84 |
| 832 | C | GLU | 631 | 25.558 | 59.475 | 1.335 | 1.00 | 36.02 |
| 833 | O | GLU | 631 | 26.437 | 60.024 | 1.991 | 1.00 | 37.52 |
| 834 | CB | GLU | 631 | 25.716 | 57.026 | 0.967 | 1.00 | 43.26 |
| 835 | CG | GLU | 631 | 25.473 | 55.592 | 1.439 | 1.00 | 53.06 |
| 836 | CD | GLU | 631 | 24.088 | 55.065 | 1.099 | 1.00 | 52.18 |
| 837 | OE1 | GLU | 631 | 23.252 | 55.830 | 0.573 | 1.00 | 55.65 |
| 838 | OE2 | GLU | 631 | 23.838 | 53.869 | 1.359 | 1.00 | 59.59 |
| 839 | N | GLN | 632 | 25.040 | 60.004 | 0.229 | 1.00 | 37.37 |
| 840 | CA | GLN | 632 | 25.483 | 61.297 | −0.301 | 1.00 | 41.31 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 841 | C | GLN | 632 | 25.334 | 62.468 | 0.673 | 1.00 | 44.67 |
| 842 | O | GLN | 632 | 26.122 | 63.416 | 0.642 | 1.00 | 39.36 |
| 843 | CB | GLN | 632 | 24.710 | 61.641 | −1.575 | 1.00 | 39.63 |
| 844 | CG | GLN | 632 | 24.887 | 60.656 | −2.720 | 1.00 | 54.67 |
| 845 | CD | GLN | 632 | 23.944 | 60.939 | −3.875 | 1.00 | 54.04 |
| 846 | OE1 | GLN | 632 | 24.051 | 61.964 | −4.552 | 1.00 | 65.04 |
| 847 | NE2 | GLN | 632 | 22.945 | 59.973 | −4.120 | 1.00 | 58.37 |
| 848 | N | ARG | 633 | 24.327 | 62.401 | 1.538 | 1.00 | 42.38 |
| 849 | CA | ARG | 633 | 24.072 | 63.483 | 2.483 | 1.00 | 46.01 |
| 850 | C | ARG | 633 | 24.797 | 63.327 | 3.817 | 1.00 | 44.06 |
| 851 | O | ARG | 633 | 24.707 | 64.194 | 4.690 | 1.00 | 43.28 |
| 852 | CB | ARG | 633 | 22.560 | 63.614 | 2.701 | 1.00 | 45.62 |
| 853 | CG | ARG | 633 | 21.804 | 63.732 | 1.385 | 1.00 | 51.99 |
| 854 | CD | ARG | 633 | 20.303 | 63.885 | 1.551 | 1.00 | 54.00 |
| 855 | NE | ARG | 633 | 19.923 | 65.164 | 2.148 | 1.00 | 62.20 |
| 856 | CZ | ARG | 633 | 18.664 | 65.565 | 2.312 | 1.00 | 62.82 |
| 857 | NH1 | ARG | 633 | 17.623 | 64.842 | 1.808 | 1.00 | 63.08 |
| 858 | NH2 | ARG | 633 | 18.318 | 66.680 | 2.975 | 1.00 | 64.33 |
| 859 | N | MET | 634 | 25.524 | 62.231 | 3.972 | 1.00 | 42.60 |
| 860 | CA | MET | 634 | 26.267 | 61.991 | 5.200 | 1.00 | 44.82 |
| 861 | C | MET | 634 | 27.734 | 62.253 | 4.897 | 1.00 | 44.81 |
| 862 | O | MET | 634 | 28.533 | 61.322 | 4.802 | 1.00 | 41.79 |
| 863 | CB | MET | 634 | 26.074 | 60.546 | 5.653 | 1.00 | 47.11 |
| 864 | CG | MET | 634 | 24.619 | 60.166 | 5.850 | 1.00 | 38.54 |
| 865 | SD | MET | 634 | 24.425 | 58.402 | 6.144 | 1.00 | 40.15 |
| 866 | CE | MET | 634 | 22.638 | 58.288 | 6.218 | 1.00 | 40.02 |
| 867 | N | THR | 635 | 28.077 | 63.525 | 4.733 | 1.00 | 45.90 |
| 868 | CA | THR | 635 | 29.448 | 63.911 | 4.417 | 1.00 | 49.64 |
| 869 | C | THR | 635 | 30.366 | 63.686 | 5.604 | 1.00 | 52.38 |
| 870 | O | THR | 635 | 31.373 | 62.981 | 5.505 | 1.00 | 56.13 |
| 871 | CB | THR | 635 | 29.493 | 65.382 | 4.014 | 1.00 | 52.46 |
| 872 | OG1 | THR | 635 | 28.707 | 65.604 | 2.851 | 1.00 | 99.90 |
| 873 | CG2 | THR | 635 | 30.883 | 65.951 | 3.656 | 1.00 | 99.90 |
| 874 | N | LEU | 636 | 30.007 | 64.308 | 6.721 | 1.00 | 54.04 |
| 875 | CA | LEU | 636 | 30.756 | 64.222 | 7.970 | 1.00 | 54.00 |
| 876 | C | LEU | 636 | 31.118 | 62.774 | 8.280 | 1.00 | 52.73 |
| 877 | O | LEU | 636 | 30.238 | 61.939 | 8.474 | 1.00 | 52.98 |
| 878 | CB | LEU | 636 | 30.018 | 64.862 | 9.170 | 1.00 | 61.18 |
| 879 | CG | LEU | 636 | 30.886 | 65.075 | 10.440 | 1.00 | 99.90 |
| 880 | CD1 | LEU | 636 | 31.840 | 66.285 | 10.304 | 1.00 | 99.90 |
| 881 | CD2 | LEU | 636 | 30.007 | 65.206 | 11.701 | 1.00 | 99.90 |
| 882 | N | PRO | 637 | 32.410 | 62.469 | 8.330 | 1.00 | 47.20 |
| 883 | CA | PRO | 637 | 32.837 | 61.103 | 8.611 | 1.00 | 47.93 |
| 884 | C | PRO | 637 | 32.365 | 60.555 | 9.969 | 1.00 | 45.20 |
| 885 | O | PRO | 637 | 32.004 | 59.376 | 10.065 | 1.00 | 41.96 |
| 886 | CB | PRO | 637 | 34.365 | 60.995 | 8.489 | 1.00 | 47.55 |
| 887 | CG | PRO | 637 | 34.792 | 62.388 | 8.982 | 1.00 | 99.90 |
| 888 | CD | PRO | 637 | 33.765 | 63.328 | 8.343 | 1.00 | 99.90 |
| 889 | N | CYS | 638 | 32.359 | 61.394 | 11.012 | 1.00 | 41.56 |
| 890 | CA | CYS | 638 | 31.923 | 60.938 | 12.337 | 1.00 | 34.71 |
| 891 | C | CYS | 638 | 30.419 | 60.645 | 12.344 | 1.00 | 33.35 |
| 892 | O | CYS | 638 | 29.985 | 59.654 | 12.927 | 1.00 | 30.89 |
| 893 | CB | CYS | 638 | 32.341 | 61.841 | 13.519 | 1.00 | 36.41 |
| 894 | SG | CYS | 638 | 31.647 | 63.515 | 13.583 | 1.00 | 99.90 |
| 895 | N | MET | 639 | 29.644 | 61.502 | 11.684 | 1.00 | 32.63 |
| 896 | CA | MET | 639 | 28.196 | 61.332 | 11.615 | 1.00 | 35.71 |
| 897 | C | MET | 639 | 27.821 | 60.152 | 10.712 | 1.00 | 35.32 |
| 898 | O | MET | 639 | 26.883 | 59.415 | 11.002 | 1.00 | 33.54 |
| 899 | CB | MET | 639 | 27.482 | 62.566 | 11.004 | 1.00 | 42.64 |
| 900 | CG | MET | 639 | 25.996 | 62.404 | 10.638 | 1.00 | 99.90 |
| 901 | SD | MET | 639 | 25.346 | 63.899 | 9.804 | 1.00 | 99.90 |
| 902 | CE | MET | 639 | 24.091 | 63.111 | 8.739 | 1.00 | 99.90 |
| 903 | N | TYR | 640 | 28.560 | 59.979 | 9.620 | 1.00 | 31.90 |
| 904 | CA | TYR | 640 | 28.315 | 58.858 | 8.708 | 1.00 | 28.99 |
| 905 | C | TYR | 640 | 28.560 | 57.587 | 9.490 | 1.00 | 25.10 |
| 906 | O | TYR | 640 | 27.802 | 56.627 | 9.404 | 1.00 | 29.55 |
| 907 | CB | TYR | 640 | 29.281 | 58.918 | 7.518 | 1.00 | 37.34 |
| 908 | CG | TYR | 640 | 29.171 | 57.750 | 6.560 | 1.00 | 40.29 |
| 909 | CD1 | TYR | 640 | 28.014 | 57.544 | 5.805 | 1.00 | 40.54 |
| 910 | CD2 | TYR | 640 | 30.233 | 56.862 | 6.397 | 1.00 | 42.80 |
| 911 | CE1 | TYR | 640 | 27.918 | 56.487 | 4.913 | 1.00 | 42.21 |
| 912 | CE2 | TYR | 640 | 30.148 | 55.798 | 5.504 | 1.00 | 45.44 |
| 913 | CZ | TYR | 640 | 28.988 | 55.618 | 4.762 | 1.00 | 44.14 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 914 | OH | TYR | 640 | 28.896 | 54.572 | 3.871 | 1.00 | 48.25 |
| 915 | N | ASP | 641 | 29.622 | 57.572 | 10.282 | 1.00 | 24.54 |
| 916 | CA | ASP | 641 | 29.907 | 56.378 | 11.043 | 1.00 | 25.44 |
| 917 | C | ASP | 641 | 28.766 | 56.107 | 12.019 | 1.00 | 28.08 |
| 918 | O | ASP | 641 | 28.423 | 54.954 | 12.269 | 1.00 | 31.55 |
| 919 | CB | ASP | 641 | 31.224 | 56.521 | 11.805 | 1.00 | 32.47 |
| 920 | CG | ASP | 641 | 31.748 | 55.265 | 12.517 | 1.00 | 99.90 |
| 921 | OD1 | ASP | 641 | 32.268 | 55.294 | 13.623 | 1.00 | 99.90 |
| 922 | OD2 | ASP | 641 | 31.547 | 54.123 | 11.794 | 1.00 | 99.90 |
| 923 | N | GLN | 642 | 28.183 | 57.165 | 12.575 | 1.00 | 25.12 |
| 924 | CA | GLN | 642 | 27.081 | 56.967 | 13.514 | 1.00 | 25.95 |
| 925 | C | GLN | 642 | 25.853 | 56.449 | 12.766 | 1.00 | 27.16 |
| 926 | O | GLN | 642 | 25.099 | 55.631 | 13.289 | 1.00 | 29.13 |
| 927 | CB | GLN | 642 | 26.776 | 58.283 | 14.226 | 1.00 | 32.01 |
| 928 | CG | GLN | 642 | 25.534 | 58.198 | 15.118 | 1.00 | 99.90 |
| 929 | CD | GLN | 642 | 25.367 | 59.502 | 15.876 | 1.00 | 99.90 |
| 930 | OE1 | GLN | 642 | 25.084 | 59.490 | 17.059 | 1.00 | 99.90 |
| 931 | NE2 | GLN | 642 | 25.556 | 60.682 | 15.111 | 1.00 | 99.90 |
| 932 | N | CYS | 643 | 25.641 | 56.940 | 11.549 | 1.00 | 26.93 |
| 933 | CA | CYS | 643 | 24.514 | 56.484 | 10.748 | 1.00 | 28.14 |
| 934 | C | CYS | 643 | 24.633 | 55.008 | 10.390 | 1.00 | 24.65 |
| 935 | O | CYS | 643 | 23.628 | 54.295 | 10.365 | 1.00 | 25.73 |
| 936 | CB | CYS | 643 | 24.377 | 57.324 | 9.477 | 1.00 | 24.73 |
| 937 | SG | CYS | 643 | 23.765 | 59.023 | 9.748 | 1.00 | 32.75 |
| 938 | N | LYS | 644 | 25.853 | 54.544 | 10.110 | 1.00 | 25.25 |
| 939 | CA | LYS | 644 | 26.062 | 53.132 | 9.792 | 1.00 | 26.29 |
| 940 | C | LYS | 644 | 25.682 | 52.271 | 10.978 | 1.00 | 27.01 |
| 941 | O | LYS | 644 | 25.217 | 51.133 | 10.827 | 1.00 | 27.73 |
| 942 | CB | LYS | 644 | 27.522 | 52.862 | 9.434 | 1.00 | 28.72 |
| 943 | CG | LYS | 644 | 27.792 | 51.395 | 9.014 | 1.00 | 99.90 |
| 944 | CD | LYS | 644 | 29.258 | 51.072 | 8.711 | 1.00 | 99.90 |
| 945 | CE | LYS | 644 | 29.388 | 49.579 | 8.381 | 1.00 | 99.90 |
| 946 | NZ | LYS | 644 | 30.760 | 49.297 | 7.922 | 1.00 | 99.90 |
| 947 | N | HIS | 645 | 25.914 | 52.808 | 12.169 | 1.00 | 28.68 |
| 948 | CA | HIS | 645 | 25.574 | 52.111 | 13.399 | 1.00 | 27.55 |
| 949 | C | HIS | 645 | 24.058 | 52.056 | 13.507 | 1.00 | 20.19 |
| 950 | O | HIS | 645 | 23.490 | 51.021 | 13.856 | 1.00 | 28.87 |
| 951 | CB | HIS | 645 | 26.107 | 52.749 | 14.715 | 1.00 | 37.30 |
| 952 | CG | HIS | 645 | 27.612 | 52.692 | 14.796 | 1.00 | 99.90 |
| 953 | ND1 | HIS | 645 | 28.464 | 52.435 | 13.772 | 1.00 | 99.90 |
| 954 | CD2 | HIS | 645 | 28.375 | 52.877 | 15.984 | 1.00 | 99.90 |
| 955 | CE1 | HIS | 645 | 29.707 | 52.477 | 14.312 | 1.00 | 99.90 |
| 956 | NE2 | HIS | 645 | 29.741 | 52.753 | 15.701 | 1.00 | 99.90 |
| 957 | N | MET | 646 | 23.410 | 53.174 | 13.213 | 1.00 | 20.28 |
| 958 | CA | MET | 646 | 21.953 | 53.226 | 13.270 | 1.00 | 23.80 |
| 959 | C | MET | 646 | 21.364 | 52.299 | 12.209 | 1.00 | 25.24 |
| 960 | O | MET | 646 | 20.358 | 51.634 | 12.444 | 1.00 | 23.42 |
| 961 | CB | MET | 646 | 21.457 | 54.660 | 13.040 | 1.00 | 23.19 |
| 962 | CG | MET | 646 | 21.841 | 55.620 | 14.177 | 1.00 | 25.74 |
| 963 | SD | MET | 646 | 21.014 | 57.221 | 13.996 | 1.00 | 29.64 |
| 964 | CE | MET | 646 | 21.961 | 57.963 | 12.711 | 1.00 | 40.66 |
| 965 | N | LEU | 647 | 22.017 | 52.247 | 11.053 | 1.00 | 27.17 |
| 966 | CA | LEU | 647 | 21.560 | 51.430 | 9.929 | 1.00 | 27.11 |
| 967 | C | LEU | 647 | 21.425 | 49.945 | 10.251 | 1.00 | 28.77 |
| 968 | O | LEU | 647 | 20.705 | 49.207 | 9.571 | 1.00 | 26.96 |
| 969 | CB | LEU | 647 | 22.502 | 51.592 | 8.740 | 1.00 | 27.64 |
| 970 | CG | LEU | 647 | 22.725 | 53.021 | 8.174 | 1.00 | 99.90 |
| 971 | CD1 | LEU | 647 | 23.610 | 52.959 | 6.921 | 1.00 | 99.90 |
| 972 | CD2 | LEU | 647 | 21.407 | 53.741 | 7.842 | 1.00 | 99.90 |
| 973 | N | TYR | 648 | 22.122 | 49.506 | 11.291 | 1.00 | 27.01 |
| 974 | CA | TYR | 648 | 22.068 | 48.111 | 11.700 | 1.00 | 29.15 |
| 975 | C | TYR | 648 | 20.655 | 47.659 | 12.025 | 1.00 | 27.44 |
| 976 | O | TYR | 648 | 20.301 | 46.504 | 11.793 | 1.00 | 26.00 |
| 977 | CB | TYR | 648 | 22.937 | 47.884 | 12.928 | 1.00 | 27.84 |
| 978 | CG | TYR | 648 | 24.436 | 48.162 | 12.771 | 1.00 | 99.90 |
| 979 | CD1 | TYR | 648 | 24.976 | 49.355 | 13.263 | 1.00 | 99.90 |
| 980 | CD2 | TYR | 648 | 25.270 | 47.239 | 12.134 | 1.00 | 99.90 |
| 981 | CE1 | TYR | 648 | 26.333 | 49.624 | 13.113 | 1.00 | 99.90 |
| 982 | CE2 | TYR | 648 | 26.628 | 47.512 | 11.984 | 1.00 | 99.90 |
| 983 | CZ | TYR | 648 | 27.158 | 48.702 | 12.474 | 1.00 | 99.90 |
| 984 | OH | TYR | 648 | 28.490 | 48.967 | 12.323 | 1.00 | 99.90 |
| 985 | N | VAL | 649 | 19.852 | 48.556 | 12.584 | 1.00 | 23.42 |
| 986 | CA | VAL | 649 | 18.493 | 48.186 | 12.934 | 1.00 | 25.19 |

TABLE 5-continued

ATOMIC COORDINATES FOR THE GR/SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 987 | C | VAL | 649 | 17.612 | 47.883 | 11.712 | 1.00 | 22.21 |
| 988 | O | VAL | 649 | 17.038 | 46.798 | 11.627 | 1.00 | 28.86 |
| 989 | CB | VAL | 649 | 17.786 | 49.291 | 13.791 | 1.00 | 25.31 |
| 990 | CG1 | VAL | 649 | 18.566 | 49.652 | 15.080 | 1.00 | 99.90 |
| 991 | CG2 | VAL | 649 | 16.350 | 48.878 | 14.193 | 1.00 | 99.90 |
| 992 | N | SER | 650 | 17.484 | 48.821 | 10.756 | 1.00 | 22.89 |
| 993 | CA | SER | 650 | 16.645 | 48.538 | 9.576 | 1.00 | 26.67 |
| 994 | C | SER | 650 | 17.123 | 47.268 | 8.877 | 1.00 | 25.60 |
| 995 | O | SER | 650 | 16.329 | 46.505 | 8.316 | 1.00 | 25.13 |
| 996 | CB | SER | 650 | 16.871 | 49.767 | 8.690 | 1.00 | 22.17 |
| 997 | OG | SER | 650 | 18.194 | 49.823 | 8.144 | 1.00 | 99.90 |
| 998 | N | SER | 651 | 18.438 | 47.055 | 8.909 | 1.00 | 29.12 |
| 999 | CA | SER | 651 | 19.039 | 45.877 | 8.287 | 1.00 | 28.65 |
| 1000 | C | SER | 651 | 18.555 | 44.601 | 8.929 | 1.00 | 30.22 |
| 1001 | O | SER | 651 | 18.250 | 43.641 | 8.228 | 1.00 | 28.51 |
| 1002 | CB | SER | 651 | 20.571 | 45.944 | 8.347 | 1.00 | 33.89 |
| 1003 | OG | SER | 651 | 21.083 | 45.792 | 9.676 | 1.00 | 99.90 |
| 1004 | N | GLU | 652 | 18.477 | 44.579 | 10.256 | 1.00 | 25.11 |
| 1005 | CA | GLU | 652 | 17.997 | 43.392 | 10.939 | 1.00 | 25.25 |
| 1006 | C | GLU | 652 | 16.513 | 43.250 | 10.723 | 1.00 | 21.49 |
| 1007 | O | GLU | 652 | 16.022 | 42.128 | 10.673 | 1.00 | 25.66 |
| 1008 | CB | GLU | 652 | 18.332 | 43.429 | 12.437 | 1.00 | 28.40 |
| 1009 | CG | GLU | 652 | 19.812 | 43.255 | 12.685 | 1.00 | 41.59 |
| 1010 | CD | GLU | 652 | 20.311 | 41.886 | 12.215 | 1.00 | 49.95 |
| 1011 | OE1 | GLU | 652 | 19.494 | 40.940 | 12.148 | 1.00 | 44.78 |
| 1012 | OE2 | GLU | 652 | 21.523 | 41.746 | 11.929 | 1.00 | 51.07 |
| 1013 | N | LEU | 653 | 15.810 | 44.381 | 10.587 | 1.00 | 24.33 |
| 1014 | CA | LEU | 653 | 14.366 | 44.377 | 10.349 | 1.00 | 26.06 |
| 1015 | C | LEU | 653 | 14.098 | 43.720 | 9.012 | 1.00 | 26.07 |
| 1016 | O | LEU | 653 | 13.183 | 42.919 | 8.888 | 1.00 | 22.03 |
| 1017 | CB | LEU | 653 | 13.777 | 45.803 | 10.351 | 1.00 | 22.64 |
| 1018 | CG | LEU | 653 | 13.974 | 46.674 | 11.621 | 1.00 | 99.90 |
| 1019 | CD1 | LEU | 653 | 13.225 | 48.005 | 11.469 | 1.00 | 99.90 |
| 1020 | CD2 | LEU | 653 | 13.515 | 45.964 | 12.905 | 1.00 | 99.90 |
| 1021 | N | HIS | 654 | 14.917 | 44.058 | 8.021 | 1.00 | 26.08 |
| 1022 | CA | HIS | 654 | 14.784 | 43.475 | 6.679 | 1.00 | 24.64 |
| 1023 | C | HIS | 654 | 15.102 | 41.986 | 6.716 | 1.00 | 26.29 |
| 1024 | O | HIS | 654 | 14.350 | 41.166 | 6.183 | 1.00 | 28.56 |
| 1025 | CB | HIS | 654 | 15.741 | 44.168 | 5.693 | 1.00 | 28.11 |
| 1026 | CG | HIS | 654 | 15.011 | 44.831 | 4.562 | 1.00 | 99.90 |
| 1027 | ND1 | HIS | 654 | 13.630 | 44.845 | 4.380 | 1.00 | 99.90 |
| 1028 | CD2 | HIS | 654 | 15.664 | 45.519 | 3.549 | 1.00 | 99.90 |
| 1029 | CE1 | HIS | 654 | 13.555 | 45.565 | 3.245 | 1.00 | 99.90 |
| 1030 | NE2 | HIS | 654 | 14.716 | 46.000 | 2.684 | 1.00 | 99.90 |
| 1031 | N | ARG | 655 | 16.215 | 41.635 | 7.356 | 1.00 | 22.16 |
| 1032 | CA | ARG | 655 | 16.655 | 40.248 | 7.453 | 1.00 | 28.14 |
| 1033 | C | ARG | 655 | 15.632 | 39.355 | 8.165 | 1.00 | 29.30 |
| 1034 | O | ARG | 655 | 15.288 | 38.265 | 7.691 | 1.00 | 29.13 |
| 1035 | CB | ARG | 655 | 18.000 | 40.212 | 8.187 | 1.00 | 31.67 |
| 1036 | CG | ARG | 655 | 18.709 | 38.870 | 8.246 | 1.00 | 41.13 |
| 1037 | CD | ARG | 655 | 19.991 | 38.988 | 9.093 | 1.00 | 46.76 |
| 1038 | NE | ARG | 655 | 20.696 | 37.673 | 9.123 | 1.00 | 99.90 |
| 1039 | CZ | ARG | 655 | 21.836 | 37.426 | 9.761 | 1.00 | 99.90 |
| 1040 | NH1 | ARG | 655 | 22.334 | 36.232 | 9.690 | 1.00 | 99.90 |
| 1041 | NH2 | ARG | 655 | 22.482 | 38.320 | 10.456 | 1.00 | 99.90 |
| 1042 | N | LEU | 656 | 15.137 | 39.816 | 9.305 | 1.00 | 29.04 |
| 1043 | CA | LEU | 656 | 14.166 | 39.042 | 10.067 | 1.00 | 27.03 |
| 1044 | C | LEU | 656 | 12.717 | 39.206 | 9.606 | 1.00 | 24.56 |
| 1045 | O | LEU | 656 | 11.843 | 38.435 | 10.014 | 1.00 | 25.98 |
| 1046 | CB | LEU | 656 | 14.250 | 39.420 | 11.556 | 1.00 | 30.03 |
| 1047 | CG | LEU | 656 | 15.510 | 39.055 | 12.345 | 1.00 | 36.08 |
| 1048 | CD1 | LEU | 656 | 15.367 | 39.505 | 13.786 | 1.00 | 28.22 |
| 1049 | CD2 | LEU | 656 | 15.715 | 37.556 | 12.295 | 1.00 | 33.46 |
| 1050 | N | GLN | 657 | 12.466 | 40.202 | 8.760 | 1.00 | 24.63 |
| 1051 | CA | GLN | 657 | 11.116 | 40.499 | 8.294 | 1.00 | 24.29 |
| 1052 | C | GLN | 657 | 10.156 | 40.706 | 9.479 | 1.00 | 28.28 |
| 1053 | O | GLN | 657 | 9.089 | 40.084 | 9.572 | 1.00 | 26.02 |
| 1054 | CB | GLN | 657 | 10.603 | 39.400 | 7.354 | 1.00 | 31.81 |
| 1055 | CG | GLN | 657 | 11.444 | 39.296 | 6.098 | 1.00 | 34.45 |
| 1056 | CD | GLN | 657 | 10.824 | 38.430 | 5.002 | 1.00 | 43.12 |
| 1057 | OE1 | GLN | 657 | 11.432 | 38.232 | 3.941 | 1.00 | 48.46 |
| 1058 | NE2 | GLN | 657 | 9.566 | 37.825 | 5.223 | 1.00 | 38.30 |
| 1059 | N | VAL | 658 | 10.561 | 41.594 | 10.384 | 1.00 | 23.00 |

TABLE 5-continued

ATOMIC COORDINATES FOR THE GR/SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1060 | CA | VAL | 658 | 9.762 | 41.941 | 11.568 | 1.00 | 23.27 |
| 1061 | C | VAL | 658 | 8.393 | 42.492 | 11.169 | 1.00 | 20.62 |
| 1062 | O | VAL | 658 | 8.270 | 43.299 | 10.243 | 1.00 | 24.25 |
| 1063 | CB | VAL | 658 | 10.506 | 42.989 | 12.436 | 1.00 | 22.34 |
| 1064 | CG1 | VAL | 658 | 9.623 | 43.484 | 13.580 | 1.00 | 22.21 |
| 1065 | CG2 | VAL | 658 | 11.756 | 42.374 | 12.981 | 1.00 | 20.16 |
| 1066 | N | SER | 659 | 7.358 | 42.043 | 11.871 | 1.00 | 21.62 |
| 1067 | CA | SER | 659 | 6.014 | 42.485 | 11.562 | 1.00 | 22.92 |
| 1068 | C | SER | 659 | 5.624 | 43.697 | 12.393 | 1.00 | 21.08 |
| 1069 | O | SER | 659 | 6.230 | 43.974 | 13.424 | 1.00 | 22.56 |
| 1070 | CB | SER | 659 | 5.014 | 41.364 | 11.837 | 1.00 | 23.84 |
| 1071 | OG | SER | 659 | 4.896 | 41.029 | 13.214 | 1.00 | 27.14 |
| 1072 | N | TYR | 660 | 4.616 | 44.417 | 11.921 | 1.00 | 22.79 |
| 1073 | CA | TYR | 660 | 4.110 | 45.589 | 12.619 | 1.00 | 26.53 |
| 1074 | C | TYR | 660 | 3.729 | 45.186 | 14.046 | 1.00 | 24.03 |
| 1075 | O | TYR | 660 | 4.017 | 45.904 | 14.994 | 1.00 | 23.00 |
| 1076 | CB | TYR | 660 | 2.883 | 46.138 | 11.863 | 1.00 | 26.89 |
| 1077 | CG | TYR | 660 | 3.117 | 46.616 | 10.426 | 1.00 | 99.90 |
| 1078 | CD1 | TYR | 660 | 2.748 | 45.797 | 9.353 | 1.00 | 99.90 |
| 1079 | CD2 | TYR | 660 | 3.703 | 47.859 | 10.174 | 1.00 | 99.90 |
| 1080 | CE1 | TYR | 660 | 2.970 | 46.214 | 8.044 | 1.00 | 99.90 |
| 1081 | CE2 | TYR | 660 | 3.924 | 48.275 | 8.863 | 1.00 | 99.90 |
| 1082 | CZ | TYR | 660 | 3.557 | 47.453 | 7.801 | 1.00 | 99.90 |
| 1083 | OH | TYR | 660 | 3.778 | 47.863 | 6.516 | 1.00 | 99.90 |
| 1084 | N | GLU | 661 | 3.096 | 44.023 | 14.191 | 1.00 | 24.42 |
| 1085 | CA | GLU | 661 | 2.660 | 43.541 | 15.509 | 1.00 | 24.69 |
| 1086 | C | GLU | 661 | 3.838 | 43.258 | 16.431 | 1.00 | 21.73 |
| 1087 | O | GLU | 661 | 3.771 | 43.539 | 17.622 | 1.00 | 23.19 |
| 1088 | CB | GLU | 661 | 1.819 | 42.269 | 15.378 | 1.00 | 27.58 |
| 1089 | CG | GLU | 661 | 0.536 | 42.386 | 14.563 | 1.00 | 32.90 |
| 1090 | CD | GLU | 661 | 0.776 | 42.657 | 13.079 | 1.00 | 38.95 |
| 1091 | OE1 | GLU | 661 | 1.753 | 42.130 | 12.509 | 1.00 | 36.30 |
| 1092 | OE2 | GLU | 661 | −0.044 | 43.378 | 12.472 | 1.00 | 49.03 |
| 1093 | N | GLU | 662 | 4.911 | 42.676 | 15.890 | 1.00 | 21.48 |
| 1094 | CA | GLU | 662 | 6.097 | 42.398 | 16.697 | 1.00 | 20.83 |
| 1095 | C | GLU | 662 | 6.795 | 43.702 | 17.061 | 1.00 | 20.85 |
| 1096 | O | GLU | 662 | 7.246 | 43.876 | 18.182 | 1.00 | 23.00 |
| 1097 | CB | GLU | 662 | 7.090 | 41.515 | 15.936 | 1.00 | 22.67 |
| 1098 | CG | GLU | 662 | 6.640 | 40.056 | 15.739 | 1.00 | 25.39 |
| 1099 | CD | GLU | 662 | 7.482 | 39.316 | 14.703 | 1.00 | 33.69 |
| 1100 | OE1 | GLU | 662 | 8.114 | 39.980 | 13.843 | 1.00 | 30.03 |
| 1101 | OE2 | GLU | 662 | 7.506 | 38.070 | 14.732 | 1.00 | 30.51 |
| 1102 | N | TYR | 663 | 6.916 | 44.604 | 16.093 | 1.00 | 21.31 |
| 1103 | CA | TYR | 663 | 7.573 | 45.888 | 16.342 | 1.00 | 22.08 |
| 1104 | C | TYR | 663 | 6.893 | 46.682 | 17.474 | 1.00 | 21.29 |
| 1105 | O | TYR | 663 | 7.564 | 47.277 | 18.327 | 1.00 | 20.03 |
| 1106 | CB | TYR | 663 | 7.540 | 46.721 | 15.070 | 1.00 | 23.06 |
| 1107 | CG | TYR | 663 | 7.851 | 48.167 | 15.290 | 1.00 | 22.01 |
| 1108 | CD1 | TYR | 663 | 9.155 | 48.583 | 15.542 | 1.00 | 22.32 |
| 1109 | CD2 | TYR | 663 | 6.831 | 49.110 | 15.260 | 1.00 | 23.62 |
| 1110 | CE1 | TYR | 663 | 9.434 | 49.925 | 15.755 | 1.00 | 27.65 |
| 1111 | CE2 | TYR | 663 | 7.101 | 50.458 | 15.474 | 1.00 | 28.88 |
| 1112 | CZ | TYR | 663 | 8.402 | 50.863 | 15.722 | 1.00 | 22.16 |
| 1113 | OH | TYR | 663 | 8.673 | 52.185 | 15.935 | 1.00 | 99.90 |
| 1114 | N | LEU | 664 | 5.567 | 46.711 | 17.455 | 1.00 | 21.31 |
| 1115 | CA | LEU | 664 | 4.806 | 47.451 | 18.468 | 1.00 | 23.49 |
| 1116 | C | LEU | 664 | 5.083 | 46.979 | 19.900 | 1.00 | 26.91 |
| 1117 | O | LEU | 664 | 5.233 | 47.802 | 20.808 | 1.00 | 20.81 |
| 1118 | CB | LEU | 664 | 3.310 | 47.384 | 18.143 | 1.00 | 24.50 |
| 1119 | CG | LEU | 664 | 2.922 | 48.148 | 16.864 | 1.00 | 23.57 |
| 1120 | CD1 | LEU | 664 | 1.452 | 47.937 | 16.521 | 1.00 | 22.54 |
| 1121 | CD2 | LEU | 664 | 3.191 | 49.647 | 17.087 | 1.00 | 27.51 |
| 1122 | N | CYS | 665 | 5.147 | 45.662 | 20.101 | 1.00 | 22.87 |
| 1123 | CA | CYS | 665 | 5.431 | 45.097 | 21.416 | 1.00 | 26.80 |
| 1124 | C | CYS | 665 | 6.902 | 45.304 | 21.783 | 1.00 | 25.96 |
| 1125 | O | CYS | 665 | 7.240 | 45.589 | 22.934 | 1.00 | 20.10 |
| 1126 | CB | CYS | 665 | 5.124 | 43.601 | 21.428 | 1.00 | 27.46 |
| 1127 | SG | CYS | 665 | 3.371 | 43.221 | 21.079 | 1.00 | 33.20 |
| 1128 | N | MET | 666 | 7.789 | 45.143 | 20.810 | 1.00 | 18.27 |
| 1129 | CA | MET | 666 | 9.187 | 45.349 | 21.107 | 1.00 | 20.73 |
| 1130 | C | MET | 666 | 9.446 | 46.800 | 21.523 | 1.00 | 18.21 |
| 1131 | O | MET | 666 | 10.282 | 47.056 | 22.376 | 1.00 | 20.04 |
| 1132 | CB | MET | 666 | 10.033 | 44.979 | 19.899 | 1.00 | 23.28 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1133 | CG | MET | 666 | 9.931 | 43.517 | 19.514 | 1.00 | 26.12 |
| 1134 | SD | MET | 666 | 10.766 | 43.239 | 17.916 | 1.00 | 30.71 |
| 1135 | CE | MET | 666 | 12.364 | 43.447 | 18.420 | 1.00 | 17.04 |
| 1136 | N | LYS | 667 | 8.730 | 47.750 | 20.934 | 1.00 | 22.26 |
| 1137 | CA | LYS | 667 | 8.958 | 49.158 | 21.285 | 1.00 | 21.99 |
| 1138 | C | LYS | 667 | 8.593 | 49.432 | 22.742 | 1.00 | 23.71 |
| 1139 | O | LYS | 667 | 9.255 | 50.224 | 23.423 | 1.00 | 20.06 |
| 1140 | CB | LYS | 667 | 8.175 | 50.091 | 20.342 | 1.00 | 24.02 |
| 1141 | CG | LYS | 667 | 8.621 | 51.548 | 20.407 | 1.00 | 31.07 |
| 1142 | CD | LYS | 667 | 8.217 | 52.309 | 19.139 | 1.00 | 38.28 |
| 1143 | CE | LYS | 667 | 6.708 | 52.411 | 18.956 | 1.00 | 39.48 |
| 1144 | NZ | LYS | 667 | 5.961 | 53.284 | 19.944 | 1.00 | 42.42 |
| 1145 | N | THR | 668 | 7.549 | 48.768 | 23.231 | 1.00 | 20.18 |
| 1146 | CA | THR | 668 | 7.158 | 48.951 | 24.623 | 1.00 | 19.22 |
| 1147 | C | THR | 668 | 8.223 | 48.345 | 25.523 | 1.00 | 21.84 |
| 1148 | O | THR | 668 | 8.587 | 48.917 | 26.548 | 1.00 | 21.05 |
| 1149 | CB | THR | 668 | 5.822 | 48.260 | 24.936 | 1.00 | 19.35 |
| 1150 | OG1 | THR | 668 | 4.778 | 48.814 | 24.146 | 1.00 | 99.90 |
| 1151 | CG2 | THR | 668 | 5.314 | 48.380 | 26.389 | 1.00 | 99.90 |
| 1152 | N | LEU | 669 | 8.733 | 47.181 | 25.140 | 1.00 | 19.81 |
| 1153 | CA | LEU | 669 | 9.769 | 46.539 | 25.937 | 1.00 | 20.73 |
| 1154 | C | LEU | 669 | 11.013 | 47.417 | 26.009 | 1.00 | 24.51 |
| 1155 | O | LEU | 669 | 11.743 | 47.380 | 26.999 | 1.00 | 21.96 |
| 1156 | CB | LEU | 669 | 10.104 | 45.149 | 25.370 | 1.00 | 21.13 |
| 1157 | CG | LEU | 669 | 8.943 | 44.165 | 25.568 | 1.00 | 20.69 |
| 1158 | CD1 | LEU | 669 | 9.239 | 42.871 | 24.849 | 1.00 | 23.72 |
| 1159 | CD2 | LEU | 669 | 8.725 | 43.908 | 27.077 | 1.00 | 21.59 |
| 1160 | N | LEU | 670 | 11.252 | 48.224 | 24.980 | 1.00 | 22.43 |
| 1161 | CA | LEU | 670 | 12.400 | 49.122 | 25.007 | 1.00 | 24.57 |
| 1162 | C | LEU | 670 | 12.195 | 50.225 | 26.025 | 1.00 | 22.02 |
| 1163 | O | LEU | 670 | 13.144 | 50.636 | 26.677 | 1.00 | 23.56 |
| 1164 | CB | LEU | 670 | 12.663 | 49.769 | 23.650 | 1.00 | 19.15 |
| 1165 | CG | LEU | 670 | 13.473 | 49.023 | 22.615 | 1.00 | 31.93 |
| 1166 | CD1 | LEU | 670 | 13.732 | 50.001 | 21.470 | 1.00 | 28.38 |
| 1167 | CD2 | LEU | 670 | 14.807 | 48.532 | 23.219 | 1.00 | 26.52 |
| 1168 | N | LEU | 671 | 10.962 | 50.710 | 26.138 | 1.00 | 18.07 |
| 1169 | CA | LEU | 671 | 10.629 | 51.743 | 27.114 | 1.00 | 20.16 |
| 1170 | C | LEU | 671 | 10.919 | 51.217 | 28.524 | 1.00 | 23.85 |
| 1171 | O | LEU | 671 | 11.313 | 51.963 | 29.427 | 1.00 | 23.95 |
| 1172 | CB | LEU | 671 | 9.144 | 52.087 | 27.013 | 1.00 | 21.07 |
| 1173 | CG | LEU | 671 | 8.548 | 52.995 | 28.099 | 1.00 | 22.15 |
| 1174 | CD1 | LEU | 671 | 9.240 | 54.359 | 28.086 | 1.00 | 21.62 |
| 1175 | CD2 | LEU | 671 | 7.050 | 53.150 | 27.871 | 1.00 | 22.53 |
| 1176 | N | LEU | 672 | 10.721 | 49.917 | 28.697 | 1.00 | 16.99 |
| 1177 | CA | LEU | 672 | 10.891 | 49.261 | 29.979 | 1.00 | 21.87 |
| 1178 | C | LEU | 672 | 12.190 | 48.477 | 30.038 | 1.00 | 24.10 |
| 1179 | O | LEU | 672 | 12.282 | 47.519 | 30.799 | 1.00 | 24.64 |
| 1180 | CB | LEU | 672 | 9.721 | 48.283 | 30.185 | 1.00 | 20.22 |
| 1181 | CG | LEU | 672 | 8.317 | 48.845 | 29.941 | 1.00 | 27.92 |
| 1182 | CD1 | LEU | 672 | 7.264 | 47.732 | 30.054 | 1.00 | 24.44 |
| 1183 | CD2 | LEU | 672 | 8.030 | 49.964 | 30.943 | 1.00 | 21.00 |
| 1184 | N | SER | 673 | 13.210 | 48.881 | 29.281 | 1.00 | 21.55 |
| 1185 | CA | SER | 673 | 14.431 | 48.072 | 29.246 | 1.00 | 26.34 |
| 1186 | C | SER | 673 | 15.616 | 48.473 | 30.129 | 1.00 | 21.48 |
| 1187 | O | SER | 673 | 16.654 | 47.815 | 30.120 | 1.00 | 25.22 |
| 1188 | CB | SER | 673 | 14.882 | 47.946 | 27.792 | 1.00 | 24.75 |
| 1189 | OG | SER | 673 | 15.366 | 49.181 | 27.251 | 1.00 | 99.90 |
| 1190 | N | SER | 674 | 15.446 | 49.532 | 30.903 | 1.00 | 20.94 |
| 1191 | CA | SER | 674 | 16.501 | 50.026 | 31.780 | 1.00 | 23.18 |
| 1192 | C | SER | 674 | 15.855 | 50.647 | 33.002 | 1.00 | 24.51 |
| 1193 | O | SER | 674 | 14.884 | 51.395 | 32.875 | 1.00 | 20.61 |
| 1194 | CB | SER | 674 | 17.349 | 51.117 | 31.062 | 1.00 | 27.14 |
| 1195 | OG | SER | 674 | 16.627 | 52.336 | 30.852 | 1.00 | 99.90 |
| 1196 | N | VAL | 675 | 16.377 | 50.324 | 34.183 | 1.00 | 23.20 |
| 1197 | CA | VAL | 675 | 15.853 | 50.899 | 35.422 | 1.00 | 22.29 |
| 1198 | C | VAL | 675 | 17.003 | 51.371 | 36.308 | 1.00 | 23.93 |
| 1199 | O | VAL | 675 | 18.163 | 51.045 | 36.053 | 1.00 | 23.93 |
| 1200 | CB | VAL | 675 | 14.995 | 49.884 | 36.192 | 1.00 | 24.86 |
| 1201 | CG1 | VAL | 675 | 13.702 | 49.465 | 35.450 | 1.00 | 99.90 |
| 1202 | CG2 | VAL | 675 | 14.532 | 50.309 | 37.613 | 1.00 | 99.90 |
| 1203 | N | PRO | 676 | 16.699 | 52.154 | 37.350 | 1.00 | 23.63 |
| 1204 | CA | PRO | 676 | 17.741 | 52.651 | 38.250 | 1.00 | 26.05 |
| 1205 | C | PRO | 676 | 18.406 | 51.512 | 39.004 | 1.00 | 30.91 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1206 | O | PRO | 676 | 17.822 | 50.433 | 39.164 | 1.00 | 27.25 |
| 1207 | CB | PRO | 676 | 16.969 | 53.583 | 39.189 | 1.00 | 28.62 |
| 1208 | CG | PRO | 676 | 15.761 | 54.002 | 38.335 | 1.00 | 25.78 |
| 1209 | CD | PRO | 676 | 15.387 | 52.647 | 37.791 | 1.00 | 28.72 |
| 1210 | N | LYS | 677 | 19.632 | 51.754 | 39.460 | 1.00 | 31.80 |
| 1211 | CA | LYS | 677 | 20.378 | 50.754 | 40.215 | 1.00 | 34.58 |
| 1212 | C | LYS | 677 | 19.609 | 50.311 | 41.453 | 1.00 | 32.37 |
| 1213 | O | LYS | 677 | 19.708 | 49.157 | 41.871 | 1.00 | 38.50 |
| 1214 | CB | LYS | 677 | 21.745 | 51.314 | 40.633 | 1.00 | 34.68 |
| 1215 | CG | LYS | 677 | 22.631 | 50.283 | 41.377 | 1.00 | 99.90 |
| 1216 | CD | LYS | 677 | 23.976 | 50.826 | 41.868 | 1.00 | 99.90 |
| 1217 | CE | LYS | 677 | 24.713 | 49.726 | 42.643 | 1.00 | 99.90 |
| 1218 | NZ | LYS | 677 | 26.075 | 50.184 | 42.968 | 1.00 | 99.90 |
| 1219 | N | ASP | 678 | 18.837 | 51.223 | 42.031 | 1.00 | 33.46 |
| 1220 | CA | ASP | 678 | 18.058 | 50.899 | 43.219 | 1.00 | 35.43 |
| 1221 | C | ASP | 678 | 16.645 | 50.442 | 42.859 | 1.00 | 37.02 |
| 1222 | O | ASP | 678 | 15.809 | 50.203 | 43.734 | 1.00 | 34.87 |
| 1223 | CB | ASP | 678 | 18.002 | 52.103 | 44.174 | 1.00 | 40.38 |
| 1224 | CG | ASP | 678 | 17.367 | 51.860 | 45.551 | 1.00 | 99.90 |
| 1225 | OD1 | ASP | 678 | 16.636 | 52.671 | 46.100 | 1.00 | 99.90 |
| 1226 | OD2 | ASP | 678 | 17.688 | 50.639 | 46.076 | 1.00 | 99.90 |
| 1227 | N | GLY | 679 | 16.380 | 50.302 | 41.565 | 1.00 | 32.49 |
| 1228 | CA | GLY | 679 | 15.063 | 49.872 | 41.144 | 1.00 | 28.49 |
| 1229 | C | GLY | 679 | 14.103 | 51.045 | 41.110 | 1.00 | 30.77 |
| 1230 | O | GLY | 679 | 14.481 | 52.171 | 41.415 | 1.00 | 29.05 |
| 1231 | N | LEU | 680 | 12.857 | 50.766 | 40.745 | 1.00 | 27.80 |
| 1232 | CA | LEU | 680 | 11.812 | 51.772 | 40.643 | 1.00 | 31.88 |
| 1233 | C | LEU | 680 | 10.938 | 51.781 | 41.896 | 1.00 | 30.49 |
| 1234 | O | LEU | 680 | 10.871 | 50.788 | 42.614 | 1.00 | 28.71 |
| 1235 | CB | LEU | 680 | 10.929 | 51.449 | 39.440 | 1.00 | 28.43 |
| 1236 | CG | LEU | 680 | 11.569 | 51.477 | 38.052 | 1.00 | 31.10 |
| 1237 | CD1 | LEU | 680 | 10.606 | 50.863 | 37.058 | 1.00 | 29.92 |
| 1238 | CD2 | LEU | 680 | 11.928 | 52.921 | 37.667 | 1.00 | 27.76 |
| 1239 | N | LYS | 681 | 10.251 | 52.892 | 42.141 | 1.00 | 33.09 |
| 1240 | CA | LYS | 681 | 9.359 | 52.979 | 43.300 | 1.00 | 33.34 |
| 1241 | C | LYS | 681 | 8.216 | 51.968 | 43.117 | 1.00 | 37.41 |
| 1242 | O | LYS | 681 | 7.767 | 51.323 | 44.075 | 1.00 | 35.58 |
| 1243 | CB | LYS | 681 | 8.779 | 54.391 | 43.419 | 1.00 | 37.62 |
| 1244 | CG | LYS | 651 | 9.834 | 55.481 | 43.433 | 1.00 | 43.12 |
| 1245 | CD | LYS | 681 | 9.273 | 56.849 | 43.827 | 1.00 | 55.06 |
| 1246 | CE | LYS | 681 | 10.419 | 57.868 | 43.884 | 1.00 | 99.90 |
| 1247 | NZ | LYS | 681 | 9.864 | 59.218 | 44.093 | 1.00 | 99.90 |
| 1248 | N | SER | 682 | 7.734 | 51.854 | 41.880 | 1.00 | 28.39 |
| 1249 | CA | SER | 682 | 6.667 | 50.925 | 41.537 | 1.00 | 29.00 |
| 1250 | C | SER | 682 | 7.282 | 49.701 | 40.864 | 1.00 | 30.23 |
| 1251 | O | SER | 682 | 6.865 | 49.312 | 39.778 | 1.00 | 26.81 |
| 1252 | CB | SER | 682 | 5.678 | 51.594 | 40.578 | 1.00 | 23.84 |
| 1253 | OG | SER | 682 | 4.977 | 52.693 | 41.139 | 1.00 | 31.90 |
| 1254 | N | GLN | 683 | 8.273 | 49.089 | 41.508 | 1.00 | 29.41 |
| 1255 | CA | GLN | 683 | 8.936 | 47.936 | 40.910 | 1.00 | 28.12 |
| 1256 | C | GLN | 683 | 7.980 | 46.776 | 40.638 | 1.00 | 30.39 |
| 1257 | O | GLN | 683 | 8.040 | 46.157 | 39.582 | 1.00 | 26.03 |
| 1258 | CB | GLN | 683 | 10.088 | 47.471 | 41.801 | 1.00 | 25.64 |
| 1259 | CG | GLN | 683 | 11.048 | 46.487 | 41.154 | 1.00 | 32.23 |
| 1260 | CD | GLN | 683 | 11.776 | 47.082 | 39.957 | 1.00 | 37.10 |
| 1261 | OE1 | GLN | 683 | 12.179 | 48.247 | 39.972 | 1.00 | 37.64 |
| 1262 | NE2 | GLN | 683 | 12.010 | 46.204 | 38.875 | 1.00 | 42.95 |
| 1263 | N | GLU | 684 | 7.107 | 46.462 | 41.592 | 1.00 | 27.88 |
| 1264 | CA | GLU | 684 | 6.155 | 45.374 | 41.386 | 1.00 | 30.26 |
| 1265 | C | GLU | 684 | 5.275 | 45.594 | 40.169 | 1.00 | 27.76 |
| 1266 | O | GLU | 684 | 5.134 | 44.699 | 39.332 | 1.00 | 28.54 |
| 1267 | CB | GLU | 684 | 5.237 | 45.203 | 42.590 | 1.00 | 31.84 |
| 1268 | CG | GLU | 684 | 4.246 | 46.371 | 42.908 | 1.00 | 99.90 |
| 1269 | CD | GLU | 684 | 3.384 | 46.270 | 44.169 | 1.00 | 99.90 |
| 1270 | OE1 | GLU | 684 | 2.605 | 47.147 | 44.516 | 1.00 | 99.90 |
| 1271 | OE2 | GLU | 684 | 3.567 | 45.114 | 44.867 | 1.00 | 99.90 |
| 1272 | N | LEU | 685 | 4.674 | 46.779 | 40.087 | 1.00 | 27.40 |
| 1273 | CA | LEU | 685 | 3.816 | 47.129 | 38.965 | 1.00 | 27.76 |
| 1274 | C | LEU | 685 | 4.627 | 47.085 | 37.676 | 1.00 | 27.08 |
| 1275 | O | LEU | 685 | 4.134 | 46.647 | 36.636 | 1.00 | 24.43 |
| 1276 | CB | LEU | 685 | 3.232 | 48.527 | 39.136 | 1.00 | 29.57 |
| 1277 | CG | LEU | 685 | 2.395 | 48.818 | 40.411 | 1.00 | 99.90 |
| 1278 | CD1 | LEU | 685 | 1.806 | 50.235 | 40.343 | 1.00 | 99.90 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1279 | CD2 | LEU | 685 | 1.265 | 47.798 | 40.626 | 1.00 | 99.90 |
| 1280 | N | PHE | 686 | 5.875 | 47.527 | 37.758 | 1.00 | 25.08 |
| 1281 | CA | PHE | 686 | 6.751 | 47.536 | 36.586 | 1.00 | 25.20 |
| 1282 | C | PHE | 686 | 7.026 | 46.127 | 36.084 | 1.00 | 22.17 |
| 1283 | O | PHE | 686 | 6.972 | 45.868 | 34.879 | 1.00 | 24.69 |
| 1284 | CB | PHE | 686 | 8.060 | 48.268 | 36.910 | 1.00 | 24.39 |
| 1285 | CG | PHE | 686 | 9.148 | 48.066 | 35.883 | 1.00 | 25.18 |
| 1286 | CD1 | PHE | 686 | 9.213 | 48.875 | 34.740 | 1.00 | 26.95 |
| 1287 | CD2 | PHE | 686 | 10.079 | 47.041 | 36.029 | 1.00 | 21.90 |
| 1288 | CE1 | PHE | 686 | 10.198 | 48.660 | 33.756 | 1.00 | 22.61 |
| 1289 | CE2 | PHE | 686 | 11.065 | 46.812 | 35.054 | 1.00 | 21.56 |
| 1290 | CZ | PHE | 686 | 11.124 | 47.622 | 33.915 | 1.00 | 23.75 |
| 1291 | N | ASP | 687 | 7.312 | 45.216 | 37.004 | 1.00 | 26.80 |
| 1292 | CA | ASP | 687 | 7.573 | 43.819 | 36.640 | 1.00 | 30.80 |
| 1293 | C | ASP | 687 | 6.365 | 43.212 | 35.929 | 1.00 | 27.28 |
| 1294 | O | ASP | 687 | 6.498 | 42.543 | 34.905 | 1.00 | 27.77 |
| 1295 | CB | ASP | 687 | 7.859 | 42.979 | 37.890 | 1.00 | 28.70 |
| 1296 | CG | ASP | 687 | 8.326 | 41.535 | 37.658 | 1.00 | 99.90 |
| 1297 | OD1 | ASP | 687 | 7.948 | 40.595 | 38.342 | 1.00 | 99.90 |
| 1298 | OD2 | ASP | 687 | 9.181 | 41.418 | 36.599 | 1.00 | 99.90 |
| 1299 | N | GLU | 688 | 5.188 | 43.418 | 36.505 | 1.00 | 29.50 |
| 1300 | CA | GLU | 688 | 3.961 | 42.897 | 35.922 | 1.00 | 27.52 |
| 1301 | C | GLU | 688 | 3.731 | 43.493 | 34.533 | 1.00 | 29.29 |
| 1302 | O | GLU | 688 | 3.318 | 42.805 | 33.610 | 1.00 | 29.26 |
| 1303 | CB | GLU | 688 | 2.762 | 43.210 | 36.826 | 1.00 | 32.59 |
| 1304 | CG | GLU | 688 | 2.653 | 42.336 | 38.078 | 1.00 | 38.26 |
| 1305 | CD | GLU | 688 | 1.528 | 42.774 | 39.012 | 1.00 | 47.34 |
| 1306 | OE1 | GLU | 688 | 0.440 | 43.140 | 38.517 | 1.00 | 51.54 |
| 1307 | OE2 | GLU | 688 | 1.720 | 42.734 | 40.248 | 1.00 | 49.88 |
| 1308 | N | ILE | 689 | 4.007 | 44.777 | 34.381 | 1.00 | 25.95 |
| 1309 | CA | ILE | 689 | 3.803 | 45.408 | 33.093 | 1.00 | 26.70 |
| 1310 | C | ILE | 689 | 4.737 | 44.798 | 32.059 | 1.00 | 26.41 |
| 1311 | O | ILE | 689 | 4.317 | 44.414 | 30.966 | 1.00 | 25.61 |
| 1312 | CB | ILE | 689 | 4.044 | 46.907 | 33.209 | 1.00 | 26.67 |
| 1313 | CG2 | ILE | 689 | 3.757 | 47.671 | 31.880 | 1.00 | 99.90 |
| 1314 | CG1 | ILE | 689 | 3.246 | 47.608 | 34.354 | 1.00 | 99.90 |
| 1315 | CD1 | ILE | 689 | 3.697 | 49.040 | 34.711 | 1.00 | 99.90 |
| 1316 | N | ARG | 690 | 6.007 | 44.684 | 32.422 | 1.00 | 26.84 |
| 1317 | CA | ARG | 690 | 6.989 | 44.124 | 31.515 | 1.00 | 29.65 |
| 1318 | C | ARG | 690 | 6.600 | 42.691 | 31.106 | 1.00 | 31.46 |
| 1319 | O | ARG | 690 | 6.645 | 42.341 | 29.931 | 1.00 | 28.49 |
| 1320 | CB | ARG | 690 | 8.366 | 44.185 | 32.177 | 1.00 | 29.38 |
| 1321 | CG | ARG | 690 | 9.522 | 43.957 | 31.232 | 1.00 | 38.40 |
| 1322 | CD | ARG | 690 | 10.844 | 44.337 | 31.875 | 1.00 | 33.58 |
| 1323 | NE | ARG | 690 | 11.947 | 44.131 | 30.940 | 1.00 | 43.23 |
| 1324 | CZ | ARG | 690 | 12.434 | 42.942 | 30.613 | 1.00 | 45.03 |
| 1325 | NH1 | ARG | 690 | 12.020 | 41.789 | 31.215 | 1.00 | 58.21 |
| 1326 | NH2 | ARG | 690 | 13.427 | 42.875 | 29.683 | 1.00 | 52.78 |
| 1327 | N | MET | 691 | 6.189 | 41.870 | 32.066 | 1.00 | 29.00 |
| 1328 | CA | MET | 691 | 5.783 | 40.497 | 31.758 | 1.00 | 29.23 |
| 1329 | C | MET | 691 | 4.586 | 40.447 | 30.814 | 1.00 | 25.05 |
| 1330 | O | MET | 691 | 4.523 | 39.601 | 29.929 | 1.00 | 27.74 |
| 1331 | CB | MET | 691 | 5.456 | 39.741 | 33.047 | 1.00 | 29.17 |
| 1332 | CG | MET | 691 | 6.626 | 39.562 | 34.038 | 1.00 | 99.90 |
| 1333 | SD | MET | 691 | 6.151 | 38.415 | 35.341 | 1.00 | 99.90 |
| 1334 | CE | MET | 691 | 7.506 | 38.731 | 36.480 | 1.00 | 99.90 |
| 1335 | N | THR | 692 | 3.631 | 41.346 | 31.015 | 1.00 | 27.46 |
| 1336 | CA | THR | 692 | 2.445 | 41.405 | 30.170 | 1.00 | 26.94 |
| 1337 | C | THR | 692 | 2.837 | 41.701 | 28.727 | 1.00 | 28.69 |
| 1338 | O | THR | 692 | 2.275 | 41.136 | 27.797 | 1.00 | 24.01 |
| 1339 | CB | THR | 692 | 1.488 | 42.485 | 30.676 | 1.00 | 33.23 |
| 1340 | OG1 | THR | 692 | 1.053 | 42.187 | 31.996 | 1.00 | 99.90 |
| 1341 | CG2 | THR | 692 | 0.183 | 42.674 | 29.872 | 1.00 | 99.90 |
| 1342 | N | TYR | 693 | 3.799 | 42.594 | 28.538 | 1.00 | 23.69 |
| 1343 | CA | TYR | 693 | 4.232 | 42.918 | 27.185 | 1.00 | 24.43 |
| 1344 | C | TYR | 693 | 5.124 | 41.845 | 26.579 | 1.00 | 25.10 |
| 1345 | O | TYR | 693 | 5.160 | 41.684 | 25.364 | 1.00 | 24.91 |
| 1346 | CB | TYR | 693 | 4.888 | 44.291 | 27.176 | 1.00 | 22.98 |
| 1347 | CG | TYR | 693 | 3.840 | 45.374 | 27.203 | 1.00 | 21.21 |
| 1348 | CD1 | TYR | 693 | 3.165 | 45.732 | 26.032 | 1.00 | 21.26 |
| 1349 | CD2 | TYR | 693 | 3.489 | 46.007 | 28.393 | 1.00 | 21.12 |
| 1350 | CE1 | TYR | 693 | 2.165 | 46.700 | 26.038 | 1.00 | 22.44 |
| 1351 | CE2 | TYR | 693 | 2.487 | 46.979 | 28.411 | 1.00 | 23.86 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1352 | CZ | TYR | 693 | 1.829 | 47.325 | 27.225 | 1.00 | 28.65 |
| 1353 | OH | TYR | 693 | 0.884 | 48.311 | 27.226 | 1.00 | 23.47 |
| 1354 | N | ILE | 694 | 5.835 | 41.101 | 27.415 | 1.00 | 23.21 |
| 1355 | CA | ILE | 694 | 6.650 | 40.015 | 26.901 | 1.00 | 29.14 |
| 1356 | C | ILE | 694 | 5.653 | 38.965 | 26.405 | 1.00 | 30.21 |
| 1357 | O | ILE | 694 | 5.832 | 38.363 | 25.350 | 1.00 | 26.87 |
| 1358 | CB | ILE | 694 | 7.584 | 39.430 | 28.003 | 1.00 | 29.35 |
| 1359 | CG1 | ILE | 694 | 8.690 | 40.443 | 28.327 | 1.00 | 23.92 |
| 1360 | CG2 | ILE | 694 | 8.219 | 38.114 | 27.542 | 1.00 | 27.00 |
| 1361 | CD1 | ILE | 694 | 9.626 | 39.992 | 29.412 | 1.00 | 22.76 |
| 1362 | N | LYS | 695 | 4.577 | 38.764 | 27.154 | 1.00 | 28.71 |
| 1363 | CA | LYS | 695 | 3.580 | 37.801 | 26.724 | 1.00 | 32.10 |
| 1364 | C | LYS | 695 | 2.890 | 38.286 | 25.458 | 1.00 | 29.94 |
| 1365 | O | LYS | 695 | 2.487 | 37.489 | 24.621 | 1.00 | 28.11 |
| 1366 | CB | LYS | 695 | 2.522 | 37.554 | 27.805 | 1.00 | 35.86 |
| 1367 | CG | LYS | 695 | 3.015 | 36.798 | 29.026 | 1.00 | 40.68 |
| 1368 | CD | LYS | 695 | 1.838 | 36.332 | 29.882 | 1.00 | 46.12 |
| 1369 | CE | LYS | 695 | 2.368 | 35.511 | 31.065 | 1.00 | 99.90 |
| 1370 | NZ | LYS | 695 | 1.257 | 35.206 | 31.985 | 1.00 | 99.90 |
| 1371 | N | GLU | 696 | 2.754 | 39.596 | 25.307 | 1.00 | 26.26 |
| 1372 | CA | GLU | 696 | 2.094 | 40.106 | 24.118 | 1.00 | 24.07 |
| 1373 | C | GLU | 696 | 2.995 | 39.939 | 22.890 | 1.00 | 25.19 |
| 1374 | O | GLU | 696 | 2.502 | 39.675 | 21.789 | 1.00 | 27.72 |
| 1375 | CB | GLU | 696 | 1.691 | 41.569 | 24.316 | 1.00 | 29.75 |
| 1376 | CG | GLU | 696 | 0.566 | 42.010 | 23.401 | 1.00 | 32.34 |
| 1377 | CD | GLU | 696 | −0.741 | 41.254 | 23.669 | 1.00 | 48.72 |
| 1378 | OE1 | GLU | 696 | −0.808 | 40.500 | 24.667 | 1.00 | 47.00 |
| 1379 | OE2 | GLU | 696 | −1.707 | 41.419 | 22.889 | 1.00 | 46.97 |
| 1380 | N | LEU | 697 | 4.306 | 40.085 | 23.073 | 1.00 | 23.97 |
| 1381 | CA | LEU | 697 | 5.250 | 39.893 | 21.974 | 1.00 | 22.66 |
| 1382 | C | LEU | 697 | 5.147 | 38.432 | 21.518 | 1.00 | 30.81 |
| 1383 | O | LEU | 697 | 5.247 | 38.138 | 20.329 | 1.00 | 24.16 |
| 1384 | CB | LEU | 697 | 6.684 | 40.158 | 22.448 | 1.00 | 22.80 |
| 1385 | CG | LEU | 697 | 7.794 | 39.746 | 21.476 | 1.00 | 25.24 |
| 1386 | CD1 | LEU | 697 | 7.669 | 40.557 | 20.215 | 1.00 | 25.51 |
| 1387 | CD2 | LEU | 697 | 9.177 | 39.940 | 22.125 | 1.00 | 27.39 |
| 1388 | N | GLY | 698 | 4.980 | 37.516 | 22.471 | 1.00 | 24.04 |
| 1389 | CA | GLY | 698 | 4.860 | 36.103 | 22.122 | 1.00 | 29.31 |
| 1390 | C | GLY | 698 | 3.637 | 35.900 | 21.243 | 1.00 | 28.39 |
| 1391 | O | GLY | 698 | 3.714 | 35.207 | 20.229 | 1.00 | 28.22 |
| 1392 | N | LYS | 699 | 2.519 | 36.528 | 21.607 | 1.00 | 29.91 |
| 1393 | CA | LYS | 699 | 1.296 | 36.425 | 20.808 | 1.00 | 27.78 |
| 1394 | C | LYS | 699 | 1.524 | 37.002 | 19.413 | 1.00 | 28.75 |
| 1395 | O | LYS | 699 | 1.047 | 36.459 | 18.420 | 1.00 | 30.96 |
| 1396 | CB | LYS | 699 | 0.141 | 37.175 | 21.469 | 1.00 | 32.36 |
| 1397 | CG | LYS | 699 | −0.319 | 36.605 | 22.790 | 1.00 | 32.65 |
| 1398 | CD | LYS | 699 | −1.435 | 37.474 | 23.360 | 1.00 | 41.08 |
| 1399 | CE | LYS | 699 | −1.870 | 36.970 | 24.710 | 1.00 | 47.72 |
| 1400 | NZ | LYS | 699 | −0.742 | 36.892 | 25.724 | 1.00 | 54.97 |
| 1401 | N | ALA | 700 | 2.254 | 38.111 | 19.334 | 1.00 | 25.66 |
| 1402 | CA | ALA | 700 | 2.515 | 38.726 | 18.035 | 1.00 | 26.89 |
| 1403 | C | ALA | 700 | 3.302 | 37.744 | 17.175 | 1.00 | 25.18 |
| 1404 | O | ALA | 700 | 3.029 | 37.591 | 15.981 | 1.00 | 24.74 |
| 1405 | CB | ALA | 700 | 3.305 | 40.026 | 18.206 | 1.00 | 22.45 |
| 1406 | N | ILE | 701 | 4.271 | 37.081 | 17.794 | 1.00 | 25.69 |
| 1407 | CA | ILE | 701 | 5.112 | 36.113 | 17.088 | 1.00 | 28.42 |
| 1408 | C | ILE | 701 | 4.237 | 34.945 | 16.627 | 1.00 | 32.00 |
| 1409 | O | ILE | 701 | 4.394 | 34.448 | 15.513 | 1.00 | 33.59 |
| 1410 | CB | ILE | 701 | 6.243 | 35.612 | 18.008 | 1.00 | 31.03 |
| 1411 | CG1 | ILE | 701 | 7.259 | 36.743 | 18.217 | 1.00 | 25.53 |
| 1412 | CG2 | ILE | 701 | 6.912 | 34.369 | 17.417 | 1.00 | 29.18 |
| 1413 | CD1 | ILE | 701 | 8.342 | 36.413 | 19.218 | 1.00 | 27.39 |
| 1414 | N | VAL | 702 | 3.311 | 34.534 | 17.488 | 1.00 | 33.82 |
| 1415 | CA | VAL | 702 | 2.409 | 33.440 | 17.168 | 1.00 | 34.58 |
| 1416 | C | VAL | 702 | 1.484 | 33.695 | 15.991 | 1.00 | 37.55 |
| 1417 | O | VAL | 702 | 0.987 | 32.754 | 15.368 | 1.00 | 37.64 |
| 1418 | CB | VAL | 702 | 1.584 | 33.033 | 18.453 | 1.00 | 99.90 |
| 1419 | CG1 | VAL | 702 | 2.450 | 32.451 | 19.597 | 1.00 | 99.90 |
| 1420 | CG2 | VAL | 702 | 0.440 | 32.002 | 18.241 | 1.00 | 99.90 |
| 1421 | N | LYS | 703 | 1.246 | 34.963 | 15.675 | 1.00 | 33.59 |
| 1422 | CA | LYS | 703 | 0.379 | 35.312 | 14.563 | 1.00 | 37.87 |
| 1423 | C | LYS | 703 | 0.909 | 34.783 | 13.231 | 1.00 | 42.05 |
| 1424 | O | LYS | 703 | 0.137 | 34.548 | 12.304 | 1.00 | 37.32 |

TABLE 5-continued

ATOMIC COORDINATES FOR THE GR/SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1425 | CB | LYS | 703 | 0.220 | 36.832 | 14.468 | 1.00 | 35.77 |
| 1426 | CG | LYS | 703 | −0.753 | 37.281 | 13.349 | 1.00 | 99.90 |
| 1427 | CD | LYS | 703 | −0.887 | 38.797 | 13.181 | 1.00 | 99.90 |
| 1428 | CE | LYS | 703 | −1.819 | 39.094 | 11.999 | 1.00 | 99.90 |
| 1429 | NZ | LYS | 703 | −2.088 | 40.542 | 11.940 | 1.00 | 99.90 |
| 1430 | N | ARG | 704 | 2.223 | 34.592 | 13.144 | 1.00 | 42.57 |
| 1431 | CA | ARG | 704 | 2.855 | 34.129 | 11.915 | 1.00 | 52.08 |
| 1432 | C | ARG | 704 | 3.857 | 33.000 | 12.122 | 1.00 | 54.79 |
| 1433 | O | ARG | 704 | 4.295 | 32.377 | 11.153 | 1.00 | 58.54 |
| 1434 | CB | ARG | 704 | 3.553 | 35.300 | 11.220 | 1.00 | 52.12 |
| 1435 | CG | ARG | 704 | 2.602 | 36.399 | 10.773 | 1.00 | 58.32 |
| 1436 | CD | ARG | 704 | 3.330 | 37.570 | 10.125 | 1.00 | 61.04 |
| 1437 | NE | ARG | 704 | 2.381 | 38.552 | 9.608 | 1.00 | 72.95 |
| 1438 | CZ | ARG | 704 | 2.717 | 39.679 | 8.985 | 1.00 | 76.45 |
| 1439 | NH1 | ARG | 704 | 4.016 | 40.006 | 8.710 | 1.00 | 80.87 |
| 1440 | NH2 | ARG | 704 | 1.724 | 40.535 | 8.609 | 1.00 | 77.97 |
| 1441 | N | GLU | 705 | 4.232 | 32.744 | 13.373 | 1.00 | 60.36 |
| 1442 | CA | GLU | 705 | 5.173 | 31.670 | 13.672 | 1.00 | 65.05 |
| 1443 | C | GLU | 705 | 4.462 | 30.478 | 14.296 | 1.00 | 67.98 |
| 1444 | O | GLU | 705 | 4.360 | 30.349 | 15.520 | 1.00 | 68.79 |
| 1445 | CB | GLU | 705 | 6.299 | 32.164 | 14.581 | 1.00 | 64.71 |
| 1446 | CG | GLU | 705 | 7.176 | 33.211 | 13.919 | 1.00 | 68.26 |
| 1447 | CD | GLU | 705 | 7.851 | 32.703 | 12.655 | 1.00 | 71.18 |
| 1448 | OE1 | GLU | 705 | 8.482 | 33.467 | 11.921 | 1.00 | 72.78 |
| 1449 | OE2 | GLU | 705 | 7.975 | 31.348 | 12.607 | 1.00 | 99.90 |
| 1450 | N | GLY | 706 | 3.967 | 29.621 | 13.410 | 1.00 | 70.37 |
| 1451 | CA | GLY | 706 | 3.248 | 28.405 | 13.752 | 1.00 | 71.87 |
| 1452 | C | GLY | 706 | 4.084 | 27.416 | 14.573 | 1.00 | 72.34 |
| 1453 | O | GLY | 706 | 3.661 | 26.978 | 15.646 | 1.00 | 71.39 |
| 1454 | N | ASN | 707 | 5.266 | 27.069 | 14.068 | 1.00 | 72.03 |
| 1455 | CA | ASN | 707 | 6.127 | 26.131 | 14.769 | 1.00 | 72.71 |
| 1456 | C | ASN | 707 | 6.392 | 26.503 | 16.219 | 1.00 | 71.15 |
| 1457 | O | ASN | 707 | 6.651 | 27.665 | 16.528 | 1.00 | 71.21 |
| 1458 | CB | ASN | 707 | 7.464 | 25.970 | 13.989 | 1.00 | 99.90 |
| 1459 | CG | ASN | 707 | 7.366 | 25.516 | 12.528 | 1.00 | 99.90 |
| 1460 | OD1 | ASN | 707 | 7.454 | 26.300 | 11.595 | 1.00 | 99.90 |
| 1461 | ND2 | ASN | 707 | 7.157 | 24.252 | 12.275 | 1.00 | 99.90 |
| 1462 | N | SER | 708 | 6.330 | 25.521 | 17.110 | 1.00 | 70.79 |
| 1463 | CA | SER | 708 | 6.571 | 25.759 | 18.531 | 1.00 | 69.40 |
| 1464 | C | SER | 708 | 8.038 | 26.104 | 18.772 | 1.00 | 68.93 |
| 1465 | O | SER | 708 | 8.369 | 26.841 | 19.706 | 1.00 | 66.12 |
| 1466 | CB | SER | 708 | 6.215 | 24.515 | 19.380 | 1.00 | 71.43 |
| 1467 | OG | SER | 708 | 7.120 | 23.424 | 19.176 | 1.00 | 99.90 |
| 1468 | N | SER | 709 | 8.912 | 25.561 | 17.929 | 1.00 | 65.17 |
| 1469 | CA | SER | 709 | 10.339 | 25.819 | 18.054 | 1.00 | 64.59 |
| 1470 | C | SER | 709 | 10.702 | 27.013 | 17.180 | 1.00 | 61.44 |
| 1471 | O | SER | 709 | 11.567 | 27.811 | 17.531 | 1.00 | 61.24 |
| 1472 | CB | SER | 709 | 11.177 | 24.591 | 17.623 | 1.00 | 65.52 |
| 1473 | OG | SER | 709 | 11.115 | 24.341 | 16.214 | 1.00 | 99.90 |
| 1474 | N | GLN | 710 | 10.031 | 27.128 | 16.038 | 1.00 | 58.29 |
| 1475 | CA | GLN | 710 | 10.272 | 28.237 | 15.129 | 1.00 | 52.84 |
| 1476 | C | GLN | 710 | 9.868 | 29.527 | 15.841 | 1.00 | 51.66 |
| 1477 | O | GLN | 710 | 10.538 | 30.553 | 15.720 | 1.00 | 45.86 |
| 1478 | CB | GLN | 710 | 9.447 | 28.068 | 13.852 | 1.00 | 55.37 |
| 1479 | CG | GLN | 710 | 9.639 | 29.168 | 12.755 | 1.00 | 99.90 |
| 1480 | CD | GLN | 710 | 8.801 | 29.099 | 11.472 | 1.00 | 99.90 |
| 1481 | OE1 | GLN | 710 | 8.894 | 29.959 | 10.612 | 1.00 | 99.90 |
| 1482 | NE2 | GLN | 710 | 7.952 | 28.118 | 11.299 | 1.00 | 99.90 |
| 1483 | N | ASN | 711 | 8.771 | 29.458 | 16.586 | 1.00 | 44.60 |
| 1484 | CA | ASN | 711 | 8.278 | 30.608 | 17.328 | 1.00 | 45.64 |
| 1485 | C | ASN | 711 | 9.227 | 30.873 | 18.485 | 1.00 | 44.47 |
| 1486 | O | ASN | 711 | 9.455 | 32.018 | 18.873 | 1.00 | 39.29 |
| 1487 | CB | ASN | 711 | 6.881 | 30.328 | 17.879 | 1.00 | 45.32 |
| 1488 | CG | ASN | 711 | 5.799 | 29.942 | 16.865 | 1.00 | 99.90 |
| 1489 | OD1 | ASN | 711 | 5.455 | 28.783 | 16.688 | 1.00 | 99.90 |
| 1490 | ND2 | ASN | 711 | 5.242 | 30.883 | 16.151 | 1.00 | 99.90 |
| 1491 | N | TRP | 712 | 9.779 | 29.796 | 19.029 | 1.00 | 43.23 |
| 1492 | CA | TRP | 712 | 10.708 | 29.884 | 20.141 | 1.00 | 42.20 |
| 1493 | C | TRP | 712 | 12.007 | 30.512 | 19.655 | 1.00 | 41.29 |
| 1494 | O | TRP | 712 | 12.572 | 31.386 | 20.314 | 1.00 | 42.13 |
| 1495 | CB | TRP | 712 | 10.974 | 28.488 | 20.708 | 1.00 | 43.71 |
| 1496 | CG | TRP | 712 | 9.763 | 27.820 | 21.365 | 1.00 | 99.90 |
| 1497 | CD1 | TRP | 712 | 8.899 | 26.892 | 20.747 | 1.00 | 99.90 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1498 | CD2 | TRP | 712 | 9.234 | 28.052 | 22.618 | 1.00 | 99.90 |
| 1499 | NE1 | TRP | 712 | 7.834 | 26.530 | 21.595 | 1.00 | 99.90 |
| 1500 | CE2 | TRP | 712 | 8.064 | 27.263 | 22.748 | 1.00 | 99.90 |
| 1501 | CE3 | TRP | 712 | 9.649 | 28.908 | 23.670 | 1.00 | 99.90 |
| 1502 | CZ2 | TRP | 712 | 7.306 | 27.317 | 23.938 | 1.00 | 99.90 |
| 1503 | CZ3 | TRP | 712 | 8.887 | 28.939 | 24.838 | 1.00 | 99.90 |
| 1504 | CH2 | TRP | 712 | 7.733 | 28.153 | 24.972 | 1.00 | 99.90 |
| 1505 | N | GLN | 713 | 12.482 | 30.063 | 18.497 | 1.00 | 35.72 |
| 1506 | CA | GLN | 713 | 13.705 | 30.607 | 17.932 | 1.00 | 36.75 |
| 1507 | C | GLN | 713 | 13.471 | 32.064 | 17.536 | 1.00 | 31.61 |
| 1508 | O | GLN | 713 | 14.390 | 32.882 | 17.555 | 1.00 | 34.73 |
| 1509 | CB | GLN | 713 | 14.140 | 29.779 | 16.718 | 1.00 | 41.06 |
| 1510 | CG | GLN | 713 | 14.425 | 28.316 | 17.080 | 1.00 | 51.40 |
| 1511 | CD | GLN | 713 | 14.813 | 27.460 | 15.891 | 1.00 | 56.24 |
| 1512 | OE1 | GLN | 713 | 15.833 | 27.698 | 15.240 | 1.00 | 66.21 |
| 1513 | NE2 | GLN | 713 | 13.872 | 26.543 | 15.379 | 1.00 | 61.83 |
| 1514 | N | ARG | 714 | 12.228 | 32.377 | 17.194 | 1.00 | 30.91 |
| 1515 | CA | ARG | 714 | 11.838 | 33.731 | 16.791 | 1.00 | 33.76 |
| 1516 | C | ARG | 714 | 11.909 | 34.647 | 18.007 | 1.00 | 29.74 |
| 1517 | O | ARG | 714 | 12.398 | 35.776 | 17.934 | 1.00 | 28.46 |
| 1518 | CB | ARG | 714 | 10.410 | 33.710 | 16.264 | 1.00 | 31.23 |
| 1519 | CG | ARG | 714 | 9.875 | 35.044 | 15.774 | 1.00 | 40.84 |
| 1520 | CD | ARG | 714 | 10.660 | 35.529 | 14.587 | 1.00 | 36.78 |
| 1521 | NE | ARG | 714 | 10.044 | 36.692 | 13.951 | 1.00 | 41.13 |
| 1522 | CZ | ARG | 714 | 10.522 | 37.255 | 12.851 | 1.00 | 35.24 |
| 1523 | NH1 | ARG | 714 | 11.641 | 36.755 | 12.245 | 1.00 | 32.73 |
| 1524 | NH2 | ARG | 714 | 9.876 | 38.307 | 12.292 | 1.00 | 33.12 |
| 1525 | N | PHE | 715 | 11.410 | 34.140 | 19.125 | 1.00 | 27.87 |
| 1526 | CA | PHE | 715 | 11.411 | 34.896 | 20.360 | 1.00 | 29.28 |
| 1527 | C | PHE | 715 | 12.853 | 35.180 | 20.724 | 1.00 | 30.03 |
| 1528 | O | PHE | 715 | 13.198 | 36.292 | 21.131 | 1.00 | 29.75 |
| 1529 | CB | PHE | 715 | 10.742 | 34.102 | 21.471 | 1.00 | 30.24 |
| 1530 | CG | PHE | 715 | 10.605 | 34.864 | 22.757 | 1.00 | 32.22 |
| 1531 | CD1 | PHE | 715 | 9.640 | 35.859 | 22.893 | 1.00 | 30.59 |
| 1532 | CD2 | PHE | 715 | 11.446 | 34.593 | 23.829 | 1.00 | 33.43 |
| 1533 | CE1 | PHE | 715 | 9.515 | 36.573 | 24.083 | 1.00 | 29.82 |
| 1534 | CE2 | PHE | 715 | 11.330 | 35.300 | 25.020 | 1.00 | 33.14 |
| 1535 | CZ | PHE | 715 | 10.360 | 36.294 | 25.147 | 1.00 | 28.67 |
| 1536 | N | TYR | 716 | 13.709 | 34.180 | 20.544 | 1.00 | 28.46 |
| 1537 | CA | TYR | 716 | 15.123 | 34.343 | 20.860 | 1.00 | 33.75 |
| 1538 | C | TYR | 716 | 15.764 | 35.435 | 20.016 | 1.00 | 30.34 |
| 1539 | O | TYR | 716 | 16.500 | 36.271 | 20.534 | 1.00 | 31.44 |
| 1540 | CB | TYR | 716 | 15.905 | 33.043 | 20.630 | 1.00 | 32.68 |
| 1541 | CG | TYR | 716 | 17.391 | 33.207 | 20.872 | 1.00 | 39.92 |
| 1542 | CD1 | TYR | 716 | 17.904 | 33.299 | 22.163 | 1.00 | 45.08 |
| 1543 | CD2 | TYR | 716 | 18.278 | 33.335 | 19.805 | 1.00 | 45.67 |
| 1544 | CE1 | TYR | 716 | 19.270 | 33.517 | 22.389 | 1.00 | 52.13 |
| 1545 | CE2 | TYR | 716 | 19.643 | 33.556 | 20.017 | 1.00 | 51.47 |
| 1546 | CZ | TYR | 716 | 20.131 | 33.646 | 21.308 | 1.00 | 51.04 |
| 1547 | OH | TYR | 716 | 21.474 | 33.869 | 21.525 | 1.00 | 54.66 |
| 1548 | N | GLN | 717 | 15.487 | 35.410 | 18.717 | 1.00 | 27.62 |
| 1549 | CA | GLN | 717 | 16.038 | 36.383 | 17.792 | 1.00 | 28.60 |
| 1550 | C | GLN | 717 | 15.598 | 37.812 | 18.104 | 1.00 | 30.83 |
| 1551 | O | GLN | 717 | 16.418 | 38.742 | 18.128 | 1.00 | 26.66 |
| 1552 | CB | GLN | 717 | 15.619 | 36.045 | 16.365 | 1.00 | 34.35 |
| 1553 | CG | GLN | 717 | 16.070 | 34.670 | 15.891 | 1.00 | 38.32 |
| 1554 | CD | GLN | 717 | 15.625 | 34.389 | 14.474 | 1.00 | 43.83 |
| 1555 | OE1 | GLN | 717 | 14.434 | 34.436 | 14.160 | 1.00 | 44.13 |
| 1556 | NE2 | GLN | 717 | 16.629 | 34.027 | 13.543 | 1.00 | 49.31 |
| 1557 | N | LEU | 718 | 14.303 | 37.983 | 18.334 | 1.00 | 26.84 |
| 1558 | CA | LEU | 718 | 13.774 | 39.309 | 18.625 | 1.00 | 25.39 |
| 1559 | C | LEU | 718 | 14.288 | 39.865 | 19.949 | 1.00 | 27.79 |
| 1560 | O | LEU | 718 | 14.634 | 41.050 | 20.032 | 1.00 | 27.31 |
| 1561 | CB | LEU | 718 | 12.242 | 39.283 | 18.616 | 1.00 | 24.65 |
| 1562 | CG | LEU | 718 | 11.635 | 38.865 | 17.267 | 1.00 | 26.51 |
| 1563 | CD1 | LEU | 718 | 10.131 | 38.939 | 17.303 | 1.00 | 29.15 |
| 1564 | CD2 | LEU | 718 | 12.187 | 39.757 | 16.171 | 1.00 | 24.41 |
| 1565 | N | THR | 719 | 14.346 | 39.025 | 20.979 | 1.00 | 26.19 |
| 1566 | CA | THR | 719 | 14.824 | 39.484 | 22.274 | 1.00 | 29.70 |
| 1567 | C | THR | 719 | 16.339 | 39.696 | 22.245 | 1.00 | 32.67 |
| 1568 | O | THR | 719 | 16.878 | 40.522 | 22.992 | 1.00 | 30.17 |
| 1569 | CB | THR | 719 | 14.411 | 38.513 | 23.424 | 1.00 | 29.72 |
| 1570 | OG1 | THR | 719 | 14.908 | 37.198 | 23.251 | 1.00 | 33.15 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1571 | CG2 | THR | 719 | 12.906 | 38.435 | 23.520 | 1.00 | 32.70 |
| 1572 | N | LYS | 720 | 17.037 | 38.976 | 21.374 | 1.00 | 29.23 |
| 1573 | CA | LYS | 720 | 18.481 | 39.162 | 21.281 | 1.00 | 29.94 |
| 1574 | C | LYS | 720 | 18.709 | 40.525 | 20.625 | 1.00 | 25.15 |
| 1575 | O | LYS | 720 | 19.630 | 41.242 | 20.971 | 1.00 | 30.87 |
| 1576 | CB | LYS | 720 | 19.122 | 38.049 | 20.435 | 1.00 | 32.66 |
| 1577 | CG | LYS | 720 | 20.649 | 38.024 | 20.484 | 1.00 | 41.23 |
| 1578 | CD | LYS | 720 | 21.154 | 37.764 | 21.902 | 1.00 | 45.10 |
| 1579 | CE | LYS | 720 | 22.671 | 37.785 | 21.969 | 1.00 | 45.88 |
| 1580 | NZ | LYS | 720 | 23.231 | 37.484 | 23.350 | 1.00 | 50.22 |
| 1581 | N | LEU | 721 | 17.849 | 40.890 | 19.682 | 1.00 | 28.84 |
| 1582 | CA | LEU | 721 | 17.962 | 42.186 | 19.014 | 1.00 | 30.79 |
| 1583 | C | LEU | 721 | 17.799 | 43.313 | 20.049 | 1.00 | 31.46 |
| 1584 | O | LEU | 721 | 18.563 | 44.282 | 20.056 | 1.00 | 28.53 |
| 1585 | CB | LEU | 721 | 16.910 | 42.303 | 17.913 | 1.00 | 29.92 |
| 1586 | CG | LEU | 721 | 16.843 | 43.583 | 17.069 | 1.00 | 36.08 |
| 1587 | CD1 | LEU | 721 | 16.109 | 43.302 | 15.767 | 1.00 | 37.87 |
| 1588 | CD2 | LEU | 721 | 16.139 | 44.675 | 17.848 | 1.00 | 34.23 |
| 1589 | N | LEU | 722 | 16.813 | 43.179 | 20.930 | 1.00 | 26.83 |
| 1590 | CA | LEU | 722 | 16.603 | 44.188 | 21.966 | 1.00 | 32.06 |
| 1591 | C | LEU | 722 | 17.838 | 44.293 | 22.860 | 1.00 | 31.54 |
| 1592 | O | LEU | 722 | 18.268 | 45.405 | 23.208 | 1.00 | 27.43 |
| 1593 | CB | LEU | 722 | 15.368 | 43.847 | 22.804 | 1.00 | 28.40 |
| 1594 | CG | LEU | 722 | 14.020 | 43.968 | 22.085 | 1.00 | 33.60 |
| 1595 | CD1 | LEU | 722 | 12.898 | 43.593 | 23.039 | 1.00 | 27.76 |
| 1596 | CD2 | LEU | 722 | 13.817 | 45.402 | 21.578 | 1.00 | 36.94 |
| 1597 | N | ASP | 723 | 18.404 | 43.144 | 23.242 | 1.00 | 30.89 |
| 1598 | CA | ASP | 723 | 19.615 | 43.141 | 24.069 | 1.00 | 31.45 |
| 1599 | C | ASP | 723 | 20.725 | 43.895 | 23.355 | 1.00 | 33.06 |
| 1600 | O | ASP | 723 | 21.418 | 44.710 | 23.967 | 1.00 | 27.21 |
| 1601 | CB | ASP | 723 | 20.131 | 41.719 | 24.340 | 1.00 | 32.85 |
| 1602 | CG | ASP | 723 | 19.307 | 40.964 | 25.374 | 1.00 | 41.09 |
| 1603 | OD1 | ASP | 723 | 18.366 | 41.546 | 25.954 | 1.00 | 34.77 |
| 1604 | OD2 | ASP | 723 | 19.617 | 39.770 | 25.609 | 1.00 | 35.56 |
| 1605 | N | SER | 724 | 20.909 | 43.607 | 22.066 | 1.00 | 23.23 |
| 1606 | CA | SER | 724 | 21.960 | 44.274 | 21.307 | 1.00 | 29.88 |
| 1607 | C | SER | 724 | 21.770 | 45.780 | 21.172 | 1.00 | 27.44 |
| 1608 | O | SER | 724 | 22.735 | 46.513 | 20.960 | 1.00 | 28.18 |
| 1609 | CB | SER | 724 | 22.114 | 43.636 | 19.917 | 1.00 | 30.74 |
| 1610 | OG | SER | 724 | 20.999 | 43.898 | 19.058 | 1.00 | 99.90 |
| 1611 | N | MET | 725 | 20.537 | 46.251 | 21.314 | 1.00 | 27.04 |
| 1612 | CA | MET | 725 | 20.295 | 47.688 | 21.211 | 1.00 | 28.38 |
| 1613 | C | MET | 725 | 21.054 | 48.489 | 22.279 | 1.00 | 29.38 |
| 1614 | O | MET | 725 | 21.465 | 49.630 | 22.043 | 1.00 | 26.74 |
| 1615 | CB | MET | 725 | 18.795 | 47.975 | 21.288 | 1.00 | 27.75 |
| 1616 | CG | MET | 725 | 17.936 | 47.376 | 20.154 | 1.00 | 99.90 |
| 1617 | SD | MET | 725 | 16.267 | 48.046 | 20.234 | 1.00 | 99.90 |
| 1618 | CE | MET | 725 | 15.466 | 46.902 | 19.103 | 1.00 | 99.90 |
| 1619 | N | HIS | 726 | 21.256 | 47.893 | 23.446 | 1.00 | 25.82 |
| 1620 | CA | HIS | 726 | 21.974 | 48.580 | 24.517 | 1.00 | 26.55 |
| 1621 | C | HIS | 726 | 23.345 | 49.086 | 24.078 | 1.00 | 28.01 |
| 1622 | O | HIS | 726 | 23.671 | 50.249 | 24.293 | 1.00 | 26.18 |
| 1623 | CB | HIS | 726 | 22.127 | 47.669 | 25.745 | 1.00 | 27.98 |
| 1624 | CG | HIS | 726 | 20.895 | 47.574 | 26.592 | 1.00 | 31.07 |
| 1625 | ND1 | HIS | 726 | 20.272 | 46.376 | 26.875 | 1.00 | 34.25 |
| 1626 | CD2 | HIS | 726 | 20.192 | 48.527 | 27.252 | 1.00 | 25.45 |
| 1627 | CE1 | HIS | 726 | 19.242 | 46.596 | 27.675 | 1.00 | 30.14 |
| 1628 | NE2 | HIS | 726 | 19.172 | 47.892 | 27.917 | 1.00 | 32.22 |
| 1629 | N | GLU | 727 | 24.148 | 48.238 | 23.446 | 1.00 | 30.88 |
| 1630 | CA | GLU | 727 | 25.476 | 48.678 | 23.017 | 1.00 | 33.37 |
| 1631 | C | GLU | 727 | 25.357 | 49.683 | 21.881 | 1.00 | 32.18 |
| 1632 | O | GLU | 727 | 26.127 | 50.639 | 21.806 | 1.00 | 28.61 |
| 1633 | CB | GLU | 727 | 26.327 | 47.486 | 22.573 | 1.00 | 41.89 |
| 1634 | CG | GLU | 727 | 25.866 | 46.713 | 21.294 | 1.00 | 99.90 |
| 1635 | CD | GLU | 727 | 26.640 | 45.457 | 20.886 | 1.00 | 99.90 |
| 1636 | OE1 | GLU | 727 | 26.334 | 44.770 | 19.921 | 1.00 | 99.90 |
| 1637 | OE2 | GLU | 727 | 27.699 | 45.178 | 21.696 | 1.00 | 99.90 |
| 1638 | N | VAL | 728 | 24.394 | 49.464 | 20.991 | 1.00 | 25.95 |
| 1639 | CA | VAL | 728 | 24.183 | 50.377 | 19.877 | 1.00 | 24.45 |
| 1640 | C | VAL | 728 | 23.817 | 51.777 | 20.382 | 1.00 | 24.31 |
| 1641 | O | VAL | 728 | 24.412 | 52.774 | 19.976 | 1.00 | 24.16 |
| 1642 | CB | VAL | 728 | 23.092 | 49.899 | 18.861 | 1.00 | 25.35 |
| 1643 | CG1 | VAL | 728 | 23.492 | 48.583 | 18.149 | 1.00 | 99.90 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1644 | CG2 | VAL | 728 | 22.782 | 50.963 | 17.778 | 1.00 | 99.90 |
| 1645 | N | VAL | 729 | 22.824 | 51.844 | 21.261 | 1.00 | 23.01 |
| 1646 | CA | VAL | 729 | 22.372 | 53.122 | 21.809 | 1.00 | 25.27 |
| 1647 | C | VAL | 729 | 23.466 | 53.875 | 22.575 | 1.00 | 22.87 |
| 1648 | O | VAL | 729 | 23.488 | 55.112 | 22.602 | 1.00 | 21.03 |
| 1649 | CB | VAL | 729 | 21.152 | 52.905 | 22.732 | 1.00 | 28.67 |
| 1650 | CG1 | VAL | 729 | 20.798 | 54.197 | 23.450 | 1.00 | 30.03 |
| 1651 | CG2 | VAL | 729 | 19.961 | 52.435 | 21.898 | 1.00 | 28.50 |
| 1652 | N | GLU | 730 | 24.366 | 53.132 | 23.200 | 1.00 | 23.37 |
| 1653 | CA | GLU | 730 | 25.459 | 53.754 | 23.940 | 1.00 | 23.75 |
| 1654 | C | GLU | 730 | 26.319 | 54.639 | 23.036 | 1.00 | 24.31 |
| 1655 | O | GLU | 730 | 26.805 | 55.687 | 23.470 | 1.00 | 23.94 |
| 1656 | CB | GLU | 730 | 26.325 | 52.689 | 24.594 | 1.00 | 23.23 |
| 1657 | CG | GLU | 730 | 27.399 | 53.266 | 25.500 | 1.00 | 34.73 |
| 1658 | CD | GLU | 730 | 28.403 | 52.304 | 26.141 | 1.00 | 99.90 |
| 1659 | OE1 | GLU | 730 | 29.321 | 52.680 | 26.858 | 1.00 | 99.90 |
| 1660 | OE2 | GLU | 730 | 28.179 | 50.996 | 25.838 | 1.00 | 99.90 |
| 1661 | N | ASN | 731 | 26.510 | 54.228 | 21.781 | 1.00 | 20.06 |
| 1662 | CA | ASN | 731 | 27.297 | 55.035 | 20.851 | 1.00 | 21.61 |
| 1663 | C | ASN | 731 | 26.511 | 56.290 | 20.509 | 1.00 | 20.55 |
| 1664 | O | ASN | 731 | 27.091 | 57.365 | 20.358 | 1.00 | 21.72 |
| 1665 | CB | ASN | 731 | 27.630 | 54.313 | 19.522 | 1.00 | 27.13 |
| 1666 | CG | ASN | 731 | 28.313 | 55.276 | 18.531 | 1.00 | 99.90 |
| 1667 | OD1 | ASN | 731 | 27.690 | 55.787 | 17.614 | 1.00 | 99.90 |
| 1668 | ND2 | ASN | 731 | 29.693 | 55.513 | 18.747 | 1.00 | 99.90 |
| 1669 | N | LEU | 732 | 25.195 | 56.156 | 20.355 | 1.00 | 18.60 |
| 1670 | CA | LEU | 732 | 24.372 | 57.322 | 20.073 | 1.00 | 19.89 |
| 1671 | C | LEU | 732 | 24.400 | 58.268 | 21.297 | 1.00 | 21.61 |
| 1672 | O | LEU | 732 | 24.496 | 59.486 | 21.145 | 1.00 | 18.84 |
| 1673 | CB | LEU | 732 | 22.936 | 56.899 | 19.764 | 1.00 | 24.80 |
| 1674 | CG | LEU | 732 | 22.703 | 55.942 | 18.590 | 1.00 | 32.83 |
| 1675 | CD1 | LEU | 732 | 21.193 | 55.824 | 18.366 | 1.00 | 30.42 |
| 1676 | CD2 | LEU | 732 | 23.369 | 56.464 | 17.329 | 1.00 | 34.48 |
| 1677 | N | LEU | 733 | 24.312 | 57.712 | 22.508 | 1.00 | 20.58 |
| 1678 | CA | LEU | 733 | 24.351 | 58.531 | 23.734 | 1.00 | 19.88 |
| 1679 | C | LEU | 733 | 25.661 | 59.317 | 23.841 | 1.00 | 23.80 |
| 1680 | O | LEU | 733 | 25.669 | 60.503 | 24.181 | 1.00 | 21.80 |
| 1681 | CB | LEU | 733 | 24.253 | 57.782 | 25.098 | 1.00 | 21.04 |
| 1682 | CG | LEU | 733 | 23.046 | 56.856 | 25.403 | 1.00 | 99.90 |
| 1683 | CD1 | LEU | 733 | 22.981 | 56.535 | 26.912 | 1.00 | 99.90 |
| 1684 | CD2 | LEU | 733 | 21.687 | 57.385 | 24.900 | 1.00 | 99.90 |
| 1685 | N | ASN | 734 | 26.774 | 58.653 | 23.543 | 1.00 | 22.67 |
| 1686 | CA | ASN | 734 | 28.066 | 59.318 | 23.616 | 1.00 | 21.83 |
| 1687 | C | ASN | 734 | 28.188 | 60.431 | 22.575 | 1.00 | 21.54 |
| 1688 | O | ASN | 734 | 28.645 | 61.526 | 22.886 | 1.00 | 20.75 |
| 1689 | CB | ASN | 734 | 29.250 | 58.341 | 23.367 | 1.00 | 20.66 |
| 1690 | CG | ASN | 734 | 29.379 | 57.211 | 24.413 | 1.00 | 99.90 |
| 1691 | OD1 | ASN | 734 | 28.890 | 57.286 | 25.529 | 1.00 | 99.90 |
| 1692 | ND2 | ASN | 734 | 30.142 | 56.095 | 23.981 | 1.00 | 99.90 |
| 1693 | N | TYR | 735 | 27.768 | 60.157 | 21.341 | 1.00 | 19.92 |
| 1694 | CA | TYR | 735 | 27.850 | 61.170 | 20.282 | 1.00 | 19.47 |
| 1695 | C | TYR | 735 | 26.977 | 62.389 | 20.650 | 1.00 | 22.05 |
| 1696 | O | TYR | 735 | 27.375 | 63.553 | 20.494 | 1.00 | 20.67 |
| 1697 | CB | TYR | 735 | 27.396 | 60.546 | 18.948 | 1.00 | 19.20 |
| 1698 | CG | TYR | 735 | 27.693 | 61.397 | 17.736 | 1.00 | 27.69 |
| 1699 | CD1 | TYR | 735 | 26.945 | 62.546 | 17.461 | 1.00 | 26.53 |
| 1700 | CD2 | TYR | 735 | 28.743 | 61.070 | 16.878 | 1.00 | 24.52 |
| 1701 | CE1 | TYR | 735 | 27.237 | 63.347 | 16.359 | 1.00 | 30.01 |
| 1702 | CE2 | TYR | 735 | 29.043 | 61.863 | 15.778 | 1.00 | 26.75 |
| 1703 | CZ | TYR | 735 | 28.285 | 62.998 | 15.525 | 1.00 | 33.34 |
| 1704 | OH | TYR | 735 | 28.416 | 63.738 | 14.398 | 1.00 | 39.29 |
| 1705 | N | CYS | 736 | 25.785 | 62.119 | 21.164 | 1.00 | 19.66 |
| 1706 | CA | CYS | 736 | 24.859 | 63.176 | 21.560 | 1.00 | 21.68 |
| 1707 | C | CYS | 736 | 25.421 | 64.067 | 22.674 | 1.00 | 20.24 |
| 1708 | O | CYS | 736 | 25.420 | 65.295 | 22.574 | 1.00 | 22.45 |
| 1709 | CB | CYS | 736 | 23.541 | 62.546 | 22.022 | 1.00 | 22.87 |
| 1710 | SG | CYS | 736 | 22.282 | 63.748 | 22.564 | 1.00 | 25.25 |
| 1711 | N | PHE | 737 | 25.901 | 63.448 | 23.738 | 1.00 | 21.55 |
| 1712 | CA | PHE | 737 | 26.445 | 64.208 | 24.862 | 1.00 | 24.47 |
| 1713 | C | PHE | 737 | 27.666 | 65.021 | 24.442 | 1.00 | 25.40 |
| 1714 | O | PHE | 737 | 27.856 | 66.143 | 24.922 | 1.00 | 28.02 |
| 1715 | CB | PHE | 737 | 26.898 | 63.269 | 26.010 | 1.00 | 24.44 |
| 1716 | CG | PHE | 737 | 27.315 | 64.017 | 27.260 | 1.00 | 99.90 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1717 | CD1 | PHE | 737 | 26.499 | 65.065 | 27.832 | 1.00 | 99.90 |
| 1718 | CD2 | PHE | 737 | 28.542 | 63.654 | 27.928 | 1.00 | 99.90 |
| 1719 | CE1 | PHE | 737 | 26.921 | 65.758 | 29.018 | 1.00 | 99.90 |
| 1720 | CE2 | PHE | 737 | 28.954 | 64.332 | 29.127 | 1.00 | 99.90 |
| 1721 | CZ | PHE | 737 | 28.149 | 65.393 | 29.667 | 1.00 | 99.90 |
| 1722 | N | GLN | 738 | 28.497 | 64.463 | 23.562 | 1.00 | 23.21 |
| 1723 | CA | GLN | 738 | 29.658 | 65.202 | 23.063 | 1.00 | 23.92 |
| 1724 | C | GLN | 738 | 29.226 | 66.424 | 22.255 | 1.00 | 25.99 |
| 1725 | O | GLN | 738 | 29.753 | 67.514 | 22.440 | 1.00 | 27.51 |
| 1726 | CB | GLN | 738 | 30.559 | 64.293 | 22.179 | 1.00 | 27.01 |
| 1727 | CG | GLN | 738 | 31.843 | 64.932 | 21.588 | 1.00 | 99.90 |
| 1728 | CD | GLN | 738 | 31.591 | 65.903 | 20.416 | 1.00 | 99.90 |
| 1729 | OE1 | GLN | 738 | 31.978 | 67.059 | 20.459 | 1.00 | 99.90 |
| 1730 | NE2 | GLN | 738 | 30.947 | 65.358 | 19.278 | 1.00 | 99.90 |
| 1731 | N | THR | 739 | 28.287 | 66.230 | 21.337 | 1.00 | 25.80 |
| 1732 | CA | THR | 739 | 27.800 | 67.322 | 20.501 | 1.00 | 25.04 |
| 1733 | C | THR | 739 | 27.089 | 68.377 | 21.331 | 1.00 | 24.51 |
| 1734 | O | THR | 739 | 27.152 | 69.566 | 21.020 | 1.00 | 28.41 |
| 1735 | CB | THR | 739 | 26.837 | 66.791 | 19.405 | 1.00 | 22.97 |
| 1736 | OG1 | THR | 739 | 27.460 | 65.817 | 18.573 | 1.00 | 23.34 |
| 1737 | CG2 | THR | 739 | 26.356 | 67.912 | 18.511 | 1.00 | 25.92 |
| 1738 | N | PHE | 740 | 26.423 | 67.928 | 22.391 | 1.00 | 23.12 |
| 1739 | CA | PHE | 740 | 25.684 | 68.804 | 23.294 | 1.00 | 23.28 |
| 1740 | C | PHE | 740 | 26.683 | 69.700 | 24.034 | 1.00 | 26.81 |
| 1741 | O | PHE | 740 | 26.466 | 70.902 | 24.160 | 1.00 | 27.75 |
| 1742 | CB | PHE | 740 | 24.899 | 67.961 | 24.302 | 1.00 | 22.97 |
| 1743 | CG | PHE | 740 | 24.055 | 68.765 | 25.255 | 1.00 | 20.82 |
| 1744 | CD1 | PHE | 740 | 22.905 | 69.411 | 24.823 | 1.00 | 21.56 |
| 1745 | CD2 | PHE | 740 | 24.442 | 68.901 | 26.584 | 1.00 | 25.72 |
| 1746 | CE1 | PHE | 740 | 22.143 | 70.187 | 25.698 | 1.00 | 26.99 |
| 1747 | CE2 | PHE | 740 | 23.690 | 69.673 | 27.468 | 1.00 | 28.83 |
| 1748 | CZ | PHE | 740 | 22.537 | 70.318 | 27.025 | 1.00 | 24.76 |
| 1749 | N | LEU | 741 | 27.770 | 69.110 | 24.527 | 1.00 | 26.30 |
| 1750 | CA | LEU | 741 | 28.799 | 69.887 | 25.225 | 1.00 | 27.51 |
| 1751 | C | LEU | 741 | 29.519 | 70.858 | 24.274 | 1.00 | 30.83 |
| 1752 | O | LEU | 741 | 29.941 | 71.946 | 24.679 | 1.00 | 31.33 |
| 1753 | CB | LEU | 741 | 29.908 | 69.003 | 25.855 | 1.00 | 30.94 |
| 1754 | CG | LEU | 741 | 29.523 | 68.182 | 27.115 | 1.00 | 99.90 |
| 1755 | CD1 | LEU | 741 | 30.665 | 67.202 | 27.464 | 1.00 | 99.90 |
| 1756 | CD2 | LEU | 741 | 29.190 | 69.075 | 28.331 | 1.00 | 99.90 |
| 1757 | N | ASP | 742 | 29.648 | 70.476 | 23.005 | 1.00 | 29.65 |
| 1758 | CA | ASP | 742 | 30.336 | 71.327 | 22.034 | 1.00 | 30.69 |
| 1759 | C | ASP | 742 | 29.348 | 72.084 | 21.156 | 1.00 | 33.21 |
| 1760 | O | ASP | 742 | 29.743 | 72.682 | 20.152 | 1.00 | 36.42 |
| 1761 | CB | ASP | 742 | 31.235 | 70.464 | 21.144 | 1.00 | 34.22 |
| 1762 | CG | ASP | 742 | 32.171 | 71.209 | 20.181 | 1.00 | 99.90 |
| 1763 | OD1 | ASP | 742 | 32.386 | 70.834 | 19.037 | 1.00 | 99.90 |
| 1764 | OD2 | ASP | 742 | 32.709 | 72.339 | 20.732 | 1.00 | 99.90 |
| 1765 | N | LYS | 743 | 27.834 | 74.903 | 21.015 | 1.00 | 37.58 |
| 1766 | CA | LYS | 743 | 28.165 | 76.351 | 20.660 | 1.00 | 43.27 |
| 1767 | C | LYS | 743 | 29.304 | 76.341 | 19.648 | 1.00 | 46.14 |
| 1768 | O | LYS | 743 | 29.279 | 77.087 | 18.665 | 1.00 | 46.04 |
| 1769 | CB | LYS | 743 | 28.506 | 77.255 | 21.851 | 1.00 | 45.98 |
| 1770 | CG | LYS | 743 | 27.451 | 77.232 | 22.956 | 1.00 | 58.17 |
| 1771 | CD | LYS | 743 | 26.030 | 77.472 | 22.426 | 1.00 | 63.03 |
| 1772 | CE | LYS | 743 | 25.032 | 77.361 | 23.586 | 1.00 | 99.90 |
| 1773 | NZ | LYS | 743 | 23.692 | 77.759 | 23.119 | 1.00 | 99.90 |
| 1774 | N | THR | 744 | 30.284 | 75.470 | 19.863 | 1.00 | 43.89 |
| 1775 | CA | THR | 744 | 31.426 | 75.374 | 18.965 | 1.00 | 44.86 |
| 1776 | C | THR | 744 | 31.055 | 74.760 | 17.623 | 1.00 | 45.61 |
| 1777 | O | THR | 744 | 31.589 | 75.140 | 16.583 | 1.00 | 44.57 |
| 1778 | CB | THR | 744 | 32.532 | 74.549 | 19.617 | 1.00 | 49.14 |
| 1779 | OG1 | THR | 744 | 32.980 | 75.173 | 20.814 | 1.00 | 99.90 |
| 1780 | CG2 | THR | 744 | 33.816 | 74.345 | 18.784 | 1.00 | 99.90 |
| 1781 | N | MET | 745 | 30.135 | 73.805 | 17.654 | 1.00 | 44.06 |
| 1782 | CA | MET | 745 | 29.702 | 73.117 | 16.446 | 1.00 | 42.19 |
| 1783 | C | MET | 745 | 28.543 | 73.819 | 15.762 | 1.00 | 40.67 |
| 1784 | O | MET | 745 | 28.123 | 73.419 | 14.680 | 1.00 | 44.90 |
| 1785 | CB | MET | 745 | 29.360 | 71.629 | 16.758 | 1.00 | 39.53 |
| 1786 | CG | MET | 745 | 29.529 | 70.678 | 15.549 | 1.00 | 99.90 |
| 1787 | SD | MET | 745 | 29.499 | 68.900 | 15.994 | 1.00 | 99.90 |
| 1788 | CE | MET | 745 | 31.285 | 68.588 | 16.215 | 1.00 | 99.90 |
| 1789 | N | SER | 746 | 28.044 | 74.878 | 16.387 | 1.00 | 38.21 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1790 | CA | SER | 746 | 26.919 | 75.618 | 15.851 | 1.00 | 35.93 |
| 1791 | C | SER | 746 | 25.688 | 74.721 | 15.769 | 1.00 | 34.57 |
| 1792 | O | SER | 746 | 24.879 | 74.855 | 14.856 | 1.00 | 33.32 |
| 1793 | CB | SER | 746 | 27.243 | 76.177 | 14.458 | 1.00 | 42.40 |
| 1794 | OG | SER | 746 | 28.273 | 77.165 | 14.476 | 1.00 | 50.36 |
| 1795 | N | ILE | 747 | 25.548 | 73.805 | 16.726 | 1.00 | 32.92 |
| 1796 | CA | ILE | 747 | 24.396 | 72.901 | 16.749 | 1.00 | 30.26 |
| 1797 | C | ILE | 747 | 23.448 | 73.310 | 17.879 | 1.00 | 31.81 |
| 1798 | O | ILE | 747 | 23.850 | 73.383 | 19.035 | 1.00 | 34.09 |
| 1799 | CB | ILE | 747 | 24.818 | 71.410 | 16.872 | 1.00 | 30.61 |
| 1800 | CG2 | ILE | 747 | 23.605 | 70.496 | 17.156 | 1.00 | 99.90 |
| 1801 | CG1 | ILE | 747 | 25.526 | 70.975 | 15.562 | 1.00 | 99.90 |
| 1802 | CD1 | ILE | 747 | 26.220 | 69.611 | 15.607 | 1.00 | 99.90 |
| 1803 | N | GLU | 748 | 22.197 | 73.600 | 17.536 | 1.00 | 28.12 |
| 1804 | CA | GLU | 748 | 21.214 | 73.984 | 18.537 | 1.00 | 27.45 |
| 1805 | C | GLU | 748 | 20.405 | 72.802 | 19.068 | 1.00 | 27.94 |
| 1806 | O | GLU | 748 | 19.952 | 71.973 | 18.288 | 1.00 | 26.23 |
| 1807 | CB | GLU | 748 | 20.238 | 75.010 | 17.965 | 1.00 | 33.68 |
| 1808 | CG | GLU | 748 | 19.118 | 75.361 | 18.944 | 1.00 | 51.81 |
| 1809 | CD | GLU | 748 | 18.123 | 76.367 | 18.393 | 1.00 | 62.71 |
| 1810 | OE1 | GLU | 748 | 18.298 | 76.824 | 17.240 | 1.00 | 63.38 |
| 1811 | OE2 | GLU | 748 | 17.160 | 76.703 | 19.123 | 1.00 | 63.52 |
| 1812 | N | PHE | 749 | 20.236 | 72.733 | 20.392 | 1.00 | 25.35 |
| 1813 | CA | PHE | 749 | 19.440 | 71.681 | 21.029 | 1.00 | 24.39 |
| 1814 | C | PHE | 749 | 18.254 | 72.387 | 21.663 | 1.00 | 26.69 |
| 1815 | O | PHE | 749 | 18.441 | 73.352 | 22.404 | 1.00 | 27.33 |
| 1816 | CB | PHE | 749 | 20.204 | 70.946 | 22.155 | 1.00 | 25.14 |
| 1817 | CG | PHE | 749 | 21.267 | 69.994 | 21.674 | 1.00 | 21.63 |
| 1818 | CD1 | PHE | 749 | 22.475 | 70.460 | 21.184 | 1.00 | 22.11 |
| 1819 | CD2 | PHE | 749 | 21.036 | 68.626 | 21.691 | 1.00 | 23.38 |
| 1820 | CE1 | PHE | 749 | 23.442 | 69.575 | 20.719 | 1.00 | 19.55 |
| 1821 | CE2 | PHE | 749 | 21.992 | 67.725 | 21.228 | 1.00 | 24.14 |
| 1822 | CZ | PHE | 749 | 23.200 | 68.201 | 20.740 | 1.00 | 22.83 |
| 1823 | N | PRO | 750 | 17.022 | 71.932 | 21.382 | 1.00 | 23.73 |
| 1824 | CA | PRO | 750 | 15.833 | 72.563 | 21.961 | 1.00 | 22.74 |
| 1825 | C | PRO | 750 | 15.766 | 72.286 | 23.474 | 1.00 | 22.33 |
| 1826 | O | PRO | 750 | 16.501 | 71.459 | 24.004 | 1.00 | 22.26 |
| 1827 | CB | PRO | 750 | 14.683 | 71.901 | 21.198 | 1.00 | 24.51 |
| 1828 | CG | PRO | 750 | 15.346 | 71.451 | 19.899 | 1.00 | 30.94 |
| 1829 | CD | PRO | 750 | 16.607 | 70.851 | 20.478 | 1.00 | 29.32 |
| 1830 | N | GLU | 751 | 14.861 | 72.976 | 24.153 | 1.00 | 25.11 |
| 1831 | CA | GLU | 751 | 14.721 | 72.860 | 25.610 | 1.00 | 22.58 |
| 1832 | C | GLU | 751 | 14.366 | 71.515 | 26.232 | 1.00 | 21.81 |
| 1833 | O | GLU | 751 | 14.968 | 71.112 | 27.220 | 1.00 | 23.58 |
| 1834 | CB | GLU | 751 | 13.704 | 73.894 | 26.097 | 1.00 | 23.00 |
| 1835 | CG | GLU | 751 | 14.072 | 75.366 | 25.825 | 1.00 | 25.08 |
| 1836 | CD | GLU | 751 | 15.381 | 75.828 | 26.459 | 1.00 | 31.26 |
| 1837 | OE1 | GLU | 751 | 15.751 | 75.341 | 27.550 | 1.00 | 31.56 |
| 1838 | OE2 | GLU | 751 | 16.034 | 76.725 | 25.879 | 1.00 | 31.17 |
| 1839 | N | MET | 752 | 13.369 | 70.820 | 25.692 | 1.00 | 20.50 |
| 1840 | CA | MET | 752 | 12.989 | 69.543 | 26.286 | 1.00 | 22.40 |
| 1841 | C | MET | 752 | 14.077 | 68.499 | 26.093 | 1.00 | 20.88 |
| 1842 | O | MET | 752 | 14.348 | 67.698 | 26.987 | 1.00 | 22.84 |
| 1843 | CB | MET | 752 | 11.659 | 69.064 | 25.692 | 1.00 | 28.13 |
| 1844 | CG | MET | 752 | 10.536 | 70.073 | 25.898 | 1.00 | 30.10 |
| 1845 | SD | MET | 752 | 8.936 | 69.576 | 25.227 | 1.00 | 36.75 |
| 1846 | CE | MET | 752 | 9.384 | 69.107 | 23.548 | 1.00 | 29.48 |
| 1847 | N | LEU | 753 | 14.719 | 68.514 | 24.932 | 1.00 | 22.18 |
| 1848 | CA | LEU | 753 | 15.778 | 67.555 | 24.665 | 1.00 | 20.40 |
| 1849 | C | LEU | 753 | 16.986 | 67.882 | 25.514 | 1.00 | 20.24 |
| 1850 | O | LEU | 753 | 17.662 | 66.988 | 26.013 | 1.00 | 20.23 |
| 1851 | CB | LEU | 753 | 16.131 | 67.658 | 23.154 | 1.00 | 24.51 |
| 1852 | CG | LEU | 753 | 17.165 | 66.660 | 22.591 | 1.00 | 99.90 |
| 1853 | CD1 | LEU | 753 | 16.675 | 65.204 | 22.693 | 1.00 | 99.90 |
| 1854 | CD2 | LEU | 753 | 17.507 | 66.994 | 21.122 | 1.00 | 99.90 |
| 1855 | N | ALA | 754 | 17.262 | 69.171 | 25.680 | 1.00 | 22.17 |
| 1856 | CA | ALA | 754 | 18.392 | 69.574 | 26.501 | 1.00 | 24.13 |
| 1857 | C | ALA | 754 | 18.157 | 69.098 | 27.942 | 1.00 | 24.76 |
| 1858 | O | ALA | 754 | 19.097 | 68.690 | 28.634 | 1.00 | 20.25 |
| 1859 | CB | ALA | 754 | 18.553 | 71.102 | 26.477 | 1.00 | 24.96 |
| 1860 | N | GLU | 755 | 16.907 | 69.162 | 28.393 | 1.00 | 21.90 |
| 1861 | CA | GLU | 755 | 16.600 | 68.727 | 29.754 | 1.00 | 25.07 |
| 1862 | C | GLU | 755 | 16.830 | 67.238 | 29.977 | 1.00 | 25.56 |

TABLE 5-continued

ATOMIC COORDINATES FOR THE GR/SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1863 | O | GLU | 755 | 17.432 | 66.860 | 30.971 | 1.00 | 26.95 |
| 1864 | CB | GLU | 755 | 15.163 | 69.086 | 30.153 | 1.00 | 26.93 |
| 1865 | CG | GLU | 755 | 14.785 | 68.556 | 31.538 | 1.00 | 30.33 |
| 1866 | CD | GLU | 755 | 15.673 | 69.098 | 32.663 | 1.00 | 45.68 |
| 1867 | OE1 | GLU | 755 | 16.238 | 70.205 | 32.515 | 1.00 | 48.37 |
| 1868 | OE2 | GLU | 755 | 15.790 | 68.424 | 33.714 | 1.00 | 40.75 |
| 1869 | N | ILE | 756 | 16.358 | 66.385 | 29.072 | 1.00 | 23.66 |
| 1870 | CA | ILE | 756 | 16.559 | 64.963 | 29.273 | 1.00 | 24.09 |
| 1871 | C | ILE | 756 | 18.031 | 64.596 | 29.179 | 1.00 | 22.11 |
| 1872 | O | ILE | 756 | 18.500 | 63.731 | 29.918 | 1.00 | 23.47 |
| 1873 | CB | ILE | 756 | 15.714 | 64.091 | 28.272 | 1.00 | 25.40 |
| 1874 | CG2 | ILE | 756 | 15.854 | 62.560 | 28.536 | 1.00 | 99.90 |
| 1875 | CG1 | ILE | 756 | 14.191 | 64.439 | 28.230 | 1.00 | 99.90 |
| 1876 | CD1 | ILE | 756 | 13.396 | 63.843 | 27.050 | 1.00 | 99.90 |
| 1877 | N | ILE | 757 | 18.775 | 65.274 | 28.301 | 1.00 | 20.76 |
| 1878 | CA | ILE | 757 | 20.201 | 64.977 | 28.158 | 1.00 | 20.13 |
| 1879 | C | ILE | 757 | 20.932 | 65.313 | 29.441 | 1.00 | 23.37 |
| 1880 | O | ILE | 757 | 21.695 | 64.500 | 29.980 | 1.00 | 25.36 |
| 1881 | CB | ILE | 757 | 20.826 | 65.763 | 26.979 | 1.00 | 19.24 |
| 1882 | CG1 | ILE | 757 | 20.290 | 65.215 | 25.661 | 1.00 | 22.39 |
| 1883 | CG2 | ILE | 757 | 22.352 | 65.650 | 27.013 | 1.00 | 18.20 |
| 1884 | CD1 | ILE | 757 | 20.522 | 66.153 | 24.469 | 1.00 | 26.26 |
| 1885 | N | THR | 758 | 20.684 | 66.509 | 29.948 | 1.00 | 23.60 |
| 1886 | CA | THR | 758 | 21.324 | 66.958 | 31.177 | 1.00 | 30.05 |
| 1887 | C | THR | 758 | 20.880 | 66.163 | 32.401 | 1.00 | 27.97 |
| 1888 | O | THR | 758 | 21.666 | 65.921 | 33.317 | 1.00 | 31.89 |
| 1889 | CB | THR | 758 | 21.042 | 68.460 | 31.398 | 1.00 | 24.81 |
| 1890 | OG1 | THR | 758 | 21.578 | 69.230 | 30.329 | 1.00 | 99.90 |
| 1891 | CG2 | THR | 758 | 21.647 | 69.091 | 32.671 | 1.00 | 99.90 |
| 1892 | N | ASN | 759 | 19.624 | 65.745 | 32.427 | 1.00 | 28.98 |
| 1893 | CA | ASN | 759 | 19.128 | 65.006 | 33.580 | 1.00 | 30.10 |
| 1894 | C | ASN | 759 | 19.657 | 63.578 | 33.713 | 1.00 | 29.70 |
| 1895 | O | ASN | 759 | 19.837 | 63.092 | 34.828 | 1.00 | 30.09 |
| 1896 | CB | ASN | 759 | 17.596 | 64.990 | 33.572 | 1.00 | 29.66 |
| 1897 | CG | ASN | 759 | 16.888 | 66.349 | 33.553 | 1.00 | 99.90 |
| 1898 | OD1 | ASN | 759 | 16.425 | 66.829 | 32.529 | 1.00 | 99.90 |
| 1899 | ND2 | ASN | 759 | 16.796 | 67.026 | 34.666 | 1.00 | 99.90 |
| 1900 | N | GLN | 760 | 19.935 | 62.906 | 32.599 | 1.00 | 26.34 |
| 1901 | CA | GLN | 760 | 20.377 | 61.526 | 32.700 | 1.00 | 23.29 |
| 1902 | C | GLN | 760 | 21.537 | 61.004 | 31.859 | 1.00 | 23.47 |
| 1903 | O | GLN | 760 | 22.127 | 59.991 | 32.231 | 1.00 | 24.44 |
| 1904 | CB | GLN | 760 | 19.199 | 60.581 | 32.419 | 1.00 | 29.83 |
| 1905 | CG | GLN | 760 | 17.964 | 60.724 | 33.272 | 1.00 | 31.14 |
| 1906 | CD | GLN | 760 | 18.228 | 60.589 | 34.752 | 1.00 | 37.37 |
| 1907 | OE1 | GLN | 760 | 19.070 | 59.800 | 35.180 | 1.00 | 33.07 |
| 1908 | NE2 | GLN | 760 | 17.354 | 61.340 | 35.577 | 1.00 | 42.40 |
| 1909 | N | ILE | 761 | 21.852 | 61.619 | 30.719 | 1.00 | 24.92 |
| 1910 | CA | ILE | 761 | 22.919 | 61.043 | 29.888 | 1.00 | 27.91 |
| 1911 | C | ILE | 761 | 24.248 | 60.745 | 30.555 | 1.00 | 27.51 |
| 1912 | O | ILE | 761 | 24.799 | 59.664 | 30.369 | 1.00 | 30.01 |
| 1913 | CB | ILE | 761 | 23.140 | 61.825 | 28.556 | 1.00 | 28.45 |
| 1914 | CG2 | ILE | 761 | 24.335 | 61.277 | 27.746 | 1.00 | 99.90 |
| 1915 | CG1 | ILE | 761 | 21.864 | 61.785 | 27.655 | 1.00 | 99.90 |
| 1916 | CD1 | ILE | 761 | 21.527 | 60.456 | 26.954 | 1.00 | 99.90 |
| 1917 | N | PRO | 762 | 24.805 | 61.698 | 31.308 | 1.00 | 27.54 |
| 1918 | CA | PRO | 762 | 26.081 | 61.376 | 31.948 | 1.00 | 27.73 |
| 1919 | C | PRO | 762 | 25.963 | 60.143 | 32.868 | 1.00 | 24.86 |
| 1920 | O | PRO | 762 | 26.847 | 59.293 | 32.895 | 1.00 | 25.75 |
| 1921 | CB | PRO | 762 | 26.399 | 62.656 | 32.715 | 1.00 | 27.68 |
| 1922 | CG | PRO | 762 | 25.760 | 63.728 | 31.833 | 1.00 | 26.00 |
| 1923 | CD | PRO | 762 | 24.403 | 63.078 | 31.631 | 1.00 | 28.16 |
| 1924 | N | LYS | 763 | 24.872 | 60.049 | 33.620 | 1.00 | 23.19 |
| 1925 | CA | LYS | 763 | 24.668 | 58.912 | 34.523 | 1.00 | 24.99 |
| 1926 | C | LYS | 763 | 24.555 | 57.617 | 33.722 | 1.00 | 26.95 |
| 1927 | O | LYS | 763 | 25.189 | 56.609 | 34.046 | 1.00 | 26.77 |
| 1928 | CB | LYS | 763 | 23.391 | 59.124 | 35.346 | 1.00 | 31.71 |
| 1929 | CG | LYS | 763 | 23.098 | 58.039 | 36.368 | 1.00 | 36.39 |
| 1930 | CD | LYS | 763 | 21.730 | 58.277 | 37.013 | 1.00 | 41.59 |
| 1931 | CE | LYS | 763 | 21.668 | 59.627 | 37.724 | 1.00 | 46.46 |
| 1932 | NZ | LYS | 763 | 20.287 | 59.994 | 38.237 | 1.00 | 52.55 |
| 1933 | N | TYR | 764 | 23.747 | 57.644 | 32.667 | 1.00 | 25.62 |
| 1934 | CA | TYR | 764 | 23.577 | 56.459 | 31.820 | 1.00 | 25.44 |
| 1935 | C | TYR | 764 | 24.904 | 56.027 | 31.211 | 1.00 | 28.84 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 1936 | O | TYR | 764 | 25.260 | 54.850 | 31.252 | 1.00 | 23.14 |
| 1937 | CB | TYR | 764 | 22.588 | 56.747 | 30.692 | 1.00 | 25.43 |
| 1938 | CG | TYR | 764 | 21.157 | 57.110 | 31.106 | 1.00 | 99.90 |
| 1939 | CD1 | TYR | 764 | 20.748 | 58.447 | 31.092 | 1.00 | 99.90 |
| 1940 | CD2 | TYR | 764 | 20.258 | 56.118 | 31.507 | 1.00 | 99.90 |
| 1941 | CE1 | TYR | 764 | 19.456 | 58.789 | 31.480 | 1.00 | 99.90 |
| 1942 | CE2 | TYR | 764 | 18.965 | 56.463 | 31.896 | 1.00 | 99.90 |
| 1943 | CZ | TYR | 764 | 18.566 | 57.796 | 31.882 | 1.00 | 99.90 |
| 1944 | OH | TYR | 764 | 17.298 | 58.130 | 32.266 | 1.00 | 99.90 |
| 1945 | N | SER | 765 | 25.633 | 56.971 | 30.624 | 1.00 | 26.45 |
| 1946 | CA | SER | 765 | 26.936 | 56.647 | 30.027 | 1.00 | 29.61 |
| 1947 | C | SER | 765 | 27.932 | 56.082 | 31.028 | 1.00 | 30.39 |
| 1948 | O | SER | 765 | 28.733 | 55.198 | 30.698 | 1.00 | 32.46 |
| 1949 | CB | SER | 765 | 27.545 | 57.887 | 29.360 | 1.00 | 27.19 |
| 1950 | OG | SER | 765 | 27.957 | 58.882 | 30.304 | 1.00 | 99.90 |
| 1951 | N | ASN | 766 | 27.897 | 56.594 | 32.249 | 1.00 | 28.14 |
| 1952 | CA | ASN | 766 | 28.813 | 56.116 | 33.266 | 1.00 | 29.10 |
| 1953 | C | ASN | 766 | 28.409 | 54.720 | 33.734 | 1.00 | 29.03 |
| 1954 | O | ASN | 766 | 29.116 | 54.104 | 34.515 | 1.00 | 32.66 |
| 1955 | CB | ASN | 766 | 28.845 | 57.089 | 34.433 | 1.00 | 25.78 |
| 1956 | CG | ASN | 766 | 29.221 | 58.540 | 34.116 | 1.00 | 99.90 |
| 1957 | OD1 | ASN | 766 | 28.382 | 59.422 | 34.006 | 1.00 | 99.90 |
| 1958 | ND2 | ASN | 766 | 30.480 | 58.839 | 33.935 | 1.00 | 99.90 |
| 1959 | N | GLY | 767 | 27.274 | 54.218 | 33.247 | 1.00 | 30.49 |
| 1960 | CA | GLY | 767 | 26.826 | 52.893 | 33.652 | 1.00 | 30.14 |
| 1961 | C | GLY | 767 | 26.212 | 52.842 | 35.048 | 1.00 | 28.27 |
| 1962 | O | GLY | 767 | 26.277 | 51.815 | 35.724 | 1.00 | 35.23 |
| 1963 | N | ASN | 768 | 25.613 | 53.942 | 35.492 | 1.00 | 27.77 |
| 1964 | CA | ASN | 768 | 25.005 | 53.977 | 36.817 | 1.00 | 31.40 |
| 1965 | C | ASN | 768 | 23.506 | 53.689 | 36.729 | 1.00 | 28.03 |
| 1966 | O | ASN | 768 | 22.691 | 54.330 | 37.391 | 1.00 | 31.74 |
| 1967 | CB | ASN | 768 | 25.266 | 55.335 | 37.472 | 1.00 | 32.66 |
| 1968 | CG | ASN | 768 | 26.730 | 55.763 | 37.620 | 1.00 | 99.90 |
| 1969 | OD1 | ASN | 768 | 27.260 | 56.553 | 36.853 | 1.00 | 99.90 |
| 1970 | ND2 | ASN | 768 | 27.441 | 55.248 | 38.587 | 1.00 | 99.90 |
| 1971 | N | ILE | 769 | 23.172 | 52.725 | 35.879 | 1.00 | 29.55 |
| 1972 | CA | ILE | 769 | 21.802 | 52.273 | 35.653 | 1.00 | 28.30 |
| 1973 | C | ILE | 769 | 21.875 | 50.778 | 35.406 | 1.00 | 31.38 |
| 1974 | O | ILE | 769 | 22.944 | 50.244 | 35.111 | 1.00 | 28.00 |
| 1975 | CB | ILE | 769 | 21.151 | 52.942 | 34.422 | 1.00 | 27.98 |
| 1976 | CG2 | ILE | 769 | 19.658 | 52.531 | 34.229 | 1.00 | 99.90 |
| 1977 | CG1 | ILE | 769 | 21.229 | 54.503 | 34.411 | 1.00 | 99.90 |
| 1978 | CD1 | ILE | 769 | 20.887 | 55.185 | 33.070 | 1.00 | 99.90 |
| 1979 | N | LYS | 770 | 20.731 | 50.112 | 35.511 | 1.00 | 28.65 |
| 1980 | CA | LYS | 770 | 20.657 | 48.673 | 35.344 | 1.00 | 27.13 |
| 1981 | C | LYS | 770 | 19.961 | 48.263 | 34.051 | 1.00 | 27.33 |
| 1982 | O | LYS | 770 | 18.737 | 48.229 | 33.971 | 1.00 | 26.71 |
| 1983 | CB | LYS | 770 | 19.922 | 48.079 | 36.543 | 1.00 | 30.31 |
| 1984 | CG | LYS | 770 | 19.641 | 46.598 | 36.440 | 1.00 | 36.48 |
| 1985 | CD | LYS | 770 | 18.845 | 46.130 | 37.649 | 1.00 | 42.65 |
| 1986 | CE | LYS | 770 | 18.386 | 44.692 | 37.468 | 1.00 | 45.66 |
| 1987 | NZ | LYS | 770 | 19.510 | 43.707 | 37.195 | 1.00 | 41.46 |
| 1988 | N | LYS | 771 | 20.743 | 47.945 | 33.013 | 1.00 | 29.35 |
| 1989 | CA | LYS | 771 | 20.153 | 47.543 | 31.738 | 1.00 | 29.76 |
| 1990 | C | LYS | 771 | 19.501 | 46.177 | 31.940 | 1.00 | 32.65 |
| 1991 | O | LYS | 771 | 20.108 | 45.300 | 32.554 | 1.00 | 31.57 |
| 1992 | CB | LYS | 771 | 21.372 | 47.462 | 30.817 | 1.00 | 32.15 |
| 1993 | CG | LYS | 771 | 21.013 | 47.119 | 29.349 | 1.00 | 99.90 |
| 1994 | CD | LYS | 771 | 22.214 | 46.965 | 28.412 | 1.00 | 99.90 |
| 1995 | CE | LYS | 771 | 21.719 | 46.557 | 27.018 | 1.00 | 99.90 |
| 1996 | NZ | LYS | 771 | 22.849 | 46.576 | 26.072 | 1.00 | 99.90 |
| 1997 | N | LEU | 772 | 18.269 | 45.986 | 31.471 | 1.00 | 26.08 |
| 1998 | CA | LEU | 772 | 17.643 | 44.678 | 31.634 | 1.00 | 28.80 |
| 1999 | C | LEU | 772 | 17.957 | 43.890 | 30.386 | 1.00 | 32.70 |
| 2000 | O | LEU | 772 | 17.814 | 44.396 | 29.272 | 1.00 | 32.54 |
| 2001 | CB | LEU | 772 | 16.125 | 44.804 | 31.825 | 1.00 | 28.21 |
| 2002 | CG | LEU | 772 | 15.741 | 45.638 | 33.053 | 1.00 | 27.44 |
| 2003 | CD1 | LEU | 772 | 14.223 | 45.661 | 33.216 | 1.00 | 25.95 |
| 2004 | CD2 | LEU | 772 | 16.400 | 45.046 | 34.305 | 1.00 | 28.60 |
| 2005 | N | LEU | 773 | 18.403 | 42.656 | 30.572 | 1.00 | 29.11 |
| 2006 | CA | LEU | 773 | 18.768 | 41.800 | 29.447 | 1.00 | 32.04 |
| 2007 | C | LEU | 773 | 17.933 | 40.528 | 29.413 | 1.00 | 33.98 |
| 2008 | O | LEU | 773 | 17.604 | 39.979 | 30.462 | 1.00 | 35.14 |

TABLE 5-continued

ATOMIC COORDINATES FOR THE GR/
SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 2009 | CB | LEU | 773 | 20.253 | 41.426 | 29.552 | 1.00 | 30.80 |
| 2010 | CG | LEU | 773 | 21.245 | 42.595 | 29.527 | 1.00 | 41.73 |
| 2011 | CD1 | LEU | 773 | 22.654 | 42.099 | 29.847 | 1.00 | 37.07 |
| 2012 | CD2 | LEU | 773 | 21.198 | 43.263 | 28.165 | 1.00 | 38.20 |
| 2013 | N | PHE | 774 | 17.580 | 40.075 | 28.211 | 1.00 | 30.93 |
| 2014 | CA | PHE | 774 | 16.815 | 38.838 | 28.065 | 1.00 | 36.94 |
| 2015 | C | PHE | 774 | 17.728 | 37.626 | 28.056 | 1.00 | 37.82 |
| 2016 | O | PHE | 774 | 17.306 | 36.518 | 28.390 | 1.00 | 40.73 |
| 2017 | CB | PHE | 774 | 16.011 | 38.820 | 26.771 | 1.00 | 33.98 |
| 2018 | CG | PHE | 774 | 14.787 | 39.666 | 26.818 | 1.00 | 31.86 |
| 2019 | CD1 | PHE | 774 | 13.620 | 39.164 | 27.384 | 1.00 | 27.98 |
| 2020 | CD2 | PHE | 774 | 14.803 | 40.967 | 26.346 | 1.00 | 29.84 |
| 2021 | CE1 | PHE | 774 | 12.488 | 39.955 | 27.478 | 1.00 | 34.01 |
| 2022 | CE2 | PHE | 774 | 13.668 | 41.769 | 26.435 | 1.00 | 31.12 |
| 2023 | CZ | PHE | 774 | 12.514 | 41.264 | 27.002 | 1.00 | 31.58 |
| 2024 | N | HIS | 775 | 18.975 | 37.839 | 27.659 | 1.00 | 39.64 |
| 2025 | CA | HIS | 775 | 19.937 | 36.755 | 27.605 | 1.00 | 43.59 |
| 2026 | C | HIS | 775 | 21.178 | 37.074 | 28.410 | 1.00 | 45.74 |
| 2027 | O | HIS | 775 | 21.780 | 38.133 | 28.258 | 1.00 | 48.72 |
| 2028 | CB | HIS | 775 | 20.286 | 36.470 | 26.149 | 1.00 | 41.38 |
| 2029 | CG | HIS | 775 | 19.079 | 36.205 | 25.308 | 1.00 | 44.29 |
| 2030 | ND1 | HIS | 775 | 18.211 | 35.169 | 25.572 | 1.00 | 49.69 |
| 2031 | CD2 | HIS | 775 | 18.541 | 36.892 | 24.274 | 1.00 | 48.24 |
| 2032 | CE1 | HIS | 775 | 17.187 | 35.231 | 24.738 | 1.00 | 50.45 |
| 2033 | NE2 | HIS | 775 | 17.364 | 36.268 | 23.940 | 1.00 | 49.57 |
| 2034 | N | GLN | 776 | 21.531 | 36.142 | 29.288 | 1.00 | 50.39 |
| 2035 | CA | GLN | 776 | 22.698 | 36.254 | 30.150 | 1.00 | 56.63 |
| 2036 | C | GLN | 776 | 23.960 | 36.339 | 29.302 | 1.00 | 53.01 |
| 2037 | O | GLN | 776 | 23.958 | 35.647 | 28.265 | 1.00 | 56.94 |
| 2038 | CB | GLN | 776 | 22.748 | 35.026 | 31.061 | 1.00 | 57.98 |
| 2039 | CG | GLN | 776 | 22.461 | 33.738 | 30.299 | 1.00 | 61.12 |
| 2040 | CD | GLN | 776 | 22.409 | 32.412 | 31.067 | 1.00 | 99.90 |
| 2041 | OE1 | GLN | 776 | 22.143 | 31.364 | 30.499 | 1.00 | 99.90 |
| 2042 | NE2 | GLN | 776 | 22.627 | 32.394 | 32.357 | 1.00 | 99.90 |
| 2043 | CB | GLU | 685 | 16.805 | 65.125 | 37.380 | 1.00 | 63.65 |
| 2044 | CG | GLU | 685 | 16.240 | 65.106 | 38.791 | 1.00 | 63.87 |
| 2045 | CD | GLU | 685 | 15.337 | 63.914 | 39.036 | 1.00 | 64.23 |
| 2046 | OE1 | GLU | 685 | 14.222 | 63.893 | 38.474 | 1.00 | 64.28 |
| 2047 | OE2 | GLU | 685 | 15.741 | 62.998 | 39.783 | 1.00 | 64.53 |
| 2048 | C | GLU | 685 | 16.202 | 67.392 | 36.510 | 1.00 | 61.94 |
| 2049 | O | GLU | 685 | 16.230 | 67.976 | 35.426 | 1.00 | 62.27 |
| 2050 | N | GLU | 685 | 18.175 | 67.207 | 37.988 | 1.00 | 62.90 |
| 2051 | CA | GLU | 685 | 17.353 | 66.483 | 36.931 | 1.00 | 62.73 |
| 2052 | N | ARG | 686 | 15.189 | 67.501 | 37.368 | 1.00 | 60.58 |
| 2053 | CA | ARG | 686 | 14.026 | 68.343 | 37.098 | 1.00 | 59.13 |
| 2054 | CB | ARG | 686 | 14.484 | 69.737 | 36.657 | 1.00 | 60.07 |
| 2055 | CG | ARG | 686 | 13.371 | 70.752 | 36.441 | 1.00 | 61.27 |
| 2056 | CD | ARG | 686 | 12.980 | 71.452 | 37.735 | 1.00 | 62.16 |
| 2057 | NE | ARG | 686 | 12.286 | 72.710 | 37.474 | 1.00 | 63.43 |
| 2058 | CZ | ARG | 686 | 11.075 | 72.803 | 36.934 | 1.00 | 64.44 |
| 2059 | NH1 | ARG | 686 | 10.244 | 71.724 | 36.777 | 1.00 | 64.89 |
| 2060 | NH2 | ARG | 686 | 10.622 | 74.033 | 36.555 | 1.00 | 65.34 |
| 2061 | C | ARG | 686 | 13.106 | 67.744 | 36.030 | 1.00 | 57.39 |
| 2062 | O | ARG | 686 | 12.108 | 67.097 | 36.352 | 1.00 | 58.48 |
| 2063 | N | HIS | 687 | 13.452 | 67.962 | 34.764 | 1.00 | 54.71 |
| 2064 | CA | HIS | 687 | 12.666 | 67.470 | 33.632 | 1.00 | 51.16 |
| 2065 | CB | HIS | 687 | 12.415 | 65.962 | 33.752 | 1.00 | 51.72 |
| 2066 | CG | HIS | 687 | 13.660 | 65.132 | 33.685 | 1.00 | 51.47 |
| 2067 | CD2 | HIS | 687 | 14.122 | 64.297 | 32.725 | 1.00 | 51.61 |
| 2068 | ND1 | HIS | 687 | 14.601 | 65.118 | 34.691 | 1.00 | 52.04 |
| 2069 | CE1 | HIS | 687 | 15.590 | 64.308 | 34.354 | 1.00 | 51.83 |
| 2070 | NE2 | HIS | 687 | 15.324 | 63.798 | 33.166 | 1.00 | 51.34 |
| 2071 | C | HIS | 687 | 11.333 | 68.204 | 33.547 | 1.00 | 48.80 |
| 2072 | O | HIS | 687 | 10.272 | 67.584 | 33.498 | 1.00 | 48.44 |
| 2073 | N | ALA | 688 | 11.400 | 69.531 | 33.519 | 1.00 | 45.79 |
| 2074 | CA | ALA | 688 | 10.208 | 70.370 | 33.454 | 1.00 | 43.75 |
| 2075 | CB | ALA | 688 | 10.613 | 71.841 | 33.459 | 1.00 | 43.70 |
| 2076 | C | ALA | 688 | 9.318 | 70.085 | 32.246 | 1.00 | 41.94 |
| 2077 | O | ALA | 688 | 8.143 | 69.755 | 32.400 | 1.00 | 40.94 |
| 2078 | N | ILE | 689 | 9.879 | 70.215 | 31.048 | 1.00 | 40.75 |
| 2079 | CA | ILE | 689 | 9.121 | 69.990 | 29.823 | 1.00 | 39.42 |
| 2080 | CB | ILE | 689 | 10.010 | 70.192 | 28.579 | 1.00 | 39.12 |
| 2081 | CG2 | ILE | 689 | 9.240 | 69.818 | 27.316 | 1.00 | 38.63 |

TABLE 5-continued

ATOMIC COORDINATES FOR THE GR/ SRC-1 MODEL USED IN MOLECULAR REPLACEMENT

| ATOM | ATOM TYPE | RESIDUE | PROTEIN # | # | X | Y | Z | OCC |
|---|---|---|---|---|---|---|---|---|
| 2082 | CG1 | ILE | 689 | 10.466 | 71.652 | 28.513 | 1.00 | 38.90 |
| 2083 | CD1 | ILE | 689 | 11.342 | 71.978 | 27.322 | 1.00 | 39.20 |
| 2084 | C | ILE | 689 | 8.483 | 68.606 | 29.772 | 1.00 | 38.83 |
| 2085 | O | ILE | 689 | 7.292 | 68.474 | 29.487 | 1.00 | 37.60 |
| 2086 | N | LEU | 690 | 9.276 | 67.579 | 30.053 | 1.00 | 38.40 |
| 2087 | CA | LEU | 690 | 8.774 | 66.213 | 30.040 | 1.00 | 38.63 |
| 2088 | CB | LEU | 690 | 9.893 | 65.247 | 30.435 | 1.00 | 39.36 |
| 2089 | CG | LEU | 690 | 9.858 | 63.847 | 29.820 | 1.00 | 40.30 |
| 2090 | CD1 | LEU | 690 | 11.172 | 63.130 | 30.105 | 1.00 | 39.81 |
| 2091 | CD2 | LEU | 690 | 8.682 | 63.064 | 30.374 | 1.00 | 41.50 |
| 2092 | C | LEU | 690 | 7.602 | 66.111 | 31.017 | 1.00 | 39.78 |
| 2093 | O | LEU | 690 | 6.543 | 65.578 | 30.679 | 1.00 | 38.83 |
| 2094 | N | HIS | 691 | 7.789 | 66.633 | 32.227 | 1.00 | 40.27 |
| 2095 | CA | HIS | 691 | 6.726 | 66.614 | 33.229 | 1.00 | 41.72 |
| 2096 | CB | HIS | 691 | 7.181 | 67.316 | 34.509 | 1.00 | 43.49 |
| 2097 | CG | HIS | 691 | 7.873 | 66.413 | 35.480 | 1.00 | 45.34 |
| 2098 | CD2 | HIS | 691 | 9.155 | 66.387 | 35.917 | 1.00 | 46.24 |
| 2099 | ND1 | HIS | 691 | 7.226 | 65.386 | 36.131 | 1.00 | 46.60 |
| 2100 | CE1 | HIS | 691 | 8.079 | 64.767 | 36.928 | 1.00 | 46.83 |
| 2101 | NE2 | HIS | 691 | 9.256 | 65.355 | 36.817 | 1.00 | 47.22 |
| 2102 | C | HIS | 691 | 5.487 | 67.312 | 32.681 | 1.00 | 41.36 |
| 2103 | O | HIS | 691 | 4.372 | 66.800 | 32.795 | 1.00 | 41.77 |
| 2104 | N | ARG | 692 | 5.692 | 68.482 | 32.085 | 1.00 | 40.51 |
| 2105 | CA | ARG | 692 | 4.592 | 69.250 | 31.511 | 1.00 | 40.58 |
| 2106 | CB | ARG | 692 | 5.131 | 70.500 | 30.815 | 1.00 | 41.97 |
| 2107 | CG | ARG | 692 | 4.061 | 71.442 | 30.275 | 1.00 | 44.31 |
| 2108 | CD | ARG | 692 | 4.690 | 72.501 | 29.383 | 1.00 | 46.39 |
| 2109 | NE | ARG | 692 | 5.286 | 71.900 | 28.191 | 1.00 | 48.87 |
| 2110 | CZ | ARG | 692 | 6.094 | 72.537 | 27.349 | 1.00 | 49.52 |
| 2111 | NH1 | ARG | 692 | 6.586 | 73.791 | 27.593 | 1.00 | 50.67 |
| 2112 | NH2 | ARG | 692 | 6.422 | 71.914 | 26.185 | 1.00 | 49.63 |
| 2113 | C | ARG | 692 | 3.823 | 68.392 | 30.508 | 1.00 | 39.77 |
| 2114 | O | ARG | 692 | 2.612 | 68.204 | 30.642 | 1.00 | 38.70 |
| 2115 | N | LEU | 693 | 4.532 | 67.870 | 29.509 | 1.00 | 38.99 |
| 2116 | CA | LEU | 693 | 3.917 | 67.031 | 28.482 | 1.00 | 39.44 |
| 2117 | CB | LEU | 693 | 4.984 | 66.418 | 27.567 | 1.00 | 38.36 |
| 2118 | CG | LEU | 693 | 5.747 | 67.337 | 26.608 | 1.00 | 38.71 |
| 2119 | CD1 | LEU | 693 | 6.769 | 66.517 | 25.841 | 1.00 | 37.17 |
| 2120 | CD2 | LEU | 693 | 4.781 | 68.014 | 25.646 | 1.00 | 37.74 |
| 2121 | C | LEU | 693 | 3.082 | 65.913 | 29.088 | 1.00 | 40.12 |
| 2122 | O | LEU | 693 | 1.998 | 65.599 | 28.598 | 1.00 | 40.20 |
| 2123 | N | LEU | 694 | 3.591 | 65.310 | 30.155 | 1.00 | 41.30 |
| 2124 | CA | LEU | 694 | 2.880 | 64.224 | 30.814 | 1.00 | 43.03 |
| 2125 | CB | LEU | 694 | 3.814 | 63.511 | 31.793 | 1.00 | 41.27 |
| 2126 | CG | LEU | 694 | 4.944 | 62.707 | 31.142 | 1.00 | 40.09 |
| 2127 | CD1 | LEU | 694 | 5.933 | 62.249 | 32.194 | 1.00 | 39.04 |
| 2128 | CD2 | LEU | 694 | 4.351 | 61.515 | 30.400 | 1.00 | 39.24 |
| 2129 | C | LEU | 694 | 1.634 | 64.710 | 31.547 | 1.00 | 45.64 |
| 2130 | O | LEU | 694 | 0.736 | 63.920 | 31.838 | 1.00 | 44.78 |
| 2131 | N | GLN | 695 | 1.575 | 66.007 | 31.832 | 1.00 | 49.29 |
| 2132 | CA | GLN | 695 | 0.436 | 66.580 | 32.546 | 1.00 | 53.51 |
| 2133 | CB | GLN | 695 | 0.780 | 67.978 | 33.075 | 1.00 | 53.94 |
| 2134 | CG | GLN | 695 | 2.068 | 68.066 | 33.890 | 1.00 | 54.96 |
| 2135 | CD | GLN | 695 | 2.065 | 67.191 | 35.133 | 1.00 | 55.61 |
| 2136 | OE1 | GLN | 695 | 3.023 | 67.202 | 35.911 | 1.00 | 55.52 |
| 2137 | NE2 | GLN | 695 | 0.874 | 66.592 | 35.592 | 1.00 | 55.62 |
| 2138 | C | GLN | 695 | −0.834 | 66.666 | 31.699 | 1.00 | 55.94 |
| 2139 | O | GLN | 695 | −1.931 | 66.813 | 32.236 | 1.00 | 55.76 |
| 2140 | N | GLU | 696 | −0.686 | 66.579 | 30.380 | 1.00 | 58.97 |
| 2141 | CA | GLU | 696 | −1.829 | 66.652 | 29.470 | 1.00 | 62.61 |
| 2142 | CB | GLU | 696 | −2.620 | 67.945 | 29.711 | 1.00 | 63.02 |
| 2143 | CG | GLU | 696 | −1.785 | 69.190 | 30.082 | 1.00 | 63.82 |
| 2144 | CD | GLU | 696 | −0.758 | 69.598 | 29.037 | 1.00 | 64.13 |
| 2145 | OE1 | GLU | 696 | −1.131 | 69.774 | 27.856 | 1.00 | 64.51 |
| 2146 | OE2 | GLU | 696 | 0.422 | 69.758 | 29.402 | 1.00 | 64.16 |
| 2147 | C | GLU | 696 | −1.374 | 66.630 | 28.019 | 1.00 | 64.98 |
| 2148 | O | GLU | 696 | −2.107 | 66.233 | 27.112 | 1.00 | 65.58 |
| 2149 | N | GLY | 697 | −0.140 | 67.073 | 27.836 | 1.00 | 67.35 |
| 2150 | CA | GLY | 697 | 0.479 | 67.171 | 26.535 | 1.00 | 70.03 |
| 2151 | C | GLY | 697 | 1.252 | 68.446 | 26.701 | 1.00 | 71.80 |
| 2152 | O | GLY | 697 | 1.323 | 69.262 | 25.756 | 1.00 | 71.76 |
| 2153 | OXT | GLY | 697 | 1.783 | 68.647 | 27.817 | 1.00 | 71.76 |

It will be understood that various details of the invention may be changed without departing from the scope of the invention. Furthermore, the foregoing description is for the purpose of illustration only, and not for the purpose of limitation—the invention being defined by the claims.

What is claimed is:

1. An isolated GR polypeptide of SEQ ID No. 8, having one or more mutations comprising a substitution of a hydrophobic amino acid residue by a hydrophilic amino acid residue in a ligand binding domain, wherein the mutation is at a residue selected from the group consisting of V552, W557, F602, L636, Y648, W712, L741, L535, V538, C638, M691, V702, Y648, Y660, L685, M691, V702, W712, L733, Y764 and combinations thereof.

2. The isolated polypeptide of claim 1, wherein the mutation is selected from the group consisting of V552K, W557S, F602S, F602D, F602E, F602Y, F602T, F602N, F602C, L636E, Y648Q, W712S, L741R, L535T, V538S, C638S, M691T, V702T, W712T and combinations thereof.

3. An isolated GR LBD polypeptide of SEQ ID No. 10, having a F602S mutation or a F602D mutation.

4. The isolated polypeptide of claim 3, wherein the polypeptide has the sequence of SEQ ID NO:12 and SEQ ID NO: 14.

* * * * *

SEQUENCE LISTING

```
<160> NUMBER OF SEQ ID NOS: 41

<210> SEQ ID NO 1
<211> LENGTH: 2334
<212> TYPE: DNA
<213> ORGANISM: Homo sapiens
<220> FEATURE:
<221> NAME/KEY: CDS
<222> LOCATION: (1)..(2334)
<223> OTHER INFORMATION:

<400> SEQUENCE: 1

atg gac tcc aaa gaa tca tta act cct ggt aga gaa gaa aac ccc agc       48
Met Asp Ser Lys Glu Ser Leu Thr Pro Gly Arg Glu Glu Asn Pro Ser
1               5                   10                  15

agt gtg ctt gct cag gag agg gga gat gtg atg gac ttc tat aaa acc       96
Ser Val Leu Ala Gln Glu Arg Gly Asp Val Met Asp Phe Tyr Lys Thr
            20                  25                  30

cta aga gga gga gct act gtg aag gtt tct gcg tct tca ccc tca ctg      144
Leu Arg Gly Gly Ala Thr Val Lys Val Ser Ala Ser Ser Pro Ser Leu
        35                  40                  45

gct gtc gct tct caa tca gac tcc aag cag cga aga ctt ttg gtt gat      192
Ala Val Ala Ser Gln Ser Asp Ser Lys Gln Arg Arg Leu Leu Val Asp
    50                  55                  60

ttt cca aaa ggc tca gta agc aat gcg cag cag cca gat ctg tcc aaa      240
Phe Pro Lys Gly Ser Val Ser Asn Ala Gln Gln Pro Asp Leu Ser Lys
65                  70                  75                  80

gca gtt tca ctc tca atg gga ctg tat atg gga gag aca gaa aca aaa      288
Ala Val Ser Leu Ser Met Gly Leu Tyr Met Gly Glu Thr Glu Thr Lys
                85                  90                  95

gtg atg gga aat gac ctg gga ttc cca cag cag ggc caa atc agc ctt      336
Val Met Gly Asn Asp Leu Gly Phe Pro Gln Gln Gly Gln Ile Ser Leu
            100                 105                 110

tcc tcg ggg gaa aca gac tta aag ctt ttg gaa gaa agc att gca aac      384
Ser Ser Gly Glu Thr Asp Leu Lys Leu Leu Glu Glu Ser Ile Ala Asn
        115                 120                 125

ctc aat agg tcg acc agt gtt cca gag aac ccc aag agt tca gca tcc      432
Leu Asn Arg Ser Thr Ser Val Pro Glu Asn Pro Lys Ser Ser Ala Ser
    130                 135                 140

act gct gtg tct gct gcc ccc aca gag aag gag ttt cca aaa act cac      480
Thr Ala Val Ser Ala Ala Pro Thr Glu Lys Glu Phe Pro Lys Thr His
145                 150                 155                 160

tct gat gta tct tca gaa cag caa cat ttg aag ggc cag act ggc acc      528
Ser Asp Val Ser Ser Glu Gln Gln His Leu Lys Gly Gln Thr Gly Thr
                165                 170                 175

aac ggt ggc aat gtg aaa ttg tat acc aca gac caa agc acc ttt gac      576
Asn Gly Gly Asn Val Lys Leu Tyr Thr Thr Asp Gln Ser Thr Phe Asp
            180                 185                 190

att ttg cag gat ttg gag ttt tct tct ggg tcc cca ggt aaa gag acg      624
Ile Leu Gln Asp Leu Glu Phe Ser Ser Gly Ser Pro Gly Lys Glu Thr
        195                 200                 205

aat gag agt cct tgg aga tca gac ctg ttg ata gat gaa aac tgt ttg      672
Asn Glu Ser Pro Trp Arg Ser Asp Leu Leu Ile Asp Glu Asn Cys Leu
    210                 215                 220
```

-continued

```
ctt tct cct ctg gcg gga gaa gac gat tca ttc ctt ttg gaa gga aac      720
Leu Ser Pro Leu Ala Gly Glu Asp Asp Ser Phe Leu Leu Glu Gly Asn
225                 230                 235                 240

tcg aat gag gac tgc aag cct ctc att tta ccg gac act aaa ccc aaa      768
Ser Asn Glu Asp Cys Lys Pro Leu Ile Leu Pro Asp Thr Lys Pro Lys
                245                 250                 255

att aag gat aat gga gat ctg gtt ttg tca agc ccc agt aat gta aca      816
Ile Lys Asp Asn Gly Asp Leu Val Leu Ser Ser Pro Ser Asn Val Thr
            260                 265                 270

ctg ccc caa gtg aaa aca gaa aaa gaa gat ttc atc gaa ctc tgc acc      864
Leu Pro Gln Val Lys Thr Glu Lys Glu Asp Phe Ile Glu Leu Cys Thr
        275                 280                 285

cct ggg gta att aag caa gag aaa ctg ggc aca gtt tac tgt cag gca      912
Pro Gly Val Ile Lys Gln Glu Lys Leu Gly Thr Val Tyr Cys Gln Ala
    290                 295                 300

agc ttt cct gga gca aat ata att ggt aat aaa atg tct gcc att tct      960
Ser Phe Pro Gly Ala Asn Ile Ile Gly Asn Lys Met Ser Ala Ile Ser
305                 310                 315                 320

gtt cat ggt gtg agt acc tct gga gga cag atg tac cac tat gac atg     1008
Val His Gly Val Ser Thr Ser Gly Gly Gln Met Tyr His Tyr Asp Met
                325                 330                 335

aat aca gca tcc ctt tct caa cag cag gat cag aag cct att ttt aat     1056
Asn Thr Ala Ser Leu Ser Gln Gln Gln Asp Gln Lys Pro Ile Phe Asn
            340                 345                 350

gtc att cca cca att ccc gtt ggt tcc gaa aat tgg aat agg tgc caa     1104
Val Ile Pro Pro Ile Pro Val Gly Ser Glu Asn Trp Asn Arg Cys Gln
        355                 360                 365

gga tct gga gat gac aac ttg act tct ctg ggg act ctg aac ttc cct     1152
Gly Ser Gly Asp Asp Asn Leu Thr Ser Leu Gly Thr Leu Asn Phe Pro
    370                 375                 380

ggt cga aca gtt ttt tct aat ggc tat tca agc ccc agc atg aga cca     1200
Gly Arg Thr Val Phe Ser Asn Gly Tyr Ser Ser Pro Ser Met Arg Pro
385                 390                 395                 400

gat gta agc tct cct cca tcc agc tcc tca aca gca aca aca gga cca     1248
Asp Val Ser Ser Pro Pro Ser Ser Ser Ser Thr Ala Thr Thr Gly Pro
                405                 410                 415

cct ccc aaa ctc tgc ctg gtg tgc tct gat gaa gct tca gga tgt cat     1296
Pro Pro Lys Leu Cys Leu Val Cys Ser Asp Glu Ala Ser Gly Cys His
            420                 425                 430

tat gga gtc tta act tgt gga agc tgt aaa gtt ttc ttc aaa aga gca     1344
Tyr Gly Val Leu Thr Cys Gly Ser Cys Lys Val Phe Phe Lys Arg Ala
        435                 440                 445

gtg gaa gga cag cac aat tac cta tgt gct gga agg aat gat tgc atc     1392
Val Glu Gly Gln His Asn Tyr Leu Cys Ala Gly Arg Asn Asp Cys Ile
    450                 455                 460

atc gat aaa att cga aga aaa aac tgc cca gca tgc cgc tat cga aaa     1440
Ile Asp Lys Ile Arg Arg Lys Asn Cys Pro Ala Cys Arg Tyr Arg Lys
465                 470                 475                 480

tgt ctt cag gct gga atg aac ctg gaa gct cga aaa aca aag aaa aaa     1488
Cys Leu Gln Ala Gly Met Asn Leu Glu Ala Arg Lys Thr Lys Lys Lys
                485                 490                 495

ata aaa gga att cag cag gcc act aca gga gtc tca caa gaa acc tct     1536
Ile Lys Gly Ile Gln Gln Ala Thr Thr Gly Val Ser Gln Glu Thr Ser
            500                 505                 510

gaa aat cct ggt aac aaa aca ata gtt cct gca acg tta cca caa ctc     1584
Glu Asn Pro Gly Asn Lys Thr Ile Val Pro Ala Thr Leu Pro Gln Leu
        515                 520                 525

acc cct acc ctg gtg tca ctg ttg gag gtt att gaa cct gaa gtg tta     1632
Thr Pro Thr Leu Val Ser Leu Leu Glu Val Ile Glu Pro Glu Val Leu
    530                 535                 540
```

-continued

```
tat gca gga tat gat agc tct gtt cca gac tca act tgg agg atc atg     1680
Tyr Ala Gly Tyr Asp Ser Ser Val Pro Asp Ser Thr Trp Arg Ile Met
545                 550                 555                 560

act acg ctc aac atg tta gga ggg cgg caa gtg att gca gca gtg aaa     1728
Thr Thr Leu Asn Met Leu Gly Gly Arg Gln Val Ile Ala Ala Val Lys
                565                 570                 575

tgg gca aag gca ata cca ggt ttc agg aac tta cac ctg gat gac caa     1776
Trp Ala Lys Ala Ile Pro Gly Phe Arg Asn Leu His Leu Asp Asp Gln
            580                 585                 590

atg acc cta ctg cag tac tcc tgg atg ttt ctt atg gca ttt gct ctg     1824
Met Thr Leu Leu Gln Tyr Ser Trp Met Phe Leu Met Ala Phe Ala Leu
        595                 600                 605

ggg tgg aga tca tat aga caa tca agt gca aac ctg ctg tgt ttt gct     1872
Gly Trp Arg Ser Tyr Arg Gln Ser Ser Ala Asn Leu Leu Cys Phe Ala
    610                 615                 620

cct gat ctg att att aat gag cag aga atg act cta ccc tgc atg tac     1920
Pro Asp Leu Ile Ile Asn Glu Gln Arg Met Thr Leu Pro Cys Met Tyr
625                 630                 635                 640

gac caa tgt aaa cac atg ctg tat gtt tcc tct gag tta cac agg ctt     1968
Asp Gln Cys Lys His Met Leu Tyr Val Ser Ser Glu Leu His Arg Leu
                645                 650                 655

cag gta tct tat gaa gag tat ctc tgt atg aaa acc tta ctg ctt ctc     2016
Gln Val Ser Tyr Glu Glu Tyr Leu Cys Met Lys Thr Leu Leu Leu Leu
            660                 665                 670

tct tca gtt cct aag gac ggt ctg aag agc caa gag cta ttt gat gaa     2064
Ser Ser Val Pro Lys Asp Gly Leu Lys Ser Gln Glu Leu Phe Asp Glu
        675                 680                 685

att aga atg acc tac atc aaa gag cta gga aaa gcc att gtc aag agg     2112
Ile Arg Met Thr Tyr Ile Lys Glu Leu Gly Lys Ala Ile Val Lys Arg
    690                 695                 700

gaa gga aac tcc agc cag aac tgg cag cgg ttt tat caa ctg aca aaa     2160
Glu Gly Asn Ser Ser Gln Asn Trp Gln Arg Phe Tyr Gln Leu Thr Lys
705                 710                 715                 720

ctc ttg gat tct atg cat gaa gtg gtt gaa aat ctc ctt aac tat tgc     2208
Leu Leu Asp Ser Met His Glu Val Val Glu Asn Leu Leu Asn Tyr Cys
                725                 730                 735

ttc caa aca ttt ttg gat aag acc atg agt att gaa ttc ccc gag atg     2256
Phe Gln Thr Phe Leu Asp Lys Thr Met Ser Ile Glu Phe Pro Glu Met
            740                 745                 750

tta gct gaa atc atc acc aat cag ata cca aaa tat tca aat gga aat     2304
Leu Ala Glu Ile Ile Thr Asn Gln Ile Pro Lys Tyr Ser Asn Gly Asn
        755                 760                 765

atc aaa aaa ctt ctg ttt cat caa aag tga                             2334
Ile Lys Lys Leu Leu Phe His Gln Lys
    770                 775


<210> SEQ ID NO 2
<211> LENGTH: 777
<212> TYPE: PRT
<213> ORGANISM: Homo sapiens

<400> SEQUENCE: 2

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
```

-continued

```
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480
```

-continued

```
Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
    770                 775
```

<210> SEQ ID NO 3
<211> LENGTH: 2334
<212> TYPE: DNA
<213> ORGANISM: Homo sapiens
<220> FEATURE:
<221> NAME/KEY: CDS
<222> LOCATION: (1)..(2334)
<223> OTHER INFORMATION:

<400> SEQUENCE: 3

```
atg gac tcc aaa gaa tca tta act cct ggt aga gaa gaa aac ccc agc       48
Met Asp Ser Lys Glu Ser Leu Thr Pro Gly Arg Glu Glu Asn Pro Ser
1               5                   10                  15

agt gtg ctt gct cag gag agg gga gat gtg atg gac ttc tat aaa acc       96
Ser Val Leu Ala Gln Glu Arg Gly Asp Val Met Asp Phe Tyr Lys Thr
            20                  25                  30

cta aga gga gga gct act gtg aag gtt tct gcg tct tca ccc tca ctg      144
```

-continued

```
Leu Arg Gly Gly Ala Thr Val Lys Val Ser Ala Ser Ser Pro Ser Leu
        35                  40                  45

gct gtc gct tct caa tca gac tcc aag cag cga aga ctt ttg gtt gat      192
Ala Val Ala Ser Gln Ser Asp Ser Lys Gln Arg Arg Leu Leu Val Asp
    50                  55                  60

ttt cca aaa ggc tca gta agc aat gcg cag cag cca gat ctg tcc aaa      240
Phe Pro Lys Gly Ser Val Ser Asn Ala Gln Gln Pro Asp Leu Ser Lys
65                  70                  75                  80

gca gtt tca ctc tca atg gga ctg tat atg gga gag aca gaa aca aaa      288
Ala Val Ser Leu Ser Met Gly Leu Tyr Met Gly Glu Thr Glu Thr Lys
                85                  90                  95

gtg atg gga aat gac ctg gga ttc cca cag cag ggc caa atc agc ctt      336
Val Met Gly Asn Asp Leu Gly Phe Pro Gln Gln Gly Gln Ile Ser Leu
            100                 105                 110

tcc tcg ggg gaa aca gac tta aag ctt ttg gaa gaa agc att gca aac      384
Ser Ser Gly Glu Thr Asp Leu Lys Leu Leu Glu Glu Ser Ile Ala Asn
        115                 120                 125

ctc aat agg tcg acc agt gtt cca gag aac ccc aag agt tca gca tcc      432
Leu Asn Arg Ser Thr Ser Val Pro Glu Asn Pro Lys Ser Ser Ala Ser
    130                 135                 140

act gct gtg tct gct gcc ccc aca gag aag gag ttt cca aaa act cac      480
Thr Ala Val Ser Ala Ala Pro Thr Glu Lys Glu Phe Pro Lys Thr His
145                 150                 155                 160

tct gat gta tct tca gaa cag caa cat ttg aag ggc cag act ggc acc      528
Ser Asp Val Ser Ser Glu Gln Gln His Leu Lys Gly Gln Thr Gly Thr
                165                 170                 175

aac ggt ggc aat gtg aaa ttg tat acc aca gac caa agc acc ttt gac      576
Asn Gly Gly Asn Val Lys Leu Tyr Thr Thr Asp Gln Ser Thr Phe Asp
            180                 185                 190

att ttg cag gat ttg gag ttt tct tct ggg tcc cca ggt aaa gag acg      624
Ile Leu Gln Asp Leu Glu Phe Ser Ser Gly Ser Pro Gly Lys Glu Thr
        195                 200                 205

aat gag agt cct tgg aga tca gac ctg ttg ata gat gaa aac tgt ttg      672
Asn Glu Ser Pro Trp Arg Ser Asp Leu Leu Ile Asp Glu Asn Cys Leu
    210                 215                 220

ctt tct cct ctg gcg gga gaa gac gat tca ttc ctt ttg gaa gga aac      720
Leu Ser Pro Leu Ala Gly Glu Asp Asp Ser Phe Leu Leu Glu Gly Asn
225                 230                 235                 240

tcg aat gag gac tgc aag cct ctc att tta ccg gac act aaa ccc aaa      768
Ser Asn Glu Asp Cys Lys Pro Leu Ile Leu Pro Asp Thr Lys Pro Lys
                245                 250                 255

att aag gat aat gga gat ctg gtt ttg tca agc ccc agt aat gta aca      816
Ile Lys Asp Asn Gly Asp Leu Val Leu Ser Ser Pro Ser Asn Val Thr
            260                 265                 270

ctg ccc caa gtg aaa aca gaa aaa gaa gat ttc atc gaa ctc tgc acc      864
Leu Pro Gln Val Lys Thr Glu Lys Glu Asp Phe Ile Glu Leu Cys Thr
        275                 280                 285

cct ggg gta att aag caa gag aaa ctg ggc aca gtt tac tgt cag gca      912
Pro Gly Val Ile Lys Gln Glu Lys Leu Gly Thr Val Tyr Cys Gln Ala
    290                 295                 300

agc ttt cct gga gca aat ata att ggt aat aaa atg tct gcc att tct      960
Ser Phe Pro Gly Ala Asn Ile Ile Gly Asn Lys Met Ser Ala Ile Ser
305                 310                 315                 320

gtt cat ggt gtg agt acc tct gga gga cag atg tac cac tat gac atg     1008
Val His Gly Val Ser Thr Ser Gly Gly Gln Met Tyr His Tyr Asp Met
                325                 330                 335

aat aca gca tcc ctt tct caa cag cag gat cag aag cct att ttt aat     1056
Asn Thr Ala Ser Leu Ser Gln Gln Gln Asp Gln Lys Pro Ile Phe Asn
            340                 345                 350
```

-continued

```
gtc att cca cca att ccc gtt ggt tcc gaa aat tgg aat agg tgc caa      1104
Val Ile Pro Pro Ile Pro Val Gly Ser Glu Asn Trp Asn Arg Cys Gln
        355                 360                 365

gga tct gga gat gac aac ttg act tct ctg ggg act ctg aac ttc cct      1152
Gly Ser Gly Asp Asp Asn Leu Thr Ser Leu Gly Thr Leu Asn Phe Pro
    370                 375                 380

ggt cga aca gtt ttt tct aat ggc tat tca agc ccc agc atg aga cca      1200
Gly Arg Thr Val Phe Ser Asn Gly Tyr Ser Ser Pro Ser Met Arg Pro
385                 390                 395                 400

gat gta agc tct cct cca tcc agc tcc tca aca gca aca aca gga cca      1248
Asp Val Ser Ser Pro Pro Ser Ser Ser Ser Thr Ala Thr Thr Gly Pro
                405                 410                 415

cct ccc aaa ctc tgc ctg gtg tgc tct gat gaa gct tca gga tgt cat      1296
Pro Pro Lys Leu Cys Leu Val Cys Ser Asp Glu Ala Ser Gly Cys His
            420                 425                 430

tat gga gtc tta act tgt gga agc tgt aaa gtt ttc ttc aaa aga gca      1344
Tyr Gly Val Leu Thr Cys Gly Ser Cys Lys Val Phe Phe Lys Arg Ala
        435                 440                 445

gtg gaa gga cag cac aat tac cta tgt gct gga agg aat gat tgc atc      1392
Val Glu Gly Gln His Asn Tyr Leu Cys Ala Gly Arg Asn Asp Cys Ile
    450                 455                 460

atc gat aaa att cga aga aaa aac tgc cca gca tgc cgc tat cga aaa      1440
Ile Asp Lys Ile Arg Arg Lys Asn Cys Pro Ala Cys Arg Tyr Arg Lys
465                 470                 475                 480

tgt ctt cag gct gga atg aac ctg gaa gct cga aaa aca aag aaa aaa      1488
Cys Leu Gln Ala Gly Met Asn Leu Glu Ala Arg Lys Thr Lys Lys Lys
                485                 490                 495

ata aaa gga att cag cag gcc act aca gga gtc tca caa gaa acc tct      1536
Ile Lys Gly Ile Gln Gln Ala Thr Thr Gly Val Ser Gln Glu Thr Ser
            500                 505                 510

gaa aat cct ggt aac aaa aca ata gtt cct gca acg tta cca caa ctc      1584
Glu Asn Pro Gly Asn Lys Thr Ile Val Pro Ala Thr Leu Pro Gln Leu
        515                 520                 525

acc cct acc ctg gtg tca ctg ttg gag gtt att gaa cct gaa gtg tta      1632
Thr Pro Thr Leu Val Ser Leu Leu Glu Val Ile Glu Pro Glu Val Leu
    530                 535                 540

tat gca gga tat gat agc tct gtt cca gac tca act tgg agg atc atg      1680
Tyr Ala Gly Tyr Asp Ser Ser Val Pro Asp Ser Thr Trp Arg Ile Met
545                 550                 555                 560

act acg ctc aac atg tta gga ggg cgg caa gtg att gca gca gtg aaa      1728
Thr Thr Leu Asn Met Leu Gly Gly Arg Gln Val Ile Ala Ala Val Lys
                565                 570                 575

tgg gca aag gca ata cca ggt ttc agg aac tta cac ctg gat gac caa      1776
Trp Ala Lys Ala Ile Pro Gly Phe Arg Asn Leu His Leu Asp Asp Gln
            580                 585                 590

atg acc cta ctg cag tac tcc tgg atg tcc ctt atg gca ttt gct ctg      1824
Met Thr Leu Leu Gln Tyr Ser Trp Met Ser Leu Met Ala Phe Ala Leu
        595                 600                 605

ggg tgg aga tca tat aga caa tca agt gca aac ctg ctg tgt ttt gct      1872
Gly Trp Arg Ser Tyr Arg Gln Ser Ser Ala Asn Leu Leu Cys Phe Ala
    610                 615                 620

cct gat ctg att att aat gag cag aga atg act cta ccc tgc atg tac      1920
Pro Asp Leu Ile Ile Asn Glu Gln Arg Met Thr Leu Pro Cys Met Tyr
625                 630                 635                 640

gac caa tgt aaa cac atg ctg tat gtt tcc tct gag tta cac agg ctt      1968
Asp Gln Cys Lys His Met Leu Tyr Val Ser Ser Glu Leu His Arg Leu
                645                 650                 655

cag gta tct tat gaa gag tat ctc tgt atg aaa acc tta ctg ctt ctc      2016
Gln Val Ser Tyr Glu Glu Tyr Leu Cys Met Lys Thr Leu Leu Leu Leu
            660                 665                 670
```

-continued

```
tct tca gtt cct aag gac ggt ctg aag agc caa gag cta ttt gat gaa      2064
Ser Ser Val Pro Lys Asp Gly Leu Lys Ser Gln Glu Leu Phe Asp Glu
        675                 680                 685

att aga atg acc tac atc aaa gag cta gga aaa gcc att gtc aag agg      2112
Ile Arg Met Thr Tyr Ile Lys Glu Leu Gly Lys Ala Ile Val Lys Arg
    690                 695                 700

gaa gga aac tcc agc cag aac tgg cag cgg ttt tat caa ctg aca aaa      2160
Glu Gly Asn Ser Ser Gln Asn Trp Gln Arg Phe Tyr Gln Leu Thr Lys
705                 710                 715                 720

ctc ttg gat tct atg cat gaa gtg gtt gaa aat ctc ctt aac tat tgc      2208
Leu Leu Asp Ser Met His Glu Val Val Glu Asn Leu Leu Asn Tyr Cys
                725                 730                 735

ttc caa aca ttt ttg gat aag acc atg agt att gaa ttc ccc gag atg      2256
Phe Gln Thr Phe Leu Asp Lys Thr Met Ser Ile Glu Phe Pro Glu Met
            740                 745                 750

tta gct gaa atc atc acc aat cag ata cca aaa tat tca aat gga aat      2304
Leu Ala Glu Ile Ile Thr Asn Gln Ile Pro Lys Tyr Ser Asn Gly Asn
        755                 760                 765

atc aaa aaa ctt ctg ttt cat caa aag tga                              2334
Ile Lys Lys Leu Leu Phe His Gln Lys
    770                 775


<210> SEQ ID NO 4
<211> LENGTH: 777
<212> TYPE: PRT
<213> ORGANISM: Homo sapiens

<400> SEQUENCE: 4

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220
```

-continued

```
Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Ser Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
```

-continued

```
            645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
            725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
    770                 775


<210> SEQ ID NO 5
<211> LENGTH: 2334
<212> TYPE: DNA
<213> ORGANISM: Homo sapiens
<220> FEATURE:
<221> NAME/KEY: CDS
<222> LOCATION: (1)..(2334)
<223> OTHER INFORMATION:

<400> SEQUENCE: 5

atg gac tcc aaa gaa tca tta act cct ggt aga gaa gaa aac ccc agc       48
Met Asp Ser Lys Glu Ser Leu Thr Pro Gly Arg Glu Glu Asn Pro Ser
1               5                   10                  15

agt gtg ctt gct cag gag agg gga gat gtg atg gac ttc tat aaa acc       96
Ser Val Leu Ala Gln Glu Arg Gly Asp Val Met Asp Phe Tyr Lys Thr
            20                  25                  30

cta aga gga gga gct act gtg aag gtt tct gcg tct tca ccc tca ctg      144
Leu Arg Gly Gly Ala Thr Val Lys Val Ser Ala Ser Ser Pro Ser Leu
        35                  40                  45

gct gtc gct tct caa tca gac tcc aag cag cga aga ctt ttg gtt gat      192
Ala Val Ala Ser Gln Ser Asp Ser Lys Gln Arg Arg Leu Leu Val Asp
    50                  55                  60

ttt cca aaa ggc tca gta agc aat gcg cag cag cca gat ctg tcc aaa      240
Phe Pro Lys Gly Ser Val Ser Asn Ala Gln Gln Pro Asp Leu Ser Lys
65                  70                  75                  80

gca gtt tca ctc tca atg gga ctg tat atg gga gag aca gaa aca aaa      288
Ala Val Ser Leu Ser Met Gly Leu Tyr Met Gly Glu Thr Glu Thr Lys
                85                  90                  95

gtg atg gga aat gac ctg gga ttc cca cag cag ggc caa atc agc ctt      336
Val Met Gly Asn Asp Leu Gly Phe Pro Gln Gln Gly Gln Ile Ser Leu
            100                 105                 110

tcc tcg ggg gaa aca gac tta aag ctt ttg gaa gaa agc att gca aac      384
Ser Ser Gly Glu Thr Asp Leu Lys Leu Leu Glu Glu Ser Ile Ala Asn
        115                 120                 125

ctc aat agg tcg acc agt gtt cca gag aac ccc aag agt tca gca tcc      432
Leu Asn Arg Ser Thr Ser Val Pro Glu Asn Pro Lys Ser Ser Ala Ser
    130                 135                 140

act gct gtg tct gct gcc ccc aca gag aag gag ttt cca aaa act cac      480
Thr Ala Val Ser Ala Ala Pro Thr Glu Lys Glu Phe Pro Lys Thr His
145                 150                 155                 160

tct gat gta tct tca gaa cag caa cat ttg aag ggc cag act ggc acc      528
```

-continued

```
Ser Asp Val Ser Ser Glu Gln Gln His Leu Lys Gly Gln Thr Gly Thr
                165                 170                 175

aac ggt ggc aat gtg aaa ttg tat acc aca gac caa agc acc ttt gac      576
Asn Gly Gly Asn Val Lys Leu Tyr Thr Thr Asp Gln Ser Thr Phe Asp
            180                 185                 190

att ttg cag gat ttg gag ttt tct tct ggg tcc cca ggt aaa gag acg      624
Ile Leu Gln Asp Leu Glu Phe Ser Ser Gly Ser Pro Gly Lys Glu Thr
        195                 200                 205

aat gag agt cct tgg aga tca gac ctg ttg ata gat gaa aac tgt ttg      672
Asn Glu Ser Pro Trp Arg Ser Asp Leu Leu Ile Asp Glu Asn Cys Leu
    210                 215                 220

ctt tct cct ctg gcg gga gaa gac gat tca ttc ctt ttg gaa gga aac      720
Leu Ser Pro Leu Ala Gly Glu Asp Asp Ser Phe Leu Leu Glu Gly Asn
225                 230                 235                 240

tcg aat gag gac tgc aag cct ctc att tta ccg gac act aaa ccc aaa      768
Ser Asn Glu Asp Cys Lys Pro Leu Ile Leu Pro Asp Thr Lys Pro Lys
                245                 250                 255

att aag gat aat gga gat ctg gtt ttg tca agc ccc agt aat gta aca      816
Ile Lys Asp Asn Gly Asp Leu Val Leu Ser Ser Pro Ser Asn Val Thr
            260                 265                 270

ctg ccc caa gtg aaa aca gaa aaa gaa gat ttc atc gaa ctc tgc acc      864
Leu Pro Gln Val Lys Thr Glu Lys Glu Asp Phe Ile Glu Leu Cys Thr
        275                 280                 285

cct ggg gta att aag caa gag aaa ctg ggc aca gtt tac tgt cag gca      912
Pro Gly Val Ile Lys Gln Glu Lys Leu Gly Thr Val Tyr Cys Gln Ala
    290                 295                 300

agc ttt cct gga gca aat ata att ggt aat aaa atg tct gcc att tct      960
Ser Phe Pro Gly Ala Asn Ile Ile Gly Asn Lys Met Ser Ala Ile Ser
305                 310                 315                 320

gtt cat ggt gtg agt acc tct gga gga cag atg tac cac tat gac atg     1008
Val His Gly Val Ser Thr Ser Gly Gly Gln Met Tyr His Tyr Asp Met
                325                 330                 335

aat aca gca tcc ctt tct caa cag cag gat cag aag cct att ttt aat     1056
Asn Thr Ala Ser Leu Ser Gln Gln Gln Asp Gln Lys Pro Ile Phe Asn
            340                 345                 350

gtc att cca cca att ccc gtt ggt tcc gaa aat tgg aat agg tgc caa     1104
Val Ile Pro Pro Ile Pro Val Gly Ser Glu Asn Trp Asn Arg Cys Gln
        355                 360                 365

gga tct gga gat gac aac ttg act tct ctg ggg act ctg aac ttc cct     1152
Gly Ser Gly Asp Asp Asn Leu Thr Ser Leu Gly Thr Leu Asn Phe Pro
    370                 375                 380

ggt cga aca gtt ttt tct aat ggc tat tca agc ccc agc atg aga cca     1200
Gly Arg Thr Val Phe Ser Asn Gly Tyr Ser Ser Pro Ser Met Arg Pro
385                 390                 395                 400

gat gta agc tct cct cca tcc agc tcc tca aca gca aca aca gga cca     1248
Asp Val Ser Ser Pro Pro Ser Ser Ser Ser Thr Ala Thr Thr Gly Pro
                405                 410                 415

cct ccc aaa ctc tgc ctg gtg tgc tct gat gaa gct tca gga tgt cat     1296
Pro Pro Lys Leu Cys Leu Val Cys Ser Asp Glu Ala Ser Gly Cys His
            420                 425                 430

tat gga gtc tta act tgt gga agc tgt aaa gtt ttc ttc aaa aga gca     1344
Tyr Gly Val Leu Thr Cys Gly Ser Cys Lys Val Phe Phe Lys Arg Ala
        435                 440                 445

gtg gaa gga cag cac aat tac cta tgt gct gga agg aat gat tgc atc     1392
Val Glu Gly Gln His Asn Tyr Leu Cys Ala Gly Arg Asn Asp Cys Ile
    450                 455                 460

atc gat aaa att cga aga aaa aac tgc cca gca tgc cgc tat cga aaa     1440
Ile Asp Lys Ile Arg Arg Lys Asn Cys Pro Ala Cys Arg Tyr Arg Lys
465                 470                 475                 480
```

-continued

```
tgt ctt cag gct gga atg aac ctg gaa gct cga aaa aca aag aaa aaa      1488
Cys Leu Gln Ala Gly Met Asn Leu Glu Ala Arg Lys Thr Lys Lys Lys
                485                 490                 495

ata aaa gga att cag cag gcc act aca gga gtc tca caa gaa acc tct      1536
Ile Lys Gly Ile Gln Gln Ala Thr Thr Gly Val Ser Gln Glu Thr Ser
            500                 505                 510

gaa aat cct ggt aac aaa aca ata gtt cct gca acg tta cca caa ctc      1584
Glu Asn Pro Gly Asn Lys Thr Ile Val Pro Ala Thr Leu Pro Gln Leu
        515                 520                 525

acc cct acc ctg gtg tca ctg ttg gag gtt att gaa cct gaa gtg tta      1632
Thr Pro Thr Leu Val Ser Leu Leu Glu Val Ile Glu Pro Glu Val Leu
    530                 535                 540

tat gca gga tat gat agc tct gtt cca gac tca act tgg agg atc atg      1680
Tyr Ala Gly Tyr Asp Ser Ser Val Pro Asp Ser Thr Trp Arg Ile Met
545                 550                 555                 560

act acg ctc aac atg tta gga ggg cgg caa gtg att gca gca gtg aaa      1728
Thr Thr Leu Asn Met Leu Gly Gly Arg Gln Val Ile Ala Ala Val Lys
                565                 570                 575

tgg gca aag gca ata cca ggt ttc agg aac tta cac ctg gat gac caa      1776
Trp Ala Lys Ala Ile Pro Gly Phe Arg Asn Leu His Leu Asp Asp Gln
            580                 585                 590

atg acc cta ctg cag tac tcc tgg atg gac ctt atg gca ttt gct ctg      1824
Met Thr Leu Leu Gln Tyr Ser Trp Met Asp Leu Met Ala Phe Ala Leu
        595                 600                 605

ggg tgg aga tca tat aga caa tca agt gca aac ctg ctg tgt ttt gct      1872
Gly Trp Arg Ser Tyr Arg Gln Ser Ser Ala Asn Leu Leu Cys Phe Ala
    610                 615                 620

cct gat ctg att att aat gag cag aga atg act cta ccc tgc atg tac      1920
Pro Asp Leu Ile Ile Asn Glu Gln Arg Met Thr Leu Pro Cys Met Tyr
625                 630                 635                 640

gac caa tgt aaa cac atg ctg tat gtt tcc tct gag tta cac agg ctt      1968
Asp Gln Cys Lys His Met Leu Tyr Val Ser Ser Glu Leu His Arg Leu
                645                 650                 655

cag gta tct tat gaa gag tat ctc tgt atg aaa acc tta ctg ctt ctc      2016
Gln Val Ser Tyr Glu Glu Tyr Leu Cys Met Lys Thr Leu Leu Leu Leu
            660                 665                 670

tct tca gtt cct aag gac ggt ctg aag agc caa gag cta ttt gat gaa      2064
Ser Ser Val Pro Lys Asp Gly Leu Lys Ser Gln Glu Leu Phe Asp Glu
        675                 680                 685

att aga atg acc tac atc aaa gag cta gga aaa gcc att gtc aag agg      2112
Ile Arg Met Thr Tyr Ile Lys Glu Leu Gly Lys Ala Ile Val Lys Arg
    690                 695                 700

gaa gga aac tcc agc cag aac tgg cag cgg ttt tat caa ctg aca aaa      2160
Glu Gly Asn Ser Ser Gln Asn Trp Gln Arg Phe Tyr Gln Leu Thr Lys
705                 710                 715                 720

ctc ttg gat tct atg cat gaa gtg gtt gaa aat ctc ctt aac tat tgc      2208
Leu Leu Asp Ser Met His Glu Val Val Glu Asn Leu Leu Asn Tyr Cys
                725                 730                 735

ttc caa aca ttt ttg gat aag acc atg agt att gaa ttc ccc gag atg      2256
Phe Gln Thr Phe Leu Asp Lys Thr Met Ser Ile Glu Phe Pro Glu Met
            740                 745                 750

tta gct gaa atc atc acc aat cag ata cca aaa tat tca aat gga aat      2304
Leu Ala Glu Ile Ile Thr Asn Gln Ile Pro Lys Tyr Ser Asn Gly Asn
        755                 760                 765

atc aaa aaa ctt ctg ttt cat caa aag tga                              2334
Ile Lys Lys Leu Leu Phe His Gln Lys
    770                 775
```

<210> SEQ ID NO 6
<211> LENGTH: 777

-continued

<212> TYPE: PRT
<213> ORGANISM: Homo sapiens

<400> SEQUENCE: 6

```
Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400
```

-continued

```
Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Asp Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
    770                 775
```

<210> SEQ ID NO 7
<211> LENGTH: 2334
<212> TYPE: DNA
<213> ORGANISM: Homo sapiens
<220> FEATURE:

-continued

```
<221> NAME/KEY: CDS
<222> LOCATION: (1)..(2334)
<223> OTHER INFORMATION:
<220> FEATURE:
<221> NAME/KEY: misc_feature
<222> LOCATION: (1)..(2334)
<223> OTHER INFORMATION: n = a or c or g or t/u

<400> SEQUENCE: 7

atg gac tcc aaa gaa tca tta act cct ggt aga gaa gaa aac ccc agc       48
Met Asp Ser Lys Glu Ser Leu Thr Pro Gly Arg Glu Glu Asn Pro Ser
1               5                   10                  15

agt gtg ctt gct cag gag agg gga gat gtg atg gac ttc tat aaa acc       96
Ser Val Leu Ala Gln Glu Arg Gly Asp Val Met Asp Phe Tyr Lys Thr
            20                  25                  30

cta aga gga gga gct act gtg aag gtt tct gcg tct tca ccc tca ctg      144
Leu Arg Gly Gly Ala Thr Val Lys Val Ser Ala Ser Ser Pro Ser Leu
        35                  40                  45

gct gtc gct tct caa tca gac tcc aag cag cga aga ctt ttg gtt gat      192
Ala Val Ala Ser Gln Ser Asp Ser Lys Gln Arg Arg Leu Leu Val Asp
    50                  55                  60

ttt cca aaa ggc tca gta agc aat gcg cag cag cca gat ctg tcc aaa      240
Phe Pro Lys Gly Ser Val Ser Asn Ala Gln Gln Pro Asp Leu Ser Lys
65                  70                  75                  80

gca gtt tca ctc tca atg gga ctg tat atg gga gag aca gaa aca aaa      288
Ala Val Ser Leu Ser Met Gly Leu Tyr Met Gly Glu Thr Glu Thr Lys
                85                  90                  95

gtg atg gga aat gac ctg gga ttc cca cag cag ggc caa atc agc ctt      336
Val Met Gly Asn Asp Leu Gly Phe Pro Gln Gln Gly Gln Ile Ser Leu
            100                 105                 110

tcc tcg ggg gaa aca gac tta aag ctt ttg gaa gaa agc att gca aac      384
Ser Ser Gly Glu Thr Asp Leu Lys Leu Leu Glu Glu Ser Ile Ala Asn
        115                 120                 125

ctc aat agg tcg acc agt gtt cca gag aac ccc aag agt tca gca tcc      432
Leu Asn Arg Ser Thr Ser Val Pro Glu Asn Pro Lys Ser Ser Ala Ser
    130                 135                 140

act gct gtg tct gct gcc ccc aca gag aag gag ttt cca aaa act cac      480
Thr Ala Val Ser Ala Ala Pro Thr Glu Lys Glu Phe Pro Lys Thr His
145                 150                 155                 160

tct gat gta tct tca gaa cag caa cat ttg aag ggc cag act ggc acc      528
Ser Asp Val Ser Ser Glu Gln Gln His Leu Lys Gly Gln Thr Gly Thr
                165                 170                 175

aac ggt ggc aat gtg aaa ttg tat acc aca gac caa agc acc ttt gac      576
Asn Gly Gly Asn Val Lys Leu Tyr Thr Thr Asp Gln Ser Thr Phe Asp
            180                 185                 190

att ttg cag gat ttg gag ttt tct tct ggg tcc cca ggt aaa gag acg      624
Ile Leu Gln Asp Leu Glu Phe Ser Ser Gly Ser Pro Gly Lys Glu Thr
        195                 200                 205

aat gag agt cct tgg aga tca gac ctg ttg ata gat gaa aac tgt ttg      672
Asn Glu Ser Pro Trp Arg Ser Asp Leu Leu Ile Asp Glu Asn Cys Leu
    210                 215                 220

ctt tct cct ctg gcg gga gaa gac gat tca ttc ctt ttg gaa gga aac      720
Leu Ser Pro Leu Ala Gly Glu Asp Asp Ser Phe Leu Leu Glu Gly Asn
225                 230                 235                 240

tcg aat gag gac tgc aag cct ctc att tta ccg gac act aaa ccc aaa      768
Ser Asn Glu Asp Cys Lys Pro Leu Ile Leu Pro Asp Thr Lys Pro Lys
                245                 250                 255

att aag gat aat gga gat ctg gtt ttg tca agc ccc agt aat gta aca      816
Ile Lys Asp Asn Gly Asp Leu Val Leu Ser Ser Pro Ser Asn Val Thr
            260                 265                 270

ctg ccc caa gtg aaa aca gaa aaa gaa gat ttc atc gaa ctc tgc acc      864
```

-continued

```
Leu Pro Gln Val Lys Thr Glu Lys Glu Asp Phe Ile Glu Leu Cys Thr
        275                 280                 285

cct ggg gta att aag caa gag aaa ctg ggc aca gtt tac tgt cag gca      912
Pro Gly Val Ile Lys Gln Glu Lys Leu Gly Thr Val Tyr Cys Gln Ala
    290                 295                 300

agc ttt cct gga gca aat ata att ggt aat aaa atg tct gcc att tct      960
Ser Phe Pro Gly Ala Asn Ile Ile Gly Asn Lys Met Ser Ala Ile Ser
305                 310                 315                 320

gtt cat ggt gtg agt acc tct gga gga cag atg tac cac tat gac atg     1008
Val His Gly Val Ser Thr Ser Gly Gly Gln Met Tyr His Tyr Asp Met
                325                 330                 335

aat aca gca tcc ctt tct caa cag cag gat cag aag cct att ttt aat     1056
Asn Thr Ala Ser Leu Ser Gln Gln Gln Asp Gln Lys Pro Ile Phe Asn
            340                 345                 350

gtc att cca cca att ccc gtt ggt tcc gaa aat tgg aat agg tgc caa     1104
Val Ile Pro Pro Ile Pro Val Gly Ser Glu Asn Trp Asn Arg Cys Gln
        355                 360                 365

gga tct gga gat gac aac ttg act tct ctg ggg act ctg aac ttc cct     1152
Gly Ser Gly Asp Asp Asn Leu Thr Ser Leu Gly Thr Leu Asn Phe Pro
    370                 375                 380

ggt cga aca gtt ttt tct aat ggc tat tca agc ccc agc atg aga cca     1200
Gly Arg Thr Val Phe Ser Asn Gly Tyr Ser Ser Pro Ser Met Arg Pro
385                 390                 395                 400

gat gta agc tct cct cca tcc agc tcc tca aca gca aca aca gga cca     1248
Asp Val Ser Ser Pro Pro Ser Ser Ser Ser Thr Ala Thr Thr Gly Pro
                405                 410                 415

cct ccc aaa ctc tgc ctg gtg tgc tct gat gaa gct tca gga tgt cat     1296
Pro Pro Lys Leu Cys Leu Val Cys Ser Asp Glu Ala Ser Gly Cys His
            420                 425                 430

tat gga gtc tta act tgt gga agc tgt aaa gtt ttc ttc aaa aga gca     1344
Tyr Gly Val Leu Thr Cys Gly Ser Cys Lys Val Phe Phe Lys Arg Ala
        435                 440                 445

gtg gaa gga cag cac aat tac cta tgt gct gga agg aat gat tgc atc     1392
Val Glu Gly Gln His Asn Tyr Leu Cys Ala Gly Arg Asn Asp Cys Ile
    450                 455                 460

atc gat aaa att cga aga aaa aac tgc cca gca tgc cgc tat cga aaa     1440
Ile Asp Lys Ile Arg Arg Lys Asn Cys Pro Ala Cys Arg Tyr Arg Lys
465                 470                 475                 480

tgt ctt cag gct gga atg aac ctg gaa gct cga aaa aca aag aaa aaa     1488
Cys Leu Gln Ala Gly Met Asn Leu Glu Ala Arg Lys Thr Lys Lys Lys
                485                 490                 495

ata aaa gga att cag cag gcc act aca gga gtc tca caa gaa acc tct     1536
Ile Lys Gly Ile Gln Gln Ala Thr Thr Gly Val Ser Gln Glu Thr Ser
            500                 505                 510

gaa aat cct ggt aac aaa aca ata gtt cct gca acg tta cca caa ctc     1584
Glu Asn Pro Gly Asn Lys Thr Ile Val Pro Ala Thr Leu Pro Gln Leu
        515                 520                 525

acc cct acc ctg gtg tca nnn ttg gag nnn att gaa cct gaa gtg tta     1632
Thr Pro Thr Leu Val Ser Xaa Leu Glu Xaa Ile Glu Pro Glu Val Leu
    530                 535                 540

tat gca gga tat gat agc tct nnn cca gac tca act nnn agg atc atg     1680
Tyr Ala Gly Tyr Asp Ser Ser Xaa Pro Asp Ser Thr Xaa Arg Ile Met
545                 550                 555                 560

act acg ctc aac atg tta gga ggg cgg caa gtg att gca gca gtg aaa     1728
Thr Thr Leu Asn Met Leu Gly Gly Arg Gln Val Ile Ala Ala Val Lys
                565                 570                 575

tgg gca aag gca ata cca ggt ttc agg aac tta cac ctg gat gac caa     1776
Trp Ala Lys Ala Ile Pro Gly Phe Arg Asn Leu His Leu Asp Asp Gln
            580                 585                 590
```

-continued

```
atg acc cta ctg cag tac tcc tgg atg nnn ctt atg gca ttt gct ctg     1824
Met Thr Leu Leu Gln Tyr Ser Trp Met Xaa Leu Met Ala Phe Ala Leu
        595                 600                 605

ggg tgg aga tca tat aga caa tca agt gca aac ctg ctg tgt ttt gct     1872
Gly Trp Arg Ser Tyr Arg Gln Ser Ser Ala Asn Leu Leu Cys Phe Ala
    610                 615                 620

cct gat ctg att att aat gag cag aga atg act nnn ccc nnn atg tac     1920
Pro Asp Leu Ile Ile Asn Glu Gln Arg Met Thr Xaa Pro Xaa Met Tyr
625                 630                 635                 640

gac caa tgt aaa cac atg ctg nnn gtt tcc tct gag tta cac agg ctt     1968
Asp Gln Cys Lys His Met Leu Xaa Val Ser Ser Glu Leu His Arg Leu
                645                 650                 655

cag gta tct nnn gaa gag tat ctc tgt atg aaa acc tta ctg ctt ctc     2016
Gln Val Ser Xaa Glu Glu Tyr Leu Cys Met Lys Thr Leu Leu Leu Leu
            660                 665                 670

tct tca gtt cct aag gac ggt ctg aag agc caa gag nnn ttt gat gaa     2064
Ser Ser Val Pro Lys Asp Gly Leu Lys Ser Gln Glu Xaa Phe Asp Glu
        675                 680                 685

att aga nnn acc tac atc aaa gag cta gga aaa gcc att nnn aag agg     2112
Ile Arg Xaa Thr Tyr Ile Lys Glu Leu Gly Lys Ala Ile Xaa Lys Arg
    690                 695                 700

gaa gga aac tcc agc cag aac nnn cag cgg ttt tat caa ctg aca aaa     2160
Glu Gly Asn Ser Ser Gln Asn Xaa Gln Arg Phe Tyr Gln Leu Thr Lys
705                 710                 715                 720

ctc ttg gat tct atg cat gaa gtg gtt gaa aat ctc nnn aac tat tgc     2208
Leu Leu Asp Ser Met His Glu Val Val Glu Asn Leu Xaa Asn Tyr Cys
                725                 730                 735

ttc caa aca ttt nnn gat aag acc atg agt att gaa ttc ccc gag atg     2256
Phe Gln Thr Phe Xaa Asp Lys Thr Met Ser Ile Glu Phe Pro Glu Met
            740                 745                 750

tta gct gaa atc atc acc aat cag ata cca aaa nnn tca aat gga aat     2304
Leu Ala Glu Ile Ile Thr Asn Gln Ile Pro Lys Xaa Ser Asn Gly Asn
        755                 760                 765

atc aaa aaa ctt ctg ttt cat caa aag tga                             2334
Ile Lys Lys Leu Leu Phe His Gln Lys
    770                 775
```

```
<210> SEQ ID NO 8
<211> LENGTH: 777
<212> TYPE: PRT
<213> ORGANISM: Homo sapiens
<220> FEATURE:
<221> NAME/KEY: misc_feature
<222> LOCATION: (535)..(535)
<223> OTHER INFORMATION: The 'Xaa' at location 535 stands for Cys, Asn,
      Tyr, Lys, Ser, Asp, Glu, Gln, Arg or Thr.
<220> FEATURE:
<221> NAME/KEY: misc_feature
<222> LOCATION: (538)..(538)
<223> OTHER INFORMATION: The 'Xaa' at location 538 stands for Cys, Asn,
      Tyr, Lys, Ser, Asp, Glu, Gln, Arg or Thr.
      .
<220> FEATURE:
<221> NAME/KEY: misc_feature
<222> LOCATION: (552)..(552)
<223> OTHER INFORMATION: The 'Xaa' at location 552 stands for Cys, Asn,
      Tyr, Lys, Ser, Asp, Glu, Gln, Arg or Thr.
      .
<220> FEATURE:
<221> NAME/KEY: misc_feature
<222> LOCATION: (557)..(557)
<223> OTHER INFORMATION: The 'Xaa' at location 557 stands for Cys, Asn,
      Tyr, Lys, Ser, Asp, Glu, Gln, Arg or Thr.
      .
<220> FEATURE:
<221> NAME/KEY: misc_feature
<222> LOCATION: (602)..(602)
```

-continued

<223> OTHER INFORMATION: The 'Xaa' at location 602 stands for Cys, Asn, Tyr, Lys, Ser, Asp, Glu, Gln, Arg or Thr.
.
<220> FEATURE:
<221> NAME/KEY: misc_feature
<222> LOCATION: (636)..(636)
<223> OTHER INFORMATION: The 'Xaa' at location 636 stands for Cys, Asn, Tyr, Lys, Ser, Asp, Glu, Gln, Arg or Thr.
.
<220> FEATURE:
<221> NAME/KEY: misc_feature
<222> LOCATION: (638)..(638)
<223> OTHER INFORMATION: The 'Xaa' at location 638 stands for Cys, Asn, Tyr, Lys, Ser, Asp, Glu, Gln, Arg or Thr.
.
<220> FEATURE:
<221> NAME/KEY: misc_feature
<222> LOCATION: (648)..(648)
<223> OTHER INFORMATION: The 'Xaa' at location 648 stands for Cys, Asn, Tyr, Lys, Ser, Asp, Glu, Gln, Arg or Thr.
.
<220> FEATURE:
<221> NAME/KEY: misc_feature
<222> LOCATION: (660)..(660)
<223> OTHER INFORMATION: The 'Xaa' at location 660 stands for Cys, Asn, Tyr, Lys, Ser, Asp, Glu, Gln, Arg or Thr.
.
<220> FEATURE:
<221> NAME/KEY: misc_feature
<222> LOCATION: (685)..(685)
<223> OTHER INFORMATION: The 'Xaa' at location 685 stands for Cys, Asn, Tyr, Lys, Ser, Asp, Glu, Gln, Arg or Thr.
.
<220> FEATURE:
<221> NAME/KEY: misc_feature
<222> LOCATION: (691)..(691)
<223> OTHER INFORMATION: The 'Xaa' at location 691 stands for Cys, Asn, Tyr, Lys, Ser, Asp, Glu, Gln, Arg or Thr.
.
<220> FEATURE:
<221> NAME/KEY: misc_feature
<222> LOCATION: (702)..(702)
<223> OTHER INFORMATION: The 'Xaa' at location 702 stands for Cys, Asn, Tyr, Lys, Ser, Asp, Glu, Gln, Arg or Thr.
.
<220> FEATURE:
<221> NAME/KEY: misc_feature
<222> LOCATION: (712)..(712)
<223> OTHER INFORMATION: The 'Xaa' at location 712 stands for Cys, Asn, Tyr, Lys, Ser, Asp, Glu, Gln, Arg or Thr.
.
<220> FEATURE:
<221> NAME/KEY: misc_feature
<222> LOCATION: (733)..(733)
<223> OTHER INFORMATION: The 'Xaa' at location 733 stands for Cys, Asn, Tyr, Lys, Ser, Asp, Glu, Gln, Arg or Thr.
.
<220> FEATURE:
<221> NAME/KEY: misc_feature
<222> LOCATION: (741)..(741)
<223> OTHER INFORMATION: The 'Xaa' at location 741 stands for Cys, Asn, Tyr, Lys, Ser, Asp, Glu, Gln, Arg or Thr.
.
<220> FEATURE:
<221> NAME/KEY: misc_feature
<222> LOCATION: (764)..(764)
<223> OTHER INFORMATION: The 'Xaa' at location 764 stands for Cys, Asn, Tyr, Lys, Ser, Asp, Glu, Gln, Arg or Thr.
<220> FEATURE:
<221> NAME/KEY: misc_feature
<222> LOCATION: (1)..(2334)
<223> OTHER INFORMATION: n = a or c or g or t/u

<400> SEQUENCE: 8

```
Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
```

-continued

```
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445
```

-continued

```
Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Xaa Leu Glu Xaa Ile Glu Pro Glu Val Leu
    530                 535                 540

Tyr Ala Gly Tyr Asp Ser Ser Xaa Pro Asp Ser Thr Xaa Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Xaa Leu Met Ala Phe Ala Leu
        595                 600                 605

Gly Trp Arg Ser Tyr Arg Gln Ser Ser Ala Asn Leu Leu Cys Phe Ala
    610                 615                 620

Pro Asp Leu Ile Ile Asn Glu Gln Arg Met Thr Xaa Pro Xaa Met Tyr
625                 630                 635                 640

Asp Gln Cys Lys His Met Leu Xaa Val Ser Ser Glu Leu His Arg Leu
                645                 650                 655

Gln Val Ser Xaa Glu Glu Tyr Leu Cys Met Lys Thr Leu Leu Leu Leu
            660                 665                 670

Ser Ser Val Pro Lys Asp Gly Leu Lys Ser Gln Glu Xaa Phe Asp Glu
        675                 680                 685

Ile Arg Xaa Thr Tyr Ile Lys Glu Leu Gly Lys Ala Ile Xaa Lys Arg
    690                 695                 700

Glu Gly Asn Ser Ser Gln Asn Xaa Gln Arg Phe Tyr Gln Leu Thr Lys
705                 710                 715                 720

Leu Leu Asp Ser Met His Glu Val Val Glu Asn Leu Xaa Asn Tyr Cys
                725                 730                 735

Phe Gln Thr Phe Xaa Asp Lys Thr Met Ser Ile Glu Phe Pro Glu Met
            740                 745                 750

Leu Ala Glu Ile Ile Thr Asn Gln Ile Pro Lys Xaa Ser Asn Gly Asn
        755                 760                 765

Ile Lys Lys Leu Leu Phe His Gln Lys
    770                 775
```

<210> SEQ ID NO 9
<211> LENGTH: 774
<212> TYPE: DNA
<213> ORGANISM: Homo sapiens
<220> FEATURE:
<221> NAME/KEY: CDS
<222> LOCATION: (1)..(774)
<223> OTHER INFORMATION:

<400> SEQUENCE: 9

```
gtt cct gca acg tta cca caa ctc acc cct acc ctg gtg tca ctg ttg       48
Val Pro Ala Thr Leu Pro Gln Leu Thr Pro Thr Leu Val Ser Leu Leu
1               5                   10                  15
```

-continued

```
gag gtt att gaa cct gaa gtg tta tat gca gga tat gat agc tct gtt       96
Glu Val Ile Glu Pro Glu Val Leu Tyr Ala Gly Tyr Asp Ser Ser Val
            20                  25                  30

cca gac tca act tgg agg atc atg act acg ctc aac atg tta gga ggg      144
Pro Asp Ser Thr Trp Arg Ile Met Thr Thr Leu Asn Met Leu Gly Gly
        35                  40                  45

cgg caa gtg att gca gca gtg aaa tgg gca aag gca ata cca ggt ttc      192
Arg Gln Val Ile Ala Ala Val Lys Trp Ala Lys Ala Ile Pro Gly Phe
    50                  55                  60

agg aac tta cac ctg gat gac caa atg acc cta ctg cag tac tcc tgg      240
Arg Asn Leu His Leu Asp Asp Gln Met Thr Leu Leu Gln Tyr Ser Trp
65                  70                  75                  80

atg ttt ctt atg gca ttt gct ctg ggg tgg aga tca tat aga caa tca      288
Met Phe Leu Met Ala Phe Ala Leu Gly Trp Arg Ser Tyr Arg Gln Ser
                85                  90                  95

agt gca aac ctg ctg tgt ttt gct cct gat ctg att att aat gag cag      336
Ser Ala Asn Leu Leu Cys Phe Ala Pro Asp Leu Ile Ile Asn Glu Gln
            100                 105                 110

aga atg act cta ccc tgc atg tac gac caa tgt aaa cac atg ctg tat      384
Arg Met Thr Leu Pro Cys Met Tyr Asp Gln Cys Lys His Met Leu Tyr
        115                 120                 125

gtt tcc tct gag tta cac agg ctt cag gta tct tat gaa gag tat ctc      432
Val Ser Ser Glu Leu His Arg Leu Gln Val Ser Tyr Glu Glu Tyr Leu
    130                 135                 140

tgt atg aaa acc tta ctg ctt ctc tct tca gtt cct aag gac ggt ctg      480
Cys Met Lys Thr Leu Leu Leu Leu Ser Ser Val Pro Lys Asp Gly Leu
145                 150                 155                 160

aag agc caa gag cta ttt gat gaa att aga atg acc tac atc aaa gag      528
Lys Ser Gln Glu Leu Phe Asp Glu Ile Arg Met Thr Tyr Ile Lys Glu
                165                 170                 175

cta gga aaa gcc att gtc aag agg gaa gga aac tcc agc cag aac tgg      576
Leu Gly Lys Ala Ile Val Lys Arg Glu Gly Asn Ser Ser Gln Asn Trp
            180                 185                 190

cag cgg ttt tat caa ctg aca aaa ctc ttg gat tct atg cat gaa gtg      624
Gln Arg Phe Tyr Gln Leu Thr Lys Leu Leu Asp Ser Met His Glu Val
        195                 200                 205

gtt gaa aat ctc ctt aac tat tgc ttc caa aca ttt ttg gat aag acc      672
Val Glu Asn Leu Leu Asn Tyr Cys Phe Gln Thr Phe Leu Asp Lys Thr
    210                 215                 220

atg agt att gaa ttc ccc gag atg tta gct gaa atc atc acc aat cag      720
Met Ser Ile Glu Phe Pro Glu Met Leu Ala Glu Ile Ile Thr Asn Gln
225                 230                 235                 240

ata cca aaa tat tca aat gga aat atc aaa aaa ctt ctg ttt cat caa      768
Ile Pro Lys Tyr Ser Asn Gly Asn Ile Lys Lys Leu Leu Phe His Gln
                245                 250                 255

aag tga                                                              774
Lys


<210> SEQ ID NO 10
<211> LENGTH: 257
<212> TYPE: PRT
<213> ORGANISM: Homo sapiens

<400> SEQUENCE: 10

Val Pro Ala Thr Leu Pro Gln Leu Thr Pro Thr Leu Val Ser Leu Leu
1               5                   10                  15

Glu Val Ile Glu Pro Glu Val Leu Tyr Ala Gly Tyr Asp Ser Ser Val
            20                  25                  30

Pro Asp Ser Thr Trp Arg Ile Met Thr Thr Leu Asn Met Leu Gly Gly
```

-continued

```
        35                  40                  45

Arg Gln Val Ile Ala Ala Val Lys Trp Ala Lys Ala Ile Pro Gly Phe
    50                  55                  60

Arg Asn Leu His Leu Asp Asp Gln Met Thr Leu Leu Gln Tyr Ser Trp
65                  70                  75                  80

Met Phe Leu Met Ala Phe Ala Leu Gly Trp Arg Ser Tyr Arg Gln Ser
                85                  90                  95

Ser Ala Asn Leu Leu Cys Phe Ala Pro Asp Leu Ile Ile Asn Glu Gln
            100                 105                 110

Arg Met Thr Leu Pro Cys Met Tyr Asp Gln Cys Lys His Met Leu Tyr
        115                 120                 125

Val Ser Ser Glu Leu His Arg Leu Gln Val Ser Tyr Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
        195                 200                 205

Val Glu Asn Leu Leu Asn Tyr Cys Phe Gln Thr Phe Leu Asp Lys Thr
    210                 215                 220

Met Ser Ile Glu Phe Pro Glu Met Leu Ala Glu Ile Ile Thr Asn Gln
225                 230                 235                 240

Ile Pro Lys Tyr Ser Asn Gly Asn Ile Lys Lys Leu Leu Phe His Gln
                245                 250                 255

Lys


<210> SEQ ID NO 11
<211> LENGTH: 1548
<212> TYPE: DNA
<213> ORGANISM: Homo sapiens
<220> FEATURE:
<221> NAME/KEY: CDS
<222> LOCATION: (1)..(774)
<223> OTHER INFORMATION:

<400> SEQUENCE: 11

gtt cct gca acg tta cca caa ctc acc cct acc ctg gtg tca ctg ttg       48
Val Pro Ala Thr Leu Pro Gln Leu Thr Pro Thr Leu Val Ser Leu Leu
1               5                   10                  15

gag gtt att gaa cct gaa gtg tta tat gca gga tat gat agc tct gtt       96
Glu Val Ile Glu Pro Glu Val Leu Tyr Ala Gly Tyr Asp Ser Ser Val
            20                  25                  30

cca gac tca act tgg agg atc atg act acg ctc aac atg tta gga ggg      144
Pro Asp Ser Thr Trp Arg Ile Met Thr Thr Leu Asn Met Leu Gly Gly
        35                  40                  45

cgg caa gtg att gca gca gtg aaa tgg gca aag gca ata cca ggt ttc      192
Arg Gln Val Ile Ala Ala Val Lys Trp Ala Lys Ala Ile Pro Gly Phe
    50                  55                  60

agg aac tta cac ctg gat gac caa atg acc cta ctg cag tac tcc tgg      240
Arg Asn Leu His Leu Asp Asp Gln Met Thr Leu Leu Gln Tyr Ser Trp
65                  70                  75                  80

atg tcc ctt atg gca ttt gct ctg ggg tgg aga tca tat aga caa tca      288
Met Ser Leu Met Ala Phe Ala Leu Gly Trp Arg Ser Tyr Arg Gln Ser
                85                  90                  95
```

-continued

```
agt gca aac ctg ctg tgt ttt gct cct gat ctg att att aat gag cag      336
Ser Ala Asn Leu Leu Cys Phe Ala Pro Asp Leu Ile Ile Asn Glu Gln
            100                 105                 110

aga atg act cta ccc tgc atg tac gac caa tgt aaa cac atg ctg tat      384
Arg Met Thr Leu Pro Cys Met Tyr Asp Gln Cys Lys His Met Leu Tyr
        115                 120                 125

gtt tcc tct gag tta cac agg ctt cag gta tct tat gaa gag tat ctc      432
Val Ser Ser Glu Leu His Arg Leu Gln Val Ser Tyr Glu Glu Tyr Leu
    130                 135                 140

tgt atg aaa acc tta ctg ctt ctc tct tca gtt cct aag gac ggt ctg      480
Cys Met Lys Thr Leu Leu Leu Leu Ser Ser Val Pro Lys Asp Gly Leu
145                 150                 155                 160

aag agc caa gag cta ttt gat gaa att aga atg acc tac atc aaa gag      528
Lys Ser Gln Glu Leu Phe Asp Glu Ile Arg Met Thr Tyr Ile Lys Glu
                165                 170                 175

cta gga aaa gcc att gtc aag agg gaa gga aac tcc agc cag aac tgg      576
Leu Gly Lys Ala Ile Val Lys Arg Glu Gly Asn Ser Ser Gln Asn Trp
            180                 185                 190

cag cgg ttt tat caa ctg aca aaa ctc ttg gat tct atg cat gaa gtg      624
Gln Arg Phe Tyr Gln Leu Thr Lys Leu Leu Asp Ser Met His Glu Val
        195                 200                 205

gtt gaa aat ctc ctt aac tat tgc ttc caa aca ttt ttg gat aag acc      672
Val Glu Asn Leu Leu Asn Tyr Cys Phe Gln Thr Phe Leu Asp Lys Thr
    210                 215                 220

atg agt att gaa ttc ccc gag atg tta gct gaa atc atc acc aat cag      720
Met Ser Ile Glu Phe Pro Glu Met Leu Ala Glu Ile Ile Thr Asn Gln
225                 230                 235                 240

ata cca aaa tat tca aat gga aat atc aaa aaa ctt ctg ttt cat caa      768
Ile Pro Lys Tyr Ser Asn Gly Asn Ile Lys Lys Leu Leu Phe His Gln
                245                 250                 255

aag tga gttcctgcaa cgttaccaca actcacccct accctggtgt cactgttgga       824
Lys

ggttattgaa cctgaagtgt tatatgcagg atatgatagc tctgttccag actcaacttg    884

gaggatcatg actacgctca acatgttagg agggcggcaa gtgattgcag cagtgaaatg    944

ggcaaaggca ataccaggtt tcaggaactt acacctggat gaccaaatga ccctactgca   1004

gtactcctgg atgtccctta tggcatttgc tctggggtgg agatcatata gacaatcaag   1064

tgcaaacctg ctgtgttttg ctcctgatct gattattaat gagcagagaa tgactctacc   1124

ctgcatgtac gaccaatgta aacacatgct gtatgtttcc tctgagttac acaggcttca   1184

ggtatcttat gaagagtatc tctgtatgaa aaccttactg cttctctctt cagttcctaa   1244

ggacggtctg aagagccaag agctatttga tgaaattaga atgacctaca tcaaagagct   1304

aggaaaagcc attgtcaaga gggaaggaaa ctccagccag aactggcagc ggttttatca   1364

actgacaaaa ctcttggatt ctatgcatga agtggttgaa aatctcctta actattgctt   1424

ccaaacattt ttggataaga ccatgagtat tgaattcccc gagatgttag ctgaaatcat   1484

caccaatcag ataccaaaat attcaaatgg aaatatcaaa aaacttctgt ttcatcaaaa   1544

gtga                                                                1548
```

<210> SEQ ID NO 12
<211> LENGTH: 257
<212> TYPE: PRT
<213> ORGANISM: Homo sapiens

<400> SEQUENCE: 12

```
Val Pro Ala Thr Leu Pro Gln Leu Thr Pro Thr Leu Val Ser Leu Leu
1               5                   10                  15
```

-continued

```
Glu Val Ile Glu Pro Glu Val Leu Tyr Ala Gly Tyr Asp Ser Ser Val
            20                  25                  30

Pro Asp Ser Thr Trp Arg Ile Met Thr Thr Leu Asn Met Leu Gly Gly
        35                  40                  45

Arg Gln Val Ile Ala Ala Val Lys Trp Ala Lys Ala Ile Pro Gly Phe
    50                  55                  60

Arg Asn Leu His Leu Asp Asp Gln Met Thr Leu Leu Gln Tyr Ser Trp
65                  70                  75                  80

Met Ser Leu Met Ala Phe Ala Leu Gly Trp Arg Ser Tyr Arg Gln Ser
                85                  90                  95

Ser Ala Asn Leu Leu Cys Phe Ala Pro Asp Leu Ile Ile Asn Glu Gln
            100                 105                 110

Arg Met Thr Leu Pro Cys Met Tyr Asp Gln Cys Lys His Met Leu Tyr
        115                 120                 125

Val Ser Ser Glu Leu His Arg Leu Gln Val Ser Tyr Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
        195                 200                 205

Val Glu Asn Leu Leu Asn Tyr Cys Phe Gln Thr Phe Leu Asp Lys Thr
    210                 215                 220

Met Ser Ile Glu Phe Pro Glu Met Leu Ala Glu Ile Ile Thr Asn Gln
225                 230                 235                 240

Ile Pro Lys Tyr Ser Asn Gly Asn Ile Lys Lys Leu Leu Phe His Gln
                245                 250                 255

Lys
```

<210> SEQ ID NO 13
<211> LENGTH: 774
<212> TYPE: DNA
<213> ORGANISM: Homo sapiens
<220> FEATURE:
<221> NAME/KEY: CDS
<222> LOCATION: (1)..(774)
<223> OTHER INFORMATION:

<400> SEQUENCE: 13

```
gtt cct gca acg tta cca caa ctc acc cct acc ctg gtg tca ctg ttg       48
Val Pro Ala Thr Leu Pro Gln Leu Thr Pro Thr Leu Val Ser Leu Leu
1               5                   10                  15

gag gtt att gaa cct gaa gtg tta tat gca gga tat gat agc tct gtt       96
Glu Val Ile Glu Pro Glu Val Leu Tyr Ala Gly Tyr Asp Ser Ser Val
            20                  25                  30

cca gac tca act tgg agg atc atg act acg ctc aac atg tta gga ggg      144
Pro Asp Ser Thr Trp Arg Ile Met Thr Thr Leu Asn Met Leu Gly Gly
        35                  40                  45

cgg caa gtg att gca gca gtg aaa tgg gca aag gca ata cca ggt ttc      192
Arg Gln Val Ile Ala Ala Val Lys Trp Ala Lys Ala Ile Pro Gly Phe
    50                  55                  60

agg aac tta cac ctg gat gac caa atg acc cta ctg cag tac tcc tgg      240
Arg Asn Leu His Leu Asp Asp Gln Met Thr Leu Leu Gln Tyr Ser Trp
65                  70                  75                  80
```

-continued

```
atg gac ctt atg gca ttt gct ctg ggg tgg aga tca tat aga caa tca       288
Met Asp Leu Met Ala Phe Ala Leu Gly Trp Arg Ser Tyr Arg Gln Ser
                85                  90                  95

agt gca aac ctg ctg tgt ttt gct cct gat ctg att att aat gag cag       336
Ser Ala Asn Leu Leu Cys Phe Ala Pro Asp Leu Ile Ile Asn Glu Gln
            100                 105                 110

aga atg act cta ccc tgc atg tac gac caa tgt aaa cac atg ctg tat       384
Arg Met Thr Leu Pro Cys Met Tyr Asp Gln Cys Lys His Met Leu Tyr
        115                 120                 125

gtt tcc tct gag tta cac agg ctt cag gta tct tat gaa gag tat ctc       432
Val Ser Ser Glu Leu His Arg Leu Gln Val Ser Tyr Glu Glu Tyr Leu
    130                 135                 140

tgt atg aaa acc tta ctg ctt ctc tct tca gtt cct aag gac ggt ctg       480
Cys Met Lys Thr Leu Leu Leu Leu Ser Ser Val Pro Lys Asp Gly Leu
145                 150                 155                 160

aag agc caa gag cta ttt gat gaa att aga atg acc tac atc aaa gag       528
Lys Ser Gln Glu Leu Phe Asp Glu Ile Arg Met Thr Tyr Ile Lys Glu
                165                 170                 175

cta gga aaa gcc att gtc aag agg gaa gga aac tcc agc cag aac tgg       576
Leu Gly Lys Ala Ile Val Lys Arg Glu Gly Asn Ser Ser Gln Asn Trp
            180                 185                 190

cag cgg ttt tat caa ctg aca aaa ctc ttg gat tct atg cat gaa gtg       624
Gln Arg Phe Tyr Gln Leu Thr Lys Leu Leu Asp Ser Met His Glu Val
        195                 200                 205

gtt gaa aat ctc ctt aac tat tgc ttc caa aca ttt ttg gat aag acc       672
Val Glu Asn Leu Leu Asn Tyr Cys Phe Gln Thr Phe Leu Asp Lys Thr
    210                 215                 220

atg agt att gaa ttc ccc gag atg tta gct gaa atc atc acc aat cag       720
Met Ser Ile Glu Phe Pro Glu Met Leu Ala Glu Ile Ile Thr Asn Gln
225                 230                 235                 240

ata cca aaa tat tca aat gga aat atc aaa aaa ctt ctg ttt cat caa       768
Ile Pro Lys Tyr Ser Asn Gly Asn Ile Lys Lys Leu Leu Phe His Gln
                245                 250                 255

aag tga                                                               774
Lys


<210> SEQ ID NO 14
<211> LENGTH: 257
<212> TYPE: PRT
<213> ORGANISM: Homo sapiens

<400> SEQUENCE: 14

Val Pro Ala Thr Leu Pro Gln Leu Thr Pro Thr Leu Val Ser Leu Leu
1               5                   10                  15

Glu Val Ile Glu Pro Glu Val Leu Tyr Ala Gly Tyr Asp Ser Ser Val
            20                  25                  30

Pro Asp Ser Thr Trp Arg Ile Met Thr Thr Leu Asn Met Leu Gly Gly
        35                  40                  45

Arg Gln Val Ile Ala Ala Val Lys Trp Ala Lys Ala Ile Pro Gly Phe
    50                  55                  60

Arg Asn Leu His Leu Asp Asp Gln Met Thr Leu Leu Gln Tyr Ser Trp
65                  70                  75                  80

Met Asp Leu Met Ala Phe Ala Leu Gly Trp Arg Ser Tyr Arg Gln Ser
                85                  90                  95

Ser Ala Asn Leu Leu Cys Phe Ala Pro Asp Leu Ile Ile Asn Glu Gln
            100                 105                 110

Arg Met Thr Leu Pro Cys Met Tyr Asp Gln Cys Lys His Met Leu Tyr
        115                 120                 125
```

-continued

```
Val Ser Ser Glu Leu His Arg Leu Gln Val Ser Tyr Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
        195                 200                 205

Val Glu Asn Leu Leu Asn Tyr Cys Phe Gln Thr Phe Leu Asp Lys Thr
    210                 215                 220

Met Ser Ile Glu Phe Pro Glu Met Leu Ala Glu Ile Ile Thr Asn Gln
225                 230                 235                 240

Ile Pro Lys Tyr Ser Asn Gly Asn Ile Lys Lys Leu Leu Phe His Gln
                245                 250                 255

Lys


<210> SEQ ID NO 15
<211> LENGTH: 774
<212> TYPE: DNA
<213> ORGANISM: Homo sapiens
<220> FEATURE:
<221> NAME/KEY: CDS
<222> LOCATION: (1)..(774)
<223> OTHER INFORMATION: n = a or c or g or t/u such that Xaa at
      positions 552, 557, 602, 636, 648, 712, 741, 535, 538, 638, 691,
      702, 648, 660, 685, 733 and 764 can indpendently be Cys, Asn, Tyr,
      Lys, Ser, Asp, Glu, Gln, Arg or Thr.
<220> FEATURE:
<221> NAME/KEY: misc_feature
<222> LOCATION: (1)..(774)
<223> OTHER INFORMATION: n = a or c or g or t/u such that Xaa at
      positions 552, 557, 602, 636, 648, 712, 741, 535, 538, 638, 691,
      702, 648, 660, 685, 733 and 764 can indpendently be Cys, Asn, Tyr,
      Lys, Ser, Asp, Glu, Gln, Arg or Thr

<400> SEQUENCE: 15

gtt cct gca acg tta cca caa ctc acc cct acc ctg gtg tca nnn ttg       48
Val Pro Ala Thr Leu Pro Gln Leu Thr Pro Thr Leu Val Ser Xaa Leu
1               5                   10                  15

gag nnn att gaa cct gaa gtg tta tat gca gga tat gat agc tct nnn       96
Glu Xaa Ile Glu Pro Glu Val Leu Tyr Ala Gly Tyr Asp Ser Ser Xaa
            20                  25                  30

cca gac tca act nnn agg atc atg act acg ctc aac atg tta gga ggg      144
Pro Asp Ser Thr Xaa Arg Ile Met Thr Thr Leu Asn Met Leu Gly Gly
        35                  40                  45

cgg caa gtg att gca gca gtg aaa tgg gca aag gca ata cca ggt ttc      192
Arg Gln Val Ile Ala Ala Val Lys Trp Ala Lys Ala Ile Pro Gly Phe
    50                  55                  60

agg aac tta cac ctg gat gac caa atg acc cta ctg cag tac tcc tgg      240
Arg Asn Leu His Leu Asp Asp Gln Met Thr Leu Leu Gln Tyr Ser Trp
65                  70                  75                  80

atg nnn ctt atg gca ttt gct ctg ggg tgg aga tca tat aga caa tca      288
Met Xaa Leu Met Ala Phe Ala Leu Gly Trp Arg Ser Tyr Arg Gln Ser
                85                  90                  95

agt gca aac ctg ctg tgt ttt gct cct gat ctg att att aat gag cag      336
Ser Ala Asn Leu Leu Cys Phe Ala Pro Asp Leu Ile Ile Asn Glu Gln
            100                 105                 110

aga atg act nnn ccc nnn atg tac gac caa tgt aaa cac atg ctg nnn      384
Arg Met Thr Xaa Pro Xaa Met Tyr Asp Gln Cys Lys His Met Leu Xaa
```

-continued

```
        115                 120                 125

gtt tcc tct gag tta cac agg ctt cag gta tct nnn gaa gag tat ctc      432
Val Ser Ser Glu Leu His Arg Leu Gln Val Ser Xaa Glu Glu Tyr Leu
    130                 135                 140

tgt atg aaa acc tta ctg ctt ctc tct tca gtt cct aag gac ggt ctg      480
Cys Met Lys Thr Leu Leu Leu Leu Ser Ser Val Pro Lys Asp Gly Leu
145                 150                 155                 160

aag agc caa gag nnn ttt gat gaa att aga nnn acc tac atc aaa gag      528
Lys Ser Gln Glu Xaa Phe Asp Glu Ile Arg Xaa Thr Tyr Ile Lys Glu
                165                 170                 175

cta gga aaa gcc att nnn aag agg gaa gga aac tcc agc cag aac nnn      576
Leu Gly Lys Ala Ile Xaa Lys Arg Glu Gly Asn Ser Ser Gln Asn Xaa
            180                 185                 190

cag cgg ttt tat caa ctg aca aaa ctc ttg gat tct atg cat gaa gtg      624
Gln Arg Phe Tyr Gln Leu Thr Lys Leu Leu Asp Ser Met His Glu Val
        195                 200                 205

gtt gaa aat ctc nnn aac tat tgc ttc caa aca ttt nnn gat aag acc      672
Val Glu Asn Leu Xaa Asn Tyr Cys Phe Gln Thr Phe Xaa Asp Lys Thr
    210                 215                 220

atg agt att gaa ttc ccc gag atg tta gct gaa atc atc acc aat cag      720
Met Ser Ile Glu Phe Pro Glu Met Leu Ala Glu Ile Ile Thr Asn Gln
225                 230                 235                 240

ata cca aaa nnn tca aat gga aat atc aaa aaa ctt ctg ttt cat caa      768
Ile Pro Lys Xaa Ser Asn Gly Asn Ile Lys Lys Leu Leu Phe His Gln
                245                 250                 255

aag tga                                                              774
Lys


<210> SEQ ID NO 16
<211> LENGTH: 257
<212> TYPE: PRT
<213> ORGANISM: Homo sapiens
<220> FEATURE:
<221> NAME/KEY: misc_feature
<222> LOCATION: (15)..(15)
<223> OTHER INFORMATION: The 'Xaa' at location 15 stands for Cys, Asn,
      Tyr, Lys, Ser, Asp, Glu, Gln, Arg or Thr.
      .
<220> FEATURE:
<221> NAME/KEY: misc_feature
<222> LOCATION: (18)..(18)
<223> OTHER INFORMATION: The 'Xaa' at location 18 stands for Cys, Asn,
      Tyr, Lys, Ser, Asp, Glu, Gln, Arg or Thr.
      .
<220> FEATURE:
<221> NAME/KEY: misc_feature
<222> LOCATION: (32)..(32)
<223> OTHER INFORMATION: The 'Xaa' at location 32 stands for Cys, Asn,
      Tyr, Lys, Ser, Asp, Glu, Gln, Arg or Thr.
      .
<220> FEATURE:
<221> NAME/KEY: misc_feature
<222> LOCATION: (37)..(37)
<223> OTHER INFORMATION: The 'Xaa' at location 37 stands for Cys, Asn,
      Tyr, Lys, Ser, Asp, Glu, Gln, Arg or Thr.
      .
<220> FEATURE:
<221> NAME/KEY: misc_feature
<222> LOCATION: (82)..(82)
<223> OTHER INFORMATION: The 'Xaa' at location 82 stands for Cys, Asn,
      Tyr, Lys, Ser, Asp, Glu, Gln, Arg or Thr.
      .
<220> FEATURE:
<221> NAME/KEY: misc_feature
<222> LOCATION: (116)..(116)
<223> OTHER INFORMATION: The 'Xaa' at location 116 stands for Cys, Asn,
      Tyr, Lys, Ser, Asp, Glu, Gln, Arg or Thr.
      .
<220> FEATURE:
```

-continued

<221> NAME/KEY: misc_feature
<222> LOCATION: (118)..(118)
<223> OTHER INFORMATION: The 'Xaa' at location 118 stands for Cys, Asn, Tyr, Lys, Ser, Asp, Glu, Gln, Arg or Thr.
.
<220> FEATURE:
<221> NAME/KEY: misc_feature
<222> LOCATION: (128)..(128)
<223> OTHER INFORMATION: The 'Xaa' at location 128 stands for Cys, Asn, Tyr, Lys, Ser, Asp, Glu, Gln, Arg or Thr.
.
<220> FEATURE:
<221> NAME/KEY: misc_feature
<222> LOCATION: (140)..(140)
<223> OTHER INFORMATION: The 'Xaa' at location 140 stands for Cys, Asn, Tyr, Lys, Ser, Asp, Glu, Gln, Arg or Thr.
.
<220> FEATURE:
<221> NAME/KEY: misc_feature
<222> LOCATION: (165)..(165)
<223> OTHER INFORMATION: The 'Xaa' at location 165 stands for Cys, Asn, Tyr, Lys, Ser, Asp, Glu, Gln, Arg or Thr.
.
<220> FEATURE:
<221> NAME/KEY: misc_feature
<222> LOCATION: (171)..(171)
<223> OTHER INFORMATION: The 'Xaa' at location 171 stands for Cys, Asn, Tyr, Lys, Ser, Asp, Glu, Gln, Arg or Thr.
.
<220> FEATURE:
<221> NAME/KEY: misc_feature
<222> LOCATION: (182)..(182)
<223> OTHER INFORMATION: The 'Xaa' at location 182 stands for Cys, Asn, Tyr, Lys, Ser, Asp, Glu, Gln, Arg or Thr.
.
<220> FEATURE:
<221> NAME/KEY: misc_feature
<222> LOCATION: (192)..(192)
<223> OTHER INFORMATION: The 'Xaa' at location 192 stands for Cys, Asn, Tyr, Lys, Ser, Asp, Glu, Gln, Arg or Thr.
.
<220> FEATURE:
<221> NAME/KEY: misc_feature
<222> LOCATION: (213)..(213)
<223> OTHER INFORMATION: The 'Xaa' at location 213 stands for Cys, Asn, Tyr, Lys, Ser, Asp, Glu, Gln, Arg or Thr.
.
<220> FEATURE:
<221> NAME/KEY: misc_feature
<222> LOCATION: (221)..(221)
<223> OTHER INFORMATION: The 'Xaa' at location 221 stands for Cys, Asn, Tyr, Lys, Ser, Asp, Glu, Gln, Arg or Thr.
.
<220> FEATURE:
<221> NAME/KEY: misc_feature
<222> LOCATION: (244)..(244)
<223> OTHER INFORMATION: The 'Xaa' at location 244 stands for Cys, Asn, Tyr, Lys, Ser, Asp, Glu, Gln, Arg or Thr.
.
<220> FEATURE:
<221> NAME/KEY: misc_feature
<222> LOCATION: (1)..(774)
<223> OTHER INFORMATION: n = a or c or g or t/u such that Xaa at positions 552, 557, 602, 636, 648, 712, 741, 535, 538, 638, 691, 702, 648, 660, 685, 733 and 764 can indpendently be Cys, Asn, Tyr, Lys, Ser, Asp, Glu, Gln, Arg or Thr

<400> SEQUENCE: 16

```
Val Pro Ala Thr Leu Pro Gln Leu Thr Pro Thr Leu Val Ser Xaa Leu
1               5                   10                  15

Glu Xaa Ile Glu Pro Glu Val Leu Tyr Ala Gly Tyr Asp Ser Ser Xaa
            20                  25                  30

Pro Asp Ser Thr Xaa Arg Ile Met Thr Thr Leu Asn Met Leu Gly Gly
        35                  40                  45

Arg Gln Val Ile Ala Ala Val Lys Trp Ala Lys Ala Ile Pro Gly Phe
```

-continued

```
    50                  55                  60

Arg Asn Leu His Leu Asp Asp Gln Met Thr Leu Leu Gln Tyr Ser Trp
65                  70                  75                  80

Met Xaa Leu Met Ala Phe Ala Leu Gly Trp Arg Ser Tyr Arg Gln Ser
                85                  90                  95

Ser Ala Asn Leu Leu Cys Phe Ala Pro Asp Leu Ile Ile Asn Glu Gln
            100                 105                 110

Arg Met Thr Xaa Pro Xaa Met Tyr Asp Gln Cys Lys His Met Leu Xaa
        115                 120                 125

Val Ser Ser Glu Leu His Arg Leu Gln Val Ser Xaa Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Xaa Phe Asp Glu Ile Arg Xaa Thr Tyr Ile Lys Glu
                165                 170                 175

Leu Gly Lys Ala Ile Xaa Lys Arg Glu Gly Asn Ser Ser Gln Asn Xaa
            180                 185                 190

Gln Arg Phe Tyr Gln Leu Thr Lys Leu Leu Asp Ser Met His Glu Val
        195                 200                 205

Val Glu Asn Leu Xaa Asn Tyr Cys Phe Gln Thr Phe Xaa Asp Lys Thr
    210                 215                 220

Met Ser Ile Glu Phe Pro Glu Met Leu Ala Glu Ile Ile Thr Asn Gln
225                 230                 235                 240

Ile Pro Lys Xaa Ser Asn Gly Asn Ile Lys Lys Leu Leu Phe His Gln
                245                 250                 255

Lys


<210> SEQ ID NO 17
<211> LENGTH: 25
<212> TYPE: PRT
<213> ORGANISM: Homo sapiens

<400> SEQUENCE: 17

Gln Glu Pro Val Ser Pro Lys Lys Lys Glu Asn Ala Leu Leu Arg Tyr
1               5                   10                  15

Leu Leu Asp Lys Asp Asp Thr Lys Asp
            20                  25


<210> SEQ ID NO 18
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: Xaa is any amino acid

<400> SEQUENCE: 18

Leu Xaa Xaa Leu Leu
1               5


<210> SEQ ID NO 19
<211> LENGTH: 67
<212> TYPE: DNA
<213> ORGANISM: Homo sapiens

<400> SEQUENCE: 19

cggcggcgcc atatgaaaaa aggtcatcat catcatcatc atggttcccc tatactaggt     60
```

-continued tattgga 67

<210> SEQ ID NO 20
<211> LENGTH: 33
<212> TYPE: DNA
<213> ORGANISM: Homo sapiens

<400> SEQUENCE: 20
cggcggcgcg gatccacgcg gaaccagatc cga 33

<210> SEQ ID NO 21
<211> LENGTH: 237
<212> TYPE: PRT
<213> ORGANISM: Homo sapiens

<400> SEQUENCE: 21

Met Lys Lys Gly His His His His His His His Gly Ser Pro Ile Leu
1 5 10 15

Gly Tyr Trp Lys Ile Lys Gly Leu Val Gln Pro Thr Arg Leu Leu Leu
20 25 30

Glu Tyr Leu Glu Glu Lys Tyr Glu Glu His Leu Tyr Glu Arg Asp Glu
35 40 45

Gly Asp Lys Trp Arg Asn Lys Lys Phe Glu Leu Gly Leu Glu Phe Pro
50 55 60

Asn Leu Pro Tyr Tyr Ile Asp Gly Asp Val Lys Leu Thr Gln Ser Met
65 70 75 80

Ala Ile Ile Arg Tyr Ile Ala Asp Lys His Asn Met Leu Gly Gly Cys
85 90 95

Pro Lys Glu Arg Ala Glu Ile Ser Met Leu Glu Gly Ala Val Leu Asp
100 105 110

Ile Arg Tyr Gly Val Ser Arg Ile Ala Tyr Ser Lys Asp Phe Glu Thr
115 120 125

Leu Lys Val Asp Phe Leu Ser Lys Leu Pro Glu Met Leu Lys Met Phe
130 135 140

Glu Asp Arg Leu Cys His Lys Thr Tyr Leu Asn Gly Asp His Val Thr
145 150 155 160

His Pro Asp Phe Met Leu Tyr Asp Ala Leu Asp Val Val Leu Tyr Met
165 170 175

Asp Pro Met Cys Leu Asp Ala Phe Pro Lys Leu Val Cys Phe Lys Lys
180 185 190

Arg Ile Glu Ala Ile Pro Gln Ile Asp Lys Tyr Leu Lys Ser Ser Lys
195 200 205

Tyr Ile Ala Trp Pro Leu Gln Gly Trp Gln Ala Thr Phe Gly Gly Gly
210 215 220

Asp His Pro Pro Lys Ser Asp Leu Val Pro Arg Gly Ser
225 230 235

<210> SEQ ID NO 22
<211> LENGTH: 32
<212> TYPE: DNA
<213> ORGANISM: Homo sapiens

<400> SEQUENCE: 22
tactcctgga tgtcccttat ggcatttgct ct 32

<210> SEQ ID NO 23
<211> LENGTH: 32
<212> TYPE: DNA

-continued

<213> ORGANISM: Homo sapiens

<400> SEQUENCE: 23
agagcaaatg ccataaggga catccaggag ta 32

<210> SEQ ID NO 24
<211> LENGTH: 32
<212> TYPE: DNA
<213> ORGANISM: Homo sapiens

<400> SEQUENCE: 24
tactcctgga tggaccttat ggcatttgct ct 32

<210> SEQ ID NO 25
<211> LENGTH: 32
<212> TYPE: DNA
<213> ORGANISM: Homo sapiens

<400> SEQUENCE: 25
agagcaaatg ccataaggtc catccaggag ta 32

<210> SEQ ID NO 26
<211> LENGTH: 252
<212> TYPE: PRT
<213> ORGANISM: Homo sapiens

<400> SEQUENCE: 26

```
Ala Leu Thr Pro Ser Pro Val Met Val Leu Glu Asn Ile Glu Pro Glu
1               5                   10                  15

Ile Val Tyr Ala Gly Tyr Asp Ser Ser Lys Pro Asp Thr Ala Glu Asn
            20                  25                  30

Leu Leu Ser Thr Leu Asn Arg Leu Ala Gly Lys Gln Met Ile Gln Val
        35                  40                  45

Val Lys Trp Ala Lys Val Leu Pro Gly Phe Lys Asn Leu Pro Leu Glu
    50                  55                  60

Asp Gln Ile Thr Leu Ile Gln Tyr Ser Trp Met Cys Leu Ser Ser Phe
65                  70                  75                  80

Ala Leu Ser Trp Arg Ser Tyr Lys His Thr Asn Ser Gln Phe Leu Tyr
                85                  90                  95

Phe Ala Pro Asp Leu Val Phe Asn Glu Glu Lys Met His Gln Ser Ala
            100                 105                 110

Met Tyr Glu Leu Cys Gln Gly Met His Gln Ile Ser Leu Gln Phe Val
        115                 120                 125

Arg Leu Gln Leu Thr Phe Glu Glu Tyr Thr Ile Met Lys Val Leu Leu
    130                 135                 140

Leu Leu Ser Thr Ile Pro Lys Asp Gly Leu Lys Ser Gln Ala Ala Phe
145                 150                 155                 160

Glu Glu Met Arg Thr Asn Tyr Ile Lys Glu Leu Arg Lys Met Val Thr
                165                 170                 175

Lys Cys Pro Asn Asn Ser Gly Gln Ser Trp Gln Arg Phe Tyr Gln Leu
            180                 185                 190

Thr Lys Leu Leu Asp Ser Met His Asp Leu Val Ser Asp Leu Leu Glu
        195                 200                 205

Phe Cys Phe Tyr Thr Phe Arg Glu Ser His Ala Leu Lys Val Glu Phe
    210                 215                 220

Pro Ala Met Leu Val Glu Ile Ile Ser Asp Gln Leu Pro Lys Val Glu
225                 230                 235                 240
```

-continued

```
Ser Gly Asn Ala Lys Pro Leu Tyr Phe His Arg Lys
                245                 250
```

<210> SEQ ID NO 27
<211> LENGTH: 252
<212> TYPE: PRT
<213> ORGANISM: Homo sapiens

<400> SEQUENCE: 27

```
Gln Leu Ile Pro Pro Leu Ile Asn Leu Leu Met Ser Ile Glu Pro Asp
1               5                   10                  15

Val Ile Tyr Ala Gly His Asp Asn Thr Lys Pro Asp Thr Ser Ser Ser
            20                  25                  30

Leu Leu Thr Ser Leu Asn Gln Leu Gly Glu Arg Gln Leu Leu Ser Val
        35                  40                  45

Val Lys Trp Ser Lys Ser Leu Pro Gly Phe Arg Asn Leu His Ile Asp
    50                  55                  60

Asp Gln Ile Thr Leu Ile Gln Tyr Ser Trp Met Ser Leu Met Val Phe
65                  70                  75                  80

Gly Leu Gly Trp Arg Ser Tyr Lys His Val Ser Gly Gln Met Leu Tyr
                85                  90                  95

Phe Ala Pro Asp Leu Ile Leu Asn Glu Gln Arg Met Lys Glu Ser Ser
            100                 105                 110

Phe Tyr Ser Leu Cys Leu Thr Met Trp Gln Ile Pro Gln Glu Phe Val
        115                 120                 125

Lys Leu Gln Val Ser Gln Glu Glu Phe Leu Cys Met Lys Val Leu Leu
    130                 135                 140

Leu Leu Asn Thr Ile Pro Leu Glu Gly Leu Arg Ser Gln Thr Gln Phe
145                 150                 155                 160

Glu Glu Met Arg Ser Ser Tyr Ile Arg Glu Leu Ile Lys Ala Ile Gly
                165                 170                 175

Leu Arg Gln Lys Gly Val Val Ser Ser Ser Gln Arg Phe Tyr Gln Leu
            180                 185                 190

Thr Lys Leu Leu Asp Asn Leu His Asp Leu Val Lys Gln Leu His Leu
        195                 200                 205

Tyr Cys Leu Asn Thr Phe Ile Gln Ser Arg Ala Leu Ser Val Glu Phe
    210                 215                 220

Pro Glu Met Met Ser Glu Val Ile Ala Ala Gln Leu Pro Lys Ile Leu
225                 230                 235                 240

Ala Gly Met Val Lys Pro Leu Leu Phe His Lys Lys
                245                 250
```

<210> SEQ ID NO 28
<211> LENGTH: 252
<212> TYPE: PRT
<213> ORGANISM: Homo sapiens

<400> SEQUENCE: 28

```
Glu Cys Gln Pro Ile Phe Leu Asn Val Leu Glu Ala Ile Glu Pro Gly
1               5                   10                  15

Val Val Cys Ala Gly His Asp Asn Asn Gln Pro Asp Ser Phe Ala Ala
            20                  25                  30

Leu Leu Ser Ser Leu Asn Glu Leu Gly Glu Arg Gln Leu Val His Val
        35                  40                  45

Val Lys Trp Ala Lys Ala Leu Pro Gly Phe Arg Asn Leu His Val Asp
    50                  55                  60
```

-continued

```
Asp Gln Met Ala Val Ile Gln Tyr Ser Trp Met Gly Leu Met Val Phe
65                  70                  75                  80

Ala Met Gly Trp Arg Ser Phe Thr Asn Val Asn Ser Arg Met Leu Tyr
                85                  90                  95

Phe Ala Pro Asp Leu Val Phe Asn Glu Tyr Arg Met His Lys Ser Arg
            100                 105                 110

Met Tyr Ser Gln Cys Val Arg Met Arg His Leu Ser Gln Glu Phe Gly
        115                 120                 125

Trp Leu Gln Ile Thr Pro Gln Glu Phe Leu Cys Met Lys Ala Leu Leu
    130                 135                 140

Leu Phe Ser Ile Ile Pro Val Asp Gly Leu Lys Asn Gln Lys Phe Phe
145                 150                 155                 160

Asp Glu Leu Arg Met Asn Tyr Ile Lys Glu Leu Asp Arg Ile Ile Ala
                165                 170                 175

Cys Lys Arg Lys Asn Pro Thr Ser Cys Ser Arg Arg Phe Tyr Gln Leu
            180                 185                 190

Thr Lys Leu Leu Asp Ser Val Gln Pro Ile Ala Arg Glu Leu His Gln
        195                 200                 205

Phe Thr Phe Asp Leu Leu Ile Lys Ser His Met Val Ser Val Asp Phe
    210                 215                 220

Pro Glu Met Met Ala Glu Ile Ile Ser Val Gln Val Pro Lys Ile Leu
225                 230                 235                 240

Ser Gly Lys Val Lys Pro Ile Tyr Phe His Thr Gln
                245                 250


<210> SEQ ID NO 29
<211> LENGTH: 286
<212> TYPE: PRT
<213> ORGANISM: Homo sapiens

<400> SEQUENCE: 29

Leu Thr Ala Asp Gln Met Val Ser Ala Leu Leu Asp Ala Glu Pro Pro
1               5                   10                  15

Ile Leu Tyr Ser Glu Tyr Asp Pro Thr Arg Pro Phe Ser Glu Ala Ser
            20                  25                  30

Met Met Gly Leu Leu Thr Asn Leu Ala Asp Arg Glu Leu Val His Met
        35                  40                  45

Ile Asn Trp Ala Lys Arg Val Pro Gly Phe Val Asp Leu Thr Leu His
    50                  55                  60

Asp Gln Val His Leu Leu Glu Cys Ala Trp Leu Glu Ile Leu Met Ile
65                  70                  75                  80

Gly Leu Val Trp Arg Ser Met Glu His Pro Gly Lys Leu Leu Phe Ala
                85                  90                  95

Pro Asn Leu Leu Leu Asp Arg Asn Gln Gly Lys Cys Val Glu Gly Met
            100                 105                 110

Val Glu Ile Phe Asp Met Leu Leu Ala Thr Ser Ser Arg Phe Arg Met
        115                 120                 125

Met Asn Leu Gln Gly Glu Glu Phe Val Cys Leu Lys Ser Ile Ile Leu
    130                 135                 140

Leu Asn Ser Gly Val Tyr Thr Phe Leu Ser Ser Thr Leu Lys Ser Leu
145                 150                 155                 160

Glu Glu Lys Asp His Ile His Arg Val Leu Asp Lys Ile Thr Asp Thr
                165                 170                 175

Leu Ile His Leu Met Ala Lys Ala Gly Leu Thr Leu Gln Gln Gln His
            180                 185                 190
```

-continued

```
Gln Arg Leu Ala Gln Leu Leu Leu Ile Leu Ser His Ile Arg His Met
        195                 200                 205

Ser Asn Lys Gly Met Glu His Leu Tyr Ser Met Lys Cys Lys Asn Val
    210                 215                 220

Val Pro Leu Tyr Asp Leu Leu Leu Glu Met Leu Asp Ala His Arg Leu
225                 230                 235                 240

His Ala Pro Thr Ser Arg Gly Gly Ala Ser Val Glu Glu Thr Asp Gln
                245                 250                 255

Ser His Leu Ala Thr Ala Gly Ser Thr Ser Ser His Ser Leu Gln Lys
            260                 265                 270

Tyr Tyr Ile Thr Gly Glu Ala Glu Gly Phe Pro Ala Thr Val
        275                 280                 285


<210> SEQ ID NO 30
<211> LENGTH: 268
<212> TYPE: PRT
<213> ORGANISM: Homo sapiens

<400> SEQUENCE: 30

Leu Ser Pro Glu Gln Leu Val Leu Thr Leu Leu Glu Ala Glu Pro Pro
1               5                   10                  15

His Val Leu Ile Ser Arg Pro Ser Ala Pro Phe Thr Glu Ala Ser Met
            20                  25                  30

Met Met Ser Leu Thr Lys Leu Ala Asp Lys Glu Leu Val His Met Ile
        35                  40                  45

Ser Trp Ala Lys Lys Ile Pro Gly Phe Val Glu Leu Ser Leu Phe Asp
    50                  55                  60

Gln Val Arg Leu Leu Glu Ser Cys Trp Met Glu Val Leu Met Met Gly
65                  70                  75                  80

Leu Met Trp Arg Ser Ile Asp His Pro Gly Lys Leu Ile Phe Ala Pro
                85                  90                  95

Asp Leu Val Leu Asp Arg Asp Glu Gly Lys Cys Val Glu Gly Ile Leu
            100                 105                 110

Glu Ile Phe Asp Met Leu Leu Ala Thr Thr Ser Arg Phe Arg Glu Leu
        115                 120                 125

Lys Leu Gln His Lys Glu Tyr Leu Cys Val Lys Ala Met Ile Leu Leu
    130                 135                 140

Asn Ser Ser Met Tyr Pro Leu Val Thr Ala Thr Gln Asp Ala Asp Ser
145                 150                 155                 160

Ser Arg Lys Leu Ala His Leu Leu Asn Ala Val Thr Asp Ala Leu Val
                165                 170                 175

Trp Val Ile Ala Lys Ser Gly Ile Ser Ser Gln Gln Gln Ser Met Arg
            180                 185                 190

Leu Ala Asn Leu Leu Met Leu Leu Ser His Val Arg His Ala Ser Asn
        195                 200                 205

Lys Gly Met Glu His Leu Leu Asn Met Lys Cys Lys Asn Val Val Pro
    210                 215                 220

Val Tyr Asp Leu Leu Leu Glu Met Leu Asn Ala His Val Leu Arg Gly
225                 230                 235                 240

Cys Lys Ser Ser Ile Thr Gly Ser Glu Cys Ser Pro Ala Glu Asp Ser
                245                 250                 255

Lys Ser Lys Glu Gly Ser Gln Asn Pro Gln Ser Gln
            260                 265
```

-continued

<210> SEQ ID NO 31
<211> LENGTH: 251
<212> TYPE: PRT
<213> ORGANISM: Homo sapiens

<400> SEQUENCE: 31

```
Gln Leu Thr Pro Thr Leu Val Ser Leu Leu Glu Val Ile Glu Pro Glu
1               5                   10                  15

Val Leu Tyr Ala Gly Tyr Asp Ser Ser Val Pro Asp Ser Thr Trp Arg
            20                  25                  30

Ile Met Thr Thr Leu Asn Met Leu Gly Gly Arg Gln Val Ile Ala Ala
        35                  40                  45

Val Lys Trp Ala Lys Ala Ile Pro Gly Phe Arg Asn Leu His Leu Asp
    50                  55                  60

Asp Gln Met Thr Leu Leu Gln Tyr Ser Trp Met Ser Leu Met Ala Phe
65                  70                  75                  80

Ala Leu Gly Trp Arg Ser Tyr Arg Gln Ser Ser Ala Asn Leu Leu Cys
                85                  90                  95

Phe Ala Pro Asp Leu Ile Ile Asn Glu Gln Arg Met Thr Leu Pro Cys
            100                 105                 110

Met Tyr Asp Gln Cys Lys His Met Leu Tyr Val Ser Ser Glu Leu His
        115                 120                 125

Arg Leu Gln Val Ser Tyr Glu Glu Tyr Leu Cys Met Lys Thr Leu Leu
    130                 135                 140

Leu Leu Ser Ser Val Pro Lys Asp Gly Leu Lys Ser Gln Glu Leu Phe
145                 150                 155                 160

Asp Glu Ile Arg Met Thr Tyr Ile Lys Glu Leu Gly Lys Ala Ile Val
                165                 170                 175

Lys Arg Glu Gly Asn Ser Ser Gln Asn Trp Gln Arg Phe Tyr Gln Leu
            180                 185                 190

Thr Lys Leu Leu Asp Ser Met His Glu Val Val Glu Asn Leu Leu Asn
        195                 200                 205

Tyr Cys Phe Gln Thr Phe Leu Asp Lys Thr Met Ser Ile Glu Phe Pro
    210                 215                 220

Glu Met Leu Ala Glu Ile Ile Thr Asn Gln Ile Pro Lys Tyr Ser Asn
225                 230                 235                 240

Gly Asn Ile Lys Lys Leu Leu Phe His Gln Lys
                245                 250
```

<210> SEQ ID NO 32
<211> LENGTH: 259
<212> TYPE: PRT
<213> ORGANISM: Homo sapiens

<400> SEQUENCE: 32

```
Gly Ser Val Pro Ala Thr Leu Pro Gln Leu Thr Pro Thr Leu Val Ser
1               5                   10                  15

Leu Leu Glu Val Ile Glu Pro Glu Val Leu Tyr Ala Gly Tyr Asp Ser
            20                  25                  30

Ser Val Pro Asp Ser Thr Trp Arg Ile Met Thr Thr Leu Asn Met Leu
        35                  40                  45

Gly Gly Arg Gln Val Ile Ala Ala Val Lys Trp Ala Lys Ala Ile Pro
    50                  55                  60

Gly Phe Arg Asn Leu His Leu Asp Asp Gln Met Thr Leu Leu Gln Tyr
65                  70                  75                  80

Ser Trp Met Ser Leu Met Ala Phe Ala Leu Gly Trp Arg Ser Tyr Arg
```

-continued

```
                85                  90                  95

Gln Ser Ser Ala Asn Leu Leu Cys Phe Ala Pro Asp Leu Ile Ile Asn
            100                 105                 110

Glu Gln Arg Met Thr Leu Pro Cys Met Tyr Asp Gln Cys Lys His Met
        115                 120                 125

Leu Tyr Val Ser Ser Glu Leu His Arg Leu Gln Val Ser Tyr Glu Glu
    130                 135                 140

Tyr Leu Cys Met Lys Thr Leu Leu Leu Leu Ser Ser Val Pro Lys Asp
145                 150                 155                 160

Gly Leu Lys Ser Gln Glu Leu Phe Asp Glu Ile Arg Met Thr Tyr Ile
                165                 170                 175

Lys Glu Leu Gly Lys Ala Ile Val Lys Arg Glu Gly Asn Ser Ser Gln
            180                 185                 190

Asn Trp Gln Arg Phe Tyr Gln Leu Thr Lys Leu Leu Asp Ser Met His
        195                 200                 205

Glu Val Val Glu Asn Leu Leu Asn Tyr Cys Phe Gln Thr Phe Leu Asp
    210                 215                 220

Lys Thr Met Ser Ile Glu Phe Pro Glu Met Leu Ala Glu Ile Ile Thr
225                 230                 235                 240

Asn Gln Ile Pro Lys Tyr Ser Asn Gly Asn Ile Lys Lys Leu Leu Phe
                245                 250                 255

His Gln Lys


<210> SEQ ID NO 33
<211> LENGTH: 257
<212> TYPE: PRT
<213> ORGANISM: Homo sapiens

<400> SEQUENCE: 33

Val Pro Ala Thr Leu Pro Gln Leu Thr Pro Thr Leu Val Ser Leu Leu
1               5                   10                  15

Glu Val Ile Glu Pro Glu Val Leu Tyr Ala Gly Tyr Asp Ser Ser Val
            20                  25                  30

Pro Asp Ser Thr Arg Arg Ile Met Thr Thr Leu Asn Met Leu Gly Gly
        35                  40                  45

Arg Gln Val Ile Ala Ala Val Lys Trp Ala Lys Ala Ile Pro Gly Phe
    50                  55                  60

Arg Asn Leu His Leu Asp Asp Gln Met Thr Leu Leu Gln Tyr Ser Trp
65                  70                  75                  80

Met Phe Leu Met Ala Phe Ala Leu Gly Trp Arg Ser Tyr Arg Gln Ser
                85                  90                  95

Ser Ala Asn Leu Leu Cys Phe Ala Pro Asp Leu Ile Ile Asn Glu Gln
            100                 105                 110

Arg Met Thr Leu Pro Cys Met Tyr Asp Gln Cys Lys His Met Leu Tyr
        115                 120                 125

Val Ser Ser Glu Leu His Arg Leu Gln Val Ser Tyr Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
```

-continued

```
        195                 200                 205

Val Glu Asn Leu Leu Asn Tyr Cys Phe Gln Thr Phe Leu Asp Lys Thr
    210                 215                 220

Met Ser Ile Glu Phe Pro Glu Met Leu Ala Glu Ile Ile Thr Asn Gln
225                 230                 235                 240

Ile Pro Lys Tyr Ser Asn Gly Asn Ile Lys Lys Leu Leu Phe His Gln
                245                 250                 255

Lys


<210> SEQ ID NO 34
<211> LENGTH: 257
<212> TYPE: PRT
<213> ORGANISM: Homo sapiens

<400> SEQUENCE: 34

Val Pro Ala Thr Leu Pro Gln Leu Thr Pro Thr Leu Val Ser Leu Leu
1               5                   10                  15

Glu Val Ile Glu Pro Glu Val Leu Tyr Ala Gly Tyr Asp Ser Ser Val
            20                  25                  30

Pro Asp Ser Thr Trp Arg Ile Met Thr Thr Leu Asn Met Leu Gly Gly
        35                  40                  45

Arg Gln Val Ile Ala Ala Val Lys Trp Ala Lys Ala Ile Pro Gly Phe
    50                  55                  60

Arg Asn Leu His Leu Asp Asp Gln Met Thr Leu Leu Gln Tyr Ser Trp
65                  70                  75                  80

Met Phe Leu Met Ala Phe Ala Leu Gly Trp Arg Ser Tyr Arg Leu Ser
                85                  90                  95

Ser Ala Asn Leu Leu Cys Phe Ala Pro Asp Leu Ile Ile Asn Glu Gln
            100                 105                 110

Arg Met Thr Leu Pro Cys Met Tyr Asp Gln Cys Lys His Met Leu Tyr
        115                 120                 125

Val Ser Ser Glu Leu His Arg Leu Gln Val Ser Tyr Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
        195                 200                 205

Val Glu Asn Leu Leu Asn Tyr Cys Phe Gln Thr Phe Leu Asp Lys Thr
    210                 215                 220

Met Ser Ile Glu Phe Pro Glu Met Leu Ala Glu Ile Ile Thr Asn Gln
225                 230                 235                 240

Ile Pro Lys Tyr Ser Asn Gly Asn Ile Lys Lys Leu Leu Phe His Gln
                245                 250                 255

Lys


<210> SEQ ID NO 35
<211> LENGTH: 257
<212> TYPE: PRT
<213> ORGANISM: Homo sapiens

<400> SEQUENCE: 35
```

-continued

```
Val Pro Ala Thr Leu Pro Gln Leu Thr Pro Thr Leu Val Ser Leu Leu
1               5                   10                  15

Glu Val Ile Glu Pro Glu Val Leu Tyr Ala Gly Tyr Asp Ser Ser Val
            20                  25                  30

Pro Asp Ser Thr Trp Arg Ile Met Thr Thr Leu Asn Met Leu Gly Gly
        35                  40                  45

Arg Gln Val Ile Ala Ala Val Lys Trp Ala Lys Ala Ile Pro Gly Phe
    50                  55                  60

Arg Asn Leu His Leu Asp Asp Gln Met Thr Leu Leu Gln Tyr Ser Trp
65                  70                  75                  80

Met Phe Leu Met Ala Phe Ala Leu Gly Trp Arg Ser Tyr Arg His Ser
                85                  90                  95

Ser Ala Asn Leu Leu Cys Phe Ala Pro Asp Leu Ile Ile Asn Glu Gln
            100                 105                 110

Arg Met Thr Leu Pro Cys Met Tyr Asp Gln Cys Lys His Met Leu Tyr
        115                 120                 125

Val Ser Ser Glu Leu His Arg Leu Gln Val Ser Tyr Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
        195                 200                 205

Val Glu Asn Leu Leu Asn Tyr Cys Phe Gln Thr Phe Leu Asp Lys Thr
    210                 215                 220

Met Ser Ile Glu Phe Pro Glu Met Leu Ala Glu Ile Ile Thr Asn Gln
225                 230                 235                 240

Ile Pro Lys Tyr Ser Asn Gly Asn Ile Lys Lys Leu Leu Phe His Gln
                245                 250                 255

Lys


<210> SEQ ID NO 36
<211> LENGTH: 257
<212> TYPE: PRT
<213> ORGANISM: Homo sapiens

<400> SEQUENCE: 36

Val Pro Ala Thr Leu Pro Gln Leu Thr Pro Thr Leu Val Ser Leu Leu
1               5                   10                  15

Glu Val Ile Glu Pro Glu Val Leu Tyr Ala Gly Tyr Asp Ser Ser Val
            20                  25                  30

Pro Asp Ser Thr Trp Arg Ile Met Thr Thr Leu Asn Met Leu Gly Gly
        35                  40                  45

Arg Gln Val Ile Ala Thr Val Lys Trp Ala Lys Ala Ile Pro Gly Phe
    50                  55                  60

Arg Asn Leu His Leu Asp Asp Gln Met Thr Leu Leu Gln Tyr Ser Trp
65                  70                  75                  80

Met Phe Leu Met Ala Phe Ala Leu Gly Trp Arg Ser Tyr Arg Gln Ser
                85                  90                  95

Ser Ala Asn Leu Leu Cys Phe Ala Pro Asp Leu Ile Ile Asn Glu Gln
            100                 105                 110
```

-continued

```
Arg Met Thr Leu Pro Cys Met Tyr Asp Gln Cys Lys His Met Leu Tyr
        115                 120                 125

Val Ser Ser Glu Leu His Arg Leu Gln Val Ser Tyr Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
        195                 200                 205

Val Glu Asn Leu Leu Asn Tyr Cys Phe Gln Thr Phe Leu Asp Lys Thr
    210                 215                 220

Met Ser Ile Glu Phe Pro Glu Met Leu Ala Glu Ile Ile Thr Asn Gln
225                 230                 235                 240

Ile Pro Lys Tyr Ser Asn Gly Asn Ile Lys Lys Leu Leu Phe His Gln
                245                 250                 255

Lys


<210> SEQ ID NO 37
<211> LENGTH: 257
<212> TYPE: PRT
<213> ORGANISM: Homo sapiens

<400> SEQUENCE: 37

Val Pro Ala Thr Leu Pro Gln Leu Thr Pro Thr Leu Val Ser Leu Leu
1               5                   10                  15

Glu Val Ile Glu Pro Glu Val Leu Tyr Ala Gly Tyr Asp Ser Ser Val
            20                  25                  30

Pro Asp Ser Thr Trp Arg Ile Met Thr Thr Leu Asn Met Leu Gly Gly
        35                  40                  45

Arg Gln Val Ile Ala Ala Val Lys Trp Ala Lys Ala Ile Pro Gly Phe
    50                  55                  60

Arg Asn Leu His Leu Asp Asp Gln Met Thr Leu Leu Gln Tyr Ser Trp
65                  70                  75                  80

Met Phe Leu Met Ala Phe Ala Leu Gly Trp Arg Ser Tyr Arg Gln Ser
                85                  90                  95

Ser Ala Asn Met Leu Cys Phe Ala Pro Asp Leu Ile Ile Asn Glu Gln
            100                 105                 110

Arg Met Thr Leu Pro Cys Met Tyr Asp Gln Cys Lys His Met Leu Tyr
        115                 120                 125

Val Ser Ser Glu Leu His Arg Leu Gln Val Ser Tyr Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
        195                 200                 205

Val Glu Asn Leu Leu Asn Tyr Cys Phe Gln Thr Phe Leu Asp Lys Thr
    210                 215                 220
```

-continued

```
Met Ser Ile Glu Phe Pro Glu Met Leu Ala Glu Ile Ile Thr Asn Gln
225                 230                 235                 240

Ile Pro Lys Tyr Ser Asn Gly Asn Ile Lys Lys Leu Leu Phe His Gln
                245                 250                 255

Lys


<210> SEQ ID NO 38
<211> LENGTH: 257
<212> TYPE: PRT
<213> ORGANISM: Homo sapiens

<400> SEQUENCE: 38

Val Pro Ala Thr Leu Pro Gln Leu Thr Pro Thr Leu Val Ser Leu Leu
1               5                   10                  15

Glu Val Ile Glu Pro Glu Val Leu Tyr Ala Gly Tyr Asp Ser Ser Val
            20                  25                  30

Pro Asp Ser Thr Trp Arg Ile Met Thr Thr Leu Asn Met Leu Gly Gly
        35                  40                  45

Arg Gln Val Ile Ala Ala Val Lys Trp Ala Lys Thr Ile Pro Gly Phe
    50                  55                  60

Arg Asn Leu His Leu Asp Asp Gln Met Thr Leu Leu Gln Tyr Ser Trp
65                  70                  75                  80

Met Leu Leu Met Ala Phe Ala Leu Gly Trp Arg Ser Tyr Arg Gln Ser
                85                  90                  95

Ser Ala Asn Leu Leu Cys Phe Ala Pro Asp Leu Ile Ile Asn Glu Gln
            100                 105                 110

Arg Met Thr Leu Pro Cys Met Tyr Asp Gln Cys Lys His Met Leu Tyr
        115                 120                 125

Val Ser Ser Glu Leu His Arg Leu Gln Val Ser Tyr Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
        195                 200                 205

Val Glu Asn Leu Leu Asn Tyr Cys Phe Gln Thr Phe Leu Asp Lys Thr
    210                 215                 220

Met Ser Ile Glu Phe Pro Glu Met Leu Ala Glu Ile Ile Thr Asn Gln
225                 230                 235                 240

Ile Pro Lys Tyr Ser Asn Gly Asn Ile Lys Lys Leu Leu Phe His Gln
                245                 250                 255

Lys


<210> SEQ ID NO 39
<211> LENGTH: 257
<212> TYPE: PRT
<213> ORGANISM: Homo sapiens

<400> SEQUENCE: 39

Val Pro Ala Thr Leu Pro Gln Leu Thr Pro Thr Leu Val Ser Leu Leu
1               5                   10                  15

Glu Val Ile Glu Pro Glu Val Leu Tyr Ala Gly Tyr Asp Ser Ser Val
            20                  25                  30
```

```
Pro Asp Ser Thr Trp Arg Ile Met Thr Thr Phe Asn Met Leu Gly Gly
        35                  40                  45

Arg Gln Val Ile Ala Ala Val Lys Trp Ala Lys Ala Ile Pro Cys Phe
    50                  55                  60

Arg Asn Leu His Leu Asp Asp Gln Met Thr Leu Leu Gln Tyr Ser Trp
65                  70                  75                  80

Met Phe Leu Met Ala Phe Ala Leu Gly Trp Arg Ser Tyr Arg Gln Ser
                85                  90                  95

Ser Ala Asn Leu Leu Cys Phe Ala Pro Asp Leu Ile Ile Asn Glu Gln
            100                 105                 110

Arg Met Thr Leu Pro Cys Met Tyr Asp Gln Cys Lys His Met Leu Tyr
        115                 120                 125

Val Ser Ser Glu Leu His Arg Leu Gln Val Ser Tyr Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
        195                 200                 205

Val Glu Asn Leu Leu Asn Tyr Cys Phe Gln Thr Phe Leu Asp Lys Thr
    210                 215                 220

Met Ser Ile Glu Phe Pro Glu Met Leu Ala Glu Ile Ile Thr Asn Gln
225                 230                 235                 240

Ile Pro Lys Tyr Ser Asn Gly Asn Ile Lys Lys Leu Leu Phe His Gln
                245                 250                 255

Lys


<210> SEQ ID NO 40
<211> LENGTH: 257
<212> TYPE: PRT
<213> ORGANISM: Homo sapiens

<400> SEQUENCE: 40

Val Pro Ala Thr Leu Pro Gln Leu Thr Pro Thr Leu Val Ser Leu Leu
1               5                   10                  15

Glu Val Ile Glu Pro Glu Val Leu Tyr Ala Gly Tyr Asp Ser Ser Val
            20                  25                  30

Pro Asp Ser Thr Trp Arg Ile Met Thr Thr Leu Asn Met Leu Gly Gly
        35                  40                  45

Arg Gln Val Ile Ala Ala Val Lys Trp Ala Lys Ala Ile Pro Gly Phe
    50                  55                  60

Arg Asn Leu His Leu Asp Asp Gln Met Thr Leu Leu Gln Tyr Ser Trp
65                  70                  75                  80

Met Phe Leu Met Ala Phe Ala Leu Gly Trp Arg Ser Tyr Arg Gln Ser
                85                  90                  95

Ser Ala Asn Leu Leu Cys Phe Ala Pro Asp Leu Ile Ile Asn Glu Gln
            100                 105                 110

Arg Met Thr Leu Pro Cys Met Tyr Asp Gln Cys Lys His Met Leu Tyr
        115                 120                 125

Val Ser Ser Glu Leu His Arg Leu Gln Val Ser Tyr Glu Glu Tyr His
    130                 135                 140
```

-continued

```
Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
        195                 200                 205

Val Glu Asn Leu Leu Asn Tyr Cys Phe Gln Thr Phe Leu Asp Lys Thr
    210                 215                 220

Met Ser Ile Glu Phe Pro Glu Thr Leu Ala Glu Ile Ile Thr Asn Gln
225                 230                 235                 240

Ile Pro Lys Tyr Ser Asn Gly Asn Ile Lys Lys Leu Leu Phe His Gln
                245                 250                 255

Lys


<210> SEQ ID NO 41
<211> LENGTH: 257
<212> TYPE: PRT
<213> ORGANISM: Homo sapiens

<400> SEQUENCE: 41

Val Pro Ala Thr Leu Pro Gln Leu Thr Pro Thr Leu Val Ser Leu Leu
1               5                   10                  15

Glu Val Ile Glu Pro Glu Val Leu Tyr Ala Gly Tyr Asp Ser Ser Val
            20                  25                  30

Pro Asp Ser Thr Trp Arg Ile Met Thr Thr Phe Asn Met Leu Gly Gly
        35                  40                  45

Arg Gln Val Ile Ala Ala Val Lys Trp Ala Lys Ala Ile Pro Gly Phe
    50                  55                  60

Arg Asn Leu His Leu Asp Asp Gln Met Thr Leu Leu Gln Tyr Ser Trp
65                  70                  75                  80

Met Phe Leu Met Ala Phe Ala Leu Gly Trp Arg Ser Tyr Arg Gln Ser
                85                  90                  95

Ser Ala Asn Leu Leu Cys Phe Ala Pro Asp Leu Ile Ile Asn Glu Gln
            100                 105                 110

Arg Met Thr Leu Pro Cys Met Tyr Asp Gln Cys Lys His Met Leu Tyr
        115                 120                 125

Val Ser Ser Glu Leu His Arg Leu Gln Val Ser Tyr Glu Glu Tyr Leu
    130                 135                 140

Cys Met Lys Thr Leu Leu Leu Leu Ser Ser Val Pro Lys Asp Gly Leu
145                 150                 155                 160

Lys Ser Gln Glu Leu Phe Asp Glu Ile Arg Met Thr Tyr Ile Lys Glu
                165                 170                 175

Leu Gly Lys Ala Ile Val Lys Arg Glu Gly Asn Ser Ser Gln Asn Trp
            180                 185                 190

Gln Arg Phe Tyr Gln Leu Thr Lys Leu Leu Asp Ser Met His Glu Val
        195                 200                 205

Val Glu Asn Leu Leu Asn Tyr Cys Phe Gln Thr Phe Leu Asp Lys Asn
    210                 215                 220

Met Ser Ile Glu Phe Pro Glu Met Leu Ala Glu Ile Ile Thr Asn Gln
225                 230                 235                 240
```

-continued

```
Ile Pro Lys Tyr Ser Asn Gly Asn Ile Lys Lys Leu Leu Phe His Gln
                245                 250                 255

Lys
```